United States Patent
Briner et al.

(10) Patent No.: US 11,813,306 B2
(45) Date of Patent: *Nov. 14, 2023

(54) CYCLIC TETRAMER COMPOUNDS AS PROPROTEIN CONVERTASE SUBTILISIN/KEXIN TYPE 9 (PCSK9) INHIBITORS FOR THE TREATMENT OF METABOLIC DISORDERS

(71) Applicant: NOVARTIS AG, Basel (CH)

(72) Inventors: Karin Briner, Cambridge, MA (US); Brian Addison Dechristopher, Belmont, MA (US); Alec Nathanson Flyer, Cambridge, MA (US); Andrei Alexandrovich Golosov, Cambridge, MA (US); Philipp Grosche, Inzlingen (DE); Eugene Yuejin Liu, Lexington, MA (US); Justin Yik Ching Mao, North Reading, MA (US); Lauren Gilchrist Monovich, Belmont, MA (US); Tajesh Jayprakash Patel, Westford, MA (US); Liansheng Su, Winchester, MA (US); Lihua Yang, Westford, MA (US); Rui Zheng, Needham, MA (US)

(73) Assignee: Novartis AG, Basel (CH)

( * ) Notice: Subject to any disclaimer, the term of this patent is extended or adjusted under 35 U.S.C. 154(b) by 112 days.

This patent is subject to a terminal disclaimer.

(21) Appl. No.: 17/200,471

(22) Filed: Mar. 12, 2021

(65) Prior Publication Data
US 2021/0252103 A1   Aug. 19, 2021

Related U.S. Application Data

(63) Continuation of application No. 16/695,843, filed on Nov. 26, 2019, now Pat. No. 11,026,993.

(60) Provisional application No. 62/924,828, filed on Oct. 23, 2019, provisional application No. 62/772,030, filed on Nov. 27, 2018.

(51) Int. Cl.
*A61K 38/12*   (2006.01)
*A61K 45/06*   (2006.01)
*C07K 5/12*    (2006.01)

(52) U.S. Cl.
CPC ............ *A61K 38/12* (2013.01); *A61K 45/06* (2013.01); *C07K 5/126* (2013.01)

(58) Field of Classification Search
CPC ......... A61K 38/12; A61K 45/06; C07K 5/126
See application file for complete search history.

(56) References Cited

U.S. PATENT DOCUMENTS

| | | |
|---|---|---|
| 6,780,968 B1 | 8/2004 | Giorgi et al. |
| 7,015,196 B1 | 3/2006 | Perrotta et al. |
| 8,492,517 B2 | 7/2013 | Yang et al. |
| 8,877,890 B2 | 11/2014 | Yang et al. |
| 2012/0252796 A1 | 10/2012 | Pingali et al. |

FOREIGN PATENT DOCUMENTS

| | | |
|---|---|---|
| CN | 108239073 A | 7/2018 |
| EP | 1297826 A1 | 4/2003 |
| WO | 9834949 A2 | 8/1998 |
| WO | 2000/008046 A1 | 2/2000 |
| WO | 2001/029066 A2 | 4/2001 |
| WO | 2010046900 A2 | 4/2010 |
| WO | 2011063366 A1 | 5/2011 |
| WO | 2014150395 A1 | 9/2014 |

OTHER PUBLICATIONS

Registry No. 835915-96-3, entered Feb. 23, 2005.
Registry No. 835915-94-1, entered Feb. 23, 2005.
Registry No. 835915-92-9, entered Feb. 23, 2005.
Registry No. 835915-91-8, entered Feb. 23, 2005.
Registry No. 835915-89-4, entered Feb. 23, 2005.
Registry No. 835915-87-2, entered Feb. 23, 2005.
Registry No. 835915-85-0, entered Feb. 23, 2005.
Registry No. 835915-83-8, entered Feb. 23, 2005.
Registry No. 835915-81-6, entered Feb. 23, 2005.
Registry No. 835915-80-5, entered Feb. 23, 2005.
Registry No. 835915-78-1, entered Feb. 23, 2005.
Registry No. 835915-75-8, entered Feb. 23, 2005.
Registry No. 835915-72-5, entered Feb. 23, 2005.
Registry No. 835915-70-3, entered Feb. 23, 2005.
Registry No. 835915-67-8, entered Feb. 23, 2005.
Registry No. 835915-64-5, entered Feb. 23, 2005.
Registry No. 835915-62-3, entered Feb. 23, 2005.
Registry No. 835915-59-8, entered Feb. 23, 2005.

(Continued)

*Primary Examiner* — Jeanette M Lieb
(74) *Attorney, Agent, or Firm* — Timothy P. O'Dea

(57) ABSTRACT

The disclosure relates to inhibitors of PCSK9 useful in the treatment of cholesterol lipid metabolism, and other diseases in which PCSK9 plays a role, having the Formula (I):

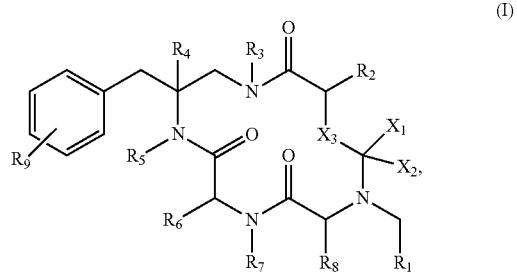

or a pharmaceutically acceptable salt, hydrate, solvate, prodrug, stereoisomer, N-oxide, or tautomer thereof, wherein $R_1$, $R_1$, $R_1$, $R_1$, $R_1$, $R_1$, $R_1$, $R_1$, $R_1$, $X_1$, $X_2$, and $X_3$ are described herein.

20 Claims, 1 Drawing Sheet

(56) References Cited

OTHER PUBLICATIONS

Registry No. 835915-57-6, entered Feb. 23, 2005.
Registry No. 835915-55-4, entered Feb. 23, 2005.
Registry No. 835915-54-3, entered Feb. 23, 2005.
Registry No. 835915-52-1, entered Feb. 23, 2005.
Registry No. 835915-50-9, entered Feb. 23, 2005.
Registry No. 835915-48-5, entered Feb. 23, 2005.
Registry No. 835915-46-3, entered Feb. 23, 2005.
Registry No. 835915-44-1, entered Feb. 23, 2005.
Registry No. 835915-42-9, entered Feb. 23, 2005.
Registry No. 835915-41-8, entered Feb. 23, 2005.
Registry No. 835915-40-7, entered Feb. 23, 2005.
Registry No. 835915-39-4, entered Feb. 23, 2005.
Registry No. 835915-38-3, entered Feb. 23, 2005.
Registry No. 835915-36-1, entered Feb. 23, 2005.
Registry No. 835915-34-9, entered Feb. 23, 2005.
Registry No. 835915-32-7, entered Feb. 23, 2005.
Registry No. 835915-30-5, entered Feb. 23, 2005.
Registry No. 835915-29-2, entered Feb. 23, 2005.
Registry No. 835915-28-1, entered Feb. 23, 2005.
Registry No. 835915-26-9, entered Feb. 23, 2005.
Registry No. 835915-21-4, entered Feb. 23, 2005.
Registry No. 835915-20-3, entered Feb. 23, 2005.
Registry No. 521949-73-5, entered May 29, 2003.
Registry No. 454707-09-6, entered Sep. 25, 2002.
Registry No. 454707-05-2, entered Sep. 25, 2002.
Registry No. 437985-42-7, entered Jul. 10, 2002.
Registry No. 437985-37-0, entered Jul. 10, 2002.
Registry No. 437985-34-7, entered Jul. 10, 2002.
Registry No. 437985-31-4, entered Jul. 10, 2002.
Registry No. 437985-27-8, entered Jul. 10, 2002.
Registry No. 437985-23-4, entered Jul. 10, 2002.
Registry No. 437985-20-1, entered Jul. 10, 2002.
Registry No. 211689-36-0, entered Sep. 24, 1998.
Registry No. 211689-35-9, entered Sep. 24, 1998.
Registry No. 211689-34-8, entered Sep. 24, 1998.
Registry No. 211689-33-7, entered Sep. 24, 1998.
Registry No. 211689-32-6, entered Sep. 24, 1998.
Registry No. 211689-30-4, entered Sep. 24, 1998.
Registry No. 211689-29-1, entered Sep. 24, 1998.
Registry No. 211689-28-0, entered Sep. 24, 1998.
Registry No. 211689-27-9, entered Sep. 24, 1998.
Registry No. 211689-26-8, entered Sep. 24, 1998.
Registry No. 211689-25-7, entered Sep. 24, 1998.
Registry No. 211689-20-2, entered Sep. 24, 1998.
Registry No. 211689-19-9, entered Sep. 24, 1998.
Registry No. 211689-18-8, entered Sep. 24, 1998.
Registry No. 211689-13-3, entered Sep. 24, 1998.
Registry No. 211689-12-2, entered Sep. 24, 1998.
Registry No. 211689-11-1, entered Sep. 24, 1998.
Registry No. 211689-10-0, entered Sep. 24, 1998.
Registry No. 211689-09-7, entered Sep. 24, 1998.
Registry No. 211689-08-6, entered Sep. 24, 1998.
Registry No. 211689-07-5, entered Sep. 24, 1998.
Registry No. 211689-06-4, entered Sep. 24, 1998.
Registry No. 211689-04-2, entered Sep. 24, 1998.
Registry No. 211689-03-1, entered Sep. 24, 1998.
Taechalertpaisarn, J., et al., "Small Molecule Inhibitors of the PCSK9-LDLR Interaction", J. Am. Chem. Soc., 2018, 140 (9):3242-3249.
Yang, J. and Miao, Y., "Substitution of Gly with Ala enhanced the melanoma uptake of technetium-99m-labeled Arg-Ala-Asp-conjugated alpha-melanocyte stimulating hormone peptide", Bioorg.& Med. Chem. Lett., 2012, 22 (4):1541-1545.
Registry No. 1350127-56-8, entered Dec. 7, 2011.
Registry No. 1349380-00-2, entered Dec. 6, 2011.
Registry No. 1349200-25-4, entered Dec. 5, 2011.
Registry No. 1348903-95-6, entered Dec. 5, 2011.
Registry No. 1348751-87-0, entered Dec. 5, 2011.
Registry No. 1348606-41-6, entered Dec. 4, 2011.
Registry No. 1348431-59-3, entered Dec. 4, 2011.
Registry No. 1348090-70-9, entered Dec. 4, 2011.
Registry No. 1347255-18-8, entered Dec. 2, 2011.
Registry No. 1223087-24-8, entered May 13, 2010.
Registry No. 1222679-25-5, entered May 13, 2010.
Registry No. 1054659-16-3, entered Sep. 29, 2008.
Registry No. 1053266-07-1, entered Sep. 26, 2008.
Registry No. 1026169-17-4, entered Jun. 8, 2008.
Registry No. 835916-01-3, entered Feb. 23, 2005.
Registry No. 835915-77-0, entered Feb. 23, 2005.
Registry No. 835915-74-7, entered Feb. 23, 2005.
Registry No. 835915-71-4, entered Feb. 23, 2005.
Registry No. 835915-69-0, entered Feb. 23, 2005.
Registry No. 835915-66-7, entered Feb. 23, 2005.
Registry No. 835915-45-2, entered Feb. 23, 2005.
Registry No. 835915-43-0, entered Feb. 23, 2005.
Registry No. 835915-37-2, entered Feb. 23, 2005.
Registry No. 835915-35-0, entered Feb. 23, 2005.
Registry No. 835915-33-8, entered Feb. 23, 2005.
Registry No. 835915-31-6, entered Feb. 23, 2005.
Registry No. 835915-27-0, entered Feb. 23, 2005.
Registry No. 211689-53-1, entered Sep. 24, 1998.
Registry No. 211689-51-9, entered Sep. 24, 1998.
Registry No. 258530-20-0, entered Mar. 8, 2000.
Registry No. 258530-19-7, entered Mar. 8, 2000.
Registry No. 258530-18-6, entered Mar. 8, 2000.
Registry No. 258530-17-5, entered Mar. 8, 2000.
Registry No. 258530-16-4, entered Mar. 8, 2000.
Registry No. 258530-15-3, entered Mar. 8, 2000.
Registry No. 258530-14-2, entered Mar. 8, 2000.
Registry No. 258530-13-1, entered Mar. 8, 2000.
Registry No. 258530-12-0, entered Mar. 8, 2000.
Registry No. 258530-11-9, entered Mar. 8, 2000.
Registry No. 258530-10-8, entered Mar. 8, 2000.
Registry No. 258530-09-5, entered Mar. 8, 2000.
Registry No. 258530-08-4, entered Mar. 8, 2000.
Registry No. 258530-07-3, entered Mar. 8, 2000.
Registry No. 258530-06-2, entered Mar. 8, 2000.
Registry No. 258530-05-1, entered Mar. 8, 2000.
Registry No. 258530-04-0, entered Mar. 8, 2000.
Registry No. 258530-03-9, entered Mar. 8, 2000.
Registry No. 258530-02-8, entered Mar. 8, 2000.
Registry No. 258530-01-7, entered Mar. 8, 2000.
Registry No. 258530-00-6, entered Mar. 8, 2000.
Registry No. 258529-99-6, entered Mar. 8, 2000.
Registry No. 258529-98-5, entered Mar. 8, 2000.
Registry No. 258529-97-4, entered Mar. 8, 2000.
Registry No. 258529-96-3, entered Mar. 8, 2000.
Registry No. 258529-95-2, entered Mar. 8, 2000.
Registry No. 258529-94-1, entered Mar. 8, 2000.
Registry No. 211689-81-5, entered Sep. 24, 1998.
Registry No. 211689-80-4, entered Sep. 24, 1998.
Registry No. 211689-75-7, entered Sep. 24, 1998.
Registry No. 211689-74-6, entered Sep. 24, 1998.
Registry No. 211689-61-1, entered Sep. 24, 1998.
Registry No. 211689-60-0, entered Sep. 24, 1998.
Registry No. 211689-59-7, entered Sep. 24, 1998.
Registry No. 211689-58-6, entered Sep. 24, 1998.
Registry No. 211689-57-5, entered Sep. 24, 1998.
Registry No. 211689-56-4, entered Sep. 24, 1998.
Registry No. 211689-55-3, entered Sep. 24, 1998.
Registry No. 211689-54-2, entered Sep. 24, 1998.
Registry No. 211689-52-0, entered Sep. 24, 1998.
Registry No. 211689-50-8, entered Sep. 24, 1998.
Registry No. 211689-49-5, entered Sep. 24, 1998.
Registry No. 211689-48-4, entered Sep. 24, 1998.
Registry No. 211689-46-2, entered Sep. 24, 1998.
Registry No. 211689-44-0, entered Sep. 24, 1998.
Registry No. 211689-43-9, entered Sep. 24, 1998.
Registry No. 211689-42-8, entered Sep. 24, 1998.
Registry No. 211689-40-6, entered Sep. 24, 1998.
Registry No. 211689-38-2, entered Sep. 24, 1998.

(56) References Cited

OTHER PUBLICATIONS

Registry No. 211689-37-1, entered Sep. 24, 1998.
Registry No. 437985-16-5, entered Jul. 10, 2002.
Registry No. 437985-07-4, entered Jul. 10, 2002.
Registry No. 437984-72-0, entered Jul. 10, 2002.
Registry No. 437984-66-2, entered Jul. 10, 2002.
Registry No. 334942-06-2, entered May 8, 2001.
Registry No. 334942-03-9, entered May 8, 2001.
Registry No. 334942-02-8, entered May 8, 2001.
Registry No. 334942-01-7, entered May 8, 2001.
Registry No. 334942-00-6, entered May 8, 2001.
Registry No. 334941-99-0, entered May 8, 2001.
Registry No. 334941-98-9, entered May 8, 2001.
Registry No. 334941-97-8, entered May 8, 2001.
Registry No. 334941-96-7, entered May 8, 2001.
Registry No. 289626-03-5, entered Sep. 18, 2000.
Registry No. 289626-02-4, entered Sep. 18, 2000.
Registry No. 289626-01-3, entered Sep. 18, 2000.
Registry No. 289626-00-2, entered Sep. 18, 2000.
Registry No. 289625-99-6, entered Sep. 18, 2000.
Registry No. 289625-98-5, entered Sep. 18, 2000.
Registry No. 289625-97-4, entered Sep. 18, 2000.
Registry No. 289625-96-3, entered Sep. 18, 2000.
Registry No. 258818-19-8, entered Mar. 9, 2000.
Registry No. 258530-65-3, entered Mar. 8, 2000.
Registry No. 258530-64-2, entered Mar. 8, 2000.
Registry No. 258530-63-1, entered Mar. 8, 2000.
Registry No. 258530-62-0, entered Mar. 8, 2000.
Registry No. 258530-43-7, entered Mar. 8, 2000.
Registry No. 258530-40-4, entered Mar. 8, 2000.
Registry No. 258530-39-1, entered Mar. 8, 2000.
Registry No. 258530-38-0, entered Mar. 8, 2000.
Registry No. 258530-37-9, entered Mar. 8, 2000.
Registry No. 258530-36-8, entered Mar. 8, 2000.
Registry No. 258530-35-7, entered Mar. 8, 2000.
Registry No. 258530-34-6, entered Mar. 8, 2000.
Registry No. 258530-33-5, entered Mar. 8, 2000.
Registry No. 258530-32-4, entered Mar. 8, 2000.
Registry No. 258530-31-3, entered Mar. 8, 2000.
Registry No. 258530-30-2, entered Mar. 8, 2000.
Registry No. 258530-29-9, entered Mar. 8, 2000.
Registry No. 258530-28-8, entered Mar. 8, 2000.
Registry No. 258530-27-7, entered Mar. 8, 2000.
Registry No. 258530-26-6, entered Mar. 8, 2000.
Registry No. 258530-25-5, entered Mar. 8, 2000.
Registry No. 258530-24-4, entered Mar. 8, 2000.
Registry No. 258530-23-3, entered Mar. 8, 2000.
Registry No. 258530-22-2, entered Mar. 8, 2000.
Registry No. 258530-21-1, entered Mar. 8, 2000.
Registry No. 258530-21-2, entered Mar. 8, 2000.
Registry No. 211689-47-3, entered Sep. 24, 1998.
Registry No. 211689-45-1, entered Sep. 24, 1998.
Registry No. 211689-41-7, entered Sep. 24, 1998.
Registry No. 211689-39-3, entered Sep. 24, 1998.
Registry No. 1224925-15-8, entered May 21, 2010.
Registry No. 1224879-01-9, entered May 21, 2010.
Registry No. 1224621-12-8, entered May 19, 2010.
Registry No. 1224621-11-7, entered May 19, 2010.
Registry No. 1224621-10-6, entered May 19, 2010.
Registry No. 1224621-09-3, entered May 19, 2010.
Registry No. 1224621-08-2, entered May 19, 2010.
Registry No. 1224621-07-1, entered May 19, 2010.
Registry No. 1224621-06-0, entered May 19, 2010.
Registry No. 1224621-05-9, entered May 19, 2010.
Registry No. 1224621-04-8, entered May 19, 2010.
Registry No. 1224621-03-7, entered May 19, 2010.
Registry No. 1224621-02-6, entered May 19, 2010.
Registry No. 1224621-01-5, entered May 19, 2010.
Registry No. 1224621-00-4, entered May 19, 2010.
Registry No. 1224620-99-8, entered May 19, 2010.
Registry No. 1224620-98-7, entered May 19, 2010.
Registry No. 1224620-97-6, entered May 19, 2010.
Registry No. 1224620-96-5, entered May 19, 2010.
Registry No. 1224620-95-4, entered May 19, 2010.
Registry No. 1224620-86-3, entered May 19, 2010.
Registry No. 1224620-82-9, entered May 19, 2010.
Registry No. 1224620-60-3, entered May 19, 2010.
Registry No. 1224620-59-0, entered May 19, 2010.
Registry No. 1224620-58-9, entered May 19, 2010.
Registry No. 1224620-57-8, entered May 19, 2010.
Registry No. 1224620-56-7, entered May 19, 2010.
Registry No. 1224620-55-6, entered May 19, 2010.
Registry No. 1224620-54-5, entered May 19, 2010.
Registry No. 1224620-53-4, entered May 19, 2010.
Registry No. 1224620-52-3, entered May 19, 2010.
Registry No. 1224620-45-4, entered May 19, 2010.
Registry No. 1224620-44-3, entered May 19, 2010.
Registry No. 1224620-37-4, entered May 19, 2010.
Registry No. 1224620-36-3, entered May 19, 2010.
Registry No. 1224620-35-2, entered May 19, 2010.
Registry No. 1224620-34-1, entered May 19, 2010.
Registry No. 1224620-27-2, entered May 19, 2010.
Registry No. 936735-70-5, entered Jun. 7, 2007.
Registry No. 835916-51-3, entered Feb. 23, 2005.
Registry No. 835916-36-4, entered Feb. 23, 2005.
Registry No. 835916-27-3, entered Feb. 23, 2005.
Registry No. 835916-25-1, entered Feb. 23, 2005.
Registry No. 835916-13-7, entered Feb. 23, 2005.
Registry No. 835916-12-6, entered Feb. 23, 2005.
Registry No. 835916-08-0, entered Feb. 23, 2005.
Altamura, Maria, et al., "New monocyclic and acyclic hNK-2 antagonists retaining the Beta-turn feature. X-ray and molecular modelling studies," Acta Crystallographica Section B: Structural Science, B62:889-896, 2006.
Fedi, Valentina, et al., "Insertion of an Aspartic Acid Moiety into Cyclic Pseudopeptides: Synthesis and Biological Characterization of Potent Antagonists for the Human Tachykinin NK-2 Receptor," J. Med. Chem., 47(27):6935-6947, 2004.
Giannotti, Danilo, et al., "Discovery of Potent Cyclic Pseudopeptide Human Tachykinin NK-2 Receptor Antagonists," J. Med. Chem., 43(22):4041-4044, 2000.
Giolotti, Alessandro, et al., "Monocyclic Human Tachykinin NK-2 Receptor Antagonists as Evolution of a Potent Bicyclic Antagonist: QSAR and Site-Directed Mutagenesis Studies," J. Med. Chem., 45(16):3418-3429, 2002.
Paoli, Paola, et al., "Solid State Investigation and Characterization of a Nepadutant Precursor: Polymorphic and Pseudopolymorphic Forms of MEN11282," Crystal Growth and Design, 16(9):5294-5304, 2016.
Valenza, Silvia, et al., "Regio- and Stereoselective Cycloadditions of Cyclic Nitrones to Maleic Diamide Forced in a Peptide: Synthesis of Potent Ligands of Human NK-2 Receptor," J. Org. Chem., 65(13):4003-4008, 2000.
Registry No. 1349380-00-2, entered Dec. 5, 2011.
Registry No. 835916-02-4, entered Feb. 23, 2005.
Registry No. 835915-99-6, entered Feb. 23, 2005.
Registry No. 835915-97-4, entered Feb. 23, 2005.
Registry No. 835915-21-1, entered Feb. 23, 2005.

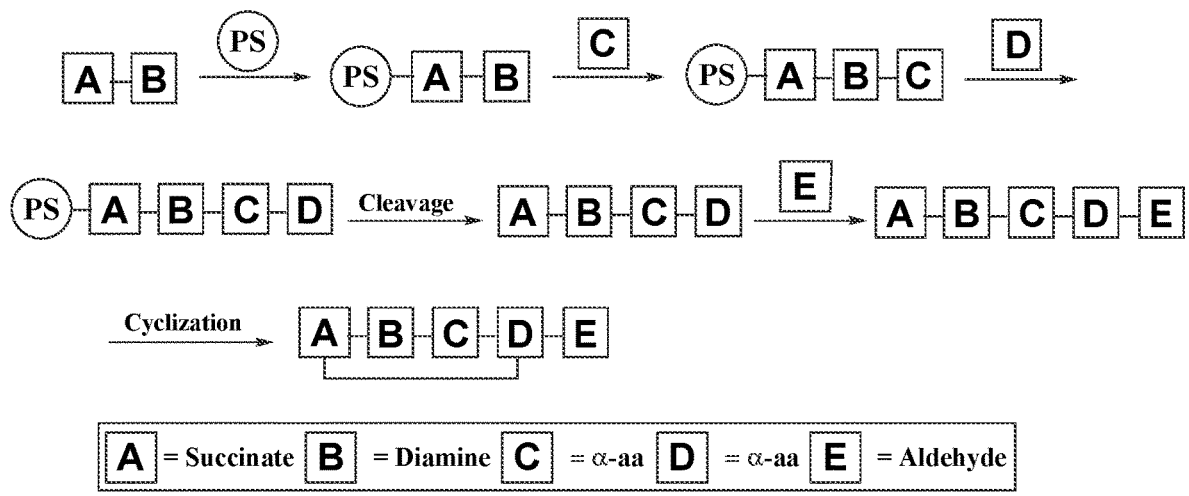

CYCLIC TETRAMER COMPOUNDS AS PROPROTEIN CONVERTASE SUBTILISIN/KEXIN TYPE 9 (PCSK9) INHIBITORS FOR THE TREATMENT OF METABOLIC DISORDERS

RELATED APPLICATIONS

This application claims is a continuation application of U.S. application Ser. No. 16/695,843, now allowed, filed on Nov. 26, 2019, which the benefit of and priority to U.S. Provisional Application No. 62/772,030, filed on Nov. 27, 2018, and 62/924,828 filed on Oct. 23, 2019, the entire contents of each of which are incorporated herein by reference in their entireties.

FIELD OF DISCLOSURE

The present disclosure is directed to modulators of proprotein convertase subtilisin/kexin type 9 (PCSK9) useful in the treatment of diseases or disorders associated with PCSK9 protease. Specifically, the disclosure is concerned with compounds and compositions, which inhibit PCSK9, methods of treating diseases or disorders associated with PCSK9, and methods of synthesis of these compounds.

BACKGROUND OF THE DISCLOSURE

Proprotein convertase subtilisin/kexin type 9 (PCSK9) is a member of the secretory subtilase, subtilisin serine protease family, and is expressed in many tissues and cell types. The PCSK9 protein contains a signal sequence, a prodomain, a catalytic domain containing a conserved triad of residues (D186, H226 and S386), and a C-terminal domain and is synthesized as a soluble 74-kDa precursor that undergoes autocatalytic cleavage in the endoplasmic reticulum. The autocatalytic activity has been shown to be required for secretion.

PCSK9 has pronounced effects on plasma low density lipoprotein cholesterol (LDL-C) levels via its modulation of hepatic low density lipoprotein receptors (LDLR), the main route by which cholesterol is removed from the circulation. PCSK9 binds the LDLR and directs it to lysosomal degradation, thereby increasing plasma LDL-C levels and, in turn, coronary heart disease (CHD) risk. (Maxwell K. N., Proc. Natl. Acad. Sci., 101, 2004, 7100-7105; Park, S. W., J. Biol. Chem. 279, 2004, 50630-50638; Lagace T. A., et. al. J. Clin. Invest. 2006, 116(11):2995-3005). Overexpression of mouse or human PCSK9 in mice has been shown to elevate total and LDL-C levels and dramatically reduce hepatic LDLR protein, without an observed effect on the levels of mRNA, SREBP, or SREBP protein nuclear to cytoplasmic ratio. (Maxwell K. N., Proc. Natl. Acad. Sci. 101, 2004, 7100-7105). Moreover, mutations in PCSK9 that cause loss of PCSK9 function in mouse models have also been shown to lower total and LDL-C levels. (Cohen, J. C., et al., N. Engl. J. Med., 354, 2006, 1264-1272). Thus, the results indicate that modulation of PCSK9 results in a reduction of LDLR protein levels.

Gene deletion of PCSK9 has also been conducted in mice. PCSK9 knockout mice show an approximate 50% reduction in plasma cholesterol levels and enhanced sensitivity to statins in reducing plasma cholesterol (Rashid, S., et al., Proc. Natl. Acad. Sci., 2005, 102:5374-5379). Human genetic data strongly support the role of PCSK9 in LDL homeostasis. The link between PCSK9 and plasma LDL-C levels was first established by the discovery of PCSK9 missense mutations in patients with an autosomal dominant form of familial hypercholesterolemia (Abifadel, M., et al., Nature, 2003, 34:154-6). Patients carrying PCSK9 gain-of-function alleles have increased plasma LDL-C levels and premature CHD, whereas those with PCSK9 loss-of-function alleles have markedly reduced plasma LDL-C and are protected from CHD.

PCSK9 also plays a role in Lipoprotein (a) (Lp(a)) metabolism. Lp(a) is a proatherogenic lipoprotein comprised of an LDL particle covalently linked to apoLp(a). Human genetic studies indicate that Lp(a) is causally associated with CHD risk. PCSK9 therapeutic antibodies have been shown to significantly reduce Lp(a) levels in patients with hypercholesterolemia. (Desai, N. R., et. al., Circulation. 2013, 128(9):962-969; Lambert, G., et. al., Clin. Sci., 2017, 131, 261-268). Patients receiving statin therapy treated with a monoclonal antibody against PCSK9 have shown up to 32% reduction in Lp(a) levels compared to placebo. (Desai N. R., et. al., Circulation. 2013, 128(9):962-969).

In addition to having cardiovascular effects, PCSK9 plays an important role in sepsis, a life-threatening condition caused by a body's response to infection. Overexpression of PCSK9 in septic mice has been shown to aggravate sepsis by increasing inflammation, while inhibition of PCSK9 has been shown to reduce mortality. (Dwivedi, D. J., et al., Shock, 2016, 46(6), 672-680). Moreover, flow cytometry studies in human HepG2 cells have shown that PCSK9 negatively regulates gram-negative lipopolysaccharide (LPS) uptake by hepatocytes through the regulation of the LDLR-mediated bacterial lipid uptake of lipoteichoic acid (LTA) and LPS through an LDL-dependent mechanism. (Grin, P. M., et al., Nature, 2018, 8(1):10496) Thus, inhibition of PCSK9 has the potential to treat sepsis by reducing the body's immune response to an infection.

Currently, there are no known small molecule inhibitors of PCSK9. The only known marketed inhibitors of PCSK9 are anti-PCSK9 antibodies. Inhibition of PCSK9 with a small molecule inhibitor therefore has the potential to be a treatment for a range of diseases, including hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, triglyceride-rich lipoproteins (TRL), elevated triglycerides, sepsis, xanthoma and other disorders. For these reasons, there remains a need for novel and potent small molecule PCSK9 inhibitors.

SUMMARY OF THE DISCLOSURE

A first aspect of the disclosure relates to compounds of Formula (I):

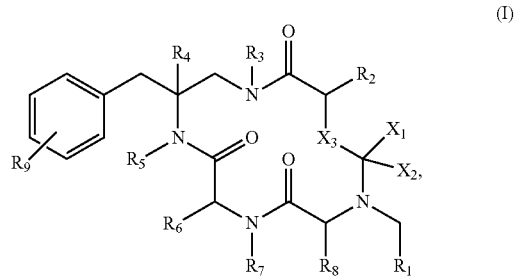

and pharmaceutically acceptable salts, hydrates, solvates, prodrugs, stereoisomers, and tautomers thereof, wherein:

$X_1$ and $X_2$ are each independently H or $(C_1-C_6)$alkyl, or $X_1$ and $X_2$ together with the carbon atom to which they are attached form =(O);

$X_3$ is —$CH_2$— when $X_1$ and $X_2$ are each independently H or $(C_1-C_6)$alkyl, or $X_1$ and $X_2$ together with the carbon atom to which they are attached form =(O), or $X_3$ is —O—, —NH— or —N$(C_1-C_6)$alkyl-, when $X_1$ and $X_2$ together with the carbon atom to which they are attached form =(O);

$R_1$ is $(C_6-C_{10})$aryl or 5- or 6-membered heteroaryl comprising 1-3 heteroatoms selected from N, O, and S, wherein the aryl and heteroaryl are substituted with —$OR_{10}$ or —$NR_{21}R_{10}$ and optionally substituted with one or more $R_{11}$;

$R_2$ is H, $(C_1-C_6)$alkyl, $(C_2-C_6)$alkenyl, $(C_1-C_6)$haloalkyl, —$NR_{12}R_{13}$, $(C_3-C_7)$carbocyclyl, $(C_3-C_7)$cycloalkenyl, 5- to 7-membered heterocyclyl comprising 1-3 heteroatoms selected from N, O, and S, $(C_6-C_{10})$aryl, or 5- or 6-membered heteroaryl comprising 1-3 heteroatoms selected from N, O, and S, wherein the alkyl is optionally substituted with one or more $R_{18}$, and the carbocyclyl, cycloalkenyl, heterocyclyl, aryl and heteroaryl are optionally substituted with one or more $R_{19}$;

$R_3$ is H, D, $(C_1-C_6)$alkyl, $(C_1-C_6)$alkoxy, $(C_1-C_6)$haloalkyl, $(C_1-C_6)$haloalkoxy, or $(C_1-C_6)$hydroxyalkyl, wherein the alkyl is optionally substituted with one or more $R_{14}$;

$R_4$ is H or $(C_1-C_6)$alkyl; or $R_3$ and $R_4$ together with the atoms to which they are attached form a 5- to 7-membered heterocyclyl ring comprising 1-3 heteroatoms selected from N, O, and S;

$R_5$ and $R_7$ are each independently H, D, $(C_1-C_6)$alkyl, $(C_1-C_6)$alkoxy, $(C_1-C_6)$haloalkyl, $(C_1-C_6)$haloalkoxy, or $(C_1-C_6)$hydroxyalkyl, wherein the $(C_1-C_6)$alkyl is optionally substituted with one or more D;

$R_6$ is $(C_1-C_6)$alkyl, $(C_1-C_6)$alkoxy, $(C_1-C_6)$haloalkyl, $(C_1-C_6)$haloalkoxy, or $(C_1-C_6)$hydroxyalkyl, wherein the alkyl is optionally substituted with one or more substituents each independently selected from $(C_1-C_6)$alkoxy, $(C_1-C_6)$haloalkoxy, —C(O)$(C_1-C_6)$alkyl, —C(O)OH, and —C(O)O$(C_1-C_6)$alkyl;

$R_8$ is H, $(C_1-C_6)$alkyl, or $(C_1-C_6)$haloalkyl, wherein the alkyl is optionally substituted with one or more substituents each independently selected from $(C_3-C_7)$carbocyclyl, 4- to 7-membered heterocyclyl comprising 1-3 heteroatoms selected from N, O, and S, —$NR_{16}R_{17}$, and —C(O)$NR_{16}R_{17}$;

$R_9$ is halogen, $(C_1-C_6)$alkyl, $(C_1-C_6)$alkoxy, $(C_1-C_6)$haloalkyl, $(C_1-C_6)$haloalkoxy, —OH, or CN;

$R_{10}$ is $(C_6-C_{10})$aryl or 5- or 6-membered heteroaryl comprising 1-3 heteroatoms selected from N, O, and S, wherein the aryl and heteroaryl are optionally substituted with one or more $R_{22}$;

each $R_{11}$ is independently at each occurrence halogen, $(C_1-C_6)$alkyl, $(C_1-C_6)$alkoxy, $(C_1-C_6)$haloalkyl, $(C_1-C_6)$haloalkoxy, —OH, or CN;

$R_{12}$ and $R_{13}$ are each independently H or $(C_1-C_6)$alkyl;

each $R_{14}$ is independently at each occurrence D, $NR_{15}R_{15'}$, $(C_3-C_7)$carbocyclyl, or 3- to 7-membered heterocyclyl comprising 1-3 heteroatoms selected from N, O, and S, wherein the carbocyclyl and heterocyclyl are optionally substituted with one or more substituents each independently selected from halogen, $(C_1-C_6)$alkyl, $(C_1-C_6)$alkoxy, $(C_1-C_6)$haloalkyl, and $(C_1-C_6)$haloalkoxy;

$R_{15}$ and $R_{15'}$ are each independently H or $(C_1-C_6)$alkyl;

$R_{16}$ and $R_{17}$ are each independently H or $(C_1-C_6)$alkyl, or $R_{16}$ and $R_{17}$ together with the nitrogen atom to which they are attached form a 4- to 7-membered heterocyclyl ring optionally comprising 1-2 additional heteroatoms selected from N, O, and S;

each $R_{18}$ is independently at each occurrence $(C_3-C_7)$carbocyclyl, 5- to 7-membered heterocyclyl comprising 1-3 heteroatoms selected from N, O, and S, $(C_6-C_{10})$aryl, or 5- or 6-membered heteroaryl comprising 1-3 heteroatoms selected from N, O, and S, wherein the carbocyclyl, heterocyclyl, aryl and heteroaryl are optionally substituted with one or more $R_{20}$;

each $R_{19}$ is independently at each occurrence halogen, $(C_1-C_6)$alkyl, $(C_1-C_6)$alkoxy, $(C_1-C_6)$haloalkyl, $(C_1-C_6)$haloalkoxy, —OH, or CN; or two $R_{19}$ together, when on adjacent atoms, form a $(C_6-C_{10})$aryl or 5- or 6-membered heteroaryl ring comprising 1-3 heteroatoms selected from N, O, and S, wherein the aryl and heteroaryl are optionally substituted with one or more substituents each independently selected from halogen, $(C_1-C_6)$alkyl, $(C_1-C_6)$alkoxy, $(C_1-C_6)$haloalkyl, $(C_1-C_6)$haloalkoxy, —OH, and CN;

each $R_{20}$ is independently at each occurrence halogen, $(C_1-C_6)$alkyl, $(C_1-C_6)$alkoxy, $(C_1-C_6)$haloalkyl, $(C_1-C_6)$haloalkoxy, oxo, —OH, or CN; or when $R_{18}$ is a carbocyclyl or a heterocyclyl, two $R_{20}$, when attached to the same carbon atom, together form =(O);

$R_{21}$ is H or $(C_1-C_6)$alkyl;

each $R_{22}$ is independently at each occurrence halogen, $(C_1-C_6)$alkyl, $(C_1-C_6)$alkoxy, $(C_1-C_6)$haloalkyl, $(C_1-C_6)$haloalkoxy, —OH, CN, $(C_6-C_{10})$aryl, or 5- or 6-membered heteroaryl comprising 1-3 heteroatoms selected from N, O, and S, wherein the aryl and heteroaryl are optionally substituted with one or more $R_{23}$;

each $R_{23}$ is independently at each occurrence halogen, $(C_1-C_6)$alkyl, $(C_1-C_6)$alkoxy, $(C_1-C_6)$haloalkyl, $(C_1-C_6)$haloalkoxy, —$CH_2(OCH_2CH_2)_{1-3}OCH_2CH_3$, —OH, CN, or 4- to 7-membered heterocyclyl comprising 1-3 heteroatoms selected from N, O, and S, wherein the heterocyclyl is optionally substituted with one or more substituents each independently selected from halogen, $(C_1-C_6)$alkyl, $(C_1-C_6)$alkoxy, $(C_1-C_6)$haloalkyl, $(C_1-C_6)$haloalkoxy, —OH, —C(O)$R_{24}R_{26}$, —$NR_{24}C(O)R_{25}$, —$NH_2$, —NH$(C_1-C_6)$alkyl, and —N$((C_1-C_6)$alkyl$)_2$, and the alkyl is optionally substituted with —$NR_{24}R_{25}$ or a 4- to 7-membered heterocyclyl comprising 1-3 heteroatoms selected from N, O, and S optionally substituted with one or more substituents each independently selected from halogen, $(C_1-C_6)$alkyl, $(C_1-C_6)$alkoxy, $(C_1-C_6)$haloalkyl, $(C_1-C_6)$haloalkoxy, —OH, —$NH_2$, —NH$(C_1-C_6)$alkyl, and —N$((C_1-C_6)$alkyl$)_2$; and $R_{24}$ and $R_{25}$ are each independently H, $(C_1-C_6)$alkyl, or $(C_3-C_7)$carbocyclyl optionally substituted with one to two $(C_1-C_6)$alkyl;

or pharmaceutically acceptable salts, hydrates, solvates, prodrugs, stereoisomers, N-oxides, or tautomers thereof.

In another aspect, the present disclosure relates to a compound of Formula (I), wherein:

$X_1$ and $X_2$ are each independently H or $(C_1-C_6)$alkyl, or $X_1$ and $X_2$ together with the carbon atom to which they are attached form =(O);

$X_3$ is —$CH_2$— when $X_1$ and $X_2$ are each independently H or $(C_1-C_6)$alkyl, or $X_1$ and $X_2$ together with the carbon atom to which they are attached form =(O), or $X_3$ is —O—, —NH— or —N$(C_1-C_6)$alkyl-, when $X_1$ and $X_2$ together with the carbon atom to which they are attached form =(O);

$R_1$ is $(C_6-C_{10})$aryl or 5- or 6-membered heteroaryl comprising 1-3 heteroatoms selected from N, O, and S, wherein the aryl and heteroaryl are substituted with —OR$_{10}$ or —NR$_{21}$R$_{10}$ and optionally substituted with one or more R$_{11}$;

R$_2$ is H, (C$_1$-C$_6$)alkyl, (C$_2$-C$_6$)alkenyl, (C$_1$-C$_6$)haloalkyl, —NR$_{12}$R$_{13}$, (C$_3$-C$_7$)carbocyclyl, (C$_3$-C$_7$)cycloalkenyl, 5- to 7-membered heterocyclyl comprising 1-3 heteroatoms selected from N, O, and S, (C$_6$-C$_{10}$)aryl, or 5- or 6-membered heteroaryl comprising 1-3 heteroatoms selected from N, O, and S, wherein the alkyl is optionally substituted with one or more R$_u$b, and the carbocyclyl, cycloalkenyl, heterocyclyl, aryl and heteroaryl are optionally substituted with one or more R$_{19}$;

R$_3$ is H, D, (C$_1$-C$_6$)alkyl, (C$_1$-C$_6$)alkoxy, (C$_1$-C$_6$)haloalkyl, (C$_1$-C$_6$)haloalkoxy, or (C$_1$-C$_6$)hydroxyalkyl, wherein the alkyl is optionally substituted with one or more R$_{14}$;

R$_4$ is H or (C$_1$-C$_6$)alkyl; or

R$_3$ and R$_4$ together with the atoms to which they are attached form a 5- to 7-membered heterocyclyl ring comprising 1-3 heteroatoms selected from N, O, and S;

R$_5$ and R$_7$ are each independently H, D, (C$_1$-C$_6$)alkyl, (C$_1$-C$_6$)alkoxy, (C$_1$-C$_6$)haloalkyl, (C$_1$-C$_6$)haloalkoxy, or (C$_1$-C$_6$)hydroxyalkyl, wherein the (C$_1$-C$_6$)alkyl is optionally substituted with one or more D;

R$_6$ is (C$_1$-C$_6$)alkyl, (C$_1$-C$_6$)alkoxy, (C$_1$-C$_6$)haloalkyl, (C$_1$-C$_6$)haloalkoxy, or (C$_1$-C$_6$)hydroxyalkyl, wherein the alkyl is optionally substituted with one or more substituents each independently selected from (C$_1$-C$_6$)alkoxy, (C$_1$-C$_6$)haloalkoxy, —C(O)(C$_1$-C$_6$)alkyl, —C(O)OH, and —C(O)O(C$_1$-C$_6$)alkyl;

R$_8$ is H, (C$_1$-C$_6$)alkyl, or (C$_1$-C$_6$)haloalkyl, wherein the alkyl is optionally substituted with one or more substituents each independently selected from (C$_3$-C$_7$)carbocyclyl, 4- to 7-membered heterocyclyl comprising 1-3 heteroatoms selected from N, O, and S, —NR$_{16}$R$_{17}$, and —C(O)NR$_{16}$R$_{17}$;

R$_9$ is halogen, (C$_1$-C$_6$)alkyl, (C$_1$-C$_6$)alkoxy, (C$_1$-C$_6$)haloalkyl, (C$_1$-C$_6$)haloalkoxy, —OH, or CN;

R$_{10}$ is (C$_6$-C$_{10}$)aryl or 5- or 6-membered heteroaryl comprising 1-3 heteroatoms selected from N, O, and S, wherein the aryl and heteroaryl are optionally substituted with one or more R$_{22}$;

each R$_{11}$ is independently at each occurrence halogen, (C$_1$-C$_6$)alkyl, (C$_1$-C$_6$)alkoxy, (C$_1$-C$_6$)haloalkyl, (C$_1$-C$_6$)haloalkoxy, —OH, or CN;

R$_{12}$ and R$_{13}$ are each independently H or (C$_1$-C$_6$)alkyl;

each R$_{14}$ is independently at each occurrence D, NR$_{15}$R$_{15'}$, (C$_3$-C$_7$)carbocyclyl, or 3- to 7-membered heterocyclyl comprising 1-3 heteroatoms selected from N, O, and S, wherein the carbocyclyl and heterocyclyl are optionally substituted with one or more substituents each independently selected from halogen, (C$_1$-C$_6$)alkyl, (C$_1$-C$_6$)alkoxy, (C$_1$-C$_6$)haloalkyl, and (C$_1$-C$_6$)haloalkoxy;

R$_{15}$ and R$_{15'}$ are each independently H or (C$_1$-C$_6$)alkyl;

R$_{16}$ and R$_{17}$ are each independently H or (C$_1$-C$_6$)alkyl, or

R$_{16}$ and R$_{17}$ together with the nitrogen atom to which they are attached form a 4- to 7-membered heterocyclyl ring comprising 1-2 additional heteroatoms selected from N, O, and S;

each R$_{18}$ is independently at each occurrence (C$_3$-C$_7$)carbocyclyl, 5- to 7-membered heterocyclyl comprising 1-3 heteroatoms selected from N, O, and S, (C$_6$-C$_{10}$)aryl, or 5- or 6-membered heteroaryl comprising 1-3 heteroatoms selected from N, O, and S, wherein the carbocyclyl, heterocyclyl, aryl and heteroaryl are optionally substituted with one or more R$_{20}$;

each R$_{19}$ is independently at each occurrence halogen, (C$_1$-C$_6$)alkyl, (C$_1$-C$_6$)alkoxy, (C$_1$-C$_6$)haloalkyl, (C$_1$-C$_6$)haloalkoxy, —OH, or CN; or two R$_{19}$ together, when on adjacent atoms, form a (C$_6$-C$_{10}$)aryl or 5- or 6-membered heteroaryl ring comprising 1-3 heteroatoms selected from N, O, and S, wherein the aryl and heteroaryl are optionally substituted with one or more substituents each independently selected from halogen, (C$_1$-C$_6$)alkyl, (C$_1$-C$_6$)alkoxy, (C$_1$-C$_6$)haloalkyl, (C$_1$-C$_6$)haloalkoxy, —OH, and CN;

each R$_{20}$ is independently at each occurrence halogen, (C$_1$-C$_6$)alkyl, (C$_1$-C$_6$)alkoxy, (C$_1$-C$_6$)haloalkyl, (C$_1$-C$_6$)haloalkoxy, oxo, —OH, or CN; or when R$_{18}$ is a carbocyclyl or a heterocyclyl, two R$_{20}$, when attached to the same carbon atom, together form =(O);

R$_{21}$ is H or (C$_1$-C$_6$)alkyl;

each R$_{22}$ is independently at each occurrence halogen, (C$_1$-C$_6$)alkyl, (C$_1$-C$_6$)alkoxy, (C$_1$-C$_6$)haloalkyl, (C$_1$-C$_6$)haloalkoxy, —OH, CN, (C$_6$-C$_{10}$)aryl, or 5- or 6-membered heteroaryl comprising 1-3 heteroatoms selected from N, O, and S, wherein the aryl and heteroaryl are optionally substituted with one or more R$_{23}$;

each R$_{23}$ is independently at each occurrence halogen, (C$_1$-C$_6$)alkyl, (C$_1$-C$_6$)alkoxy, (C$_1$-C$_6$)haloalkyl, (C$_1$-C$_6$)haloalkoxy, —CH$_2$(OCH$_2$CH$_2$)$_{1-3}$OCH$_2$CH$_3$, —OH, CN, or 4- to 7-membered heterocyclyl comprising 1-3 heteroatoms selected from N, O, and S, wherein the heterocyclyl is optionally substituted with one or more substituents each independently selected from halogen, (C$_1$-C$_6$)alkyl, (C$_1$-C$_6$)alkoxy, (C$_1$-C$_6$)haloalkyl, (C$_1$-C$_6$)haloalkoxy, —OH, —C(O)R$_{24}$R$_{25}$, —NR$_{24}$C(O)R$_{25}$, —NH$_2$, —NH(C$_1$-C$_6$)alkyl, and —N((C$_1$-C$_6$)alkyl)$_2$, and the alkyl is optionally substituted with —NR$_{24}$R$_{25}$ or a 4- to 7-membered heterocyclyl comprising 1-3 heteroatoms selected from N, O, and S optionally substituted with one or more substituents each independently selected from halogen, (C$_1$-C$_6$)alkyl, (C$_1$-C$_6$)alkoxy, (C$_1$-C$_6$)haloalkyl, (C$_1$-C$_6$)haloalkoxy, —OH, —NH$_2$, —NH(C$_1$-C$_6$)alkyl, and —N((C$_1$-C$_6$)alkyl)$_2$; and R$_{24}$ and R$_{25}$ are each independently H, (C$_1$-C$_6$)alkyl, or (C$_3$-C$_7$)carbocyclyl;

or pharmaceutically acceptable salts, hydrates, solvates, prodrugs, stereoisomers, N-oxides, or tautomers thereof.

Another aspect of the present disclosure relates to a compound of Formula (I), or a pharmaceutically acceptable salt thereof, for use in the treatment, prevention, amelioration or delay of progression of a PCSK9-mediated disease or disorder or for use in the treatment, prevention, amelioration or delay of progression of a disease or disorder requiring inhibition of PCSK9 or of PCSK9 activity In another aspect, the present disclosure relates to the use of a compound of Formula (I), or a pharmaceutically acceptable salt thereof, for the treatment, prevention, amelioration or delay of progression of a PCSK9-mediated disease or disorder or for the treatment, prevention, amelioration or delay of progression of a disease or disorder requiring inhibition of PCSK9 or of PCSK9 activity.

Another aspect of the present disclosure relates to the use of a compound of Formula (I), or a pharmaceutically acceptable salt thereof, in the manufacture of a medicament for the treatment, prevention, amelioration or delay of progression of a PCSK9-mediated disease or disorder or for the treatment, prevention, amelioration or delay of progression of a disease or disorder requiring inhibition of PCSK9 or of PCSK9 activity.

In another aspect, the present disclosure relates a method for treating, preventing, ameliorating or delaying the progression of a PCSK9-mediated disease or disorder comprising the step of administering to a patient in need thereof a therapeutically effective amount of a compound of Formula (I), or a pharmaceutically acceptable salt thereof, according to the disclosure, or a pharmaceutically acceptable salt thereof.

Another aspect of the present disclosure relates to a method for treating, preventing, ameliorating or delaying the progression of a PCSK9-mediated disease or a disorder or of disease or disorder requiring inhibition of PCSK9 or of PCSK9 activity comprising the step of administering to a patient in need thereof a therapeutically effective amount of a compound of Formula (I), or a pharmaceutically acceptable salt thereof, according to the disclosure, or a pharmaceutically acceptable salt thereof.

In another aspect, the present disclosure relates a method of treating, preventing, inhibiting, or eliminating hypercholesterolemia, hyperlipidemia, hypertriglyceridemia, sitosterolemia, atherosclerosis, arteriosclerosis, coronary heart disease, peripheral vascular disease, vascular inflammation, xanthoma, peripheral arterial disease, sepsis, elevated Lp(a), elevated LDL, elevated TRL, or elevated triglycerides comprising the step of administering to a patient in need thereof a therapeutically effective amount of a compound of Formula (I), or a pharmaceutically acceptable salt thereof.

Another aspect of the present disclosure relates to a method of (i) reducing Lp(a), (ii) reducing Lp(a) plasma levels, (iii) reducing Lp(a) serum levels, (iv) reducing serum TRL or LDL levels, (v) reducing serum triglyceride levels, (vi) reducing LDL-C, (vii) reducing total plasma apoB concentrations, (viii) reducing LDL apoB, (ix) reducing TRL apoB, or (x) reducing non HDL-C comprising the step of administering to a patient in need thereof a therapeutically effective amount of a compound of Formula (I), or a pharmaceutically acceptable salt thereof.

In another aspect, the present disclosure also relates to a method of (i) reducing LDL-C, (ii) reducing total apolipoprotein B (apoB) concentrations, (iii) reducing LDL apoB, (iv) reducing TRL apoB, or (v) reducing non HDL-C and combinations thereof, in a patient in need thereof, wherein the method comprising administering a therapeutically effective amount of a compound of Formula (I), or a pharmaceutically acceptable salt thereof, to the patient.

Another aspect of the present disclosure relates to a method of reducing the total plasma concentration of a marker selected from (i) LDL-C, (ii) apoB, (iii) LDL apoB, (iv) TRL apoB and (v) non HDL-C and combinations thereof, in a patient in need thereof, wherein the method comprising administering a therapeutically effective amount of a compound of Formula (I), or a pharmaceutically acceptable salt thereof, to the patient.

In another aspect, the present disclosure relates to a pharmaceutical composition comprising (e.g., a therapeutically effective amount of) a compound of Formula (I), or a pharmaceutically acceptable salt thereof, and one or more pharmaceutically acceptable carriers or excipients.

Another aspect of the present disclosure relates to a pharmaceutical composition comprising (e.g., a therapeutically effective amount of) a compound of Formula (I), or a pharmaceutically acceptable salt thereof, and one or more pharmaceutically acceptable carriers or excipients for use in the treatment of a PCSK9-mediated disease or disorder.

In another aspect, the present disclosure relates to a method of modulating PCSK9 comprising administering to a patient in need thereof a compound of Formula (I), or a pharmaceutically acceptable salt thereof.

Another aspect of the present disclosure relates to a method of inhibiting PCSK9 comprising administering to a patient in need thereof a compound of Formula (I), or a pharmaceutically acceptable salt thereof. In another aspect, the present disclosure relates to a method of inhibiting PCSK9 activity comprising administering to a patient in need thereof a compound of Formula (I), or a pharmaceutically acceptable salt thereof.

In another aspect, the present disclosure relates to a method for treating a PCSK9-mediated disease or disorder comprising the step of administering to a patient in need thereof a therapeutically effective amount of a compound of Formula (I), or a pharmaceutically acceptable salt thereof.

Another aspect of the present disclosure relates to a method of reducing LDL-C in a patient in need thereof, the method comprising administering a therapeutically effective amount of a compound of Formula (I), or a pharmaceutically acceptable salt thereof to the patient, thereby reducing LDL-C in the patient.

In another aspect, the present disclosure relates to a compound of Formula (I), or a pharmaceutically acceptable salt thereof, for use in the treatment of a PCSK9-mediated disease or disorder.

Another aspect of the present disclosure relates to a compound of Formula (I), or a pharmaceutically acceptable salt thereof, for use in the treatment of a PCSK9-mediated disease or disorder which is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

In another aspect, the present disclosure relates to the use of a compound of Formula (I), or a pharmaceutically acceptable salt thereof, or a pharmaceutically acceptable salt thereof, in the manufacture of a medicament for treating a PCSK9-mediated disease or disorder.

Another aspect of the present disclosure relates to a compound of Formula (I), or a pharmaceutically acceptable salt thereof, for use in the manufacture of a medicament for treating a disease associated with inhibiting PCSK9 activity.

In another aspect, the present disclosure relates to the use of a compound of Formula (I), or a pharmaceutically acceptable salt thereof, in the treatment of a disease associated with the inhibition of PCSK9 activity.

In certain aspects, the PCSK9 modulating or inhibiting compounds of the disclosure may be administered alone or in combination with other compounds, including other PCSK9 modulating or inhibiting agents, or other therapeutic agents.

Accordingly, in another aspect, the present disclosure relates to a combination, comprising (e.g. a therapeutically effective amount of) a compound of formula (I), or a pharmaceutically acceptable salt thereof, and one or more therapeutically active agents.

Another aspect of the present disclosure relates to a process for the manufacture of a compound of Formula (II), or pharmaceutically acceptable salts, hydrates, solvates, stereoisomers, N-oxides, or tautomers thereof,

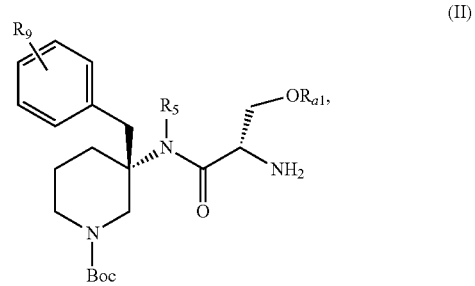

(II)

wherein $R_{a1}$ and $R_5$ are each independently ($C_1$-$C_6$ alkyl) and $R_9$ is as defined above for Formula (I), comprising:

(a) alkylating a compound of Formula (IIa), or pharmaceutically acceptable salts, hydrates, solvates, stereoisomers, N-oxides, or tautomers thereof,

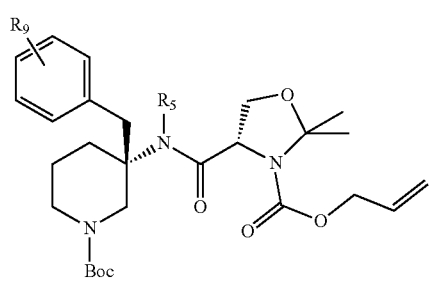

wherein $R_5$ is H and $R_9$ is as defined above for Formula (I),
with an alkyl halide (e.g., methyl iodide, ethyl iodide, etc.) and a base (e.g., NaH) in a solvent (e.g., DMF, acetonitrile, etc.), and at low temperature to provide a compound of formula (IIb),

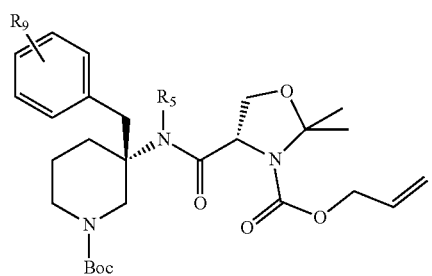

wherein $R_5$ is ($C_1$-$C_6$ alkyl) and $R_9$ is as defined above for Formula (I), or pharmaceutically acceptable salts, hydrates, solvates, stereoisomers, N-oxides, or tautomers thereof, (b) reacting the compound of Formula (IIb), or pharmaceutically acceptable salts, hydrates, solvates, stereoisomers, N-oxides, or tautomers thereof, with an acid (e.g., trifluoroacetic acid) in a solvent (e.g., dichloromethane), followed by Boc$_2$O and a base (e.g., N,N-diisopropylethylamine (DIPEA)) to form a compound of formula (IIc),

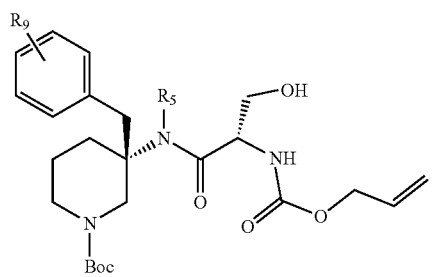

wherein $R_5$ is ($C_1$-$C_6$ alkyl) and $R_9$ is as defined above for Formula (I), or pharmaceutically acceptable salts, hydrates, solvates, stereoisomers, N-oxides, or tautomers thereof;

(c) alkylating the compound of Formula (IIc), or pharmaceutically acceptable salts, hydrates, solvates, stereoisomers, N-oxides, or tautomers thereof, with a alkylating agent (e.g., methyl iodide, ethyl iodide, etc.), in a solvent (e.g., DMF, acetonitrile, etc.), and optionally a metal oxide (e.g., silver (I) oxide (AgO), etc.), to provide a compound of Formula (IId),

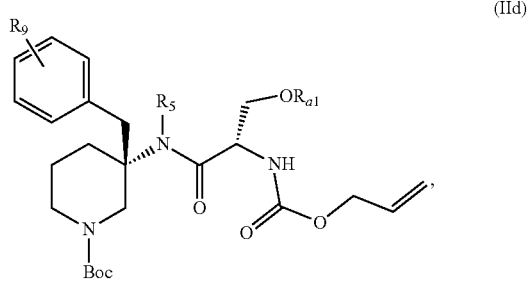

wherein $R_{a1}$ and $R_5$ are each independently ($C_1$-$C_6$ alkyl) and $R_9$ is as defined above for Formula (I) or pharmaceutically acceptable salts, hydrates, solvates, stereoisomers, N-oxides, or tautomers thereof; and (d) deallylating the compound of Formula (IId), with a palladium catalyst (e.g., tetrakis(triphenylphosphine) palladium(0) (Pd(PPh$_3$)$_4$), etc.) and N,N-dimethyltrimethylsilylamine in a solvent (e.g., DCM, etc.) to provide the compound of Formula (II). In one embodiment, the palladium catalyst is tetrakis (triphenylphosphine) palladium(0) (Pd(PPh$_3$)$_4$).

In another aspect, the present disclosure relates to the a process for the manufacture of a compound of Formula (II), or pharmaceutically acceptable salts, hydrates, solvates, stereoisomers, N-oxides, or tautomers thereof,

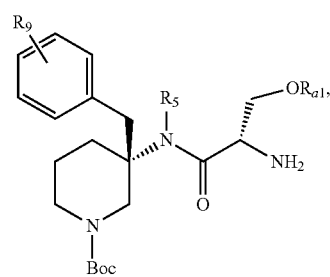

wherein $R_{a1}$ is H, $R_5$ is ($C_1$-$C_6$ alkyl), and $R_9$ is as defined above for Formula (I), comprising reacting a compound of Formula (IIb):

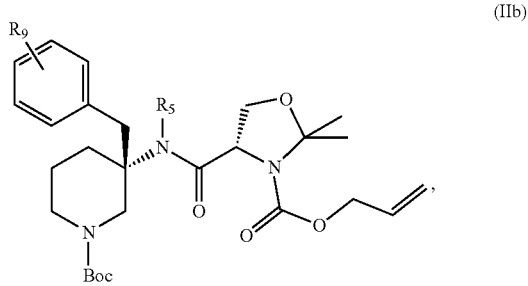

wherein $R_5$ is ($C_1$-$C_6$ alkyl) and $R_9$ is as defined above for Formula (I), with a palladium catalyst (e.g., tetrakis(triphenylphosphine) palladium(0) (Pd(PPh$_3$)$_4$), etc.) and N,N-dimethyltrimethylsilylamine in a solvent (e.g., DCM, etc.) to provide the compound of Formula (II). In one embodiment, the palladium catalyst is tetrakis(triphenylphosphine) palladium(0) (Pd(PPh$_3$)$_4$).

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar to or equivalent to those described herein can be used in the practice and testing of the disclosure, suitable methods and materials are described below. All publications, patent applications, patents, and other references mentioned herein are incorporated by reference. The references cited herein are not admitted to be prior art to the claimed disclosure. In the case of conflict, the present specification, including definitions, will control. In addition, the materials, methods, and examples are illustrative only and not intended to be limiting.

Other features and advantages of the disclosure will be apparent from the following detailed description and claims.

BRIEF DESCRIPTION OF THE DRAWING

FIG. 1 is a scheme depicting the general synthesis procedure for the assembly of cyclic tetramer compounds of the disclosure.

DETAILED DESCRIPTION OF THE DISCLOSURE

The present disclosure relates to compounds and compositions that are capable of modulating the activity of PCSK9. The disclosure features methods of treating, preventing or ameliorating a disease or disorder in which PCSK9 plays a role by administering to a patient in need thereof a therapeutically effective amount of a compound of Formula (I), or a pharmaceutically acceptable salt, hydrate, solvate, stereoisomer, or tautomer thereof. The methods of the present disclosure can be used in the treatment of a variety of PCSK9 dependent diseases and disorders by modulating or inhibiting PCSK9. Inhibition or modulation of PCSK9 provides a novel approach to the treatment, prevention, or amelioration of diseases including, but not limited to, hypercholesterolemia, hyperlipidemia, hypertriglyceridemia, sitosterolemia, atherosclerosis, arteriosclerosis, coronary heart disease, peripheral vascular disease (including aortic diseases and cerebrovascular disease), peripheral arterial disease, vascular inflammation, elevated Lp(a), elevated LDL, elevated TRL, elevated triglycerides, sepsis, and xanthoma.

The compounds of the disclosure, by inhibiting PCSK9, have utility in the treatment of hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL (e.g., elevated VLDL and/or chylomicrons), elevated triglycerides, sepsis, and xanthoma.

For example, the compounds of formula (I) of the disclosure bind to PCSK9 and thereby inhibit PCSK9 and/or PCSK9 activity, since PCSK9 cannot any longer bind to the low density lipoprotein receptors (LDLR) or any other target receptors. For example, if PCSK9 is blocked, more LDLRs are recycled and are present on the surface of cells to remove LDL-particles from the extracellular fluid. Therefore, blocking PCSK9 can lower blood LDL-particle concentrations.

Accordingly, compounds of the present disclosure may therefore be potentially useful in the treatment, prevention, amelioration or delay of progression of a PCSK9-mediated disease or disorder, or a disease or disorder in which PCSK9 plays a role, as well as conditions, diseases and disorders benefitting from modulating PCSK9 or PCSK9 activity.

In addition, compounds of the present disclosure may therefore be potentially useful in the treatment, prevention, amelioration or delay of progression of a disease or disorder requiring inhibition of PCSK9 or of PCSK9 activity.

Such diseases and disorders include diseases or disorders selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL (e.g., elevated VLDL and/or chylomicrons), elevated triglycerides, sepsis, and xanthoma.

Various embodiments of the disclosure are described herein. It will be recognized that features specified in each embodiment may be combined with other specified features of other embodiments to provide further embodiments.

In a first aspect of the disclosure, the compounds of Formula (I) are described:

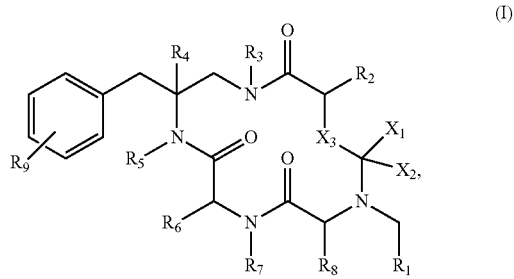

(I)

and pharmaceutically acceptable salts, hydrates, solvates, prodrugs, stereoisomers, N-oxides, and tautomers thereof, wherein $R_1$, $R_2$, $R_3$, $R_4$, $R_5$, $R_6$, $R_7$, $R_8$, $R_9$, $X_1$, $X_2$, and $X_3$ are as described herein above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

Chemical Nomenclature, Terms, and Conventions

In the groups, radicals, or moieties defined below, the number of carbon atoms is often specified preceding the group, and for example, $(C_1-C_{10})$ alkyl means an alkyl group or radical having 1 to 10 carbon atoms. In general, for groups comprising two or more subgroups, the last named group is the radical attachment point, for example, "alkylaryl" means a monovalent radical of the formula alkyl-aryl-, while "arylalkyl" means a monovalent radical of the formula aryl-alkyl-. Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups. The articles "a" and "an" are used in this disclosure to refer to one or more than one (e.g., to at least one) of the grammatical object of the article. By way of example, "an element" means one element or more than one element.

The term "and/or" is used in this disclosure to mean either "and" or "or" unless indicated otherwise.

The term "optionally substituted" means that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus, the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, $(C_1-C_6)$alkyl, $(C_1-C_6)$alkoxy, $(C_1-C_6)$haloalkyl, $(C_1-C_6)$haloalkoxy, —O$(C_2-C_6)$alkenyl, —O$(C_2-C_6)$alkynyl, $(C_2-C_6)$alkenyl, $(C_2-C_6)$alkynyl, —OH, —OP(O)(OH)$_2$, —OC(O)$(C_1-C_6)$alkyl, —C(O)$(C_1-C_6)$alkyl, —OC(O)O$(C_1-C_6)$alkyl, —NH$_2$, —NH$((C_1-C_6)$alkyl), —N$((C_1-C_6)$alkyl)$_2$, —NHC(O)$(C_1-C_6)$alkyl, —C(O)NH$(C_1-C_6)$alkyl, —S(O)$_2$ $(C_1-C_6)$alkyl, —S(O)NH$(C_1-C_6)$alkyl, and S(O)N$((C_1-C_6)$ alkyl)$_2$. The substituents can themselves be optionally substituted. "Optionally substituted" as used herein also refers to substituted or unsubstituted whose meaning is described below.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

The term "unsubstituted" means that the specified group bears no substituents.

Unless otherwise specifically defined, "aryl" means a cyclic, aromatic hydrocarbon group having 1 to 3 aromatic rings, including monocyclic or bicyclic groups such as phenyl, biphenyl, or naphthyl. When containing two aromatic rings (bicyclic, etc.), the aromatic rings of the aryl group are optionally joined at a single point (e.g., biphenyl), or fused (e.g., naphthyl). The aryl group is optionally substituted by one or more substituents, e.g., 1 to 5 substituents, at any point of attachment. Exemplary substituents include, but are not limited to, —H, -halogen, —CN, —O—$(C_1-C_6)$alkyl, $(C_1-C_6)$alkyl, —O—$(C_2-C_6)$alkenyl, —O—$(C_2-C_6)$alkynyl, $(C_2-C_6)$alkenyl, $(C_2-C_6)$alkynyl, —OH, —OP(O)(OH)$_2$, —OC(O)$(C_1-C_6)$alkyl, —C(O)$(C_1-C_6)$alkyl, —OC(O)O$(C_1-C_6)$ alkyl, NH$_2$, NH$((C_1-C_6)$alkyl), N$((C_1-C_6)$alkyl)$_2$, —S(O)$_2$—$(C_1-C_6)$alkyl, —S(O)NH$(C_1-C_6)$alkyl, and S(O)N$((C_1-C_6)$alkyl)$_2$. The substituents are themselves optionally substituted. Furthermore, when containing two fused rings, the aryl groups optionally have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyridyl N-oxide, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1$\Delta^2$-pyrrolo[2,1-b]pyrimidine, dibenzo[b,d] thiophene, pyridin-2-one, furo[3,2-c]pyridinyl, furo[2,3-c] pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[I,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d] imidazol-2-one, 3,4-dihydro-2H-pyrazolo[1,5-b][1,2] oxazinyl, 4,5,6,7-tetrahydropyrazolo[1,5-a]pyridinyl, thiazolo[5,4d]thiazolyl, imidazo[2,1-b][1,3,4]thiadiazolyl, thieno[2,3-b]pyrrolyl, 3H-indolyl, and derivatives thereof. Furthermore, when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-IH-isoquinolinyl, 2,3-dihydrobenzofuran, indolinyl, indolyl, and dihydrobenzoxanyl.

"Halogen" or "halo" mean fluorine, chlorine, bromine, or iodine.

"Alkyl" means a straight or branched chain saturated hydrocarbon containing 1-12 carbon atoms. Examples of a ($C_1$-$C_6$)alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" means a straight or branched chain saturated hydrocarbon containing 1-12 carbon atoms containing a terminal "O" in the chain, e.g., —O(alkyl). Examples of alkoxy groups include, without limitation, methoxy, ethoxy, propoxy, butoxy, t-butoxy, or pentoxy groups.

"Alkenyl" means a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted and may be straight or branched.

"Alkynyl" means a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

"Cycloalkyl" means a monocyclic or polycyclic saturated carbon ring containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A ($C_3$-$C_8$)cycloalkyl is a cycloalkyl group containing between 3 and 8 carbon atoms. A cycloalkyl group can be fused (e.g., decalin) or bridged (e.g., norbomane).

"Carbocyclyl" means a monocyclic or polycyclic saturated or partially unsaturated carbon ring containing 3-18 carbon atoms (e.g., cycloalkyl, cycloalkenyl, cycloalkynyl, etc). Examples of carbocyclyl groups include, without limitations, cyclopropyl, cyclobutyl, cyclobutenyl, cyclopentyl, cyclopentenyl, cyclohexyl, cyclohexenyl cycloheptanyl, cyclooctanyl, norboranyl, norborenyl, bicyclo[2.2.2]octanyl, or bicyclo[2.2.2]octenyl and derivatives thereof. A ($C_3$-$C_8$) carbocyclyl is a carbocyclyl group containing between 3 and 8 carbon atoms. A carbocyclyl group can be fused (e.g., decalin) or bridged (e.g., norbomane).

The term "cycloalkenyl" means a partially unsaturated carbon ring containing 3-18 carbon atoms, preferably 4 to 12 carbons and 1 or 2 double bonds. Exemplary cycloalkenyl groups include cyclopentenyl, cyclohexenyl, cycloheptenyl, cyclooctenyl, cyclohexadienyl, and cycloheptadienyl. A ($C_3$-$C_8$) cycloalkenyl is a cycloalkenyl group containing between 3 and 8 carbon atoms and at least one double bond.

"Heterocycloalkyl" means a saturated monocyclic or polycyclic ring containing carbon and at least one heteroatom selected from oxygen, nitrogen, or sulfur (O, N, or S) and wherein there is not delocalized n electrons (aromaticity) shared among the ring carbon or heteroatoms. The heterocycloalkyl ring structure may be substituted by one or more substituents. The substituents can themselves be optionally substituted. Examples of heterocycloalkyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, 1,4-dioxanyl, dihydrofuranyl, 1,3-dioxolanyl, imidazolidinyl, imidazolinyl, dithiolanyl, and homotropanyl.

"Heterocyclyl" means a saturated (e.g., heterocycloalkyl ring) or partially unsaturated monocyclic or polycyclic ring containing carbon and at least one heteroatom selected from oxygen, nitrogen, or sulfur (O, N, or S) and wherein there is not delocalized n electrons (aromaticity) shared among the ring carbon or heteroatoms. The heterocyclyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, dihydropyrrolidinyl, pyridin-2(1H)-one, dihydropyridinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, 1,4-dioxanyl, dihydrofuranyl, 1,3-dioxolanyl, imidazolidinyl, imidazolinyl, dithiolanyl, and homotropanyl.

"Hydroxyalkyl" means an alkyl group substituted with one or more —OH groups. Examples of hydroxyalkyl groups include HO—$CH_2$—, HO—$CH_2CH_2$—, and $CH_2$—CH(OH)—.

"Haloalkyl" means an alkyl group substituted with one or more halogens. Examples of haloalkyl groups include, but are not limited to, trifluoromethyl, difluoromethyl, pentafluoroethyl, trichloromethyl, etc.

"Haloalkoxy" means an alkoxy group substituted with one or more halogens. Examples of haloalkyl groups include, but are not limited to, trifluoromethoxy, difluoromethoxy, pentafluoroethoxy, trichloromethoxy, etc.

"Cyano" means a substituent having a carbon atom joined to a nitrogen atom by a triple bond, e.g., C≡N.

The term "oxo" as used herein refers to an "—$O^{\ominus}$" group.

The term "N-oxide" refers to an oxygen atom bound by a single bond (e.g., "oxo") to a nitrogen atom (e.g., N—$O^{\ominus}$).

"Amino" means a substituent containing at least one nitrogen atom (e.g., $NH_2$).

Salt, Prodrug, Derivative, and Solvate Terms and Conventions

"Prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder, et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

"Pharmaceutically acceptable prodrug" as used herein means a prodrug of a compound of the disclosure which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

"Salt" means an ionic form of the parent compound or the product of the reaction between the parent compound with a suitable acid or base to make the acid salt or base salt of the parent compound. Salts of the compounds of the present disclosure can be synthesized from the parent compounds, which contain a basic or acidic moiety, by conventional chemical methods. Generally, the salts are prepared by reacting the free base or acid parent compound with stoichiometric amounts or with an excess of the desired salt-forming inorganic or organic acid or base in a suitable solvent or various combinations of solvents.

"Pharmaceutically acceptable salt" means a salt of a compound of the disclosure which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present disclosure are useful in both free base and salt form, in practice, the use of the salt form amounts to use of the base form. Lists of suitable salts are found in, e.g., S. M. Birge, et. al., J. Pharm. Sci., 1977, 66, pp. 1-19, which is hereby incorporated by reference in its entirety.

"Pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

"Pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

"Solvate" means a complex of variable stoichiometry formed by a solute, for example, a compound of Formula (I) and solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, such solvents selected for the purpose of the disclosure do not interfere with the biological activity of the solute. Solvates encompasses both solution-phase and isolatable solvates. Representative solvates include hydrates, ethanolates, methanolates, and the like.

"Hydrate" means a solvate wherein the solvent molecule(s) is/are water. The compounds of the present disclosure as discussed below include the free base or acid thereof, their salts, solvates, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

Isomer Terms and Conventions

"Isomers" means compounds having the same number and kind of atoms, and hence the same molecular weight, but differing with respect to the arrangement or configuration of the atoms in space. The term includes stereoisomers and geometric isomers.

"Stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the disclosure which may give rise to stereoisomerism, the disclosure contemplates stereoisomers and mixtures thereof. The compounds of the disclosure and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

"Enantiomers" means a pair of stereoisomers that are non-superimposable mirror images of each other.

"Diastereoisomers" or "diastereomers" mean optical isomers which are not mirror images of each other.

"Racemic mixture" or "racemate" mean a mixture containing equal parts of individual enantiomers.

"Non-racemic mixture" means a mixture containing unequal parts of individual enantiomers.

"Geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C=N double bonds, cyclic structures, and the like may be present in the compounds of the disclosure, the disclosure contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, Advanced Organic Chemistry: Reactions, Mechanisms, and Structure, 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as x-ray crystallography, $^1$H NMR, and $^{13}$C NMR.

Some of the compounds of the disclosure can exist in more than one tautomeric form. As mentioned above, the compounds of the disclosure include all such tautomers.

It is well known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the disclosure from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

Pharmaceutical Administration and Treatment Terms and Conventions

A "patient" or "subject" is a mammal, e.g., a human, mouse, rat, guinea pig, dog, cat, horse, cow, pig, or nonhuman primate, such as a monkey, chimpanzee, baboon or, rhesus. In certain embodiments, the subject is a primate. In yet other embodiments, the subject is a human.

The terms "pharmaceutically effective amount" or "therapeutically effective amount" or "effective amount" means an amount of a compound according to the disclosure which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound according to the disclosure which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the disclosure, and the age, body weight, general health, sex, and diet of the patient. Such a therapeutically effective amount can be determined routinely by one of ordinary skill in the art having regard to their own knowledge, the prior art, and this disclosure.

As used herein, the term "pharmaceutical composition" refers to a compound of the disclosure, or a pharmaceutically acceptable salt, hydrate, solvate, stereoisomer, or tautomer thereof, together with at least one pharmaceutically acceptable carrier, in a form suitable for oral or parenteral administration.

"Carrier" encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

"Combination" refers to either a fixed combination in one dosage unit form, or a combined administration where a compound of the present disclosure and at least one combination partner (e.g. another drug as explained below, also referred to as "therapeutic agent" or "co-agent") may be administered independently at the same time or separately within time intervals, especially where these time intervals allow that the combination partners show a beneficial effect from the co-action of these therapeutic agents. The beneficial effect of the combination includes, but is not limited to, a cooperative, e.g., synergistic, effect and/or a pharmacokinetic or pharmacodynamic co-action, or any combination thereof, resulting from the combination of therapeutic agents. In one embodiment, administration of these therapeutic agents in combination is carried out over a defined time period (e.g., minutes, hours, days or weeks depending upon the combination selected)."

The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time.

The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g., a compound of the present disclosure and a combination partner, are both administered to a patient simultaneously in the form of a single entity or dosage. The term "non-fixed combination" means that the therapeutic agents, e.g., a compound of the present disclosure and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agents.

A subject is "in need of" a treatment if such subject would benefit biologically, medically, or in quality of life from such treatment (preferably, a human).

The term "PCSK9" or "proprotein convertase subtilisin/kexin type 9" interchangeably refer to a naturally-occurring human proprotein convertase belonging to the proteinase K subfamily of the secretory subtilase family. PCSK9 is synthesized as a soluble zymogen that undergoes autocatalytic intramolecular processing in the endoplasmic reticulum, and is thought to function as a proprotein convertase. PCSK9 plays a role in cholesterol homeostasis and may have a role in the differentiation of cortical neurons. Mutations in the PCSK9 gene are a cause of autosomal dominant familial hypercholesterolemia. (Burnett and Hooper, Clin. Biochem. Rev. (2008) 29(1):11-26)

As used herein, the term "inhibit", "inhibition", or "inhibiting" refers to the reduction or suppression of a given condition, symptom, or disorder, or disease, or a significant decrease in the baseline activity of a biological activity or process.

As used herein, the term "treat", "treating", or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing", or "prevention" of any disease or disorder refers to the prophylactic treatment of the disease or disorder; or delaying the onset or progression of the disease or disorder.

"Pharmaceutically acceptable" means that the substance or composition must be compatible chemically and/or toxicologically, with the other ingredients comprising a formulation, and/or the mammal being treated therewith.

"Disorder" means, and is used interchangeably with, the terms disease, condition, or illness, unless otherwise indicated.

"Administer", "administering", or "administration" means to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

"Prodrug" means a compound which is convertible in vivo by metabolic means (e.g., by hydrolysis) to a disclosed compound.

"Compounds of the present disclosure", "Compounds of Formula (I)", "compounds of the disclosure", and equivalent expressions (unless specifically identified otherwise) refer to compounds of Formulae (I), (Ia), (Ib), (Ic), (Id), (Ie), (If), (Ig), (Ih), (Ii), (Ij), (Ik), (Im), and (Io) as herein described including the tautomers, the prodrugs, salts particularly the pharmaceutically acceptable salts, and the solvates and hydrates thereof, where the context so permits thereof, as well as all stereoisomers (including diastereoisomers and enantiomers), rotamers, tautomers, and isotopically labelled compounds (including deuterium ("D") substitutions), as well as inherently formed moieties (e.g., polymorphs, solvates and/or hydrates). For purposes of this disclosure, solvates and hydrates are generally considered compositions. In general and preferably, the compounds of the disclosure and the formulas designating the compounds of the disclosure are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

"intermediates of the present disclosure", "intermediates of the disclosure", and equivalent expressions (unless specifically identified otherwise) refer to compounds of Formulae (IIIa), (IIIb), (IIIc), (IIId), (IIIe), (IIIf), (IIIg), (IIIh), (IIIi), and (IIIj) as herein described including the tautomers, the prodrugs, salts particularly the pharmaceutically acceptable salts, and the solvates and hydrates thereof, where the context so permits thereof, as well as all stereoisomers (including diastereoisomers and enantiomers), rotamers, tautomers, and isotopically labelled compounds (including deuterium ("D") substitutions), as well as inherently formed moieties (e.g., polymorphs, solvates and/or hydrates). For purposes of this disclosure, solvates and hydrates are generally considered compositions. In general and preferably, the intermediates of the disclosure and the formulas designating the intermediates of the disclosure are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

"Stable compound" or "stable structure" means a compound that is sufficiently robust to survive isolation to a useful degree of purity from a reaction mixture, and formulation into an efficacious therapeutic or diagnostic agent. For example, a compound, which would have a "dangling valency" or is a carbanion is not a compound contemplated by the disclosure. In a specific embodiment, the term "about" or "approximately" means within 20%, preferably within 10%, and more preferably within 5% of a given value or range.

As used herein, a "modulator of PCSK9" refers to a compound or molecule that is able to modulate PCSK9 biological activity or function, and/or downstream pathway(s) mediated by PCSK9 activity.

As used herein, an "inhibitor of PCSK9" refers to a compound or molecule that is able to inhibit PCSK9 biological activity or function, and/or downstream pathway(s) mediated by PCSK9 signaling. An inhibitor of PCSK9 activity encompasses compounds that block, antagonize, suppress or reduce (to any degree including significantly) PCSK9 biological activity, including downstream pathways mediated by PCSK9 activity.

As used herein, "disorders or diseases responsive to the inhibition of PCSK9," "disorders and conditions responsive to the inhibition of PCSK9," "disorders and conditions responsive to the inhibition of PCSK9 activity," "disorders responsive to the inhibition of PCSK9," "disorders responsive to the inhibition of PCSK9 activity," "disorders in which PCSK9 plays a role," and like terms include hypercholesterolemia, hyperlipidemia, hypertriglyceridemia, sitosterolemia, atherosclerosis, arteriosclerosis, coronary heart disease, peripheral vascular disease (including aortic diseases and cerebrovascular disease), peripheral arterial disease, vascular inflammation, elevated Lp(a), elevated LDL, elevated TRL, elevated triglycerides, sepsis, and xanthoma.

As used herein, "Inhibition of PCSK9 activity," or "inhibition of PCSK9," refers to a decrease in the PCSK9 activity, e.g., by administration of the compound of the disclosure.

The term "hypercholesterolemia" or "dyslipidemia" includes, e.g., familial and non-familial hypercholesterolemia. Familial hypercholesterolemia (FH) is an autosomal dominant disorder characterized by elevation of serum cholesterol bound to low density lipoprotein (LDL). Familial hypercholesterolemia includes both heterozygous FH and homozygous FH.

Hypercholesterolemia (or dyslipidemia) is the presence of high levels of cholesterol in the blood. It is a form of hyperlipidemia (elevated levels of lipids in the blood) and hyperlipoproteinemia (elevated levels of lipoproteins in the blood).

Hyperlipidemia is an elevation of lipids in the bloodstream. These lipids include cholesterol, cholesterol esters, phospholipids and triglycerides. Hyperlipidemia includes for example, type I, IIa, IIb, III, IV and V.

Hypertriglyceridemia denotes high blood levels of triglycerides. Elevated levels of triglycerides are associated with atherosclerosis, even in the absence of hypercholesterolemia, and predispose to cardiovascular disease.

"Sitosterolemia" or "phytosterolemia" is a rare autosomal recessively inherited lipid metabolic disorder characterized by hyperabsorption of sitosterol from the gastrointestinal tract and decreased biliary excretion of dietary sterols (i.e., leading to hypercholesterolemia, tendon and tuberous xanthomas, premature development of atherosclerosis) and altered cholesterol synthesis.

"Atherosclerosis" includes hardening of arteries associated with deposition of fatty substances, cholesterol, cellular waste products, calcium and fibrin in the inner lining of an artery. The buildup that results is called plaque.

"Atherosclerosis" or "arteriosclerotic vascular disease (ASVD)" is a specific form of arteriosclerosis involving thickening, hardening and loss of elasticity of the walls of arteries as a result of invasion and accumulation of white blood cells, containing both living, active white blood cells (producing inflammation) and remnants of dead cells, including cholesterol and triglycerides. Atherosclerosis is therefore a syndrome affecting arterial blood vessels due to a chronic inflammatory response of white blood cells in the walls of arteries.

"Coronary heart disease," also known as atherosclerotic artery disease, atherosclerotic cardiovascular disease, coronary heart disease or ischemic heart disease is the most common type of heart disease and cause of heart attacks. The disease is caused by plaque building up along the inner walls of the arteries of the heart, which narrows the lumen of arteries and reduces blood flow to the heart.

"Xanthoma" is a cutaneous manifestation of lipidosis in which lipids accumulate in large foam cells within the skin. Xanthomas are associated with hyperlipidemias.

The term "elevated Lp(a) concentration", as used herein, refers to a serum Lp(a) concentration above 30 mg/dl (75 nmol/L). "Elevated serum Lp(a)" means a serum Lp(a) level greater than about 14 mg/dL. In certain embodiments, a patient is considered to exhibit elevated serum Lp(a) if the level of serum Lp(a) measured in the patient is greater than about 15 mg/dL, about 20 mg/dL, about 25 mg/dL, about 30 mg/dL, about 35 mg/dL, about 40 mg/dL, about 45 mg/dL, about 50 mg/dL, about 60 mg/dL, about 70 mg/dL, about 80 mg/dL, about 90 mg/dL, about 100 mg/dL, about 20 mg/dL, about 140 mg/dL, about 150 mg dL, about 180 mg/dL, or about 200 mg/dL The serum Lp(a) level can be measured in a patient post-prandial. In some embodiments, the Lp(a) level is measured after a period of time of fasting (e.g., after fasting for 8 hrs, 8 hrs, 10 hrs, 12 hrs or more). Exemplary methods for measuring serum Lp(a) in a patient include, but are not limited to, rate immunonephelometry, ELISA, nephelometry, immunoturbidimetry, and dissociation-enhanced lanthanide fluorescent immunoassay, although any clinically acceptable diagnostic method can be used in the context of the present disclosure.

By "elevated triglyceride levels" or "ETL" is meant any degree of triglyceride levels that is determined to be undesirable or is targeted for modulation.

"Sepsis" is a systemic reaction characterized by arterial hypotension, metabolic acidosis, decreased systemic vascular resistance, tachypnea, and organ dysfunction. Sepsis can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). The term "sepsis" also encompasses fungemia (i.e., fungi in the blood), viremia (i.e., viruses or virus particles in the blood), and parasitemia (i.e., helminthic or protozoan parasites in the blood). Thus, septicemia and septic shock (acute circulatory failure resulting from septicemia often associated with multiple organ failure and a high mortality rate) may be caused by a number of organisms.

Specific Embodiments of Compounds of Formula (I)

The present disclosure relates to compounds or pharmaceutically acceptable salts, hydrates, solvates, stereoisomers, or tautomers thereof, capable of modulating PCSK9, which are useful for the treatment of diseases and disorders associated with modulation of a PCSK9 protein or enzyme. In another embodiment, the present disclosure relates to compounds or pharmaceutically acceptable salts, hydrates, solvates, prodrugs, stereoisomers, or tautomers thereof, capable of inhibiting PCSK9, which are useful for the treatment of diseases and disorders associated with inhibition of a PCSK9 protein or enzyme. The disclosure further relates to compounds, or pharmaceutically acceptable salts, hydrates, solvates, stereoisomers, or tautomers thereof, which are useful for inhibiting PCSK9.

In one embodiment, the compounds of Formula (I) have the structure of Formula (Ia):

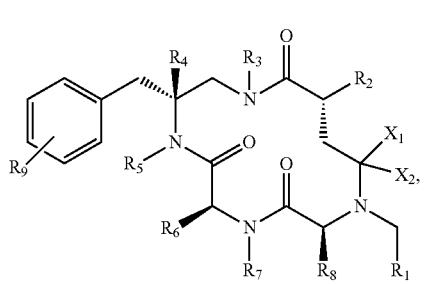

(Ia)

and pharmaceutically acceptable salts, hydrates, solvates, prodrugs, stereoisomers, N-oxides, and tautomers thereof.

In another embodiment, the compounds of Formula (I) have the structure of Formula (Ib):

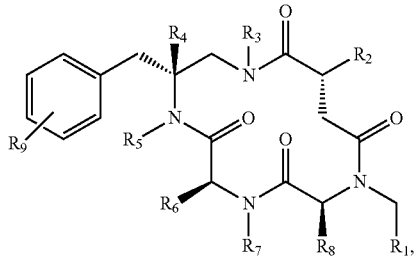

(Ib)

and pharmaceutically acceptable salts, hydrates, solvates, prodrugs, stereoisomers, N-oxides, and tautomers thereof.

In another embodiment, the compounds of Formula (I) have the structure of Formula (Ic):

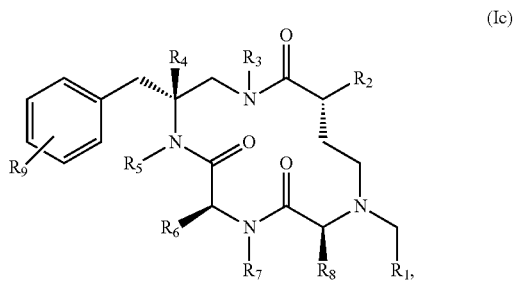

(Ic)

and pharmaceutically acceptable salts, hydrates, solvates, prodrugs, stereoisomers, N-oxides, and tautomers thereof.

In another embodiment, the compounds of Formula (I) have the structure of Formula (Id):

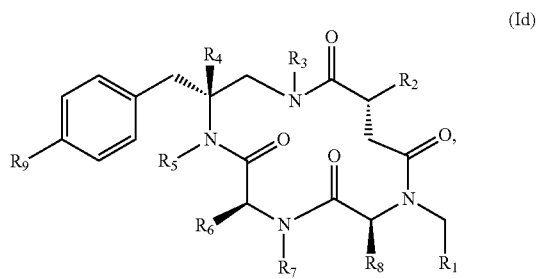

(Id)

and pharmaceutically acceptable salts, hydrates, solvates, prodrugs, stereoisomers, N-oxides, and tautomers thereof.

In another embodiment, the compounds of Formula (I) have the structure of Formula (Ie):

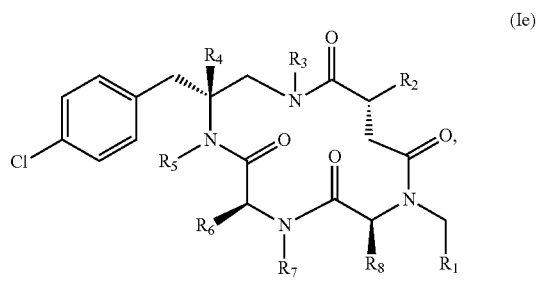

(Ie)

and pharmaceutically acceptable salts, hydrates, solvates, prodrugs, stereoisomers, N-oxides, and tautomers thereof.

In another embodiment, the compounds of Formula (I) have the structure of Formula (If):

(If)

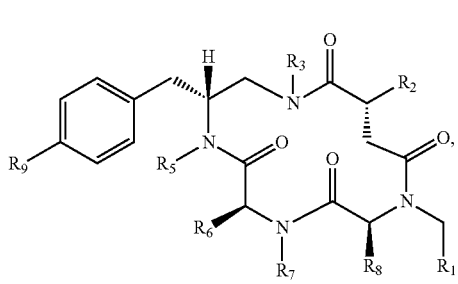

and pharmaceutically acceptable salts, hydrates, solvates, prodrugs, stereoisomers, N-oxides, and tautomers thereof.

In another embodiment, the compounds of Formula (I) have the structure of Formula (Ig):

(Ig)

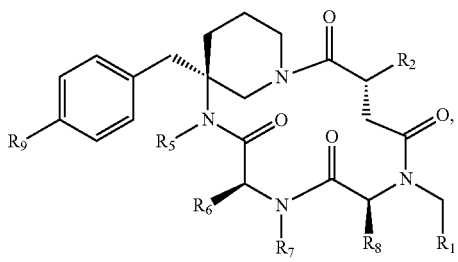

and pharmaceutically acceptable salts, hydrates, solvates, prodrugs, stereoisomers, N-oxides, and tautomers thereof.

In another embodiment, the compounds of Formula (I) have the structure of Formula (Ih):

(Ih)

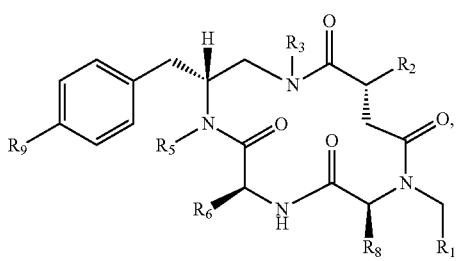

and pharmaceutically acceptable salts, hydrates, solvates, prodrugs, stereoisomers, N-oxides, and tautomers thereof.

In another embodiment, the compounds of Formula (I) have the structure of Formula (Ii):

(Ii)

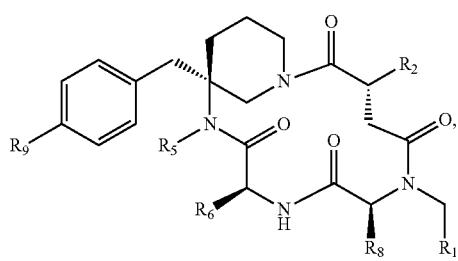

and pharmaceutically acceptable salts, hydrates, solvates, prodrugs, stereoisomers, N-oxides, and tautomers thereof.

In another embodiment, the compounds of Formula (I) have the structure of Formula (Ij):

(Ij)

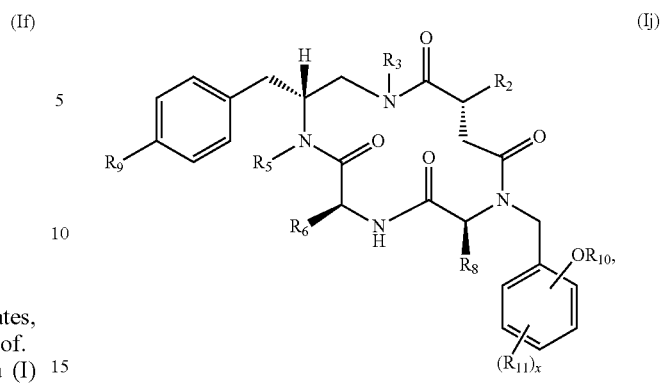

wherein x is 0, 1, or 2; and pharmaceutically acceptable salts, hydrates, solvates, prodrugs, stereoisomers, N-oxides, and tautomers thereof.

In another embodiment, the compounds of Formula (I) have the structure of Formula (Ik):

(Ik)

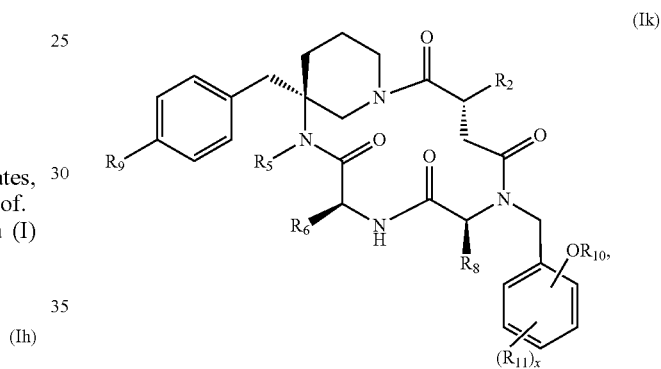

wherein x is 0, 1, or 2; and pharmaceutically acceptable salts, hydrates, solvates, prodrugs, stereoisomers, N-oxides, and tautomers thereof.

In another embodiment, the compounds of Formula (I) have the structure of Formula (Im):

(Im)

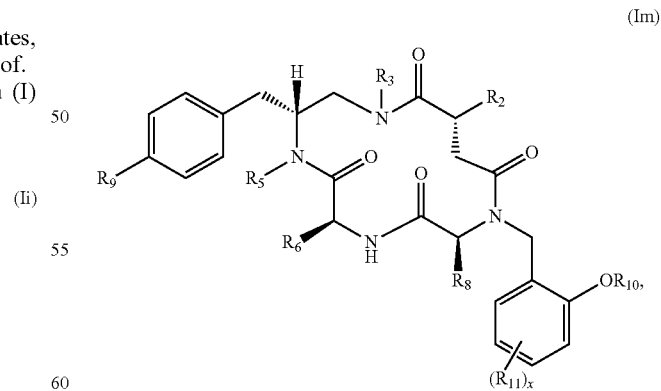

wherein x is 0, 1, or 2; and pharmaceutically acceptable salts, hydrates, solvates, prodrugs, stereoisomers, N-oxides, and tautomers thereof.

In another embodiment, the compounds of Formula (I) have the structure of Formula (Io):

(Io)

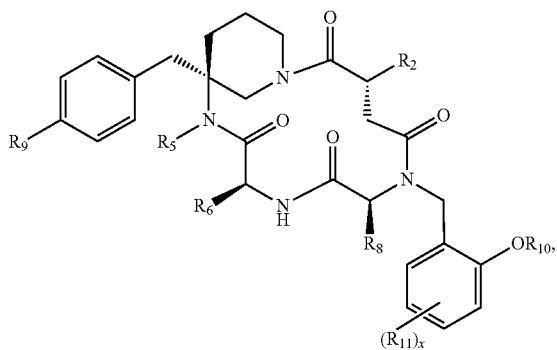

wherein x is 0, 1, or 2; and pharmaceutically acceptable salts, hydrates, solvates, prodrugs, stereoisomers, N-oxides, and tautomers thereof.

In some embodiments of the Formulae above (e.g., Formula (I), Formula (Ia), Formula (Ib), Formula (Ic), Formula (Id), Formula (Ie), Formula (If), Formula (Ig), Formula (Ih), Formula (Ii): Formula (Ij), Formula (Ik), Formula (Im), and/or Formula (Io)), $X_1$ and $X_2$ are each independently H or $(C_1-C_6)$alkyl, or $X_1$ and $X_2$ together with the carbon atom to which they are attached form =(O);

$X_3$ is —$CH_2$— when $X_1$ and $X_2$ are each independently H or $(C_1-C_6)$alkyl, or $X_1$ and $X_2$ together with the carbon atom to which they are attached form =(O), or $X_3$ is —O—, —NH— or —N$(C_1-C_6)$alkyl-, when $X_1$ and $X_2$ together with the carbon atom to which they are attached form =(O);

$R_1$ is $(C_6-C_{10})$aryl or 5- or 6-membered heteroaryl comprising 1-3 heteroatoms selected from N, O, and S, wherein the aryl and heteroaryl are substituted with —$OR_{10}$ or —$NR_{21}R_{10}$ and optionally substituted with one to four $R_{11}$;

$R_2$ is H, $(C_1-C_6)$alkyl, $(C_2-C_6)$alkenyl, $(C_1-C_6)$haloalkyl, —$NR_{12}R_{13}$, $(C_3-C_7)$carbocyclyl, $(C_3-C_7)$cycloalkenyl, 5- to 7-membered heterocyclyl comprising 1-3 heteroatoms selected from N, O, and S, $(C_6-C_{10})$aryl, or 5- or 6-membered heteroaryl comprising 1-3 heteroatoms selected from N, O, and S, wherein the alkyl is optionally substituted with one to four $R_{18}$, and the carbocyclyl, cycloalkenyl, heterocyclyl, aryl and heteroaryl are optionally substituted with one to four $R_{19}$;

$R_3$ is H, D, $(C_1-C_6)$alkyl, $(C_1-C_6)$alkoxy, $(C_1-C_6)$haloalkyl, $(C_1-C_6)$haloalkoxy, or $(C_1-C_6)$hydroxyalkyl, wherein the alkyl is optionally substituted with one to four $R_{14}$;

$R_4$ is H or $(C_1-C_6)$alkyl; or $R_3$ and $R_4$ together with the atoms to which they are attached form a 5- to 7-membered heterocyclyl ring comprising 1-3 heteroatoms selected from N, O, and S;

$R_5$ and $R_7$ are each independently H, D, $(C_1-C_6)$alkyl, $(C_1-C_6)$alkoxy, $(C_1-C_6)$haloalkyl, $(C_1-C_6)$haloalkoxy, or $(C_1-C_6)$hydroxyalkyl, wherein the $(C_1-C_6)$alkyl is optionally substituted with one to four D;

$R_6$ is $(C_1-C_6)$alkyl, $(C_1-C_6)$alkoxy, $(C_1-C_6)$haloalkyl, $(C_1-C_6)$haloalkoxy, or $(C_1-C_6)$hydroxyalkyl, wherein the alkyl is optionally substituted with one to four substituents each independently selected from $(C_1-C_6)$alkoxy, $(C_1-C_6)$haloalkoxy, —C(O)$(C_1-C_6)$alkyl, —C(O)OH, and —C(O)O$(C_1-C_6)$alkyl;

$R_8$ is H, $(C_1-C_6)$alkyl, or $(C_1-C_6)$haloalkyl, wherein the alkyl is optionally substituted with one to four substituents each independently selected from $(C_3-C_7)$carbocyclyl, 4- to 7-membered heterocyclyl comprising 1-3 heteroatoms selected from N, O, and S, —$NR_{16}R_{17}$, and —C(O)$NR_{16}R_{17}$;

$R_9$ is halogen, $(C_1-C_6)$alkyl, $(C_1-C_6)$alkoxy, $(C_1-C_6)$haloalkyl, $(C_1-C_6)$haloalkoxy, —OH, or CN;

$R_{10}$ is $(C_6-C_{10})$aryl or 5- or 6-membered heteroaryl comprising 1-3 heteroatoms selected from N, O, and S, wherein the aryl and heteroaryl are optionally substituted with one to four $R_{22}$;

each $R_{11}$ is independently at each occurrence halogen, $(C_1-C_6)$alkyl, $(C_1-C_6)$alkoxy, $(C_1-C_6)$haloalkyl, $(C_1-C_6)$haloalkoxy, —OH, or CN;

$R_{12}$ and $R_{13}$ are each independently H or $(C_1-C_6)$alkyl;

each $R_{14}$ is independently at each occurrence D, $NR_{15}R_{15'}$, $(C_3-C_7)$carbocyclyl, or 3- to 7-membered heterocyclyl comprising 1-3 heteroatoms selected from N, O, and S, wherein the carbocyclyl and heterocyclyl are optionally substituted with one to four substituents each independently selected from halogen, $(C_1-C_6)$alkyl, $(C_1-C_6)$alkoxy, $(C_1-C_6)$haloalkyl, and $(C_1-C_6)$haloalkoxy;

$R_{15}$ and $R_{15'}$ are each independently H or $(C_1-C_6)$alkyl;

$R_{16}$ and $R_{17}$ are each independently H or $(C_1-C_6)$alkyl, or $R_{16}$ and $R_{17}$ together with the nitrogen atom to which they are attached form a 4- to 7-membered heterocyclyl ring optionally comprising 1-2 additional heteroatoms selected from N, O, and S;

each $R_{18}$ is independently at each occurrence $(C_3-C_7)$carbocyclyl, 5- to 7-membered heterocyclyl comprising 1-3 heteroatoms selected from N, O, and S, $(C_6-C_{10})$aryl, or 5- or 6-membered heteroaryl comprising 1-3 heteroatoms selected from N, O, and S, wherein the carbocyclyl, heterocyclyl, aryl and heteroaryl are optionally substituted with one to four $R_{20}$;

each $R_{19}$ is independently at each occurrence halogen, $(C_1-C_6)$alkyl, $(C_1-C_6)$alkoxy, $(C_1-C_6)$haloalkyl, $(C_1-C_6)$haloalkoxy, —OH, or CN; or two $R_{19}$ together, when on adjacent atoms, form a $(C_6-C_{10})$aryl or 5- or 6-membered heteroaryl ring comprising 1-3 heteroatoms selected from N, O, and S, wherein the aryl and heteroaryl are optionally substituted with one to four substituents each independently selected from halogen, $(C_1-C_6)$alkyl, $(C_1-C_6)$alkoxy, $(C_1-C_6)$haloalkyl, $(C_1-C_6)$haloalkoxy, —OH, and CN;

each $R_{20}$ is independently at each occurrence halogen, $(C_1-C_6)$alkyl, $(C_1-C_6)$alkoxy, $(C_1-C_6)$haloalkyl, $(C_1-C_6)$haloalkoxy, oxo, —OH, or CN; or when $R_{18}$ is a carbocyclyl or a heterocyclyl, two $R_{20}$, when attached to the same carbon atom, together form =(O);

$R_{21}$ is H or $(C_1-C_6)$alkyl;

each $R_{22}$ is independently at each occurrence halogen, $(C_1-C_6)$alkyl, $(C_1-C_6)$alkoxy, $(C_1-C_6)$haloalkyl, $(C_1-C_6)$haloalkoxy, —OH, CN, $(C_6-C_{10})$aryl, or 5- or 6-membered heteroaryl comprising 1-3 heteroatoms selected from N, O, and S, wherein the aryl and heteroaryl are optionally substituted with one to four $R_{23}$;

each $R_{23}$ is independently at each occurrence halogen, $(C_1-C_6)$alkyl, $(C_1-C_6)$alkoxy, $(C_1-C_6)$haloalkyl, $(C_1-C_6)$haloalkoxy, —$CH_2(OCH_2CH_2)_{1-3}OCH_2CH_3$, —OH, CN, or 4- to 7-membered heterocyclyl comprising 1-3 heteroatoms selected from N, O, and S, wherein the heterocyclyl is optionally substituted with one to four substituents each independently selected from halogen, $(C_1-C_6)$alkyl, $(C_1-C_6)$alkoxy, $(C_1-C_6)$haloalkyl, $(C_1-C_6)$haloalkoxy, —OH, —C(O)$R_{24}R_{25}$, —$NR_{24}C(O)R_{25}$, —$NH_2$, —NH$(C_1-C_6)$alkyl, and —N$((C_1-C_6)$alkyl$)_2$, and the alkyl is optionally substituted with —$NR_{24}R_{25}$ or a 4- to 7-membered heterocyclyl comprising 1-3 heteroatoms selected from N, O, and S optionally substituted with one to four substituents each independently selected from halogen, $(C_1-C_6)$alkyl, $(C_1-C_6)$alkoxy, $(C_1-C_6)$haloalkyl, $(C_1-C_6)$haloalkoxy, —OH, —NH$_2$, —NH$(C_1-C_6)$alkyl, and —N$((C_1-C_6)$alkyl$)_2$; and $R_{24}$ and $R_{25}$ are each independently H, $(C_1-C_6)$alkyl, or $(C_3-C_7)$carbocyclyl;

or pharmaceutically acceptable salts, hydrates, solvates, prodrugs, stereoisomers, N-oxides, or tautomers thereof.

In some embodiments of the Formulae above, $X_1$ and $X_2$ are each independently H or $(C_1-C_6)$alkyl, or $X_1$ and $X_2$ together with the carbon atom to which they are attached form =(O);

$X_3$ is —CH$_2$— when $X_1$ and $X_2$ are each independently H or $(C_1-C_6)$alkyl, or $X_1$ and $X_2$ together with the carbon atom to which they are attached form =(O), or $X_3$ is —O—, —NH— or —N$(C_1-C_6)$alkyl-, when $X_1$ and $X_2$ together with the carbon atom to which they are attached form =(O);

$R_1$ is $(C_6-C_{10})$aryl or 5- or 6-membered heteroaryl comprising 1-3 heteroatoms selected from N, O, and S, wherein the aryl and heteroaryl are substituted with —OR$_{10}$ or —NR$_{21}$R$_{10}$ and optionally substituted with one to four $R_{11}$;

$R_2$ is H, $(C_1-C_6)$alkyl, $(C_2-C_6)$alkenyl, $(C_1-C_6)$haloalkyl, —NR$_{12}$R$_{13}$, $(C_3-C_7)$carbocyclyl, $(C_3-C_7)$cycloalkenyl, 5- to 7-membered heterocyclyl comprising 1-3 heteroatoms selected from N, O, and S, $(C_6-C_{10})$aryl, or 5- or 6-membered heteroaryl comprising 1-3 heteroatoms selected from N, O, and S, wherein the alkyl is optionally substituted with one to four Rub, and the carbocyclyl, cycloalkenyl, heterocyclyl, aryl and heteroaryl are optionally substituted with one to four $R_{19}$;

$R_3$ is H, D, $(C_1-C_6)$alkyl, $(C_1-C_6)$alkoxy, $(C_1-C_6)$haloalkyl, $(C_1-C_6)$haloalkoxy, or $(C_1-C_6)$hydroxyalkyl, wherein the alkyl is optionally substituted with one to four $R_{14}$;

$R_4$ is H or $(C_1-C_6)$alkyl; or $R_3$ and $R_4$ together with the atoms to which they are attached form a 5- to 7-membered heterocyclyl ring comprising 1-3 heteroatoms selected from N, O, and S;

$R_5$ and $R_7$ are each independently H, D, $(C_1-C_6)$alkyl, $(C_1-C_6)$alkoxy, $(C_1-C_6)$haloalkyl, $(C_1-C_6)$haloalkoxy, or $(C_1-C_6)$hydroxyalkyl, wherein the $(C_1-C_6)$alkyl is optionally substituted with one to four D;

$R_6$ is $(C_1-C_6)$alkyl, $(C_1-C_6)$alkoxy, $(C_1-C_6)$haloalkyl, $(C_1-C_6)$haloalkoxy, or $(C_1-C_6)$hydroxyalkyl, wherein the alkyl is optionally substituted with one to four substituents each independently selected from $(C_1-C_6)$alkoxy, $(C_1-C_6)$haloalkoxy, —C(O)$(C_1-C_6)$alkyl, —C(O)OH, and —C(O)O$(C_1-C_6)$alkyl;

$R_8$ is H, $(C_1-C_6)$alkyl, or $(C_1-C_6)$haloalkyl, wherein the alkyl is optionally substituted with one to four substituents each independently selected from $(C_3-C_7)$carbocyclyl, 4- to 7-membered heterocyclyl comprising 1-3 heteroatoms selected from N, O, and S, —NR$_{16}$R$_{17}$, and —C(O)NR$_{16}$R$_{17}$;

$R_9$ is halogen, $(C_1-C_6)$alkyl, $(C_1-C_6)$alkoxy, $(C_1-C_6)$haloalkyl, $(C_1-C_6)$haloalkoxy, —OH, or CN;

$R_{10}$ is $(C_6-C_{10})$aryl or 5- or 6-membered heteroaryl comprising 1-3 heteroatoms selected from N, O, and S, wherein the aryl and heteroaryl are optionally substituted with one to four $R_{22}$;

each $R_{11}$ is independently at each occurrence halogen, $(C_1-C_6)$alkyl, $(C_1-C_6)$alkoxy, $(C_1-C_6)$haloalkyl, $(C_1-C_6)$haloalkoxy, —OH, or CN;

$R_{12}$ and $R_{13}$ are each independently H or $(C_1-C_6)$alkyl;

each $R_{14}$ is independently at each occurrence D, NR$_{15}$R$_{15'}$, $(C_3-C_7)$carbocyclyl, or 3- to 7-membered heterocyclyl comprising 1-3 heteroatoms selected from N, O, and S, wherein the carbocyclyl and heterocyclyl are optionally substituted with one to four substituents each independently selected from halogen, $(C_1-C_6)$alkyl, $(C_1-C_6)$alkoxy, $(C_1-C_6)$haloalkyl, and $(C_1-C_6)$haloalkoxy;

$R_{15}$ and $R_{15'}$ are each independently H or $(C_1-C_6)$alkyl;

$R_{16}$ and $R_{17}$ are each independently H or $(C_1-C_6)$alkyl, or $R_{16}$ and $R_{17}$ together with the nitrogen atom to which they are attached form a 4- to 7-membered heterocyclyl ring comprising 1-2 additional heteroatoms selected from N, O, and S;

each $R_{18}$ is independently at each occurrence $(C_3-C_7)$carbocyclyl, 5- to 7-membered heterocyclyl comprising 1-3 heteroatoms selected from N, O, and S, $(C_6-C_{10})$aryl, or 5- or 6-membered heteroaryl comprising 1-3 heteroatoms selected from N, O, and S, wherein the carbocyclyl, heterocyclyl, aryl and heteroaryl are optionally substituted with one to four $R_{20}$;

each $R_{19}$ is independently at each occurrence halogen, $(C_1-C_6)$alkyl, $(C_1-C_6)$alkoxy, $(C_1-C_6)$haloalkyl, $(C_1-C_6)$haloalkoxy, —OH, or CN; or two $R_{19}$ together, when on adjacent atoms, form a $(C_6-C_{10})$aryl or 5- or 6-membered heteroaryl ring comprising 1-3 heteroatoms selected from N, O, and S, wherein the aryl and heteroaryl are optionally substituted with one to four substituents each independently selected from halogen, $(C_1-C_6)$alkyl, $(C_1-C_6)$alkoxy, $(C_1-C_6)$haloalkyl, $(C_1-C_6)$haloalkoxy, —OH, and CN;

each $R_{20}$ is independently at each occurrence halogen, $(C_1-C_6)$alkyl, $(C_1-C_6)$alkoxy, $(C_1-C_6)$haloalkyl, $(C_1-C_6)$haloalkoxy, oxo, —OH, or CN; or when $R_{18}$ is a carbocyclyl or a heterocyclyl, two $R_{20}$, when attached to the same carbon atom, together form =(O);

$R_{21}$ is H or $(C_1-C_6)$alkyl;

each $R_{22}$ is independently at each occurrence halogen, $(C_1-C_6)$alkyl, $(C_1-C_6)$alkoxy, $(C_1-C_6)$haloalkyl, $(C_1-C_6)$haloalkoxy, —OH, CN, $(C_6-C_{10})$aryl, or 5- or 6-membered heteroaryl comprising 1-3 heteroatoms selected from N, O, and S, wherein the aryl and heteroaryl are optionally substituted with one to four $R_{23}$;

each $R_{23}$ is independently at each occurrence halogen, $(C_1-C_6)$alkyl, $(C_1-C_6)$alkoxy, $(C_1-C_6)$haloalkyl, $(C_1-C_6)$haloalkoxy, —CH$_2$(OCH$_2$CH$_2$)$_{1-3}$OCH$_2$CH$_3$, —OH, CN, or 4- to 7-membered heterocyclyl comprising 1-3 heteroatoms selected from N, O, and S, wherein the heterocyclyl is optionally substituted with one to four substituents each independently selected from halogen, $(C_1-C_6)$alkyl, $(C_1-C_6)$alkoxy, $(C_1-C_6)$haloalkyl, $(C_1-C_6)$haloalkoxy, —OH, —C(O)R$_{24}$R$_{25}$, —NR$_{24}$C(O)R$_{25}$, —NH$_2$, —NH$(C_1-C_6)$alkyl, and —N$((C_1-C_6)$alkyl$)_2$, and the alkyl is optionally substituted with —NR$_{24}$R$_{25}$ or a 4- to 7-membered heterocyclyl comprising 1-3 heteroatoms selected from N, O, and S optionally substituted with one to four substituents each independently selected from halogen, $(C_1-C_6)$alkyl, $(C_1-C_6)$alkoxy, $(C_1-C_6)$haloalkyl, $(C_1-C_6)$haloalkoxy, —OH, —NH$_2$, —NH$(C_1-C_6)$alkyl, and —N$((C_1-C_6)$alkyl$)_2$; and $R_{24}$ and $R_{25}$ are each independently H, $(C_1-C_6)$alkyl, or $(C_3-C_7)$carbocyclyl;

or pharmaceutically acceptable salts, hydrates, solvates, prodrugs, stereoisomers, N-oxides, or tautomers thereof.

In some embodiments of the Formulae above, $X_1$ is H or $(C_1-C_6)$alkyl. In another embodiment $X_1$ is H. In yet another embodiment, $X_1$ is $(C_1-C_6)$alkyl.

In some embodiments of the Formulae above, $X_2$ is H or $(C_1-C_6)$alkyl. In another embodiment $X_2$ is H. In yet another embodiment, $X_2$ is $(C_1-C_6)$alkyl.

In some embodiments of the Formulae above, $X_1$ and $X_2$ together with the carbon atom to which they are attached form =(O).

In some embodiments of the Formulae above, $X_1$ is H and $X_2$ is H. In another embodiment, $X_1$ is H and $X_2$ is $(C_1-C_6)$alkyl. In yet another embodiment, $X_1$ is $(C_1-C_6)$alkyl and $X_2$ is $(C_1-C_6)$alkyl.

In some embodiments of the Formulae above, $X_3$ is —O—, —NH— or —N($C_1-C_6$)alkyl-, when $X_1$ and $X_2$ together with the carbon atom to which they are attached form =(O). In another embodiment, $X_3$ is —N($C_1-C_6$)alkyl-, when $X_1$ and $X_2$ together with the carbon atom to which they are attached form =(O). In yet another embodiment, $X_3$ is —O—, when $X_1$ and $X_2$ together with the carbon atom to which they are attached form =(O). In another embodiment, $X_3$ is —NH—, when $X_1$ and $X_2$ together with the carbon atom to which they are attached form =(O). In yet another embodiment, $X_3$ is —$CH_2$— when $X_1$ and $X_2$ are each independently H or $(C_1-C_6)$alkyl, or $X_1$ and $X_2$ together with the carbon atom to which they are attached form =(O). In another embodiment, $X_3$ is —$CH_2$— when $X_1$ and $X_2$ are each independently H or $(C_1-C_6)$alkyl. In yet another embodiment, $X_3$ is —$CH_2$— when $X_1$ and $X_2$ together with the carbon atom to which they are attached form =(O).

In some embodiments of the Formulae above, $R_1$ is $(C_6-C_{10})$aryl or 5- or 6-membered heteroaryl comprising 1-3 heteroatoms selected from N, O, and S, wherein the aryl and heteroaryl are substituted with —$OR_{10}$ or —$NR_{21}R_{10}$ and optionally substituted with one to three $R_{11}$. In another embodiment, $R_1$ is phenyl or 5- or 6-membered heteroaryl comprising 1-3 heteroatoms selected from N, O, and S, wherein the phenyl and heteroaryl are substituted with —$OR_{10}$ or —$NR_{21}R_{10}$ and optionally substituted with one to three $R_{11}$. In yet another embodiment, $R_1$ is $(C_6-C_{10})$aryl, or 5-membered heteroaryl comprising 1-3 heteroatoms selected from N, O, and S, wherein the aryl and heteroaryl are substituted with —$OR_{10}$ or —$NR_{21}R_{10}$ and optionally substituted with one to three $R_{11}$. In another embodiment, $R_1$ is phenyl or 5-membered heteroaryl comprising 1-3 heteroatoms selected from N, O, and S, wherein the phenyl and heteroaryl are substituted with —$OR_{10}$ or —$NR_{21}R_{10}$ and optionally substituted with one to three $R_{11}$.

In yet another embodiment, $R_1$ is $(C_6-C_{10})$aryl, or 6-membered heteroaryl comprising 1-3 heteroatoms selected from N, O, and S, wherein the aryl and heteroaryl are substituted with —$OR_{10}$ or —$NR_{21}R_{10}$ and optionally substituted with one to three $R_{11}$. In another embodiment, $R_1$ is phenyl, or 6-membered heteroaryl comprising 1-3 heteroatoms selected from N, O, and S, wherein the phenyl and heteroaryl are substituted with —$OR_{10}$ or —$NR_{21}R_{10}$ and optionally substituted with one to three $R_{11}$. In another embodiment, $R_1$ is $(C_6-C_{10})$aryl substituted with —$OR_{10}$ or —$NR_{21}R_{10}$ and optionally substituted with one to three $R_{11}$. In yet another embodiment, $R_1$ is phenyl substituted with —$OR_{10}$ or —$NR_{21}R_{10}$ and optionally substituted with one to three $R_{11}$. In another embodiment, $R_1$ is $(C_6-C_{10})$aryl substituted with —$OR_{10}$ or —$NR_{21}R_{10}$ and substituted with one to three $R_{11}$. In yet another embodiment, $R_1$ is phenyl substituted with —$OR_{10}$ or —$NR_{21}R_{10}$ and substituted with one to three $R_{11}$.

In another embodiment, $R_1$ is $(C_6-C_{10})$aryl substituted with —$NR_{21}R_{10}$ and optionally substituted with one to three $R_{11}$. In yet another embodiment, $R_1$ is phenyl substituted with —$NR_{21}R_{10}$ and optionally substituted with one to three $R_{11}$. In another embodiment, $R_1$ is $(C_6-C_{10})$aryl substituted with —$NR_{21}R_{10}$ and substituted with one to three $R_{11}$. In yet another embodiment, $R_1$ is phenyl substituted with —$NR_{21}R_{10}$ and substituted with one to three $R_{11}$. In another embodiment, $R_1$ is $(C_6-C_{10})$aryl substituted with —$OR_{10}$ and optionally substituted with one to three $R_{11}$. In another embodiment, $R_1$ is phenyl substituted with —$OR_{10}$ and optionally substituted with one to three $R_{11}$. In yet another embodiment, $R_1$ is $(C_6-C_{10})$aryl substituted with —$OR_{10}$ and substituted with one to three $R_{11}$. In another embodiment, $R_1$ is phenyl substituted with —$OR_{10}$ and substituted with one to three $R_{11}$.

In some embodiments of the Formulae above, $R_2$ is H, $(C_1-C_6)$alkyl, $(C_2-C_6)$alkenyl, $(C_1-C_6)$haloalkyl, —$NR_{12}R_{13}$, $(C_3-C_7)$carbocyclyl, $(C_3-C_7)$cycloalkenyl, 5- to 7-membered heterocyclyl comprising 1-3 heteroatoms selected from N, O, and S, $(C_6-C_{10})$aryl, or 5- or 6-membered heteroaryl comprising 1-3 heteroatoms selected from N, O, and S, wherein the alkyl is optionally substituted with one to three $R_{18}$, and the carbocyclyl, heterocyclyl, aryl and heteroaryl are optionally substituted with one to four $R_{19}$. In another embodiment, $R_2$ is H, $(C_1-C_3)$alkyl, $(C_2-C_4)$alkenyl, $(C_1-C_6)$haloalkyl, —$NR_{12}R_{13}$, $(C_3-C_7)$carbocyclyl, $(C_3-C_7)$cycloalkenyl, 5- to 7-membered heterocyclyl comprising 1-3 heteroatoms selected from N, O, and S, $(C_6-C_{10})$aryl, or 5- or 6-membered heteroaryl comprising 1-3 heteroatoms selected from N, O, and S, wherein the alkyl is optionally substituted with one to three $R_{18}$, and the carbocyclyl, heterocyclyl, aryl and heteroaryl are optionally substituted with one to four $R_{19}$. In yet another embodiment, $R_2$ is H, $(C_1-C_3)$alkyl, $(C_1-C_6)$haloalkyl, —$NR_{12}R_{13}$, $(C_3-C_7)$carbocyclyl, 5- to 7-membered heterocyclyl comprising 1-3 heteroatoms selected from N, O, and S, $(C_6-C_{10})$aryl, or 5- or 6-membered heteroaryl comprising 1-3 heteroatoms selected from N, O, and S, wherein the alkyl is optionally substituted with one to three $R_{18}$, and the carbocyclyl, heterocyclyl, aryl and heteroaryl are optionally substituted with one to four $R_{19}$.

In another embodiment, $R_2$ is H, $(C_1-C_3)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to three $R_{18}$, and the carbocyclyl and heterocyclyl are optionally substituted with one to four $R_{19}$. In another embodiment, $R_2$ is H, $(C_1-C_6)$alkyl, or —$NR_{12}R_{13}$, wherein the alkyl is optionally substituted with one to three $R_{18}$. In another embodiment, $R_2$ is H, $(C_1-C_6)$alkyl, $(C_1-C_6)$haloalkyl, or —$NR_{12}R_{13}$. In yet another embodiment, $R_2$ is H, $(C_1-C_3)$alkyl, $(C_1-C_6)$haloalkyl, $(C_3-C_7)$carbocyclyl, 5- to 7-membered heterocyclyl comprising 1-3 heteroatoms selected from N, O, and S, wherein the alkyl is optionally substituted with one to three $R_{18}$, and the carbocyclyl and heterocyclyl are optionally substituted with one to four $R_{19}$. In another embodiment, $R_2$ is $(C_1-C_3)$alkyl optionally substituted with one to three $R_{18}$. In yet another embodiment, $R_2$ is $(C_1-C_3)$alkyl substituted with one to three $R_{18}$. In another embodiment, $R_2$ is $(C_3-C_7)$carbocyclyl or 5- to 7-membered heterocyclyl comprising 1-3 heteroatoms selected from N, O, and S, wherein the carbocyclyl and heterocyclyl are optionally substituted with one to four $R_{19}$.

In another embodiment, $R_2$ is $(C_1-C_3)$alkyl, $(C_1-C_6)$haloalkyl, $(C_3-C_7)$carbocyclyl, or 5- to 7-membered heterocyclyl comprising 1-3 heteroatoms selected from N, O, and S, wherein the alkyl is optionally substituted with one to three $R_{18}$, and the carbocyclyl and heterocyclyl are optionally substituted with one to four $R_{19}$. In another embodiment, $R_2$ is $(C_1-C_3)$alkyl, $(C_1-C_6)$haloalkyl, $(C_3-C_7)$carbocyclyl, 5- to 7-membered heterocyclyl comprising 1-3 heteroatoms selected from N, O, and S, wherein the alkyl is substituted with one to three $R_{18}$, and the carbocyclyl and heterocyclyl are optionally substituted with one to four $R_{19}$.

In some embodiments of the Formulae above, $R_3$ is H, D, $(C_1-C_4)$alkyl, $(C_1-C_4)$alkoxy, $(C_1-C_4)$haloalkyl, $(C_1-C_4)$haloalkoxy, or $(C_1-C_4)$hydroxyalkyl, wherein the alkyl is optionally substituted with one to three $R_{14}$. In another embodiment, $R_3$ is H, D, $(C_1-C_4)$alkyl, $(C_1-C_4)$haloalkyl, or $(C_1-C_4)$hydroxyalkyl, wherein the alkyl is optionally substituted with one to three $R_{14}$. In yet another embodiment, $R_3$ is H, D, $(C_1-C_4)$alkyl, or $(C_1-C_4)$haloalkyl, wherein the alkyl is optionally substituted with one to three $R_{14}$. In another embodiment, $R_3$ is H, D, or $(C_1-C_4)$alkyl optionally substituted with one to three $R_{14}$. In yet another embodiment, $R_3$ is H, D, or $(C_1-C_4)$alkyl optionally substituted with one or two $R_{14}$. In another embodiment, $R_3$ is H or $(C_1-C_4)$alkyl optionally substituted with one or two $R_{14}$. In yet another embodiment, $R_3$ is H. In another embodiment, $R_3$ is $(C_1-C_4)$alkyl optionally substituted with one or two $R_{14}$. In yet another embodiment, $R_3$ is H or $(C_1-C_4)$alkyl. In another embodiment, $R_3$ is $(C_1-C_4)$alkyl.

In some embodiments of the Formulae above, $R_4$ is H or $(C_1-C_3)$alkyl. In another embodiment, $R_4$ is $(C_1-C_3)$alkyl. In yet another embodiment, $R_4$ is H, methyl, ethyl, n-propyl, or i-propyl. In another embodiment, $R_4$ is H, methyl or ethyl. In yet another embodiment, $R_4$ is H or methyl. In another embodiment, $R_4$ is H.

In some embodiments of the Formulae above, $R_3$ and $R_4$ together with the atoms to which they are attached form a 5- or 6-membered heterocyclyl ring comprising 1-3 heteroatoms selected from N, O, and S. In another embodiment, $R_3$ and $R_4$ together with the atoms to which they are attached form a 6- or 7-membered heterocyclyl ring comprising 1-3 heteroatoms selected from N, O, and S. In yet another embodiment, $R_3$ and $R_4$ together with the atoms to which they are attached form a 5-membered heterocyclyl ring comprising 1-3 heteroatoms selected from N, O, and S. In another embodiment, $R_3$ and $R_4$ together with the atoms to which they are attached form a 7-membered heterocyclyl ring comprising 1-3 heteroatoms selected from N, O, and S. In yet another embodiment, $R_3$ and $R_4$ together with the atoms to which they are attached form a 6-membered heterocyclyl ring comprising 1-3 heteroatoms selected from N, O, and S.

In some embodiments of the Formulae above, $R_5$ is H, D, $(C_1-C_3)$alkyl, $(C_1-C_3)$alkoxy, $(C_1-C_3)$haloalkyl, $(C_1-C_3)$haloalkoxy, or $(C_1-C_3)$hydroxyalkyl, wherein the $(C_1-C_3)$alkyl is optionally substituted with one or more (i.e., one to seven) D. In another embodiment, $R_5$ is H, D, $(C_1-C_3)$alkyl, $(C_1-C_3)$haloalkyl, or $(C_1-C_3)$hydroxyalkyl, wherein the $(C_1-C_6)$alkyl is optionally substituted with one or more D. In yet another embodiment, $R_5$ is H, D, $(C_1-C_3)$alkyl, $(C_1-C_3)$alkoxy, $(C_1-C_3)$haloalkoxy, or $(C_1-C_3)$hydroxyalkyl, wherein the $(C_1-C_6)$alkyl is optionally substituted with one or more D. In another embodiment, $R_5$ is H, D, $(C_1-C_3)$alkyl, or $(C_1-C_3)$haloalkyl, wherein the $(C_1-C_6)$alkyl is optionally substituted with one or more D. In yet another embodiment, $R_5$ is H, D, or $(C_1-C_3)$alkyl. In another embodiment, $R_5$ is H or $(C_1-C_3)$alkyl. In yet another embodiment, $R_5$ is H or $(C_1-C_2)$alkyl. In another embodiment, $R_5$ is H, methyl, or ethyl. In yet another embodiment, $R_5$ is H or methyl. In another embodiment, $R_5$ is H. In yet another embodiment, $R_5$ is methyl.

In some embodiments of the Formulae above, $R_6$ is $(C_1-C_3)$alkyl, $(C_1-C_3)$alkoxy, $(C_1-C_3)$haloalkyl, $(C_1-C_3)$haloalkoxy, or $(C_1-C_3)$hydroxyalkyl, wherein the alkyl is optionally substituted with one to three substituents each independently selected from $(C_1-C_6)$alkoxy, $(C_1-C_6)$haloalkoxy, —C(O)($C_1-C_6$)alkyl, —C(O)OH, and —C(O)O($C_1-C_6$)alkyl. In another embodiment, $R_6$ is $(C_1-C_3)$alkyl, $(C_1-C_3)$alkoxy, $(C_1-C_3)$haloalkyl, $(C_1-C_3)$haloalkoxy, or $(C_1-C_3)$hydroxyalkyl, wherein the alkyl is optionally substituted with one to three substituents each independently selected from $(C_1-C_3)$alkoxy, $(C_1-C_3)$haloalkoxy, —C(O)($C_1-C_3$)alkyl, —C(O)OH, and —C(O)O($C_1-C_3$)alkyl. In yet another embodiment, $R_6$ is $(C_1-C_3)$alkyl, $(C_1-C_3)$haloalkyl, or $(C_1-C_3)$hydroxyalkyl, wherein the alkyl is optionally substituted with one to three substituents each independently selected from $(C_1-C_3)$alkoxy, $(C_1-C_3)$haloalkoxy, —C(O)($C_1-C_3$)alkyl, —C(O)OH, and —C(O)O($C_1-C_3$)alkyl. In another embodiment, $R_6$ is $(C_1-C_3)$alkyl, $(C_1-C_3)$alkoxy, $(C_1-C_3)$haloalkoxy, or $(C_1-C_3)$hydroxyalkyl, wherein the alkyl is optionally substituted with one to three substituents each independently selected from $(C_1-C_3)$alkoxy, $(C_1-C_3)$haloalkoxy, —C(O)($C_1-C_3$)alkyl, —C(O)OH, and —C(O)O($C_1-C_3$)alkyl.

In another embodiment, $R_6$ is $(C_1-C_3)$alkyl, or $(C_1-C_3)$haloalkyl, wherein the alkyl is optionally substituted with one to three substituents each independently selected from $(C_1-C_3)$alkoxy, $(C_1-C_3)$haloalkoxy, —C(O)($C_1-C_3$)alkyl, —C(O)OH, and —C(O)O($C_1-C_3$)alkyl. In yet another embodiment, $R_6$ is $(C_1-C_3)$alkyl optionally substituted with one to three substituents each independently selected from $(C_1-C_3)$alkoxy, $(C_1-C_3)$haloalkoxy, —C(O)($C_1-C_3$)alkyl, —C(O)OH, and —C(O)O($C_1-C_3$)alkyl. In another embodiment, $R_6$ is $(C_1-C_3)$alkyl substituted with one to three substituents each independently selected from $(C_1-C_3)$alkoxy, $(C_1-C_3)$haloalkoxy, —C(O)($C_1-C_3$)alkyl, —C(O)OH, and —C(O)O($C_1-C_3$)alkyl. In yet another embodiment, $R_6$ is $(C_1-C_3)$alkyl optionally substituted with one to three substituents each independently selected from $(C_1-C_3)$alkoxy, $(C_1-C_3)$haloalkoxy, —C(O)($C_1-C_3$)alkyl, and —C(O)OH. In another embodiment, $R_6$ is $(C_1-C_3)$alkyl substituted with one to three substituents each independently selected from $(C_1-C_3)$alkoxy, $(C_1-C_3)$haloalkoxy, —C(O)($C_1-C_3$)alkyl, and —C(O)OH.

In some embodiments of the Formulae above, $R_7$ is H, D, $(C_1-C_3)$alkyl, $(C_1-C_3)$alkoxy, $(C_1-C_3)$haloalkyl, $(C_1-C_3)$haloalkoxy, or $(C_1-C_3)$hydroxyalkyl, wherein the $(C_1-C_6)$alkyl is optionally substituted with one or more D. In another embodiment, $R_7$ is H, D, $(C_1-C_3)$alkyl, $(C_1-C_3)$haloalkyl, or $(C_1-C_3)$hydroxyalkyl, wherein the $(C_1-C_6)$alkyl is optionally substituted with one or more D. In yet another embodiment, $R_7$ is H, D, $(C_1-C_3)$alkyl, $(C_1-C_3)$alkoxy, $(C_1-C_3)$haloalkoxy, or $(C_1-C_3)$hydroxyalkyl, wherein the $(C_1-C_6)$alkyl is optionally substituted with one or more D. In another embodiment, $R_7$ is H, D, $(C_1-C_3)$alkyl, or $(C_1-C_3)$haloalkyl, wherein the $(C_1-C_6)$alkyl is optionally substituted with one or more D. In yet another embodiment, $R_7$ is H, D, or $(C_1-C_3)$alkyl. In another embodiment, $R_7$ is H or $(C_1-C_3)$alkyl. In yet another embodiment, $R_7$ is H or $(C_1-C_2)$alkyl. In another embodiment, $R_7$ is H, methyl, or ethyl. In yet another embodiment, $R_7$ is H or methyl. In another embodiment, $R_7$ is H. In yet another embodiment, $R_7$ is methyl.

In some embodiments of the Formulae above, $R_8$ is H, $(C_1-C_5)$alkyl, or $(C_1-C_5)$haloalkyl, wherein the alkyl is optionally substituted with one to three substituents each independently selected from $(C_3-C_7)$carbocyclyl, 4- to 7-membered heterocyclyl comprising 1-3 heteroatoms selected from N, O, and S, —$NR_{16}R_{17}$, and —C(O)$NR_{16}R_{17}$. In another embodiment, $R_8$ is H, $(C_1-C_5)$alkyl, or $(C_1-C_5)$haloalkyl, wherein the alkyl is optionally substituted with one to three substituents each independently selected from 4- to 7-membered heterocyclyl comprising 1-3 heteroatoms selected from N, O, and S, —$NR_{16}R_{17}$, and —C(O)NR$_{16}$R$_{17}$. In another embodiment, R$_8$ is H, (C$_1$-C$_5$)alkyl, or (C$_1$-C$_5$)haloalkyl, wherein the alkyl is optionally substituted with one to three substituents each independently selected from (C$_3$-C$_7$)carbocyclyl, 5- to 7-membered heterocyclyl comprising 1-3 heteroatoms selected from N, O, and S, —NR$_{16}$R$_{17}$, and —C(O)NR$_{16}$R$_{17}$. In another embodiment, R$_8$ is H, (C$_1$-C$_5$)alkyl, or (C$_1$-C$_5$)haloalkyl, wherein the alkyl is optionally substituted with one to three substituents each independently selected from 5- to 7-membered heterocyclyl comprising 1-3 heteroatoms selected from N, O, and S, —NR$_{16}$R$_{17}$, and —C(O)NR$_{16}$R$_{17}$.

In some embodiments of the Formulae above, R$_9$ is halogen, (C$_1$-C$_3$)alkyl, (C$_1$-C$_3$)alkoxy, (C$_1$-C$_3$)haloalkyl, (C$_1$-C$_3$)haloalkoxy, —OH, or CN. In another embodiment, R$_9$ is halogen, (C$_1$-C$_3$)alkyl, (C$_1$-C$_3$)haloalkyl, —OH, or CN. In yet another embodiment, R$_9$ is halogen, (C$_1$-C$_3$)alkoxy, (C$_1$-C$_3$)haloalkoxy, —OH, or CN. In another embodiment, R$_9$ is halogen, (C$_1$-C$_3$)alkyl, (C$_1$-C$_3$)haloalkyl, or (C$_1$-C$_3$)haloalkoxy. In yet another embodiment, R$_9$ is halogen, (C$_1$-C$_3$)alkyl, or (C$_1$-C$_3$)haloalkyl. In another embodiment, R$_9$ is halogen, or (C$_1$-C$_3$)alkyl. In yet another embodiment, R$_9$ is halogen or (C$_1$-C$_3$)haloalkyl. In another embodiment, R$_9$ is halogen. In yet another embodiment, R$_9$ is F, Cl or Br. In another embodiment, R$_9$ is F or Cl. In yet another embodiment, R$_9$ is F. In yet another embodiment, R$_9$ is 01.

In some embodiments of the Formulae above, R$_{10}$ is (C$_6$-C$_{10}$)aryl or 5- or 6-membered heteroaryl comprising 1-3 heteroatoms selected from N, O, and S, wherein the aryl and heteroaryl are optionally substituted with one to three R$_{22}$. In another embodiment, R$_{10}$ is phenyl or 5- or 6-membered heteroaryl comprising 1-3 heteroatoms selected from N, O, and S, wherein the phenyl and heteroaryl are optionally substituted with one to three R$_{22}$. In yet another embodiment, R$_{10}$ is (C$_6$-C$_{10}$)aryl or 5- or 6-membered heteroaryl comprising 1-3 heteroatoms selected from N, O, and S, wherein the aryl and heteroaryl are substituted with one to three R$_{22}$. In another embodiment, R$_{10}$ is phenyl or 5- or 6-membered heteroaryl comprising 1-3 heteroatoms selected from N, O, and S, wherein the phenyl and heteroaryl are substituted with one to three R$_{22}$.

In another embodiment, R$_{10}$ is (C$_6$-C$_{10}$)aryl or 5-membered heteroaryl comprising 1-3 heteroatoms selected from N, O, and S, wherein the aryl and heteroaryl are optionally substituted with one to three R$_{22}$. In another embodiment, R$_{10}$ is (C$_6$-C$_{10}$)aryl or 6-membered heteroaryl comprising 1-3 heteroatoms selected from N, O, and S, wherein the aryl and heteroaryl are optionally substituted with one to three R$_{22}$. In yet another embodiment, R$_{10}$ is (C$_6$-C$_{10}$)aryl or 5-membered heteroaryl comprising 1-3 heteroatoms selected from N, O, and S, wherein the aryl and heteroaryl are substituted with one to three R$_{22}$. In another embodiment, R$_{10}$ is (C$_6$-C$_{10}$)aryl or 6-membered heteroaryl comprising 1-3 heteroatoms selected from N, O, and S, wherein the aryl and heteroaryl are substituted with one to three R$_{22}$.

In another embodiment, R$_{10}$ is phenyl or 5-membered heteroaryl comprising 1-3 heteroatoms selected from N, O, and S, wherein the phenyl and heteroaryl are optionally substituted with one to three R$_{22}$. In yet another embodiment, R$_{10}$ is phenyl or 6-membered heteroaryl comprising 1-3 heteroatoms selected from N, O, and S, wherein the phenyl and heteroaryl are optionally substituted with one to three R$_{22}$. In another embodiment, R$_{10}$ is phenyl or 5-membered heteroaryl comprising 1-3 heteroatoms selected from N, O, and S, wherein the phenyl and heteroaryl are substituted with one to three R$_{22}$. In yet another embodiment, R$_{10}$ is phenyl or 6-membered heteroaryl comprising 1-3 heteroatoms selected from N, O, and S, wherein the phenyl and heteroaryl are substituted with one to three R$_{22}$.

In another embodiment, R$_{10}$ is (C$_6$-C$_{10}$)aryl optionally substituted with one to three R$_{22}$. In another embodiment, R$_{10}$ is (C$_6$-C$_{10}$)aryl substituted with one to three R$_{22}$. In another embodiment, R$_{10}$ is 5- or 6-membered heteroaryl comprising 1-3 heteroatoms selected from N, O, and S, optionally substituted with one to three R$_{22}$. In yet another embodiment, R$_{10}$ is 5- or 6-membered heteroaryl comprising 1-3 heteroatoms selected from N, O, and S, substituted with one to three R$_{22}$. In another embodiment, R$_{10}$ is 5-membered heteroaryl comprising 1-3 heteroatoms selected from N, O, and S, optionally substituted with one to three R$_{22}$. In yet another embodiment, R$_{10}$ is 6-membered heteroaryl comprising 1-3 heteroatoms selected from N, O, and S, optionally substituted with one to three R$_{22}$. In another embodiment, R$_{10}$ is 5-membered heteroaryl comprising 1-3 heteroatoms selected from N, O, and S, substituted with one to three R$_{22}$. In yet another embodiment, R$_{10}$ is 6-membered heteroaryl comprising 1-3 heteroatoms selected from N, O, and S, substituted with one to three R$_{22}$. In another embodiment, R$_{10}$ is phenyl or pyridinyl, wherein the phenyl and pyridinyl are optionally substituted with one to three R$_{22}$. In yet another embodiment, R$_{10}$ is phenyl or pyridinyl, wherein the phenyl and pyridinyl are substituted with one to three R$_{22}$.

In some embodiments of the Formulae above, each R$_{11}$ is independently at each occurrence halogen, (C$_1$-C$_3$)alkyl, (C$_1$-C$_3$)alkoxy, (C$_1$-C$_3$)haloalkyl, (C$_1$-C$_3$)haloalkoxy, —OH, or CN. In another embodiment, each R$_{11}$ is independently at each occurrence halogen, (C$_1$-C$_3$)alkyl, (C$_1$-C$_3$)alkoxy, (C$_1$-C$_3$)haloalkyl, or (C$_1$-C$_3$)haloalkoxy. In yet another embodiment, each R$_{11}$ is independently at each occurrence halogen, —OH, or CN. In another embodiment, each R$_{11}$ is independently at each occurrence halogen, (C$_1$-C$_3$)alkyl, or (C$_1$-C$_3$)haloalkyl. In another embodiment, each R$_{11}$ is independently at each occurrence halogen, (C$_1$-C$_3$)alkyl, (C$_1$-C$_3$)alkoxy, or (C$_1$-C$_3$)haloalkoxy. In yet another embodiment, each R$_{11}$ is independently at each occurrence halogen, (C$_1$-C$_3$)alkyl, (C$_1$-C$_3$)haloalkyl, or (C$_1$-C$_3$)haloalkoxy. In another embodiment, each R$_{11}$ is independently at each occurrence halogen, (C$_1$-C$_3$)haloalkyl, or (C$_1$-C$_3$)haloalkoxy. In yet another embodiment, each R$_{11}$ is independently at each occurrence halogen.

In some embodiments of the Formulae above, R$_{12}$ is H or (C$_1$-C$_6$)alkyl. In another embodiment, R$_{12}$ is H or (C$_1$-C$_3$)alkyl. In yet another embodiment, R$_{12}$ is H. In another embodiment, R$_{12}$ is (C$_1$-C$_3$)alkyl. In yet another embodiment, R$_{12}$ is methyl, ethyl, n-propyl, or i-propyl. In another embodiment, R$_{12}$ is methyl or ethyl. In yet another embodiment, R$_{12}$ is methyl. In some embodiments of the Formulae above, R$_{13}$ is H or (C$_1$-C$_6$)alkyl. In another embodiment, R$_{13}$ is H or (C$_1$-C$_3$)alkyl. In yet another embodiment, R$_{13}$ is H. In another embodiment, R$_{13}$ is (C$_1$-C$_3$)alkyl. In yet another embodiment, R$_{13}$ is methyl, ethyl, n-propyl, or i-propyl. In another embodiment, R$_{13}$ is methyl or ethyl. In yet another embodiment, R$_{13}$ is methyl.

In some embodiments of the Formulae above, R$_{12}$ is H and R$_{13}$ is H. In another embodiment, R$_{12}$ is H and R$_{13}$ is (C$_1$-C$_3$)alkyl. In yet another embodiment, R$_{12}$ is (C$_1$-C$_3$)alkyl and R$_{13}$ is H. In another embodiment, R$_{12}$ is (C$_1$-C$_3$)alkyl and R$_{13}$ is (C$_1$-C$_3$)alkyl. In yet another embodiment, R$_{12}$ is methyl and R$_{13}$ is methyl.

In some embodiments of the Formulae above, each R$_{14}$ is independently at each occurrence D, —NR$_{15}$R$_{15'}$, (C$_3$-C$_7$)carbocyclyl, or 3- to 7-membered heterocyclyl comprising 1-3 heteroatoms selected from N, O, and S, wherein the carbocyclyl and heterocyclyl are optionally substituted with one to three substituents each independently selected from halogen, $(C_1-C_6)$alkyl, $(C_1-C_6)$alkoxy, $(C_1-C_6)$haloalkyl, and $(C_1-C_6)$haloalkoxy. In another embodiment, each $R_{14}$ is independently at each occurrence D, —$NR_{15}R_{15'}$, $(C_3-C_7)$carbocyclyl, or 3- to 7-membered heterocyclyl comprising 1-3 heteroatoms selected from N, O, and S, wherein the carbocyclyl and heterocyclyl are optionally substituted with one to three substituents each independently selected from halogen, $(C_1-C_3)$alkyl, $(C_1-C_3)$alkoxy, $(C_1-C_3)$haloalkyl, and $(C_1-C_3)$haloalkoxy. In yet another embodiment, each $R_{14}$ is independently at each occurrence —$NR_{15}R_{15'}$, $(C_3-C_7)$carbocyclyl, or 3- to 7-membered heterocyclyl comprising 1-3 heteroatoms selected from N, O, and S, wherein the carbocyclyl and heterocyclyl are optionally substituted with one to three substituents each independently selected from halogen, $(C_1-C_3)$alkyl, $(C_1-C_3)$alkoxy, $(C_1-C_3)$haloalkyl, and $(C_1-C_3)$haloalkoxy.

In another embodiment, each $R_{14}$ is independently at each occurrence —$NR_{15}R_{15'}$ or $(C_3-C_7)$carbocyclyl optionally substituted with one to three substituents each independently selected from halogen, $(C_1-C_3)$alkyl, $(C_1-C_3)$alkoxy, $(C_1-C_3)$haloalkyl, and $(C_1-C_3)$haloalkoxy. In yet another embodiment, each $R_{14}$ is independently at each occurrence —$NR_{15}R_{15'}$ or $(C_3-C_7)$carbocyclyl optionally substituted with one to three substituents each independently selected from halogen, $(C_1-C_3)$alkyl, and $(C_1-C_3)$haloalkyl. In another embodiment, each $R_{14}$ is independently at each occurrence —$NR_{15}R_{15'}$ or $(C_3-C_7)$carbocyclyl optionally substituted with one to three $(C_1-C_3)$alkyl.

In some embodiments of the Formulae above, $R_{15}$ is H or $(C_1-C_6)$alkyl. In another embodiment, $R_{15}$ is H or $(C_1-C_3)$alkyl. In yet another embodiment, $R_{15}$ is H. In another embodiment, $R_{15}$ is $(C_1-C_3)$alkyl. In yet another embodiment, $R_{15}$ is methyl, ethyl, n-propyl, or i-propyl. In another embodiment, $R_{15}$ is methyl or ethyl. In yet another embodiment, $R_{15}$ is methyl.

In some embodiments of the Formulae above, $R_{15'}$ is H or $(C_1-C_6)$alkyl. In another embodiment, $R_{15'}$ is H or $(C_1-C_3)$alkyl. In yet another embodiment, $R_{15'}$ is H. In another embodiment, $R_{15'}$ is $(C_1-C_3)$alkyl. In yet another embodiment, $R_{15'}$ is methyl, ethyl, n-propyl, or i-propyl. In another embodiment, $R_{15'}$ is methyl or ethyl. In yet another embodiment, $R_{15'}$ is methyl.

In some embodiments of the Formulae above, $R_{15}$ is H and $R_{15'}$ is H. In another embodiment, $R_{15}$ is H and $R_{15'}$ is $(C_1-C_3)$alkyl. In yet another embodiment, $R_{15}$ is $(C_1-C_3)$alkyl and $R_{15'}$ is H. In another embodiment, $R_{15}$ is $(C_1-C_3)$alkyl and $R_{15'}$ is $(C_1-C_3)$alkyl. In yet another embodiment, $R_{15}$ is methyl and $R_{15'}$ is methyl.

In some embodiments of the Formulae above, $R_{16}$ is H or $(C_1-C_3)$alkyl. In another embodiment, $R_{16}$ is H. In another embodiment, $R_{16}$ is $(C_1-C_3)$alkyl. In yet another embodiment, $R_{16}$ is H, methyl, ethyl, n-propyl, or i-propyl. In another embodiment, $R_{16}$ is methyl, ethyl, n-propyl, or i-propyl. In yet another embodiment, $R_{16}$ is H, methyl or ethyl. In another embodiment, $R_{16}$ is methyl or ethyl. In yet another embodiment, $R_{16}$ is H or methyl. In another embodiment, $R_{16}$ is methyl. In yet another embodiment, $R_{16}$ is H or $(C_1-C_3)$alkyl; or $R_{16}$ and $R_{17}$ together with the nitrogen atom to which they are attached form a 4- to 7-membered heterocyclyl ring comprising 1-2 additional heteroatoms selected from N, O, and S. In yet another embodiment, $R_{16}$ is H or $(C_1-C_3)$alkyl; or $R_{16}$ and $R_{17}$ together with the nitrogen atom to which they are attached form a 4- to 7-membered heterocyclyl ring optionally comprising 1-2 additional heteroatoms selected from N, O, and S.

In some embodiments of the Formulae above, $R_{17}$ is H or $(C_1-C_3)$alkyl. In another embodiment, $R_{17}$ is H. In another embodiment, $R_{17}$ is $(C_1-C_3)$alkyl. In yet another embodiment, $R_{17}$ is H, methyl, ethyl, n-propyl, or i-propyl. In another embodiment, $R_{17}$ is methyl, ethyl, n-propyl, or i-propyl. In yet another embodiment, $R_{17}$ is H, methyl or ethyl. In another embodiment, $R_{17}$ is methyl or ethyl. In yet another embodiment, $R_{17}$ is H or methyl. In another embodiment, $R_{17}$ is methyl.

In some embodiments of the Formulae above, $R_{16}$ and $R_{17}$ together with the nitrogen atom to which they are attached form a 4- to 7-membered heterocyclyl ring comprising 1-2 additional heteroatoms selected from N, O, and S. In another embodiment, $R_{16}$ and $R_{17}$ together with the nitrogen atom to which they are attached form a 4- to 6-membered heterocyclyl ring comprising 1-2 additional heteroatoms selected from N, O, and S. In yet another embodiment, $R_{16}$ and $R_{17}$ together with the nitrogen atom to which they are attached form a 4- or 5-membered heterocyclyl ring comprising 1-2 additional heteroatoms selected from N, O, and S.

In some embodiments of the Formulae above, $R_{16}$ and $R_{17}$ together with the nitrogen atom to which they are attached form a 4- to 7-membered heterocyclyl ring optionally comprising 1-2 additional heteroatoms selected from N, O, and S. In another embodiment, $R_{16}$ and $R_{17}$ together with the nitrogen atom to which they are attached form a 4- to 6-membered heterocyclyl ring optionally comprising 1-2 additional heteroatoms selected from N, O, and S. In yet another embodiment, $R_{16}$ and $R_{17}$ together with the nitrogen atom to which they are attached form a 4- or 5-membered heterocyclyl ring optionally comprising 1-2 additional heteroatoms selected from N, O, and S.

In some embodiments of the Formulae above, each $R_{18}$ is independently at each occurrence $(C_3-C_7)$carbocyclyl, 5- to 7-membered heterocyclyl comprising 1-3 heteroatoms selected from N, O, and S, $(C_6-C_{10})$aryl, or 5- or 6-membered heteroaryl comprising 1-3 heteroatoms selected from N, O, and S, wherein the carbocyclyl, heterocyclyl, aryl and heteroaryl are optionally substituted with one to four $R_{20}$. In another embodiment, each $R_{18}$ is independently at each occurrence $(C_3-C_7)$carbocyclyl or 5- to 7-membered heterocyclyl, wherein the carbocyclyl and heterocyclyl are optionally substituted with one to four $R_{20}$. In yet another embodiment, each $R_{18}$ is independently at each occurrence $(C_3-C_7)$carbocyclyl or $(C_6-C_{10})$aryl, wherein the carbocyclyl and aryl are optionally substituted with one to four $R_{20}$. In another embodiment, each $R_{18}$ is independently at each occurrence 5- to 7-membered heterocyclyl comprising 1-3 heteroatoms selected from N, O, and S or 5- or 6-membered heteroaryl comprising 1-3 heteroatoms selected from N, O, and S, wherein the heterocyclyl and heteroaryl are optionally substituted with one to four $R_{20}$.

In another embodiment, each $R_{18}$ is independently at each occurrence $(C_6-C_{10})$aryl or 5- or 6-membered heteroaryl comprising 1-3 heteroatoms selected from N, O, and S, wherein the aryl and heteroaryl are substituted with one to three $R_{20}$. In yet another embodiment, each $R_{18}$ is independently at each occurrence phenyl or 5- or 6-membered heteroaryl comprising 1-3 heteroatoms selected from N, O, and S, wherein the phenyl and heteroaryl are substituted with one to three $R_{20}$. In another embodiment, each $R_{18}$ is independently at each occurrence $(C_6-C_{10})$aryl or 5- or 6-membered heteroaryl comprising 1-3 heteroatoms selected from N, O, and S, wherein the aryl and heteroaryl are optionally substituted with one to three $R_{20}$. In yet another embodiment, each $R_{18}$ is independently at each occurrence phenyl or 5- or 6-membered heteroaryl comprising 1-3 heteroatoms selected from N, O, and S, wherein the phenyl and heteroaryl are optionally substituted with one to three $R_{20}$.

In some embodiments of the Formulae above, $R_{19}$ is halogen, $(C_1-C_3)$alkyl, $(C_1-C_3)$alkoxy, $(C_1-C_3)$haloalkyl, $(C_1-C_3)$haloalkoxy, —OH, or CN. In another embodiment, $R_{19}$ is halogen, $(C_1-C_3)$alkyl, $(C_1-C_3)$alkoxy, $(C_1-C_3)$haloalkyl, or $(C_1-C_3)$haloalkoxy. In another embodiment, $R_{19}$ is halogen, $(C_1-C_3)$alkyl, $(C_1-C_3)$haloalkyl, —OH, or CN. In another embodiment, $R_{19}$ is halogen, $(C_1-C_3)$alkyl, $(C_1-C_3)$alkoxy, $(C_1-C_3)$haloalkyl, $(C_1-C_3)$haloalkoxy, or —OH. In another embodiment, $R_{19}$ is halogen, $(C_1-C_3)$alkyl, $(C_1-C_3)$alkoxy, $(C_1-C_3)$haloalkyl, $(C_1-C_3)$haloalkoxy, or CN. In another embodiment, $R_{19}$ is halogen, $(C_1-C_3)$alkyl, $(C_1-C_3)$alkoxy, $(C_1-C_3)$haloalkyl, —OH, or CN. In another embodiment, $R_{19}$ is halogen, $(C_1-C_3)$alkyl, $(C_1-C_3)$alkoxy, $(C_1-C_3)$haloalkoxy, —OH, or CN. In another embodiment, $R_{19}$ is halogen, $(C_1-C_3)$alkyl, $(C_1-C_3)$haloalkyl, $(C_1-C_3)$haloalkoxy, —OH, or CN. In another embodiment, $R_{19}$ is halogen, $(C_1-C_3)$alkyl, or $(C_1-C_3)$haloalkyl. In another embodiment, $R_{19}$ is halogen or $(C_1-C_3)$alkyl.

In some embodiments of the Formulae above, two $R_{19}$ together, when on adjacent atoms, form a $(C_6-C_{10})$aryl or 5- or 6-membered heteroaryl ring comprising 1-3 heteroatoms selected from N, O, and S, wherein the aryl and heteroaryl are optionally substituted with one or more substituents each independently selected from halogen, $(C_1-C_6)$alkyl, $(C_1-C_6)$alkoxy, $(C_1-C_6)$haloalkyl, $(C_1-C_6)$haloalkoxy, —OH, and CN. In another embodiment, two $R_{19}$ together, when on adjacent atoms, form a $(C_6-C_{10})$aryl optionally substituted with one or more substituents each independently selected from halogen, $(C_1-C_6)$alkyl, $(C_1-C_6)$alkoxy, $(C_1-C_6)$haloalkyl, $(C_1-C_6)$haloalkoxy, —OH, and CN. In yet another embodiment, two $R_{19}$ together, when on adjacent atoms, form a 5- or 6-membered heteroaryl ring comprising 1-3 heteroatoms selected from N, O, and S, optionally substituted with one or more substituents each independently selected from halogen, $(C_1-C_6)$alkyl, $(C_1-C_6)$alkoxy, $(C_1-C_6)$haloalkyl, $(C_1-C_6)$haloalkoxy, —OH, and CN. In another embodiment, two $R_{19}$ together, when on adjacent atoms, form a phenyl or 5- or 6-membered heteroaryl ring comprising 1-3 heteroatoms selected from N, O, and S, wherein the phenyl and heteroaryl are optionally substituted with one or more substituents each independently selected from halogen, $(C_1-C_6)$alkyl, $(C_1-C_6)$alkoxy, $(C_1-C_6)$haloalkyl, $(C_1-C_6)$haloalkoxy, —OH, and CN.

In another embodiment, two $R_{19}$ together, when on adjacent atoms, form a phenyl optionally substituted with one or more substituents each independently selected from halogen, $(C_1-C_6)$alkyl, $(C_1-C_6)$alkoxy, $(C_1-C_6)$haloalkyl, $(C_1-C_6)$haloalkoxy, —OH, and CN. In yet another embodiment, two $R_{19}$ together, when on adjacent atoms, together form a 5-membered heteroaryl ring comprising 1-3 heteroatoms selected from N, O, and S, optionally substituted with one or more substituents each independently selected from halogen, $(C_1-C_6)$alkyl, $(C_1-C_6)$alkoxy, $(C_1-C_6)$haloalkyl, $(C_1-C_6)$haloalkoxy, —OH, and CN. In another embodiment, two $R_{19}$ together, when on adjacent atoms, a 6-membered heteroaryl ring comprising 1-3 heteroatoms selected from N, O, and S, optionally substituted with one or more substituents each independently selected from halogen, $(C_1-C_6)$alkyl, $(C_1-C_6)$alkoxy, $(C_1-C_6)$haloalkyl, $(C_1-C_6)$haloalkoxy, —OH, and CN.

In some embodiments of the Formulae above, each $R_{20}$ is independently at each occurrence halogen, $(C_1-C_3)$alkyl, $(C_1-C_3)$alkoxy, $(C_1-C_3)$haloalkyl, $(C_1-C_3)$haloalkoxy, oxo, —OH, or CN. In another embodiment, each $R_{20}$ is independently at each occurrence halogen, $(C_1-C_3)$alkyl, $(C_1-C_3)$haloalkyl, oxo —OH, or CN. In yet another embodiment, each $R_{20}$ is independently at each occurrence halogen, $(C_1-C_3)$alkyl, $(C_1-C_3)$alkoxy, $(C_1-C_3)$haloalkyl, or $(C_1-C_3)$haloalkoxy. In another embodiment, each $R_{20}$ is independently at each occurrence halogen, $(C_1-C_3)$alkyl, oxo, —OH, or CN. In yet another embodiment, each $R_{20}$ is independently at each occurrence halogen, $(C_1-C_3)$alkyl, $(C_1-C_3)$alkoxy, —OH, or CN. In another embodiment, each $R_{20}$ is independently at each occurrence halogen, $(C_1-C_3)$alkyl, $(C_1-C_3)$alkoxy, $(C_1-C_3)$haloalkoxy, —OH, or CN. In yet another embodiment, each $R_{20}$ is independently at each occurrence halogen, $(C_1-C_3)$alkyl, $(C_1-C_3)$alkoxy, $(C_1-C_3)$haloalkyl, or $(C_1-C_3)$haloalkoxy.

In another embodiment, each $R_{20}$ is independently at each occurrence halogen, $(C_1-C_3)$alkyl, or $(C_1-C_3)$haloalkyl. In yet another embodiment, each $R_{20}$ is independently at each occurrence halogen, $(C_1-C_3)$alkyl, $(C_1-C_3)$alkoxy. In another embodiment, each $R_{20}$ is independently at each occurrence halogen, $(C_1-C_3)$alkyl, $(C_1-C_3)$alkoxy, or $(C_1-C_3)$haloalkoxy. In yet another embodiment, each $R_{20}$ is independently at each occurrence halogen, $(C_1-C_3)$alkyl, or oxo. In another embodiment, each $R_{20}$ is independently at each occurrence halogen or $(C_1-C_3)$alkyl. In yet another embodiment, each $R_{20}$ is independently at each occurrence $(C_1-C_3)$alkyl, $(C_1-C_3)$alkoxy, $(C_1-C_3)$haloalkyl, or $(C_1-C_3)$haloalkoxy. In another embodiment, each $R_{20}$ is independently at each occurrence $(C_1-C_3)$alkyl or $(C_1-C_3)$haloalkyl.

In some embodiments of the Formulae above, each $R_{20}$ is independently at each occurrence halogen, $(C_1-C_3)$alkyl, or oxo; or when $R_{18}$ is a carbocyclyl or a heterocyclyl, two $R_{20}$, when attached to the same carbon atom, together form =(O). In another embodiment, each $R_{20}$ is independently at each occurrence halogen or $(C_1-C_3)$alkyl; or when $R_{18}$ is a carbocyclyl or a heterocyclyl, two $R_{20}$, when attached to the same carbon atom, together form =(O). In some embodiments of the Formulae above, when $R_{18}$ is a carbocyclyl or a heterocyclyl, two $R_{20}$, when attached to the same carbon atom, together form =(O). In another embodiment, when $R_{18}$ is a carbocyclyl, two $R_{20}$, when attached to the same carbon atom, together form =(O). In another embodiment, when $R_{18}$ is a heterocyclyl, two $R_{20}$, when attached to the same carbon atom, together form =(O). In another embodiment, $R_{18}$ is carbocyclyl or heterocyclyl substituted with one to three $R_{20}$, and two $R_{20}$, when attached to the same carbon atom, together form =(O). In another embodiment, $R_{18}$ is carbocyclyl substituted with one to three $R_{20}$, and two $R_{20}$, when attached to the same carbon atom, together form =(O). In another embodiment, $R_{18}$ is heterocyclyl substituted with one to three $R_{20}$, and two $R_{20}$, when attached to the same carbon atom, together form =(O).

In some embodiments of the Formulae above, $R_{21}$ is H or $(C_1-C_3)$alkyl. In another embodiment, $R_{21}$ is H. In another embodiment, $R_{21}$ is $(C_1-C_3)$alkyl. In yet another embodiment, $R_{21}$ is H, methyl, ethyl, n-propyl, or i-propyl. In another embodiment, $R_{21}$ is methyl, ethyl, n-propyl, or i-propyl. In yet another embodiment, $R_{21}$ is H, methyl or ethyl. In another embodiment, $R_{21}$ is methyl or ethyl. In yet another embodiment, $R_{21}$ is H or methyl. In another embodiment, $R_{21}$ is methyl.

In some embodiments of the Formulae above, each $R_{22}$ is independently at each occurrence halogen, $(C_1-C_3)$alkyl, $(C_1-C_3)$alkoxy, $(C_1-C_3)$haloalkyl, $(C_1-C_3)$haloalkoxy, —OH, CN, $(C_6-C_{10})$aryl, or 5- or 6-membered heteroaryl comprising 1-3 heteroatoms selected from N, O, and S, wherein the aryl and heteroaryl are optionally substituted with one to three $R_{23}$. In another embodiment, each $R_{22}$ is independently at each occurrence halogen, $(C_1$-$C_3)$alkyl, $(C_1$-$C_3)$alkoxy, $(C_1$-$C_3)$haloalkyl, $(C_1$-$C_3)$haloalkoxy, $(C_6$-$C_{10})$aryl, or 5- or 6-membered heteroaryl comprising 1-3 heteroatoms selected from N, O, and S, wherein the aryl and heteroaryl are optionally substituted with one to three $R_{23}$. In yet another embodiment, each $R_{22}$ is independently at each occurrence halogen, $(C_1$-$C_3)$alkyl, $(C_1$-$C_3)$haloalkyl, —OH, CN, $(C_6$-$C_{10})$aryl, or 5- or 6-membered heteroaryl comprising 1-3 heteroatoms selected from N, O, and S, wherein the aryl and heteroaryl are optionally substituted with one to three $R_{23}$. In another embodiment, each $R_{22}$ is independently at each occurrence halogen, $(C_1$-$C_3)$alkyl, $(C_1$-$C_3)$alkoxy, $(C_1$-$C_3)$haloalkoxy, —OH, CN, $(C_6$-$C_{10})$aryl, or 5- or 6-membered heteroaryl comprising 1-3 heteroatoms selected from N, O, and S, wherein the aryl and heteroaryl are optionally substituted with one to three $R_{23}$.

In another embodiment, each $R_{22}$ is independently at each occurrence halogen, $(C_1$-$C_3)$alkyl, $(C_1$-$C_3)$haloalkyl, $(C_6$-$C_{10})$aryl, or 5- or 6-membered heteroaryl comprising 1-3 heteroatoms selected from N, O, and S, wherein the aryl and heteroaryl are optionally substituted with one to three $R_{23}$. In yet another embodiment, each $R_{22}$ is independently at each occurrence halogen, $(C_1$-$C_3)$alkyl, $(C_1$-$C_3)$alkoxy, $(C_1$-$C_3)$haloalkoxy, $(C_6$-$C_{10})$aryl, or 5- or 6-membered heteroaryl comprising 1-3 heteroatoms selected from N, O, and S, wherein the aryl and heteroaryl are optionally substituted with one to three $R_{23}$. In another embodiment, each $R_{22}$ is independently at each occurrence halogen, $(C_1$-$C_3)$alkyl, $(C_6$-$C_{10})$aryl, or 5- or 6-membered heteroaryl comprising 1-3 heteroatoms selected from N, O, and S, wherein the aryl and heteroaryl are optionally substituted with one to three $R_{23}$. In yet another embodiment, each $R_{22}$ is independently at each occurrence halogen, $(C_1$-$C_3)$alkyl, or $(C_6$-$C_{10})$aryl optionally substituted with one to three $R_{23}$. In yet another embodiment, each $R_{22}$ is independently at each occurrence halogen, $(C_1$-$C_3)$alkyl, or 5- or 6-membered heteroaryl comprising 1-3 heteroatoms selected from N, O, and S optionally substituted with one to three $R_{23}$. In another embodiment, each $R_{22}$ is independently at each occurrence halogen, $(C_1$-$C_3)$alkyl, or 5- or 6-membered heteroaryl comprising 1-3 heteroatoms selected from N, O, and S optionally substituted with one to three $R_{23}$.

In another embodiment, each $R_{22}$ is independently at each occurrence halogen, $(C_1$-$C_3)$alkyl, or 5-membered heteroaryl comprising 1-3 heteroatoms selected from N, O, and S optionally substituted with one to three $R_{23}$. In yet another embodiment, each $R_{22}$ is independently at each occurrence halogen, $(C_1$-$C_3)$alkyl, or 6-membered heteroaryl comprising 1-3 heteroatoms selected from N, O, and S optionally substituted with one to three $R_{23}$. In another embodiment, each $R_{22}$ is independently at each occurrence halogen, $(C_1$-$C_3)$alkyl, or 5-membered heteroaryl comprising 1-3 heteroatoms selected from N, O, and S substituted with one to three $R_{23}$. In yet another embodiment, each $R_{22}$ is independently at each occurrence halogen, $(C_1$-$C_3)$alkyl, or 6-membered heteroaryl comprising 1-3 heteroatoms selected from N, O, and S substituted with one to three $R_{23}$. In another embodiment, each $R_{22}$ is independently at each occurrence halogen, $(C_1$-$C_3)$alkyl, or imidazolyl optionally substituted with one to three $R_{23}$. In yet another embodiment, each $R_{22}$ is independently at each occurrence halogen, $(C_1$-$C_3)$alkyl, or imidazolyl substituted with one to three $R_{23}$.

In some embodiments of the Formulae above, each $R_{23}$ is independently at each occurrence halogen, $(C_1$-$C_3)$alkyl, $(C_1$-$C_3)$alkoxy, $(C_1$-$C_3)$haloalkyl, $(C_1$-$C_3)$haloalkoxy, —$CH_2(OCH_2CH_2)_{1-3}OCH_2CH_3$, —OH, CN, or 4- to 7-membered heterocyclyl comprising 1-3 heteroatoms selected from N, O, and S, wherein the heterocyclyl is optionally substituted with one to three substituents each independently selected from halogen, $(C_1$-$C_6)$alkyl, $(C_1$-$C_6)$alkoxy, $(C_1$-$C_6)$haloalkyl, $(C_1$-$C_6)$haloalkoxy, —OH, —$C(O)R_{24}R_{25}$, —$NR_{24}C(O)R_{25}$, —$NH_2$, —$NH(C_1$-$C_6)$alkyl, and —$N((C_1$-$C_6)$alkyl$)_2$, and the alkyl is optionally substituted with —$NR_{24}R_{25}$ or a 4- to 7-membered heterocyclyl comprising 1-3 heteroatoms selected from N, O, and S optionally substituted with one to three substituents each independently selected from halogen, $(C_1$-$C_6)$alkyl, $(C_1$-$C_6)$alkoxy, $(C_1$-$C_6)$haloalkyl, $(C_1$-$C_6)$haloalkoxy, —OH, —$NH_2$, —$NH(C_1$-$C_6)$alkyl, and —$N((C_1$-$C_6)$alkyl$)_2$.

In another embodiment, each $R_{23}$ is independently at each occurrence halogen, $(C_1$-$C_3)$alkyl, $(C_1$-$C_3)$alkoxy, $(C_1$-$C_3)$haloalkyl, $(C_1$-$C_3)$haloalkoxy, —OH, CN, or 4- to 7-membered heterocyclyl comprising 1-3 heteroatoms selected from N, O, and S, wherein the heterocyclyl is substituted with one to three substituents each independently selected from halogen, $(C_1$-$C_6)$alkyl, $(C_1$-$C_6)$alkoxy, $(C_1$-$C_6)$haloalkyl, $(C_1$-$C_6)$haloalkoxy, —OH, —$C(O)R_{24}R_{25}$, —$NR_{24}C(O)R_{25}$, —$NH_2$, —$NH(C_1$-$C_6)$alkyl, and —$N((C_1$-$C_6)$alkyl$)_2$, and the alkyl is optionally substituted with —$NR_{24}R_{25}$ or a 4- to 7-membered heterocyclyl comprising 1-3 heteroatoms selected from N, O, and S optionally substituted with one to three substituents each independently selected from halogen, $(C_1$-$C_6)$alkyl, $(C_1$-$C_6)$alkoxy, $(C_1$-$C_6)$haloalkyl, $(C_1$-$C_6)$haloalkoxy, —OH, —$NH_2$, —$NH(C_1$-$C_6)$alkyl, and —$N((C_1$-$C_6)$alkyl$)_2$.

In another embodiment, each $R_{23}$ is independently at each occurrence halogen, $(C_1$-$C_3)$alkyl, $(C_1$-$C_3)$haloalkyl, —$CH_2(OCH_2CH_2)_{1-3}OCH_2CH_3$, —OH, CN, or 4- to 7-membered heterocyclyl comprising 1-3 heteroatoms selected from N, O, and S, wherein the heterocyclyl is optionally substituted with one to three substituents each independently selected from halogen, $(C_1$-$C_6)$alkyl, $(C_1$-$C_6)$alkoxy, $(C_1$-$C_6)$haloalkyl, $(C_1$-$C_6)$haloalkoxy, —OH, —$C(O)R_{24}R_{25}$, —$NR_{24}C(O)R_{25}$, —$NH_2$, —$NH(C_1$-$C_6)$alkyl, and —$N((C_1$-$C_6)$alkyl$)_2$, and the alkyl is optionally substituted with —$NR_{24}R_{25}$ or a 4- to 7-membered heterocyclyl comprising 1-3 heteroatoms selected from N, O, and S optionally substituted with one to three substituents each independently selected from halogen, $(C_1$-$C_6)$alkyl, $(C_1$-$C_6)$alkoxy, $(C_1$-$C_6)$haloalkyl, $(C_1$-$C_6)$haloalkoxy, —OH, —$NH_2$, —$NH(C_1$-$C_6)$alkyl, and —$N((C_1$-$C_6)$alkyl$)_2$.

In another embodiment, each $R_{23}$ is independently at each occurrence halogen, $(C_1$-$C_3)$alkyl, $(C_1$-$C_3)$haloalkyl, —OH, CN, or 4- to 7-membered heterocyclyl comprising 1-3 heteroatoms selected from N, O, and S, wherein the heterocyclyl is optionally substituted with one to three substituents each independently selected from halogen, $(C_1$-$C_6)$alkyl, $(C_1$-$C_6)$alkoxy, $(C_1$-$C_6)$haloalkyl, $(C_1$-$C_6)$haloalkoxy, —OH, —$C(O)R_{24}R_{25}$, —$NR_{24}C(O)R_{25}$, —$NH_2$, —$NH(C_1$-$C_6)$alkyl, and —$N((C_1$-$C_6)$alkyl$)_2$, and the alkyl is optionally substituted with —$NR_{24}R_{25}$ or a 4- to 7-membered heterocyclyl comprising 1-3 heteroatoms selected from N, O, and S optionally substituted with one to three substituents each independently selected from halogen, $(C_1$-$C_6)$alkyl, $(C_1$-$C_6)$alkoxy, $(C_1$-$C_6)$haloalkyl, $(C_1$-$C_6)$haloalkoxy, —OH, —$NH_2$, —$NH(C_1$-$C_6)$alkyl, and —$N((C_1$-$C_6)$alkyl$)_2$.

In another embodiment, each $R_{23}$ is independently at each occurrence halogen, $(C_1$-$C_3)$alkyl, $(C_1$-$C_3)$alkoxy, $(C_1$-$C_3)$haloalkyl, $(C_1$-$C_3)$haloalkoxy, or 4- to 7-membered heterocyclyl comprising 1-3 heteroatoms selected from N, O, and S, wherein the heterocyclyl is optionally substituted with one to three substituents each independently selected from halogen, $(C_1$-$C_6)$alkyl, $(C_1$-$C_6)$alkoxy, $(C_1$-$C_6)$haloalkyl, $(C_1-C_6)$haloalkoxy, —OH, —C(O)$R_{24}R_{25}$, —$NR_{24}$C(O) $R_{25}$, —$NH_2$, —NH($C_1-C_6$)alkyl, and —N(($C_1-C_6$)alkyl)$_2$, and the alkyl is optionally substituted with —$NR_{24}R_{25}$ or a 4- to 7-membered heterocyclyl comprising 1-3 heteroatoms selected from N, O, and S optionally substituted with one to three substituents each independently selected from halogen, ($C_1-C_6$)alkyl, ($C_1-C_6$)alkoxy, ($C_1-C_6$)haloalkyl, ($C_1-C_6$)haloalkoxy, —OH, —$NH_2$, —NH($C_1-C_6$)alkyl, and —N(($C_1-C_6$)alkyl)$_2$.

In another embodiment, each $R_{23}$ is independently at each occurrence halogen, ($C_1-C_3$)alkyl, or 4- to 7-membered heterocyclyl comprising 1-3 heteroatoms selected from N, O, and S, wherein the heterocyclyl is optionally substituted with one to three substituents each independently selected from halogen, ($C_1-C_6$)alkyl, ($C_1-C_6$)alkoxy, ($C_1-C_6$)haloalkyl, ($C_1-C_6$)haloalkoxy, —OH, —C(O)$R_{24}R_{25}$, —$NR_{24}$C(O)$R_{25}$, —$NH_2$, —NH($C_1-C_6$)alkyl, and —N(($C_1-C_6$)alkyl)$_2$, and the alkyl is optionally substituted with —$NR_{24}R_{25}$ or a 4- to 7-membered heterocyclyl comprising 1-3 heteroatoms selected from N, O, and S optionally substituted with one to three substituents each independently selected from halogen, ($C_1-C_6$)alkyl, ($C_1-C_6$)alkoxy, ($C_1-C_6$)haloalkyl, ($C_1-C_6$)haloalkoxy, —OH, —$NH_2$, —NH($C_1-C_6$)alkyl, and —N(($C_1-C_6$)alkyl)$_2$. In yet another embodiment, each $R_{23}$ is independently at each occurrence ($C_1-C_3$)alkyl or 4- to 7-membered heterocyclyl comprising 1-3 heteroatoms selected from N, O, and S, wherein the heterocyclyl is optionally substituted with one to three substituents each independently selected from halogen, ($C_1-C_6$)alkyl, ($C_1-C_6$)alkoxy, ($C_1-C_6$)haloalkyl, ($C_1-C_6$)haloalkoxy, —OH, —C(O)$R_{24}R_{25}$, —$NR_{24}$C(O)$R_{25}$, —$NH_2$, —NH($C_1-C_6$)alkyl, and —N(($C_1-C_6$)alkyl)$_2$, and the alkyl is optionally substituted with —$NR_{24}R_{25}$ or a 4- to 7-membered heterocyclyl comprising 1-3 heteroatoms selected from N, O, and S optionally substituted with one to three substituents each independently selected from halogen, ($C_1-C_6$)alkyl, ($C_1-C_6$)alkoxy, ($C_1-C_6$)haloalkyl, ($C_1-C_6$)haloalkoxy, —OH, —$NH_2$, —NH($C_1-C_6$)alkyl, and —N(($C_1-C_6$)alkyl)$_2$.

In another embodiment, each $R_{23}$ is independently at each occurrence ($C_1-C_3$)alkyl or 4- to 7-membered heterocyclyl comprising 1-3 heteroatoms selected from N, O, and S, wherein the heterocyclyl is substituted with one to three substituents each independently selected from halogen, ($C_1-C_6$)alkyl, ($C_1-C_6$)alkoxy, ($C_1-C_6$)haloalkyl, ($C_1-C_6$)haloalkoxy, —OH, —C(O)$R_{24}R_{25}$, —$NR_{24}$C(O)$R_{26}$, —$NH_2$, —NH($C_1-C_6$)alkyl, and —N(($C_1-C_6$)alkyl)$_2$, and the alkyl is optionally substituted with —$NR_{24}R_{25}$ or a 4- to 7-membered heterocyclyl comprising 1-3 heteroatoms selected from N, O, and S optionally substituted with one to three substituents each independently selected from halogen, ($C_1-C_6$)alkyl, ($C_1-C_6$)alkoxy, ($C_1-C_6$)haloalkyl, ($C_1-C_6$)haloalkoxy, —OH, —$NH_2$, —NH($C_1-C_6$)alkyl, and —N(($C_1-C_6$)alkyl)$_2$. In yet another embodiment, each $R_{23}$ is independently at each occurrence ($C_1-C_3$)alkyl or 4- to 7-membered heterocyclyl comprising 1-3 heteroatoms selected from N, O, and S, wherein the heterocyclyl is optionally substituted with one to three substituents each independently selected from ($C_1-C_6$)alkyl, ($C_1-C_6$)haloalkyl, —OH, —C(O) $R_{24}R_{25}$, —$NR_{24}$C(O)$R_{25}$, —$NH_2$, —NH($C_1-C_6$)alkyl, and —N(($C_1-C_6$)alkyl)$_2$, and the alkyl is optionally substituted with —$NR_{24}R_{25}$ or a 4- to 7-membered heterocyclyl comprising 1-3 heteroatoms selected from N, O, and S optionally substituted with one to three substituents each independently selected from halogen, ($C_1-C_6$)alkyl, ($C_1-C_6$)haloalkyl, —OH, —$NH_2$, —NH($C_1-C_6$) alkyl, and —N(($C_1-C_6$)alkyl)$_2$.

In another embodiment, each $R_{23}$ is independently at each occurrence ($C_1-C_3$)alkyl or 4- to 7-membered heterocyclyl comprising 1-3 heteroatoms selected from N, O, and S, wherein the heterocyclyl is optionally substituted with one to three substituents each independently selected from ($C_1-C_6$)alkyl, ($C_1-C_6$)haloalkyl, —OH, —$NH_2$, —NH($C_1-C_6$) alkyl, and —N(($C_1-C_6$)alkyl)$_2$, and the alkyl is optionally substituted with —$NR_{24}R_{25}$ or a 4- to 7-membered heterocyclyl comprising 1-3 heteroatoms selected from N, O, and S optionally substituted with one to three substituents each independently selected from ($C_1-C_6$)alkyl, ($C_1-C_6$)haloalkyl, —OH, —$NH_2$, —NH($C_1-C_6$)alkyl, and —N(($C_1-C_6$)alkyl)$_2$. In yet another embodiment, each $R_{23}$ is independently at each occurrence ($C_1-C_3$)alkyl or 4- to 7-membered heterocyclyl comprising 1-3 heteroatoms selected from N, O, and S, wherein the heterocyclyl is optionally substituted with one to three substituents each independently selected from ($C_1-C_6$)alkyl, —OH, —$NH_2$, —NH($C_1-C_6$)alkyl, and —N(($C_1-C_6$)alkyl)$_2$, and the alkyl is optionally substituted with —$NR_{24}R_{25}$ or a 4- to 7-membered heterocyclyl comprising 1-3 heteroatoms selected from N, O, and S optionally substituted with one to three substituents each independently selected from ($C_1-C_6$)alkyl, —OH, —$NH_2$, —NH($C_1-C_6$) alkyl, and —N(($C_1-C_6$)alkyl)$_2$.

In another embodiment, each $R_{23}$ is independently at each occurrence ($C_1-C_3$)alkyl or 4- to 7-membered heterocyclyl comprising 1-3 heteroatoms selected from N, O, and S, wherein the heterocyclyl is optionally substituted with one to three ($C_1-C_6$)alkyl, and the alkyl is optionally substituted with —$NR_{24}R_{25}$ or a 4- to 7-membered heterocyclyl comprising 1-3 heteroatoms selected from N, O, and S optionally substituted with one to three substituents each independently selected from —OH, —$NH_2$, —NH($C_1-C_6$)alkyl, and —N(($C_1-C_6$)alkyl)$_2$. In yet another embodiment, each $R_{23}$ is independently at each occurrence ($C_1-C_3$)alkyl or 4- to 7-membered heterocyclyl comprising 1-3 heteroatoms selected from N, O, and S, wherein the heterocyclyl is optionally substituted with one to three ($C_1-C_6$)alkyl, and the alkyl is optionally substituted with —$NR_{24}R_{25}$ or a 4- to 7-membered heterocyclyl comprising 1-3 heteroatoms selected from N, O, and S optionally substituted with one to three substituents each independently selected from —OH, and —N(($C_1-C_6$)alkyl)$_2$.

In some embodiments of the Formulae above, $R_{24}$ is H, ($C_1-C_3$)alkyl, or ($C_3-C_7$)carbocyclyl optionally substituted with one to two ($C_1-C_6$)alkyl. In another embodiment, $R_{24}$ is H, ($C_1-C_3$)alkyl, or ($C_3-C_7$)carbocyclyl optionally substituted with one to two ($C_1-C_3$)alkyl. In another embodiment, $R_{24}$ is H, ($C_1-C_3$)alkyl, or ($C_3-C_7$)carbocyclyl. In another embodiment, $R_{24}$ is H, ($C_1-C_3$)alkyl, or ($C_3-C_5$)carbocyclyl. In yet another embodiment, $R_{24}$ is H or ($C_1-C_3$)alkyl. In another embodiment, $R_{24}$ is H. In another embodiment, $R_{24}$ is ($C_1-C_3$)alkyl. In yet another embodiment, $R_{24}$ is ($C_3-C_5$) carbocyclyl optionally substituted with one to two ($C_1-C_6$) alkyl. In yet another embodiment, $R_{24}$ is ($C_3-C_5$)carbocyclyl. In another embodiment, $R_{24}$ is H, methyl, ethyl, n-propyl, or i-propyl. In yet another embodiment, $R_{24}$ is methyl, ethyl, n-propyl, or i-propyl. In another embodiment, $R_{24}$ is H, methyl, ethyl, cyclopropyl, cyclobutyl, or cyclopentyl, wherein the cyclopropyl, cyclobutyl, and cyclopentyl are optionally substituted with one to two ($C_1-C_3$)alkyl. In yet another embodiment, $R_{24}$ is H, methyl, ethyl, cyclopropyl or cyclobutyl, wherein the cyclopropyl and cyclobutyl are optionally substituted with one to two ($C_1-C_3$)alkyl. In another embodiment, $R_{24}$ is H, methyl, ethyl, cyclopropyl, cyclobutyl, or cyclopentyl. In yet another embodiment, $R_{24}$ is H, methyl, ethyl, cyclopropyl or cyclobutyl. In another embodiment, $R_{24}$ is H, methyl or ethyl. In another embodiment, $R_{24}$ is methyl or ethyl. In yet another embodiment, $R_{24}$ is H or methyl. In another embodiment, $R_{24}$ is methyl.

In some embodiments of the Formulae above, $R_{25}$ is H, $(C_1-C_3)$alkyl, or $(C_3-C_7)$carbocyclyl optionally substituted with one to two $(C_1-C_6)$alkyl. In another embodiment, $R_{25}$ is H, $(C_1-C_3)$alkyl, or $(C_3-C_7)$carbocyclyl optionally substituted with one to two $(C_1-C_3)$alkyl. In another embodiment, $R_{25}$ is H, $(C_1-C_3)$alkyl, or $(C_3-C_7)$carbocyclyl. In another embodiment, $R_{25}$ is H, $(C_1-C_3)$alkyl, or $(C_3-C_5)$carbocyclyl. In yet another embodiment, $R_{25}$ is H or $(C_1-C_3)$alkyl. In another embodiment, $R_{25}$ is H. In another embodiment, $R_{25}$ is $(C_1-C_3)$alkyl. In yet another embodiment, $R_{25}$ is $(C_3-C_5)$carbocyclyl optionally substituted with one to two $(C_1-C_6)$alkyl. In yet another embodiment, $R_{25}$ is $(C_3-C_5)$carbocyclyl. In another embodiment, $R_{25}$ is H, methyl, ethyl, n-propyl, or i-propyl. In yet another embodiment, $R_{25}$ is methyl, ethyl, n-propyl, or i-propyl. In another embodiment, $R_{25}$ is H, methyl, ethyl, cyclopropyl, cyclobutyl, or cyclopentyl, wherein the cyclopropyl, cyclobutyl, and cyclopentyl are optionally substituted with one to two $(C_1-C_3)$alkyl. In yet another embodiment, $R_{25}$ is H, methyl, ethyl, cyclopropyl or cyclobutyl, wherein the cyclopropyl and cyclobutyl are optionally substituted with one to two $(C_1-C_3)$alkyl. In another embodiment, $R_{25}$ is H, methyl, ethyl, cyclopropyl, cyclobutyl, or cyclopentyl. In yet another embodiment, $R_{25}$ is H, methyl, ethyl, cyclopropyl or cyclobutyl. In another embodiment, $R_{25}$ is H, methyl or ethyl. In another embodiment, $R_{25}$ is methyl or ethyl. In yet another embodiment, $R_{25}$ is H or methyl. In another embodiment, $R_{25}$ is methyl.

In some embodiments of the Formulae above, $R_4$ is H or $(C_1-C_6)$alkyl. In another embodiment, $R_4$ is H or $(C_1-C_6)$alkyl and $R_5$ is H or $(C_1-C_6)$alkyl. In another embodiment, $R_4$ is H or $(C_1-C_6)$alkyl, $R_5$ is H or $(C_1-C_6)$alkyl, and $R_7$ is H or $(C_1-C_6)$alkyl. In another embodiment, $R_4$ is H or $(C_1-C_6)$alkyl, $R_5$ is H or $(C_1-C_6)$alkyl, $R_7$ is H or $(C_1-C_6)$alkyl, and $R_9$ is halogen. In another embodiment, $R_4$ is H or $(C_1-C_6)$alkyl, $R_5$ is H or $(C_1-C_6)$alkyl, $R_7$ is H or $(C_1-C_6)$alkyl, and $R_9$ is chloro. In another embodiment, $R_4$ is H and $R_5$ is H or $(C_1-C_6)$alkyl. In another embodiment, $R_4$ is H, $R_5$ is H or $(C_1-C_6)$alkyl, and $R_7$ is H or $(C_1-C_6)$alkyl. In another embodiment, $R_4$ is H, $R_5$ is H or $(C_1-C_6)$alkyl, $R_7$ is H or $(C_1-C_6)$alkyl, and $R_9$ is halogen. In another embodiment, $R_4$ is H, $R_5$ is H or $(C_1-C_6)$alkyl, $R_7$ is H or $(C_1-C_6)$alkyl, and $R_9$ is chloro.

In some embodiments of the Formulae above, $R_4$ is H or $(C_1-C_6)$alkyl and $R_5$ is $(C_1-C_6)$alkyl. In another embodiment, $R_4$ is H or $(C_1-C_6)$alkyl, $R_5$ is $(C_1-C_6)$alkyl, and $R_7$ is H or $(C_1-C_6)$alkyl. In another embodiment, $R_4$ is H or $(C_1-C_6)$alkyl, $R_5$ is $(C_1-C_6)$alkyl, $R_7$ is H or $(C_1-C_6)$alkyl, and $R_9$ is halogen. In another embodiment, $R_4$ is H or $(C_1-C_6)$alkyl, $R_5$ is $(C_1-C_6)$alkyl, $R_7$ is H or $(C_1-C_6)$alkyl, and $R_9$ is chloro. In another embodiment, $R_4$ is H and $R_5$ is $(C_1-C_6)$alkyl. In another embodiment, $R_4$ is H, $R_5$ is $(C_1-C_6)$alkyl, and $R_7$ is H or $(C_1-C_6)$alkyl. In another embodiment, $R_4$ is H, $R_5$ is $(C_1-C_6)$alkyl, $R_7$ is H or $(C_1-C_6)$alkyl, and $R_9$ is halogen. In another embodiment, $R_4$ is H, $R_5$ is $(C_1-C_6)$alkyl, $R_7$ is H or $(C_1-C_6)$alkyl, and $R_9$ is chloro. In some embodiments of the Formulae above, $R_4$ is H or $(C_1-C_6)$alkyl, $R_5$ is H or $(C_1-C_6)$alkyl, and $R_7$ is $(C_1-C_6)$alkyl. In another embodiment, $R_4$ is H or $(C_1-C_6)$alkyl, $R_5$ is H or $(C_1-C_6)$alkyl, $R_7$ is $(C_1-C_6)$alkyl, and $R_9$ is halogen. In another embodiment, $R_4$ is H or $(C_1-C_6)$alkyl, $R_5$ is H or $(C_1-C_6)$alkyl, $R_7$ is $(C_1-C_6)$alkyl, and $R_9$ is chloro. In another embodiment, $R_4$ is H, $R_5$ is H or $(C_1-C_6)$alkyl, $R_7$ is $(C_1-C_6)$alkyl, and $R_9$ is chloro.

In some embodiments of the Formulae above, $R_4$ is H or $(C_1-C_6)$alkyl, $R_5$ is $(C_1-C_6)$alkyl, and $R_7$ is $(C_1-C_6)$alkyl. In another embodiment, $R_4$ is H or $(C_1-C_6)$alkyl, $R_5$ is $(C_1-C_6)$alkyl, $R_7$ is $(C_1-C_6)$alkyl, and $R_9$ is halogen. In another embodiment, $R_4$ is H or $(C_1-C_6)$alkyl, $R_5$ is $(C_1-C_6)$alkyl, $R_7$ is $(C_1-C_6)$alkyl, and $R_9$ is chloro. In another embodiment, $R_4$ is H, $R_5$ is $(C_1-C_6)$alkyl, and $R_7$ is $(C_1-C_6)$alkyl. In another embodiment, $R_4$ is H, $R_5$ is $(C_1-C_6)$alkyl, $R_7$ is $(C_1-C_6)$alkyl, and $R_9$ is halogen. In another embodiment, $R_4$ is H, $R_5$ is $(C_1-C_6)$alkyl, $R_7$ is $(C_1-C_6)$alkyl, and $R_9$ is chloro.

In some embodiments of the Formulae above, $R_5$ is H or $(C_1-C_6)$alkyl. In another embodiment, $R_5$ is H or $(C_1-C_6)$alkyl and $R_7$ is H or $(C_1-C_6)$alkyl. In another embodiment, $R_5$ is H or $(C_1-C_6)$alkyl, $R_7$ is H or $(C_1-C_6)$alkyl, and $R_9$ is halogen. In another embodiment, $R_4$ is H or $(C_1-C_6)$alkyl, $R_5$ is H or $(C_1-C_6)$alkyl, $R_7$ is H or $(C_1-C_6)$alkyl, and $R_9$ is chloro.

In some embodiments of the Formulae above, $R_5$ is $(C_1-C_6)$alkyl. In another embodiment, $R_5$ is $(C_1-C_6)$alkyl and $R_7$ is H or $(C_1-C_6)$alkyl. In another embodiment, $R_5$ is $(C_1-C_6)$alkyl, $R_7$ is H or $(C_1-C_6)$alkyl, and $R_9$ is halogen. In another embodiment, $R_5$ is $(C_1-C_6)$alkyl, $R_7$ is H or $(C_1-C_6)$alkyl, and $R_9$ is chloro. In another embodiment, $R_5$ is H or $(C_1-C_6)$alkyl and $R_7$ is $(C_1-C_6)$alkyl. In another embodiment, $R_5$ is H or $(C_1-C_6)$alkyl, $R_7$ is $(C_1-C_6)$alkyl, and $R_9$ is halogen. In another embodiment, $R_5$ is H or $(C_1-C_6)$alkyl, $R_7$ is $(C_1-C_6)$alkyl, and $R_9$ is chloro. In another embodiment, $R_5$ is $(C_1-C_6)$alkyl and $R_7$ is $(C_1-C_6)$alkyl. In another embodiment, $R_5$ is $(C_1-C_6)$alkyl, $R_7$ is $(C_1-C_6)$alkyl, and $R_9$ is halogen. In another embodiment, $R_5$ is $(C_1-C_6)$alkyl, $R_7$ is $(C_1-C_6)$alkyl, and $R_9$ is chloro.

In some embodiments of the Formulae above, $R_4$ is H or $(C_1-C_6)$alkyl and $R_7$ is H or $(C_1-C_6)$alkyl. In another embodiment, $R_4$ is H or $(C_1-C_6)$alkyl, $R_7$ is H or $(C_1-C_6)$alkyl, and $R_9$ is halogen. In another embodiment, $R_4$ is H or $(C_1-C_6)$alkyl, $R_7$ is H or $(C_1-C_6)$alkyl, and $R_9$ is chloro. In another embodiment, $R_4$ is H and $R_7$ is H or $(C_1-C_6)$alkyl. In another embodiment, $R_4$ is H, $R_7$ is H or $(C_1-C_6)$alkyl, and $R_9$ is halogen. In another embodiment, $R_4$ is H, $R_7$ is H or $(C_1-C_6)$alkyl, and $R_9$ is chloro. In some embodiments of the Formulae above, $R_4$ is H or $(C_1-C_6)$alkyl and $R_7$ is $(C_1-C_6)$alkyl. In another embodiment, $R_4$ is H or $(C_1-C_6)$alkyl, $R_7$ is $(C_1-C_6)$alkyl, and $R_9$ is halogen. In another embodiment, $R_4$ is H or $(C_1-C_6)$alkyl, $R_7$ is $(C_1-C_6)$alkyl, and $R_9$ is chloro. In another embodiment, $R_4$ is H and $R_7$ is $(C_1-C_6)$alkyl. In another embodiment, $R_4$ is H, $R_7$ is $(C_1-C_6)$alkyl, and $R_9$ is halogen. In another embodiment, $R_4$ is H, $R_7$ is $(C_1-C_6)$alkyl, and $R_9$ is chloro.

In some embodiments of the Formulae above, $R_4$ is H or $(C_1-C_6)$alkyl, $R_5$ is H or $(C_1-C_6)$alkyl, and $R_9$ is halogen. In another embodiment, $R_4$ is H or $(C_1-C_6)$alkyl, $R_5$ is H or $(C_1-C_6)$alkyl, and $R_9$ is chloro. In another embodiment, $R_4$ is H, $R_5$ is H or $(C_1-C_6)$alkyl, and $R_9$ is halogen. In another embodiment, $R_4$ is H, $R_5$ is H or $(C_1-C_6)$alkyl, and $R_9$ is chloro. In another embodiment, $R_4$ is H or $(C_1-C_6)$alkyl, $R_5$ is $(C_1-C_6)$alkyl, and $R_9$ is halogen. In another embodiment, $R_4$ is H or $(C_1-C_6)$alkyl, $R_5$ is $(C_1-C_6)$alkyl, and $R_9$ is chloro. In another embodiment, $R_4$ is H, $R_5$ is $(C_1-C_6)$alkyl, and $R_9$ is halogen. In another embodiment, $R_4$ is H, $R_5$ is $(C_1-C_6)$alkyl, and $R_9$ is chloro.

In some embodiments of the Formulae above, $R_4$ is H or $(C_1-C_6)$alkyl and $R_9$ is halogen. In another embodiment, $R_4$ is H or $(C_1-C_6)$alkyl and $R_9$ is chloro. In another embodiment, $R_4$ is H and $R_9$ is halogen. In another embodiment, $R_4$ is H and $R_9$ is chloro. In another embodiment, $R_5$ is H or $(C_1-C_6)$alkyl and $R_9$ is halogen. In another embodiment, $R_5$ is H or $(C_1-C_6)$alkyl and $R_9$ is chloro. In another embodiment, $R_5$ is $(C_1-C_6)$alkyl and $R_9$ is halogen. In another embodiment, $R_5$ is $(C_1-C_6)$alkyl and $R_9$ is chloro. In another embodiment, $R_7$ is H or $(C_1-C_6)$alkyl and $R_9$ is halogen. In another embodiment, $R_7$ is H or $(C_1-C_6)$alkyl and $R_9$ is chloro. In another embodiment, $R_7$ is $(C_1-C_6)$alkyl and $R_9$ is halogen. In another embodiment, $R_7$ is $(C_1-C_6)$alkyl and $R_9$ is chloro.

In some embodiments of the Formulae above, $X_1$ and $X_2$ together with the carbon atom to which they are attached form =(O), and $X_3$ is —$CH_2$—. In another embodiment, $X_1$ and $X_2$ together with the carbon atom to which they are attached form =(O), $X_3$ is —$CH_2$—, and $R_9$ is Cl. In another embodiment, $X_1$ and $X_2$ together with the carbon atom to which they are attached form =(O), $X_3$ is —$CH_2$—, $R_9$ is Cl, and $R_4$ is H. In yet another embodiment, $X_1$ and $X_2$ together with the carbon atom to which they are attached form =(O), $X_3$ is —$CH_2$—, $R_9$ is Cl, $R_4$ is H, and $R_7$ is H. In another embodiment, $X_1$ and $X_2$ together with the carbon atom to which they are attached form =(O), $X_3$ is —$CH_2$—, $R_9$ is Cl, $R_4$ is H, $R_7$ is H, and $R_5$ is H or $(C_1-C_4)$alkyl. In yet another embodiment, $X_1$ and $X_2$ together with the carbon atom to which they are attached form =(O), $R_9$ is Cl, $R_4$ is H, $R_7$ is H, $R_5$ is H or $(C_1-C_4)$alkyl, and $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$.

In another embodiment, $X_1$ and $X_2$ together with the carbon atom to which they are attached form =(O), $X_3$ is —$CH_2$—, $R_9$ is Cl, $R_4$ is H, $R_7$ is H, and $R_5$ is H or $(C_1-C_4)$alkyl. In yet another embodiment, $X_1$ and $X_2$ together with the carbon atom to which they are attached form =(O), $R_9$ is Cl, $R_4$ is H, $R_7$ is H, $R_5$ is H or $(C_1-C_4)$alkyl, and $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$. In another embodiment, $X_1$ and $X_2$ together with the carbon atom to which they are attached form =(O), $X_3$ is —$CH_2$—, $R_9$ is Cl, $R_4$ is H, $R_7$ is H, $R_5$ is H or $(C_1-C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, and $R_2$ is H, $(C_1-C_6)$alkyl, —$NR_{12}R_{13}$, $(C_1-C_6)$haloalkyl, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$.

In another embodiment, $X_1$ and $X_2$ together with the carbon atom to which they are attached form =(O), $X_3$ is —$CH_2$—, $R_9$ is Cl, $R_4$ is H, $R_7$ is H, $R_5$ is H or $(C_1-C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, and $R_3$ is H, $(C_1-C_6)$haloalkyl, or $(C_1-C_6)$alkyl optionally substituted with one to three $R_{14}$. In yet another embodiment, $X_1$ and $X_2$ together with the carbon atom to which they are attached form =(O), $X_3$ is —$CH_2$—, $R_9$ is Cl, $R_4$ is H, $R_7$ is H, $R_5$ is H or $(C_1-C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_3$ is H, $(C_1-C_6)$haloalkyl, or $(C_1-C_6)$alkyl optionally substituted with one to three $R_{14}$, and $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —$C(O)(C_1-C_6)$alkyl, —$C(O)$OH, and —$C(O)O(C_1-C_6)$alkyl.

In another embodiment, $X_1$ and $X_2$ together with the carbon atom to which they are attached form =(O), $X_3$ is —$CH_2$—, $R_9$ is Cl, $R_4$ is H, $R_7$ is H, $R_5$ is H or $(C_1-C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_3$ is H, $(C_1-C_6)$haloalkyl, or $(C_1-C_6)$alkyl optionally substituted with one to three $R_{14}$, $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —$C(O)(C_1-C_6)$alkyl, —$C(O)$OH, and —$C(O)O(C_1-C_6)$alkyl, and $R_8$ is H, $(C_1-C_6)$haloalkyl, or $(C_1-C_6)$alkyl optionally substituted with one to three substituents each independently selected from 4- to 7-membered heterocyclyl comprising 1-3 heteroatoms selected from N, O, and S and —$C(O)NR_{16}R_{17}$.

In yet another embodiment, $X_1$ and $X_2$ together with the carbon atom to which they are attached form =(O), $X_3$ is —$CH_2$—, $R_9$ is Cl, $R_4$ is H, $R_7$ is H, $R_5$ is H or $(C_1-C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_3$ is H, $(C_1-C_6)$haloalkyl, or $(C_1-C_6)$alkyl optionally substituted with one to three more $R_{14}$, $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —$C(O)(C_1-C_6)$alkyl, —$C(O)$OH, and —$C(O)O(C_1-C_6)$alkyl, $R_8$ is H, $(C_1-C_6)$haloalkyl, or $(C_1-C_6)$alkyl optionally substituted with one to three substituents each independently selected from 4- to 7-membered heterocyclyl comprising 1-3 heteroatoms selected from N, O, and S and —$C(O)NR_{16}R_{17}$, and $R_{10}$ is phenyl, or 5- or 6-membered heteroaryl comprising 1-3 heteroatoms selected from N, O, and S, wherein the aryl and heteroaryl are optionally substituted with one to three $R_{22}$.

In another embodiment, $X_1$ and $X_2$ together with the carbon atom to which they are attached form =(O), $X_3$ is —$CH_2$—, $R_9$ is Cl, $R_4$ is H, $R_7$ is H, and $R_5$ is H or methyl. In another embodiment, $X_1$ and $X_2$ together with the carbon atom to which they are attached form =(O), $R_9$ is Cl, $R_4$ is H, $R_7$ is H, $R_5$ is H or methyl, and $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$. In yet another embodiment, $X_1$ and $X_2$ together with the carbon atom to which they are attached form =(O), $R_9$ is Cl, $R_4$ is H, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, and $R_2$ is H, $(C_1$-$C_6)$alkyl, $(C_1$-$C_6)$haloalkyl, —$NR_{12}R_{13}$, $(C_3$-$C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$.

In another embodiment, $X_1$ and $X_2$ together with the carbon atom to which they are attached form =(O), $X_3$ is —$CH_2$—, $R_9$ is Cl, $R_4$ is H, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1$-$C_6)$alkyl, $(C_1$-$C_6)$haloalkyl, —$NR_{12}R_{13}$, $(C_3$-$C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, and $R_3$ is H, $(C_1$-$C_6)$haloalkyl, or $(C_1$-$C_6)$alkyl optionally substituted with one to three $R_{14}$. In yet another embodiment, $X_1$ and $X_2$ together with the carbon atom to which they are attached form =(O), $X_3$ is —$CH_2$—, $R_9$ is Cl, $R_4$ is H, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1$-$C_6)$alkyl, $(C_1$-$C_6)$haloalkyl, —$NR_{12}R_{13}$, $(C_3$-$C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_3$ is H, $(C_1$-$C_6)$haloalkyl, or $(C_1$-$C_6)$alkyl optionally substituted with one to three $R_{14}$, and $R_6$ is $(C_1$-$C_6)$hydroxyalkyl or $(C_1$-$C_6)$alkyl optionally substituted with one to three substituents each independently selected from $(C_1$-$C_6)$alkoxy, $(C_1$-$C_6)$haloalkoxy, —$C(O)(C_1$-$C_6)$alkyl, —$C(O)OH$, and —$C(O)O(C_1$-$C_6)$alkyl.

In another embodiment, $X_1$ and $X_2$ together with the carbon atom to which they are attached form =(O), $X_3$ is —$CH_2$—, $R_9$ is Cl, $R_4$ is H, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1$-$C_6)$alkyl, $(C_1$-$C_6)$haloalkyl, —$NR_{12}R_{13}$, $(C_3$-$C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_3$ is H, $(C_1$-$C_6)$haloalkyl, or $(C_1$-$C_6)$alkyl optionally substituted with one to three $R_{14}$, $R_6$ is $(C_1$-$C_6)$hydroxyalkyl or $(C_1$-$C_6)$alkyl optionally substituted with one to three substituents each independently selected from $(C_1$-$C_6)$alkoxy, $(C_1$-$C_6)$haloalkoxy, —$C(O)(C_1$-$C_6)$alkyl, —$C(O)OH$, and —$C(O)O(C_1$-$C_6)$alkyl, and $R_8$ is H, $(C_1$-$C_6)$haloalkyl, or $(C_1$-$C_6)$alkyl optionally substituted with one to three substituents each independently selected from 4- to 7-membered heterocyclyl comprising 1-3 heteroatoms selected from N, O, and S and —$C(O)NR_{16}R_{17}$.

In yet another embodiment, $X_1$ and $X_2$ together with the carbon atom to which they are attached form =(O), $X_3$ is —$CH_2$—, $R_9$ is Cl, $R_4$ is H, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1$-$C_6)$alkyl, $(C_1$-$C_6)$haloalkyl, —$NR_{12}R_{13}$, $(C_3$-$C_7)$carbocyclyl, or 5- to 7-membered heterocyclyl comprising 1-3 heteroatoms selected from N, O, and S, wherein the alkyl is optionally substituted with one to four Rib, and the carbocyclyl and heterocyclyl are optionally substituted with one to four $R_{19}$, $R_3$ is H, $(C_1$-$C_6)$haloalkyl, or $(C_1$-$C_6)$alkyl optionally substituted with one to three $R_{14}$, $R_6$ is $(C_1$-$C_6)$hydroxyalkyl or $(C_1$-$C_6)$alkyl optionally substituted with one to three substituents each independently selected from $(C_1$-$C_6)$alkoxy, $(C_1$-$C_6)$haloalkoxy, —$C(O)(C_1$-$C_6)$alkyl, —$C(O)OH$, and —$C(O)O(C_1$-$C_6)$alkyl, $R_8$ is H, $(C_1$-$C_6)$haloalkyl, or $(C_1$-$C_6)$alkyl optionally substituted with one to three substituents each independently selected from 4- to 7-membered heterocyclyl comprising 1-3 heteroatoms selected from N, O, and S and —$C(O)NR_{16}R_{17}$, and $R_{10}$ is phenyl, or 5- or 6-membered heteroaryl comprising 1-3 heteroatoms selected from N, O, and S, wherein the aryl and heteroaryl are optionally substituted with one to three $R_{22}$, and $R_{10}$ is phenyl, or 5- or 6-membered heteroaryl comprising 1-3 heteroatoms selected from N, O, and S, wherein the aryl and heteroaryl are optionally substituted with one to three $R_{22}$.

In some embodiments of the Formulae above, $X_1$ is H and $X_2$ is H and $X_3$ is —$CH_2$—. In another embodiment, $X_1$ is H and $X_2$ is H, $X_3$ is —$CH_2$—, and $R_9$ is Cl. In another embodiment, $X_1$ is H and $X_2$ is H, $R_9$ is Cl, and $R_4$ is H. In yet another embodiment, $X_1$ is H and $X_2$ is H, $X_3$ is —$CH_2$—, $R_9$ is Cl, $R_4$ is H, and $R_7$ is H. In another embodiment, $X_1$ is H and $X_2$ is H, $X_3$ is —$CH_2$—, $R_9$ is Cl, $R_4$ is H, $R_7$ is H, and $R_5$ is H or $(C_1$-$C_4)$alkyl. In yet another embodiment, $X_1$ is H and $X_2$ is H, $X_3$ is —$CH_2$—, $R_9$ is Cl, $R_4$ is H, $R_7$ is H, $R_5$ is H or $(C_1$-$C_4)$alkyl, and $R_1$ is phenyl, or 5- or 6-membered heteroaryl comprising 1-3 heteroatoms selected from N, O, and S, wherein the aryl and heteroaryl are substituted with —$OR_{10}$ and optionally substituted with one to three $R_{11}$. In another embodiment, $X_1$ is H and $X_2$ is H, $X_3$ is —$CH_2$—, $R_9$ is Cl, $R_4$ is H, $R_7$ is H, $R_5$ is H or $(C_1$-$C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, and $R_2$ is H, $(C_1$-$C_6)$alkyl, $(C_1$-$C_6)$haloalkyl, —$NR_{12}R_{13}$, $(C_3$-$C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four Rig.

In yet another embodiment, $X_1$ is H and $X_2$ is H, $X_3$ is —$CH_2$—, $R_9$ is Cl, $R_4$ is H, $R_7$ is H, $R_5$ is H or $(C_1$-$C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1$-$C_6)$alkyl, $(C_1$-$C_6)$haloalkyl, —$NR_{12}R_{13}$, $(C_3$-$C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, and $R_3$ is H, $(C_1-C_6)$haloalkyl, or $(C_1-C_6)$alkyl optionally substituted with one to three $R_{14}$. In another embodiment, $X_1$ is H and $X_2$ is H, $X_3$ is —$CH_2$—, $R_9$ is Cl, $R_4$ is H, $R_7$ is H, $R_5$ is H or $(C_1-C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_3$ is H, $(C_1-C_6)$haloalkyl, or $(C_1-C_6)$alkyl optionally substituted with one to three $R_{14}$, and $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —$C(O)(C_1-C_6)$alkyl, —$C(O)OH$, and —$C(O)O(C_1-C_6)$alkyl.

In yet another embodiment, $X_1$ is H and $X_2$ is H, $X_3$ is —$CH_2$—, $R_9$ is Cl, $R_4$ is H, $R_7$ is H, $R_5$ is H or $(C_1-C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_3$ is H, $(C_1-C_6)$haloalkyl, or $(C_1-C_6)$alkyl optionally substituted with one to three $R_{14}$, $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —$C(O)(C_1-C_6)$alkyl, —$C(O)OH$, and —$C(O)O(C_1-C_6)$alkyl, and $R_8$ is H, $(C_1-C_6)$haloalkyl, or $(C_1-C_6)$alkyl optionally substituted with one to three substituents each independently selected from 4- to 7-membered heterocyclyl comprising 1-3 heteroatoms selected from N, O, and S and —$C(O)NR_{16}R_{17}$.

In another embodiment, $X_1$ is H and $X_2$ is H, $X_3$ is —$CH_2$—, $R_9$ is Cl, $R_4$ is H, $R_7$ is H, $R_5$ is H or $(C_1-C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four Rib, and the carbocyclyl and heterocyclyl are optionally substituted with one to four $R_{19}$, $R_3$ is H, $(C_1-C_6)$haloalkyl, or $(C_1-C_6)$alkyl optionally substituted with one to three $R_{14}$, $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —$C(O)(C_1-C_6)$alkyl, —$C(O)OH$, and —$C(O)O(C_1-C_6)$alkyl, $R_8$ is H, $(C_1-C_6)$haloalkyl, or $(C_1-C_6)$alkyl optionally substituted with one to three substituents each independently selected from 4- to 7-membered heterocyclyl comprising 1-3 heteroatoms selected from N, O, and S and —$C(O)NR_{16}R_{17}$, and $R_{10}$ is phenyl, or 5- or 6-membered heteroaryl comprising 1-3 heteroatoms selected from N, O, and S, wherein the aryl and heteroaryl are optionally substituted with one to three $R_{22}$, and $R_{10}$ is phenyl, or 5- or 6-membered heteroaryl comprising 1-3 heteroatoms selected from N, O, and S, wherein the aryl and heteroaryl are optionally substituted with one to three $R_{22}$.

In some embodiments of the Formulae above, $X_1$ is H and $X_2$ is H, $X_3$ is —$CH_2$—, $R_9$ is Cl, $R_4$ is H, $R_7$ is H, and $R_5$ is H or methyl. In another embodiment, $X_1$ is H and $X_2$ is H, $R_9$ is Cl, $R_4$ is H, $R_7$ is H, $R_5$ is H or methyl, and $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$. In yet another embodiment, $X_1$ is H and $X_2$ is H, $R_9$ is Cl, $R_4$ is H, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, and $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$.

In another embodiment, $X_1$ is H and $X_2$ is H, $X_3$ is —$CH_2$—, $R_9$ is Cl, $R_4$ is H, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, and $R_3$ is H, $(C_1-C_6)$haloalkyl, or $(C_1-C_6)$alkyl optionally substituted with one to three $R_{14}$. In yet another embodiment, $X_1$ is H and $X_2$ is H, $X_3$ is —$CH_2$—, $R_9$ is Cl, $R_4$ is H, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_3$ is H, $(C_1-C_6)$haloalkyl, or $(C_1-C_6)$alkyl optionally substituted with one to three $R_{14}$, and $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —$C(O)(C_1-C_6)$alkyl, —$C(O)OH$, and —$C(O)O(C_1-C_6)$alkyl.

In another embodiment, $X_1$ is H and $X_2$ is H, $X_3$ is —$CH_2$—, $R_9$ is Cl, $R_4$ is H, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_3$ is H, $(C_1-C_6)$haloalkyl, or $(C_1-C_6)$alkyl optionally substituted with one to three $R_{14}$, $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —C(O)$(C_1-C_6)$alkyl, —C(O)OH, and —C(O)O$(C_1-C_6)$alkyl, and $R_8$ is H, $(C_1-C_6)$haloalkyl, or $(C_1-C_6)$alkyl optionally substituted with one to three substituents each independently selected from 4- to 7-membered heterocyclyl comprising 1-3 heteroatoms selected from N, O, and S and —C(O)$NR_{16}R_{17}$.

In yet another embodiment, $X_1$ is H and $X_2$ is H, $X_3$ is —$CH_2$—, $R_9$ is Cl, $R_4$ is H, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_3$ is H, $(C_1-C_6)$haloalkyl, or $(C_1-C_6)$alkyl optionally substituted with one to three $R_{14}$, $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —C(O)$(C_1-C_6)$alkyl, —C(O)OH, and —C(O)O$(C_1-C_6)$alkyl, $R_8$ is H, $(C_1-C_6)$haloalkyl, or $(C_1-C_6)$alkyl optionally substituted with one to three substituents each independently selected from 4- to 7-membered heterocyclyl comprising 1-3 heteroatoms selected from N, O, and S and —C(O)$NR_{16}R_{17}$, and $R_{10}$ is phenyl, or 5- or 6-membered heteroaryl comprising 1-3 heteroatoms selected from N, O, and S, wherein the aryl and heteroaryl are optionally substituted with one to three $R_{22}$, and $R_{10}$ is phenyl, or 5- or 6-membered heteroaryl comprising 1-3 heteroatoms selected from N, O, and S, wherein the aryl and heteroaryl are optionally substituted with one to three $R_{22}$.

In some embodiments of the Formulae above, $X_1$ and $X_2$ together with the carbon atom to which they are attached form =(O), $X_3$ is —$CH_2$—, $R_9$ is Cl, and $R_3$ and $R_4$ together with the atoms to which they are attached form a 5- to 7-membered heterocyclyl ring comprising 1-3 heteroatoms selected from N, O, and S. In another embodiment, $X_1$ and $X_2$ together with the carbon atom to which they are attached form =(O), $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and S, and $R_7$ is H. In yet another embodiment, $X_1$ and $X_2$ together with the carbon atom to which they are attached form =(O), $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, and $R_5$ is H or $(C_1-C_4)$alkyl. In another embodiment, $X_1$ and $X_2$ together with the carbon atom to which they are attached form =(O), $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or $(C_1-C_4)$alkyl, and $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$.

In another embodiment, $X_1$ and $X_2$ together with the carbon atom to which they are attached form =(O), $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or $(C_1-C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, and $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$. In yet another embodiment, $X_1$ and $X_2$ together with the carbon atom to which they are attached form =(O), $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and 5, $R_7$ is H, $R_5$ is H or $(C_1-C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, and $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —C(O)$(C_1-C_6)$alkyl, —C(O)OH, and —C(O)O$(C_1-C_6)$alkyl.

In another embodiment, $X_1$ and $X_2$ together with the carbon atom to which they are attached form =(O), $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or $(C_1-C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —C(O)$(C_1-C_6)$alkyl, —C(O)OH, and —C(O)O$(C_1-C_6)$alkyl, and $R_8$ is H, $(C_1-C_6)$haloalkyl, or $(C_1-C_6)$alkyl optionally substituted with one to three substituents each independently selected from 4- to 7-membered heterocyclyl comprising 1-3 heteroatoms selected from N, O, and S and —C(O)$NR_{16}R_{17}$.

In yet another embodiment, $X_1$ and $X_2$ together with the carbon atom to which they are attached form =(O), $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or $(C_1-C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —C(O)$(C_1-C_6)$alkyl, —C(O)OH, and —C(O)O$(C_1-C_6)$alkyl, $R_8$ is H, $(C_1-C_6)$haloalkyl, or $(C_1-C_6)$alkyl optionally substituted with one to three substituents each independently selected from 4- to 7-membered heterocyclyl comprising 1-3 heteroatoms selected from N, O, and S and —C(O)NR$_{16}$R$_{17}$, and $R_{10}$ is phenyl, or 5- or 6-membered heteroaryl comprising 1-3 heteroatoms selected from N, O, and S, wherein the aryl and heteroaryl are optionally substituted with one to three $R_{22}$, and $R_{10}$ is phenyl, or 5- or 6-membered heteroaryl comprising 1-3 heteroatoms selected from N, O, and S, wherein the aryl and heteroaryl are optionally substituted with one to three $R_{22}$.

In some embodiments of the Formulae above, $X_1$ and $X_2$ together with the carbon atom to which they are attached form =(O), $X_3$ is —CH$_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, and $R_5$ is H or methyl. In another embodiment, $X_1$ and $X_2$ together with the carbon atom to which they are attached form =(O), $X_3$ is —CH$_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or methyl, and $R_1$ is phenyl, or 5- or 6-membered heteroaryl comprising 1-3 heteroatoms selected from N, O, and S, wherein the phenyl and heteroaryl are substituted with —OR$_{10}$ and optionally substituted with one to three $R_{11}$.

In yet another embodiment, $X_1$ and $X_2$ together with the carbon atom to which they are attached form =(O), $X_3$ is —CH$_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —OR$_{10}$ and optionally substituted with one to three $R_{11}$, and $R_2$ is H, $(C_1-C_6)$alkyl, $(C_1-C_6)$haloalkyl —NR$_{12}$R$_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$.

In another embodiment, $X_1$ and $X_2$ together with the carbon atom to which they are attached form =(O), $X_3$ is —CH$_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —OR$_{10}$ and optionally substituted with one to three $R_{11}$, $R_2$ is H, $(C_1-C_6)$alkyl, $(C_1-C_6)$haloalkyl, —NR$_{12}$R$_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, and $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —C(O)$(C_1-C_6)$alkyl, —C(O)OH, and —C(O)O$(C_1-C_6)$alkyl.

In another embodiment, $X_1$ and $X_2$ together with the carbon atom to which they are attached form =(O), $X_3$ is —CH$_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —OR$_{10}$ and optionally substituted with one to three $R_{11}$, $R_2$ is H, $(C_1-C_6)$alkyl, $(C_1-C_6)$haloalkyl, —NR$_{12}$R$_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —C(O)$(C_1-C_6)$alkyl, —C(O)OH, and —C(O)O$(C_1-C_6)$alkyl, and $R_8$ is H, $(C_1-C_6)$haloalkyl, or $(C_1-C_6)$alkyl optionally substituted with one to three substituents each independently selected from 4- to 7-membered heterocyclyl comprising 1-3 heteroatoms selected from N, O, and S and —C(O)NR$_{16}$R$_{17}$.

In yet another embodiment, $X_1$ and $X_2$ together with the carbon atom to which they are attached form =(O), $X_3$ is —CH$_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or methyl, $R_1$ is phenyl, or 5- or 6-membered heteroaryl comprising 1-3 heteroatoms selected from N, O, and S, wherein the phenyl and heteroaryl are substituted with —OR$_{10}$ and optionally substituted with one to three $R_{11}$, $R_2$ is H, $(C_1-C_6)$alkyl, $(C_1-C_6)$haloalkyl, —NR$_{12}$R$_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —C(O)$(C_1-C_6)$alkyl, —C(O)OH, and —C(O)O$(C_1-C_6)$alkyl, $R_8$ is H, $(C_1-C_6)$haloalkyl, or $(C_1-C_6)$alkyl optionally substituted with one to three substituents each independently selected from 4- to 7-membered heterocyclyl comprising 1-3 heteroatoms selected from N, O, and S and —C(O)NR$_{16}$R$_{17}$, and $R_{10}$ is phenyl, or 5- or 6-membered heteroaryl comprising 1-3 heteroatoms selected from N, O, and S, wherein the aryl and heteroaryl are optionally substituted with one to three $R_{22}$.

In some embodiments of the Formulae above, $X_1$ is H and $X_2$ is H, $X_3$ is —CH$_2$—, $R_9$ is Cl, and $R_3$ and $R_4$ together with the atoms to which they are attached form a 5- to 7-membered heterocyclyl ring comprising 1-3 heteroatoms selected from N, O, and S. In another embodiment, $X_1$ is H and $X_2$ is H, $X_3$ is —CH$_2$—, $R_9$ is Cl, $R_3$ and $R_4$ together with the atoms to which they are attached form a 5- to 7-membered heterocyclyl ring comprising 1-3 heteroatoms selected from N, O, and S, and $R_7$ is H. In yet another embodiment, $X_1$ is H and $X_2$ is H, $X_3$ is —CH$_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, and $R_5$ is H or $(C_1-C_4)$alkyl. In another embodiment, $X_1$ is H and $X_2$ is H, $X_3$ is —CH$_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or $(C_1-C_4)$alkyl, and $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$.

In another embodiment, $X_1$ is H and $X_2$ is H, $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or $(C_1\text{-}C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, and $R_2$ is H, $(C_1\text{-}C_6)$alkyl, $(C_1\text{-}C_6)$haloalkyl, —$NR_{12}R_{13}$, $(C_3\text{-}C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$.

In yet another embodiment, $X_1$ is H and $X_2$ is H, $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or $(C_1\text{-}C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1\text{-}C_6)$alkyl, $(C_1\text{-}C_6)$haloalkyl, —$NR_{12}R_{13}$, $(C_3\text{-}C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, and $R_6$ is $(C_1\text{-}C_6)$hydroxyalkyl or $(C_1\text{-}C_6)$alkyl optionally substituted with one to three substituents each independently selected from $(C_1\text{-}C_6)$alkoxy, $(C_1\text{-}C_6)$haloalkoxy, —$C(O)(C_1\text{-}C_6)$alkyl, —$C(O)OH$, and —$C(O)O(C_1\text{-}C_6)$alkyl.

In another embodiment, $X_1$ is H and $X_2$ is H, $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or $(C_1\text{-}C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1\text{-}C_6)$alkyl, $(C_1\text{-}C_6)$haloalkyl, —$NR_{12}R_{13}$, $(C_3\text{-}C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_6$ is $(C_1\text{-}C_6)$hydroxyalkyl or $(C_1\text{-}C_6)$alkyl optionally substituted with one to three substituents each independently selected from $(C_1\text{-}C_6)$alkoxy, $(C_1\text{-}C_6)$haloalkoxy, —$C(O)(C_1\text{-}C_6)$alkyl, —$C(O)OH$, and —$C(O)O(C_1\text{-}C_6)$alkyl, and $R_8$ is H, $(C_1\text{-}C_6)$haloalkyl, or $(C_1\text{-}C_6)$alkyl optionally substituted with one to three substituents each independently selected from 4- to 7-membered heterocyclyl comprising 1-3 heteroatoms selected from N, O, and S and —$C(O)NR_{16}R_{17}$.

In yet another embodiment, $X_1$ is H and $X_2$ is H, $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or $(C_1\text{-}C_4)$alkyl, $R_1$ is phenyl, or 5- or 6-membered heteroaryl comprising 1-3 heteroatoms selected from N, O, and S, wherein the phenyl and heteroaryl are substituted with —$OR_{10}$ and optionally substituted with one to three $R_{11}$, $R_2$ is H, $(C_1\text{-}C_6)$alkyl, $(C_1\text{-}C_6)$haloalkyl, —$NR_{12}R_{13}$, $(C_3\text{-}C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_6$ is $(C_1\text{-}C_6)$hydroxyalkyl or $(C_1\text{-}C_6)$alkyl optionally substituted with one to three substituents each independently selected from $(C_1\text{-}C_6)$alkoxy, $(C_1\text{-}C_6)$haloalkoxy, —$C(O)(C_1\text{-}C_6)$alkyl, —$C(O)OH$, and —$C(O)O(C_1\text{-}C_6)$alkyl, $R_8$ is H, $(C_1\text{-}C_6)$haloalkyl, or $(C_1\text{-}C_6)$alkyl optionally substituted with one to three substituents each independently selected from 4- to 7-membered heterocyclyl comprising 1-3 heteroatoms selected from N, O, and S and —$C(O)NR_{16}R_{17}$, and $R_{10}$ is phenyl, or 5- or 6-membered heteroaryl comprising 1-3 heteroatoms selected from N, O, and S, wherein the aryl and heteroaryl are optionally substituted with one to three $R_{22}$.

In some embodiments of the Formulae above, $X_1$ is H and $X_2$ is H, $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or methyl, and $R_1$ is phenyl, or 5- or 6-membered heteroaryl comprising 1-3 heteroatoms selected from N, O, and S, wherein the aryl and heteroaryl are substituted with —$OR_{10}$ and optionally substituted with one to three $R_{11}$. In another embodiment, $X_1$ is H and $X_2$ is H, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or methyl, $R_1$ is phenyl, or 5- or 6-membered heteroaryl comprising 1-3 heteroatoms selected from N, O, and S, wherein the aryl and heteroaryl are substituted with —$OR_{10}$ and optionally substituted with one to three $R_{11}$, and $R_2$ is H, $(C_1\text{-}C_6)$alkyl, $(C_1\text{-}C_6)$haloalkyl, —$NR_{12}R_{13}$, $(C_3\text{-}C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$.

In yet another embodiment, $X_1$ is H and $X_2$ is H, $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or methyl, $R_1$ is phenyl, or 5- or 6-membered heteroaryl comprising 1-3 heteroatoms selected from N, O, and S, wherein the aryl and heteroaryl are substituted with —$OR_{10}$ and optionally substituted with one to three $R_{11}$, $R_2$ is H, $(C_1\text{-}C_6)$alkyl, $(C_1\text{-}C_6)$haloalkyl, —$NR_{12}R_{13}$, $(C_3\text{-}C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, and $R_6$ is $(C_1\text{-}C_6)$hydroxyalkyl or $(C_1\text{-}C_6)$alkyl optionally substituted with one to three substituents each independently selected from $(C_1\text{-}C_6)$alkoxy, $(C_1\text{-}C_6)$haloalkoxy, —$C(O)(C_1\text{-}C_6)$alkyl, —$C(O)OH$, and —$C(O)O(C_1\text{-}C_6)$alkyl.

In another embodiment, $X_1$ is H and $X_2$ is H, $X_3$ is —$CH_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or methyl, $R_1$ is phenyl, or 5- or 6-membered heteroaryl comprising 1-3 heteroatoms selected from N, O, and S, wherein the aryl and heteroaryl are substituted with —$OR_{10}$ and optionally substituted with one to three $R_{11}$, $R_2$ is H, $(C_1\text{-}C_6)$alkyl, $(C_1\text{-}C_6)$haloalkyl, —$NR_{12}R_{13}$, $(C_3\text{-}C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —C(O)$(C_1-C_6)$alkyl, —C(O)OH, and —C(O)O$(C_1-C_6)$alkyl, and $R_8$ is H, $(C_1-C_6)$haloalkyl, or $(C_1-C_6)$alkyl optionally substituted with one to three substituents each independently selected from 4- to 7-membered heterocyclyl comprising 1-3 heteroatoms selected from N, O, and S and —C(O)$NR_{16}R_{17}$.

In another embodiment, $X_1$ is H and $X_2$ is H, $X_3$ is —CH$_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or methyl, $R_1$ is phenyl, or 5- or 6-membered heteroaryl comprising 1-3 heteroatoms selected from N, O, and S, wherein the aryl and heteroaryl are substituted with —$OR_{10}$ and optionally substituted with one to three $R_{11}$, $R_2$ is H, $(C_1-C_6)$alkyl, $(C_1-C_6)$haloalkyl, —$NR_{12}R_{13}$, $(C_3-C_7)$carbocyclyl, or 5- to 7-membered heterocyclyl comprising 1-3 heteroatoms selected from N, O, and S, wherein the alkyl is optionally substituted with one to four $R_{18}$, and the carbocyclyl and heterocyclyl are optionally substituted with one to four $R_{19}$, $R_6$ is $(C_1-C_6)$hydroxyalkyl or $(C_1-C_6)$alkyl optionally substituted with one to three substituents each independently selected from $(C_1-C_6)$alkoxy, $(C_1-C_6)$haloalkoxy, —C(O)$(C_1-C_6)$alkyl, —C(O)OH, and —C(O)O$(C_1-C_6)$alkyl, $R_8$ is H, $(C_1-C_6)$haloalkyl, or $(C_1-C_6)$alkyl optionally substituted with one to three substituents each independently selected from 4- to 7-membered heterocyclyl comprising 1-3 heteroatoms selected from N, O, and S and —C(O)$NR_{16}R_{17}$, and $R_{10}$ is phenyl, or 5- or 6-membered heteroaryl comprising 1-3 heteroatoms selected from N, O, and S, wherein the aryl and heteroaryl are optionally substituted with one to three $R_{22}$.

In another embodiment, $X_1$ and $X_2$ together with the carbon atom to which they are attached form =(O), $X_3$ is —CH$_2$—, $R_9$ is Cl, $R_3$ and $R_4$ together with the atoms to which they are attached form a 5- to 7-membered heterocyclyl ring comprising 1-3 heteroatoms selected from N, O, and S, $R_7$ is H, $R_5$ is H or methyl, $R_1$ is phenyl substituted with —$OR_{10}$ and optionally substituted with one to three $R_{11}$, $R_2$ is $(C_1-C_6)$alkyl, or $(C_3-C_7)$carbocyclyl, wherein the alkyl is optionally substituted with one to four $R_{18}$, and the carbocyclyl is optionally substituted with one to four $R_{19}$, $R_6$ is $(C_1-C_6)$hydroxyalkyl, $R_8$ is $(C_1-C_6)$alkyl optionally substituted with one to three substituents each independently selected from 4- to 7-membered heterocyclyl comprising 1-3 heteroatoms selected from N, O, and S and —C(O)$NR_{16}R_{17}$, and $R_{10}$ is phenyl are substituted with one to three $R_{22}$.

Embodiment 1. A compound according to Formula (I).

Embodiment 2. The compound according to Embodiment 1, wherein $R_4$ is H or $(C_1-C_6)$alkyl.

Embodiment 3. The compound according to Embodiment 1 or 2, wherein $R_4$ is H.

Embodiment 4. The compound according to Embodiment 1, wherein $R_3$ and $R_4$ together with the atoms to which they are attached form a 5- to 7-membered heterocyclyl ring comprising 1-3 heteroatoms selected from N, O, and S.

Embodiment 5. The compound according to Embodiment 1 or 3, wherein $R_3$ and $R_4$ together with the atoms to which they are attached form a 6-membered heterocyclyl ring comprising 1-3 heteroatoms selected from N, O, and S.

Embodiment 6. The compound according to any one of Embodiments 1-5, wherein $R_5$ is H or $(C_1-C_6)$alkyl.

Embodiment 7. The compound according to any one of Embodiments 1-6, wherein $R_5$ is $(C_1-C_6)$alkyl.

Embodiment 8. The compound according to any one of Embodiments 1-7, wherein $R_7$ is H or $(C_1-C_6)$alkyl.

Embodiment 9. The compound according to any one of Embodiments 1-8, wherein $R_7$ is $(C_1-C_6)$alkyl.

Embodiment 10. The compound according to any one of Embodiments 1-9, wherein $R_9$ is halogen.

Embodiment 11. The compound according to any one of Embodiments 1-10, wherein $R_9$ is chloro.

Embodiment 12. The compound according to any one of Embodiments 1-11, wherein $R_8$ is $(C_1-C_6)$alkyl optionally substituted with one to three substituents each independently selected from $(C_3-C_7)$carbocyclyl, 4- to 7-membered heterocyclyl comprising 1-3 heteroatoms selected from N, O, and S, —$NR_{16}R_{17}$, and —C(O)$NR_{16}R_{17}$.

Embodiment 13. The compound according to any one of Embodiments 1-12, wherein $R_8$ is $(C_1-C_6)$alkyl.

Embodiment 14. The compound according to Embodiment 1, having a Formula (Ia), Formula (Ib), Formula (Ic), Formula (Id), Formula (Ie), Formula (If), Formula (Ig), Formula (Ih), or Formula (Ii).

Embodiment 15. The compound according to any one of Embodiments 1-14, wherein $R_1$ is phenyl substituted with —$OR_{10}$ and optionally substituted with one to three $R_{11}$.

Embodiment 16. The compound according to any one of Embodiments 1-14, wherein $R_1$ is pyridinyl substituted with —$OR_{10}$ and optionally substituted with one to three $R_{11}$.

Embodiment 17. The compound according to Embodiment 1, having a Formula (Ij), Formula (Ik), Formula (Im), or Formula (Io), wherein x is 0, 1, or 2.

Embodiment 18. The compound according to any one of Embodiments 1-17, wherein $R_{10}$ is phenyl substituted with one to three $R_{22}$.

Embodiment 19. The compound according to any one of Embodiments 1-17, wherein $R_{10}$ is pyridinyl substituted with one to three $R_{22}$.

Embodiment 20. The compound (Cmd) according to Embodiment 1 selected from:

| Cmd No. | Compound Name |
|---|---|
| 1 | (3R, 7S, 10S, 13R)-6-(4-chloro-2-(4-(1-methyl-2-(pyrrolidin-1-ylmethyl)-1H-imidazol-5-yl)phenoxy)benzyl)-13-(4-chlorobenzyl)-10-(hydroxymethyl)-7-methyl-3-(pyridin-2-ylmethyl)-1,6,9,12-tetraazabicyclo[11.3.1]heptadecane-2,5,5,8,11-tetraone; |
| 2 | (3S, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone; |
| 3 | 2-(((3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-2,5,8,11-tetraoxo-1,6,9,12-tetraazabicyclo[11.3.1]heptadecan-3-yl)methyl)pyridine 1-oxide; |

-continued

| Cmd No. | Compound Name |
|---|---|
| 4 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7-methyl-3-((6-methylpyridin-2-Amethyl)-1,6,9,12-tetraazabicyclo[11.3.1]heptadecane-2,5,8,11-tetraone |
| 5 | (3S, 7S, 10S, 13R)-6-(4-chloro-2-(4-(2-((cyclobutylamino)methyl)-1-methyl-1H-imidazol-5-yl)phenoxy)-6-fluorobenzyl)-13-(4-chlorobenzyl)-10-(hydroxymethyl)-7-methyl-3-(2,2,2-trifluoroethyl)-1,6,9,12-tetraazabicyclo[11.3.1]heptadecane-2,5,8,11-tetraone; |
| 6 | (3S, 7S, 10S, 13R)-6-(2-(4-(2-((tert-butylamino)methyl)-1-methyl-1H-imidazol-5-yl)phenoxy)-4-chlorobenzyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone; |
| 7 | (3S, 7S, 10S, 13R)-6-(4-chloro-2-(4-(4-((dimethylamino)methyl)-5-methyl-1H-imidazol-1-yl)phenoxy)benzyl)-13-(4-chlorobenzyl)-3-((S)-2,3-dihydro-1H-inden-1-yl)-10-(hydroxymethyl)-7-methyl-1,6,9,12-tetraazabicyclo[11.3.1]heptadecane-2,5,8,11-tetraone; |
| 8 | (3S, 7S, 10S, 13R)-6-(4-chloro-2-((6-(2-((dimethylamino)methyl)-1-methyl-1H-imidazol-5-Apyridin-3-yl)oxy)-6-fluorobenzyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone; |
| 9 | (3S, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone; |
| 10 | (3R, 7S, 10S, 13R)-6-(4-chloro-2-fluoro-6-(4-(1-methyl-2-(pyrrolidin-1-ylmethyl)-1H-imidazol-5-yl)phenoxy)benzyl)-13-(4-chlorobenzyl)-3-(cyclopropylmethyl)-10-(hydroxymethyl)-7-methyl-1,6,9,12-tetraazabicyclo[11.3.1]heptadecane-2,5,8,11-tetraone; |
| 11 | (3R, 7S, 10S, 13R)-3-benzyl-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7-methyl-1,6,9,12-tetraazabicyclo[11.3.11]-heptadecane-2,5,8,11-tetraone; |
| 12 | (3S, 7S, 10S, 13R)-6-(4-chloro-2-((6-(2-((dimethylamino)methyl)-1-methyl-1H-imidazol-5-yl)pyridin-3-yl)oxy)benzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone; |
| 13 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7, 12-dimethyl-3-((6-methylpyridin-2-yl)methyl)-1,6,9,12-tetraazabicyclo-2,5,8,11-tetraone; |
| 14 | (3R, 7S, 10S, 13R)-6-(4-chloro-2-fluoro-6-(4-(1-methyl-2-(pyrrolidin-1-ylmethyl)-1H-imidazol-5-yl)phenoxy)benzyl)-13-(4-chlorobenzyl)-10-(methoxymethyl)-7,12-dimethyl-3-((6-methylpyridin-2-Amethyl)-1,6,9,12-tetraazabicyclo[11.3.1]heptadecane-2,5,8,11-tetraone; |
| 15 | (3S, 7S, 10S, 13R)-6-(4-chloro-2-fluoro-6-(4-(1-methyl-2-(pyrrolidin-1-ylmethyl)-1H-imidazol-5-yl)phenoxy)benzyl)-13-(4-chlorobenzyl)-10-(hydroxymethyl)-7-methyl-3-(2,2,2-trifluoroethyl)-1,6,9,12-tetraazabicyclo[11.3.1]heptadecane-2,5,8,11-tetraone; |
| 16 | (3S, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-3-((R)-6,7-dihydro-5H-cyclopenta[b]pyridin-5-yl)-10-(hydroxymethyl)-7-methyl-1,6,9,12-tetraazabicyclo[11.3.1]heptadecane-2,5,8,11-tetraone; |
| 17 | (3R, 7S, 10S, 13R)-3-benzyl-6-((5-chloro-3-(4-(2-((dimethylamino)methyl)-1-methyl-1H-imidazol-5-yl)phenoxy)pyridin-2-yl)methyl)-13-(4-chlorobenzyl)-10-(methoxymethyl)-7-methyl-1,6,9,12-tetraazabicyclo[11.3.1]heptadecane-2,5,8,11-tetraone; |
| 18 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7,12-dimethyl-3-(pyridin-2-ylmethyl)-1,6,9,12-tetraazabicyclo[11.3.1]heptadecane-2,5,8,11-tetraone; |
| 19 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-3-(pyridin-3-ylmethyl)-1,6,9,12-tetraazabicyclo[11.3.1]heptadecane-2,5,8,11-tetraone; |
| 20 | (3S, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7,12-dimethyl-3-(2,2,2-trifluoroethyl)-1,6,9,12-tetraazabicyclo[11.3.1]heptadecane-2,5,8,11-tetraone; |
| 21 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7-methyl-3-(pyridin-2-ylmethyl)-1,6,9,12-tetraazabicyclo[11.3.1]heptadecane-2,5,8,11-tetraone; |
| 22 | (3S, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone; |

-continued

| Cmd No. | Compound Name |
|---|---|
| 23 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7-methyl-3-(pyridin-3-ylmethyl)-1,6,9,12-tetraazabicyclo[11.3.1]heptadecane-2,5,8,11-tetraone; |
| 24 | (3R, 7S, 10S, 13R)-6-(4-chloro-2-((6-(2-((dimethylamino)methyl)-1-methyl-1H-imidazol-5-yl)pyridin-3-yl)oxy)benzyl)-13-(4-chlorobenzyl)-10-(methoxymethyl)-7,12-dimethyl-3-((6-methylpyridin-2-yl)methyl)-1,6,9,12-tetraazabicyclo[11.3.1]heptadecane-2,5,8,11-tetraone; |
| 25 | (3R, 7S, 10S, 13R)-3-benzyl-6-(4-chloro-2-(4-(2-((dimethylamino)methyl)-1-methyl-1H-imidazol-5-yl)phenoxy)-3-fluorobenzyl)-13-(4-chlorobenzyl)-10-(hydroxymethyl)-7-methyl-1,6,9,12-tetraazabicyclo[11.3.1]heptadecane-2,5,8,11-tetraone; |
| 26 | (3R, 7S, 10S, 13R)-6-(4-chloro-2-(4-(1-methyl-2-(pyrrolidin-1-ylmethyl)-1H-imidazol-5-yl)phenoxy)benzyl)-13-(4-chlorobenzyl)-3-ethyl-10-(hydroxymethyl)-7-methyl-1,6,9,12-tetraazabicyclo[11.3.1]heptadecane-2,5,8,11-tetraone; |
| 27 | (3R, 7S, 10S, 13R)-3-benzyl-6-(4-chloro-24(6-(2-((dimethylamino)methyl)-1-methyl-1H-imidazol-5-Apyridin-3-yl)oxy)benzyl)-13-(4-chlorobenzyl)-10-(methoxymethyl)-7, 12-dimethyl-1,6,9,12-tetraazabicyclo[11.3.1]heptadecane-2,5,8,11-tetraone; |
| 28 | (3S, 7S, 10S, 13R)-6-(2-(4-(2-(azetidin-1-ylmethyl)-1-methyl-1H-imidazol-5-yl)phenoxy)-4-chloro-6-fluorobenzyl)-13-(4-chlorobenzyl)-10-(hydroxymethyl)-7-methyl-3-(2,2,2-trifluoroethyl)-1,6,9,12-tetraazabicyclo[11.3.1]heptadecane-2,5,8,11-tetraone; |
| 29 | (3S, 7S, 10S, 13R)-6-((5-chloro-3-(4-(2-((dimethylamino)methyl)-1-methyl-1H-imidazol-5-yl)phenoxy)pyridin-2-yl)methyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone; |
| 30 | (3R, 7S, 10S, 13R)-6-(4-chloro-2-(4-(1-methyl-2-(pyrrolidin-1-ylmethyl)-1H-imidazol-5-yl)phenoxy)benzyl)-13-(4-chlorobenzyl)-10-((difluoromethoxy)methyl)-7-methyl-3-(pyridin-2-ylmethyl)-1,6,9,12-tetraazabicyclo[11.3.1]heptadecane-2,5,8,11-tetraone; |
| 31 | (3S, 7S, 10S, 13R)-6-(4-chloro-2-((5-(2-((dimethylamino)methyl)-1-methyl-1H-imidazol-5-yl)pyridin-2-yl)oxy)benzyl)-13-(4-chlorobenzyl)-3-((R)-2,3-dihydro-1H-inden-1-yl)-10-(hydroxymethyl)-7-methyl-1,6,9,12-tetraazabicyclo[11.3.1]heptadecane-2,5,8,11-tetraone; |
| 31a | (3S, 7S, 10S, 13R)-6-(4-chloro-2-((5-(2-((dimethylamino)methyl)-1-methyl-1H-imidazol-5-yl)pyridin-2-yl)oxy)benzyl)-13-(4-chlorobenzyl)-3-((S)-2,3-dihydro-1H-inden-1-yl)-10-(hydroxymethyl)-7-methyl-1,6,9,12-tetraazabicyclo[11.3.1]heptadecane-2,5,8,11-tetraone; |
| 32 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-3-(pyridin-2-ylmethyl)-1,6,9,12-tetraazabicyclo[11.3.1]heptadecane-2,5,8,11-tetraone; |
| 33 | (3S, 7S, 10S, 13R)-6-(2-(4-(2-(azetidin-1-ylmethyl)-1-methyl-1H-imidazol-5-yl)phenoxy)-4-chlorobenzyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone; |
| 34 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-3-(2,6-difluorobenzyl)-10-(hydroxymethyl)-7-methyl-1,6,9,12-tetraazabicyclo[11.3.1]heptadecane-2,5,8,11-tetraone; |
| 35 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7-methyl-3-(oxazol-2-ylmethyl)-1,6,9,12-tetraazabicyclo[11.3.1]heptadecane-2,5,8,11-tetraone; |
| 36 | (7S, 10S, 13R)-6-(4-chloro-2-(4-(2-((dimethylamino)methyl)-1-methyl-1H-imidazol-5-yl)phenoxy)-6-(2,2,2-trifluoroethoxy)benzyl)-13-(4-chlorobenzyl)-10-(hydroxymethyl)-7-methyl-1,6,9,12-tetraazabicyclo[11.3.1]heptadecane-2,5,8,11-tetraone; |
| 37 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7,12-dimethyl-3-(2,4,6-trifluorobenzyl)-1,6,9,12-tetraazabicyclo[11.3.1]heptadecane-2,5,8,11-tetraone; |
| 38 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7,12-dimethyl-3-((6-methylpyridin-2-yl)methyl)-1,6,9,12-tetraazabicyclo[11.3.1]heptadecane-2,5,8,11-tetraone; |
| 39 | (3R, 7S, 10S, 13R)-3-benzyl-6-(4-chloro-2-fluoro-6-(4-(5-methyl-4-(pyrrolidin-1-ylmethyl)-1H-imidazol-1-yl)phenoxy)benzyl)-13-(4-chlorobenzyl)-10-(methoxymethyl)-7-methyl-1,6,9,12-tetraazabicyclo[11.3.1]heptadecane-2,5,8,11-tetraone; |
| 40 | (3R, 7S, 10S, 13R)-3-((E)-but-2-en-1-yl)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-1,6,9,12-tetraazabicyclo[11.3.1]heptadecane-2,5,8,11-tetraone; |

-continued

| Cmd No. | Compound Name |
|---|---|
| 41 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-3-((6-methylpyridin-2-yl)methyl)-1,6,9,12-tetraazabicyclo[11.3.1]heptadecane-2,5,8,11-tetraone; |
| 42 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-3-(cyclopropylmethyl)-10-(hydroxymethyl)-7-methyl-1,6,9,12-tetraazabicyclo[11.3.1]heptadecone-2,5,8,11-tetraone; |
| 43 | (3R, 7S, 10S, 13R)-3-benzyl-6-(4-chloro-2-(4-(2-((dimethylamino)methyl)-1-methyl-1H-imidazol-5-yl)-3-fluorophenoxy)benzyl)-13-(4-chlorobenzyl)-10-(hydroxymethyl)-7-methyl-1,6,9,12-tetraazabicyclo[11.3.1]heptadecane-2,5,8,11-tetraone; |
| 44 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7-methyl-3-((1-methyl-6-oxo-1,6-dihydropyridin-2-Amethyl)-1,6,9,12-tetraazabicyclo[11.3.1]heptadecane-2,5,8,11-tetraone; |
| 45 | (3S, 7S, 10S, 13R)-6-(4-chloro-2-(4-(2-((cyclobutylamino)methyl)-1-methyl-1H-imidazol-5-yl)phenoxy)-6-fluorobenzyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone; |
| 46 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-3-(2,4,6-trifluorobenzyl)-1,6,9,12-tetraazabicyclo[11.3.1]heptadecane-2,5,8,11-tetraone; |
| 47 | (3R, 7S, 10S, 13R)-6-(4-chloro-2-(4-(1-methyl-2-(morpholinomethyl)-1H-imidazol-5-yl)phenoxy)benzyl)-13-(4-chlorobenzyl)-10-(hydroxymethyl)-7-methyl-3-(pyridin-3-ylmethyl)-1,6,9,12-tetraazabicyclo[11.3.1]heptadecane-2,5,8,11-tetraone; |
| 48 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7-methyl-3-(2,3,4-trifluorobenzyl)-1,6,9,12-tetraazabicyclo[11.3.1]heptadecane-2,5,8,11-tetraone; |
| 49 | (3S, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-3-((S)-2,3-dihydro-1H-inden-1-yl)-10-(hydroxymethyl)-7-methyl-1,6,9,12-tetraazabicyclo[11.3.1]heptadecane-2,5,8,11-tetraone; |
| 50 | (3R, 7S, 10S, 13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-1,6,9,12-tetraazabicyclo[11.3.1]heptadecane-2,5,8,11-tetraone; |
| 51 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7-methyl-3-propyl-1,6,9,12-tetraazabicyclo[11.3.1]heptadecane-2,5,8,11-tetraone; |
| 52 | (3R, 7S, 10S, 13R)-3-benzyl-6-(4-chloro-2-((6-(2-((dimethylamino)methyl)-1-methyl-1H-imidazol-5-yl)pyridin-3-yl)oxy)benzyl)-13-(4-chlorobenzyl)-10-(methoxymethyl)-7-methyl-1,6,9,12-tetraazabicyclo[11.3.1]heptadecane-2,5,8,11-tetraone; |
| 53 | (3R, 7S, 10S, 13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7,12-dimethyl-1,6,9,12-tetraazabicyclo[11.3.1]heptadecane-2,5,8,11-tetraone; |
| 54 | (3R, 7S, 10S, 13R)-3-benzyl-6-(4-chloro-2-(4-(2-((dimethylamino)methyl)-1-methyl-1H-imidazol-5-yl)phenoxy)-5-fluorobenzyl)-13-(4-chlorobenzyl)-10-(hydroxymethyl)-7-methyl-1,6,9,12-tetraazabicyclo[11.3.1]heptadecane-2,5,8,11-tetraone; |
| 55 | (3S, 7S, 10S, 13R)-13-(4-chlorobenzyl)-34(S)-2,3-dihydro-1H-inden-1-yl)-6-(2-(4-(2-((dimethylamino)methyl)-1-methyl-1H-imidazol-5-yl)phenoxy)benzyl)-10-(hydroxymethyl)-7-methyl-1,6,9,12-tetraazabicyclo[11.3.1]heptadecane-2,5,8,11-tetraone; |
| 56 | (3R, 7S, 10S, 13R)-3-benzyl-6-(4-chloro-2-(4-(5-((dimethylamino)methyl)-4-methyl-4H-1,2,4-triazol-3-yl)phenoxy)benzyl)-13-(4-chlorobenzyl)-10-(hydroxymethyl)-7-methyl-1,6,9,12-tetraazabicyclo[11.3.1]heptadecane-2,5,8,11-tetraone; |
| 57 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-3-(pyridin-2-ylmethyl)-1,6,9,12-tetraazabicyclo[11.3.1]heptadecane-2,5,8,11-tetraone; |
| 58 | (3S, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-3-(2,2-difluoroethyl)-10-(hydroxymethyl)-7-methyl-1,4,6,9,12-pentaazabicyclo[11.3.1]heptadecane-2,5,8,11-tetraone; |
| 59 | (3R, 7S, 10S, 13R)-3-benzyl-6-(4-chloro-2-(4-(2-(((S)-3-hydroxypyrrolidin-1-yl)methyl)-1-methyl-1H-imidazol-5-yl)phenoxy)benzyl)-13-(4-chlorobenzyl)-10-(methoxymethyl)-7-methyl-1,6,9,12-tetraazabicyclo+11.3.1+heptadecane-2,5,8,11-tetraone; |
| 60 | (3S, 7S, 10S, 13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-1,4,6,9,12-pentaazabicyclo[11.3.1]heptadecane-2,5,8,11-tetraone; |

| Cmd No. | Compound Name |
|---|---|
| 61 | (3R, 7S, 10S, 13R)-3-benzyl-6-(4-chloro-2-(4-(24(4-hydroxypiperidin-1-yl)methyl)-1-methyl-1H-imidazol-5-yl)phenoxy)benzyl)-13-(4-chlorobenzyl)-10-(methoxymethyl)-7-methyl-1,6,9,12-tetraazabicyclo[11.3.1]heptadecane-2,5,8,11-tetraone; |
| 62 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-3-(4-(trifluoromethyl)benzyl)-1,6,9,12-tetraazabicyclo[11.3.1]heptadecane-2,5,8,11-tetraone; |
| 63 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-3-ethyl-10-(methoxymethyl)-7-methyl-1,6,9,12-tetraazabicyclo[11.3.1\heptadecane-2,5,8,11-tetraone; |
| 64 | (3S, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-((S)-1-hydroxyethyl)-7-methyl-3-(2,2,2-trifluoroethyl)-1,6,9,12-tetraazabicyclo[11.3.1]heptadecane-2,5,8,11-tetraone; |
| 65 | (3R, 7S, 10S, 13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7,12-dimethyl-1,6,9,12-tetraazabicyclo[11.3.]heptadecane-2,5,8,11-tetraone; |
| 66 | 2-(((3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-2,5,8,11-tetraoxo-1,6,9,12-tetraazabicyclo[11.3.1]heptadecan-3-yl)methyl)pyridine 1-oxide; |
| 67 | (3S, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-3-isopropyl-7-methyl-1,4,6,9,12-pentaazabicyclo[11.3.1]heptadecane-2,5,8,11-tetraone; |
| 68 | (3S, 7S, 10S, 13R)-6-(4-chloro-2-(4-(1-methyl-2-(pyrrolidin-1-yl-methyl)-1H-imidazol-5-yl)phenoxy)benzyl)-13-(4-chlorobenzyl)-3-((R)-2,3-dihydro-1H-inden-1-yl)-10-(hydroxymethyl)-7-methyl-1,6,9,12-tetraazabicyclo[11.3.1]heptadecane-2,5,8,11-tetraone; |
| 69 | (3S, 7S, 10S, 13R)-6-(4-chloro-2-(4-(1-methyl-2-(1-methylazetidin-3-yl)-1H-imidazol-5-yl)phenoxy)benzyl)-13-(4-chlorobenzyl)-3-((S)-2,3-dihydro-1H-inden-1-yl)-10-(hydroxymethyl)-7-methyl-1,6,9,12-tetraazabicyclo[11.3.1]heptadecane-2,5,8,11-tetraone; |
| 70 | (3S, 7S,10S, 13R)-6-(4-chloro-2-(4-(2-((R)-1-(dimethylamino)ethyl)-1-methyl-1H-imidazol-5-yl)phenoxy)benzyl)-13-(4-chlorobenzyl)-3-((S)-2,3-dihydro-1H-inden-1-yl)-10-(hydroxymethyl)-7-methyl-1,6,9,12-tetraazabicyclo[11.3.1]heptadecane-2,5,8,11-tetraone; |
| 71 | (3R, 7S, 10S, 13R)-3-benzyl-6-(4-chloro-2-((6-(2-((dimethylamino)methyl)-1-methyl-1H-imidazol-5-yl)pyridin-3-yl)oxy)benzyl)-13-(4-chlorobenzyl)-10-(hydroxymethyl)-7,12-dimethyl-1,6,9,12-tetraazabicyclo[11.3.1]heptadecane-2,5,8,11-tetraone; |
| 72 | (3R, 7S, 10S, 13R)-3-benzyl-6-(4-chloro-2-(4-(2-(((S)-3-(dimethylamino)pyrrolidin-1-yl)methyl)-1-methyl-1H-imidazol-5-yl)phenoxy)benzyl)-13-(4-chlorobenzyl)-10-(methoxymethyl)-7-methyl-1,6,9,12-tetraazabicyclo[11.3.1]heptadecane-2,5,8,11-tetraone; |
| 73 | (3S, 7S, 10S, 13R)-13-(4-chlorobenzyl)-34(S)-2,3-dihydro-1H-inden-1-yl)-6-(2-(4-(2-((dimethylamino)methyl)-1-methyl-1H-imidazol-5-yl)phenoxy)-5-fluorobenzyl)-10-(hydroxymethyl)-7-methyl-1,6,9,12-tetraazabicyclo[11.3.1]heptadecane-2,5,8,11-tetraone; |
| 73a | (3S, 7S, 10S, 13R)-13-(4-chlorobenzyl)-34(S)-2,3-dihydro-1H-inden-1-yl)-6-(2-(4-(2-((dimethylamino)methyl)-1-methyl-1H-imidazol-5-yl)phenoxy)-4-fluorobenzyl)-10-(hydroxymethyl)-7-methyl-1,6,9,12-tetraazabicyclo[11.3.1]heptadecane-2,5,8,11-tetraone; |
| 74 | (3S, 7S, 10S, 13R)-6-(4-chloro-2-(4-(1-methyl-2-(pyrrolidin-1-ylmethyl)-1H-imidazol-5-yl)phenoxy)benzyl)-13-(4-chlorobenzyl)-3-((S)-2,3-dihydro-1H-inden-1-yl)-10-(hydroxymethyl)-7-methyl-1,6,9,12-tetraazabicyclo[11.3.1]heptadecane-2,5,8,11-tetraone; |
| 75 | (3R, 7S, 10S, 13R)-3-benzyl-13-(4-chlorobenzyl)-6-(2,4-difluoro-6-(4-(1-methyl-2-(pyrrolidin-1-ylmethyl)-1H-imidazol-5-yl)phenoxy)benzyl)-10-(hydroxymethyl)-7-methyl-1,6,9,12-tetraazabicyclo[11.3.1]heptadecane-2,5,8,11-tetraone; |
| 76 | (3R, 7S, 10S, 13R)-3-benzyl-6-(4-chloro-2-(4-(1-methyl-2-((4-methylpiperazin-1-yl)methyl)-1H-imidazol-5-yl)phenoxy)benzyl)-13-(4-chlorobenzyl)-10-(methoxymethyl)-7-methyl-1,6,9,12-tetraazabicyclo[11.3.1]heptadecane-2,5,8,11-tetraone; |
| 77 | (3S, 7S, 10S, 13R)-6-(4-chloro-2-(4-(1-methyl-2-(1-methyl-2,5-dihydro-1H-pyrrol-3-yl)-1H-imidazol-5-yl)phenoxy)benzyl)-13-(4-chlorobenzyl)-3-((S)-2,3-dihydro-1H-inden-1-yl)-10-(hydroxymethyl)-7-methyl-1,6,9,12-tetraazabicyclo[11.3.1]heptadecane-2,5,8,11-teraone; |
| 78 | (3S, 7S, 10S, 13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-4-oxa-1,6,9,12-tetraazabicyclo[11.3.11]heptadecane-2,5,8,11-tetraone; |
| 79 | (3R, 7S, 10S, 13R)-3-benzyl-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-1,6,9,12-tetraazabicyclo[11.3.1]heptadecane-2,5,8,11-tetraone; |

| Cmd No. | Compound Name |
|---|---|
| 80 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7-methyl-3-(3-(trifluoromethyl)benzyl)-1,6,9,12-tetraazabicyclo[11.3.1]heptadecane-2,5,8,11-tetraone; |
| 81 | (2S, 5S, 8R, 12S)-1-(4-chloro-2-(4-(2-((dimethylamino)methyl)-1-methyl-1H-imidazol-5-yl)phenoxy)benzyl)-8-(4-chlorobenzyl)-5-(hydroxymethyl)-2,7,10-trimethyl-12-((1R,3S)-3-methyl-2,3-dihydro-1H-inden-1-yl)-1,4,7,10-tetraazacyclotetradecane-3,6,11,14-tetraone; |
| 82 | (3S, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-3-(2,2,2-trifluoroethyl)-1,6,9,12-tetraazabicyclo[11.3.1]heptadecane-2,5,8,11-tetraone; |
| 83 | (3S, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-3-(2,2,2-trifluoroethyl)-1,6,9,12-tetraazabicyclo[11.3.1]heptadecane-2,5,8,11-tetraone; |
| 84 | (3S, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-3-((S)-2,3-dihydro-1H-inden-1-yl)-10-(hydroxymethyl)-7-methyl-1,6,9,12-tetraazabicyclo[11.3.1]heptadecane-2,5,8,11-tetraone; |
| 85 | (3R, 7S, 10S, 13R)-3-benzyl-6-((5-chloro-34(6-(2-((dimethylamino)methyl)-1-methyl-1H-imidazol-5-yl)pyridin-3-yl)oxy)pyridin-2-yl)methyl)-13-(4-chlorobenzyl)-10-(methoxymethyl)-7,12-dimethyl-1,6,9,12-tetraazabicyclo[11.3.1]heptadecane-2,5,8,11-tetraone; |
| 86 | (2S, 5S, 8R, 12S)-1-(4-chloro-2-(4-(1-methyl-2-(pyrrolidin-1-ylmethyl)-1H-imidazol-5-yl)phenoxy)benzyl)-8-(4-chlorobenzyl)-12-((R)-2,3-dihydro-1H-inden-1-yl)-5-(hydroxymethyl)-2,7,10-trimethyl-1,4,7,10-tetraazacyclotetradecane-3,6,11,14-tetraone; |
| 87 | (3R, 7S, 10S, 13R)-3-benzyl-6-(4-chloro-2-(4-(2-((dimethylamino)methyl)-1-methyl-1H-imidazol-5-yl)-2-fluorophenoxy)-6-fluorobenzyl)-13-(4-chlorobenzyl)-10-(hydroxymethyl)-7-methyl-1,6,9,12-tetraazabicyclo[11.3.1]heptadecane-2,5,8,11-tetraone; |
| 88 | (3S, 7S, 10S, 13R)-6-(4-chloro-2-(4-(2-((dimethylamino)methyl)-1-ethyl-1H-imidazol-5-yl)phenoxy)-6-fluorobenzyl)-13-(4-chlorobenzyl)-10-(hydroxymethyl)-7-methyl-3-(2,2,2-trifluoroethyl)-1,6,9,12-tetraazabicyclo[11.3.1]heptadecane-2,5,8,11-tetraone; |
| 89 | (2S, 5S, 8R, 12R)-12-benzyl-1-(4-chloro-2-(4-(1-methyl-2-(pyrrolidin-1-ylmethyl)-1H-imidazol-5-yl)phenoxy)benzyl)-8-(4-chlorobenzyl)-5-(hydroxymethyl)-2,7-dimethyl-1,4,7,10-tetraazacyclotetradecane-3,6,11,14-tetraone; |
| 90 | (3S, 7S, 10S, 13R)-13-(4-chlorobenzyl)-34(S)-2,3-dihydro-1H-inden-1-yl)-6-(2-(4-(2-((dimethylamino)methyl)-1-methyl-1H-imidazol-5-yl)phenoxy)-5-(trifluoromethyl)benzyl)-10-(hydroxymethyl)-7-methyl-1,6,9,12-tetraazabicyclo[11.3.1]heptadecane-2,5,8,11-tetraone; |
| 90a | (3S, 7S, 10S, 13R)-13-(4-chlorobenzyl)-34(S)-2,3-dihydro-1H-inden-1-yl)-6-(2-(4-(2-((dimethylamino)methyl)-1-methyl-1H-imidazol-5-yl)phenoxy)-4-(trifluoromethyl)benzyl)-10-(hydroxymethyl)-7-methyl-1,6,9,12-tetraazabicyclo[11.3.1]heptadecane-2,5,8,11-tetraone; |
| 91 | (2S, 5S, 8R, 12S)-1-(4-chloro-2-(4-(2-((dimethylamino)methyl)-1-methyl-1H-imidazol-5-yl)phenoxy)benzyl)-8-(4-chlorobenzyl)-12-((R)-2,3-dihydro-1H-inden-1-yl)-5-(hydroxymethyl)-2,7,10-trimethyl-1,4,7,10-tetraazacyclotetradecane-3,6,11,14-tetraone; |
| 92 | (2S, 5S, 8R, 12R)-12-benzyl-1-(4-chloro-2-(4-(1-methyl-2-(pyrrolidin-1-ylmethyl)-1H-imidazol-5-yl)phenoxy)benzyl)-8-(4-chlorobenzyl)-5-(methoxymethyl)-2,7-dimethyl-1,4,7,10-tetraazacyclotetradecane-3,6,11,14-tetraone; |
| 93 | (2S, 5S, 8R, 12S)-1-(4-chloro-2-(4-(1-methyl-2-(pyrrolidin-1-ylmethyl)-1H-imidazol-5-yl)phenoxy)benzyl)-8-(4-chlorobenzyl)-5-(hydroxymethyl)-2,7,10-trimethyl-12-((1R, 3S)-3-methyl-2,3-dihydro-1H-inden-1-yl)-1,4,7,10-tetraazacyclotetradecane-3,6,11,14-tetraone; |
| 94 | (3R, 7S, 10S, 13R)-6-(4-chloro-2-((6-(2-((dimethylamino)methyl)-1-methyl-1H-imidazol-5-yl)pyridin-3-yl)oxy)benzyl)-13-(4-chlorobenzyl)-10-(methoxymethyl)-7,12-dimethyl-3-(pyridin-2-ylmethyl)-1,6,9,12-tetraazabicyclo[11.3.1]heptadecane-2,5,8,11-tetraone; |
| 95 | (3S, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-3-((S)-2,3-dihydro-1H-inden-1-yl)-10-(methoxymethyl)-7-methyl-1,6,9,12-tetraazabicyclo[11.3.1]heptadecane-2,5,8,11-tetraone; |
| 96 | (3S, 7S, 10S, 13R)-6-(4-chloro-2-(4-(1-methyl-2-(pyrrolidin-1-ylmethyl)-1H-imidazol-5-yl)phenoxy)benzyl)-13-(4-chlorobenzyl)-3-((R)-2,3-dihydro-1H-inden-1-yl)-10-(methoxymethyl)-7-methyl-1,6,9,12-tetraazabicyclo[11.3.1]heptadecane-2,5,8,11-tetraone; |
| 97 | (3S, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-((R)-1-hydroxyethyl)-7-methyl-3-(2,2,2-trifluoroethyl)-1,6,9,12-tetraazabicyclo[11.3.1]heptadecane-2,5,8,1-tetraone; |

-continued

| Cmd No. | Compound Name |
|---|---|
| 98 | (3R, 7S, 10S, 13R)-3-benzyl-13-(4-chlorobenzyl)-6-(2,4-dichloro-6-(4-(2-((dimethylamino)methyl)-1-methyl-1H-imidazol-5-yl)phenoxy)benzyl)-10-(hydroxymethyl)-7-methyl-1,6,9,12-tetraazabicyclo+11.3.111-tetraone; |
| 99 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-3,7,12-trimethyl-1,6,9,12-tetraazabicyclo+11.3.1+heptadecane-2,5,8,11-tetraone; |
| 100 | (3S, 10S, 13R)-6-(5-chloro-2-(4-(2-((dimethylamino)methyl)-1-methyl-1H-imidazol-5-yl)phenoxy)benzyl)-13-(4-chlorobenzyl)-3-((S)-2,3-dihydro-1H-inden-1-yl)-10-(hydroxymethyl)-1,6,9,12-tetraazabicyclo[11.3.1]heptadecane-2,5,8,11-tetraone; |
| 100a | (3S, 10S, 13R)-6-(4-chloro-2-(4-(2-((dimethylamino)methyl)-1-methyl-1H-imidazol-5-yl)phenoxy)benzyl)-13-(4-chlorobenzyl)-3-((S)-2,3-dihydro-1H-inden-1-yl)-10-(hydroxymethyl)-1,6,9,12-tetraazabicyclo[11.3.1]heptadecane-2,5,8,11-tetraone; |
| 101 | (2S, 5S, 8R, 12S)-1-(4-chloro-2-(4-(1-methyl-2-(pyrrolidin-1-ylmethyl)-1H-imidazol-5-yl)phenoxy)benzyl)-8-(4-chlorobenzyl)-12-((R)-2,3-dihydro-1H-inden-1-yl)-5-(methoxymethyl)-2,7,10-trimethyl-1,4,7,10-tetraazacyclotetradecane-3,6,11,14-tetraone; |
| 102 | (2S, 5S, 8R, 12S)-1-(4-chloro-2-(4-(1-methyl-2-(pyrrolidin-1-ylmethyl)-1H-imidazol-5-yl)phenoxy)benzyl)-8-(4-chlorobenzyl)-12-((R)-2,3-dihydrobenzofuran-3-yl)-5-(hydroxymethyl)-2,7,10-trimethyl-1,4,7,10-tetraazacyclotetradecane-3,6,11,14-tetraone; |
| 103 | (2S, 5S, 8R, 12S)-1-(4-chloro-2-(4-(1-methyl-2-(pyrrolidin-1-ylmethyl)-1H-imidazol-5-yl)phenoxy)benzyl)-8-(4-chlorobenzyl)-5-(hydroxymethyl)-12-((R)-7-methoxy-2,3-dihydrobenzofuran-3-yl)-2,7,10-trimethyl-1,4,7,10-tetraazacyclotetradecane-3,6,11,14-tetraone |
| 104 | (3S, 7S, 10S, 13R)-3-benzyl-6-(4-chloro-2-(4-(24(2-(2-ethoxyethoxy)ethoxy)methyl)-1-methyl-1H-imidazol-5-yl)phenoxy)benzyl)-13-(4-chlorobenzyl)-10-(hydroxymethyl)-7-methyl-1,4,6,9,12-pentaazabicyclo[11.3.1]heptadecane-2,5,8,11-tetraone; |
| 105 | (3R, 7S, 10S, 13R)-3-benzyl-6-(4-chloro-2-(4-(2-((dimethylamino)methyl)-1-methyl-1H-imidazol-5-yl)phenoxy)benzyl)-13-(4-chlorobenzyl)-7-(2-fluoroethyl)-10-(methoxymethyl)-1,6,9,12-tetraazabicyclo[11.3.1]heptadecane-2,5,8,11-tetraone; |
| 106 | (2S, 5S, 8R, 12R)-12-benzyl-1-(4-chloro-2-(3,5-difluoro-4-(1-methyl-2-(pyrrolidin-1-ylmethyl)-1H-imidazol-5-yl)phenoxy)benzyl)-8-(4-chlorobenzyl)-5-(hydroxymethyl)-2,7,10-trimethyl-1,4,7,10-tetraazacyclotetradecane-3,6,11,14-tetraone; |
| 107 | (2S, 5S, 8R, 12S)-1-(4-chloro-2-(4-(1-methyl-2-(pyrrolidin-1-ylmethyl)-1H-imidazol-5-yl)phenoxy)benzyl)-8-(4-chlorobenzyl)-5-(hydroxymethyl)-2,7,10-trimethyl-12-((R)-1-phenylethyl)-1,4,7,10-tetraazacyclotetradecane-3,6,11,14-tetraone |
| 108 | (2S, 5S, 8R, 12R)-12-benzyl-1-(4-chloro-2-(4-(1-methyl-2-(pyrrolidin-1-ylmethyl)-1H-imidazol-5-yl)phenoxy)benzyl)-8-(4-chlorobenzyl)-5-(hydroxymethyl)-2,7,10-trimethyl-1,4,7, 10-tetraazacyclotetradecane-3,6,11,14-tetraone; |
| 109 | (3R, 7S, 10S, 13R)-3-benzyl-6-(4-chloro-2-(4-(2-((dimethylamino)methyl)-1-methyl-1H-imidazol-5-yl)phenoxy)benzyl)-13-(4-chlorobenzyl)-10-((S)-1-hydroxyethyl)-7-methyl-1,6,9,12-tetraazabicyclo[11.3.1]heptadecane-2,5,8,11-tetraone; |
| 110 | (2S, 5S, 8R, 12S)-1-(4-chloro-2-(4-(1-methyl-2-(pyrrolidin-1-ylmethyl)-1H-imidazol-5-yl)phenoxy)benzyl)-8-(4-chlorobenzyl)-12-((R)-7-methoxy-2,3-dihydrobenzofuran-3-yl)-5-(methoxymethyl)-2,7,10-trimethyl-1,4,7,10-tetraazacyclotetradecane-3,6,11,14-tetraone; |
| 111 | (2S, 5S, 8R, 12S)-1-(4-chloro-2-(4-(1-methyl-2-(pyrrolidin-1-ylmethyl)-1H-imidazol-5-yl)phenoxy)benzyl)-8-(4-chlorobenzyl)-12-((R)-3,3-dimethyl-2,3-dihydro-1H-inden-1-yl)-5-(methoxymethyl)-2,7,10-trimethyl-1,4,7,10-tetraazacyclotetradecane-3,6,11,14-tetraone; |
| 112 | (2S, 5S, 8R, 12R)-1-(4-chloro-2-(4-(1-methyl-2-(pyrrolidin-1-ylmethyl)-1H-imidazol-5-yl)phenoxy)-6-(2,2,2-trifluoroethoxy)benzyl)-8-(4-chlorobenzyl)-12-ethyl-5-(hydroxymethyl)-2,7-dimethyl-1,4,7,10-tetraazacyclotetradecane-3,6,11,14-tetraone; |
| 113 | (2S, 5S, 8R, 12S)-1-(4-chloro-2-(4-(1-methyl-2-(pyrrolidin-1-ylmethyl)-1H-imidazol-5-yl)phenoxy)benzyl)-8-(4-chlorobenzyl)-10-(3,3-difluoropropyl)-124(R)-2,3-dihydro-1H-inden-1-yl)-5-(methoxymethyl)-2,7-dimethyl-1,4,7,10-tetraazacyclotetradecane-3,6,11,14-tetraone; |
| 114 | (2S, 5S, 8R, 12R)-12-benzyl-1-(4-chloro-2-(4-(1-methyl-2-(pyrrolidin-1-ylmethyl)-1H-imidazol-5-yl)phenoxy)benzyl)-8-(4-chlorobenzyl)-5-(methoxymethyl)-2,7,10-trimethyl-1,4,7,10-tetraazacyclotetradecane-3,6,11,14-tetraone; |
| 115 | (2S, 5S, 8R, 12S)-1-(4-chloro-2-(4-(1-methyl-2-(pyrrolidin-1-ylmethyl)-1H-imidazol-5-yl)phenoxy)benzyl)-8-(4-chlorobenzyl)-12-((R)-2,3-dihydro-1H-inden-1-yI)-5-(methoxymethyl)-2,7-dimethyl-10-((1-methylcyclopropyl)methyl)-1,4,7,10-tetraazacyclotetradecane-3,6,11,14-tetraone; |
| 116 | (2S, 5S, 8R, 12R)-12-benzyl-1-(4-chloro-2-(4-(1-methyl-2-(pyrrolidin-1-ylmethyl)-1H-imidazol-5-yl)phenoxy)benzyl)-8-(4-chlorobenzyl)-10-(3-(dimethylamino)propyl)-5-(methoxymethyl)-2,7-dimethyl-1,4,7,10-tetraazacyclotetradecane-3,6,11,14-tetraone; |
| 117 | (2S, 5S, 8R, 12R)-12-benzyl-1-(4-chloro-2-(3,5-difluoro-4-(1-methyl-2-(pyrrolidin-1-ylmethyl)-1H-imidazol-5-yl)phenoxy)benzyl)-8-(4-chlorobenzyl)-5-(methoxymethyl)-2,7,10-trimethyl-1,4,7,10-tetraazacyclotetradecane-3,6,11,14-tetraone; |

-continued

| Cmd No. | Compound Name |
|---|---|
| 118 | (2S, 5S, 8S, 12S)-8-(4-chlorobenzyl)-12-((S)-2,3-dihydro-1H-inden-1-yl)-1-(2-(4-(2-((dimethylamino)methyl)-1-methyl-1H-imidazol-5-yl)phenoxy)-4-ethylbenzyl)-5-(hydroxymethyl)-2,7,10-trimethyl-1,4,7,10-tetraazacyclotetradecane-3,6,11,14-tetraone; |
| 119 | (2S, 5S, 8R, 12S)-8-(4-chlorobenzyl)-12-((S)-2,3-dihydro-1H-inden-1-yl)-1-(2-(4-(2-((dimethylamino)methyl)-1-methyl-1H-imidazol-5-yl)phenoxy)-4-ethylbenzyl)-5-(hydroxymethyl)-2,7,10-trimethyl-1,4,7,10-tetraazacyclotetradecane-3,6,11,14-tetraone; |
| 120 | (3R, 7S, 10S, 13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7-methyl-1,6,9,12-tetraazabicyclo[11.3.1]heptadecane-2,8,11-trione; |
| 121 | (2S, 5R, 8R, 12S)-8-(4-chlorobenzyl)-124(S)-2,3-dihydro-1H-inden-1-yl)-1-(2-(4-(2-((dimethylamino)methyl)-1-methyl-1H-imidazol-5-yl)phenoxy)-4-ethylbenzyl)-5-(hydroxymethyl)-2,7,10-trimethyl-1,4,7,10-tetraazacyclotetradecane-3,6,11,14-tetraone; |
| 122 | (3R, 7S, 10R, 13R)-3-benzyl-6-(4-chloro-2-((6-(2-((dimethylamino)methyl)-1-methyl-1H-imidazol-5-yl)pyridin-3-yl)oxy)benzyl)-13-(4-chlorobenzyl)-10-(methoxymethyl)-7-methyl-1,6,9,12-tetraazabicyclo[11.3.1]heptadecane-2,5,8,11-tetraone; |
| 123 | (3S, 10S, 13R)-13-(4-chlorobenzyl)-3-((S)-2,3-dihydro-1H-inden-1-yl)-6-(4-(4-(2-((dimethylamino)methyl)-1-methyl-1H-imidazol-5-yl)phenoxy)-2-fluorobenzyl)-10-(hydroxymethyl)-1,6,9,12-tetraazabicyclo[11.3.1]heptadecane-2,5,8,11-tetraone; |
| 123a | (3S, 7S, 10S, 13R)-13-(4-chlorobenzyl)-34(S)-2,3-dihydro-1H-inden-1-yl)-6-(4-(4-(2-((dimethylamino)methyl)-1-methyl-1H-imidazol-5-yl)phenoxy)-2-fluorobenzyl)-10-(hydroxymethyl)-7-methyl-1,6,9,12-tetraazabicyclo[11.3.1]heptadecane-2,5,8,11-tetraone; |
| 124 | (2S, 5S, 8R, 12R)-1-(4-chloro-2-(4-(1-methyl-2-(pyrrolidin-1-ylmethyl)-1H-imidazol-5-yl)phenoxy)benzyl)-8-(4-chlorobenzyl)-12-ethyl-5-(hydroxymethyl)-2,7-dimethyl-1,4,7,10-tetraazacyclotetradecane-3,6,11,14-tetraone; |
| 125 | (2S, 5S, 8R, 12S)-1-(4-chloro-2-(4-(2-((dimethylamino)methyl)-1-methyl-1H-imidazol-5-yl)phenoxy)benzyl)-8-(4-chlorobenzyl)-12-((R)-2,3-dihydro-1H-inden-1-yl)-5-(methoxymethyl)-7,10-dimethyl-2-(2-morpholinoethyl)-1,4,7,10-tetraazacyclotetradecane-3,6,11,14-tetraone; |
| 126 | (2S)-N-((3R, 8S, 11R)-3-benzyl-11-(4-chlorobenzyl)-10-methyl-2,5,9-trioxo-6-oxa-1,10-diazabicyclo[9.3.1]pentadecan-8-yl)-2-((4-chloro-2-(4-(2-((dimethylamino)methyl)-1-methyl-1H-imidazol-5-yl)phenoxy)benzyl)amino)propanamide; |
| 127 | (2S, 5S, 8R, 12S)-1-(4-chloro-2-(4-(2-((dimethylamino)methyl)-1-methyl-1H-imidazol-5-yl)phenoxy)benzyl)-8-(4-chlorobenzyl)-12-((R)-2,3-dihydro-1H-inden-1-yl)-5-(methoxymethyl)-7,10-dimethyl-2-(3-morpholinopropyl)-1,4,7,10-tetraazacyclotetradecane-3,6,11,14-tetraone; |
| 128 | (2S, 5S, 8R, 12R)-1-(4-chloro-2-(4-(1-methyl-2-(pyrrolidin-1-ylmethyl)-1H-imidazol-5-yl)phenoxy)benzyl)-8-(4-chlorobenzyl)-12-ethyl-5-(hydroxymethyl)-2,7,10-trimethyl-1,4,7, 10-tetraazacyclotetradecane-3,6,11,114-tetraone; |
| 129 | (2S, 5S, 8R, 12R)-12-benzyl-1-(4-chloro-2-(4-(1-methyl-2-(pyrrolidin-1-ylmethyl)-1H-imidazol-5-yl)phenoxy)benzyl)-8-(4-chlorobenzyl)-2,7,10-trimethyl-5-(2-oxopropyl)-1,4,7,10-tetraazacyclotetradecane-3,6,11,14-tetraone; |
| 130 | (2S)-N-((3S, 8R, 11R)-8-benzyl-11-(4-chlorobenzyl)-10-methyl-2,6,9-trioxo-5-oxa-1,10-diazabicyclo[9.3.1]pentadecan-3-yl)-2-((4-chloro-2-(4-(2-((dimethylamino)methyl)-1-methyl-1H-imidazol-5-yl)phenoxy)benzyl)amino)propanamide; |
| 131 | (2S, 5S, 8R, 12S)-1-(4-chloro-2-(4-(2-((dimethylamino)methyl)-1-methyl-1H-imidazol-5-yl)phenoxy)benzyl)-8-(4-chlorobenzyl)-12-((R)-2,3-dihydro-1H-inden-1-yl)-5-(methoxymethyl)-7,10-dimethyl-2-(4-morpholinobutyl)-1,4,7,10-tetraazacyclotetradecane-3,6,11,14-tetraone; |
| 132 | (2S, 5S, 8R, 12S)-2-(3-(azetidin-1-yl)-3-oxopropyl)-1-(4-chloro-2-(4-(1-methyl-2-(pyrrolidin-1-ylmethyl)-1H-imidazol-5-yl)phenoxy)benzyl)-8-(4-chlorobenzyl)-12-((R)-3,3-dimethyl-2,3-dihydro-1H-inden-1-yl)-5-(methoxymethyl)-7,10-dimethyl-1,4,7,10-tetraazacyclotetradecane-3,6,11,14-tetraone; |
| 133 | (3R, 7S, 10S, 13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-3-isopropyl-7-methyl-1,6,9,12-tetraazabicyclo[11.3.1]heptadecane-2,5,8,11-tetraone; |
| 134 | (2S, 5S, 8R, 12R)-1-(4-chloro-2-(4-(1-methyl-2-(pyrrolidin-1-ylmethyl)-1H-imidazol-5-yl)phenoxy)benzyl)-8-(4-chlorobenzyl)-12-(dimethylamino)-5-(methoxymethyl)-2,7,10-trimethyl-1,4,7,10-tetraazacyclotetradecane-3,6,11,14-tetraone; |
| 135 | 2-((2S, 5S, 8R, 12R)-12-benzyl-1-(4-chloro-2-(4-(1-methyl-2-(pyrrolidin-1-ylmethyl)-1H-imidazol-5-yl)phenoxy)benzyl)-8-(4-chlorobenzyl)-2,7,10-trimethyl-3,6,11,14-tetraoxo-1,4,7,10-tetraazacyclotetradecan-5-yl)acetic acid |
| 136 | (3S, 7S, 10S, 13R)-6-(2-(4-(2-((tert-butylamino)methyl)-1-methyl-1H-imidazol-5-yl)phenoxy)-4-chloro-6-fluorobenzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone; |

| Cmd No. | Compound Name |
|---|---|
| 137 | (3S, 7S, 10S, 13R)-6-(2-(4-(2-((tert-butyl(methyl)amino)methyl)-1-methyl-1H-imidazol-5-yl)phenoxy)-4-chloro-6-fluorobenzyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone; |
| 138 | (3S, 7S, 10S, 13R)-6-(2-(4-(2-((tert-butylamino)methyl)-1-methyl-1H-imidazol-5-yl)phenoxy)-4-chloro-6-fluorobenzyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone; |
| 139 | (3S, 7S, 10S, 13R)-6-(4-chloro-2-(4-(2-((cyclobutyl(methyl)amino)methyl)-1-methyl-1H-imidazol-5-yl)phenoxy)-6-fluorobenzyl)-13-(4-chlorobenzyl)-10-(hydroxymethyl)-7-methyl-3-(2,2,2-trifluoroethyl)-1,6,9,12-tetraazabicyclo[11.3.1]heptadecane-2,5,8,11-tetraone; |
| 140 | (3S, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-3-cyclobutyl-10-(methoxymethyl)-7,12-dimethyl-1,6,9,12-tetraazabicyclo[11.3.1]heptadecane-2,5,8,11-tetraone; |
| 141 | (3S, 7S, 10S, 13R)-6-(2-(4-(2-((tert-butyl(methyl)amino)methyl)-1-methyl-1H-imidazol-5-yl)phenoxy)-4-chloro-6-fluorobenzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone; |
| 142 | (3R, 7S, 10S, 13R)-6-(2-(4-(2-((tert-butylamino)methyl)-1-methyl-1H-imidazol-5-yl)phenoxy)-4-chloro-6-fluorobenzyl)-13-(4-chlorobenzyl)-3-(cyclopropylmethyl)-10-(methoxymethyl)-7-methyl-1,6,9,12-tetraazabicyclo[11.3.1]heptadecane-2,5,8,11-tetraone; |
| 143 | (3S, 7S, 10S, 13R)-6-(2-(4-(2-((tert-butyl(methyl)amino)methyl)-1-methyl-1H-imidazol-5-yl)phenoxy)-4-chlorobenzyl)-13-(4-chlorobenzyl)-10-(hydroxymethyl)-7-methyl-3-(2,2,2-trifluoroethyl)-1,6,9,12-tetraazabicyclo[11.3.1]heptadecane-2,5,8,11-tetraone; |
| 144 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7-methyl-3-((1-methylcyclopropyl)methyl)-1,6,9,12-tetraazabicyclo[11.3.1]heptadecane-2,5,8,11-tetraone; |
| 145 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-3-(cyclopropylmethyl)-10-(hydroxymethyl)-7-methyl-1,6,9,12-tetraazabicyclo[11.3.1]heptadecane-2,5,8,11-tetraone; |
| 146 | (3S, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-3-(2,2-difluoropropyl)-10-(hydroxymethyl)-7-methyl-1,6,9,12-tetraazabicyclo[11.3.1]heptadecane-2,5,8,11-tetraone; |
| 147 | (3S, 7S, 10S, 13R)-6-(2-(4-(2-((tert-butylamino)methyl)-1-methyl-1H-imidazol-5-yl)phenoxy)-4-chlorobenzyl)-13-(4-chlorobenzyl)-10-(hydroxymethyl)-7-methyl-3-(2,2,2-trifluoroethyl)-1,6,9,12-tetraazabicyclo[11.3.1]heptadecane-2,5,8,11-tetraone; |
| 148 | (3R, 7S, 10S, 13R)-6-(2-(4-(2-((tert-butylamino)methyl)-1-methyl-1H-imidazol-5-yl)phenoxy)-4-chlorobenzyl)-13-(4-chlorobenzyl)-3-(cyclopropylmethyl)-10-(hydroxymethyl)-7-methyl-1,6,9,12-tetraazabicyclo[11.3.1]heptadecane-2,5,8,11-tetraone; |
| 149 | (3R, 7S, 10S, 13R)-3-benzyl-6-(2-(4-(2-((tert-butylamino)methyl)-1-methyl-1H-imidazol-5-yl)phenoxy)-4-chlorobenzyl)-13-(4-chlorobenzyl)-10-(methoxymethyl)-7-methyl-1,6,9,12-tetraazabicyclo[11.3.1]heptadecane-2,5,8,11-tetraone; |
| 150 | (3R, 7S, 10S, 13R)-3-benzyl-6-(4-chloro-2-(4-(1-methyl-2-((methylamino)methyl)-1H-imidazol-5-yl)phenoxy)benzyl)-13-(4-chlorobenzyl)-10-(hydroxymethyl)-7-methyl-1,6,9, 12-tetraazabicyclo[11.3.1]heptadecane-2,5,8,11-tetraone; |
| 151 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-3-(2,2,2-trifluoroethyl)-1,6,9,12-tetraazabicyclo[11.3.1]heptadecane-2,5,8,11-tetraone; |
| 152 | (3S, 7S, 10S, 13R)-6-(4-chloro-2-(4-(2-((ethyl(1-methylcyclopropyl)amino)methyl)-1-methyl-1H-imidazol-5-yl)phenoxy)-6-fluorobenzyl)-13-(4-chlorobenzyl)-10-(hydroxymethyl)-7-methyl-3-(2,2,2-trifluoroethyl)-1,6,9,12-tetraazabicyclo[11.3.1]heptadecane-2,5,8,11-tetraone; |
| 153 | (3R, 7S, 10S, 13R)-6-(4-chloro-2-(4-(2-((cyclobutylamino)methyl)-1-methyl-1H-imidazol-5-yl)phenoxy)-6-fluorobenzyl)-13-(4-chlorobenzyl)-3-(cyclopropylmethyl)-10-(hydroxymethyl)-7-methyl-1,6,9,12-tetraazabicyclo[11.3.1]heptadecane-2,5,8,11-tetraone; |
| 154 | (3R, 7S, 10S, 13R)-6-(2-(4-(2-((tert-butylamino)methyl)-1-methyl-1H-imidazol-5-yl)phenoxy)-4-chloro-6-fluorobenzyl)-13-(4-chlorobenzyl)-3-(cyclopropylmethyl)-10-(hydroxymethyl)-7-methyl-1,6,9,12-tetraazabicyclo[11.3.1]heptadecane-2,5,8,11-tetraone; |
| 155 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-3-(cyclobutylmethyl)-10-(hydroxymethyl)-7-methyl-1,6,9,12-tetraazabicyclo[11.3.1]heptadecane-2,5,8,11-tetraone; |

| Cmd No. | Compound Name |
|---|---|
| 156 | (3S, 7S, 10S, 13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7-methyl-4-oxa-1,6,9,12-tetraazabicyclo[11.3.1]heptadecane-2,5,8,11-tetraone; |
| 157 | (3S, 7S, 10S, 13R)-6-(2-(4-(2-(azetidin-1-ylmethyl)-1-methyl-1H-imidazol-5-yl)phenoxy)-4-chloro-6-fluorobenzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone; |
| 158 | (3S, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-3-(2,2-difluoropropyl)-10-(methoxymethyl)-7,12-dimethyl-1,6,9,12-tetraazabicyclo[11.3.1]heptadecane-2,5,8,11-tetraone; |
| 159 | (3R, 7S, 10S, 13R)-3-benzyl-6-(4-chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-1,6,9,12-tetraazabicyclo[11.3.1]heptadecane-2,5,8,11-tetraone; |
| 160 | (3S, 7S, 10S, 13R)-6-(4-chloro-2-(4-(2-((cyclobutyl(methyl)amino)methyl)-1-methyl-1H-imidazol-5-yl)phenoxy)-6-fluorobenzyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone; |
| 161 | (3S, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-3-(3,3-difluorocyclobutyl)-10-(hydroxymethyl)-7-methyl-1,6,9,12-tetraazabicyclo[11.3.1]heptadecane-2,5,8,11-tetraone; |
| 162 | (3R, 7S, 10S, 13R)-6-(2-(4-(2-((tert-butyl(methyl)amino)methyl)-1-methyl-1H-imidazol-5-yl)phenoxy)-4-chlorobenzyl)-13-(4-chlorobenzyl)-3-(cyclopropylmethyl)-10-(hydroxymethyl)-7-methyl-1,6,9,12-tetraazabicyclo[11.3.1]heptadecane-2,5,8,11-tetraone; |
| 163 | (3R, 7S, 10S, 13R)-6-(2-(4-(2-((tert-butyl(methyl)amino)methyl)-1-methyl-1H-imidazol-5-yl)phenoxy)-4-chloro-6-fluorobenzyl)-13-(4-chlorobenzyl)-3-(cyclopropylmethyl)-10-(hydroxymethyl)-7-methyl-1,6,9,12-tetraazabicyclo[11.3.1]heptadecane-2,5,8,11-tetraone; |
| 164 | (3S, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-3-(3,3-difluorocyclobutyl)-10-(hydroxymethyl)-7,12-dimethyl-1,6,9,12-tetraazabicyclo[11.3.1]heptadecane-2,5,8,11-tetraone; |
| 165 | (3S, 7S, 10S, 13R)-6-(2-(4-(2-((tert-butylamino)methyl)-1-methyl-1H-imidazol-5-yl)phenoxy)-4-chloro-6-fluorobenzyI)-13-(4-chlorobenzyl)-3-(3,3-difluorocyclobutyl)-10-(methoxymethyl)-7,12-dimethyl-1,6,9,12-tetraazabicyclo[11.3.1]-2,5,8,11-tetraone; |
| 166 | (3S, 7S, 10S, 13R)-6-(2-(4-(2-(aminomethyl)-1-methyl-1H-imidazol-5-yl)phenoxy)-4-chloro-6-fluorobenzyl)-13-(4-chlorobenzyl)-3-(3,3-difluorocyclobutyl)-10-(methoxymethyl)-7,12-dimethyl-1,6,9,12-tetraazabicyclo[11.3.1]heptadecane-2,5,8,11-tetraone; |
| 167 | (3R, 7S, 10S, 13R)-6-(4-chloro-2-fluoro-6-(4-(1-methyl-2-((methylamino)methyl)-1H-imidazol-5-yl)phenoxy)benzyl)-13-(4-chlorobenzyl)-10-(methoxymethyl)-7,12-dimethyl-3-((6-methylpyridin-2-yl)methyl)-1,6,9,12-tetraazabicyclo[11.3.1]heptadecane-2,5,8,11-tetraone; |
| 168 | 2-(((3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-2,5,8,11-tetraoxo-1,6,9,12-tetraazabicyclo[11.3.1]heptadecan-3-yl)methyl)-6-methylpyridine 1-oxide; |
| 169 | (3S, 7S, 10S, 13R)-6-(2-(4-(2-((tert-butyl(methyl)amino)methyl)-1-methyl-1H-imidazol-5-yl)phenoxy)-4-chloro-6-fluorobenzyl)-13-(4-chlorobenzyl)-3-(3,3-difluorocyclobutyl)-10-(methoxymethyl)-7,12-dimethyl-1,6,9,12-tetraazabicyclo[11.3.1]heptadecane-2,5,8,11-tetraone; |
| 170 | (3R, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-3-((6-methylpyridin-2-yl)methyl)-1,6,9,12-tetraazabicyclo[11.3.1]heptadecane-2,5,8,11-tetraone; |
| 171 | (3S, 7S, 10S, 13R)-6-(4-chloro-2-((6-(2-((dimethylamino)methyl)-1-methyl-1H-imidazol-5-yl)pyridin-3-yl)oxy)-6-(fluorobenzyl)-13-(4-chlorobenzyl)-3-(3,3-difluorocyclobutyl)-10-(methoxymethyl)-7,12-dimethyl-1,6,9,12-tetraazabicyclo[11.3.1]heptadecane-2,5,8,11-tetraone; |
| 172 | (3S, 7S, 10S, 13R)-6-(4-chloro-2-fluoro-6-(4-(1-methyl-2-((methylamino)methyl)-1H-imidazol-5-yl)phenoxy)benzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone; |
| 173 | (3S, 7S, 10S, 13R)-6-(4-chloro-2-((6-(2-((dimethylamino)methyl)-1-methyl-1H-imidazol-5-Apyridin-3-yl)oxy)-6-fluorobenzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone; |
| 174 | (3S, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-3-(tetrahydro-2H-pyran-4-yl)-1,6,9,12-tetraazabicyclo[11.3.1]heptadecane-2,5,8,11-tetraone; |

| Cmd No. | Compound Name |
|---|---|
| 175 | (3S, 7S, 10S, 13R)-6-(4-chloro-2-(4-(2-((dimethylamino)methyl)-1-methyl-1H-imidazol-5-yl)phenoxy)-6-fluorobenzyl)-13-(4-chlorobenzyl)-10-((difluoromethoxy)methyl)-7,12-dimethyl-3-(2,2,2-trifluoroethyl)-1,6,9,12-tetraazabicyclo[11.3.1]heptadecane-2,5,8,11-tetraone; |
| 176 | (3S, 7R, 10S, 13R)-6-(4-chloro-2-((6-(2-((dimethylamino)methyl)-1-methyl-1H-imidazol-5-yl)pyridin-3-yl)oxy)-6-fluorobenzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone; |
| 177 | (3S, 7S, 10S, 13R)-6-(4-chloro-2-fluoro-6-(4-(1-methyl-2-((methylamino)methyl)-1H-imidazol-5-yl)phenoxy)benzyl)-13-(4-chlorobenzyl)-10-(hydroxymethyl)-7,12-dimethyl-3-(2,2,2-trifluoroethyl)-1,6,9,12-tetraazabicyclo[11.3.1]heptadecane-2,5,8,11-tetraone; and |
| 178 | (3R, 7S, 10S, 13R)-7-(2-aminoethyl)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-1,6,9,12-tetraazabicyclo[11.3.1]heptadecane-2,5,8,11-tetraone. |

Embodiment 21. A pharmaceutical composition comprising a therapeutically effective amount of a compound according to any one of Embodiments 1-20, or a pharmaceutically acceptable salt thereof, and one or more pharmaceutically acceptable carriers or excipients.

Embodiment 22. A combination comprising a compound according to any one of Embodiments 1-20, or a pharmaceutically acceptable salt thereof, and one or more additional therapeutically active agents.

Embodiment 23. The combination according to Embodiment 22, wherein the additional therapeutically active agent is a statin.

Embodiment 24. The pharmaceutical composition according to Embodiment 21 or combination according to Embodiment 22 or 23, for use in the treatment, prevention, amelioration, or delay in the progression of a PCSK9-mediated disease or disorder.

Embodiment 25. The pharmaceutical composition or the combination according to Embodiment 24, wherein said PCSK9-mediated disease or disorder or the disease or disorder requiring inhibition of PCSK9 activity is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

Embodiment 26. A method of modulating PCSK9 comprising administering to a patient in need thereof a compound of any one of Embodiments 1-20, or a pharmaceutically acceptable salt thereof.

Embodiment 27. A method of inhibiting PCSK9 comprising administering to a patient in need thereof a compound of any one of Embodiments 1-20, or a pharmaceutically acceptable salt thereof.

Embodiment 28. A method for treating, preventing, ameliorating or delaying the progression of a PCSK9-mediated disease or disorder comprising the step of administering to a patient in need thereof a therapeutically effective amount of a compound according to any one of Embodiments 1-20, or a pharmaceutically acceptable salt thereof.

Embodiment 29. The method of Embodiment 28, wherein said PCSK9-mediated disease or disorder is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

Embodiment 30. A method of (i) reducing Lp(a), (ii) reducing Lp(a) plasma levels, (iii) reducing Lp(a) serum levels, (iv) reducing serum TRL or LDL levels, (v) reducing serum triglyceride levels, (vi) reducing LDL-C, (vii) reducing total plasma apoB concentrations, (viii) reducing LDL apoB, (ix) reducing TRL apoB, or (x) reducing non HDL-C, the method comprising administering to a patient in need thereof a therapeutically effective amount of a compound of any one of Embodiments 1-20, or a pharmaceutically acceptable salt thereof to the patient, thereby reducing LDL-C in the patient.

Embodiment 31. The method of any one Embodiments 26-30, wherein administering is performed orally, parentally, subcutaneously, by injection, or by infusion.

Embodiment 32. A compound according to any one of Embodiments 1-20, or a pharmaceutically acceptable salt thereof, for use in the treatment of a PCSK9-mediated disease or disorder.

Embodiment 33. A compound according to any one of Embodiments 1-20, or a pharmaceutically acceptable salt thereof, for use in the treatment, prevention, amelioration or delay of progression or for use in the treatment, prevention, amelioration or delay of progression of a disease or disorder requiring inhibition of PCSK9.

Embodiment 34. Use of a compound according to any one of Embodiments 1-20, or a pharmaceutically acceptable salt thereof, for the treatment, prevention, amelioration or delay of progression of a PCSK9-mediated disease or disorder or for the treatment, prevention, amelioration or delay of progression of a disease or disorder requiring inhibition of PCSK9.

Embodiment 35. Use of a compound according to any one of Embodiments 1-20, or a pharmaceutically acceptable salt thereof, in the manufacture of a medicament for the treatment, prevention, amelioration or delay of progression of a PCSK9-mediated disease or disorder or for the treatment, prevention, amelioration or delay of progression of a disease or disorder requiring inhibition of PCSK9.

Embodiment 36. A method for treating, preventing, ameliorating or delaying the progression of a PCSK9-mediated disease or disorder or of disease or disorder requiring inhibition of PCSK9 or of PCSK9 activity comprising the step of administering to a patient in need thereof a therapeutically effective amount of a compound according to any one of Embodiments 1-20, or a pharmaceutically acceptable salt thereof.

Embodiment 37. The compound for use according to Embodiment 33, the use of a compound according to Embodiment 34 or 35, or the method for according to Embodiment 36, wherein said PCSK9-mediated disease or disorder or the disease or disorder requiring inhibition of PCSK9 is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

Embodiment 38. The compound according to Embodiment 1 selected from:
(3R,7S,10S,13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7,12-dimethyl-3-(pyridin-2-ylmethyl)-1,6,9,12-tetraazabicyclo[11.3.1]heptadecane-2,5,8,11-tetraone;
(3R,7S,10S,13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-3-(pyridin-2-ylmethyl)-1,6,9,12-tetraazabicyclo[11.3.1]heptadecane-2,5,8,11-tetraone;
(3R,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-1,6,9,12-tetraazabicyclo[11.3.1]heptadecane-2,5,8,11-tetraone;
(3S,7S,10S,13R)-6-(4-chloro-2-(4-(2-((dimethylamino)methyl)-1-methyl-1H-imidazol-5-yl)phenoxy)-6-fluorobenzyl)-13-(4-chlorobenzyl)-3-((S)-2,3-dihydro-1H-inden-1-yl)-10-(hydroxymethyl)-7-methyl-1,6,9,12-tetraazabicyclo[11.3.1]heptadecane-2,5,8,11-tetraone;
(3R,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7,12-dimethyl-1,6,9,12-tetraazabicyclo[11.3.1]heptadecane-2,5,8,11-tetraone;
(3R,7S,10S,13R)-3-benzyl-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7-methyl-1,6,9,12-tetraazabicyclo[11.3.1]heptadecane-2,5,8,11-tetraone;
(3R,7S,10S,13R)-3-benzyl-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-1,6,9,12-tetraazabicyclo[11.3.1]heptadecane-2,5,8,11-tetraone;
(3S,7S,10S,13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone;
(3S,7S,10S,13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-3-(2,2,2-trifluoroethyl)-1,6,9,12-tetraazabicyclo[11.3.1]heptadecane-2,5,8,11-tetraone;
(3S,7S,10S,13R)-6-(4-chloro-2-fluoro-6-(4-(1-methyl-2-((methylamino)methyl)-1H-imidazol-5-yl)phenoxy)benzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone; and
(3S,7S,10S,13R)-6-(4-chloro-2-fluoro-6-(4-(1-methyl-2-((methylamino)methyl)-1H-imidazol-5-yl)phenoxy)benzyl)-13-(4-chlorobenzyl)-10-(hydroxymethyl)-7,12-dimethyl-3-(2,2,2-trifluoroethyl)-1,6,9,12-tetraazabicyclo[11.3.1]heptadecane-2,5,8,11-tetraone;
or a pharmaceutically acceptable salt, hydrate, solvate, prodrug, stereoisomer, N-oxide, or tautomer thereof.

Embodiment 39. A pharmaceutical composition comprising a therapeutically effective amount of a compound according to any one of Embodiments 1-20 and Embodiment 38, or a pharmaceutically acceptable salt thereof, and a pharmaceutically acceptable carrier or excipient.

Embodiment 40. The pharmaceutical composition of Embodiment 39 further comprising at least one additional pharmaceutical agent.

Embodiment 41. The pharmaceutical composition of Embodiment 39 or Embodiment 40 for use in the treatment of a PCSK9-mediated disease or disorder.

Embodiment 42. A method of modulating PCSK9 comprising administering to a patient in need thereof a compound of any one of Embodiments 1-20 and Embodiment 38, or a pharmaceutically acceptable salt thereof.

Embodiment 43. A method of inhibiting PCSK9 comprising administering to a patient in need thereof a compound of any one of Embodiments 1-20 and Embodiment 38, or a pharmaceutically acceptable salt thereof.

Embodiment 44. A method of inhibiting PCSK9 activity comprising administering to a patient in need thereof a compound of any one of Embodiments 1-20 and Embodiment 38, or a pharmaceutically acceptable salt thereof.

Embodiment 45. A method for treating a PCSK9-mediated disease or disorder comprising the step of administering to a patient in need thereof a therapeutically effective amount of a compound according to any one of the Embodiments 1-20 and Embodiment 38, or a pharmaceutically acceptable salt thereof.

Embodiment 46. The method of Embodiment 45, wherein said PCSK9-mediated disease or disorder is selected from hypercholesterolemia, hyperlipidemia, hypertriglyceridemia, sitosterolemia, atherosclerosis, arteriosclerosis, coronary heart disease, peripheral vascular disease, vascular inflammation, and xanthoma.

Embodiment 47. A method of reducing LDL-C in a patient in need thereof, the method comprising administering a therapeutically effective amount of a compound of any one of Embodiments 1-20 and Embodiment 38, or a pharmaceutically acceptable salt thereof to the patient, thereby reducing LDL-C in the patient.

Embodiment 48. The method of any one of Embodiments 42 to 47, wherein administering is performed orally, parentally, subcutaneously, by injection, or by infusion.

Embodiment 49. A compound according to any one of Embodiments 1-20 and Embodiment 38, or a pharmaceutically acceptable salt thereof, for use in the treatment of a PCSK9-mediated disease or disorder.

Embodiment 50. A compound according to any one of Embodiments 1-20 and Embodiment 38, or a pharmaceutically acceptable salt thereof, for use in the treatment of a PCSK9-mediated disease or disorder which is selected from hypercholesterolemia, hyperlipidemia, hypertriglyceridemia, sitosterolemia, atherosclerosis, arteriosclerosis, coronary heart disease, peripheral vascular disease, vascular inflammation, and xanthoma.

Embodiment 51. Use of a compound according to any one of Embodiments 1-20 and Embodiment 38, or a pharmaceutically acceptable salt thereof, in the manufacture of a medicament for treating a PCSK9-mediated disease or disorder.

Embodiment 52. The use of claim 51, wherein said PCSK9-mediated disease or disorder is selected from hypercholesterolemia, hyperlipidemia, hypertriglyceridemia, sitosterolemia, atherosclerosis, arteriosclerosis, coronary heart disease, peripheral vascular disease, vascular inflammation, and xanthoma.

Embodiment 53. A compound according to any one of Embodiments 1-20 and Embodiment 38, or a pharmaceutically acceptable salt thereof, for use in the manufacture of a medicament for treating a disease associated with inhibiting PCSK9 activity.

Embodiment 54. Use of a compound according to any one of Embodiments 1-20 and Embodiment 38, or a pharmaceutically acceptable salt thereof, in the treatment of a disease associated with the inhibition of PCSK9 activity.

Embodiment 55. The use of Embodiment 54, wherein said disease associated with the inhibition of PCSK9 activity is selected from hypercholesterolemia, hyperlipidemia, hypertriglyceridemia, sitosterolemia, atherosclerosis, arteriosclerosis, coronary heart disease, peripheral vascular disease, vascular inflammation, and xanthoma.

Embodiment 56. A process for the manufacture of a compound of Formula (II), or a pharmaceutically acceptable salt, hydrate, solvate, stereoisomer, N-oxide, or tautomer thereof,

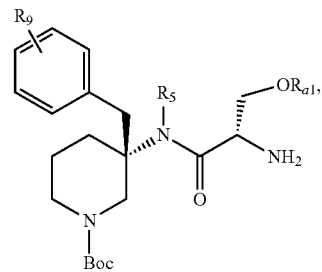

(II)

wherein $R_{a1}$ and $R_5$ are each independently $(C_1-C_6$ alkyl) and $R_9$ is as defined above for Formula (I), comprising:

(d) alkylating a compound of Formula (IIa), or a pharmaceutically acceptable salt, hydrate, solvate, stereoisomer, N-oxide, or tautomer thereof,

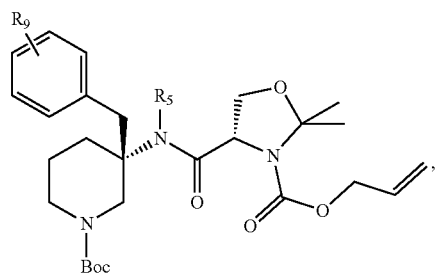

(IIa)

wherein $R_5$ is H and $R_9$ is as defined above for Formula (I), with an alkyl halide and a base in a solvent, and at low temperature to provide a compound of formula (IIb),

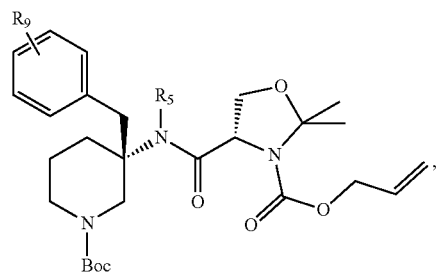

(IIb)

wherein $R_5$ is $(C_1-C_6$ alkyl) and $R_9$ is as defined above for Formula (I), or a pharmaceutically acceptable salt, hydrate, solvate, stereoisomer, N-oxide, or tautomer thereof, (e) reacting the compound of Formula (IIb), or a pharmaceutically acceptable salt, hydrate, solvate, stereoisomer, N-oxide, or tautomer thereof, with an acid in a solvent, followed by $Boc_2O$ and a base to form a compound of formula (IIc),

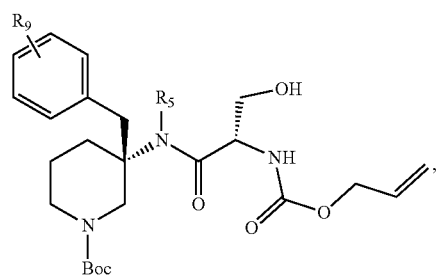

(IIc)

wherein $R_5$ is $(C_1-C_6$ alkyl) and $R_9$ is as defined above for Formula (I), a pharmaceutically acceptable salt, hydrate, solvate, stereoisomer, N-oxide, or tautomer thereof;

(f) alkylating the compound of Formula (IIc), or a pharmaceutically acceptable salt, hydrate, solvate, stereoisomer, N-oxide, or tautomer thereof, with a alkylating agent, in a solvent, and optionally a metal oxide to provide a compound of Formula (IId),

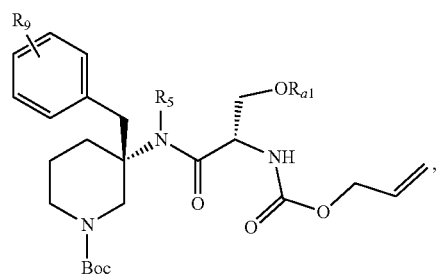

(IId)

wherein $R_{a1}$ and $R_5$ are each independently $(C_1-C_6$ alkyl) and $R_9$ is as defined above for Formula (I), or a pharmaceutically acceptable salt, hydrate, solvate, stereoisomer, N-oxide, or tautomer thereof; and (d), deallylating the compound of Formula (IId), with a palladium catalyst and N,N-dimethyltrimethylsilylamine in a solvent to provide the compound of Formula (II).

Embodiment 57. The process of Embodiment 56, wherein the solvent in step (a) is DMF.

Embodiment 58. The process of Embodiment 56 or Embodiment 57, wherein the temperature in step (a) is about 0° C.

Embodiment 59. The process of any one of Embodiments 56 to Embodiment 58, wherein the acid in step (b) is trifluoroacetic acid (TFA).

Embodiment 60. The process of any one of Embodiment 56-59, wherein a metal oxide is used in step (c).

Embodiment 61. The process of Embodiment 60, wherein the metal oxide is silver (I) oxide (Ag$_2$O).

Embodiment 62. The process of any one of Embodiment 56-61, wherein the palladium catalyst in step (d) is tetrakis(triphenylphosphine) palladium(0).

Embodiment 63. A process for the manufacture of a compound of Formula (II), or a pharmaceutically acceptable salt, hydrate, solvate, stereoisomer, N-oxide, or tautomer thereof,

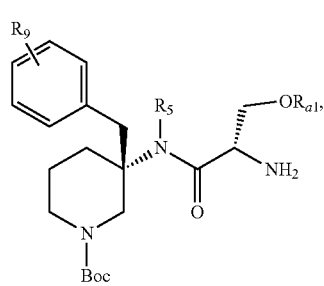

(II)

wherein $R_{a1}$ is H, $R_5$ is ($C_1$-$C_6$ alkyl), and $R_9$ is as defined above for Formula (I), comprising reacting a compound of Formula (IIb):

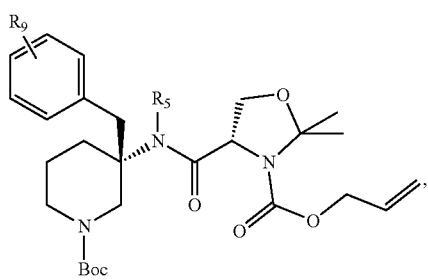

(IIb)

wherein $R_5$ is ($C_1$-$C_6$ alkyl) and $R_9$ is as defined above for Formula (I), with a palladium catalyst and N,N-dimethyltrimethylsilylamine in a solvent to provide the compound of Formula (II).

Embodiment 64. The process of Embodiment 63, wherein the solvent in dichloromethane.

Embodiment 65. The process of Embodiment 63 or Embodiment 64, wherein the palladium catalyst is tetrakis(triphenylphosphine) palladium(0).

In another embodiment, the compounds of Formula (I) are selected from:

(3R,7S,10S,13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7,12-dimethyl-3-(pyridin-2-ylmethyl)-1,6,9,12-tetraazabicyclo[11.3.1]heptadecane-2,5,8,11-tetraone;

(3R,7S,10S,13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-3-(pyridin-2-ylmethyl)-1,6,9,12-tetraazabicyclo[11.3.1]heptadecane-2,5,8,11-tetraone;

(3R,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-1,6,9,12-tetraazabicyclo[11.3.1]heptadecane-2,5,8,11-tetraone;

(3S,7S,10S,13R)-6-(4-chloro-2-(4-(2-((dimethylamino)methyl)-1-methyl-1H-imidazol-5-yl)phenoxy)-6-fluorobenzyl)-13-(4-chlorobenzyl)-3-((S)-2,3-dihydro-1H-inden-1-yl)-10-(hydroxymethyl)-7-methyl-1,6,9,12-tetraazabicyclo[11.3.1]heptadecane-2,5,8,11-tetraone;

(3R,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7,12-dimethyl-1,6,9,12-tetraazabicyclo[11.3.1]heptadecane-2,5,8,11-tetraone;

(3R,7S,10S,13R)-3-benzyl-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7-methyl-1,6,9,12-tetraazabicyclo[11.3.1]heptadecane-2,5,8,11-tetraone; and (3R,7S,10S,13R)-3-benzyl-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-1,6,9,12-tetraazabicyclo[11.3.1]heptadecane-2,5,8,11-tetraone.

Another aspect of the present disclosure relates to an intermediate of Formula (IIIa):

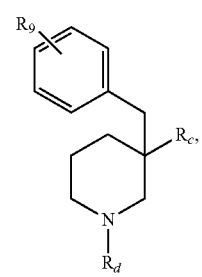

(IIIa)

or a pharmaceutically acceptable salt, hydrate, solvate, stereoisomer, N-oxide, or tautomer thereof, wherein: $R_c$ is —NH$_2$, —NH($C_1$-$C_6$)alkyl, —C(O)NH$_2$, or

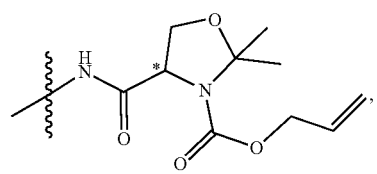 [SMILES: *NC(=O)C1COC(C)(C)N1C(=O)OCC=C]

wherein * denotes a chiral center, $R_d$ is H or a nitrogen protecting group (e.g., tert-butyloxycarbonyl (Boc), 9-fluorenylmethyloxycarbonyl (Fmoc), etc.), and $R_9$ is as defined above for Formula (I). In one embodiment, $R_d$ is a nitrogen protecting group. In another embodiment, $R_d$ is tert-butyloxycarbonyl (Boc). In another embodiment, $R_d$ is H.

Another aspect of the present disclosure relates to an intermediate of Formula (IIIb):

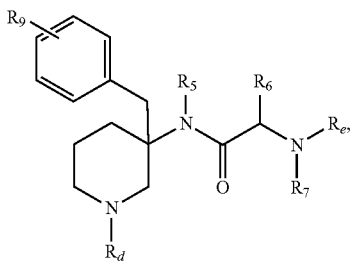

(IIIb)

or a pharmaceutically acceptable salt, hydrate, solvate, stereoisomer, N-oxide, or tautomer thereof, wherein: $R_d$ is H or a nitrogen protecting group (e.g., tert-butyloxycarbonyl (Boc), 9-fluorenylmethyloxycarbonyl (Fmoc), etc.), $R_e$ is H or —C(O)OCH$_2$CH=CH$_2$, $R_7$ is H, and $R_5$, $R_6$, and $R_9$ are as defined above for Formula (I). In one embodiment, $R_d$ is a nitrogen protecting group. In another embodiment, $R_d$ is tert-butyloxycarbonyl (Boc). In another embodiment, $R_d$ is H.

Another aspect of the present disclosure relates to an intermediate of Formula (IIIc):

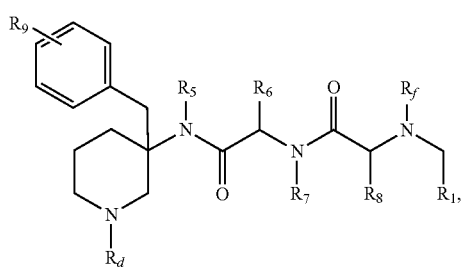

(IIIc)

or a pharmaceutically acceptable salt, hydrate, solvate, stereoisomer, N-oxide, or tautomer thereof, wherein: $R_d$ and $R_f$ are each independently H or a nitrogen protecting group (e.g., tert-butyloxycarbonyl (Boc), 9-fluorenylmethyloxycarbonyl (Fmoc), etc.), and $R_1$, $R_5$, $R_6$, $R_7$, $R_8$, and $R_9$ are as defined above for Formula (I). In one embodiment, $R_d$ is a nitrogen protecting group. In another embodiment, $R_d$ is tert-Butyloxycarbonyl (Boc). In another embodiment, $R_d$ is H. In one embodiment, $R_f$ is a nitrogen protecting group. In another embodiment, $R_f$ is tert-butyloxycarbonyl (Boc). In another embodiment, $R_f$ is H.

Another aspect of the present disclosure relates to an intermediate of Formula (IIId):

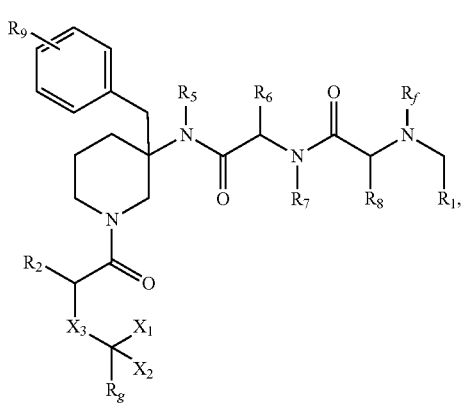

(IIId)

or a pharmaceutically acceptable salt, hydrate, solvate, stereoisomer, N-oxide, or tautomer thereof, wherein: $R_f$ is H or a nitrogen protecting group (e.g., tert-butyloxycarbonyl (Boc), 9-fluorenylmethyloxycarbonyl (Fmoc), etc.), $R_g$ is —OH or —O(C$_1$-C$_6$)alkyl, $X_1$ and $X_2$ together with the carbon atom to which they are attached form =(O), $X_3$ is —CH$_2$—, and $R_1$, $R_2$, $R_5$, $R_6$, $R_7$, $R_8$, and $R_9$ are as defined above for Formula (I). In one embodiment, $R_f$ is a nitrogen protecting group. In another embodiment, $R_f$ is tert-butyloxycarbonyl (Boc). In another embodiment, $R_f$ is H.

Another aspect of the present disclosure relates to an intermediate of Formula (IIIe) or (IIIf):

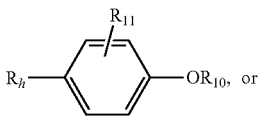

(IIIe)

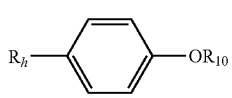

(IIIf)

or a pharmaceutically acceptable salt, hydrate, solvate, stereoisomer, N-oxide, or tautomer thereof, wherein: $R_H$ is —OH, —O(C$_1$-C$_6$)alkyl, —Otriflate, or halogen, and $R_{10}$ and $R_{11}$ are as defined above for Formula (I).

Another aspect of the present disclosure relates to an intermediate of Formula (IIIg) or (IIIh):

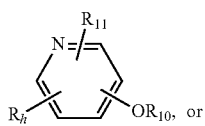

(IIIg)

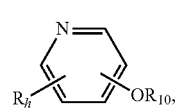

(IIIh)

or a pharmaceutically acceptable salt, hydrate, solvate, stereoisomer, N-oxide, or tautomer thereof, wherein: $R_H$ is —OH, —O(C$_1$-C$_6$)alkyl, —Otriflate, or halogen, and $R_{10}$ and $R_{11}$ are as defined above for Formula (I).

Another aspect of the present disclosure relates to an intermediate of Formula (IIIi) or

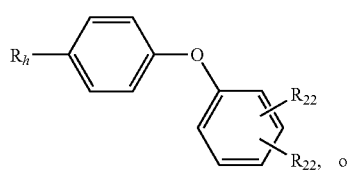

(IIIi)

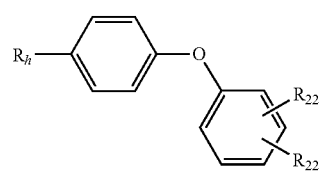

(IIIj)

or a pharmaceutically acceptable salt, hydrate, solvate, stereoisomer, N-oxide, or tautomer thereof, wherein: $R_H$ is —OH, —O($C_1$-$C_6$)alkyl, —Otriflate, or halogen, and $R_{22}$ is as defined above for Formula (I).

Another aspect of the present disclosure relates to an intermediate selected from:

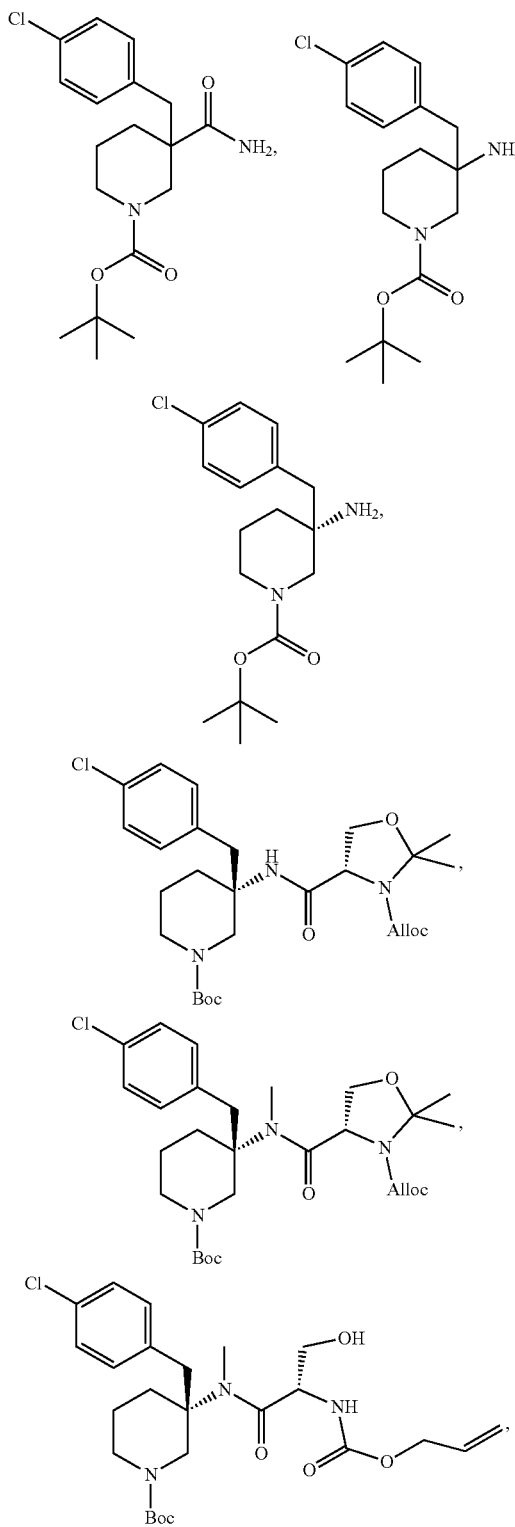

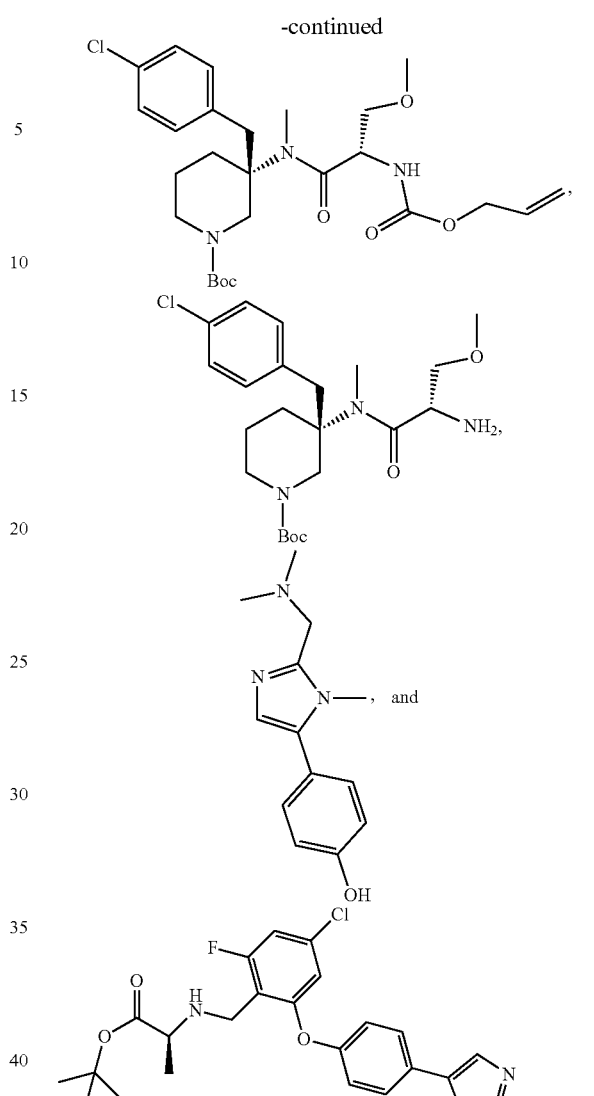

or a pharmaceutically acceptable salt, hydrate, solvate, stereoisomer, N-oxide, or tautomer thereof.

In another embodiment of the disclosure, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

In another embodiment of the disclosure, the Intermediates (IIIa), (IIIb), (IIIc) and (IIId) are enantiomers. In some embodiments the intermediates are the (S)-enantiomer. In other embodiments the intermediates are the (R)-enantiomer. In yet other embodiments, the intermediates may be (+) or (−) enantiomers.

In another embodiment of the disclosure, the compounds of Formula (I) are diastereomers. In another embodiment of the disclosure, the Intermediates of Formulae (IIIa), (IIIb), (IIIc) and (IIId) are diastereomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds and intermediates of the disclosure, and pharmaceutically acceptable salts, hydrates, solvates, stereoisomers and prodrugs thereof may exist in their tautomeric form (for example, as an amide or imino ether). All such tautomeric forms are contemplated herein as part of the present disclosure.

The compounds and intermediates of the disclosure may contain asymmetric or chiral centers, and, therefore, exist in different stereoisomeric forms. It is intended that all stereoisomeric forms of the compounds and intermediates of the disclosure as well as mixtures thereof, including racemic mixtures, form part of the present disclosure. In addition, the present disclosure embraces all geometric and positional isomers. For example, if a compound or intermediate of the disclosure incorporates a double bond or a fused ring, both the cis- and trans-forms, as well as mixtures, are embraced within the scope of the disclosure. Each compound or intermediate herein disclosed includes all the enantiomers that conform to the general structure of the compound or intermediate. The compounds or intermediates may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the disclosure may be atropisomers (e.g., substituted biaryls) and are considered as part of this disclosure. Enantiomers can also be separated by use of a chiral HPLC column.

It is also possible that the compounds and intermediates of the disclosure may exist in different tautomeric forms, and all such forms are embraced within the scope of the disclosure. Also, for example, all keto-enol and imine-enamine forms of the compounds are included in the disclosure.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the disclosure. Also, for example, all keto-enol and imine-enamine forms of the compounds are included in the disclosure.) Individual stereoisomers of the compounds of the disclosure may, for example, be substantially free of other isomers, or may be admixed, for example, as racemates or with all other, or other selected, stereoisomers. The chiral centers of the present disclosure can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula (I) may form salts which are also within the scope of this disclosure. Reference to a compound of the Formula herein is understood to include reference to salts thereof, unless otherwise indicated.

The present disclosure relates to compounds which are modulators of PCSK9. In one embodiment, the compounds of the present disclosure are inhibitors of PCSK9.

The disclosure is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Activity of the Compounds

The activity of compounds according to the present disclosure as PCSK9 inhibitors can be assessed using a time resolved fluorescence resonance energy transfer (TR-FRET) assay. This time resolved fluorescence resonance energy transfer (TR-FRET) assay measures the ability of a compounds of the present disclosure to interfere with the binding of human PCSK9 to human LDLR, providing measures of both potency (IC50) and efficacy (Amax).

Solutions of varying concentrations are prepared by diluting a compound of the disclosure in dimethylsulfoxide (DMSO) and the resulting solutions are pipetted into a plate. DMSO is used as a negative control. An intermediate plate is prepared in by transferring a known amount of each compound solution and of the control from the compound plate into a corresponding well containing assay buffer and mixing thoroughly. A third plate is then prepared to be used for the assay by adding Human PCSK9 Alexa Fluor 647, followed by a known amount of each solution from the intermediate plate. Unlabeled human PCSK9 in assay buffer containing DMSO is used as a positive control for the assay. Following incubation, Human LDLR extracellular domain-Europium Kryptate is added to each well of the assay plate and the resulting mixture is incubated for an additional period of time. The TR-FRET signal is measured and the FRET ratio (FRET/Europium) is used to calculate the $IC_{50}$ and Amax of the compounds.

Method of Synthesizing the Compounds

The compounds of the present disclosure may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander Interscience, 1994).

The compounds described herein may be made from commercially available starting materials or synthesized using known organic, inorganic, and/or enzymatic processes.

Preparation of Compounds

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereof as appreciated by those skilled in the art. Preferred methods include but are not limited to those methods described below. Compounds of the present disclosure can be synthesized by following the steps outlined in General Schemes 1 and 2 which comprise different sequences of assembling intermediates 1-a, 1-b, 1-c, 1-d, 1-e, 1-f, 1-g, 1-h, 1-i, 2-a, 2-b, 2-c, 2-d, and 2-e. Starting materials are either commercially available or made by known procedures in the reported literature or as illustrated.

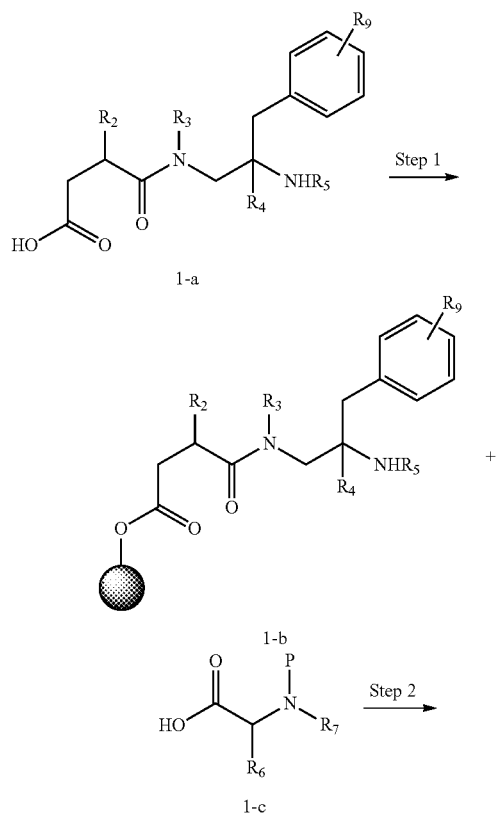

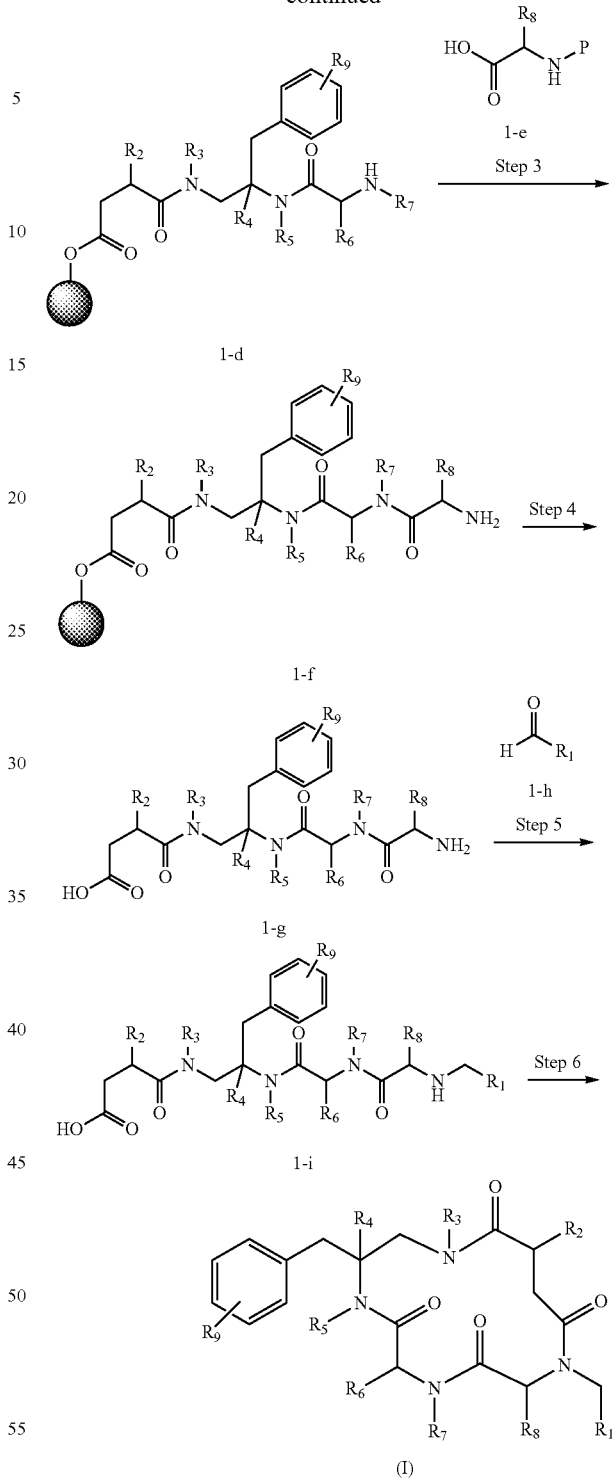

wherein $R_1$, $R_2$, $R_3$, $R_4$, $R_5$, $R_6$, $R_7$, $R_8$, and $R_9$ are defined in Formula (I), $X_3$ is $CH_2$, $X_1$ and $X_2$ together with the carbon atom to which they are attached form =(O), and P is an amine protecting group (e.g., tert-butyloxycarbonyl (Boc), 9-fluorenylmethyloxycarbonyl (Fmoc), etc.).

The general way of preparing compounds of Formula (I) by using intermediates 1-a, 1-b, 1-c, 1-d, 1-e, 1-f, 1-g, 1-h, and 1-i is outlined in General Scheme 1. Treatment of 1-a with PS-2-chlorotrityl chloride resin in the presence of a base (e.g., triethylamine (TEA), N,N-diisopropylethylamine (DIPEA), etc.) and in a solvent (e.g., dichloromethane (DCM), dimethylformamide (DMF), etc.) provides 1-b. Synthesis of intermediate 1-d can be accomplished by coupling of 1-b with 1-c under standard coupling conditions using an amide coupling reagent (e.g., 2-(1H-Benzotriazol-1-yl)-1,1,3,3-tetramethyluronium-tetrafluoroborate (TBTU), O-(1H-6-chlorobenzotriazole-1-yl)-1,1,3,3-tetramethyluronium hexafluorophosphate (HCTU), or O-(7-azobenzotriazol-1-yl)-1,1,3,3-tetramethyluroniumhexafluorophosphate (HATU), etc.) and optionally a base (e.g., TEA, DIPEA, etc.) in a solvent (e.g., N-methylpyrrolidine (NMP) or DMF) on a resin (e.g., TentaGel™ S RAM resin) followed by removal of amine protection group P (e.g., treatment with 4-methylpiperidine/DMA for removal of Fmoc group). Coupling of 1-d and acid 1-e using an amide coupling reagent (e.g., TBTU, HCTU, HATU, etc.) and optionally a base (e.g., TEA, DIPEA, etc.) followed by deprotection (e.g., treatment with 4-methylpiperidine/DMA for removal of Fmoc group or TFA for removal of Boc group) provides 1-f.

Cleavage of 1-f from the resin by repetitive treatment with 1,1,1,3,3,3-Hexafluoropropan-2-ol (HFIP) in a solvent (e.g., DCM) provides 1-g. Reductive amination of amine 1-g and aldehyde 1-h in the presence of a reducing agent (e.g., sodium triacetoxyborohydride, sodium cyanoborohydride, sodium borohydride, etc.) optionally an acid (e.g., acetic acid (AcOH)) in a solvent (e.g., methanol (MeOH) and/or DCM), provides 1-i. Cyclization of 1-i using standard coupling conditions, e.g., an amide coupling reagent (e.g., HATU, HOAt, TBTU, and/or HCTU), optionally a base (e.g., 2,6-lutidine, TEA, DIPEA, etc.) in a solvent (e.g., DCM, NMP, DMF, etc.) provides the desired compound of Formula (I).

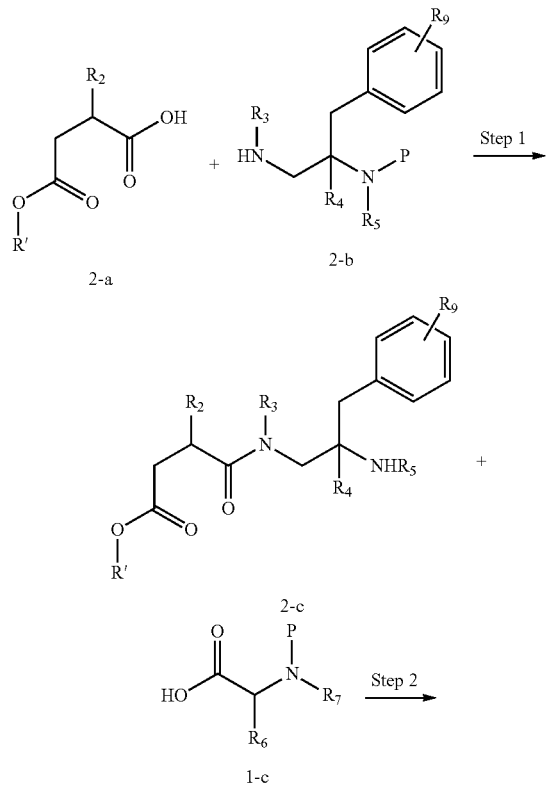

General Scheme 2

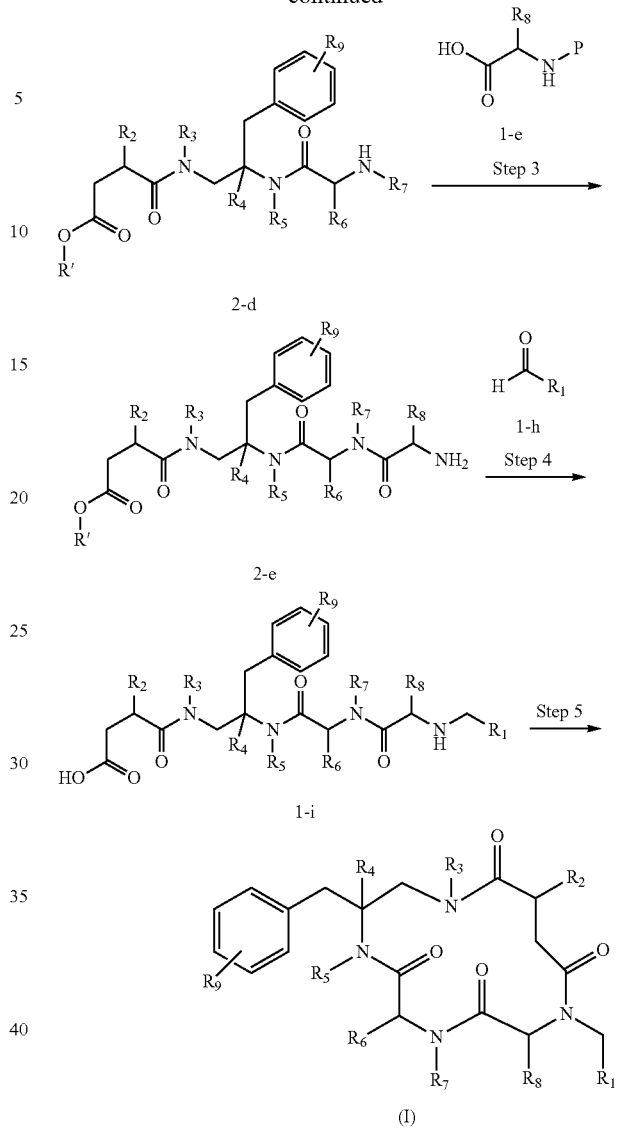

wherein $R_1$, $R_2$, $R_3$, $R_4$, $R_5$, $R_6$, $R_7$, $R_8$, and $R_9$ are defined in Formula (I), $X_3$ is $CH_2$, $X_1$ and $X_2$ together with the carbon atom to which they are attached form $=(O)$, R' is an alkyl group, and P is an amine protecting group (e.g., tert-butyloxycarbonyl (Boc), 9-fluorenylmethyloxycarbonyl (Fmoc), etc.).

Alternatively, compounds of Formula (I) can be prepared by using intermediates 1-c, 1-e, 1-h, 1-i, 2-a, 2-b, 2-c, 2-d, and 2-e as outlined in General Scheme 2. Synthesis of intermediate 2-c can be accomplished by coupling of 2-a with 2-b under standard coupling conditions using an amide coupling reagent (e.g., TBTU, HCTU, HATU, etc.) and optionally a base (e.g., TEA, DIPEA, etc.) in a solvent (e.g., NMP, DMF, etc.) followed by removal of amine protection group P (e.g., treatment with 4-methylpiperidine/DMA for removal of Fmoc group). Coupling of amine 2-c and acid 1-c using an amide coupling reagent (e.g., TBTU, HCTU, HATU, etc.) and optionally a base (e.g., TEA, DIPEA, etc.) followed by deprotection (e.g., treatment with 4-methylpiperidine/DMA for removal of Fmoc group or TFA for removal of Boc group) provides 2-d. The coupling and deprotection steps are repeated in step 3 using the standard coupling conditions described above to provide intermediate 2-e. Reductive amination of amine 2-e and aldehyde 1-h in the presence of a reducing agent, e.g., sodium triacetoxyborohydride, sodium cyanoborohydride, or sodium borohydride, and optionally an acid (e.g., AcOH) in a solvent (e.g., MeOH and/or DCM) followed by hydrolysis of the ester using an acid (e.g., TFA) in a solvent (e.g., DCM) provides 1-i. Cyclization of 1-i using standard coupling conditions, e.g., an amide coupling reagent (e.g., HATU, HOAt, TBTU, and/or HCTU), optionally a base (e.g., 2,6-lutidine, TEA or DIPEA) in a solvent (e.g., DCM, NMP or DMF) provides the desired compound of Formula (I).

It should be understood that in the description and formula shown above, the various groups $X_1$, $X_2$, $X_3$, $R_1$, $R_2$, $R_3$, $R_4$, $R_5$, $R_6$, $R_7$, $R_8$, and $R_9$, and other variables are as defined above, except where otherwise indicated. Furthermore, for synthetic purposes, the compounds of General Schemes 1 and 2 are mere representative with elected radicals to illustrate the general synthetic methodology of the compounds of Formula (I) as defined herein.

Methods of Using the Disclosed Compounds

Another aspect of the disclosure is directed to a method of modulating PCSK9. The method comprises administering to a patient in need thereof an effective amount of a compound of Formula (I), or a pharmaceutically acceptable salt, hydrate, solvate, stereoisomer, or tautomer thereof or a pharmaceutical composition comprising a compound of Formula (I), or a pharmaceutically acceptable salt, hydrate, solvate, stereoisomer, or tautomer thereof, and a pharmaceutically acceptable carrier.

In another aspect, the disclosure is directed to a method of inhibiting PCSK9. The method involves administering to a patient in need thereof an effective amount of a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier.

Another aspect of the disclosure relates to a method of treating, preventing, inhibiting, or eliminating a disease or disorder in which PCSK9 plays a role. The method comprises administering to a patient in need of a treatment for diseases or disorders in which PCSK9 plays a role an effective amount of a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier.

Another aspect of the present disclosure relates to a method of treating, preventing, inhibiting, or eliminating a disease or disorder in a patient associated with the inhibition of PCSK9, the method comprising administering to a patient in need thereof an effective amount of a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier.

In another aspect, the present disclosure relates to a method of treating, preventing, inhibiting, or eliminating a PCSK9-mediated disease or disorder. The method comprises administering to a patient in need of a treatment for a PCSK9-mediated disease or disorder an effective amount of a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier.

Another aspect of the present disclosure relates to a method of treating, preventing, inhibiting, or eliminating hypercholesterolemia, hyperlipidemia, hypertriglyceridemia, sitosterolemia, atherosclerosis, arteriosclerosis, coronary heart disease, peripheral vascular disease, vascular inflammation, xanthoma, peripheral arterial disease, sepsis, elevated Lp(a), elevated LDL, elevated TRL, or elevated triglycerides. The method comprises administering to a patient in need of a treatment an effective amount of a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier.

In another aspect, the present disclosure relates to a method of reducing Lp(a), reducing Lp(a) plasma levels, reducing Lp(a) serum levels, reducing serum TRL or LDL levels, reducing serum triglyceride levels, reducing LDL-C, reducing total plasma apoB concentrations, reducing LDL apoB, reducing TRL apoB, or reducing non HDL-C. The method comprises administering to a patient in need thereof an effective amount of a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier.

In another aspect, the present disclosure relates to a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier for use in the treatment, prevention, inhibition, or elimination of a disease or disorder in which PCSK9 plays a role.

Another aspect of the present disclosure relates to a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier for use in the treatment, prevention, inhibition, or elimination of a disease associated with inhibiting PCSK9.

Another aspect of the present disclosure relates to a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier for use in the treatment, prevention, inhibition, or elimination of hypercholesterolemia, hyperlipidemia, hypertriglyceridemia, sitosterolemia, atherosclerosis, arteriosclerosis, coronary heart disease, peripheral vascular disease, vascular inflammation, xanthoma, peripheral arterial disease, sepsis, elevated Lp(a), elevated LDL, elevated TRL, or elevated triglycerides.

In another aspect, the present disclosure relates to a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier for use in the reduction of Lp(a), in the reduction of Lp(a) plasma levels, in the reduction of Lp(a) serum levels, in the reduction of serum TRL or LDL levels, in the reduction of serum triglyceride levels, in the reduction of LDL apoB, in the reduction of TRL apoB, or in the reduction of non HDL-C.

Another aspect of the present disclosure relates to the use of a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier for treating, preventing, inhibiting, or eliminating a disease or disorder in which PCSK9 plays a role.

In another aspect, the present disclosure relates to the use of a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier in the manufacture of a medicament for inhibiting PCSK9.

In another aspect, the present disclosure relates to the use of a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier in the manufacture of a medicament for treating, preventing, inhibiting, or eliminating hypercholesterolemia, hyperlipidemia, hypertriglyceridemia, sitosterolemia, atherosclerosis, arteriosclerosis, coronary heart disease, peripheral vascular disease, vascular inflammation, xanthoma, peripheral arterial disease, sepsis, elevated Lp(a), elevated LDL, elevated TRL, or elevated triglycerides.

Another aspect of the present disclosure relates to the use of a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier in the manufacture of a medicament for reducing Lp(a), reducing Lp(a) plasma levels, reducing Lp(a) serum levels, reducing serum TRL or LDL levels, reducing serum triglyceride levels, reducing LDL apoB, reducing TRL apoB, or reducing non HDL-C.

In another aspect, the present disclosure relates to a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier for use in the manufacture of a medicament for treating a disease associated with inhibiting PCSK9.

Another aspect of the present disclosure relates to a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier for use in the manufacture of a medicament for treating a disease in which PCSK9 plays a role.

In another aspect, the present disclosure relates to a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier for use in the manufacture of a medicament for treating, preventing, inhibiting, or eliminating hypercholesterolemia, hyperlipidemia, hypertriglyceridemia, sitosterolemia, atherosclerosis, arteriosclerosis, coronary heart disease, peripheral vascular disease, vascular inflammation, xanthoma, peripheral arterial disease, sepsis, elevated Lp(a), elevated LDL, elevated TRL, or elevated triglycerides.

Another aspect of the present disclosure relates to a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier for use in the manufacture of a medicament for reducing Lp(a), reducing Lp(a) plasma levels, reducing Lp(a) serum levels, reducing serum TRL or LDL levels, reducing serum triglyceride levels, reducing LDL apoB, reducing TRL apoB, or reducing non HDL-C.

In another aspect, the present disclosure relates to the use of an inhibitor of PCSK9 for the preparation of a medicament used in the treatment, prevention, inhibition or elimination of hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, or xanthoma.

Another aspect of the present disclosure relates to a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier for use in the treatment of a PCSK9-mediated disease or disorder.

Another aspect of the present disclosure relates to a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier for use in the treatment of a PCSK9-mediated disease or disorder which is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

In another aspect, the present disclosure relates to the use of a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier in the manufacture of a medicament for treating a PCSK9-mediated disease or disorder.

Another aspect of the present disclosure relates to a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier for use in the manufacture of a medicament for treating a PCSK9-mediated disease or disorder.

In another aspect, the present disclosure relates to the use of a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier for use as a medicament.

The present disclosure also relates to the use of an inhibitor of PCSK9 for the preparation of a medicament used in the treatment, prevention, inhibition, or elimination of a disease or condition in which PCSK9 plays a role, wherein the medicament comprises a compound of Formula (I).

In another aspect, the present disclosure relates to a method for the manufacture of a medicament for treating, preventing, inhibiting, or eliminating a disease or condition mediated by PCSK9, wherein the medicament comprises a compound of Formula (I), or a pharmaceutically acceptable salt, hydrate, solvate, stereoisomer, or tautomer, or a pharmaceutical composition comprising a compound of Formula (I), or a pharmaceutically acceptable salt, hydrate, solvate, stereoisomer, or tautomer thereof, and a pharmaceutically acceptable carrier.

In some embodiments of the methods above, the PCSK9-mediated disease or disorder, the disease or disorder in which PCSK9 plays a role, the disease or disorder in a patient associated with the inhibition of PCSK9, and the disease associated with inhibiting PCSK9 is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

The compounds of the present disclosure find use in reducing or lowering low density lipoprotein cholesterol (LDL-C) in an individual in need thereof. The individual may have persistently elevated levels of LDL-C. In some embodiments, the individual has LDL-C plasma levels consistently above 70 mg/dL, for example above 80, 90, 100, 110, 120, 130, 140, 150, 160, 170, 180, or 190 mg/dL, or higher. The compounds of the present disclosure may also be used to reduce or lower non-high density lipoprotein cholesterol (non-HDL-C) or total cholesterol in an individual in need thereof.

The present disclosure also relates to methods for improving blood cholesterol markers associated with increased risk of heart disease. These markers include high total cholesterol, high LDL, high total cholesterol to HDL ratio and high LDL to HDL ratio. A total cholesterol of less than 200 mg/dL is considered desirable, 200-239 mg/dL is considered borderline high and 240 mg/dL and above is considered high.

In a further aspect, the disclosure provides methods of reducing LDL-C, non-HDL-C and/or total cholesterol in an individual in need thereof, the method comprising administering a therapeutically effective amount to the individual a compound or a pharmaceutical composition comprising a compound disclosed herein and a pharmaceutically acceptable carrier as described herein.

In another embodiment, the present disclosure relates to a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, of the present disclosure and a pharmaceutically acceptable carrier used for the treatment of diseases including, but not limited to, hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

In one embodiment, are provided methods of treating a disease or disorder in which PCSK9 plays a role including hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma comprising administering to a patient suffering from at least one of said diseases or disorder a compound of Formula (I), or a pharmaceutically acceptable salt, hydrate, solvate, stereoisomer, or tautomer thereof, or a pharmaceutical composition comprising a compound of Formula (I), or a pharmaceutically acceptable salt, hydrate, solvate, stereoisomer, or tautomer thereof, and a pharmaceutically acceptable carrier.

The disclosed compounds of the disclosure can be administered in effective amounts to treat or prevent a disorder and/or prevent the development thereof in subjects.

The disclosed compounds of the disclosure can be administered in effective amounts to treat or prevent a disorder and/or prevent the development thereof in subjects.

Administration, Pharmaceutical Compositions, and Dosing of the Disclosed Compounds Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Another aspect of the disclosure is directed to pharmaceutical compositions comprising a compound of Formula (I), or a pharmaceutically acceptable salt, hydrate, solvate, stereoisomer, or tautomer thereof, and a pharmaceutically acceptable carrier. The pharmaceutical acceptable carrier may further include an excipient, diluent, or surfactant. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present disclosure can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, of the disclosed pharmaceutical compositions, or of the disclosed combinations, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present disclosure can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

Combination Therapy

The compounds of the disclosure can be administered in therapeutically effective amounts in a combinational therapy with one or more therapeutic agents (pharmaceutical combinations) or modalities, e.g., non-drug therapies. For example, synergistic effects can occur with other cardiovascular agents, antihypertensive agents, coronary vasodilators, and diuretic substances. Where the compounds of the application are administered in conjunction with other therapies, dosages of the co-administered compounds will of course vary depending on the type of co-drug employed, on the specific drug employed, on the condition being treated and so forth.

The compound of the present disclosure may be administered either simultaneously with, or before or after, one or more other therapeutic agent. The compound of the present disclosure may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the present disclosure.

In one embodiment, the disclosure provides a product comprising a compound of the present disclosure and at least one other therapeutic agent as a combined preparation for simultaneous, separate or sequential use in therapy. In one embodiment, the therapy is the treatment of a disease or condition mediated by PCSK9. Products provided as a combined preparation include a composition comprising the compound of the present disclosure and the other therapeutic agent(s) together in the same pharmaceutical composition, or the compound of the present disclosure and the other therapeutic agent(s) in separate form, e.g. in the form of a kit.

In another aspect, the disclosure includes a compound of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Im), Formula (Io), a compound according to any one of embodiment No. 1 to No. 20 or Embodiment 38, or any embodiment of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Im), and/or Formula (Io) described herein, or a pharmaceutically acceptable salt thereof, for use in a combination therapy. A compound, composition, medicament and compounds for use of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Im), Formula (Io), a compound according to any one of embodiment No. 1 to No. 20 or Embodiment 38, or any embodiment of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Im), and/or Formula (Io) described herein, or a pharmaceutically acceptable salt thereof, may also be used to advantage in combination with one or more other therapeutic agents.

Another aspect of the disclosure is directed to pharmaceutical compositions comprising a compound of Formula (I), or a pharmaceutically acceptable salt, hydrate, solvate, stereoisomer, or tautomer thereof, a pharmaceutically acceptable carrier, and one or more therapeutic agents. The pharmaceutical acceptable carrier may further include an excipient, diluent, or surfactant.

Combination therapy includes the administration of the subject compounds in further combination with other biologically active ingredients (such as, but not limited to, a second agent such as, but not limited to, a cardiovascular agent, an adrenergic blocker, an antihypertensive agent, an angiotensin system inhibitor, an angiotensin-converting enzyme (ACE) inhibitor, a coronary vasodilator, a diuretic, or an adrenergic stimulant or a second agent that targets PCSK9) and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

In some embodiments, compounds of the application can be used in combination with agents known to be beneficial for reducing cholesterol, including LDL-C, non-HDL-C, triglyceride-lowering agents, and total cholesterol and/or raising HDL-C.

Exemplary therapeutic agents that may be used in combination with the compounds of the disclosure, include, but are not limited to, hypolipidemic agents, niacin and analogs thereof, bile acid sequestrants, a thyroid hormone mimetic, thyroid hormone receptor (THR) β-selective agonist, a microsomal triglyceride transfer protein (MTP) inhibitor, an acyl CoA:diacylglycerol acyltransferase 1 (DGAT1) inhibitor, a Niemann Pick C1-like 1 (NPC1-L1) inhibitor, an agonist of ATP Binding Cassette (ABC) proteins G5 or G8, an inhibitory nucleic acid targeting PCSK9, an inhibitory nucleic acid targeting apoB100, apoA-I up-regulator/inducer, ABCA1 stabilizer or inducer, phospholipid transfer protein (PLTP) inhibitor, fish oil, anti-diabetic agent, anti-obesity agent, agonists of peroxisome proliferator-activator receptors, ATP citrate lyase (ACL) inhibitor, and anti-hypertensive agents.

Examples of hypolipidemic agents that may be used in combination with the compounds of the disclosure include, but are not limited to, an HMG-CoA reductase inhibitor, squalene synthase inhibitors, LXR agonist, FXR agonist, fibrates, cholesterol absorption inhibitors, nicotinic acid bile acid binding resins, nicotinic acid and other GPR109 agonists and aspirin.

HMG-CoA reductase inhibitors (i.e., statins) are a class of drugs used to lower cholesterol levels by inhibiting the enzyme HMG-CoA reductase, which plays a central role in the production of cholesterol in the liver. Increased cholesterol levels have been associated with cardiovascular diseases and statins are therefore used in the prevention of these diseases. Exemplary statins include, but are not limited to, atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or pharmaceutically acceptable salts thereof.

Fibrates or fibric acid derivatives lower triglycerides and raise HDL cholesterol. They may have little effect on LDL cholesterol. For example, Gemfibrozil or fenofibrate is prescribed for people who have very high triglycerides or who have low HDL and high triglycerides. Gemfibrozil may be used to reduce the risk of heart attack in people with coronary artery disease (CAD) who have low HDL and high triglycerides. Examples of fibrates include, but are not limited to, clofibrate, gemfibrozil, fenofibrate, ciprofibrate, and bezafibrate.

Cholesterol absorption inhibitors are a class of compounds that prevents the uptake of cholesterol from the small intestine into the circulatory system, and, in turn, reduce plasma LDL-C concentrations. Increased cholesterol levels are associated with increased CVD risk; thus, cholesterol absorption inhibitors are used with the goal of reducing CVD risk. A non-limiting example of a cholesterol absorption inhibitor is Ezetimibe, previously known as "Sch-58235". Another example is Sch-48461. Both compounds are developed by Schering-Plough.

Examples of bile acid sequestrants that may be used in combination with the compounds of the disclosure include, but are not limited to, cholestyramine, colestipol, and colesvelam.

A non-limiting example of a thyroid hormone mimetic that may be used in combination with the compounds of the disclosure is compound KB2115.

A non-limiting example of a thyroid hormone receptor (THR) β-selective agonist that may be used in combination with the compounds of the disclosure is MGL-3196.

DGAT is an enzyme that catalyzes the last step in triacylglycerol biosynthesis. DGAT catalyzes the coupling of a 1,2-diacylglycerol with a fatty acyl-CoA resulting in Coenzyme A and triacylglycerol. Two enzymes that display DGAT activity have been identified: DGAT1 (acyl coA-diacylglycerol acyl transferase 1, see Cases et al, Proc. Natl. Acad. Sci. 95:13018-13023, 1998) and DGAT2 (acyl coA-diacylglycerol acyl transferase 2, see Cases et al, J. Biol. Chem. 276:38870-38876, 2001). DGAT1 and DGAT2 do not share significant protein sequence homology. Importantly, DGAT1 knockout mice are protected from high fat diet-induced weight gain and insulin resistance (Smith et al, Nature Genetics 25:87-90, 2000). The phenotype of the DGAT1 knockout mice suggests that a DGAT1 inhibitor has utility for the treatment of obesity and obesity-associated complications. DGAT1 inhibitors useful in said combination are compounds and analogs generically and specifically disclosed e.g. in WO2007/126957 and WO2009/040410, in particular in the compound claims and the final products of the working examples, the subject-matter of the final products, the pharmaceutical preparations and the claims.

Examples of DGAT1 inhibitors suitable for use in combination with compounds of the present disclosure, include but are not limited to, {4-[4-(3-Methoxy-5-phenylamino-pyridin-2-yl)-phenyl]-cyclohexyl}-acetic acid, (4-{4-[5-(1-Methyl-1H-pyrazol-3-ylamino)-pyridin-2-yl]-phenyl}-cyclohexyl)-acetic acid, (4-{4-[5-(5-Fluoro-6-methoxy-pyridin-3-ylamino)-pyridin-2-yl]-phenyl}-cyclohexyl)-acetic acid, (4-{5-[5-(6-Trifluoromethyl-pyridin-3-ylamino)-pyridin-2-yl]-spirocyclohexylidenyl-1,1'-indanyl}-acetic acid, (4-{4-[5-(Benzooxazol-2-ylamino)-pyridin-2-yl]-phenyl}-cyclohexyl)-acetic acid, 4-(4-{4-[2-(3-Chlorophenylamino)-oxazol-5-yl]-phenyl}-cyclohexyl)-butyric acid, (4-{4-[5-(6-Trifluoromethyl-pyridin-3-ylamino)-pyridin-2-yl]-phenyl}-cyclohexyl)-acetic acid, (6-{4-[4-(2H-Tetrazol-5-ylmethyl)-cyclohexyl]-phenyl}-pyridazin-3-yl)-(6-trifluoromethyl-pyridin-3-yl)-amine, 3-(4-{4-[6-(6-Trifluoromethyl-pyridin-3-ylamino)-pyridazin-3-yl]-phenyl}-cyclohexylmethyl)-4H-[1,2,4]oxadiazol-5-one, (1-{4-[6-(3-Trifluoromethyl-phenylamino)-pyridazin-3-yl]-phenyl}-piperidin-4-yl)-acetic acid, (4-{4-[4-Methyl-6-(6-trifluoromethyl-pyridin-3-ylamino)-pyridazin-3-yl]-phenyl}-cyclohexyl)-acetic acid, (4-{4-[5-(6-Trifluoromethyl-pyridin-3-ylamino)-pyrazin-2-yl]-phenyl}-cyclohexyl)-acetic acid, 6-[5-(4-Chloro-phenyl)-[1,3,4]oxadiazol-2-yl]-2-(2,6-dichloro-phenyl)-1H-benzoimidazole, 6-(5-Cyclohexyl-[1,3,4]oxadiazol-2-yl)-2-(2,6-dichloro-phenyl)-1H-benzoimidazole, 6-(5-Butyl-[1,3,4]oxadiazol-2-yl)-2-(2,6-dichloro-phenyl)-1H-benzoimidazole, 2-(2,6-Dichloro-phenyl)-6-[5-(5-methyl-pyridin-3-yl)-[1,3,4]oxadiazol-2-yl]-1H-benzoimidazole, 6-[5-(4-Chloro-phenyl)-[1,3,4]oxadiazol-2-yl]-2-(2,6-dimethyl-4-morpholin-4-yl-phenyl)-1H-benzoimidazole, 6-[5-(4-Chloro-phenyl)-[1,3,4]oxadiazol-2-yl]-2-(3,5-dichloro-pyridin-4-yl)-1H-benzoimidazole, 3-(4-{5-[5-(4-Methoxy-phenyl)-[1,3,4]oxadiazol-2-yl]-1H-benzoimidazol-2-yl}-3,5-dimethyl-phenyl)-2,2-dimethyl-propionic acid, 3-(4-{6-[5-(4-Methoxy-phenyl)-[1,3,4]oxadiazol-2-yl]-1H-benzoimidazol-2-yl}-3,5-dimethyl-phenyl)-propionic acid, 3-(4-{6-[5-(4-methoxyphenylamino)-[1,3,4]oxadiazol-2-yl]-1H-benzimidazol-2-yl}-3,5-dimethylphenyl)-propionic acid, [3-(4-{6-[5-(4-Chloro-phenyl)-[1,3,4]oxadiazol-2-yl]-1H-benzoimidazol-2-yl}-3,5-dimethyl-phenyl)-propyl]-phosphonic acid, 2-(2,6-Dichloro-phenyl)-6-(4,5-diphenyl-oxazol-2-yl)-1H-benzoimidazole, (4-{6-[5-(4-Chloro-phenyl)-[1,3,4]oxadiazol-2-yl]-1H-benzoimidazol-2-yl}-3,5-dimethyl-phenoxy)-acetic acid, 2-(2,6-Dichloro-phenyl)-6-(5-pyrrolidin-1-yl-[1,3,4]oxadiazol-2-yl)-1H-benzoimidazole, and 3,5-Dimethyl-4-{6-[5-(4-trifluoromethyl-phenylamino)-[1,3,4]oxadiazol-2-yl]-1H-benzoimidazol-2-yl}-phenol.

A non-limiting example of a Niemann Pick C1-like 1 (NPC1-L1) inhibitor that may be used in combination with the compounds of the disclosure is ezetimibe.

Apolipoprotein A-I is a protein that in humans is encoded by the APOA1 gene. It has a specific role in lipid metabolism. Apolipoprotein A-I is the major protein component of high density lipoprotein (HDL) in plasma. Chylomicrons secreted from enterocytes also contain ApoA-I but it is quickly transferred to HDL in the bloodstream. The protein promotes cholesterol efflux from tissues to the liver for excretion. It is a cofactor for lecithin cholesterolacyltransferase (LCAT) which is responsible for the formation of most plasma cholesteryl esters. Infusion of a variant of apoA-I in humans has been shown to regress atherosclerotic plaque, as assessed by intravascular ultrasound; thus, apoA-I reduces CVD risk and has the ability to both slow progression and induce regression of atherosclerosis. A non-limiting example of an apoA-I up-regulator/inducer is RVX208.

ATP-binding cassette transporter, ABCA1 (member 1 of human transporter sub-family ABCA), also known as the cholesterol efflux regulatory protein (CERP) is a protein which in humans is encoded by the ABCA1 gene. This transporter is a major regulator of cellular cholesterol and phospholipid homeostasis. A non-limiting example of an ABCA1 regulator is Probucol. Probucol lowers the level of cholesterol in the bloodstream by increasing the rate of LDL catabolism. Additionally, probucol may inhibit cholesterol synthesis and delay cholesterol absorption. Probucol is a powerful antioxidant, which inhibits the oxidation of cholesterol in LDLs; this slows the formation of foam cells, which contribute to atherosclerotic plaques.

The liver X receptor (LXR) is a member of the nuclear receptor family of transcription factors and is closely related to nuclear receptors such as PPAR, FXR and RXR. Liver X receptors (LXRs) are important regulators of cholesterol, fatty acids and glucose homeostasis. LXR agonists are effective for treatment of murine models of atherosclerosis, diabetes, anti-inflammation and Alzheimer's disease. Treatment with LXR agonists (including but not limited to, hypocholamide, T0901317, GW3965, or N,N-dimethyl-3-beta-hydroxy-cholenamide (DMHCA)) lowers the cholesterol level in serum and liver and inhibits the development of atherosclerosis in murine disease models. Examples of LXR agonists include, but are not limited to, GW3965 (a synthetic nonsteroidal liver X receptor (LXR) agonist/activator) and T0901317 (a dual LXR, FXR agonist).

The farnesoid X receptor (FXR), also known as NR1H4 (nuclear receptor subfamily 1, group H, member 4) is a nuclear hormone receptor with activity similar to that seen in other steroid receptors such as estrogen or progesterone but more similar in form to PPAR, LXR and RXR. Activation of the nuclear receptor FXR is known to improve hyperglycemia and hyperlipidemia. A non-limiting example of a FXR agonist is GW4064 (3-(2,6-Dichlorophenyl)-4-(3'-carboxy-2-chlorostilben-4-yl)oxymethyl-5-isopropylisoxazole).

Phospholipid transfer protein (PLTP) is a protein that in humans is encoded by the PLTP gene. The protein encoded by this gene is one of at least two lipid transfer proteins found in human plasma, with CETP being the other. The encoded protein transfers phospholipids from triglyceride-rich lipoproteins to HDL. In addition to regulating the size of HDL particles, this protein may be involved in cholesterol metabolism. At least two transcript variants encoding different isoforms have been found for this gene. Because PLTP influences the metabolism of both triglyceride-rich lipoproteins and HDL, modulation of this transfer protein has the potential to alter cardiovascular disease risk.

Fish oil is derived from the tissues of oily fish. Fish oils contain the omega-3 fatty acids eicosapentaenoic acid (EPA) and docosahexaenoic acid (DHA), precursors of eicosanoids that are known to have many health benefits. Fish oil and other omega-3 sources are most highly recommended for the following conditions: hypertriglyceridemia, secondary cardiovascular disease and prevention of high blood pressure. For example, Lovaza® is used along with a low-fat and low-cholesterol diet to lower very high triglycerides (fats) in your blood. Examples of omega-3 fatty acids that may be used in combination with the compounds of the disclosure include, but are not limited to Lovaza® and Vascepa® (icosapent ethyl).

Examples of anti-diabetic agents that may be used in combination with the compounds of the disclosure include, but are not limited to, insulin, insulin derivatives and mimetics; insulin secretagogues such as the sulfonylureas; insulinotropic sulfonylurea receptor ligands such as meglitinides, e.g., nateglinide and repaglinide; protein tyrosine phosphatase-1B (PTP-1B) inhibitors including, but not limited to, PTP-112; GSK3 (glycogen synthase kinase-3) inhibitors including, but not limited to, SB-517955, SB-4195052, SB-216763, NN-57-05441 and NN-57-05445; RXR ligands including, but not limited to, GW-0791 and AGN-194204; sodium-dependent glucose cotransporter inhibitors including, but not limited to, T-1095; glycogen phosphorylase A inhibitors including, but not limited to, BAY R3401; biguanides including, but not limited to, metformin; alpha-glucosidase inhibitors including, but not limited to, acarbose; GLP-1 (glucagon like peptide-1), GLP-1 analogs including, but not limited to, Exendin-4 and GLP-1 mimetics; and DPPIV (dipeptidyl peptidase IV) inhibitors including, but not limited to, vildagliptin.

Examples of sulfonylureas include, but are not limited to, tolbutamide, chlorpropamide, tolazamide, acetohexamide, 4-chloro-N-[(1-pyrolidinylamino)carbonyl]-benzenesulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, amaryl, and tolylcyclamide, or pharmaceutically acceptable salts thereof.

DPP-IV (dipeptidyl peptidase IV) is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. Examples of DPP-IV inhibitors also include, but are not limited to, generically and specifically DPP-IV inhibitors disclosed in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications.

GLP-1 (glucagon like peptide-1) is an insulinotropic protein which is described, e.g., by W. E. Schmidt et al. in *Diabetologia*, 28, 1985, 704-707 and in U.S. Pat. No. 5,705,483. The term "GLP-1 agonists" includes variants and analogs of GLP-1(7-36)NH$_2$ which are disclosed in particular in U.S. Pat. Nos. 5,120,712, 5,118,666, 5,512,549, WO 91/11457 and by C. Orskov, et al, in *J. Biol. Chem.*, 264 (1989) 12826. Further examples include GLP-1(7-37), in which compound the carboxy-terminal amide functionality of Arg$^{36}$ is displaced with Gly at the 37$^{th}$ position of the GLP-1(7-36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37)OH, VAL$^8$-GLP-1(7-37), GLY$^8$-GLP-1(7-37), THR$^8$-GLP-1(7-37), MET$^8$-GLP-1(7-37) and 4-imidazopropionyl-GLP-1. Special preference is also given to the GLP agonist analog exendin-4, described by Greig, et al., in *Diabetologia*, 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenyl]methyl}-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-(3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Examples of anti-obesity agents that may be used in combination with the compounds of the disclosure include, but are not limited to, orlistat, sibutramine, phentermine and Cannabinoid Receptor 1 (CB1) antagonists e.g. rimonabant.

Examples of agonists of peroxisome proliferator-activator receptors that may be used in combination with the compounds of the disclosure include, but are not limited to, fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof.

Examples of hypolipidemic agents that may be used in combination with the compounds of the disclosure include, but are not limited to, an HMG-CoA reductase inhibitor, squalene synthase inhibitors, LXR agonist, FXR agonist, fibrates, cholesterol absorption inhibitors, nicotinic acid bile acid binding resins, bempedoic acid, nicotinic acid and other GPR109 agonists, and aspirin.

Examples of anti-hypertensive agents that may be used in combination with the compounds of the disclosure include, but are not limited to, loop diuretics; angiotensin converting enzyme (ACE); inhibitors of the Na—K-ATPase membrane pump; neutralendopeptidase (NEP) inhibitors; ACE/NEP inhibitors; angiotensin II antagonists; renin inhibitors; β-adrenergic receptor blockers; inotropic agents; calcium channel; aldosterone receptor antagonists; and aldosterone synthase inhibitors.

Examples of loop diuretics that may be used in combination with the compounds of the disclosure include, but are not limited to, ethacrynic acid, furosemide and torsemide.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include, but are not limited to, alacepril, benazepril, benazeprilat, captopril, ceronapril, cilazapril, delapril, enalapril, enaprilat, fosinopril, imidapril, lisinopril, moexipril, moveltopril, perindopril, quinapril, ramipril, spirapril, temocapril, and trandolapril, or a pharmaceutically acceptable salt thereof.

A non-limiting example of an inhibitor of the Na—K-ATPase membrane pump is digoxin.

The term "NEP inhibitor" refers to a compound that inhibits neutral endopeptidase (NEP). Examples include, but are not limited to, Candoxatril, Candoxatrilat, Dexecadotril, Ecadotril, Racecadotril, Sampatrilat, Fasidotril, Omapatrilat, Gemopatrilat, Daglutril, SCH-42495, SCH-32615, UK-447841, AVE-0848, PL-37, and (2R,4S)-5-Biphenyl-4-yl-4-(3-carboxy-propionylamino)-2-methyl-pentanoic acid ethyl ester, or a pharmaceutically acceptable salt thereof. NEP inhibitors also include Phosphono/biaryl substituted dipeptide derivatives, as disclosed in U.S. Pat. No. 5,155,100. NEP inhibitors also include N-mercaptoacyl phenylalanine derivative as disclosed in PCT application WO 2003/104200. NEP inhibitors also include dual-acting antihypertensive agents as disclosed in PCT applications WO 2008/133896, WO 2009/035543, or WO 2009/134741. Other examples include compounds disclosed in U.S. application Ser. Nos. 12/788,794; 12/788,766, and 12/947,029. NEP inhibitors also include compounds disclosed in WO 2010/136474, WO 2010/136493, WO 2011/061271, WO 2012/065953, WO 2012/065956, WO 2014/126979, and WO 2014/015965. Other examples of NEP inhibitors are compounds disclosed in WO2015116786, WO2015116760, WO2014138053, WO2014025891, WO2013184934, WO2013067163, WO2012166389, WO2012166387, WO2012112742, and WO2012082853.

The term "ACE/NEP inhibitors" refers to a compound that inhibits both angiotensin converting enzyme(ACE) and neutral endopeptidase (NEP). Examples of ACE/NEP inhibitors that may be used in combination with the compounds of the disclosure include, but are not limited to, omapatrilat, sampatrilat, and fasidotril.

The class of angiotensin II antagonists or $AT_1$ receptor antagonists comprises compounds having differing structural features, essentially preferred are the non-peptidic ones. Examples of angiotensin II antagonists that may be used in combination with the compounds of the disclosure include, but are not limited to, valsartan, losartan, candesartan, eprosartan, irbesartan, saprisartan, tasosartan, telmisartan, the compounds with the designation E-1477 and ZD-8731 of the following formulae

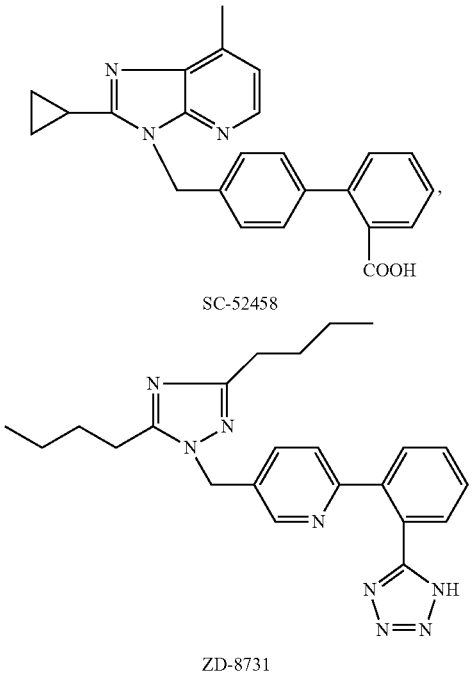

or, in each case, a pharmaceutically acceptable salt thereof.

The term "renin inhibitor" includes ditekiren (chemical name: [1S-[1R,2R,4R(1R,2R)]]-1-[(1,1-dimethylethoxy) carbonyl]-L-prolyl-L-phenylalanyl-N-[2-hydroxy-5-methyl-1-(2-methylpropyl)-4-[[[2-methyl-1-[[(2 pyridinylmethyl)amino]carbonyl]butyl]amino]carbonyl]hexyl]-N-alfa-methyl-L-histidinamide); terlakiren (chemical name: [R—(R,S)]—N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); Aliskiren (chemical name: (2S,4s,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl) nonanamide) and zankiren (chemical name: [1S-[1R[R(R)], 2S,3r]]-[1-(cyclohexylmethyl)-2,3-dihydroxy-5-m ethylhexyl]-alfa-[[2-[[(4-methyl-1-piperazinyl)sulfonyl] methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

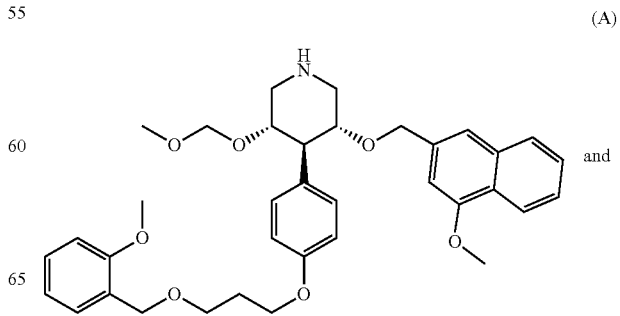

(A)

and

-continued (B)

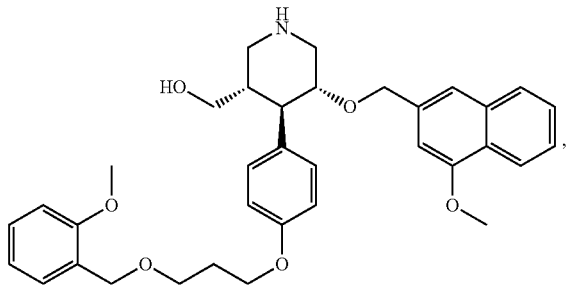

or pharmaceutically acceptable salts thereof. The term "aliskiren", if not defined specifically, is to be understood both as the free base and as a salt thereof, especially a pharmaceutically acceptable salt thereof, most preferably a hemi-fumarate salt thereof.

Examples of β-adrenergic receptor blockers that may be used in combination with the compounds of the disclosure include, but are not limited to, acebutolol, atenolol, betaxolol, bisoprolol, metoprolol, nadolol, propranolol, sotalol, and timolol.

Examples of inotropic agents that may be used in combination with the compounds of the disclosure include, but are not limited to, digoxin, dobutamine, and milrinone; Inotropes as used herein include, for example, dobutamine, isoproterenol, milrinone, amirinone, levosimendan, epinephrine, norepinephrine, isoproterenol, and digoxin.

Examples of calcium channel blockers that may be used in combination with the compounds of the disclosure include, but are not limited to, amlodipine, bepridil, diltiazem, felodipine, nicardipine, nimodipine, nifedipine, nisoldipine and verapamil.

The class of aldosterone synthase inhibitors comprises both steroidal and non-steroidal aldosterone synthase inhibitors, the latter being most preferred. The class of aldosterone synthase inhibitors comprises compounds having differing structural features. Examples of aldosterone synthase inhibitor that can be used in combination with the compounds of the present disclosure include, but are not limited to, the (+)-enantiomer of the hydrochloride of fadrozole (U.S. Pat. Nos. 4,617,307 and 4,889,861) of formula

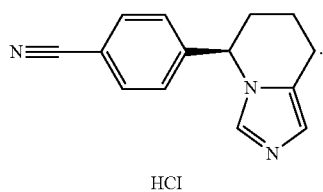 [SMILES: N#Cc1ccc([C@H]2CCCc3cncn32)cc1 ; "HCI"]

HCl or, if appropriable, a pharmaceutically acceptable salt thereof; and compounds and analogs generically and specifically disclosed e.g. in US2007/0049616, in particular in the compound claims and the final products of the working examples, the subject-matter of the final products, the pharmaceutical preparations and the claims are hereby incorporated into the present application by reference to this publication. Examples of aldosterone synthase inhibitors that can be used in combination with the compounds of the present disclosure include, but are not limited to, without limitation 4-(6,7-dihydro-5H-pyrrolo[1,2-c]imidazol-5-yl)-3-methylbenzonitrile; 5-(2-chloro-4-cyanophenyl)-6,7-dihydro-5H-pyrrolo[1,2-c]imidazole-5-carboxylic acid (4-methoxybenzyl)methylamide; 4'-fluoro-6-(6,7,8,9-tetrahydro-5H-imidazo[1,5-a]azepin-5-yl)biphenyl-3-carbonitrile; 5-(4-Cyano-2-methoxyphenyl)-6,7-dihydro-5H-pyrrolo[1,2-c]imidazole-5-carboxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c]imidazole-5-carboxylic acid 4-fluorobenzyl ester; 5-(4-Cyano-2-trifluoromethoxyphenyl)-6,7-dihydro-5H-pyrrolo[1,2-c]imidazole-5-carboxylic acid methyl ester; 5-(4-Cyano-2-methoxyphenyl)-6,7-dihydro-5H-pyrrolo[1,2-c]imidazole-5-carboxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-c]imidazol-5-yl)-2-methoxybenzonitrile; 3-Fluoro-4-(7-methylene-6,7-dihydro-5H-pyrrolo[1,2-c]imidazol-5-yl)benzonitrile; cis-3-Fluoro-4-[7-(4-fluoro-benzyl)-5,6,7,8-tetrahydro-imidazo[1,5-a]pyridin-5-yl]benzonitrile; 4'-Fluoro-6-(9-methyl-6,7,8,9-tetrahydro-5H-imidazo[1,5-a]azepin-5-yl)biphenyl-3-carbonitrile; 4'-Fluoro-6-(9-methyl-6,7,8,9-tetrahydro-5H-imidazo[1,5-a]azepin-5-yl)biphenyl-3-carbonitrile or in each case, the (R) or (S) enantiomer thereof; or if appropriable, a pharmaceutically acceptable salt thereof.

The term aldosterone synthase inhibitors also include, but are not limited to, compounds and analogs disclosed in WO2008/076860, WO2008/076336, WO2008/076862, WO2008/027284, WO2004/046145, WO2004/014914, and WO2001/076574.

Furthermore, Aldosterone synthase inhibitors also include, but are not limited to, compounds and analogs disclosed in U.S. patent applications US2007/0225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695. Preferred aldosterone synthase inhibitors suitable for use in the present disclosure include, without limitation 8-(4-Fluorophenyl)-5,6-dihydro-8H-imidazo[5,1-c1[1,41oxazine; 4-(5,6-Dihydro-8H-imidazo[5,1-c][1,4]oxazin-8-yl)-2-fluorobenzonitrile; 4-(5,6-Dihydro-8H-imidazo[5,1-c][1,4]oxazin-8-yl)-2,6-difluorobenzonitrile; 4-(5,6-Dihydro-8H-imidazo[5,1-c][1,4]oxazin-8-yl)-2-methoxybenzonitrile; 3-(5,6-Dihydro-8H-imidazo[5,1-c][1,4]oxazin-8-yl)benzonitrile; 4-(5,6-Dihydro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl)benzonitrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitrile; 8-[4-(1H-Tetrazol-5-yl)phenyl1-5,6-dihydro-8H-imidazo[5,1-c][1,4]oxazine as developed by Speedel or in each case, the (R) or (S) enantiomer thereof; or if appropriable, a pharmaceutically acceptable salt thereof.

Aldosterone synthase inhibitors useful in said combination include, but are not limited to, compounds and analogs generically and specifically disclosed e.g. in WO 2009/156462 and WO 2010/130796, in particular in the compound claims and the final products of the working examples, the subject-matter of the final products, the pharmaceutical preparations and the claims. Preferred Aldosterone Synthase inhibitors suitable for combination in the present disclosure include, 3-(6-Fluoro-3-methyl-2-pyridin-3-yl-1H-indol-1-ylmethyl)-benzonitrile hydrochloride, 1-(4-

Methanesulfonyl-benzyl)-3-methyl-2-pyridin-3-yl-1H-indole, 2-(5-Benzyloxy-pyridin-3-yl)-6-chloro-1-methyl-1H-indole, 5-(3-Cyano-1-methyl-1H-indol-2-yl)-nicotinic acid ethyl ester, N-[5-(6-chloro-3-cyano-1-methyl-1H-indol-2-yl)-pyridin-3-ylmethyl]-ethanesulfonamide, Pyrrolidine-1-sulfonic acid 5-(6-chloro-3-cyano-1-methyl-1H-indol-2-yl)-pyridin-3-ylester, N-Methyl-N-[5-(1-methyl-1H-indol-2-yl)-pyridin-3-ylmethyl]-methanesulfonamide, 6-Chloro-1-methyl-2-{5-[(2-pyrrolidin-1-yl-ethylamino)-methyl]-pyridin-3-yl}-1H-indole-3-carbonitrile, 6-Chloro-2-[5-(4-methanesulfonyl-piperazin-1-ylmethyl)-pyridin-3-yl]-1-methyl-1H-indole-3-carbonitrile, 6-Chloro-1-methyl-2-{5-[(1-methyl-piperidin-4-ylamino)-methyl]-pyridin-3-yl}-1H-indole-3-carbonitrile, Morpholine-4-carboxylic acid [5-(6-chloro-3-cyano-1-methyl-1H-indol-2-yl)-pyridin-3-ylmethyl]-amide, N-5-(6-Chloro-1-methyl-1H-indol-2-yl)-pyridin-3-ylmethyl]-ethanesulfonamide, C,C,C-Trifluoro-N-[5-(1-methyl-1H-indol-2-yl)-pyridin-3-ylmethyl]-methanesulfonamide, N-[5-(3-Chloro-4-cyano-phenyl)-pyridin-3-yl]-4-trifluoromethyl-benzenesulfonamide, N-[5-(3-Chloro-4-cyano-phenyl)-pyridin-3-yl]-1-phenyl-methanesulfonamide, N-(5-(3-chloro-4-cyanophenyl)pyridin-3-yl)butane-1-sulfonamide, N-(1-(5-(4-cyano-3-methoxyphenyl)pyridin-3-yl)ethyl)ethanesulfonamide, N-((5-(3-chloro-4-cyanophenyl)pyridin-3-yl)(cyclopropyl)methyl)ethanesulfonamide, N-(cyclopropyl(5-(1H-indol-5-yl)pyridin-3-yl)methyl)ethanesulfonamide, N-(cyclopropyl(5-naphtalen-1-yl-pyridin-3-yl)methyl)ethanesulfonamide, Ethanesulfonic acid [5-(6-chloro-1-methyl-1H-pyrrolo[2,3-b]pyridin-2-yl)-pyridin-3-ylmethyl]-amide and Ethanesulfonic acid {[5-(3-chloro-4-cyano-phenyl)-pyridin-3-yl]-cyclopropyl-methyl}-ethyl-amide.

Lipid-lowering agents are known in the art, and described, e.g., in *Goodman and Gilman's The Pharmacological Basis of Therapeutics*, 11th Ed., Brunton, Lazo and Parker, Eds., McGraw-Hill (2006); 2009 *Physicians' Desk Reference* (*PDR*), for example, in the 63rd (2008) Eds., Thomson PDR.

"Combination therapy" is intended to embrace administration of these therapeutic agents in a sequential manner, wherein each therapeutic agent is administered at a different time and in any order, or in alternation and in any order, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

In accordance with the foregoing, the present disclosure also provides a therapeutic combination, e.g., a kit, kit of parts, e.g., for use in any method as defined herein, comprising a compound of Formula (I), or a pharmaceutically acceptable salt thereof, to be used concomitantly or in sequence with at least one pharmaceutical composition comprising at least another therapeutic agent, selected from a hypolipidemic agent, niacin or analogs thereof, a bile acid sequestrant, a thyroid hormone mimetic, a thyroid hormone receptor (THR) β-selective agonist, a microsomal triglyceride transfer protein (MTP) inhibitor, an acyl CoA:diacylglycerol acyltransferase (DGAT) inhibitor, a Niemann Pick C1-like 1 (NPC1-L1) inhibitor, an agonist of ATP Binding Cassette (ABC) proteins G5 or G8, an inhibitory nucleic acid targeting PCSK9, an inhibitory nucleic acid targeting apoB100, apoA-I up-regulator/inducer, an ABCA1 stabilizer or inducer, phospholipid transfer protein (PLTP) inhibitor, fish oil, an antidiabetic agent, an anti-obesity agent, an agonist of peroxisome proliferator-activator receptors, ATP citrate lyase (ACL) inhibitor, and an anti-hypertensive agent, or a pharmaceutically acceptable salt thereof. The kit may comprise instructions for its administration. The combination can be a fixed combination (e.g. in the same pharmaceutical composition) or a free combination (e.g. in separate pharmaceutical compositions).

Similarly, the present disclosure provides a kit of parts comprising: (i) a pharmaceutical composition of the disclosure; and (ii) a pharmaceutical composition comprising a compound selected from a hypolipidemic agent, niacin or analogs thereof, a bile acid sequestrant, a thyroid hormone mimetic, a thyroid hormone receptor (THR) β-selective agonist, a microsomal triglyceride transfer protein (MTP) inhibitor, an acyl CoA:diacylglycerol acyltransferase (DGAT) inhibitor, a Niemann Pick C1-like 1 (NPC1-L1) inhibitor, an agonist of ATP Binding Cassette (ABC) proteins G5 or G8, an inhibitory nucleic acid targeting PCSK9, an inhibitory nucleic acid targeting apoB100, apoA-I up-regulator/inducer, an ABCA1 stabilizer or inducer, phospholipid transfer protein (PLTP) inhibitor, fish oil, an antidiabetic agent, an anti-obesity agent, an agonist of peroxisome proliferator-activator receptors, ATP citrate lyase (ACL) inhibitor, and an anti-hypertensive agent, or a pharmaceutically acceptable salt thereof, in the form of two separate units of the components (i) to (ii).

Likewise, the present disclosure provides a method as defined above comprising co-administration, e.g., concomitantly or in sequence, of a therapeutically effective amount of a compound of Formula (I), or a pharmaceutically acceptable salt thereof, and a second drug substance, said second drug substance being a hypolipidemic agent, niacin or analogs thereof, a bile acid sequestrant, a thyroid hormone mimetic, a thyroid hormone receptor (THR) β-selective agonist, a microsomal triglyceride transfer protein (MTP) inhibitor, an acyl CoA:diacylglycerol acyltransferase (DGAT) inhibitor, a Niemann Pick C1-like 1 (NPC1-L1) inhibitor, an agonist of ATP Binding Cassette (ABC) proteins G5 or G8, an inhibitory nucleic acid targeting PCSK9, an inhibitory nucleic acid targeting apoB100, apoA-I up-regulator/inducer, an ABCA1 stabilizer or inducer, phospholipid transfer protein (PLTP) inhibitor, fish oil, an antidiabetic agent, an anti-obesity agent, an agonist of peroxisome proliferator-activator receptors, ATP citrate lyase (ACL) inhibitor, and an anti-hypertensive agent, e.g., as indicated above.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. Proton nuclear magnetic resonance (NMR) spectra were obtained on either Bruker or Varian spectrometers at 300 or 400 MHz. Spectra are given in ppm (δ) and coupling constants, J, are reported in Hertz. Tetramethylsilane (TMS) was used as an internal standard.

| Abbreviations | |
| --- | --- |
| ACN, AcN | Acetonitrile |
| AcOEt | Ethyl acetate |
| AcOH | Acetic acid |
| AcOtBu | tert-Butylethylacetate |
| Arg | Arginine |
| BME | 8-Mercaptoethanol |
| Boc | tert-Butyloxycarbonyl |
| Boc$_2$O | Di-tert-butyl-dicarbonate |
| DBU | 1,8-Diazabicyclo[5.4.0]undec-7-ene |
| DCE | 1,2-Dichloroethane |
| DCM | Dichloromethane |
| DEAD | Diethylazodicarboxylate |
| DIAD | Diisopropylazodicarboxylate |
| DIC | N,N'-Diisopropylcarbodiimide |
| DIEA, DIPEA | N,N-Diisopropylethylamine |
| DMA | N,N-Dimethylacetamide |
| DMAP | 4-Dimethylaminopyridine |
| DME | 1,2-Dimethoxyethane |
| DMF | N,N-Dimethylformamide |
| DMSO | Dimethylsulfoxide |
| DMT-MM | 4-(4,6-Dimethoxy-1,3,5-triazin-2-yl)-4-methylmorpholinium chloride |
| DPPA | Diphenylphosphorylazide |
| EDC | N-(3-Dimethylaminopropyl)-N-ethylcarbodiimide HCl |
| EtOAc, EA | Ethyl acetate |
| EtOH | Ethanol |
| Fmoc | 9-Fluorenylmethyloxycarbonyl |
| FmocOSu | 9-Fluorenylmethyl-N-hydroxysuccinimide |
| HATU | 1-[Bis(dimethylamino)methylene]-1H-1,2,3-triazolo[4,5-b]pyridinium 3-oxid hexafluorophosphate |
| HCTU | O-(6-Chlorobenzotriazol-1-yl)-N,N,N',N'-tetramethyluronium hexafluorophosphate |
| HFIP | 1,1,1,3,3,3-Hexafluoropropan-2-ol |
| HOAt | 1-Hydroxy-7-azabenzotriazole |
| HOBt | 1-Hydroxybenzotriazole |
| IPA | 2-propanol |
| KHMDS | Potassium hexamethyldisilazane |
| KN(TMS)$_2$ | Potassium hexamethyldisilazane |
| KOtBu, tBuOK | Potassium tert-butylate |
| LCMS | Liquid chromatography mass spectrometry |
| LiHMDS | Lithium hexamethyldisilazane |
| mCPBA | meta-Chloroperbenzoic acid |
| MeI | Methyl iodide |
| MeOH | Methanol |
| MMPP | Magnesium monoperoxyphthalate |
| NaBH(OAc)$_3$ | Sodium triacetoxyborohydride |
| NaOAc | Sodium acetate |
| NaOMe | Sodium methanolate |
| NBS | N-Bromosuccinimide |
| nBuOH | n-Butanol |
| NIS | N-Iodosuccinimide |
| NMP | N-Methylpyrrolidine |
| Np | 4-Nitrophenyl |
| Ns | 4-Nosyl |
| o/n | over night |
| P1-tBu | Phosphazene base P1-t-Bu-tris(tetramethylene), tert-butylimino-tri(pyrrolidino)phosphorane |
| Pd(dtbpf)Cl$_2$ | [1,1'-Bis(di-tert-butylphosphino)ferrocene]dichloropalladium(II) |
| Pd(PPh$_3$)$_4$ | tetrakis(triphenylphosphine)palladium(0) |
| Pmc | 2,2,5,7,8-Pentamethylchroman-6-sulfonyl |
| PPHF | Pyridinium poly(hydrogen fluoride) |
| PS | Polystyrene |
| PTSA | para-Toluenesulfonic acid |
| PyOxim | (((1-Cyano-2-ethoxy-2-oxoethylidene)amino)oxy)tri(pyrrolidin-1-yl)phosphonium hexafluorophosphate(V) |
| Rt, rt | Retention time |
| Ser | Serine |
| SFC | Supercritical fluid chromatography |
| STAB | Sodium triacetoxyborohydride |
| TBAF | Tetrabutylammoniumfluoride |
| TBS | tert-Butyldimethylsilyl |
| TBTA | Tris[(1-benzyl-1H-1,2,3-triazol-4-Amethyl]amine |
| TBTU | 2-(1H-Benzotriazol-1-yl)-1,1,3,3-tetramethyluronium-tetrafluoroborate |
| TEA | Triethylamine |
| TFA | Trifluoroacetic acid |
| TFFH | Tetramethylfluoroform-amidinium hexafluorophosphate |
| THF | Tetrahydrofuran |
| TMOF | Trimethylorthoformate |
| TMSOTf | Trimethylsilyltriflate |
| TosBIC | alpha-Tosylbenzyl isocyanide |
| TOSMIC | Toluenesulfonylmethyl isocyanide |
| t$_R$ | Retention time |
| TTPA | Tris(N,N-tetramethylene)phosphoric acid triamide |

Purification Methods:

The final products were purified by preparative reversed-phase HPLC suing a Waters XBridge Prep C18 OBD Column, 5 μm, 30 mm×250 mm, Part No. 186004025. The following mobile phases were used:

Eluent A: 0.1% TFA in H$_2$O and eluent B: ACN

Eluent A: 0.01 M HCl in H$_2$O and eluent B: ACN

Gradients were designed based on the specific requirements of the separation problem. Pure products were lyophilized from ACN/H$_2$O and obtained, depending on the used eluents, as a free base or the corresponding trifluoroacetate, formate or hydrochloride. In several cases the salt form was changed using the following methods:

The TFA salt was partitioned between EtOAc and 5% aq. NaHCO$_3$. The organic phase was washed with 5% aq. NaHCO$_3$ (2×) and brine, dried over Na$_2$SO$_4$, filtered and evaporated to dryness in vacuo. The residue was dissolved in ACN/H$_2$O (1:1) and 1 M HCl (~1.5-3 eq per basic center), then lyophilized to afford the hydrochloride of the product as a white solid.

Analytical methods: The products were analyzed by the analytical methods described below.

Analytical method 1

Agilent 1100/1200 ALS system/Waters ZQD MS system
Eluent A: 0.05% Trifluoroacetic acid in $H_2O$
Eluent B: Acetonitrile
Column temperature: 40° C.
Flow: 2.0 mL/min
Column: SunFire C18, 3.5 μm, 3.0 × 30 mm
Gradient:

| Time | Eluent A [%] | Eluent B [%] |
|---|---|---|
| 0.00 | 95 | 5 |
| 1.70 | 5 | 95 |
| 2.00 | 5 | 95 |
| 2.10 | 95 | 5 |

Analytical method 2

Waters Acquity UPLC system/Waters SQD MS system
Eluent A: 5 mM Ammonium hydroxide in $H_2O$
Eluent B: 5 mM Ammonium hydroxide in acetonitrile
Column temperature: 50° C.
Flow: 1.0 mL/min
Column: Acquity UPLC BEH C18, 1.7 μm, 2.1 × 50 mm
Gradient:

| Time | Eluent A [%] | Eluent B [%] |
|---|---|---|
| 0.00 | 98 | 2 |
| 4.40 | 2 | 98 |
| 5.15 | 2 | 98 |
| 5.19 | 98 | 2 |

Analytical method 3

Waters Acquity UPLC system/Waters Xevo G2 Qtof MS system
Eluent A: 0.1% Formic acid in $H_2O$
Eluent B: 0.1% Formic acid in acetonitrile
Column temperature: 50° C.
Flow: 1.0 mL/min
Column: Acquity UPLC BEH C18, 1.7 μm, 2.1 × 50 mm
Gradient:

| Time | Eluent A [%] | Eluent B [%] |
|---|---|---|
| 0.00 | 98 | 2 |
| 0.06 | 98 | 2 |
| 1.76 | 2 | 98 |
| 2.00 | 2 | 98 |
| 2.16 | 98 | 2 |

Analytical method 4

Waters Acquity UPLC system/Waters SQD MS system
Eluent A: 0.1% Formic acid in $H_2O$
Eluent B: 0.1% Formic acid in acetonitrile
Column temperature: 50° C.
Flow: 1.0 mL/min
Column: Acquity UPLC BEH C18, 1.7 μm, 2.1 × 50 mm
Gradient:

| Time | Eluent A [%] | Eluent B [%] |
|---|---|---|
| 0.00 | 98 | 2 |
| 4.40 | 2 | 98 |
| 5.15 | 2 | 98 |
| 5.19 | 98 | 2 |

Analytical method 5

Waters Acquity UPLC system/Waters SQD MS system
Eluent A: 5 mM Ammonium hydroxide in $H_2O$
Eluent B: 5 mM Ammonium hydroxide in acetonitrile
Column temperature: 50° C.
Flow: 1.0 mL/min
Column: Acquity UPLC BEH C18, 1.7 μm, 2.1 × 30 mm
Gradient:

| Time | Eluent A [%] | Eluent B [%] |
|---|---|---|
| 0.00 | 98 | 2 |
| 0.10 | 98 | 2 |
| 1.50 | 2 | 98 |
| 1.80 | 2 | 98 |
| 1.90 | 98 | 2 |
| 2.00 | 98 | 2 |

Analytical method 6

Waters Acquity UPLC system/Waters Xevo G2 Qtof MS system
Eluent A: 0.1% Formic acid in $H_2O$
Eluent B: 0.1% Formic acid in acetonitrile
Column temperature: 50° C.
Flow: 1.0 mL/min
Column: Acquity UPLC BEH C18, 1.7 μm, 2.1 × 50 mm
Gradient:

| Time | Eluent A [%] | Eluent B [%] |
|---|---|---|
| 0.00 | 98 | 2 |
| 4.40 | 2 | 98 |
| 5.15 | 2 | 98 |
| 5.19 | 98 | 2 |

Analytical method 7

Waters Acquity UPLC system/Waters SQD MS system
Eluent A: 0.1% Formic acid in $H_2O$
Eluent B: 0.1% Formic acid in acetonitrile
Column temperature: 50° C.
Flow: 1.0 mL/min
Column: Acquity UPLC BEH C18, 1.7 μm, 2.1 × 30 mm
Gradient:

| Time | Eluent A [%] | Eluent B [%] |
|---|---|---|
| 0.00 | 98 | 2 |
| 0.10 | 98 | 2 |
| 1.50 | 2 | 98 |
| 1.80 | 2 | 98 |
| 1.90 | 98 | 2 |
| 2.00 | 98 | 2 |

Analytical method 8

Agilent 1100/1200 ALS system/Waters ZQD MS system
Eluent A: 5 mM Ammonium hydroxide in $H_2O$
Eluent B: Acetonitrile
Column temperature: 40° C.
Flow: 2.0 mL/min
Column: XBridge C18, 3.5 μm, 3.0 × 30 mm
Gradient:

| Time | Eluent A [%] | Eluent B [%] |
|---|---|---|
| 0.00 | 95 | 5 |
| 1.70 | 5 | 95 |
| 2.00 | 5 | 95 |
| 2.10 | 95 | 5 |

Analytical method 9

Waters Acquity UPLC/Waters QTof MS system
Eluent A: 0.05% Trifluoroacetic acid in $H_2O$
Eluent B: 0.04% Trifluoroacetic acid in acetonitrile
Column temperature: 80° C.
Flow: 0.5 mL/min
Column: Acquity UPLC CSH C18, 1.7 μm, 2.1 mm × 100 mm
Gradient:

Analytical methods: The products were analyzed by the analytical methods described below.

| Time | Eluent A [%] | Eluent B [%] |
| --- | --- | --- |
| 0.00 | 95 | 5 |
| 0.20 | 95 | 5 |
| 9.40 | 2 | 98 |
| 9.80 | 2 | 98 |
| 9.90 | 95 | 5 |
| 10.00 | 95 | 5 |

Analytical method 10

Waters Acquity UPLC/SQD MS system
Eluent A: 0.05% Formic acid and 3.75 mM ammonium acetate in $H_2O$
Eluent B: 0.04% Formic acid in acetonitrile
Column temperature: 60° C.
Flow: 1.0 mL/min
Column: Acquity UPLC HSS T3, 1.8 mm, 2.1 mm × 50 mm
Gradient:

| Time | Eluent A [%] | Eluent B [%] |
| --- | --- | --- |
| 0.00 | 95 | 5 |
| 1.40 | 2 | 98 |
| 1.80 | 2 | 98 |
| 1.90 | 95 | 5 |
| 2.00 | 95 | 5 |

Analytical method 11

Waters Acquity UPLC/SQD MS system
Eluent A: 0.05% Formic acid and 3.75 mM ammonium acetate in $H_2O$
Eluent B: 0.04% Formic acid in acetonitrile
Column temperature: 60° C.
Flow: 1.0 mL/min
Column: Acquity UPLC HSS T3, 1.8 mm, 2.1 mm × 50 mm
Gradient:

| Time | Eluent A [%] | Eluent B [%] |
| --- | --- | --- |
| 0.00 | 99 | 1 |
| 1.40 | 2 | 98 |
| 1.80 | 2 | 98 |
| 1.90 | 99 | 1 |
| 2.00 | 99 | 1 |

Analytical method 12

Waters Acquity UPLC/SQD MS system
Eluent A: 0.05% Formic acid and 3.75 mM ammonium acetate in $H_2O$
Eluent B: 0.04% Formic acid in acetonitrile
Column temperature: 60° C.
Flow: 1.0 mL/min
Column: Acquity UPLC HSS T3, 1.8 mm, 2.1 mm × 50 mm
Gradient:

| Time | Eluent A [%] | Eluent B [%] |
| --- | --- | --- |
| 0.00 | 95 | 5 |
| 9.40 | 2 | 98 |
| 9.80 | 2 | 98 |
| 9.90 | 95 | 5 |
| 10.00 | 95 | 5 |

Analytical method 13

Waters Acquity UPLC/Waters QTof MS system
Eluent A: 0.05% Trifluoroacetic acid in $H_2O$
Eluent B: 0.04% Trifluoroacetic acid in acetonitrile
Column temperature: 80° C.
Flow: 0.8 mL/min
Column: Acquity UPLC CSH C18, 1.7 μm, 2.1 mm × 100 mm
Gradient:

Analytical methods: The products were analyzed by the analytical methods described below.

| Time | Eluent A [%] | Eluent B [%] |
| --- | --- | --- |
| 0.00 | 95 | 5 |
| 0.20 | 95 | 5 |
| 9.40 | 2 | 98 |
| 9.80 | 2 | 98 |
| 9.90 | 95 | 5 |
| 10.00 | 95 | 5 |

Analytical method 14

Waters Acquity UPLC/Waters QTof MS system
Eluent A: 0.05% Trifluoroacetic acid in $H_2O$
Eluent B: 0.04% Trifluoroacetic acid in acetonitrile
Column temperature: 80° C.
Flow: 0.5 mL/min
Column: Acquity UPLC CSH C18, 1.7 μm, 2.1 mm × 100 mm
Gradient:

| Time | Eluent A [%] | Eluent B [%] |
| --- | --- | --- |
| 0.00 | 95 | 5 |
| 0.20 | 95 | 5 |
| 9.40 | 2 | 98 |
| 10.40 | 2 | 98 |
| 10.50 | 95 | 5 |
| 11.00 | 95 | 5 |

Analytical method 15

Waters Acquity UPLC/SQD MS system
Eluent A: 0.05% Formic acid and 3.75 mM ammonium acetate in $H_2O$
Eluent B: 0.04% Formic acid in acetonitrile
Column temperature: 60° C.
Flow: 0.8 mL/min
Column: Acquity UPLC HSS T3, 1.8 mm, 2.1 mm × 50 mm
Gradient:

| Time | Eluent A [%] | Eluent B [%] |
| --- | --- | --- |
| 0.00 | 95 | 5 |
| 9.40 | 2 | 98 |
| 9.80 | 2 | 98 |
| 9.90 | 95 | 5 |
| 10.00 | 95 | 5 |

Example 1: General Synthesis Procedure for Assembly of Tetramer Compounds

The cyclic and linear tetramer compounds (e.g., Compound 86 in Example 2) were assembled on solid phase and in solution from blocks A (succinate), B (diamine), C (α-amino acid (α-aa)), D (α-amino acid (α-aa)), and E (aldehyde) as shown in the synthetic scheme in FIG. 1. The synthesis of building blocks A-E used for the syntheses is described herein below. The letter of the building block refers to the specific position in the final compound (See FIG. 1). For the solid phase strategies, PS-2-Chlorotrityl chloride resin was used. A variety of coupling reagents were used for amide formation, e.g., HATU, PyOxim, TBTU, DMT-MM and Ghosez's reagent (1-chloro-N,N,2-trimethyl-1-propenylamine).

Coupling of succinate A with diamine B using standard coupling conditions (e.g., an amide coupling reagent in a solvent) followed by removal of the Fmoc protecting group under basic conditions provided A-B (See FIG. 1). Polymer bound dimer A-B was obtained by attachment of building block A-B to the solid phase (PS) by coupling of the acid group on A of building block A-B with an amine on the resin using standard coupling conditions (e.g., an amide coupling reagent in a solvent) followed by deprotection of the amine on B of building block A-B (e.g., removal of an F-moc protecting group under basic conditions or a Boc protecting group under acidic conditions) (See FIG. 1). The deprotection and coupling steps were repeated followed by cleavage from the resin (e.g., by treatment with HFIP) to provide Intermediate A-B-C-D (See FIG. 1). Reductive amination of Intermediate A-B-C-D with aldehyde E using a reducing agent (e.g., sodium cyano borohydride or sodium borohydride) in a solvent provides Intermediate A-B-C-D-E (See FIG. 1). Cyclization under standard coupling conditions using an amide coupling reagent followed by deprotection provides the cyclic tetramer compound.

Example 2: Synthesis of Building Block A—Succinates

Example 2.1: Synthesis of (R)-2-benzyl-4-(tert-butoxy)-4-oxobutanoic acid (A1)

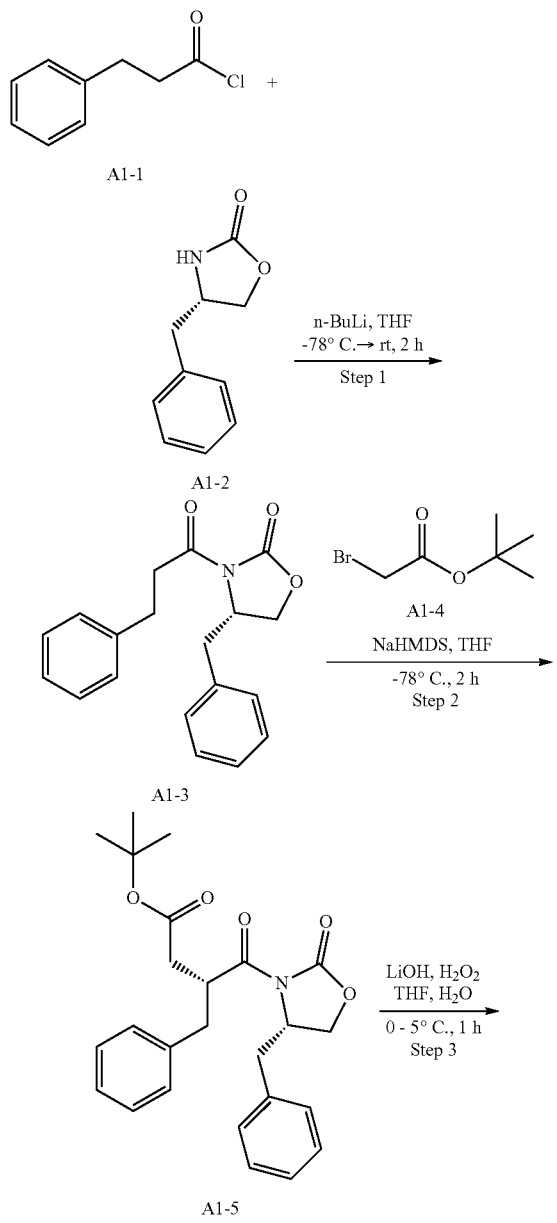

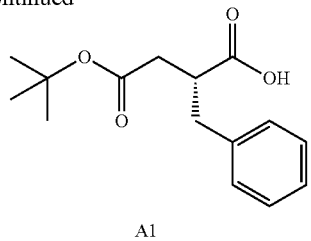

Step 1. (S)-4-Benzyl-3-(3-phenylpropanoyl)oxazolidin-2-one (A1-3)

To a stirred solution of (S)-4-benzyloxazolidin-2-one (A1-2, 500 g, 2.821 mol) in THF (9 L) at −78° C. was added n-BuLi (2.5 M in hexane) (1.24 L, 3.103 mol) over a period of 30 min. The reaction mixture was then stirred at −78° C. for 30 min and a solution of 3-phenylpropanoyl chloride (A1-1, 571 g, 3.38 mol) in THF (1 L) was added over a period of 1 h at −78 to −60° C. The resulting mixture was stirred for 2 h and then allowed to warm up slowly to rt. The reaction mixture was cooled to 0° C., quenched with sat. aq. NH$_4$Cl (500 mL) and the product was extracted with DCM (2×1.5 L). The combined organic phases were washed with 0.5 N NaOH (1 L) and brine (1 L), dried over Na$_2$SO$_4$, filtered, and concentrated to dryness in vacuo. The crude product was triturated with petroleum ether (5 L) for 1 h and the resulting suspension was filtered. The residue was washed with petroleum ether (500 mL) and dried under vacuum to afford compound A1-1 (815 g, 93%) as an off-white solid. Analytical method 7; $t_R$=1.53 min; [M+H]$^+$=310.2.

Step 2. (R)-tert-butyl 3-benzyl-4-((S)-4-benzyl-2-oxooxazolidin-3-yl)-4-oxobutanoate (A1-5)

To a stirred solution of A1-3 (500 g, 1.616 mol) in THF (7 L) at −78° C. was added 1 M NaHMDS in THF (1.94 L, 1.939 mol) over a period of 30 min. The reaction mixture was then stirred for 1 h at −78° C. and a solution of tert-butyl 2-bromo acetate (A1-4, 472.8 g, 2.424 mol) in THF (500 mL) was added dropwise over a period of 30 min at −78° C. The resulting mixture was stirred for 2 h and then quenched with sat. aq. NH$_4$Cl (500 mL). The product was extracted with EtOAc (2×1.5 L). The combined organic phases were washed with brine (2 L), dried over Na$_2$SO$_4$, filtered, and concentrated in vacuo. The crude material was triturated with methanol (800 mL) for 1 h. The suspension was filtered and the resulting residue was washed with methanol (200 mL) and dried under vacuum to afford Intermediate A1-5 (410 g, 60%) as an off-white solid. Analytical method 7; $t_R$=1.78 min; [M-tBu+H]$^+$=368.3.

Step 3. (R)-2-benzyl-4-(tert-butoxy)-4-oxobutanoic acid (A1)

To a stirred solution of A1-5 (250 g, 0.59 mol) in THF (9 L) at 0-5° C. was added 30% H$_2$O$_2$ (267 mL, 2.37 mol). The resulting mixture was stirred for 30 min at 0-5° C. and then a solution of LiOH·H$_2$O (49.5 g, 1.18 mol) in H$_2$O (3 L) was added. The reaction mixture was stirred at 0-5° C. for 1 h and then quenched by addition of sat. aq. sodium sulfite (1.6 L) and sat. sodium bicarbonate (1.6 L). The resulting mixture was concentrated in vacuo (removal of THF). H$_2$O (3 L) was added and the aqueous phase was washed with DCM (2×1 L) to remove any impurities. The aqueous phase was cooled to 5° C. and acidified to pH ~1.5 with 6 M HCl (1 L). The aqueous phase was extracted with ethyl acetate (3×1 L). The combined organic phases were washed with brine (1 L), dried over $Na_2SO_4$, filtered, and concentrated to dryness in vacuo to afford Intermediate A1 as an oil (125 g, 82%).

Analytical method 7; $t_R$=1.78 min; [M−H]⁻=263.5. ¹H NMR (400 MHz, chloroform-d) δ ppm 1.42 (s, 9H), 2.36 (dd, J=16.93, 4.58 Hz, 1H), 2.48-2.62 (m, 1H), 2.71-2.83 (m, 1H), 3.00-3.18 (m, 2H), 7.12-7.35 (m, 6H).

The following Building Blocks (BB) in Table 1 were synthesized according to the procedure described in Example 2.1 for Building Block A1.

TABLE 1

Succinates - Building block A

| BB No. | Structure/Chemical Name | Starting Material | LCMS |
|---|---|---|---|
| A2 | (R)-4-(tert-butoxy)-4-oxo-2-(pyridin-3-ylmethyl)butanoic acid | Starting from A2-1 (see Example 2.2) | Analytical method 10<br>$t_R$ = 0.61 min<br>[M + H]⁺ = 266.1 |
| A3 | (S)-4-(tert-butoxy)-2-((R)-2,3-dihydro-1H-inden-1-yl)-4-oxobutanoic acid | Starting from A3-1-Diastereomeric mixture separated after Step 2 by silica gel flash chromatography and separated diastereomers (structure confirmed by X-ray crystallography) onto the next step. | Analytical method 10<br>$t_R$ = 1.09 min<br>[M − H]⁻ = 289.2 |
| A4 | (S)-4-(tert-butoxy)-2-((S)-2,3-dihydro-1H-inden-1-yl)-4-oxobutanoic acid | Starting from A3-1-Diastereomeric mixture separated after Step 2 by silica gel flash chromatography and separated diastereomers (structure confirmed by X-ray crystallography) was taken onto the next step. | Analytical method 10<br>$t_R$ = 1.11 min<br>[M − H]⁻ = 289.3 |
| A5 | (S)-4-(tert-butoxy)-2-((R)-3,3-dimethyl-2,3-dihydro-1H-inden-1-yl)-4-oxobutanoic acid | Starting from A5-3-Diastereomeric mixture separated after Step 2 by silica gel flash chromatography and (R,S)-diastereomer (confirmed by X-ray crystallography) was taken onto the next step. | Analytical method 10<br>$t_R$ = 1.21 min<br>[M − H]⁻ = 317.2 |

TABLE 1-continued

Succinates - Building block A

| BB No. | Structure/Chemical Name | Starting Material | LCMS |
|---|---|---|---|
| A6 | 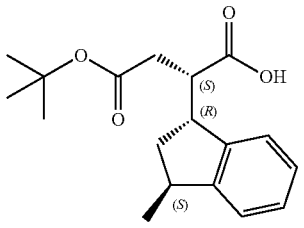<br>(S)-4-(tert-butoxy)-2-((1R,3S)-3-methyl-2,3-dihydro-1H-inden-1-yl)-4-oxobutanoic acid | Starting from A6-6-Diastereomeric mixture separated after Step 2 by silica gel flash chromatography and desired diastereomer (confirmed by X-ray crystallography) was taken onto the next step. | Analytical method 15<br>$t_R$ = 5.65 min<br>$[M - H]^-$ = 303.1 |
| A7 | 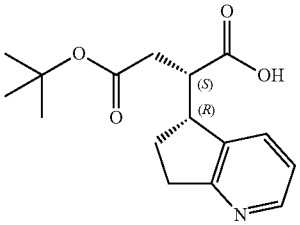<br>(S)-4-(tert-butoxy)-2-((R)-6,7-dihydro-5H-cyclopenta[b]pyridin-5-yl)-4-oxobutanoic acid | Starting from A7-4. | Analytical method 10<br>$t_R$ = 0.67 min<br>$[M + H]^+$ = 292.1 |
| A8 | 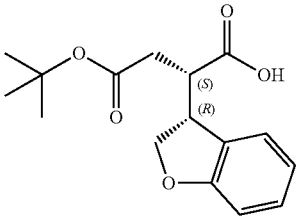<br>(S)-4-(tert-butoxy)-2-((R)-2,3-dihydrobenzofuran-3-yl)-4-oxobutanoic acid | Starting from A8-4-Diastereomeric mixture separated after Step 2 by silica gel flash chromatography and (R,S)-diastereomer (confirmed by X-ray crystallography) was taken onto the next step. | Analytical method 15<br>$t_R$ = 4.57 min<br>$[M - H]^-$ = 291.1 |
| A9 | 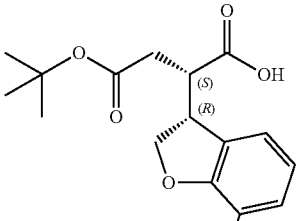<br>(S)-4-(tert-butoxy)-2-((R)-7-methoxy-2,3-dihydrobenzofuran-3-yl)-4-oxobutanoic acid | Starting from A9-1-Diastereomeric mixture separated after Step 2 by silica gel flash chromatography and desired diastereomer (confirmed by X-ray crystallography) was taken onto the next step. | Analytical method 10<br>$t_R$ = 0.96 min<br>$[M - H]^-$ = 321.2 |
| A10 | 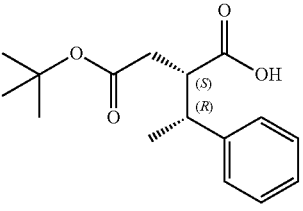<br>(S)-4-(tert-butoxy)-4-oxo-2-((R)-1-phenylethyl)butanoic acid | Starting from A10-1. | Analytical method 12<br>$t_R$ = 4.16 min<br>$[M - H]^-$ = 277.1 |

TABLE 1-continued

Succinates - Building block A

| BB No. | Structure/Chemical Name | Starting Material | LCMS |
|---|---|---|---|
| A11 | (R)-4-(tert-butoxy)-2-ethyl-4-oxobutanoic acid | Starting from butyryl chloride. | Analytical method 10 $t_R = 0.89$ min $[M - H]^- = 201.2$ |
| A12 | (R)-3-(methoxycarbonyl)-4-methylpentanoic acid | Commercially Available | — |
| A13 | R)-2-((((9H-fluoren-9-yl)methoxy)carbonyl)amino)-4-(tert-butoxy)-4-oxobutanoic acid | Commercially Available | — |

Example 2.2: Synthesis of (S)-4-benzyl-3-(3-(pyridin-3-yl)propanoyl)oxazolidin-2-one (A2-1)

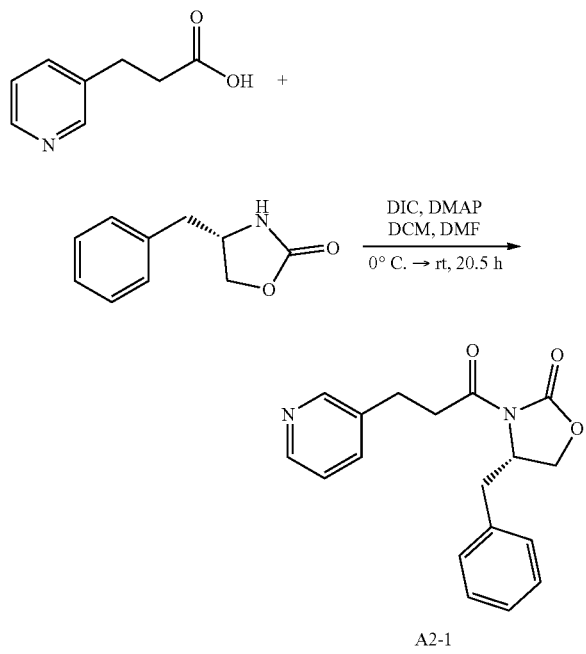

To 3-(pyridin-3-yl)propanoic acid (7.56 g, 50 mmol), (S)-4-benzyloxazolidin-2-one (8.86 g, 50.0 mmol) and DMAP (1.833 g, 15.0 mmol) was added DCM (150 mL) and the resulting mixture was stirred at rt for 20 min and then cooled to 0° C. The acid was not dissolved to a significant extent. A solution of DIC (10.91 mL, 70.0 mmol) in DCM (10 mL) was then added dropwise at 0° C. However, the acid was still only partially dissolved. DMF (75 mL) was added and the mixture was stirred for 20.5 h and then allowed to warm up to rt. The solution was concentrated to dryness in vacuo and the residue was suspended in DCM. The suspension was filtered and the residue was washed with DCM. The filtrate was concentrated to dryness in vacuo. The crude product was purified by flash silica gel chromatography (eluent A: heptane/DIEA (98:2); eluent B: EtOAc/DIEA (98:2)). Pure fractions were combined and concentrated to dryness in vacuo and the residue was dissolved in toluene and the solution was concentrated to dryness in vacuo. This treatment was repeated twice. A2-1 (11.56 g, 37.3 mmol, 75% yield) was obtained as a mixture of an oil and crystals. Analytical method 10; $t_R$=0.77 min; $[M+H]^+$=311.1.

The following Intermediates (Int) or Building Blocks (BB) in Table 2 were synthesized according to the procedure described in Example 2.2 for Intermediate A2-1

Table 2:

| BB No. | Structure | Name | Starting material | LCMS |
|---|---|---|---|---|
| A3-1 | 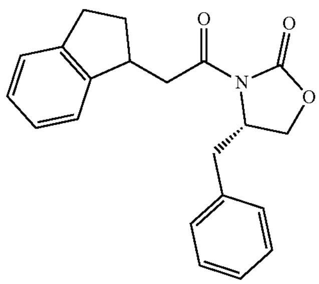 [SMILES: O=C(CC1CCc2ccccc21)N1C(=O)OC[C@@H]1Cc1ccccc1] | (4S)-4-benzyl-3-(2-(2,3-dihydro-1H-inden-1-yl)acetyl)oxazolidin-2-one (diastereomeric mixture) | Starting from 2-(2,3-dihydro-1H-inden-1-yl)acetic acid | Analytical method 10 $t_R$ = 1.26 min [M + H]$^+$ = 336.2 |
| A5-3 | 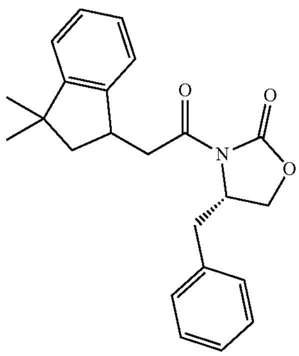 [SMILES: CC1(C)CC(CC(=O)N2C(=O)OC[C@@H]2Cc2ccccc2)c2ccccc21] | (4S)-4-benzyl-3-(2-(3,3-dimethyl-2,3-dihydro-1H-inden-1-yl)acetyl)oxazolidin-2-one (diastereomeric mixture) | Starting from A5-2 (see Example 2.3) | Analytical method 10 $t_R$ = 1.35 min [M + H]$^+$ = 364.2 |
| A7-4 | 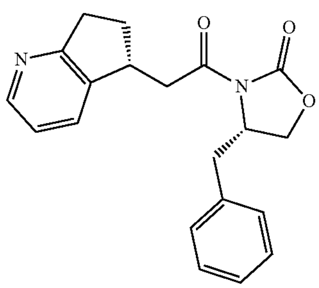 [SMILES: O=C(C[C@H]1CCc2ncccc21)N1C(=O)OC[C@@H]1Cc1ccccc1] | (S)-4-benzyl-3-(2-((R)-6,7-dihydro-5H-cyclopenta[b]pyridin-5-yl)acetyl)oxazolidin-2-one | Starting from A7-3 | Analytical method 10 $t_R$ = 0.82 min [M + H]$^+$ = 337.3 |
| A8-4 | 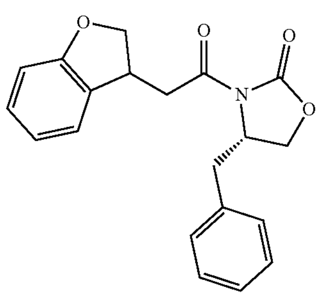 [SMILES: O=C(CC1COc2ccccc21)N1C(=O)OC[C@@H]1Cc1ccccc1] | (S)-4-benzyl-3-(2-((R)-2,3-dihydrobenzofuran-3-yl)acetyl)oxazolidin-2-one (diastereomeric mixture) | Starting from A8-3 | Analytical method 15 $t_R$ = 5.62 min [M + H]$^+$ = 338.2 |
| A9-1 | 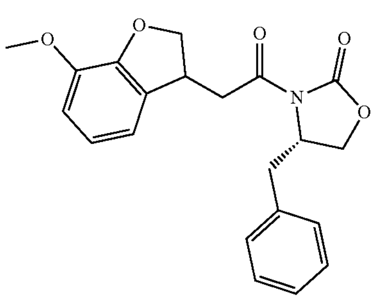 [SMILES: COc1cccc2c1OCC2CC(=O)N1C(=O)OC[C@@H]1Cc1ccccc1] | (4S)-4-benzyl-3-(2-(7-methoxy-2,3-dihydrobenzofuran-3-yl)acetyl)oxazolidin-2-one (diastereomeric mixture) | Starting from 2-(7-methoxy-2,3-dihydrobenzofuran-3-yl)acetic acid | Analytical method 15 $t_R$ = 5.39/5.46 min [M + NH$_4$]$^+$ = 385.3 |

| BB No. | Structure | Name | Starting material | LCMS |
|---|---|---|---|---|
| A10-1 | 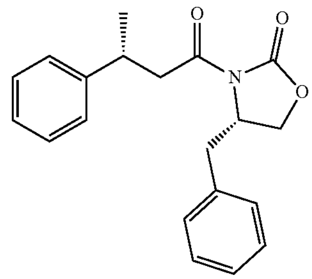 [SMILES: C[C@H](CC(=O)N1C(=O)OC[C@@H]1Cc1ccccc1)c1ccccc1] | (S)-4-benzyl-3-((R)-3-phenylbutanoyl)-oxazolidin-2-one | Starting from (R)-3-phenylbutanoic acid | Analytical method 12 $t_R$ = 4.98 min [M + H]$^+$ = 324.3 |

Example 2.3: Synthesis of 2-(3,3-dimethyl-2,3-dihydro-1H-inden-1-yl)acetic acid (A5-2)

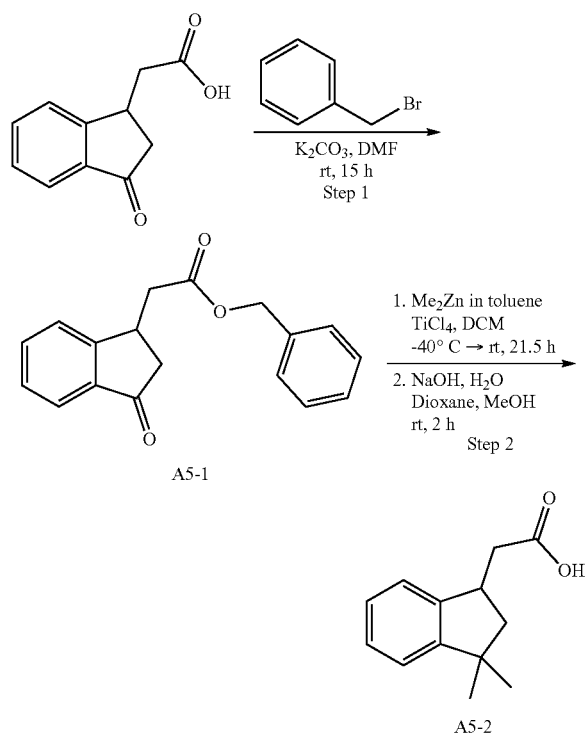

Step 1. Benzyl 2-(3-oxo-2,3-dihydro-1H-inden-1-yl)acetate (A5-1)

To 2-(3-oxo-2,3-dihydro-1H-inden-1-yl)acetic acid (3.80 g, 20.0 mmol) and K$_2$CO$_3$ (2.76 g, 20.00 mmol) were added DMF (50 mL) and benzyl bromide (2.379 mL, 20.00 mmol). The reaction was stirred for 15 h at rt, then partitioned between EtOAc (300 mL) and 5% aq. NaHCO$_3$ (250 mL). The organic phase was washed with 5% aq. NaHCO$_3$ (3×50 mL) and brine (30 mL), dried over Na$_2$SO$_4$, filtered, and concentrated to dryness in vacuo to afford A5-1 (5.66 g, 20.0 mmol, ~100% yield) as a beige oil. The crude product was used in the next step without purification. Analytical method 10; $t_R$=1.06 min; [M+H]$^+$=281.2.

Step 2. 2-(3,3-Dimethyl-2,3-dihydro-1H-inden-1-yl)acetic acid (A5-2)

Step 2-1: To a solution of TiCl$_4$ (1.103 mL, 10.00 mmol) in DCM (25 mL) at −40° C. was added slowly 2 M dimethylzinc in toluene (7.50 mL, 15.00 mmol). After stirring at −40° C. for 10 min a solution of A5-1 (1402 mg, 5.0 mmol) in DCM (5 mL) was added. The resulting solution was stirred for 8 h and then allowed to warm slowly to 0° C. Stirring was continued for 13.5 h allowing the reaction to warm to rt. The reaction was quenched by the addition of H$_2$O (2 mL) and MeOH (2 mL). H$_2$O (10 mL) and DCM (10 mL) were added and the phases were separated. The organic phase was washed with H$_2$O (10 mL) and brine (10 mL), then concentrated to dryness in vacuo.

Step 2-2: To the crude residue from Step 2-1 dissolved in dioxane (20 mL) and MeOH (5 mL) was added 1 M NaOH (10.0 mL, 10.0 mmol) and the resulting mixture was stirred for 2 h at rt becoming a clear solution. Dioxane and MeOH were removed in vacuo and the residue was partitioned between EtOAc (100 mL) and 1 M aq. HCl (20 mL). The organic phase was washed with 5% aq. KHSO$_4$ (2×20 mL) and brine (15 mL), dried over Na$_2$SO$_4$, filtered, and concentrated to dryness in vacuo. The crude product was purified by silica gel flash chromatography (eluent A: heptane/AcOH (99:1); eluent B: EtOAc/AcOH (99:1)). Pure fractions were combined and concentrated to dryness in vacuo. The residue was dissolved in toluene and concentrated to dryness in vacuo. This treatment was repeated twice to afford A5-2 (769 mg, 3.76 mmol, 75% yield) as a yellowish solid. The product was taken to the next step without further purification. Analytical method 10; $t_R$=1.00 min; [M−H]$^−$=203.2.

Example 2.4: Synthesis of (S)-4-benzyl-3-(2-((1R,3S)-3-methyl-2,3-dihydro-1H-inden-1-yl)acetyl)oxazolidin-2-one (A6-6)

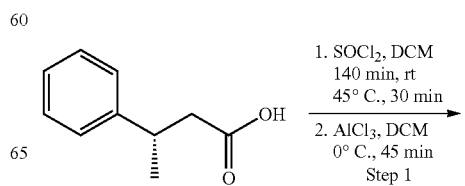

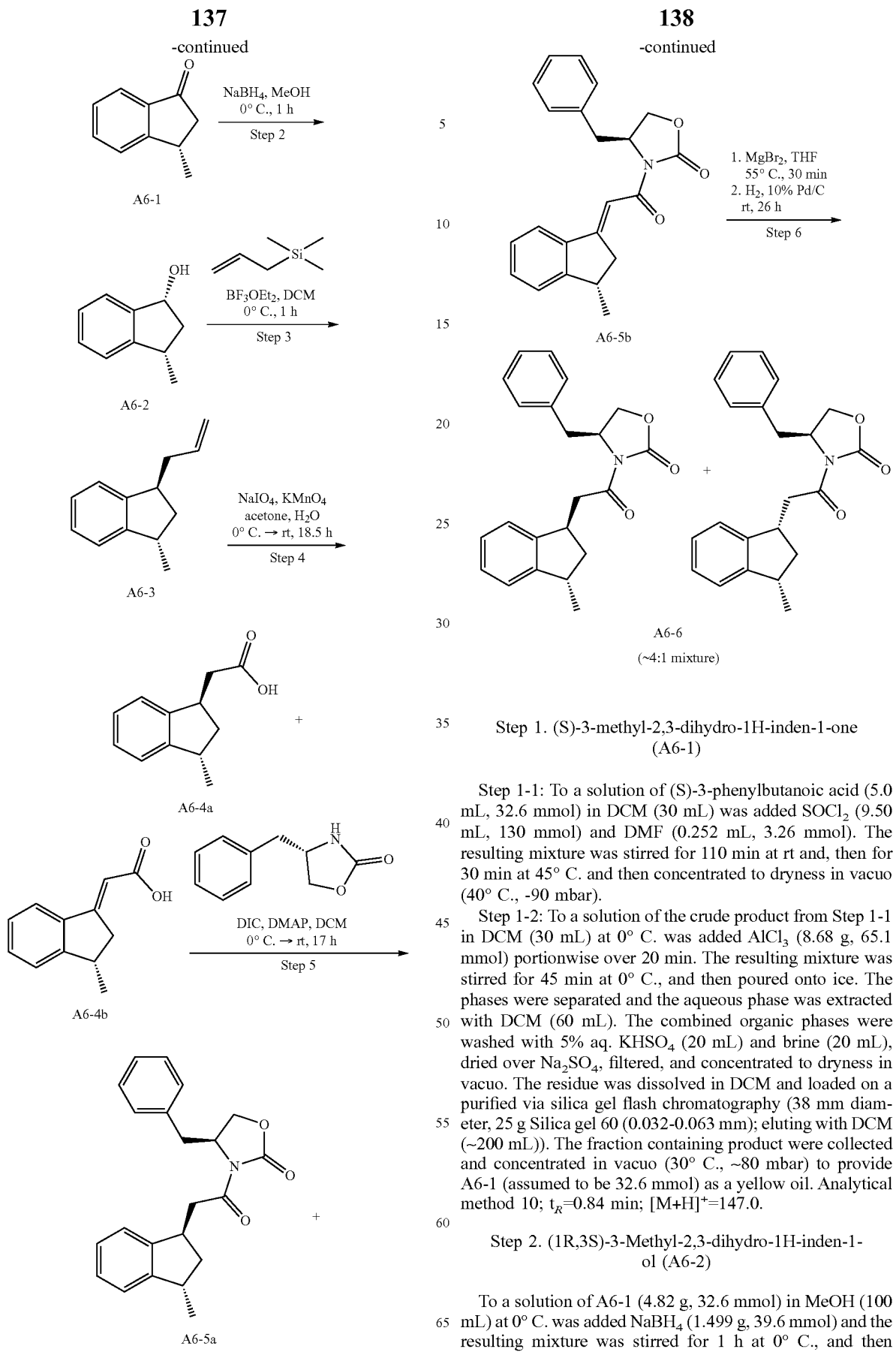

Step 1. (S)-3-methyl-2,3-dihydro-1H-inden-1-one (A6-1)

Step 1-1: To a solution of (S)-3-phenylbutanoic acid (5.0 mL, 32.6 mmol) in DCM (30 mL) was added SOCl$_2$ (9.50 mL, 130 mmol) and DMF (0.252 mL, 3.26 mmol). The resulting mixture was stirred for 110 min at rt and, then for 30 min at 45° C. and then concentrated to dryness in vacuo (40° C., ~90 mbar).

Step 1-2: To a solution of the crude product from Step 1-1 in DCM (30 mL) at 0° C. was added AlCl$_3$ (8.68 g, 65.1 mmol) portionwise over 20 min. The resulting mixture was stirred for 45 min at 0° C., and then poured onto ice. The phases were separated and the aqueous phase was extracted with DCM (60 mL). The combined organic phases were washed with 5% aq. KHSO$_4$ (20 mL) and brine (20 mL), dried over Na$_2$SO$_4$, filtered, and concentrated to dryness in vacuo. The residue was dissolved in DCM and loaded on a purified via silica gel flash chromatography (38 mm diameter, 25 g Silica gel 60 (0.032-0.063 mm); eluting with DCM (~200 mL)). The fraction containing product were collected and concentrated in vacuo (30° C., ~80 mbar) to provide A6-1 (assumed to be 32.6 mmol) as a yellow oil. Analytical method 10; $t_R$=0.84 min; [M+H]$^+$=147.0.

Step 2. (1R,3S)-3-Methyl-2,3-dihydro-1H-inden-1-ol (A6-2)

To a solution of A6-1 (4.82 g, 32.6 mmol) in MeOH (100 mL) at 0° C. was added NaBH$_4$ (1.499 g, 39.6 mmol) and the resulting mixture was stirred for 1 h at 0° C., and then quenched by the addition of 5% aq. NaHCO$_3$ (5 mL) and H₂O (10 mL). The MeOH was removed in vacuo and the resulting residue was partitioned between EtOAc (100 mL) and 5% aq. NaHCO₃ (15 mL). The organic phase was washed with 5% aq. NaHCO₃ (2×10 mL) and brine (10 mL), dried over Na₂SO₄, filtered, and concentrated to dryness in vacuo (30° C.; 65 mbar) to afford A6-2 (4.645 g, 31.3 mmol, 96% yield) as a white solid. The crude product was used in the next step. Analytical method 15; $t_R$=3.28 min; [M−OH]⁺=131.1.

Step 3. (1S,3S)-1-Allyl-3-methyl-2,3-dihydro-1H-indene (A6-3)

To a solution of A6-2 (4.64 g, 31.3 mmol) and allyltrimethylsilane (14.98 mL, 94 mmol) in DCM (dry, 70 mL) at 0° C. was added BF₃—OEt₂ (3.97 mL, 31.3 mmol) dropwise over 5 min. The resulting mixture was stirred for 1 h at 0° C., and then quenched by the addition of 5% aq. NaHCO₃ (200 mL). The phases were separated and the aqueous phase was extracted with DCM (50 mL). The combined organic phases were washed with 5% aq. NaHCO₃ (2×20 mL) and brine (20 mL), dried over Na₂SO₄, filtered, and concentrated to dryness in vacuo (40° C., ~45 mbar) to afford A6-3 (containing ~16% of cis-isomer according to ¹H-NMR; 5.22 g, 30.3 mmol, 97% yield) as a yellowish oil. The crude product was used in the next step. Analytical method 10; $t_R$=1.40 min.

Step 4. 2-((1R,3S)-3-Methyl-2,3-dihydro-1H-inden-1-yl)acetic acid and dehydro analogue (A6-4)

To a solution of A6-3 (5.22 g, 30.3 mmol) in acetone (130 mL) was added portionwise a slurry of sodium periodate (22.68 g, 106 mmol) and KMnO₄ (2.87 g, 18.18 mmol) in H₂O (200 mL) over 25 min. The reaction was stirred for 20 min at 0° C., and then further acetone (70 mL) was added. After stirring for 50 min at rt, KMnO₄ (2.87 g, 18.18 mmol) in H₂O (30 mL) was added and stirring was continued for 80 min. Further acetone (100 mL), H₂O (100 mL), KMnO₄ (2.87 g, 18.18 mmol) and sodium periodate (6.48 g, 30.3 mmol) were added and the reaction was stirred for 15 h 35 min at rt. The reaction mixture was filtered, the acetone was removed in vacuo and the resulting residue was acidified by addition of 2 M aq. HCl (50 mL). The aqueous phase was extracted with EtOAc (2×100 mL). The combined organic phases were washed with brine (20 mL), dried over Na₂SO₄, filtered, and concentrated to dryness in vacuo. The crude product was purified by flash silica gel chromatography (eluent A: heptane/AcOH (99:1); eluent B: EtOAc/AcOH (99:1)) to afford the desired product A6-4a together with a dehydro analogue A6-4b (2.579 g, 13.56 mmol, 45% yield) as a yellow oil. The product was used in the next step without further purification. Analytical method 15; A6-4a: $t_R$=4.15 min, [M−H]⁻=189.1; A6-4b: $t_R$=3.99 min, [M−H]⁻=187.1.

Step 5. (S)-4-Benzyl-3-(2-((1R,3S)-3-methyl-2,3-dihydro-1H-inden-1-yl)acetyl)oxazolidin-2-one and dehydro analogue (A6-5)

A6-4 (A6-4a and A6-4b, 2.579 g, 13.56 mmol), (S)-4-benzyloxazolidin-2-one (2.402 g, 13.56 mmol) and DMAP (0.497 g, 4.07 mmol) were dissolved in DCM (40 mL). The solution was cooled down to 0° C. under an atmosphere of nitrogen and DIC (2.96 mL, 18.98 mmol) was added dropwise. The resulting mixture was stirred for 17 h and then allowed to warm up slowly to rt. The resulting suspension was filtered and washed with DCM. The filtrate was concentrated to dryness in vacuo. The crude product was purified by flash silica gel chromatography (eluent A: heptane; eluent B: EtOAc) to afford A6-5 (as a mixture of A6-5a and A6-5b; 3.983 g, 11.40 mmol, 84% yield) as a reddish oil. The product was used in the next step without further purification. Analytical method 15; A6-5a: $t_R$=6.63 min, [M+H]⁺=350.2; A6-5b: $t_R$=6.51 min, [M+H]⁺=348.2.

Step 6. (S)-4-Benzyl-3-(2-((1R,3S)-3-methyl-2,3-dihydro-1H-inden-1-yl)acetyl)oxazolidin-2-one and Cis Analogue (A6-6)

To A6-5 (3.983 g, 11.40 mmol) dissolved in THF (80 mL) was added magnesium bromide (2.73 g, 14.82 mmol) and the resulting mixture was stirred for 30 min at 55° C. becoming a clear solution. After cooling to rt, 10% Pd/C (0.364 g, 0.342 mmol) was added and the resulting suspension was stirred for 26 h under an H₂-atmosphere, and then filtered through HyFlo. The filtrate was concentrated in vacuo and the residue was partitioned between EtOAc (100 mL) and 5% aq. NaHCO₃ (20 mL). The organic phase was washed with 5% aq. NaHCO₃ (2×20 mL) and brine (15 mL), dried over Na₂SO₄, filtered, and concentrated to dryness in vacuo to afford A6-6 (as a mixture containing ~20% of cis-isomer) (3.594 g, 10.29 mmol, 90% yield) as a yellow oil. The product was used in the next step without purification. Analytical method 15; $t_R$=6.61; [M+H]⁺=350.2.

Example 2.5: Synthesis of 2-(6,7-dihydro-5H-cyclopenta[b]pyridin-5-yl)acetic acid (A7-3)

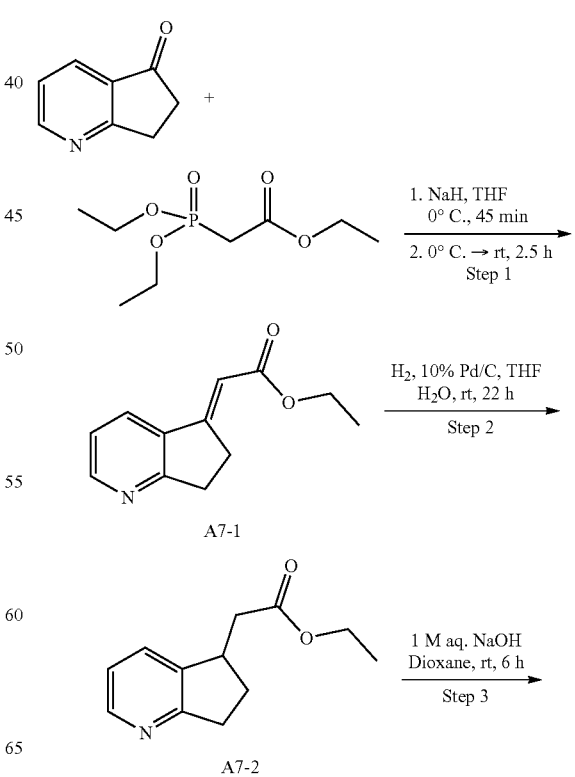

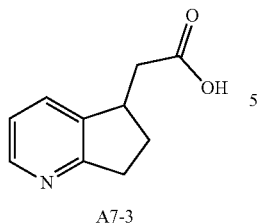

A7-3

Step 1. Ethyl 2-(6,7-dihydro-5H-cyclopenta[b]pyridin-5-ylidene)acetate (A7-1)

To a suspension of NaH (2.072 g, 51.8 mmol) in THF (60 mL) at 0° C. was added ethyl 2-(diethoxyphosphoryl)-acetate (10.28 mL, 51.8 mmol) dropwise over 40 min. The resulting mixture was stirred for 5 min at 0° C., and then 6,7-dihydro-5H-cyclopenta[b]pyridin-5-one (4.93 g, 37 mmol) in THF (40 mL) was added dropwise over 15 min. The cooling bath was removed and the reaction was stirred for 2.5 h at rt, and then quenched by addition of 2 M aq. HCl (25.0 mL, 50.0 mmol). The THF was removed in vacuo and the resulting residue was partitioned between EtOAc (250 mL) and 5% aq. NaHCO$_3$ (100 mL). The organic phase was washed with 5% aq. NaHCO$_3$ (2×40 mL) and 5% aq. NaHCO$_3$/brine (1:1) (60 mL). n-Butanol (50 mL) and brine (50 mL) were added and the phases were separated. The organic phase was dried over Na$_2$SO$_4$, filtered, and concentrated to dryness in vacuo to afford A7-1 (assumed to be 37 mmol) as green-black oil. The crude product was used in the next step. Analytical method 10; $t_R$=0.79 min and 0.84 min; [M+H]$^+$=204.0.

Step 2. Ethyl 2-(6,7-dihydro-5H-cyclopenta[b]pyridin-5-yl)acetate (A7-2)

To A7-1 (37 mmol) dissolved in THF (100 mL) was added a suspension of 10% Pd/C (0.788 g, 0.740 mmol) in H$_2$O (10 mL) and the resulting mixture was stirred for 22 h under a H$_2$-atmosphere, and then filtered through HyFlo. The filtrate was concentrated to dryness in vacuo and the crude product was purified by flash silica gel chromatography (eluent A: heptane/DIEA (98:2); eluent B: EtOAc/DIEA (98:2)). Pure fractions were combined and concentrated to dryness in vacuo to afford A7-2 (2.805 g, 13.67 mmol, 37% yield for 2 steps) as a red-brown oil. Analytical method 11; $t_R$=0.73 min; [M+H]$^+$=206.1.

Step 3. 2-(6,7-Dihydro-5H-cyclopenta[b]pyridin-5-yl)acetic acid (A7-3)

To A7-2 (2.805 g, 13.67 mmol) dissolved in dioxane (30 mL) was added 1 M NaOH (27.3 mL, 27.3 mmol) and the resulting mixture was stirred for 6 h at rt, becoming a clear solution.

The dioxane was removed in vacuo, sat. aq. KH$_2$PO$_4$ (50 mL) was added, and the aqueous phase was extracted with EtOAc (17×30 mL). The combined organic phases were washed with brine (30 mL), dried over Na$_2$SO$_4$, filtered, and concentrated to dryness in vacuo to afford A7-3-Batch 1 (1.928 g, 10.88 mmol, 80% yield) as a light beige solid. The aqueous phase was concentrated to dryness in vacuo. The resulting residue was suspended in DMA and the suspension was filtered. The residue was washed with DMA and the filtrate was concentrated to dryness in vacuo to afford A7-3-Batch 2 (425 mg, 2.398 mmol, 18% yield) as a brown lacquer. The crude product was used in the next step without further purification. Analytical method 11: $t_R$=0.44 min; [M+H]$^+$=178.0.

Example 2.6: Synthesis of 2-(2,3-dihydrobenzofuran-3-yl)acetic acid (A8-3)

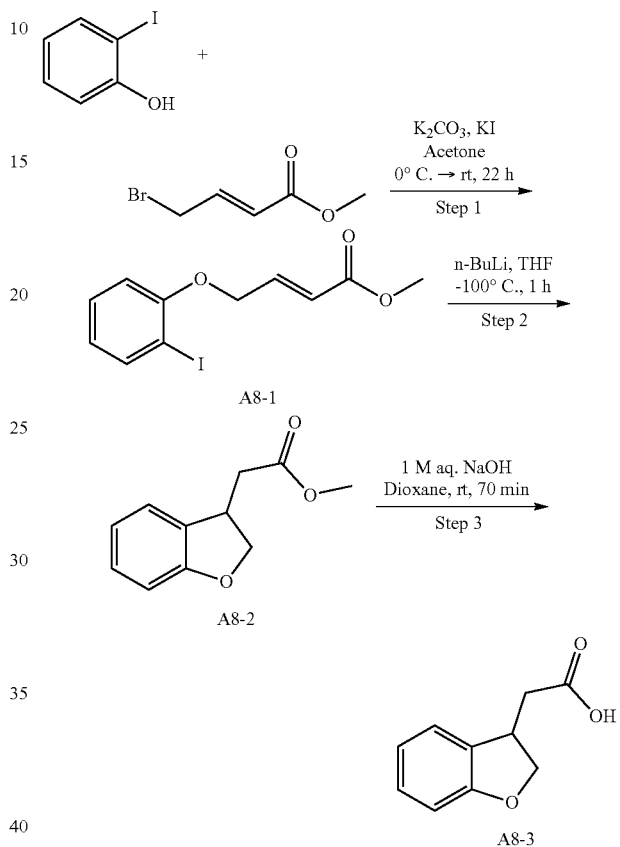

Step 1. Methyl (E)-4-(2-iodophenoxy)but-2-enoate (A8-1)

To 2-iodophenol (17.60 g, 80 mmol), K$_2$CO$_3$ (11.06 g, 80 mmol) and KI (13.28 g, 80 mmol) was added acetone (80 mL) and the mixture was cooled to 0° C. A solution of (E)-methyl 4-bromobut-2-enoate (9.56 mL, 80 mmol) in acetone (40 mL) was added dropwise over a period of 15 min. After 30 min stirring at 0° C. the cooling bath was removed and stirring was continued for 21.5 h. The reaction was filtered and acetone was removed in vacuo. The residue was partitioned between EtOAc (150 mL) and 1 M NaOH (15 mL). The organic phase was washed with 1 M NaOH (4×15 mL) and brine (15 mL), dried over Na$_2$SO$_4$, filtered, and concentrated to dryness in vacuo to afford A8-1 (23.368 g, 73.5 mmol, 92% yield) as a brown oil which was used in the nest step without purification. Analytical method 10; $t_R$=1.14 min; [M+H]$^+$=319.0.

Step 2. Methyl 2-(2,3-dihydrobenzofuran-3-yl)acetate (A8-2)

To A8-1 (19.72 g, 62 mmol) dissolved in THF (210 mL) under an argon atmosphere and cooled to −100° C. under an argon atmosphere was added a solution of 1.6 M BuLi in hexane (42.6 mL, 68.2 mmol) in THF (30 mL) dropwise over 1 h 45 min at −100° C. The resulting mixture was stirred for 1 h at −100° C. and then quenched by the addition of sat. aq. NH₄Cl (40 mL). The reaction mixture was concentrated in vacuo until the bulk of the THF was removed. The mixture was partitioned between EtOAc (500 mL) and 5% aq. KHSO₄ (50 mL). The organic phase was washed with 5% aq. KHSO₄ (2×25 mL) and brine (25 mL), dried over Na₂SO₄, filtered, and concentrated to dryness in vacuo to yield A8-2 (assumed to be 62 mmol) as a yellow oil. The crude product was used in the next step. Another batch of A8-2 (10 mmol) was synthesized from A8-1 (10 mmol). Analytical method 10; t$_R$=0.91 min; [M+H]⁺=193.0.

Step 3. 2-(2,3-Dihydrobenzofuran-3-yl)acetic acid (A8-3)

To A8-2 (72 mmol) dissolved in dioxane (100 mL) was added 1 M NaOH (144 mL, 144 mmol) and the resulting mixture was stirred for 70 min at rt. The reaction mixture was partitioned between EtOAc (150 mL) and 2 M aq. HCl (80 mL) and the aqueous phase was washed with EtOAc (2×50 mL). The combined organic phases were washed with 5% aq. KHSO₄ (2×30 mL) and brine (20 mL), dried over Na₂SO₄, filtered, and concentrated to dryness in vacuo to afford A8-3 (assumed to be 72.0 mmol) as a brown solid. The crude product was used in the next step without purification. Analytical method 10; t$_R$=[M−H]⁻=177.0.

Example 2.7: Synthesis of (S)-2-(2-(tert-Butoxy)-2-oxoethyl)-4,4,4-trifluorobutanoic acid (A14)

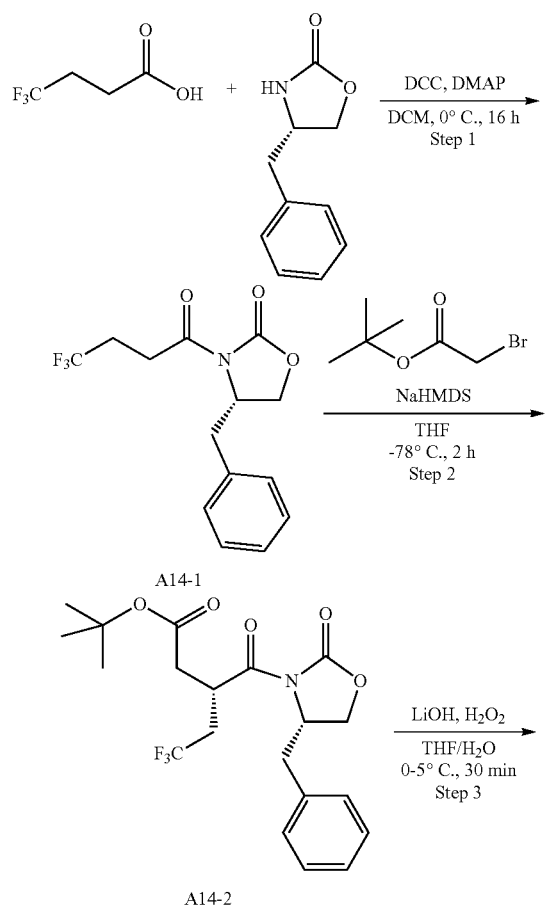

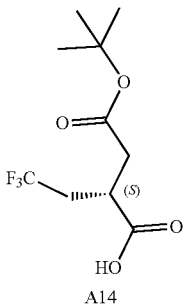

Step 1. (S)-4-Benzyl-3-(4,4,4-trifluorobutanoyl) oxazolidin-2-one A14-1

To solution of (S)-4-benzyloxazolidin-2-one (1.871 g, 10.56 mmol), DMAP (0.25 g, 2.11 mmol), and 4,4,4-trifluorobutanoic acid (1.5 g, 10.56 mmol) in DCM (21 mL) at 0° C. was added DCC (2.17 g, 6.49 mmol). The resulting mixture was stirred at room temperature for 16 h. The resulting milky mixture was filtered and the filter cake was washed with DCM. The filtrate was concentrated and the obtained white solid was taken up in EtOAc. The organic phase was washed with sat. NaHCO₃ and dried over Na₂SO₄, filtered, and concentrated. The crude product was purified by flash column chromatography on silica gel (eluting with 0-50% EtOAc in heptane) to yield the desired compound A14-1 after drying (2.7 g, 85%).

Step 2. tert-Butyl (S)-3-((S)-4-benzyl-2-oxooxazolidine-3-carbonyl)-5,5,5-trifluoropentanoate A14-2

To a stirred solution of (S)-4-benzyl-3-(4,4,4-trifluorobutanoyl)oxazolidin-2-one (2.7 g, 8.96 mmol) in THF (60 L) at −78° C., was added 1.0 M NaHMDS in THF (10.75 mL, 10.75 mmol) slowly over a period of 10 minutes and the resulting mixture was stirred for 1 h at −78° C. t-Butyl-2-bromoacetate (2.62 g, 13.44 mmol) was then added drop wise at −78° C. and stirred for 2 h. The reaction mixture was quenched with saturated aq. NH₄Cl and extracted twice with ethyl acetate. The combined organic phases were washed with brine, dried over anhydrous sodium sulfate, filtered, and concentrated under reduced pressure. The crude material was purified by flash column chromatography on silica gel (eluting with 0-50% EtOAc in heptane) to yield the desired compound A14-2 (2.22 g, 60%).

Step 3. (S)-2-(2-(tert-Butoxy)-2-oxoethyl)-4,4,4-trifluorobutanoic acid (A14)

To a stirred solution of tert-butyl (S)-3-((S)-4-benzyl-2-oxooxazolidine-3-carbonyl)-5,5,5-trifluoropentanoate (2.22 g, 5.34 mmol) in THF (28.5 mL) at 0-5° C. was added 30% H₂O₂ (2.18 mL, 21.37 mmol) and stirred for 30 minutes at same temperature. A solution of LiOH·H₂O (0.512 g, 21.37 mmol) in water (7.12 mL) was then added at 0-5° C. and stirring was continued for 1 h. The reaction mixture was quenched with a saturated aqueous solution of sodium sulfite (1.6 L) and a saturated aqueous solution of sodium bicarbonate (1.6 L). The solvent was removed under reduced pressure, diluted with water, and washed with DCM to remove the impurities. The aqueous phase was cooled to 5° C. and acidified (pH ~1.5) with 6 M HCl and the product was extracted with ethyl acetate (3×). The combined organic phases were washed with brine, and dried over anhydrous sodium sulfate, filtered, and concentrated under vacuum to afford the desired compound A14 (1.27 g, 93%) which was carried onto the next step without purification.

Example 2.8: Synthesis of (R)-2-(4-(tert-Butoxy)-2-carboxy-4-oxobutyl)pyridine-I-oxide (A15)

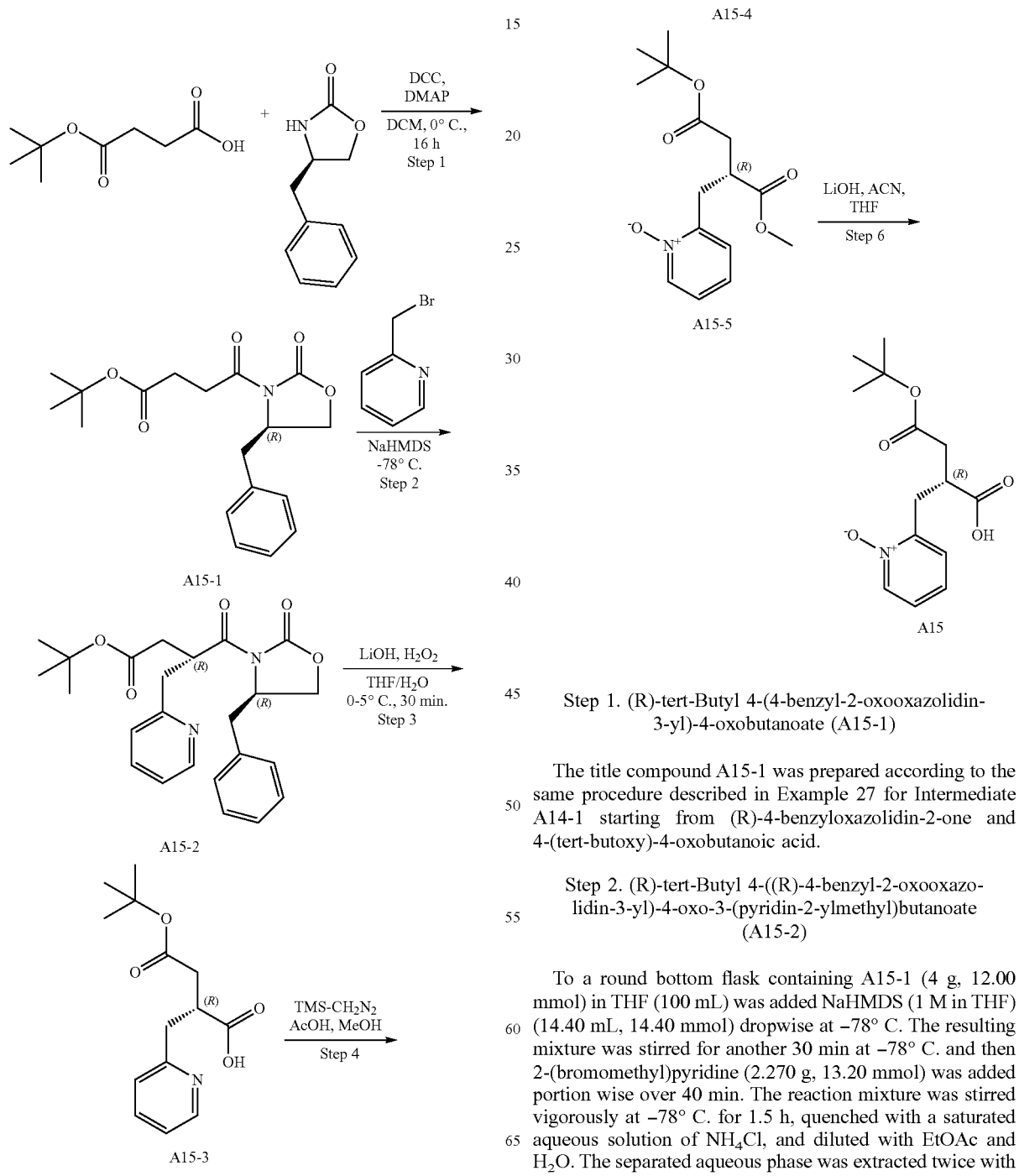

Step 1. (R)-tert-Butyl 4-(4-benzyl-2-oxooxazolidin-3-yl)-4-oxobutanoate (A15-1)

The title compound A15-1 was prepared according to the same procedure described in Example 27 for Intermediate A14-1 starting from (R)-4-benzyloxazolidin-2-one and 4-(tert-butoxy)-4-oxobutanoic acid.

Step 2. (R)-tert-Butyl 4-((R)-4-benzyl-2-oxooxazo-lidin-3-yl)-4-oxo-3-(pyridin-2-ylmethyl)butanoate (A15-2)

To a round bottom flask containing A15-1 (4 g, 12.00 mmol) in THF (100 mL) was added NaHMDS (1 M in THF) (14.40 mL, 14.40 mmol) dropwise at −78° C. The resulting mixture was stirred for another 30 min at −78° C. and then 2-(bromomethyl)pyridine (2.270 g, 13.20 mmol) was added portion wise over 40 min. The reaction mixture was stirred vigorously at −78° C. for 1.5 h, quenched with a saturated aqueous solution of NH₄Cl, and diluted with EtOAc and H₂O. The separated aqueous phase was extracted twice with EtOAc. The combined organic phases were washed with brine, dried over sodium sulfate, filtered, and concentrated to afford the crude product. The crude product was purified by flash column chromatography on silica gel (eluting with 0-100% EtOAc/heptane, product eluted ~60% EtOAc) to afford the A15-2 as a reddish oil (solidified upon storage, 3.68 g, 72%).

Step 3. (R)-4-(tert-Butoxy)-4-oxo-2-(pyridin-2-ylmethyl)butanoic acid (A15-3)

The title compound A15-3 (1.95 g, 85%) was prepared according to the procedure described in Example 2.7, Step 3 for intermediate A14 starting from A15-2 (3.68 g, 8.67 mmol). The material was used in the next step without purification, Step 4. (R)-4-tert-Butyl 1-methyl 2-(pyridin-2-ylmethyl)succinate (A15-4)

To a solution of A15-3 (1.95 g, 7.35 mmol) in anhydrous MeOH (12 mL) and cooled in an ice bath was added TMSCH$_2$N$_2$ in hexane (11 mL, 22.0 mmol). The resulting mixture was then warmed to room temperature and stirred for 1 h. An additional 6 mL of TMSCH$_2$N$_2$ was added and stirring was continued for another 30 min. The reaction mixture was then quenched with acetic acid (8 mL, 140 mmol) and saturated aq. sodium bicarbonate solution and extracted three times with EtOAc. The combined organic phases were dried over sodium sulfate, filtered, and concentrated to afford A15-4 (1.83 g, 89%) which was used in the next step without purification.

Step 5. (R)-2-(4-(tert-Butoxy)-2-(methoxycarbonyl)-4-oxobutyl)pyridine 1-oxide (A15-5)

To a solution of A15-4 (1.83 g, 6.55 mmol) in DCM (50 mL) at 0° C. was added mCPBA (2.94 g, 13.10 mmol). The resulting mixture was stirred at 0° C. for 1 h, and then at RT for 1 h. A saturated aqueous solution of NaHCO$_3$ was added and the reaction mixture was extracted three times with EtOAc. The organic phases were combined, dried over Na$_2$SO$_4$, filtered, and concentrated. The crude product was purified by flash column chromatography on silica gel (eluting with 0-15% MeOH/DCM, product eluted ~15% MeOH) to give desired product A15-5 as a light brown oil (1.5 g, 78%).

Step 6. (R)-2-(4-(tert-Butoxy)-2-carboxy-4-oxobutyl)pyridine-1-oxide (A15)

To a solution of A15-5 (1.5 g, 5.08 mmol) in THF (36 mL) and ACN (12 mL) was added 1 M LiOH aqueous solution (10.16 mL, 10.16 mmol). The resulting mixture was stirred at RT overnight and then concentrated under reduced pressure (in a bath at 25° C.). The obtained residue was acidified to pH 4 with 4 M HCl and extracted three times with DCM. The combined organic phases were dried over Na$_2$SO$_4$, filtered, and concentrated to afford A15 (1.55 g, 98%) as a light thick brown oil which was used in the next step without purification.

Example 2.9: Synthesis of (R)-2-(2-(tert-Butoxy)-2-oxoethyl)pentanoic acid (A16)

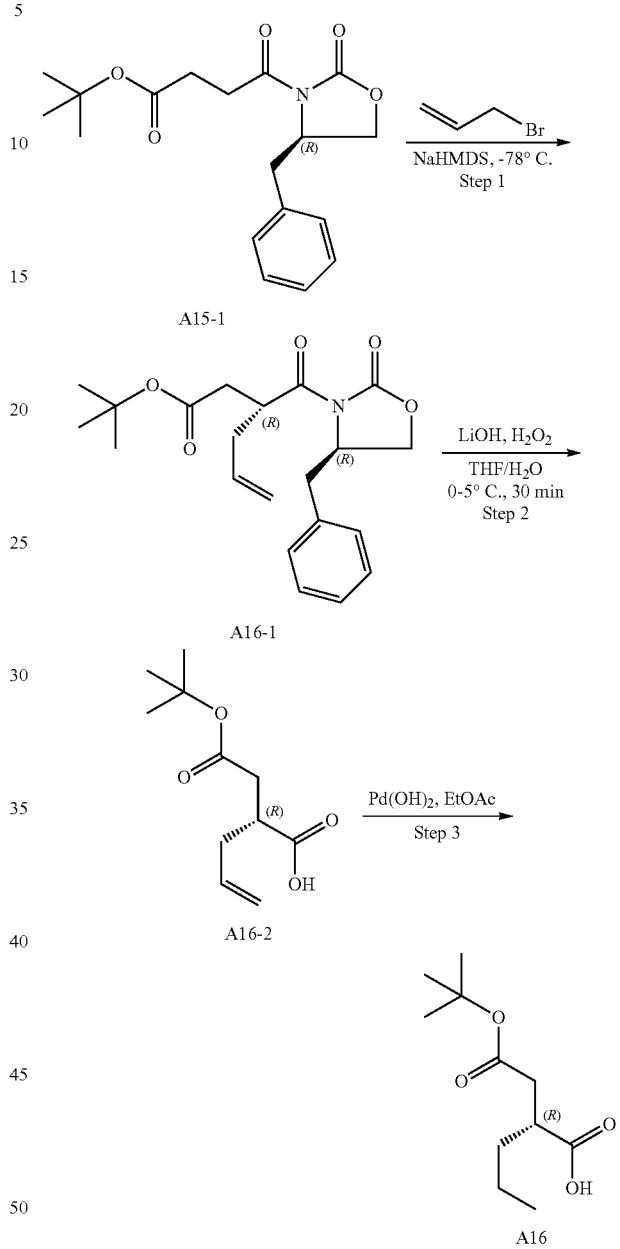

Step 1 and 2. (R)-2-(2-(tert-Butoxy)-2-oxoethyl)pent-4-enoic acid (A16-2)

The title compound A16-2 was prepared according to the procedure described in Example 2.8, Steps 2 and 3, for A15 starting from intermediate A15-1.

Step 3. (R)-2-(2-(tert-Butoxy)-2-oxoethyl)pentanoic acid (A16)

To a mixture of A16-2 (500 mg, 2.33 mmol) in EtOAc (10 mL) was added Pd(OH)$_2$ (100 mg, 2.33 mmol). The resulting mixture was flushed with hydrogen three times and stirred at RT overnight under a hydrogen atmosphere. The reaction mixture was then filtered through a pad of Celite®, and the filtrate was concentrated to afford A16 as a crude product after drying under high vacuum (695 mg, quantitative yield). The material was used in the next step without purification.

Example 2.10: Synthesis of (R)-2-(4-(tert-butoxy)-2-carboxy-4-oxobutyl)-6-methylpyridine 1-oxide (A34)

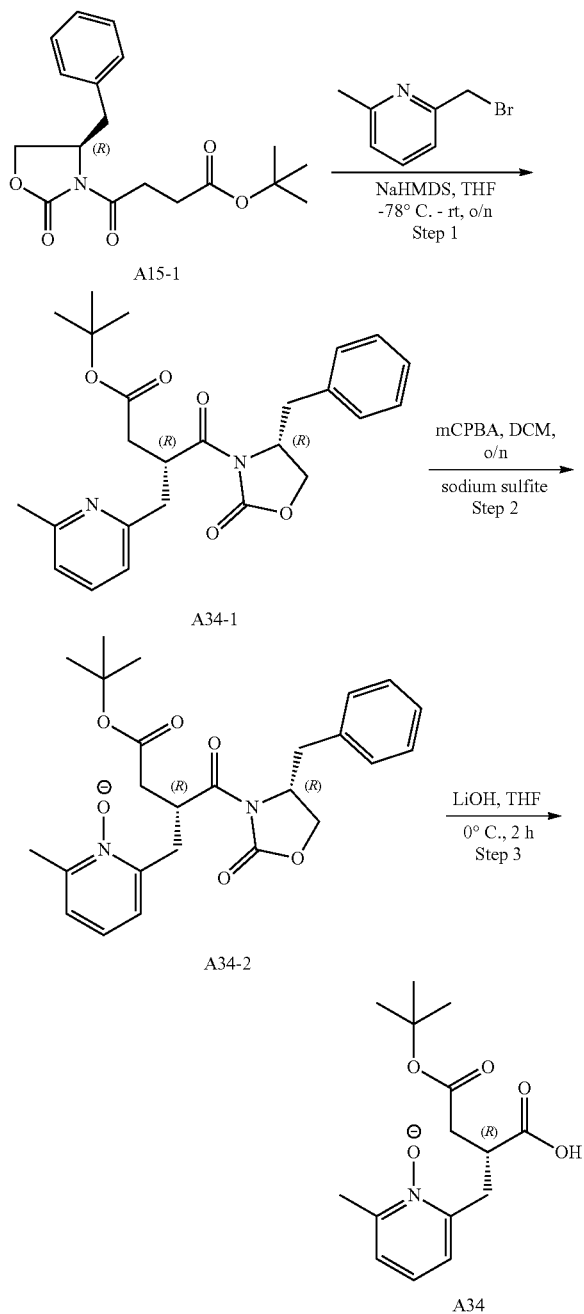

Step 1. (R)-tert-butyl 4-((R)-4-benzyl-2-oxooxazolidin-3-yl)-3-((6-methylpyridin-2-yl)methyl)-4-oxobutanoate (A34-1)

To A15-1 (31.19 g, 94 mmol) in THF (104 mL) was added NaHMDS (1M in THF) (112 mL, 112 mmol) dropwise at −78° C. The reaction mixture was stirred for another 30 min at −78° C. Then 2-(bromomethyl)-6-methylpyridine (19.15 g, 103 mmol in 15 mL THF+20 mL DMSO red solution) was added dropwise over 20 min. After the addition, the reaction (containing a lot of solid inside) was stirred at −78° C. and then warmed to rt overnight, resulting a dark red solution. The reaction mixture was quenched with sat. NH$_4$Cl solution at rt, and diluted with EtOAc/H$_2$O. The aqueous phase was saturated with salt and extracted with EtOAc. All the organic phases were combined, dried over Na$_2$SO$_4$, filtered and concentrated. The crude product was purified by flash chromatography on 330 g silica gel column, eluting with 0-80% EtOAc/heptane. A second 330 g gold column was used to purify the fractions with impurity (eluting with 30-50% EtOAc/heptane) and 26.33 g (60 mmol, 64.2% yield) of the title product A34-1 was isolated. Analytical method 5, $t_R$=1.19, min, [M+H]$^+$=439.5.

Step 2. 2-((R)-2-((R)-4-benzyl-2-oxooxazolidine-3-carbonyl)-4-(tert-butoxy)-4-oxobutyl)-6-methyl-1I4-pyridin-1-olate (A34-2)

To a solution of A34-1 (26.33 g, 60.0 mmol) in DCM (300 mL) was added mCPBA (26.9 g, 120 mmol) as a solid in one portion and the reaction mixture was stirred at room temperature overnight. Once LCMS showed complete consumption of starting material and a peak consistent with clean conversion to desired product. The reaction mixture was treated with sodium sulfite (7.57 g, 60 mmol) in water (~25 mL), and then was poured into saturated sodium bicarbonate solution. The aqueous phase extracted with DCM twice. The combined organic phases were washed with sat. aq. NaHCO$_3$ again, dried over sodium sulfate, filtered, and concentrated. The crude residue was purified by flash chromatography (330 g column, absorbed onto silica, eluting with 0-10% MeOH in DCM), to provide the desired product A34-2 (24.39 g, 53.7 mmol, 89% yield). Analytical method 5, $t_R$=1.02, min, [M+H]$^+$=455.4.

Step 3. (R)-2-(4-(tert-butoxy)-2-carboxy-4-oxobutyl)-6-methyl-1I4-pyridin-1-olate (A34)

To a round bottom flask containing A34-2 (24.39 g, 53.7 mmol) suspended in THF (286 ml) and cooled to 0° C. was added hydrogen peroxide (21.93 mL, 215 mmol), followed by lithium hydroxide (5.14 g, 215 mmol) in water (72 mL), keeping the internal temperature below 5° C. and the resulting mixture was stirred at 0° C. After 2 h, LCMS showed complete consumption os starting material (only hydrolyzed oxazolidinone). The reaction mixture was quenched by adding sat. aq. sodium thiosulfate and then allowed to stir overnight. The mixture was concentrated to remove the THF, partitioned with DCM, and transferred to a separatory funnel. The phases were separated, and the aqueous phase was extracted with DCM (2×). These organic phases were discarded. The aqueous phase was acidified to pH=1 using 1 M HCl and then partitioned with EtOAc. The phases were separated, and the aqueous phase was extracted with EtOAc (2×). The combined (EtOAc) organic phases were washed with brine, dried over sodium sulfate, filtered, and concentrated to provide 10.95 g (37.1 mmol, 69.1% yield) of the desired material A34. Analytical method 5, $t_R$=0.43, min, [M+H]$^+$=296.3.

The following intermediates in Table 2A were made according to the procedures described herein above for the succinate building blocks using the appropriate starting materials unless otherwise mentioned:

TABLE 2A

| BB No. | Structure/Chemical Name |
|---|---|
| A17 | 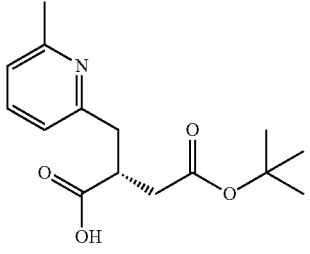 [SMILES: Cc1cccc(C[C@H](CC(=O)OC(C)(C)C)C(=O)O)n1]<br>(R)-4-(tert-Butoxy)-2-((6-methylpyridin-2-yl)methyl)-4-oxobutanoic acid |
| A18 | 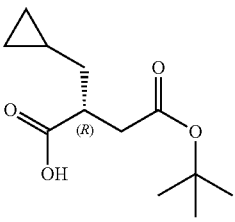<br>(R)-4-(tert-Butoxy)-2-(cyclopropylmethyl)-4-oxobutanoic acid |
| A11 | 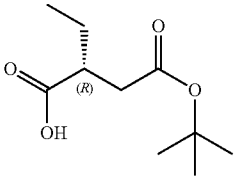<br>(R)-4-(tert-Butoxy)-2-ethyl-4-oxobutanoic acid |
| A19 | 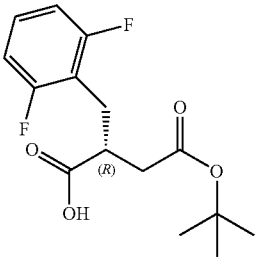<br>(R)-4-(tert-Butoxy)-2-(2,6-difluorobenzyl)-4-oxobutanoic acid |
| A20 | 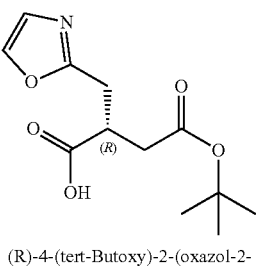<br>(R)-4-(tert-Butoxy)-2-(oxazol-2-ylmethyl)-4-oxobutanoic acid |

TABLE 2A-continued

| BB No. | Structure/Chemical Name |
|---|---|
| A21 | 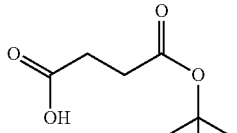<br>4-(tert-Butoxy)-4-oxobutanoic acid |
| A22 | 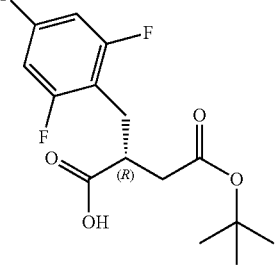<br>(R)-4-(tert-Butoxy)-4-oxo-2-(2,4,6-trifluorobenzyl)butanoic acid |
| A23 | 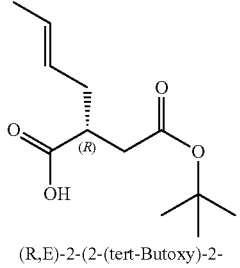<br>(R,E)-2-(2-(tert-Butoxy)-2-oxoethyl)hex-4-enoic acid |
| A24 | 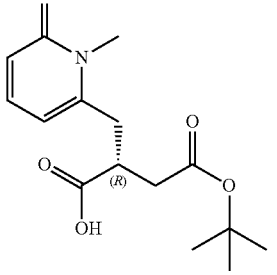<br>(R)-4-(tert-Butoxy)-2-((1-methyl-6-oxo-1,6-dihydropyridin-2-yl)methyl)-4-oxobutanoic acid |
| A25 | 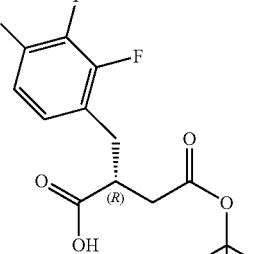<br>(R)-4-(tert-Butoxy)-4-oxo-2-(2,3,4-trifluorobenzyl)butanoic acid |

TABLE 2A-continued

| BB No. | Structure/Chemical Name |
|---|---|
| A26 | 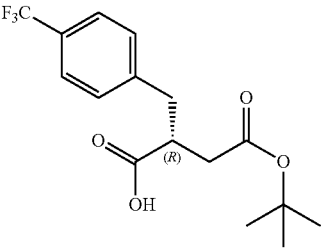 (R)-4-(tert-Butoxy)-4-oxo-2-(4-(trifluoromethyl)benzyl)butanoic acid |
| A27 | (R)-4-(tert-Butoxy)-4-oxo-2-(3-(trifluoromethyl)benzyl)butanoic acid |
| A28 | (R)-4-(tert-Butoxy)-2-methyl-4-oxobutanoic acid |
| A29 | (S)-4-(tert-Butoxy)-2-(3,3-difluorocyclobutyl)-4-oxobutanoic acid |
| A30 | (S)-4-(tert-Butoxy)-2-cyclobutyl-4-oxobutanoic acid |
| A31 | 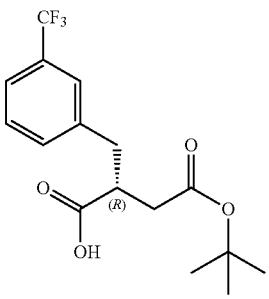 (S)-2-(2-(tert-Butoxy)-2-oxoethyl)-4,4-difluoropentanoic acid |
| A32 | (R)-4-(tert-Butoxy)-2-((1-methylcyclopropyl)methyl)-4-oxobutanoic acid |
| A33 | (R)-4-(tert-Butoxy)-2-(cyclobutylmethyl)-4-oxobutanoic acid |
| A34 | 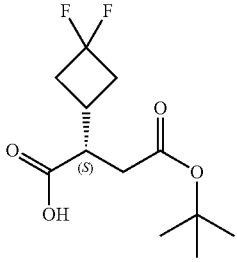 (R)-2-(4-(tert-butoxy)-2-carboxy-4-oxobutyl)-6-methylpyridine 1-oxide |
| A35 | 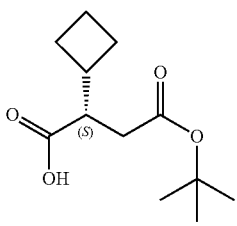 (S)-4-(tert-butoxy)-4-oxo-2-(tetrahydro-2H-pyran-4-yl)butanoic acid |

Example 3: Synthesis of Building Block B—Diamines

Example 3.1: Synthesis of tert-butyl (R)-(1-(4-chlorophenyl)-3-(methylamino)propan-2-yl)(methyl)carbamate (B1)

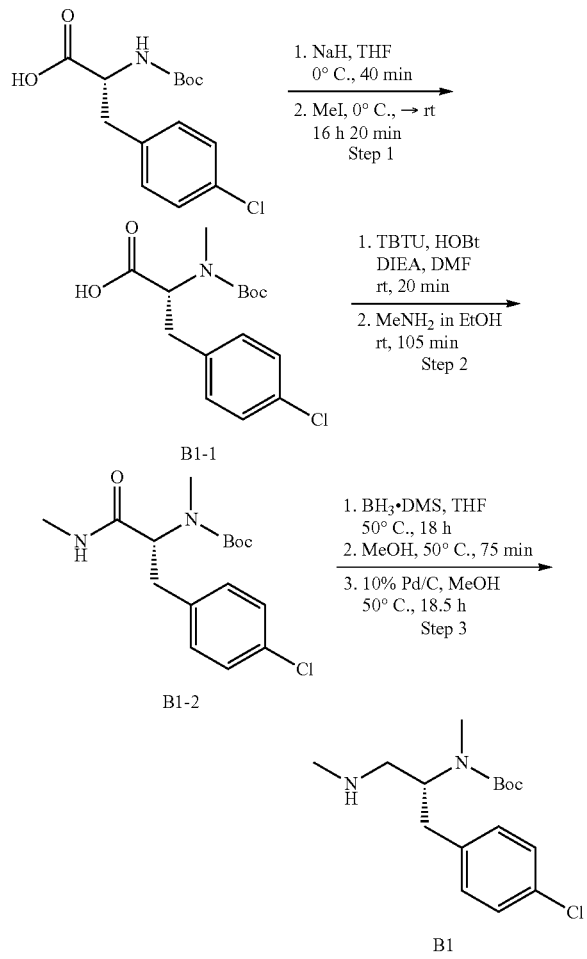

Step 1. (R)-2-((tert-Butoxycarbonyl)(methyl)amino)-3-(4-chlorophenyl)propanoic acid (B1-1)

To N-Boc-D-Phe(4-Cl)—OH (2.30 g, 7.67 mmol) dissolved in THF (25 mL) and cooled to 0° C. was added NaH (0.921 g, 23.02 mmol) and the resulting suspension was stirred for 40 min at 0° C. Methyl iodide (3.84 mL, 61.4 mmol) was then added and stirring was continued for 16 h and 20 min. The reaction mixture was warmed to rt and then quenched by the addition of $H_2O$ (2 mL) and then partitioned between EtOAc (70 mL) and 5% aq. $KHSO_4$ (40 mL). The organic phase was washed with 5% aq. $KHSO_4$ (2×15 mL) and brine (15 mL), dried over $Na_2SO_4$, filtered, and concentrated to dryness in vacuo to yield B1-1 (assumed to be 7.67 mmol) as a beige oil. The crude product was used in the next step without purification. Analytical method 10; $t_R$=1.05 min; [M−H]⁻=312.1.

Step 2. tert-Butyl (R)-(3-(4-chlorophenyl)-1-(methylamino)-1-oxopropan-2-yl)(methyl)carbamate (B1-2)

To B1-1 (3.83 mmol), TBTU (1.599 g, 4.98 mmol) and HOBT (0.587 g, 3.83 mmol) dissolved in DMF (25 mL) was added DIEA (1.539 mL, 8.81 mmol) and the resulting solution was stirred for 20 min at rt. Methylamine in EtOH (33%, 0.954 mL, 7.66 mmol) was added and the reaction mixture was stirred for 105 min at rt and concentrated in vacuo. The resulting residue was partitioned between EtOAc (70 mL) and 5% aq. $NaHCO_3$ (20 mL). The organic phase was washed with 5% aq. $NaHCO_3$ (2×15 mL) and brine (15 mL), dried over $Na_2SO_4$, filtered, and concentrated to dryness in vacuo to afford B1-2 (assumed to be 3.83 mmol) as a yellowish solid. The crude product was used in the next step without purification. Analytical method 10; $t_R$=1.06 min; [M+H]⁺=327.1.

Step 3. tert-Butyl (R)-(1-(4-chlorophenyl)-3-(methylamino)propan-2-yl)(methyl)carbamate (B1)

Step 3-1: B1-2 (3.83 mmol) was dissolved in THF (20 mL) and $BH_3$-DMS (1.091 mL, 11.49 mmol) was added. The reaction was stirred for 18 h at 50° C.

Step 3-2: The reaction mixture from Step 3-1 was quenched by the addition of MeOH (mL). The resulting solution was stirred for 75 min at 50° C., and then concentrated to dryness in vacuo.

Step 3-3: To the residue from Step 3-2 dissolved in MeOH (25 mL) was added 10% Pd/C (0.122 g, 0.115 mmol) in $H_2O$ (2 mL) and the resulting suspension was stirred for 18.5 at 50° C., and then filtered through HyFlo. The filtrate was concentrated to dryness in vacuo to afford B1 (1.183 g, 3.78 mmol, 99% yield for 3 steps) as a yellowish oil. The crude product was used in the next step without purification. Analytical method 10; $t_R$=0.80 min; [M+H]⁺=313.2.

The following Building Blocks (BB) in Table 3 were synthesized according to the procedure described in Example 3.1 for Building Block B1.

TABLE 3

| Building block B - Diamines | | | | |
|---|---|---|---|---|
| BB No. | Structure | Chemical Name | Starting material | LCMS |
| B3 | | tert-butyl (R)-(1-amino-3-(4-chlorophenyl)propan-2-yl)(methyl)carbamate | Starting from B1-1 and using 32% aq. $NH_3$. | Analytical method 10 $t_R$ = 0.77 min [M + H]⁺ = 299.2 |

TABLE 3-continued

Building block B - Diamines

| BB No. | Structure | Chemical Name | Starting material | LCMS |
|---|---|---|---|---|
| B4 | (structure shown) | tert-butyl (R)-(1-(4-chlorophenyl)-3-((3,3-difluoropropyl)amino)propan-2-yl)(methyl)carbamate | Starting from B1-1 and using 3,3-difluoropropan-1-amine. | Analytical method 10 $t_R$ = 0.85 min $[M + H]^+$ = 377.3 |
| B5 | (structure shown) | tert-butyl (R)-(1-(4-chlorophenyl)-3-(((1-methylcyclopropyl)methyl)amino)propan-2-yl)(methyl)carbamate | Starting from B1-5 | Analytical method 10 $t_R$ = 0.90 min $[M + H]^+$ = 367.4 |
| B6 | (structure shown) | tert-butyl (R)-(1-(4-chlorophenyl)-3-((3-(dimethylamino)propyl)amino)propan-2-yl)(methyl)carbamate | Starting from B1-1 and using 3-dimethylaminopropyl amine | Analytical method 10 $t_R$ = 0.67 min $[M + H]^+$ = 384.2 |

Example 3.2: Synthesis of tert-butyl (R)-(1-(4-chlorophenyl)-3-(1-methylcyclopropane-1-carboxamido)propan-2-yl)(methyl)carbamate (B5-1)

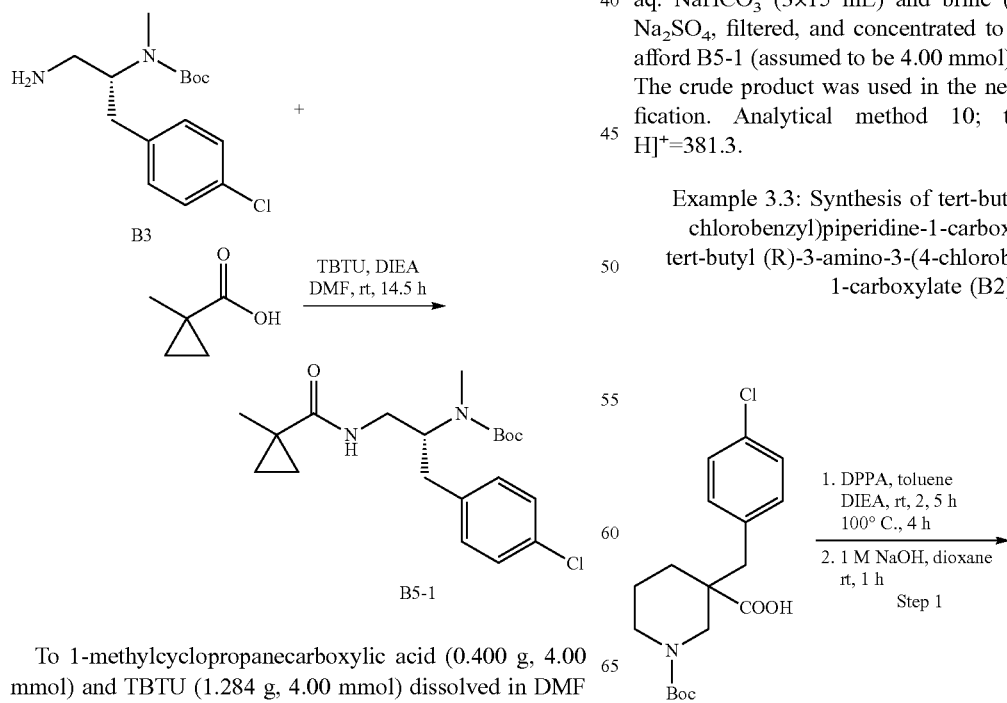

To 1-methylcyclopropanecarboxylic acid (0.400 g, 4.00 mmol) and TBTU (1.284 g, 4.00 mmol) dissolved in DMF (5 mL) was added DIEA (1.40 mL; 8.00 mmol) and the resulting solution was stirred for 5 min at rt. A solution of B3 in DMF (5 mL) was then added and stirring was continued for 14.5 h at rt. H₂O (1 mL) was added and the resulting mixture was partitioned between EtOAc (75 mL) and 5% aq. NaHCO₃ (15 mL). The organic phase was washed with 5% aq. NaHCO₃ (3×15 mL) and brine (10 mL), dried over Na₂SO₄, filtered, and concentrated to dryness in vacuo to afford B5-1 (assumed to be 4.00 mmol) as a light brown oil. The crude product was used in the next step without purification. Analytical method 10; $t_R$=1.17 min; $[M+H]^+$=381.3.

Example 3.3: Synthesis of tert-butyl 3-amino-3-(4-chlorobenzyl)piperidine-1-carboxylate (B8) and tert-butyl (R)-3-amino-3-(4-chlorobenzyl)piperidine-1-carboxylate (B2)

-continued

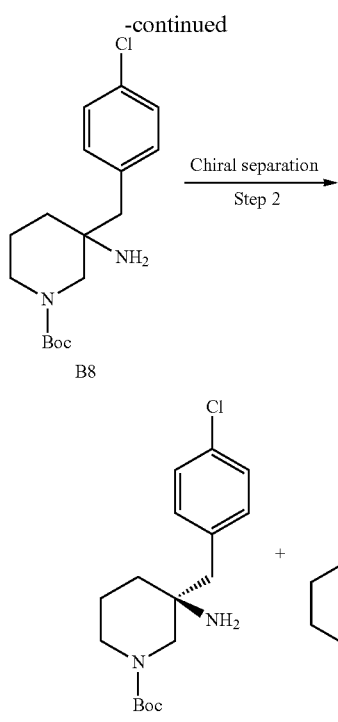

B8

Step 1. tert-Butyl 3-amino-3-(4-chlorobenzyl)piperidine-1-carboxylate (B8)

Step 1-1: To 1-(tert-Butoxycarbonyl)-3-(4-chlorobenzyl)piperidine-3-carboxylic acid (6.905 g, 19.51 mmol) dissolved in toluene (100 mL) and DIEA (5.11 ml, 29.3 mmol) was added diphenyl phosphoryl azide (5.48 ml, 25.4 mmol) and the resulting mixture was stirred for 2.5 h at rt, and then for 4 h at 100° C. The reaction mixture was partitioned between EtOAc (300 mL) and 5% aq. NaHCO$_3$ (60 mL). The organic phase was washed with 5% aq. NaHCO$_3$ (3×60 mL) and brine (50 mL), dried over Na$_2$SO$_4$, filtered, and concentrated to dryness in vacuo.

Step 1-2: To the residue from Step 1-1 dissolved in dioxane (200 mL) was added 1 M NaOH (195 ml, 195 mmol). The resulting mixture was stirred for 1 h at rt, and then concentrated to dryness in vacuo. The resulting residue was partitioned between EtOAc (250 mL) and 5% aq. Na$_2$CO$_3$ (20 mL) and aqueous phase was extracted with EtOAc (70 mL). The combined organic phases were washed with 5% aq. Na$_2$CO$_3$ (40 mL) and brine (40 mL) dried over Na$_2$SO$_4$, filtered, and concentrated to dryness in vacuo to afford the racemate B8 as a yellow oil (assumed to be 19.5 mmol) which was used in the next step without further purification. Analytical method 10; $t_R$=0.80 min; [M+H]$^+$=325.2.

Step 2. tert-Butyl (R)-3-amino-3-(4-chlorobenzyl)piperidine-1-carboxylate (B2)

The racemate B8 (19.5 mmol) was separated by preparative SFC (Instrument: Thar 200 preparative SFC) using the following conditions: Column: ChiralPak AD, 300×50 mm I.D., 10 μm; eluent A: CO$_2$; eluent B: EtOH (0.1% NH$_4$OH); gradient: B 45%; flow rate: 200 mL/min; back pressure: 100 bar; column temperature: 38° C.; cycle time: ~9 min; compound was dissolved in ~130 mL MeOH; injection: 10 mL per injection. B2 (slower eluting isomer) (2.66 g; 7.78 mmol; 40%) was obtained as a colorless oil. Partial crystallization occurred upon storage allowing for the structural confirmation by X-ray crystallography. Analytical method 10; $t_R$=0.77 min; [M+H]$^+$=325.3.

Example 3.3: Synthesis of (R)-3-(4-chlorobenzyl)piperidin-3-amine hydrochloride (B7)

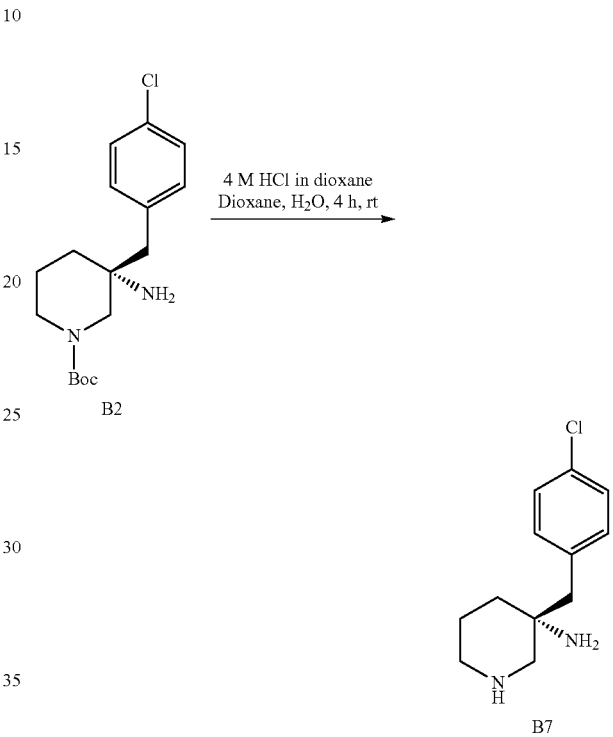

To B2 (2.09 g, 6.43 mmol) dissolved in dioxane (10 mL) was added 4 M HCl in dioxane (50 mL) and H$_2$O (5 mL) and the resulting solution was stirred for 4 h at rt. The reaction mixture was concentrated to dryness in vacuo to afford B7 (1.818 g, 6.11 mmol, 95% yield) as a light beige foam. The crude product was used in the next step without purification. Analytical method 10; $t_R$=0.40 min; [M+H]$^+$=225.1.

Example 4: Synthesis of Building Block AB

Example 4.1: Synthesis of (S)-4-(((R)-2-((((9H-fluoren-9-yl)methoxy)carbonyl)(methyl) amino)-3-(4-chlorophenyl)-propyl)(methyl)amino)-3-((R)-2,3-dihydro-1H-inden-1-yl)-4-oxobutanoic acid (AB1)

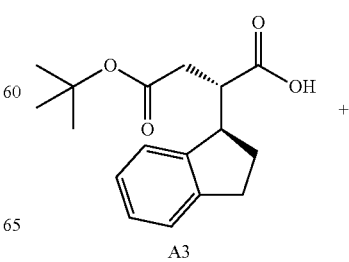

A3

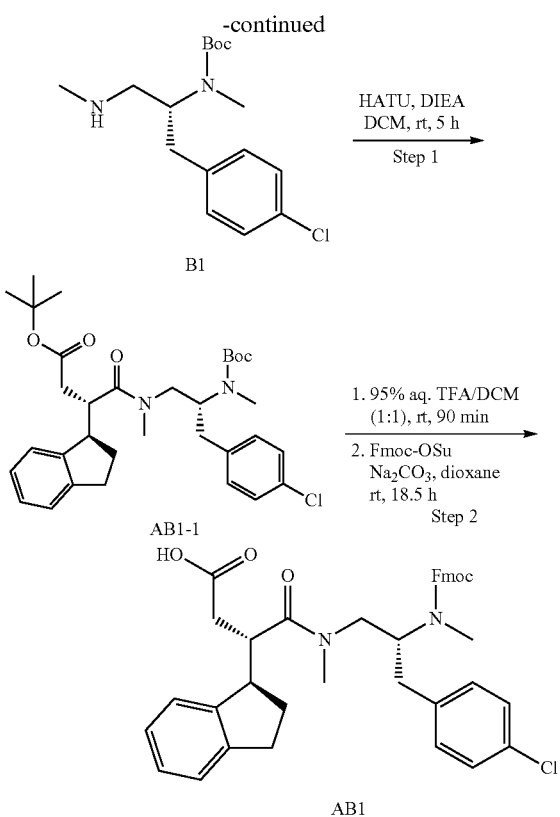

Step 1. tert-Butyl (S)-4-(((R)-2-((tert-butoxycarbonyl)(methyl)amino)-3-(4-chlorophenyl)propyl)(methyl)-amino)-3-((R)-2,3-dihydro-1H-inden-1-yl)-4-oxobutanoate (AB1-1)

To A3 (417 mg, 1.436 mmol) dissolved in DCM (20 mL) was added HATU (601 mg, 1.580 mmol) and DIEA (0.301 mL, 1.723 mmol) and the resulting mixture was stirred for 30 min at rt. A solution of B1 (642 mg, 1.867 mmol) in DCM (10 mL) and DIEA (0.752 mL, 4.31 mmol) was then added and the reaction mixture was stirred for 4 h at rt. Additional B1 (99 mg, 0.287 mmol) was added and stirring at rt was continued for 1 h. The reaction mixture was concentrated in vacuo and the resulting residue was partitioned between EtOAc (60 mL) and 5% aq. NaHCO$_3$ (10 mL). The organic phase was washed with 5% aq. NaHCO$_3$ (2×10 mL), 5% aq. KHSO$_4$ (10 mL) and brine (10 mL), dried over Na$_2$SO$_4$, filtered, and concentrated to dryness in vacuo to afford AB1-1 (assumed to be 1.436 mmol) as a yellow oil. The crude product was used in the next step without purification. Analytical method 10; $t_R$=1.55 min; [M+H]$^+$=585.4.

Step 2. (S)-4-(((R)-2-((((9H-Fluoren-9-yl)methoxy)carbonyl)(methyl)amino)-3-(4-chlorophenyl)propyl)-(methyl)amino)-3-((R)-2,3-dihydro-1H-inden-1-yl)-4-oxobutanoic acid (AB1)

Step 2-1: AB1-1 (1.435 mmol) was dissolved in 95% aq. TFA/DCM (1:1) (20 mL) and the resulting solution was stirred for 90 min at rt and then concentrated to dryness in vacuo.

Step 2-2: To the residue from Step 2-1 dissolved in dioxane (16 mL) was added 0.5 M aq. Na$_2$CO$_3$ (8.61 mL, 4.31 mmol) and a solution of Fmoc-OSu (0.484 g, 1.435 mmol) in dioxane (10 mL). The resulting mixture was stirred for 18.5 h at rt and then quenched by the addition of 2 M aq. HCl (10 mL). The dioxane was removed in vacuo, EtOAc (75 mL) was added, and the phases were separated. The organic phase was washed with 5% aq. KHSO$_4$ (2×10 mL) and brine (10 mL), dried over Na$_2$SO$_4$, filtered, and concentrated to dryness in vacuo. The crude product was purified by flash silica gel chromatography (eluent A: heptane/AcOH (99:1); eluent B: EtOAc/AcOH (99:1)). Pure fractions were combined and concentrated to dryness in vacuo. The residue was partitioned between EtOAc (70 mL) and 5% aq. NaHCO$_3$ (5 mL). The organic phase was washed with 5% aq. NaHCO$_3$ (3×5 mL), 5% aq. KHSO$_4$ (10 mL) and brine (10 mL), dried over Na$_2$SO$_4$, filtered, and concentrated to dryness in vacuo to afford AB1 (661 mg, 1.015 mmol, 71% yield for 2 steps) as a colorless lacquer. Analytical method 10; $t_R$=1.41 min; [M+H]$^+$=651.2.

The following Building Blocks (BB) in Table 4 were synthesized according to the procedure described in Example 4.1 for Building Block AB1 and Example 4.3 for Building Block AB14 from the monomer Building Blocks A and B in Table 1 and Table 3.

TABLE 4

| | Building block AB | | |
|---|---|---|---|
| BB No. | Structure/Chemical Name | Chemical Name | Synthesis Protocol/ LCMS |
| AB2 | ![structure] | 4-(((R)-2-((((9H-fluoren-9-yl)methoxy)carbonyl)(methyl) amino)-3-(4-chlorophenyl)propyl)amino)-3-benzyl-4-oxobutanoic acid | Example 4.1-starting from A1 and B3; Boc removal done with 4M HCl in dioxane (led to partial succinimide formation which was hydrolysed using aq. NaOH prior to Fmoc-protection/Analytical method 10 $t_R$ = 1.29 min [M + H]$^+$ = 611.2 |

TABLE 4-continued

Building block AB

| BB No. | Structure/Chemical Name | Chemical Name | Synthesis Protocol/ LCMS |
|---|---|---|---|
| AB3 | (S)- | (S)-4-(((R)-2-((((9H-fluoren-9-yl)methoxy)carbonyl)(methyl)amino)-3-(4-chlorophenyl)propyl)(methyl)amino)-3-((1R,3S)-3-methyl-2,3-dihydro-1H-inden-1-yl)-4-oxobutanoic acid | Example 4.1-starting from A6 and B1/ Analytical method 15 $t_R$ = 7.58 min $[M + H]^+$ = 665.2 |
| AB4 | | (S)-4-(((R)-2-((((9H-fluoren-9-yl)methoxy)carbonyl)(methyl)amino)-3-(4-chlorophenyl)propyl)(methyl)amino)-3-((R)-2,3-dihydrobenzfuran-3-yl)-4-oxobutanoic acid | Example 4.1-starting from A8 and B1/ Analytical method 15 $t_R$ = 6.91 min $[M + H]^+$ = 653.3 |
| AB5 | | (S)-4-(((R)-2-((((9H-fluoren-9-yl)methoxy)carbonyl)(methyl)amino)-3-(4-chlorophenyl)propyl)(methyl)amino)-3-((R)-7-methoxy-2,3-dihydrobenzofuran-3-yl)-4-oxobutanoic acid | Example 4.1-starting from A9 and B1/ Analytical method 15 $t_R$ = 6.72 min $[M + H]^+$ = 683.2 |
| AB6 | | (3S,4R)-3-(((R)-2-((((9H-fluoren-9-yl)methoxy)carbonyl)(methyl)amino)-3-(4-chlorophenyl)propyl)(methyl)carbamoyl)-4-phenylpentanoic acid | Example 4.1-starting from A10 and B1/ Analytical method 10 $t_R$ = 1.37 min $[M + H]^+$ = 639.4 |
| AB7 | | (S)-4-(((R)-2-((((9H-fluoren-9-yl)methoxy)carbonyl)(methyl)amino)-3-(4-chlorophenyl)propyl)(methyl)amino)-3-((R)-3,3-dimethyl-2,3-dihydro-1H-inden-1-yl)-4-oxobutanoic acid | Example 4.1-starting from A5 and B1/ Analytical method 10 $t_R$ = 1.47 min $[M + H]^+$ = 679.4 |
| AB8 | | (R)-3-(((R)-2-((((9H-fluoren-9-yl)methoxy)carbonyl)(methyl)amino)-3-(4-chlorophenyl)propyl)carbamoyl)pentanoic acid | Example 4.1-starting from A11 and B3/ Analytical method 9 $t_R$ = 6.34 min $[M + H]^+$ = 549.2 |

TABLE 4-continued

Building block AB

| BB No. | Structure/Chemical Name | Chemical Name | Synthesis Protocol/ LCMS |
|---|---|---|---|
| AB9 | | (R)-3-(((R)-2-((((9H-fluoren-9-yl)methoxy)carbonyl)(methyl)amino)-3-(4-chlorophenyl)propyl)(methyl)carbamoyl)pentanoic acid | Example 4.1-starting from A11 and B1/ Analytical method 10 $t_R$ = 1.28 min $[M + H]^+$ = 563.3 |
| AB10 | | (S)-4-(((R)-2-((((9H-fluoren-9-yl)methoxy)carbonyl)(methyl)amino)-3-(4-chlorophenyl)propyl)(3,3-difluoropropyl)amino)-3-((R)-2,3-dihydro-1H-inden-1-yl)-4-oxobutanoic acid | Example 4.1-starting from A3 and B4; coupling done for 121 h at rt, then for 111 h at 60° C. Fmoc-Cl used instead of Fmoc-OSu./ Analytical method 10 $t_R$ = 1.42 min $[M + H]^+$ = 715.5 |
| AB11 | | (S)-4-(((R)-2-((((9H-fluoren-9-yl)methoxy)carbonyl)(methyl)amino)-3-(4-chlorophenyl)propyl)((1-methylcyclopropyl)methyl)amino)-3-((R)-2,3-dihydro-1H-inden-1-yl)-4-oxobutanoic acid | Example 4.1-starting from A3 and B5/ Analytical method 10 $t_R$ = 1.52 min $[M + H]^+$ = 705.5 |
| AB12 | | (R)-4-(((R)-2-((((9H-fluoren-9-yl)methoxy)carbonyl)(methyl)amino)-3-(4-chlorophenyl)propyl)(3-(dimethylamino)propyl)amino)-3-benzyl-4-oxobutanoic acid | Example 4.1-starting from A1 and B6/ Analytical method 10 $t_R$ = 1.13 min $[M + H]^+$ = 696.4 |
| AB13 | | (R)-4-(((R)-2-((((9H-fluoren-9-yl)methoxy)carbonyl)(methyl)amino)-3-(4-chlorophenyl)propyl)(methyl)amino)-3-(dimethylamino)-4-oxobutanoic acid | Example 4.1-starting from A13-2 (see Example 4.2) and B1/ Analytical method 10 $t_R$ = 1.04 min $[M + H]^+$ = 578.2 |
| AB15 | | (S)-4-((R)-3-((((9H-fluoren-9-yl)methoxy)carbonyl)amino)-3-(4-chlorobenzyl)piperidin-1-yl)-3-((R)-6,7-dihydro-5H-cyclopenta[b]pyridin-5-yl)-4-oxobutanoic acid | Example 4.3-starting from A4 and B7/ Analytical method 10 $t_R$ = 1.23 min $[M + H]^+$ = 664.4 |

TABLE 4-continued

Building block AB

| BB No. | Structure/Chemical Name | Chemical Name | Synthesis Protocol/ LCMS |
|---|---|---|---|
| AB16 | | (S)-4-((R)-3-((((9H-fluoren-9-yl)methoxy)carbonyl)amino)-3-(4-chlorobenzyl)piperidin-1-yl)-3-((S)-2,3-dihydro-1H-inden-1-yl)-4-oxobutanoic acid | Example 4.3-starting from A4 and B7/ Analytical method 10 $t_R$ = 1.44 min $[M + H]^+$ = 663.4 |

Example 4.2: Synthesis of tert-butyl (R)-4-(((R)-2-((tert-butoxycarbonyl)(methyl)amino)-3-(4-chlorophenyl)propyl)-(methyl)amino)-3-(dimethylamino)-4-oxobutanoate (AB13-2)

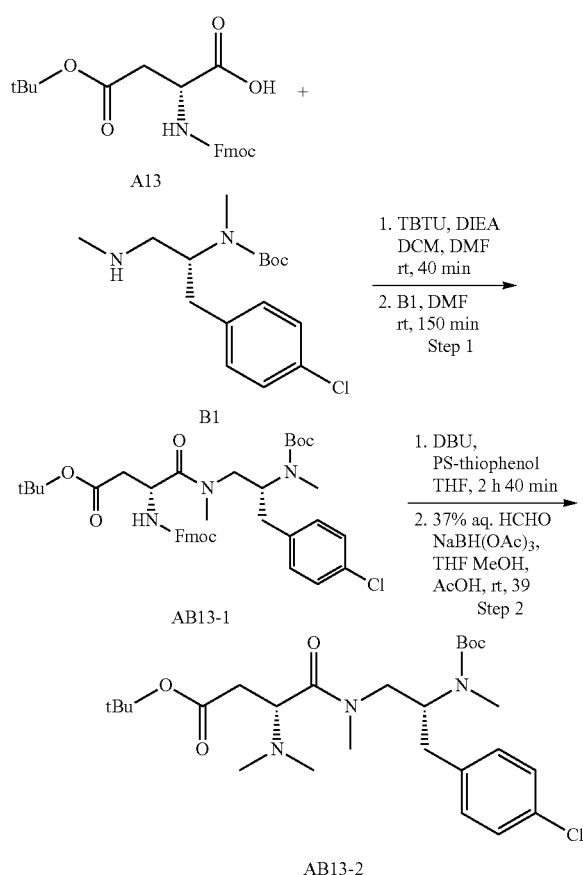

Step 1. tert-Butyl (R)-3-((((9H-fluoren-9-yl)methoxy)carbonyl)amino)-4-(((R)-2-((tert-butoxycarbonyl)-(methyl)amino)-3-(4-chlorophenyl)propyl)(methyl)amino)-4-oxobutanoate (AB13-1)

To A13 (362 mg, 0.88 mmol) and TBTU (311 mg, 0.968 mmol) dissolved in DCM/DMF (2:1) (15 mL) and was added DIEA (0.231 mL, 1.320 mmol) and the resulting solution was stirred for 40 min at rt. A solution of B1 (391 mg, 1.250 mmol) in DMF (2.5 mL) was added and stirring was continued for 150 min at rt. The reaction mixture was concentrated in vacuo and then partitioned between EtOAc (60 mL) and 5% aq. NaHCO$_3$ (20 mL). The organic phase was washed with 5% aq. NaHCO$_3$ (3×10 mL) and brine (10 mL), dried over Na$_2$SO$_4$, filtered, and concentrated to dryness in vacuo to afford AB13-1 (~0.88 mmol) as a yellowish oil. The crude product was used in the next step without purification. Analytical method 10; $t_R$=1.54 min; [M+H]$^+$=706.5.

Step 2. tert-Butyl (R)-4-(((R)-2-((tert-butoxycarbonyl)(methyl)amino)-3-(4-chlorophenyl)propyl)(methyl)-amino)-3-(dimethylamino)-4-oxobutanoate (AB13-2)

Step 2-1: To AB13-1 (0.88 mmol) dissolved in THF (20 mL) was added PS-thiophenol (852 mg, 1.320 mmol) and DBU (0.027 mL, 0.176 mmol) and the resulting suspension was stirred for 2 h 40 min at rt. The solution was filtered off and the resin was carefully washed with DCM. The combined filtrates were concentrated to dryness in vacuo.

Step 2-2: To the residue from Step 2-1 dissolved in THF (20 mL) was added 37% aq. HCHO (0.262 mL, 3.52 mmol) and the resulting solution was stirred for 20 min at rt. NaBH(OAc)$_3$ (0.746 g, 3.52 mmol) was then added and the reaction mixture was stirred for 15 h 40 min at rt. Additional 37% aq. HCHO (0.262 mL, 3.52 mmol) was added and stirring was continued for 1 h 20 min at rt. Additional NaBH(OAc)$_3$ (0.746 g, 3.52 mmol) was added and stirring was continued for 4 h. MeOH (2 mL) was added and stirring was continued for 90 min. AcOH (0.101 mL, 1.760 mmol) was added and the mixture was stirred for 3 h. Additional 37% aq. HCHO (0.262 mL, 3.52 mmol) and NaBH(OAc)$_3$ (0.746 g, 3.52 mmol) were added and stirring at rt was continued for 13.5 h. The reaction mixture was concentrated in vacuo and the resulting residue was partitioned between EtOAc (50 mL) and 5% aq. Na$_2$CO$_3$ (15 mL). The organic phase was washed with 5% aq. Na$_2$CO$_3$ (2×10 mL) and brine (10 mL), dried over Na$_2$SO$_4$, filtered, and concentrated to dryness in vacuo. The crude product was purified by flash silica gel chromatography (eluent A: heptane/DIEA (98:2); eluent B: EtOAc/DIEA (98:2)). Pure fractions were combined and concentrated to dryness in vacuo to afford AB13-2 (335 mg, 0.654 mmol, 74% for 2 steps) as a colorless oil. Analytical method 10; $t_R$=1.09 min; [M+H]$^+$=512.0.

Example 4.3: Synthesis of (R)-4-((R)-3-((((9H-fluoren-9-yl)methoxy)carbonyl)amino)-3-(4-chlorobenzyl)piperidin-1-yl)-4-oxo-3-(pyridin-3-ylmethyl)butanoic acid (AB14)

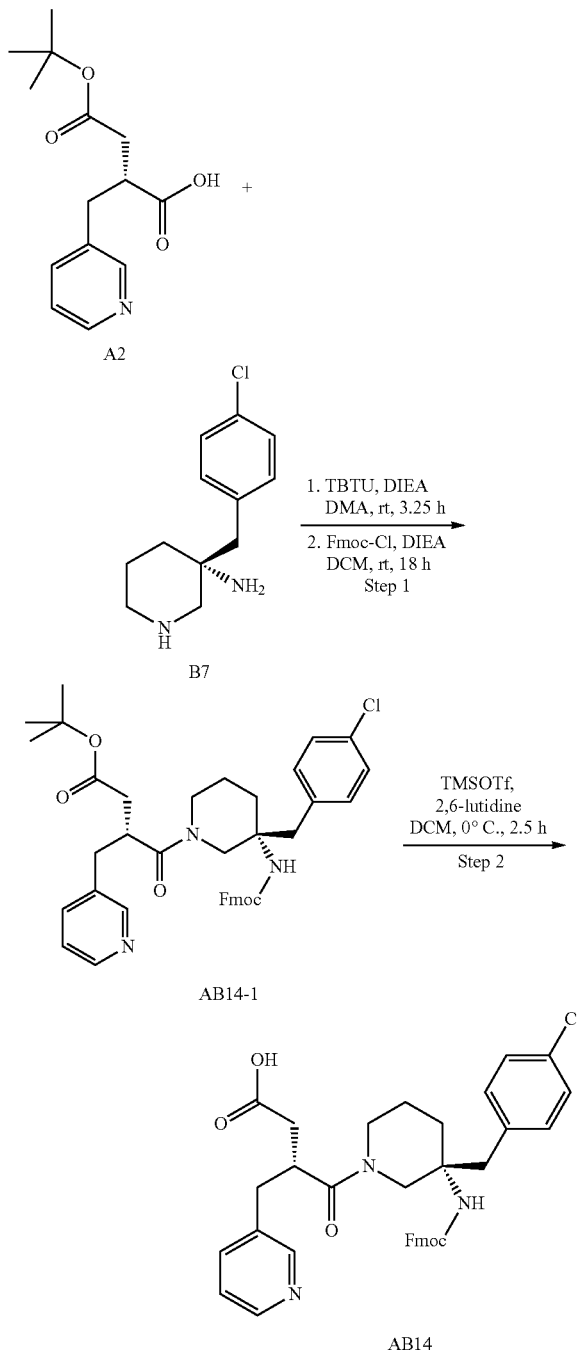

Step 1. tert-Butyl (R)-4-((R)-3-((((9H-fluoren-9-yl)methoxy)carbonyl)amino)-3-(4-chlorobenzyl)piperidin-1-yl)-4-oxo-3-(pyridin-3-ylmethyl)butanoate (AB14-1)

Step 1-1: To a solution of A2 (491 mg, 1.500 mmol) and TBTU (482 mg, 1.500 mmol) in DMA (10 mL) was added DIEA (0.341 mL, 1.950 mmol). The resulting mixture was stirred for 5 min at rt, and then a solution of B7 (446 mg, 1.50 mmol) in DMA (10 mL) and DIEA (1.048 mL, 6.00 mmol) was added. The reaction mixture was stirred for 3.25 h at rt, and then the DMA was removed in vacuo. The resulting residue was partitioned between EtOAc (70 mL) and 5% aq. NaHCO$_3$ (10 mL). The organic phase was washed with 5% NaHCO$_3$ (3×10 mL) and brine (10 mL), dried over Na$_2$SO$_4$, filtered, and concentrated to dryness in vacuo to afford a light brown oil.

Step 1-2: To the residue from Step 1-1 dissolved in DCM (10 mL) was added DIEA (0.524 mL, 3.00 mmol) and a solution of Fmoc-Cl (388 mg, 1.500 mmol) in DCM (5 mL). The reaction mixture was stirred for 18 h at rt, and then concentrated in vacuo. The resulting residue was partitioned between EtOAc (60 mL) and 5% aq. NaHCO$_3$ (10 mL). The organic phase was washed with 5% aq. NaHCO$_3$ (2×10 mL) and brine (10 mL), dried over Na$_2$SO$_4$, filtered, and concentrated to dryness in vacuo. The crude product was purified by flash silica gel chromatography (eluent A: heptane/DIEA (98:2); eluent B: EtOAc/DIEA (98:2)). Pure fractions were combined and concentrated to dryness in vacuo. The residue was dissolved in DCM and the solution was concentrated to dryness in vacuo to afford AB14-1 (775 mg, 1.116 mmol, 74% yield) as a white foam. Analytical method 10; t$_R$=1.47 min; [M+H]$^+$=694.5.

Step 2. (R)-4-((R)-3-((((9H-Fluoren-9-yl)methoxy)carbonyl)amino)-3-(4-chlorobenzyl)piperidin-1-yl)-4-oxo-3-(pyridin-3-ylmethyl)butanoic acid (AB14)

To a solution of AB14-1 (774 mg, 1.115 mmol) and 2,6-lutidine (1.298 mL, 11.15 mmol) in DCM (15 mL) at 0° C. was added TMSOTf (1.007 mL, 5.57 mmol) dropwise and the reaction mixture was stirred for 2.5 h at 0° C. EtOAc (60 mL) and 5% aq. NaHCO$_3$ (5 mL) were added and the phases were separated. The organic phase was washed with 5% aq. NaHCO$_3$ (3×5 mL) and brine (10 mL). The combined aqueous phases were extracted with EtOAc (2×25 mL). The combined organic phases were washed with brine (10 mL) and combined with the first organic phase. The combined organic phases were dried over Na$_2$SO$_4$, filtered, and concentrated to dryness in vacuo. The residue was dissolved in DCM and the solution was concentrated to dryness in vacuo to afford AB14 (~1.115 mmol) as a beige foam. The crude product was used in the next step without further purification. Analytical method 10; t$_R$=1.20 min; [M+H]$^+$=638.3.

Example 4.4: Synthesis of methyl (S)-4-((R)-3-amino-3-(4-chlorobenzyl)piperidin-1-yl)-3-((R)-2,3-dihydro-1H-inden-1-yl)-4-oxobutanoate (AB17)

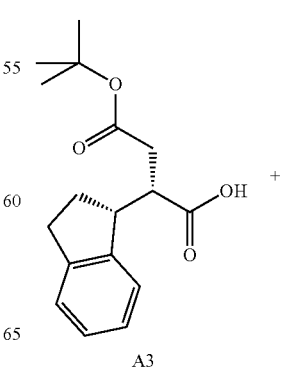

A3

-continued

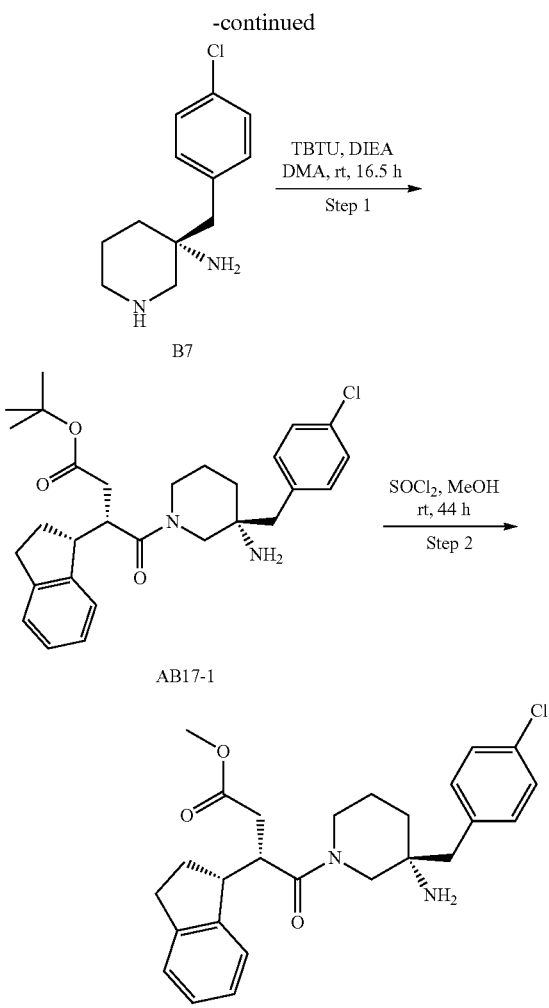

Step 1. tert-Butyl (R)-4-((R)-3-amino-3-(4-chlorobenzyl)piperidin-1-yl)-4-oxo-3-(pyridin-3-ylmethyl)butanoate (AB17-1)

To a solution of A3 (93 mg, 320 µmol) and TBTU (103 mg, 320 µmol) in DMA (4 mL) was added DIEA (0.073 mL, 416 µmol). The resulting solution was stirred for 15 min at rt and then a solution of B7 (117 mg, 320 µmol) in DMA (3 mL) and DIEA (0.291 mL, 1664 µmol) was added. The reaction mixture was stirred for 16.5 h at rt and then partitioned between EtOAc (50 mL) and 5% aq. NaHCO$_3$ (10 mL). The organic phase was washed with 5% NaHCO$_3$ (2×10 mL) and brine (10 mL), dried over Na$_2$SO$_4$, filtered, and concentrated to dryness in vacuo to afford AB17-1 (assumed to be 0.32 mmol). The crude product was used in the next step without purification. Analytical method 10; $t_R$=1.12 min; [M+H]$^+$=497.2.

Step 2. Methyl (S)-4-((R)-3-amino-3-(4-chlorobenzyl)piperidin-1-yl)-3-((R)-2,3-dihydro-1H-inden-1-yl)-4-oxobutanoate (AB17)

To AB17-1 (0.30 mmol) dissolved in MeOH (10 mL) was added SOCl$_2$ (0.219 mL, 3.00 mmol) and the resulting mixture was stirred for 3.5 h at rt. Additional SOC$_2$ (0.438 mL, 6.00 mmol) was added, and stirring at rt was continued for 24 h. More SOC$_2$ (0.438 mL, 6.00 mmol) was added and the resulting mixture was stirred for 16.5 at rt, and then concentrated to dryness in vacuo. The obtained residue was partitioned between EtOAc (50 mL) and 5% aq. NaHCO$_3$ (10 mL). The organic phase was washed with 5% aq. NaHCO$_3$ (2×10 mL) and brine (10 mL), dried over Na$_2$SO$_4$, filtered, and concentrated to dryness in vacuo to afford AB17 (123 mg, 0.270 mmol, 90% yield for 2 steps) as a yellow oil. The product was used in the next step without purification. Analytical method 10; $t_R$=0.96 min; [M+H]$^+$=455.2.

Example 5: Building Block C-α-Amino Acids

Table 5 shows the α-amino acids used as Building Block C.

TABLE 5

Building block C-α-amino acids

| BB No. | Structure | Chemical Name | LCMS |
|---|---|---|---|
| C1 | 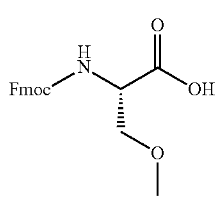 | N-(((9H-fluoren-9-yl)methoxy)carbonyl)-O-methyl-L-serine | Commercially available |
| C2 | 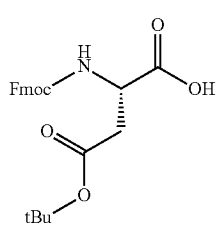 | (S)-2-((((9H-fluoren-9-yl)methoxy)carbonyl)amino)-4-(tert-butoxy)-4-oxobutanoic acid | Commercially available |

TABLE 5-continued

Building block C-α-amino acids

| BB No. | Structure | Chemical Name | LCMS |
|---|---|---|---|
| C3 | 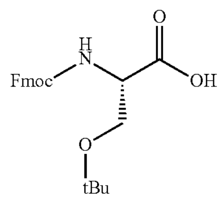 | N-(((9H-fluoren-9-yl)methoxy)carbonyl)-O-(tert-butyl)-L-serine | Commercially available |
| C4 | 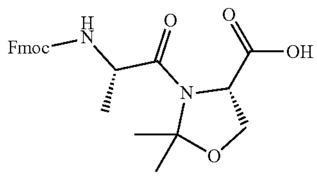 | (S)-3-((((9H-fluoren-9-yl)methoxy)carbonyl)-L-alanyl)-2,2-dimethyloxazolidine-4-carboxylic acid | Commercially available |

Example 6: Building Block D-α-Amino Acids

Example 6.1: Synthesis of (S)-2-((((9H-fluoren-9-yl)methoxy)carbonyl)amino)-6-morpholinohexanoic acid trifluoroacetate (D2)

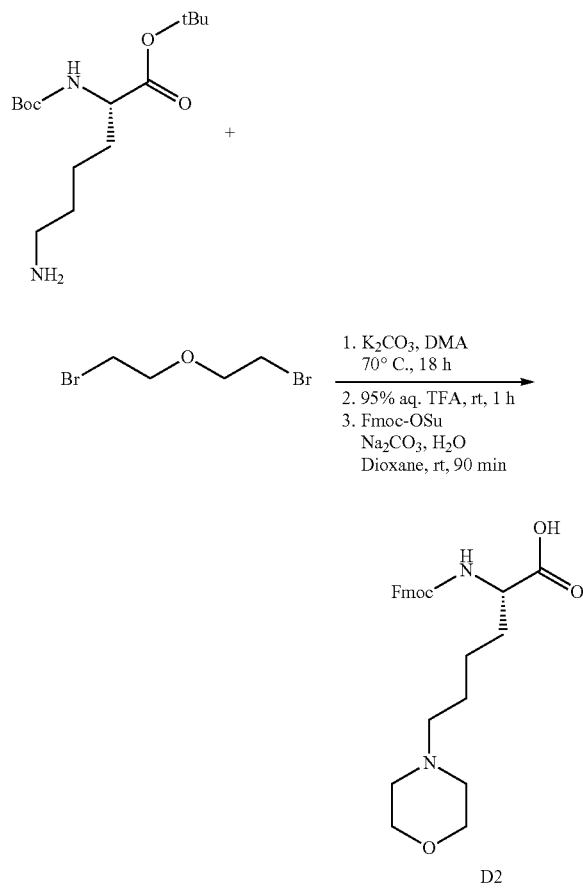

D2

Step 1-1: To Boc-Lys-OtBu HCl (339 mg, 1.00 mmol) and $K_2CO_3$ (415 mg, 3.00 mmol) were added DMA (8 mL) and 1-bromo-2-(2-bromoethoxy)ethane (0.126 mL, 1.000 mmol). The resulting suspension was stirred for 18 h at 70° C., and then partitioned between EtOAc (60 mL) and 5% aq. $NaHCO_3$ (10 mL). The organic phase was washed with 5% aq. $NaHCO_3$ (2×10 mL) and brine (10 mL), dried over $Na_2SO_4$, filtered, and concentrated to dryness in vacuo. The crude product was used in the next step without purification.

Step 1-2: The residue from Step 1-1 was dissolved in 95% aq. TFA (10 mL) and the resulting solution was stirred for 1 h at rt, and then concentrated to dryness in vacuo. The crude product was used in the next step without purification.

Step 1-3: To the residue from Step 1-2 dissolved in dioxane (5 mL) and $H_2O$ (2 mL) was added 0.5 M aq. $Na_2CO_3$ (6.00 mL, 3.00 mmol) and a solution of Fmoc-OSu (304 mg, 0.900 mmol) in dioxane (2 mL). The reaction mixture was stirred for 90 min at rt and then quenched by the addition of 2 M aq. HCl (3 mL). The dioxane was removed in vacuo and the crude residue was partitioned between EtOAc (50 mL) and $H_2O$ (10 mL). The organic phase was washed with brine (10 mL). The combined aqueous phases were extracted with EtOAc (20 mL) and the resulting organic phase was washed with brine (5 mL). The combined organic phases were dried over $Na_2SO_4$, filtered, and concentrated to dryness in vacuo. The crude product was purified by preparative reverse-phase HPLC (eluent A: 0.1% TFA in $H_2O$; eluent B: ACN). Pure fractions were combined and lyophilized to afford 02 (264.5 mg, 0.479 mmol, 48% yield) as a white solid. Analytical method 10; $t_R$=0.71 min; $[M+H]^+$=439.3.

Table 6 shows the α-amino acids used as Building Block D.

TABLE 6

Building block D-α-amino acids

| BB No. | Structure | Chemical Name | Synthesis/LCMS |
|---|---|---|---|
| D1 | Fmoc-NH-CH(CH₃)-COOH | (((9H-fluoren-9-yl)methoxy)carbonyl)-L-alanine | Commercially available |
| D3 | Fmoc-NH-CH(COOH)-CH₂CH₂CH₂-N(morpholine) | (S)-2-((((9H-fluoren-9-yl)methoxy)carbonyl)amino)-5-morpholinopentanoic acid | Example 6.1-starting from (S)-tert-butyl 5-amino-2-((tert-butoxycarbonyl)amino)pentanoate hydrochloride; crude product suspended in EtOAc/heptane; EtOAc removed in vacuo until only small amount of product in supernatant. Supernatant was removed and residue washed with heptane, then dried in vacuo/ Analytical method 10 $t_R$ = 0.71 min [M + H]⁺ = 425.2 |
| D4 | Fmoc-NH-CH(COOH)-CH₂CH₂-N(morpholine) | (S)-2-((((9H-fluoren-9-yl)methoxy)carbonyl)amino)-4-morpholinobutanoic acid | Example 6.1-starting from (S)-tert-butyl 4-amino-2-((tert-butoxycarbonyl)amino)pentanoate hydrochloride; crude product suspended in EtOAc/heptane; EtOAc removed in vacuo until only small amount of product in supernatant. Supernatant was removed and residue washed with heptane, then dried in vacuo/ Analytical method 10 $t_R$ = 0.75 min [M + H]⁺ = 411.2 |
| D6 | Fmoc-NH-CH(COOH)-CH₂CH₂-COO-tBu | (S)-2-((((9H-fluoren-9-yl)methoxy)carbonyl)amino)-5-(tert-butoxy)-5-oxopentanoic acid | Commercially Available |
| D7 | Boc-NH-CH(CH₃)-COOH | (tert-butoxycarbonyl)-L-alanine | Commercially Available |

Example 6.2: Synthesis of (S)-2-((((9H-fluoren-9-yl)methoxy)carbonyl)amino)-4-fluorobutanoic acid (D5)

-continued

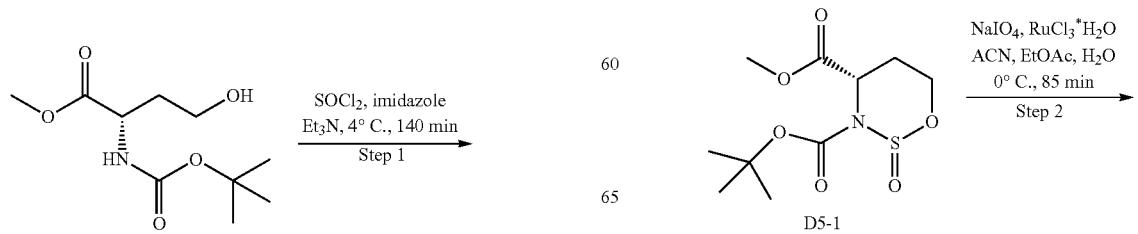

-continued

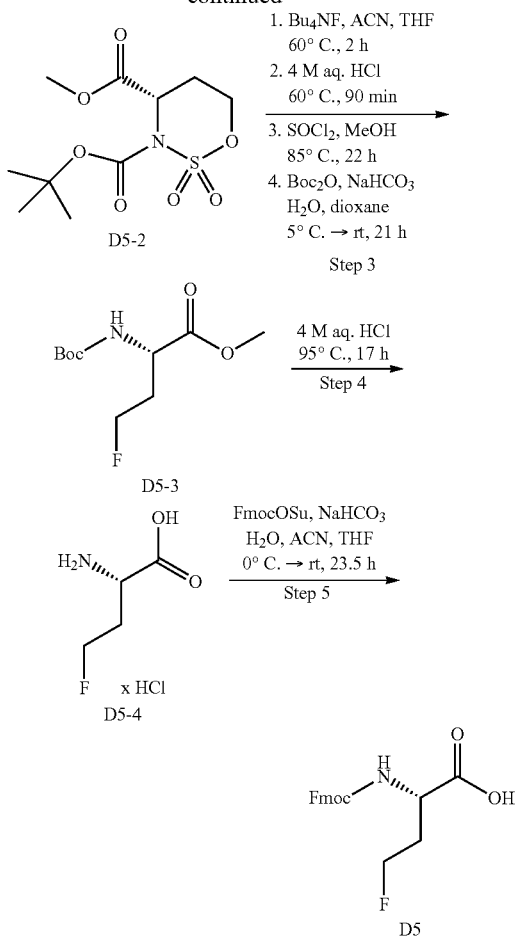

Step 1. 3-(tert-Butyl) 4-methyl (4S)-1,2,3-oxathiazinane-3,4-dicarboxylate 2-oxide (D5-1)

To a solution of imidazole (173.4 g, 2.55 mol) and triethylamine (132.0 mL, 939 mmol) in DCM (3 L) at 4° C. was added SOCl$_2$ (65 mL) dropwise over 1 h. The suspension was stirred for 25 min at 4° C. and a solution of methyl (tert-butoxycarbonyl)-L-homoserinate (110.65 g, 90% content, 427.0 mmol) in DCM (0.5 L) was added over 30 min. The reaction mixture was stirred at 4° C. for 2 h 20 min and then quenched by the addition of H$_2$O (1.2 L). The phases were separated and the aqueous phase was extracted with DCM (0.5 L). The combined organic phases were washed with H$_2$O (1 L) and brine (1 L), dried over Na$_2$SO$_4$, filtered, and concentrated to dryness in vacuo. The crude product was purified by silica gel chromatography. D5-1 was obtained as a yellow oil (78.14 g, 279.8 mmol, 66% yield).

Step 2. 3-(tert-Butyl) 4-methyl (4S)-1,2,3-oxathiazinane-3,4-dicarboxylate 2-oxide (D5-2)

To a solution of D5-1 (97.3 g, 348.4 mmol) in ACN (1.8 L) and EtOAc (180 mL) at 0° C. was added RuCl$_3$·H$_2$O (4.19 g, 20.2 mmol), followed by a cooled cloudy solution of NaIO$_4$ (149.0 g, 696.7 mmol) in H$_2$O (800 mL) over 15 min. The reaction mixture was stirred for 85 min at 0° C., and then Et$_2$O (1400 mL) was added. The resulting suspension was filtered and the phases were separated. The aqueous phase was extracted with Et$_2$O (2×800 mL). The combined organic phases were washed with NaHCO$_3$ solution (1000 mL) and brine, dried over Na$_2$SO$_4$, filtered, and concentrated to dryness in vacuo to afford D5-2 (92.75 g, 282.7 mmol, 90% purity by NMR, 81% yield) as a white solid. The crude product was taken to the next step without purification.

Step 3. Methyl (S)-2-((tert-butoxycarbonyl)amino)-4-fluorobutanoate (D5-3)

To D5-2 (92.75 g, 90% purity, 282.7 mmol) dissolved in ACN (1 L) was added slowly at rt 1 M Tetrabutylammoniumfluoride in THF (466.5 mL; 466.5 mmol) and the reaction mixture was stirred for 2 h at 60° C. The solvent was evaporated in vacuo and the obtained oil was mixed with 4 M aq. HCl (800 mL) and heated to 60° C. with stirring for 90 min. The reaction mixture was concentrated to dryness in vacuo. The resulting residue was co-evaporated with toluene to dryness to give a viscous yellow oil. The crude intermediate was dissolved in MeOH (1200 mL) and SOCl$_2$ (102.6 mL, 1.41 mol) was added at 5° C. and the resulting mixture was stirred under reflux for 22 h. After complete consumption of starting materials, the solvent was removed in vacuo and the crude product was co-evaporated with toluene to dryness.

To the obtained oil dissolved in 1 M aq. NaHCO$_3$ and dioxane (200 mL) at 5° C. was added a solution of Boc$_2$O (124.1 g, 568.6 mmol) in dioxane (100 mL) and the resulting mixture was allowed to warm to rt and stirred for 21 h. H$_2$O (500 mL) and Et$_2$O (500 mL) were added and the phases were separated. The aqueous phase was extracted with Et$_2$O (2×500 mL). The combined organic phases were washed with H$_2$O (500 mL) and brine (300 mL), dried over Na$_2$SO$_4$, filtered, and concentrated to dryness in vacuo. The crude product was purified by silica gel chromatography. D5-3 (55.0 g, 233.8 mmol, 83% yield) was obtained as a yellow oil.

Step 4. (S)-2-Amino-4-fluorobutanoic acid (D5-4)

D5-3 (55.0 g, 233.8 mmol) was dissolved in 4 M HCl (1000 mL) and the reaction mixture was stirred for 17 h at 95° C. and then concentrated in vacuo. Further drying was achieved by co-evaporation with toluene. D5-4 (33.94 g, 194 mmol, 90% purity, 83% yield) was obtained as a yellow solid.

Step 5. (S)-2-((((9H-Fluoren-9-yl)methoxy)carbonyl)amino)-4-fluorobutanoic acid (D5)

To D5-4 (33.9 g, 194 mmol) dissolved in 0.5 M aq. NaHCO$_3$ (1 L, 500 mmol) was added ACN/THF (4:1). The resulting mixture was cooled to 0° C. and a solution of Fmoc-OSu (75.35 g, 223.4 mmol) in ACN/THF (4:1) (500 mL) was added. The reaction mixture was allowed to warm to rt and stirred for 23.5 h. Ice (1000 mL) was added and the reaction mixture was carefully acidified to pH of −2-3 by the addition of conc. HCl (25 mL). Et$_2$O (2 L) was added and the phases were separated. The aqueous phase was extracted with Et$_2$O (600 mL). The combined organic phases were washed with H$_2$O (600 mL) and brine, dried over Na$_2$SO$_4$, filtered, and concentrated to dryness in vacuo. The crude product was purified by silica gel chromatography. Pure fractions were combined and concentrated to dryness in vacuo. The resulting residue was suspended in toluene (150 mL) and the suspension concentrated to dryness in vacuo.

This step was repeated twice. D5 (17.5 g, 50.7 mmol, 26% yield) was obtained as an off-white solid. Analytical method 10; $t_R$=0.96 min; [M+H]$^+$=344.1. $^1$H NMR (600 MHz, DMSO-d$_6$) δ 12.75 (s, 1H), 7.88 (d, J=7.5 Hz, 2H), 7.71 (t, J=7.2 Hz, 2H), 7.40 (t, J=7.4 Hz, 2H), 7.32 (t, J=7.4 Hz, 2H), 4.55 (dt, J=9.7, 5.0 Hz, 0.5H), 4.48 (dt, J=9.7, 4.8 Hz, 1H), 4.40 (td, J=8.9, 4.4 Hz, 0.5H), 4.30 (d, J=7.1 Hz, 2H), 4.22 (t, J=7.0 Hz, 1H), 4.06 (td, J=9.6, 4.4 Hz, 1H), 2.14 (dtt, J=19.0, 8.7, 4.4 Hz, 1H), 1.92 (dtd, J=31.2, 10.2, 5.1 Hz, 1H).

Example 7: Building Block E—Aldehydes

Example 7.1: Synthesis of 4-chloro-2-(4-(1-methyl-2-(pyrrolidin-1-ylmethyl)-1H-imidazol-5-yl)phenoxy)-benzaldehyde (E2)

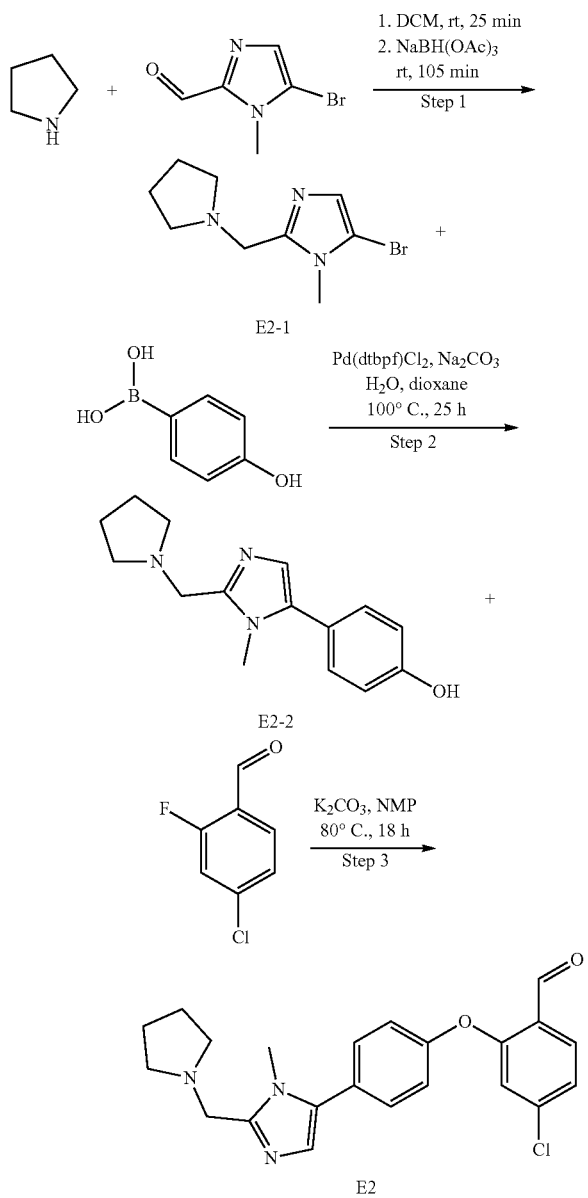

Step 1. 5-Bromo-1-methyl-2-(pyrrolidin-1-ylmethyl)-1H-imidazole (E2-1)

To a solution of 5-bromo-1-methyl-1H-imidazole-2-carbaldehyde (1.890 g, 10.0 mmol) in DCM (70 mL) was added pyrrolidine (1.643 mL, 20.0 mmol). After stirring for 25 min at rt NaBH(OAc)$_3$ (8.48 g, 40.0 mmol) was added. The reaction mixture was stirred for 105 min at rt, and then concentrated to dryness in vacuo. The resulting residue was partitioned between EtOAc (250 mL) and 1 M aq. NaOH (50 mL). The organic phase was washed with 1 M NaOH (2×40 mL) and brine (20 mL), dried over Na$_2$SO$_4$, filtered, and concentrated to dryness in vacuo to afford E2-1 (assumed to be 10.0 mmol) as a yellow solid. The crude product was used in the next step without purification. Analytical method 11; $t_R$=0.66 min; [M+H]$^+$=244.1.

Step 2. 4-(1-Methyl-2-(pyrrolidin-1-ylmethyl)-1H-imidazol-5-yl)phenol (E2-2)

To E2-1 (10.0 mmol), (4-hydroxyphenyl)boronic acid (2.76 g, 20.0 mmol) and [1,1'-bis(di-tert-butylphosphino)-ferrocene]dichloropalladium(II) (0.978 g, 1.50 mmol) were added dioxane (30 mL) and 1 M aq. Na$_2$CO$_3$ (30 mL) and the resulting mixture was stirred for 4 h at 100° C. under an N$_2$-atmosphere. Additional (4-hydroxyphenyl)boronic acid (1.379 g, 10.0 mmol) was added and stirring at 100° C. was continued for 135 min. Additional (4-hydroxyphenyl)boronic acid (1.379 g, 10.0 mmol) and [1,1'-bis(di-tert-butylphosphino)ferrocene]-dichloropalladium(II) (0.244 g, 0.375 mmol) were then added and stirring at 100° C. was continued for 18.75 h. EtOAc (250 mL) and H$_2$O (50 mL) were added and the mixture was filtered through Hyflo. The phases were separated and the organic phase was washed with 5% aq. NaHCO$_3$ (3×40 mL) and brine (40 mL), dried over Na$_2$SO$_4$, filtered, and concentrated to dryness in vacuo. The crude product was purified by flash silica gel chromatography (eluent A: EtOAc/MeOH/DIEA (95:5:2); eluent B: EtOAc/MeOH/DIEA (85:15:2)) to give E2-2 (2.28 g, 8.86 mmol, 89% yield over 2 steps) as a brown solid. Analytical method 11; $t_R$=0.76 min; [M+H]$^+$=258.1.

Step 3. 4-Chloro-2-(4-(1-methyl-2-(pyrrolidin-1-ylmethyl)-1H-imidazol-5-yl)phenoxy)benzaldehyde (E2)

To E2-2 (1.029 g, 4 mmol) and 4-chloro-2-fluorobenzaldehyde (0.824 g, 5.20 mmol) dissolved in NMP (20 mL) was added K$_2$CO$_3$ (1.437 g, 10.40 mmol). The resulting mixture was stirred for 18 h at 80° C., and then partitioned between EtOAc (125 mL) and H$_2$O (20 mL). The organic phase was washed with 5% aq. NaHCO$_3$ (3×10 mL) and brine (10 mL), dried with Na$_2$SO$_4$, filtered, and concentrated to dryness in vacuo. The crude product was purified by flash silica gel chromatography (eluent A: EtOAc/DIEA (98:2); eluent B: EtOAc/MeOH/DIEA (90:10:2)) to give E2 (1.25 g, 3.16 mmol, 79% yield) as a brown oil. Analytical method 10; $t_R$=0.79 min; [M+H]$^+$=396.2.

E9 was synthesized according to the procedure described to E2 in Example 7.1 starting from E9-4, (4-hydroxyphenyl) boronic acid, and 4-chloro-2-fluorobenzaldehyde as starting materials.

Example 7.2: 4-Chloro-2-(4-(1-methyl-2-(morpholinomethyl)-1H-imidazol-5-yl)phenoxy)benzaldehyde (E3)

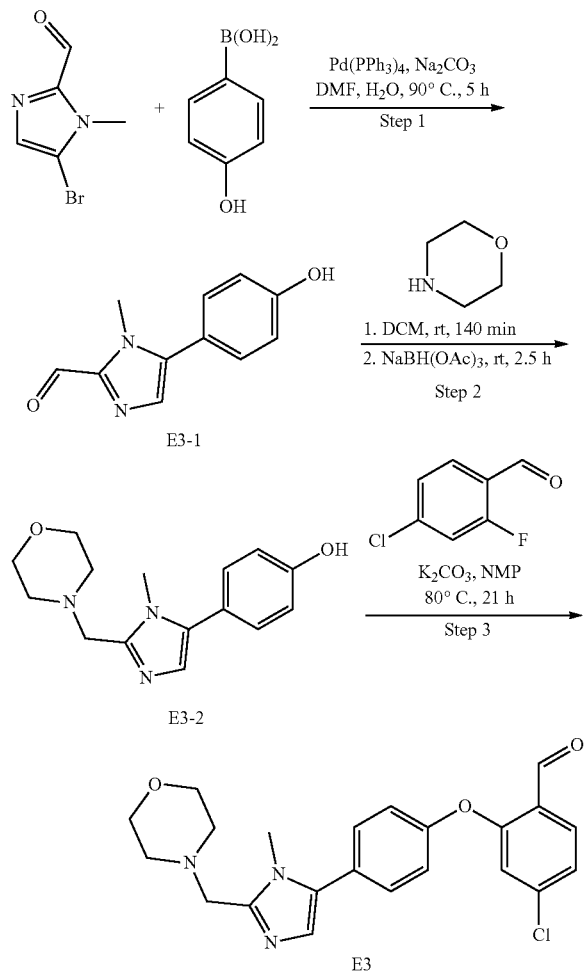

Step 1. 5-(4-Hydroxyphenyl)-1-methyl-1H-imidazole-2-carbaldehyde (E3-1)

A mixture of 5-bromo-1-methyl-1H-imidazole-2-carbaldehyde (1.890 g, 10 mmol), (4-hydroxyphenyl)boronic acid (2.76 g, 20.00 mmol) and Pd(PPh$_3$)$_4$ (0.578 g, 0.500 mmol) in DMF (40 mL) and 1 M aq. Na$_2$CO$_3$ (30 mL, 30.0 mmol) was stirred for 5 h at 90° C. under an N$_2$-atmosphere. The mixture was filtered through HyFlo and the filtrate was partitioned between EtOAc (100 mL) and H$_2$O (50 mL). The aqueous phase was extracted with EtOAc (3×50 mL). The combined organic phases were washed with brine (20 mL), dried over Na$_2$SO$_4$, filtered, and concentrated to dryness in vacuo to afford E3-1 (assumed to be 10 mmol) as an olive-colored solid. The crude product was used in the next step without purification. Analytical method 10; $t_R$=0.60 min; [M+H]$^+$=203.1.

Step 2. 4-(1-Methyl-2-(morpholinomethyl)-1H-imidazol-5-yl)phenol (E3-2)

To E3-1 (2.5 mmol) were added DCM (10 mL) and morpholine (0.431 mL, 5.00 mmol). The resulting mixture was stirred for 140 min at rt, and then NaBH(OAc)$_3$ (1060 mg, 5.00 mmol) was added. The reaction mixture was stirred for 2.5 h at rt, then partitioned between EtOAc (70 mL) and 5% aq. NaHCO$_3$ (15 mL). The aqueous phase was extracted with EtOAc (2×20 mL). The combined organic phases were washed with brine (5 mL), dried over Na$_2$SO$_4$, filtered, and concentrated to dryness in vacuo to afford E3-2 (677 mg, 2.477 mmol, 99% yield for 2 steps) as a light olive-colored solid. The crude product was used in the next step without purification. Analytical method 10; $t_R$=0.42 min; [M+H]$^+$=274.2.

Step 3. 4-Chloro-2-(4-(1-methyl-2-(morpholinomethyl)-1H-imidazol-5-yl)phenoxy)benzaldehyde (E3)

To 4-chloro-2-fluorobenzaldehyde (550 mg, 3.47 mmol) and K$_2$CO$_3$ (890 mg, 6.44 mmol) was added a solution of E3-2 (677 mg, 2.477 mmol) in NMP (10 mL). The suspension was stirred for 21 h at 80° C. The reaction mixture was partitioned between EtOAc (60 mL) and H$_2$O (15 mL). The organic phase was washed with 5% aq. NaHCO$_3$ (2×10 mL) and brine (10 mL), dried over Na$_2$SO$_4$, filtered, and concentrated to dryness in vacuo. The crude product was purified by flash silica gel chromatography (eluent A: EtOAc/DIEA (98:2); eluent B: EtOAc/MeOH/DIEA (85:15:2)). Pure fractions were combined and concentrated to dryness in vacuo to afford E3 (579 mg, 1.406 mmol, 57% yield) as a beige solid. Analytical method 10; $t_R$=0.81 min; [M+H]$^+$=412.1.

The following Building Blocks (BB) in Table 7 were synthesized according to the procedure described in Example 7.1 for Building Block E2, Example 7.2 for Building Block E3, Example 7.7 for Building Block E12, Example 7.10 for Building Block E17, and Example 7.14 for Building Block E23.

TABLE 7

Building block F-Aldehydes

| BB No. | Structure/Chemical Name | Synthesis/LCMS |
|---|---|---|
| E1 | 4-chloro-2-(4-(2-((dimethylamino)methyl)-1-methyl-1H-imidazol-5-yl)phenoxy)benzaldehyde | Example 7.1-Starting from dimethylamine, 5-bromo-1-methyl-1H-imidazole-2-carbaldehyde, (4-hydroxyphenyl)boronic acid, and 4-chloro-2-fluorobenzaldehyde or Example 7.3-starting from E3-1, dimethylamine and 4-chloro-2-fluorobenzaldehyde/ Analytical method 10 $t_R$ = 0.74 min [M + H]$^+$ = 370.2 |

TABLE 7-continued

Building block F-Aldehydes

| BB No. | Structure/Chemical Name | Synthesis/ LCMS |
|---|---|---|
| E4 | 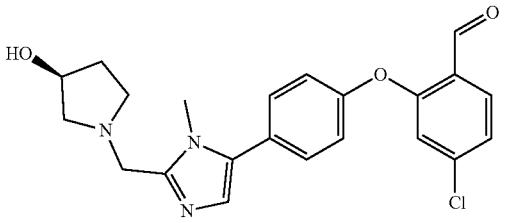 [SMILES: Cn1c(-c2ccc(Oc3cc(Cl)ccc3C=O)cc2)cnc1CN1CC[C@H](O)C1](S)-4-chloro-2-(4-(2-((3-hydroxypyrrolidin-1-yl)methyl)-1-methyl-1H-imidazol-5-yl)phenoxy)benzaldehyde | Example 7.2-Starting from E3-1, (S)-pyrrolidin-3-ol and 4-chloro-2-fluorobenzaldehyde/ Analytical method 10 $t_R$ = 0.71 min $[M + H]^+$ = 412.3 |
| E5 | 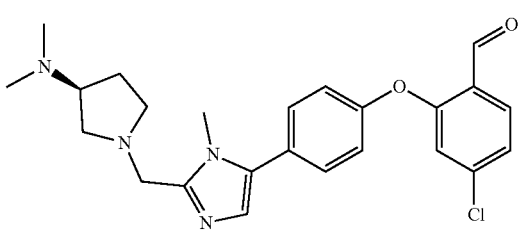 [SMILES: CN(C)[C@H]1CCN(Cc2ncc(-c3ccc(Oc4cc(Cl)ccc4C=O)cc3)n2C)C1](S)-4-chloro-2-(4-(2-((3-(dimethylamino)pyrrolidin-1-yl)methyl)-1-methyl-1H-imidazol-5-yl)phenoxy)benzaldehyde | Example 7.2-Starting from E3-1, (S)-N,N-dimethylpyrrolidin-3-amine and 4-chloro-2-fluorobenzaldehyde/ Analytical method 10 $t_R$ = 0.53 min $[M + H]^+$ = 439.3 |
| E6 | 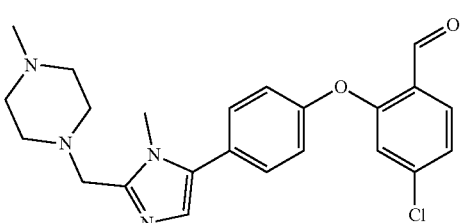4-chloro-2-(4-(1-methyl-2-((4-methylpiperazin-1-yl)methyl)-1H-imidazol-5-yl)phenoxy)benzaldehyde | Example 7.2-Starting from E3-1, 1-methylpiperazine and 4-chloro-2-fluorobenzaldehyde/ Analytical method 10 $t_R$ = 0.57 min $[M + H]^+$ = 425.3 |
| E7 | 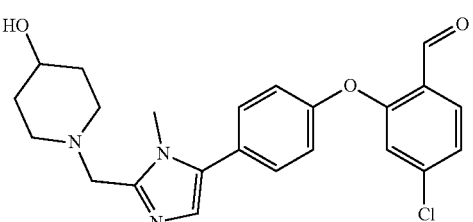4-chloro-2-(4-(2-((4-hydroxypiperidin-1-yl)methyl)-1-methyl-1H-imidazol-5-yl)phenoxy)benzaldehyde | Example 7.2-Starting from E3-1, piperidin-4-ol and 4-chloro-2-fluorobenzaldehyde/ Analytical method 10 $t_R$ = 0.70 min $[M + H]^+$ = 426.2 |

TABLE 7-continued

Building block F-Aldehydes

| BB No. | Structure/Chemical Name | Synthesis/ LCMS |
|---|---|---|
| E8 | 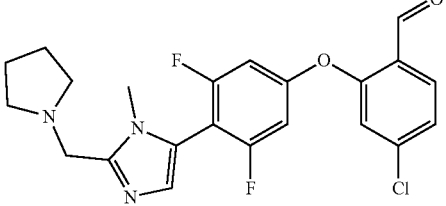<br>4-chloro-2-(3,5-difluoro-4-(1-methyl-2-(pyrrolidin-1-ylmethyl)-1H-imidazol-5-yl)phenoxy)benzaldehyde | Example 7.2-Starting from E8-3 (see Example 7.3) and 4-chloro-2-fluorobenzaldehyde/<br>Analytical method 10<br>$t_R$ = 0.82 min<br>$[M + H]^+$ = 432.1 |
| E9 | 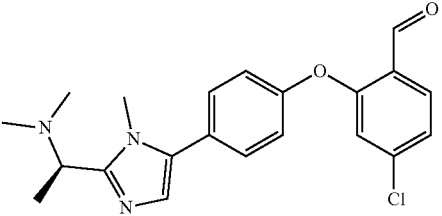 [SMILES: C[C@H](c1ncc(-c2ccc(Oc3cc(Cl)ccc3C=O)cc2)n1C)N(C)C]<br>(R)-4-chloro-2-(4-(2-(1-(dimethylamino)ethyl)-1-methyl-1H-imidazol-5-yl)phenoxy)benzaldehyde | Example 7.1-Starting from E9-4 (see Example 7.4), (4-hydroxyphenyl)boronic acid and 4-chloro-2-fluorobenzaldehyde/<br>Analytical method 5<br>$t_R$ = 1.03 min<br>$[M + H]^+$ = 384.3. |
| E10 | 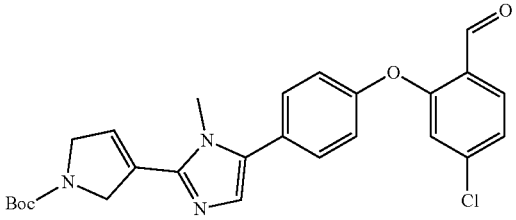 [SMILES: Cn1c(-c2ccc(Oc3cc(Cl)ccc3C=O)cc2)cnc1C1=CCN(C(=O)OC(C)(C)C)C1]<br>tert-butyl 3-(5-(4-(5-chloro-2-formylphenoxy)phenyl)-1-methyl-1H-imidazol-2-yl)-2,5-dihydro-1H-pyrrole-1-carboxylate | Example 7.1-Starting from E10-4 (see Example 7.5), (4-benzylphenyl)boronic acid and 4-chloro-2-fluorobenzaldehyde/<br>Analytical method 10<br>$t_R$ = 1.14 min<br>$[M + H]^+$ = 480.2 |
| E13 | 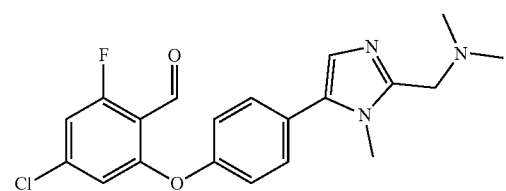 [SMILES: CN(C)Cc1ncc(-c2ccc(Oc3cc(Cl)cc(F)c3C=O)cc2)n1C]<br>4-Chloro-2-(4-(2-((dimethylamino)methyl)-1-methyl-1H-imidazol-5-yl)phenoxy)-6-fluorobenzaldehyde | Example 7.7, Step 3-Starting from corresponding phenol and 4-chloro-2,6-difluorobenzaldehyde (1.2 eq) |
| E16 | 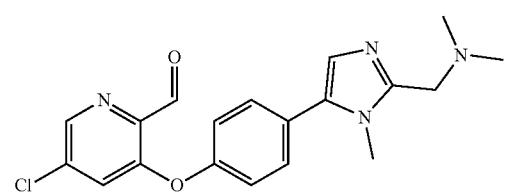 [SMILES: CN(C)Cc1ncc(-c2ccc(Oc3cc(Cl)cnc3C=O)cc2)n1C]<br>5-Chloro-3-(4-(2-((dimethylamino)methyl)-1-methyl-1H-imidazol-5-yl)phenoxy)picolinaldehyde | Example 7.7, Step 3-Starting from corresponding phenol and 5-chloro-3-fluoropicolinaldehyde (1.0 eq) |

TABLE 7-continued

Building block F-Aldehydes

| BB No. | Structure/Chemical Name | Synthesis/LCMS |
|---|---|---|
| E18 | tert-Butyl ((5-(4-(5-chloro-3-fluoro-2-formylphenoxy)phenyl)-1-methyl-1H-imidazol-2-yl)methyl)(cyclobutyl)carbamate | Example 7.10-Starting from cyclobutylamine |
| E20 | 4-Chloro-2-(4-(2-((dimethylamino)methyl)-1-methyl-1H-imidazol-5-yl)phenoxy)-3-fluorobenzaldehyde | Example 7.7, Step 3-Starting from the corresponding phenol and 4-chloro-2,3-difluorobenzaldehyde |
| E24 | 4-Chloro-2-(4-(2-((dimethylamino)methyl)-1-methyl-1H-imidazol-5-yl)phenoxy)-5-fluorobenzaldehyde | Example 7.7, Step 3-Starting from the corresponding phenol and 4-chloro-2,5-difluorobenzaldehyde |
| E25 | 2-(4-(2-((dimethylamino)methyl)-1-methyl-1H-imidazol-5-yl)phenoxy)benzaldehyde | Example 7.7, Step 3-Starting from the corresponding phenol and 2-fluorobenzaldehyde |
| E28 | 2-(4-(2-((Dimethylamino)methyl)-1-methyl-1H-imidazol-5-yl)phenoxy)-4-fluorobenzaldehyde | Example 7.7, Step 3-Starting from the corresponding phenol and 2,4-difluorobenzaldehyde |

TABLE 7-continued

Building block F-Aldehydes

| BB No. | Structure/Chemical Name | Synthesis/ LCMS |
|---|---|---|
| E30 | 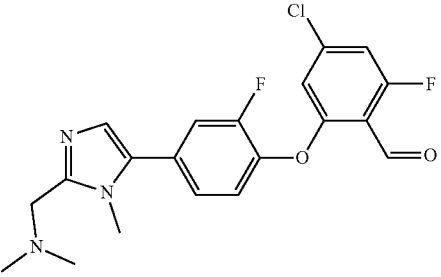 [SMILES: CN(C)Cc1ncc(-c2ccc(Oc3cc(Cl)cc(F)c3C=O)c(F)c2)n1C]<br>4-Chloro-2-(4-(2-((dimethylamino)methyl)-1-methyl-1H-imidazol-5-yl)-2-fluorophenoxy)-6-fluorobenzaldehyde | Example 7.14, Steps 1 to 4-Starting from ((4-(benzyloxy)-3-fluorophenyl)boronic acid |
| E32 | 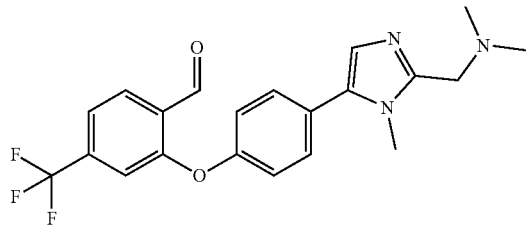 [SMILES: CN(C)Cc1ncc(-c2ccc(Oc3cc(C(F)(F)F)ccc3C=O)cc2)n1C]<br>2-(4-(2-((Dimethylamino)methyl)-1-methyl-1H-imidazol-5-yl)phenoxy)-4-(trifluoromethyl)benzaldehyde | Example 7.7, Step 3-Starting from the corresponding phenol and 2-fluoro-4-(trifluoromethyl)benzaldehyde |
| E33 | 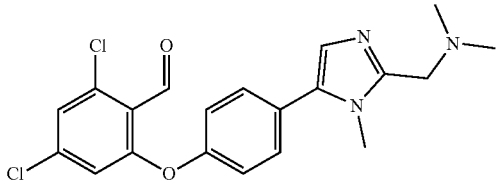 [SMILES: CN(C)Cc1ncc(-c2ccc(Oc3cc(Cl)cc(Cl)c3C=O)cc2)n1C]<br>2,4-Dichloro-6-(4-(2-((dimethylamino)methyl)-1-methyl-1H-imidazol-5-yl)phenoxy)benzaldehyde | Example 7.7, Step 3-Starting from the corresponding phenol and 2,4-dichloro-6-fluorobenzaldehyde |
| E35 | 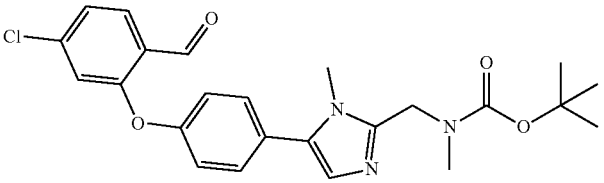 [SMILES: CN(Cc1ncc(-c2ccc(Oc3cc(Cl)ccc3C=O)cc2)n1C)C(=O)OC(C)(C)C]<br>tert-Butyl((5-(4-(5-chloro-2-formylphenoxy)phenyl)-1-methyl-1H-imidazol-2-yl)methyl)(methyl)carbamate | Example 7.7, Step 1 & Example 7.10, Steps 1 & 2-Starting from E3-1 and methylamine |

Example 7.3: Synthesis of 3,5-difluoro-4-(1-methyl-2-(pyrrolidin-1-ylmethyl)-1H-imidazol-5-yl)phenol (E8-3)

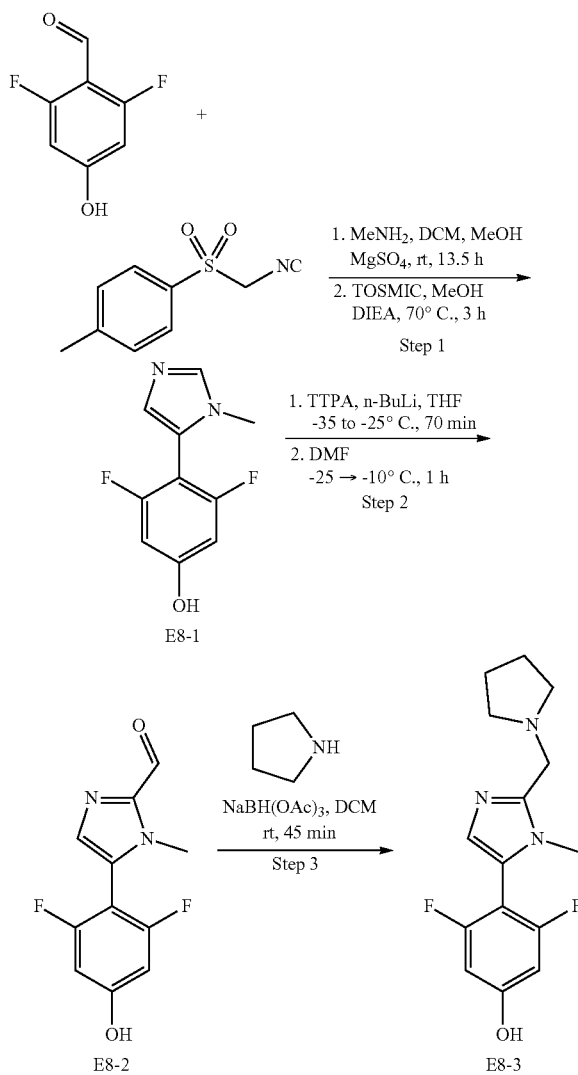

Step 1. 3,5-Difluoro-4-(1-methyl-1H-imidazol-5-yl)phenol (E8-1)

Step 1-1: To 2,6-difluoro-4-hydroxybenzaldehyde (949 mg, 6.00 mmol) dissolved in DCM (20 mL) was added 2 M methylamine in methanol (9.00 mL, 18.00 mmol) followed by MgSO$_4$ (4333 mg, 36.0 mmol). The resulting suspension was stirred for 13.5 h at rt, and then filtered. The obtained residue was washed with DCM (~40 mL) and the filtrate was concentrated to dryness in vacuo to afford an orange-brown solid which was used in the next step without purification.

Step 1-2: To TOSMIC (1523 mg, 7.80 mmol) was added a solution of the residue of Step 1-1 in MeOH (15 mL) and DIEA (3.14 mL, 18.00 mmol). The resulting mixture was stirred for 3 h at 70° C., and then concentrated to dryness in vacuo. The crude product was purified by flash silica gel chromatography (eluent A: EtOAc/MeOH/DIEA (95:5:2); eluent B: EtOAc/MeOH/DIEA (90:10:2)) to yield E8-1 (960 mg, 4.57 mmol, 76% yield) as a beige solid. Analytical method 11; $t_R$=0.71 min; [M+H]$^+$=211.1.

Step 2. 5-(2,6-Difluoro-4-hydroxyphenyl)-1-methyl-1H-imidazole-2-carbaldehyde (E8-2)

To E8-1 (0.420 g, 2.00 mmol) dissolved in THF (5 mL) and TTPA (5 mL) (tris(N,N-tetramethylene)phosphoric acid triamide) and cooled to −30° C. was added n-BuLi (1.6 M in hexanes) (7.50 mL, 12.00 mmol) dropwise. The reaction mixture was stirred for 65 min at −25 to −35° C. (some gel formed upon addition of n-BuLi). Additional TTPA (1.0 mL) and n-BuLi (1.6 M in hexanes) (1.25 mL, 2.00 mmol) were added and stirring at −25° C. was continued for 5 min. DMF (1.55 mL, 20.0 mmol) was then added dropwise and the resulting mixture was stirred for 1 h and then allowed to warm to −10° C. The reaction mixture was quenched by the addition of AcOH (0.916 mL, 16.0 mmol) and partitioned between EtOAc (50 mL) and 5% NaHCO$_3$ (15 mL). The organic phase was washed with 5% aq. NaHCO$_3$ (2×10 mL) and brine (10 mL), dried over Na$_2$SO$_4$, filtered, and concentrated to dryness in vacuo to afford E8-2 (~2.0 mmol) as a yellow oil. The crude product was used in the next step without purification. Analytical method 11; $t_R$=1.10 min; [M+H]$^+$=239.1.

Step 3. 3,5-Difluoro-4-(1-methyl-2-(pyrrolidin-1-ylmethyl)-1H-imidazol-5-yl)phenol (E8-3)

E8-2 (2.0 mmol) was dissolved in DCM (20 mL) and pyrrolidine (0.331 mL, 4.00 mmol). The resulting solution was stirred for 5 min at rt, and NaBH(OAc)$_3$ (0.848 g, 4.00 mmol) was added. The reaction mixture was stirred for 45 min at rt, and then partitioned between EtOAc (40 mL) and 1 M aq. HCl (10 mL). The organic phase was extracted with 1 M aq. HCl (3×10 mL). The combined aqueous phases were basified to pH=8-9 by the addition of 4 M aq. NaOH and then washed with EtOAc (3×40 mL). The combined organic phases were washed with brine (20 mL), dried over Na$_2$SO$_4$, filtered, and concentrated to dryness in vacuo to afford E8-3 (~2.0 mmol) as a yellow oil. The crude product was used in the next step without purification. Analytical method 11; $t_R$=0.84 min; [M+H]$^+$=294.2.

Example 7.4: Synthesis of (R)-1-(5-bromo-1-methyl-1H-imidazol-2-yl)-N,N-dimethylethan-1-amine (E9-4)

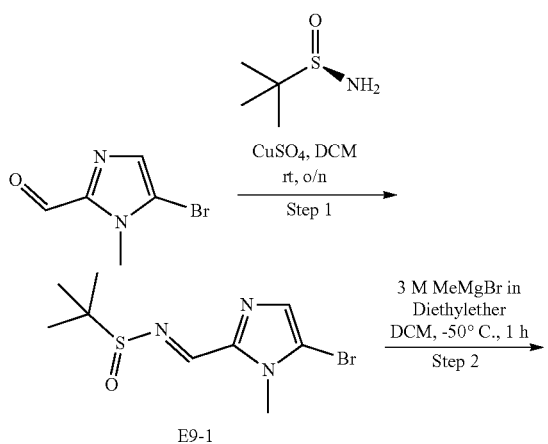

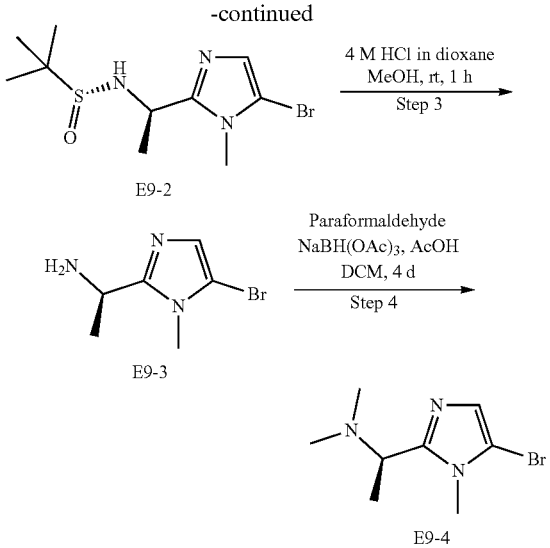

Step 1. (R,E)-N-((5-Bromo-1-methyl-1H-imidazol-2-yl)methylene)-2-methylpropane-2-sulfinamide (E9-1)

To 5-bromo-1-methyl-1H-imidazole-2-carbaldehyde (3 g, 15.87 mmol) in anhydrous DCM (40 mL) was added (R)-2-methylpropane-2-sulfinamide (2.116 g, 17.46 mmol) and anhydrous copper sulfate (5.07 g, 31.7 mmol). The resulting mixture was stirred at rt overnight, and then filtered through a pad of Celite®, flushing with DCM. The filtrate was concentrated in vacuo and the crude product was purified by flash silica gel chromatography (eluting with 0→100% EtOAc in heptane) to afford E9-1 (4 g, 13.69 mmol, 86% yield) as a white solid. Analytical method 5; $t_R$=0.83 min; $[M+H]^+$=294.2.

Step 2. (R)—N—((R)-1-(5-Bromo-1-methyl-1H-imidazol-2-yl)ethyl)-2-methylpropane-2-sulfinamide (E9-2)

To a solution of E9-1 (2.7 g, 9.24 mmol) in anhydrous DCM (50 mL) at −50° C. was added 3 M MeMgBr in diethyl ether (7.08 mL, 21.25 mmol) via a syringe and the resulting mixture was stirred at −50° C. for 1 h, and then quenched with sat. aq. NH₄Cl. After warming to rt, the reaction mixture was diluted with sat. aq. NaHCO₃ (50 mL) and extracted with DCM (2×60 mL). The combined organic phases were dried over Na₂SO₄, filtered, and concentrated to dryness in vacuo to afford a white solid. The product was recrystallized from EtOAc/heptane to afford E9-2 (2.03 g, 6.59 mmol, 71% yield) as a white power. Analytical method 5; $t_R$=0.68 min; $[M+H]^+$=310.1.

Step 3. (R)-1-(5-Bromo-1-methyl-1H-imidazol-2-yl)ethanamine hydrochloride (E9-3)

To a suspension of E9-2 (2.02 g, 6.55 mmol) in anhydrous MeOH (10 mL) was added 4 M HCl in dioxane (6.55 mL, 26.2 mmol). The resulting mixture turned clear and was stirred at rt for 1 h. Diethyl ether (100 mL) was added leading to the formation of a precipitate. The precipitate was collected by filtration to afford E9-3 (~6.55 mmol) as a white powder. The crude material was used in the next step without purification. Analytical method 5; $t_R$=0.51 min; $[M+H]^+$=203.9.

Step 4. (R)-1-(5-Bromo-1-methyl-1H-imidazol-2-yl)-N,N-dimethylethanamine (E9-4)

To E9-3 (6.55 mmol) was added anhydrous DCM (50 mL), paraformaldehyde (1.967 g, 65.5 mmol), NaBH(OAc)₃ (3.47 g, 16.38 mmol) and AcOH (5 mL). The resulting mixture was stirred at rt over two days. Additional NaBH(OAc)₃, (1600 mg, 7.55 mmol) and paraformaldehyde (600 mg, 20.0 mmol) were added. The reaction mixture was stirred overnight, then quenched with 2 N aq. Na₂CO₃ (100 mL) and extracted with DCM (2×100 mL). The combined organic phases were dried over Na₂SO₄, filtered, and concentrated to dryness in vacuo to afford E9-4 (1.46 g, 3.14 mmol, 48% yield for 2 steps) as a yellow oil. The crude material was used in the next step without purification. Analytical method 5; $t_R$=0.66 min; $[M+H]^+$=233.9.

Example 7.5: Synthesis of tert-butyl 3-(5-(4-hydroxyphenyl)-1-methyl-1H-imidazol-2-yl)-2,5-dihydro-1H-pyrrole-1-carboxylate (E10-4)

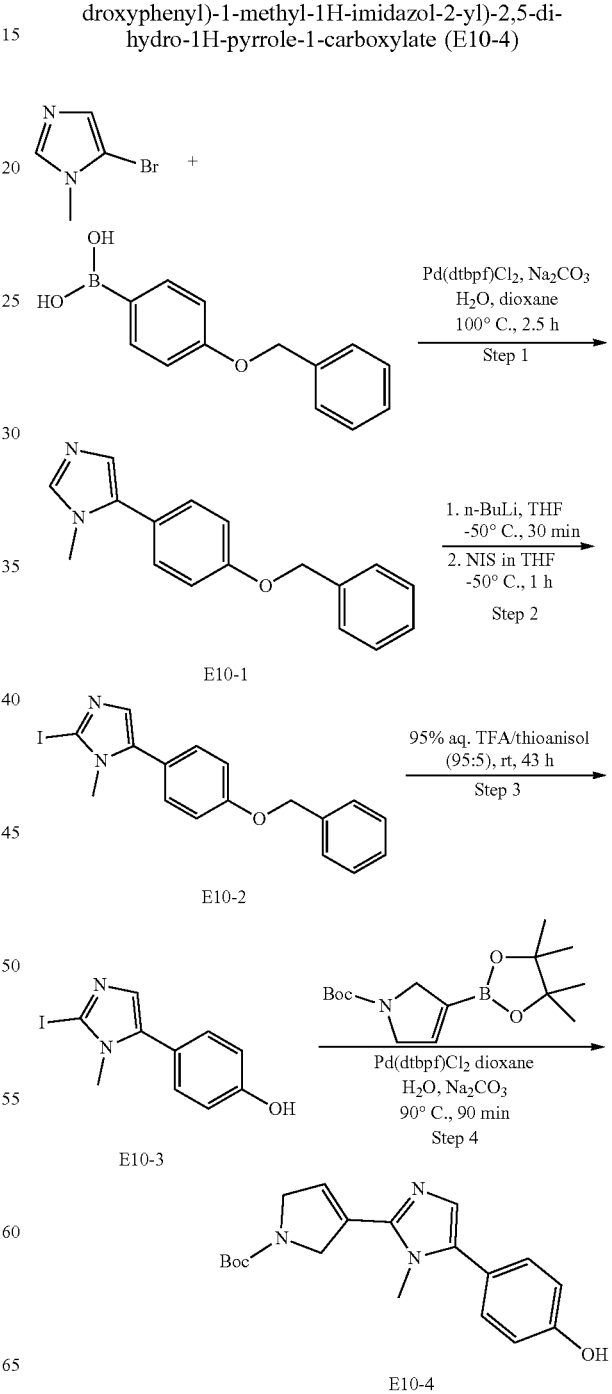

Step 1. 5-(4-(Benzyloxy)phenyl)-1-methyl-1H-imidazole (E10-1)

To (4-(benzyloxy)phenyl)boronic acid (2.281 g, 10.00 mmol), 5-bromo-1-methyl-1H-imidazole (1.610 g, 10.00 mmol) and [1,1'-bis(di-tert-butylphosphino)ferrocene]dichloropalladium(II) (0.326 g, 0.500 mmol) were added dioxane (25 mL) and 1 M aq. $Na_2CO_3$ (25 mL, 25.00 mmol). The resulting mixture was stirred for 2.5 h at 100° C. in an $N_2$-atmosphere, and then partitioned between EtOAc (200 mL) and $H_2O$ (20 mL). The organic phase was washed with 5% aq. $NaHCO_3$ (3×25 mL) and brine, dried over $Na_2SO_4$, filtered, and concentrated to dryness in vacuo. The crude product was purified by flash silica gel chromatography (eluent A: EtOAc/DIEA (98:2); eluent B: EtOAc/MeOH/DIEA (90:10:2)) to afford E10-1 (1.173 g, 4.44 mmol, 44% yield). Analytical method 10; $t_R$=0.75 min; $[M+H]^+$=265.2.

Step 2. 5-(4-(Benzyloxy)phenyl)-2-iodo-1-methyl-1H-imidazole (E10-2)

To E10-1 (538 mg, 2.035 mmol) dissolved in THF (50 mL) cooled to −50° C. and under an $N_2$-atmosphere was added 1.6 M n-BuLi in hexane (1.781 mL, 2.85 mmol) dropwise over 10 min at −50° C. After 20 min stirring at −50° C., additional 1.6 M n-BuLi in hexane (0.509 mL, 0.814 mmol) was added dropwise over 5 min. The brown suspension turned into a red solution. After stirring for 10 min at −50° C., N-iodosuccinimide (641 mg, 2.85 mmol) in THF (5 mL) was added dropwise over 10 min. The reaction mixture was stirred for 1 h at −50° C., and then quenched by addition of $H_2O$ (10 mL). The THF was removed in vacuo and the resulting residue was partitioned between EtOAc (80 mL) and 5% aq. $NaHCO_3$ (10 mL). The organic phase was washed with 5% aq. $NaHCO_3$ (2×5 mL). The combined aqueous phases were washed with EtOAc (2×20 mL). The combined organic phases were washed with brine (15 mL), dried over $Na_2SO_4$, filtered, and concentrated to dryness in vacuo. The crude product was purified by flash silica gel chromatography (eluent A: heptane/DIEA (98:2); eluent B: EtOAc/DIEA (98:2)) to yield E10-2 (372 mg, 0.953 mmol, 47% yield) as a beige solid. Analytical method 10; $t_R$=1.12 min; $[M+H]^+$=391.0.

Step 3. 4-(2-Iodo-1-methyl-1H-imidazol-5-yl)phenol (E10-3)

E10-2 (405.3 mg, 1.039 mmol) was dissolved in 95% aq. TFA/thioanisol (95:5) (20 mL) and the resulting mixture was stirred for 43 h at rt, and then concentrated to dryness in vacuo. The obtained residue was partitioned between EtOAc (70 mL) and 5% aq. $NaHCO_3$ (10 mL). The organic phase was washed with 5% aq. $NaHCO_3$ (3×10 mL) and brine (10 mL), dried over $Na_2SO_4$, filtered, and concentrated to dryness in vacuo. The crude residue was purified by flash silica gel chromatography (eluent A: heptane/DIEA (98:2); eluent 1: EtOAc/DIEA; eluent B2: EtOAc/MeOH/DIEA (90:10:2)) to afford E10-3 (165 mg, 0.55 mmol, 53% yield). Analytical method 10; $t_R$=0.55 min; $[M-H]^-$=299.0.

Step 4. tert-Butyl 3-(5-(4-hydroxyphenyl)-1-methyl-1H-imidazol-2-yl)-2,5-dihydro-1H-pyrrole-1-carboxylate (E10-4)

To E10-3 (450 mg, 1.50 mmol; from several batches), tert-butyl 3-(4,4,5,5-tetramethyl-1,3,2-dioxaborolan-2-yl)-2,5-dihydro-1H-pyrrole-1-carboxylate (531 mg, 1.800 mmol) and [1,1'-bis(di-tert-butylphosphino)ferrocene]-dichloropalladium(II) (48.9 mg, 0.075 mmol) was added dioxane (8 mL) and 1 M aq. $Na_2CO_3$ (4.50 mL, 4.50 mmol). The resulting mixture was stirred under an $N_2$-atmosphere for 90 min at 90° C., and then partitioned between EtOAc (50 mL) and $H_2O$ (10 mL). The organic phase was washed with 5% $NaHCO_3$ (2×10 mL) and brine (10 mL), dried over $Na_2SO_4$, filtered, and concentrated to dryness in vacuo to afford E10-4 (~1.50 mmol) as a brown solid. The crude product was used in the next step without purification. Analytical method 10; $t_R$=0.72 min; $[M+H]^+$=342.2.

Example 7.6: Synthesis of 4-chloro-2-(4-(1-methyl-2-(pyrrolidin-1-ylmethyl)-1H-imidazol-5-yl)phenoxy)-6-(2,2,2-trifluoroethoxy)benzaldehyde (E11)

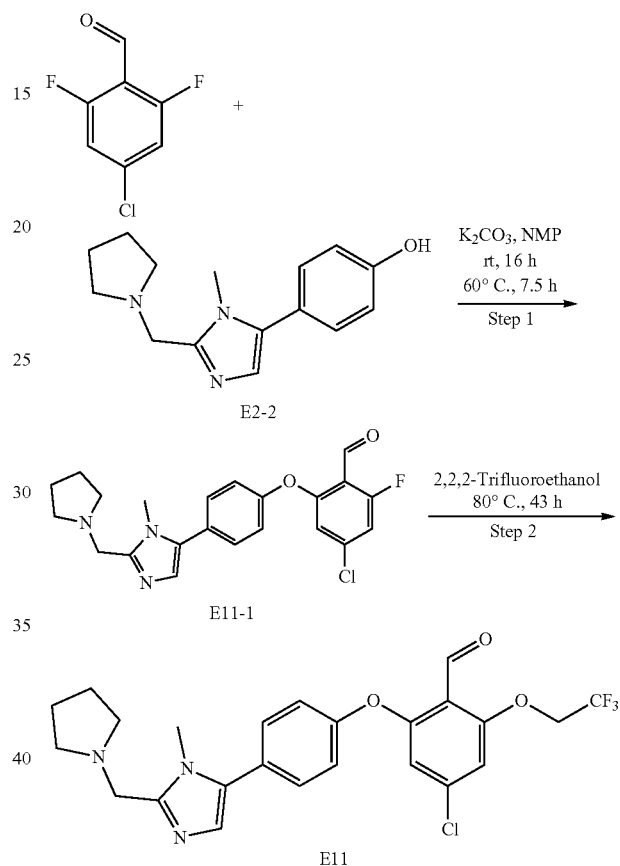

Step 1. 4-Chloro-2-fluoro-6-(4-(1-methyl-2-(pyrrolidin-1-ylmethyl)-1H-imidazol-5-yl)phenoxy)benzaldehyde (E11-1)

To 4-chloro-2,6-difluorobenzaldehyde (88 mg, 0.50 mmol), E2-2 (129 mg, 0.500 mmol) and $K_2CO_3$ (207 mg, 1.500 mmol) was added NMP (2.5 mL) and the resulting suspension was stirred at rt for 16 h, and then at 60° C. for 7.5 h. The solution containing E11-1 was taken onto the next step.

Step 2. 4-Chloro-2-(4-(1-methyl-2-(pyrrolidin-1-ylmethyl)-1H-imidazol-5-yl)phenoxy)-6-(2,2,2-trifluoro-ethoxy)-benzaldehyde (E11)

2,2,2-Trifluoroethanol (0.044 mL, 0.600 mmol) was added to the solution containing E11-1 and the resulting mixture was stirred at 80° C. for 22 h. Additional 2,2,2-trifluoroethanol (0.044 mL, 0.600 mmol) was added and stirring at 80° C. was continued for 21 h. The reaction mixture was partitioned between EtOAc (50 mL) and $H_2O$ (10 mL). The organic phase was washed with 5% aq. $NaHCO_3$ (3×10 mL) and brine, dried over $Na_2SO_4$, filtered, and concentrated to dryness in vacuo. The crude product was purified by flash silica gel chromatography (eluent A: EtOAc/DIEA (98:2); eluent B: EtOAc/MeOH/DIEA (90:10:2)) to afford E11 (165 mg, 0.334 mmol, 67% yield for 2 steps). Analytical method 10; $t_R$=0.87 min; [M+H]$^+$=494.2.

Example 7.7: Synthesis of 2-(4-(2-(azetidin-1-ylmethyl)-1-methyl-1H-imidazol-5-yl)phenoxy)-4-chlorobenzaldehyde (E12)

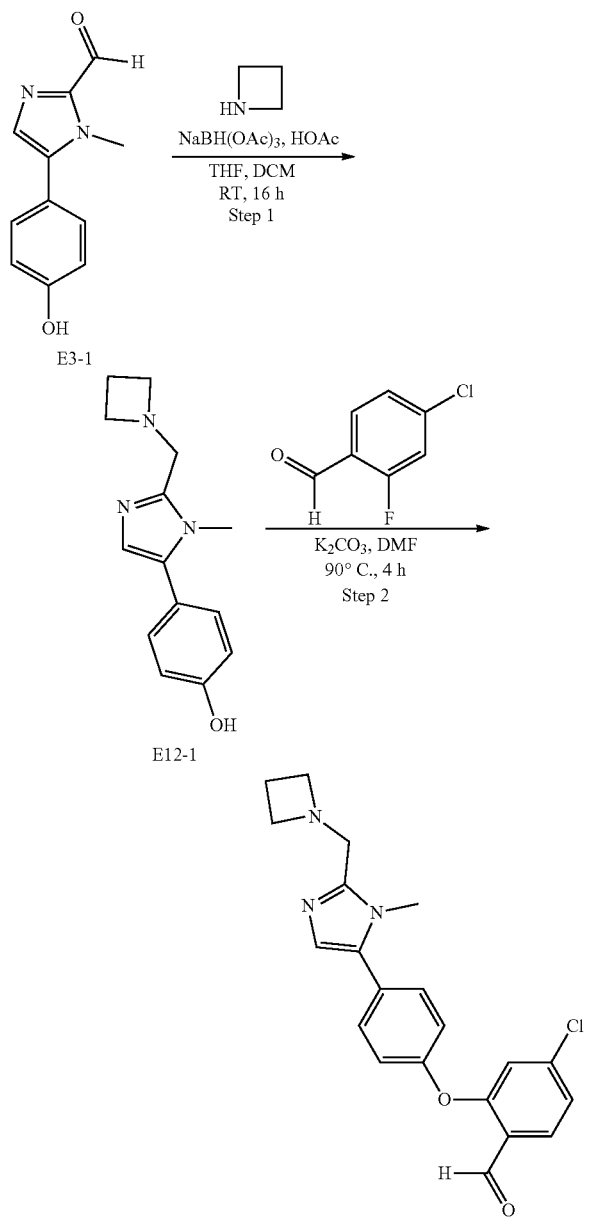

Step 1. 4-(2-(Azetidin-1-ylmethyl)-1-methyl-1H-imidazol-5-yl)phenol (E12-1)

To a solution of E3-1 (500 mg, 2.47 mmol) in THF (25 mL) was added azetidine (0.33 mL, 4.95 mmol) and acetic acid (0.42 mL, 7.42 mmol). The resulting mixture was stirred at RT for 1 h, and then NaBH(OAc)$_3$ (1.15 g, 5.44 mmol) was added in one portion. The reaction mixture was stirred at RT for overnight, quenched with MeOH, and concentrated. The crude product was taken up in 20% IPA in DCM and washed with saturated sodium bicarbonate once. The aqueous phase was then extracted again with 20% IPA in DCM. The combined organic phases were dried over sodium sulfate, filtered, and concentrated to afford E12-1 as a foam after drying (602 mg, quantitative yield). The material was carried to the next step without purification. Analytical method 5: $t_R$=0.77 min; MS [M+H]$^+$=244.2.

Step 2. 2-(4-(2-(Azetidin-1-ylmethyl)-1-methyl-1H-imidazol-5-yl)phenoxy)-4-chlorobenzaldehyde (E12)

Into a round-bottom flask was placed E12-1 (171 mg, 0.70 mmol) and potassium carbonate (486 mg, 3.51 mol) in N,N-dimethylformamide (3.5 mL). The resulting mixture was stirred for 30 min at room temperature and then 4-chloro-2-fluorobenzaldehyde (123 mg, 3.51 mmol) was added. The resulting solution was stirred for 2.5 h at 90° C. using an oil bath, cooled to room temperature, diluted with water, and extracted with EtOAc (3×). The combined organic phases were washed with half saturated NaHCO$_3$ solution and brine, dried over Na$_2$SO$_4$, filtered, and concentrated. The crude residue was purified by flash column chromatography on silica gel eluting with dichloromethane/methanol to give E12 (150 mg, 56%). Analytical method 5: $t_R$=0.99 min [M+H]$^+$=382.2.

Example 7.8: Synthesis of 4-Chloro-2-((6-(2-((dimethylamino)methyl)-1-methyl-1H-imidazol-5-yl)pyridin-3-yl)oxy)benzaldehyde (E14)

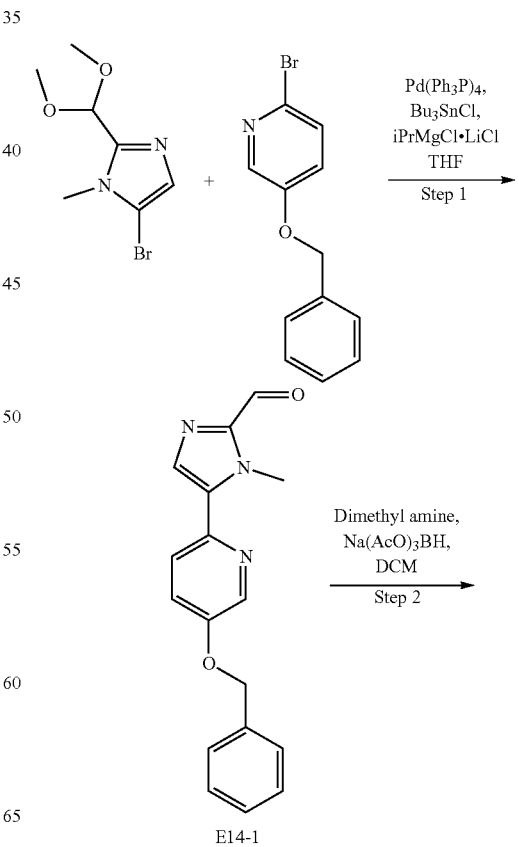

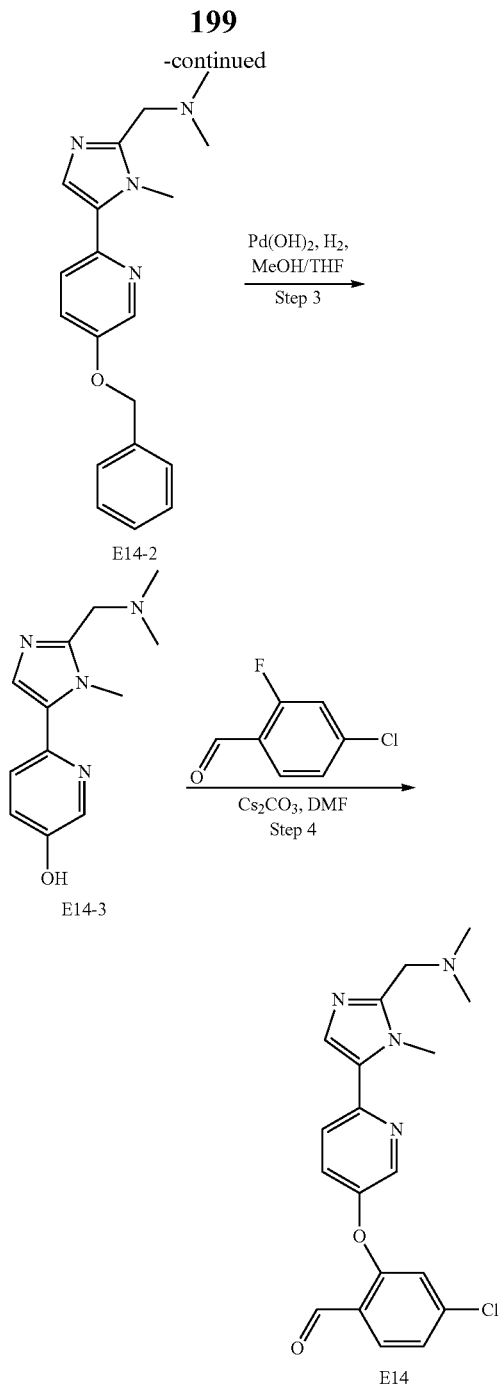

Step 1. 5-(5-(Benzyloxy)pyridin-2-yl)-1-methyl-1H-imidazole-2-carbaldehyde (E14-1)

To a mixture of 5-bromo-2-(dimethoxymethyl)-1-methyl-1H-imidazole (6.2 g, 26.4 mmol) in THF (80 mL) at −78° C. under an atmosphere of nitrogen was added i-PrMgCl—LiCl complex (1.3 M in THF, 24.35 mL, 31.6 mmol) and the resulting mixture was stirred for 15 min at −78° C. (cloudy mixture). Bu$_3$SnCl (8.15 mL, 29.0 mmol) was then added and stirring was continued for 15 min at −78° C. (clear solution) and rt for 1 h (clear solution). 5-(benzyloxy)-2-bromopyridine (8.36 g, 31.6 mmol) and Pd(PPh$_3$)$_4$ (3.05 g, 2.64 mmol) were added and the resulting mixture was diluted with 50 mL dioxane, flushed with nitrogen three times, and refluxed at 105° C. for 2-3 days.

After cooling to rt, the reaction mixture was filtered through Celite®. The filtrate was quenched at 0° C. with 0.5 N HCl (50 mL) and the organic solvent was removed under reduced pressure. EtOAc was added to extract the product. The combined organic phases were washed with water, brine, and dried over Na$_2$SO$_4$, filtered, and concentrated. The crude product was purified by flash column chromatography on silica gel (300 g) eluting with 10% MeOH/DCM. The fractions containing the desired compound were combined and concentrated under reduced pressure. To the residue was added 50 mL THF, 2.5 mL water and 25 mL of 6 N HCl. The resulting mixture was stirred at RT overnight, heated at 80° C. for 6 h, cooled, neutralized with a saturated aqueous solution of NaHCO$_3$, and extracted with EtOAc (300 mL). The combined organic phases were concentrated under reduced pressure. The residue was purified by flash column chromatography (300 g silica gel column, eluting with 50-90% EtOAc/heptane) to afford E14-1 (5.8 g, 95%). $^1$H NMR (400 MHz, DMSO-d$_6$) δ 9.75 (s, 1H), 8.50 (d, J=2.8 Hz, 1H), 7.84 (d, J=8.8 Hz, 1H), 7.72 (s, 1H), 7.62 (dd, J=8.8, 3.0 Hz, 1H), 7.53-7.47 (m, 2H), 7.45-7.39 (m, 2H), 7.39-7.33 (m, 1H), 5.27 (s, 2H), 4.20 (s, 3H).

Step 2. 1-(5-(5-(Benzyloxy)pyridin-2-yl)-1-methyl-1H-imidazol-2-yl)-N,N-dimethylmethanamine (E14-2)

A mixture of E14-1 (4.35 g, 14.83 mmol) and dimethylamine (2 M in THF, 44.5 mL, 89 mmol) in DCM (200 mL) was stirred at room temperature for 1 hour. NaBH(OAc)$_3$ (9.43 g, 44.5 mmol) was then added in several portions and the resulting mixture was stirred at room temperature for 1 hour and then quenched with 0.5 mL AcOH and 1 mL of water. The phases were separated and the organic phase was washed with a saturated solution of NaHCO$_3$ and water, dried over sodium sulfate, filtered, and concentrated. The crude product was purified by flash column chromatography (330 g silica gel column eluting with −20-50% MeOH/DCM) to afford E14-2 (5 g, 99%). $^1$H NMR (400 MHz, DMSO-d$_6$) δ 8.39 (d, J=2.9 Hz, 1H), 7.63 (d, J=8.8 Hz, 1H), 7.54-7.46 (m, 3H), 7.46-7.38 (m, 2H), 7.39-7.30 (m, 1H), 7.21 (s, 1H), 5.22 (s, 2H), 3.87 (s, 3H), 3.48 (s, 2H), 2.16 (s, 6H).

Step 3. 6-(2-((Dimethylamino)methyl)-1-methyl-1H-imidazol-5-yl)pyridin-3-ol (E14-3)

To a solution of 1-(5-(5-(benzyloxy)pyridin-2-yl)-1-methyl-1H-imidazol-2-yl)-N,N-dimethylmethanamine (E14-2, 4.4 g, 13.65 mmol) in MeOH (60 mL) and THF (20 mL) was added Pd(OH)$_2$ (10% on carbon, 0.575 g, 4.09 mmol) and the resulting mixture was flushed with hydrogen three times and stirred under an atmosphere of hydrogen using a balloon for 4 hours.

After complete consumption of starting material was observed by LCMS, the reaction mixture was flushed with nitrogen, filtered through Celite®, and the Celite® pad was washed with MeOH. The filtrate was concentrated and dried under high vacuum to afford E14-3 (2.0 g, −80% purity) and 1.53 g (~85% purity) of 14-3 which was used in the next step without purification; $^1$H NMR (400 MHz, DMSO-d$_6$) δ 10.01 (s, 1H), 8.17 (d, J=2.9 Hz, 1H), 7.49 (d, J=8.2 Hz, 1H), 7.21 (dd, J=8.7, 2.9 Hz, 1H), 7.12 (s, 1H), 3.85 (s, 3H), 3.48 (s, 2H), 2.16 (s, 6H).

Step 4. 4-Chloro-2-((6-(2-((dimethylamino)methyl)-1-methyl-1H-imidazol-5-yl)pyridin-3-yl)oxy)benzaldehyde (E14)

A flask containing E14-3 (1 g, 4.31 mmol), 4-chloro-2-fluorobenzaldehyde (0.887 g, 5.60 mmol) and Cs$_2$CO$_3$ (1.824 g, 5.60 mmol), DMF (5 mL) was flushed with nitrogen three times and heated at 60° C. for 16 h. Once complete consumption of starting material and formation of product (LCMS showed product at t$_R$=0.92 min) was observed, the reaction mixture was filtered and concentrated to afford a crude oil. The crude product was purified by reverse phase flash column (eluting 5-80% water/ACN with 0.1% NH$_4$OH). The fractions containing the desired product were combined and concentrated under vacuum. A saturated solution of NaHCO$_3$ (50 mL) was added and the resulting mixture was extracted with EtOAc (2×100 mL). The combined organic phases were washed with a saturated aqueous solution of NaHCO$_3$ (2×50 mL), water, brine, dried over Na$_2$SO$_4$, filtered, and concentrated under reduced pressure to afford the product E14 (1.04 g, 2.80 mmol, 65%). $^1$H NMR (400 MHz, DMSO-d$_6$) δ 10.36 (s, 1H), 8.55 (d, J=2.9 Hz, 1H), 7.89 (d, J=8.4 Hz, 1H), 7.80 (d, J=8.2 Hz, 1H), 7.70 (dd, J=8.8, 2.9 Hz, 1H), 7.42 (dd, J=8.3, 1.9 Hz, 1H), 7.38 (s, 1H), 7.16 (d, J=1.9 Hz, 1H), 3.94 (s, 3H), 3.51 (s, 2H), 2.17 (s, 6H).

Example 7.9: Synthesis of 2-(4-(2-((Dimethylamino)methyl)-1-methyl-1H-imidazol-5-yl)phenoxy)-4-ethylbenzaldehyde (E15)

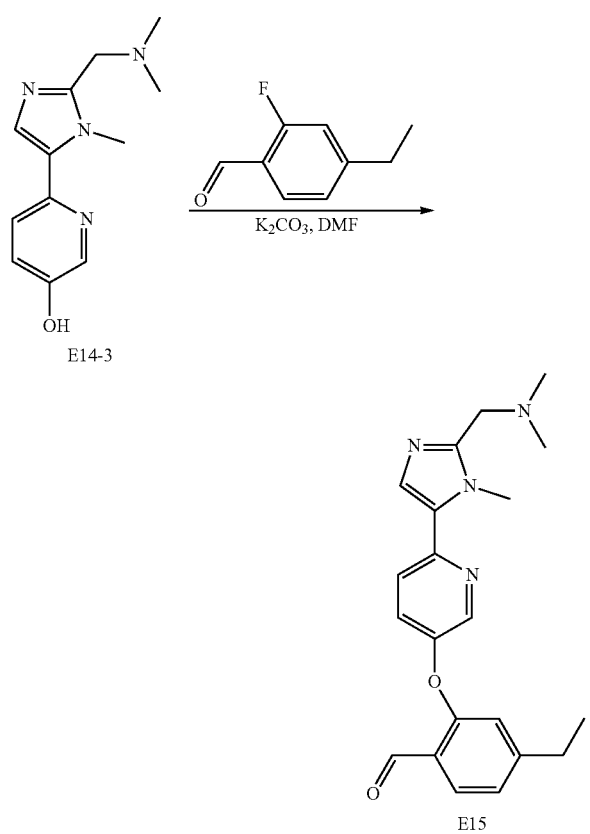

To a mixture of E14-3 (456 mg, 1.972 mmol) and 4-ethyl-2-fluorobenzaldehyde (300 mg, 1.972 mmol) in anhydrous DMF (5 mL) was added K$_2$CO$_3$ (2180 mg, 15.77 mmol). The resulting mixture was heated and stirred at 90° C. under an atmosphere of nitrogen for >5 h or longer to allow the reaction to go to completion. The reaction mixture was cooled to room temperature, diluted with 15 mL of water, and extracted with 2×15 mL of EtOAc. The combined organic phases were washed with 3×10 mL of water, and 2×15 mL of a 1.0 N solution of aqueous HCl. The aqueous phases were combined and basified with 1 M K$_2$CO$_3$ solution to afford a cloudy mixture. The aqueous phase was then extracted with 2×20 mL of EtOAc, dried over sodium sulfate, filtered, and concentrated. The crude product was purified by flash column chromatography on silica gel (330 g column, eluting with 10% MeOH/DCM) to afford E15 as yellow oil (300 mg, 41.9%).

Example 7.10: Synthesis of tert-Butyl ((5-(4-(5-chloro-3-fluoro-2-formylphenoxy)phenyl)-1-methyl-1H-imidazol-2-yl)methyl)carbamate (E17)

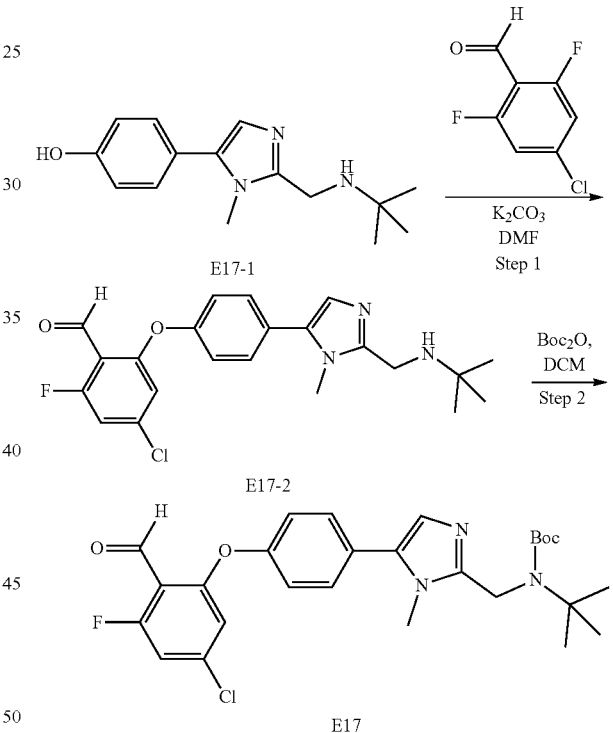

4-(2-((tert-Butylamino)methyl)-1-methyl-1H-imidazol-5-yl)phenol (E17-1) was prepared according to the procedure described in Example 7.7, Step 1 for Building block E12 starting from the corresponding aldehyde and tert-butylamine.

Step 1. 2-(4-(2-((tert-Butylamino)methyl)-1-methyl-1H-imidazol-5-yl)phenoxy)-4-chloro-6-fluorobenzaldehyde (E17-2)

The title compound E17-2 was prepared according to the procedure described in Example 7.7, Step 2 for Building block E12 starting from 4-(2-((tert-Butylamino)methyl)-1-methyl-1H-imidazol-5-yl)phenol (E17-1) and 1.2 eq of 4-chloro-2,6-difluorobenzaldehyde.

Step 2. tert-Butyl((5-(4-(5-chloro-3-fluoro-2-formylphenoxy)phenyl)-1-methyl-1H-imidazol-2-yl)methyl)carbamate (E17)

To a solution of E17-2 (1.27 g, 3.05 mmol) in DCM (20 mL) was added Boc₂O (1 g, 4.58 mmol) in one portion. The resulting mixture was stirred at RT overnight, and then another 0.5 eq of Boc₂O was added to ensure complete conversion of starting material to product. The reaction mixture was then quenched with water and extracted twice with DCM. The organic phase was dried over sodium sulfate, filtered, and concentrated to afford E17 as a light yellow foam (1.5 g, 95%). The crude product was of sufficient purity to be used in the next step without purification.

Example 7.11: Synthesis of 4-Chloro-2-(4-(4-((dimethylamino)methyl)-5-methyl-1H-imidazol-1-yl)phenoxy)benzaldehyde (E19)

Step 1. 1-(1-(4-(Benzyloxy)phenyl)-5-methyl-1H-imidazol-4-yl)-N,N-dimethylmethanamine E19-2

The title compound E19-2 was prepared according to the procedure described in Example 7.7, Step 2 for Building block E12 starting from E19-1 and using THF as the solvent.

Step 2. 4-(4-((Dimethylamino)methyl)-5-methyl-1H-imidazol-1-yl)phenol B11-3

To a round bottom flask containing E19-2 (1.45 g, 4.51 mmol) and THF (12 mL) and MeOH (12 mL) was added Pearlman catalyst (Pd(OH)₂, 290 mg, 2.07 mmol) and the resulting mixture was stirred under an atmosphere of hydrogen for 3 h. The reaction mixture was the flushed with nitrogen, filtered through a pad of Celite®, and concentrated to afford E19-3 after drying (1.02 g, 98%). The product was of sufficient purity to be carried to the next step without purification.

Step 3. 4-Chloro-2-(4-(4-((dimethylamino)methyl)-5-methyl-1H-imidazol-1-yl)phenoxy)benzaldehyde (E19)

The title compound E19 was prepared according to the procedure described in Example 7.7, Step 2 for Building block E12 starting from E19-3.

Example 7.12: Synthesis of 1-(4-(Benzyloxy)phenyl)-5-methyl-1H-imidazole-4-carbaldehyde, (E19-1)

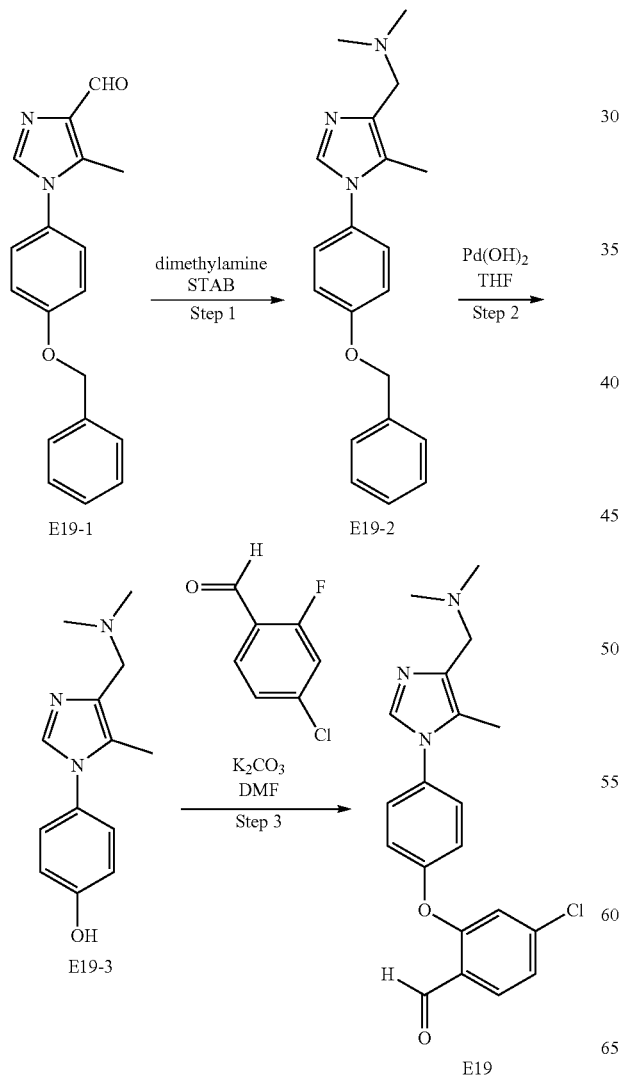

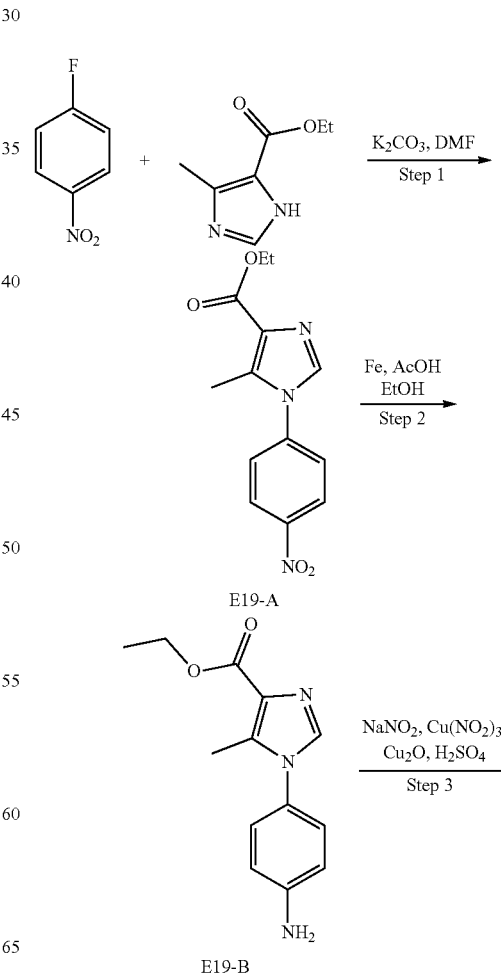

-continued

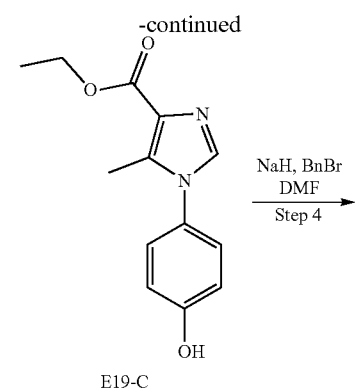

E19-C

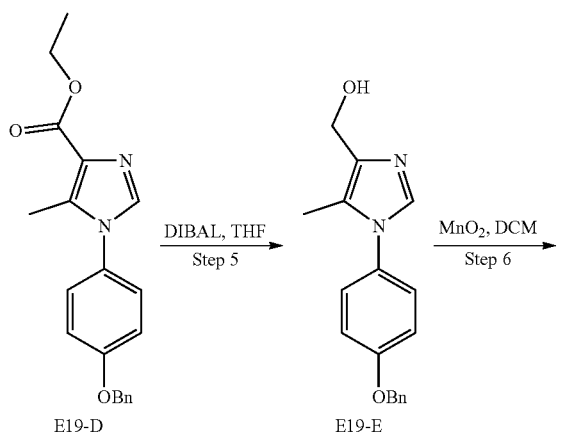

E19-D    E19-E

![E19-1 structure]

E19-1

Step 1. Ethyl 5-methyl-1-(4-nitrophenyl)-1H-imidazole-4-carboxylate (E19-A)

To a round bottom flask containing 1-fluoro-4-nitrobenzene (100 g, 0.71 mol) and ethyl 4-methyl-1H-imidazole-5-carboxylate (101 g, 0.71 mol) in DMF (800 mL) was added potassium carbonate (392 g, 2.84 mmol) and the resulting mixture was heated to 100° C. and stirred for 4 h. The reaction mixture was then cooled to RT and poured into an ice bath to afford a slurry. The mixture was filtered and the filter cake dried under high vacuum to afford E19-A as a pale yellow solid (170 g, 87%). $^1$H NMR (400 MHz, DMSO-d$_6$): δ 8.42 (d, J=6.8 Hz, 2H), 8.01 (s, 1H), 7.83 (d, J=6.8 Hz, 2H), 4.27 (q, J=7.2 Hz, 2H), 2.47 (s, 3H), 1.30 (t, J=7.2 Hz, 2H).

Step 2. Ethyl 1-(4-aminophenyl)-5-methyl-1H-imidazole-4-carboxylate (E19-B)

To a cooled mixture of B19-A (85 g, 0.31 mol) in ethanol (700 mL) and in an ice bath was added acetic acid (200 mL) followed by iron powder (69 g, 1.24 mol). The ice bath was then removed and the resulting mixture was heated to 100° C. for 1 h and then allowed to cool to room temperature. The reaction mixture was concentrated under reduced pressure and partitioned between DCM and water. The organic phase was dried over Na$_2$SO$_4$, filtered, and concentrated under reduced pressure to afford E19-B as a gummy material (55 g, 73%) which was used in the next step without purification. $^1$H NMR (400 MHz, CDCl$_3$): δ 7.56 (s, 1H), 7.02 (d, J=8.0 Hz, 2H), 6.75 (d, J=8.4 Hz, 2H), 6.20 (bs, 2H), 4.38 (q, J=7.2 Hz, 2H), 2.41 (s, 3H), 1.41 (t, J=7.2 Hz, 2H).

Step 3. Ethyl 1-(4-hydroxyphenyl)-5-methyl-1H-imidazole-4-carboxylate (E19-C)

To a cooled mixture of E19-B (25 g, 0.10 mol) in water (2 L) and in an ice bath was added sulfuric acid (35%, 100 mL). The resulting mixture was stirred for 10 min before NaNO$_2$ (14 g, 0.23 mol) was added. The reaction mixture was stirred at 0° C. for another 10 min and urea (6.13 g, 0.10 mol) was added. The mixture was then allowed to warm to RT and an aqueous solution of Cu(NO$_3$)$_2$ (370 g, 1.53 mol, 0.5M) was added, followed by solid Cu$_2$O (7.3 g, 0.05 mol). The resulting mixture was stirred at RT for 3 h and then quenched with aqueous ammonia and repeatedly extracted with 10% methanol in DCM. The combined organic phases were dried over Na$_2$SO$_4$, filtered, and concentrated under reduced pressure to afford E19-C as an off-white solid (16 g, 64%). The crude compound was used in next step without further purification.

Step 4. Ethyl 1-(4-(benzyloxy)phenyl)-5-methyl-1H-imidazole-4-carboxylate (E19-D)

To an ice-cold suspension of NaH (2.85 g, 71.4 mmol) in DMF (75 mL) was added a solution of E19-C (16 g, 65 mmol) in DMF (75 mL) and the resulting mixture was allowed to warm to RT and then stirred for 1 h before benzyl bromide (13.3 g, 78 mmol) was added. The reaction mixture was stirred at RT for >2 h, quenched with ice-cold water, and extracted twice with EtOAc. The organic phase was dried over Na$_2$SO$_4$, filtered, and concentrated under reduced pressure. The crude product was purified by flash column chromatography (eluting with 40% EtOAc in ether) to afford E19-D as a pale yellow solid (8 g, 37%). $^1$H NMR (400 MHz, CDCl$_3$): δ 7.50 (s, 1H), 7.48-7.36 (m, 5H), 7.18 (d, J=8.8 Hz, 2H), 7.08 (d, J=8.8 Hz, 2H), 5.12 (s, 2H), 4.39 (q, J=7.2 Hz, 2H), 2.43 (s, 3H), 1.42 (t, J=7.2 Hz, 2H).

Step 5. (1-(4-(Benzyloxy)phenyl)-5-methyl-1H-imidazol-4-yl)methanol (E19-E)

To a cooled solution of B19-D (10 g, 30 mmol) in THF (150 mL) and in an ice bath was added DIBAL-H (1M in toluene, 98 mL, 98 mmol) and the resulting mixture was stirred in an ice bath for 2 h and then quenched with water (21 mL) and 15% aqueous solution of NaOH (6 mL). The reaction mixture was then warmed to RT gradually, stirred for 15 min, filtered, and the filtrate was concentrated under reduced pressure to afford E19-E as an off-white solid after drying (8 g, 91%). $^1$H NMR (400 MHz, DMSO-$d_6$): δ 7.59 (s, 1H), 7.48 (d, J=6.8 Hz, 2H), 7.41 (t, J=7.2 Hz, 2H), 7.36-7.30 (m, 3H), 7.14 (dd, J, =2.0 Hz, $J_2$=6.8 Hz, 2H), 5.17 (s, 2H), 4.70 (t, J=5.6 Hz, 1H), 4.34 (d, J=5.6 Hz, 1H), 2.09 (s, 3H).

Step 6. 1-(4-(Benzyloxy)phenyl)-5-methyl-1H-imidazole-4-carbaldehyde (E19-1)

To a solution of oxalyl chloride (4.7 mL, 54 mmol) in CH$_2$Cl$_2$ (80 mL) cooled to −78° C. was added DMSO (7.7 mL, 108 mmol) dropwise. The resulting mixture was stirred at −78° C. for 10 min. before a solution of E19-E (8 g, 27 mmol) in CH$_2$Cl$_2$ (60 mL) was added dropwise. The reaction mixture was stirred at −78° C. for 10 min and then Et$_3$N (23 mL, 162 mmol) was added dropwise. The reaction mixture was allowed to warm to RT, stirred for >3 h, diluted with water, and extracted with DCM twice. The combined organic phases were dried over Na$_2$SO$_4$, filtered, and concentrated under reduced pressure to afford a crude product. The crude material was purified using a Grace prep HPLC system (eluting with 0-100% petroleum ether/EtOAc) to afford E19-1 as an off-white solid after concentrating the pure fractions under reduced pressure (4 g, 50%). $^1$H NMR (400 MHz, CDCl$_3$): δ 9.88 (s, 1H), 7.92 (s, 1H), 7.49-7.35 (m, 7H), 7.19 (d, J=6.8 Hz, 2H), 5.19 (s, 2H), 2.39 (s, 3H).

Example 7.13: Synthesis of 4-Chloro-2-(4-(2-((dimethylamino)methyl)-1-methyl-1H-imidazol-5-yl)phenoxy)-6-(2,2,2-trifluoroethoxy)benzaldehyde (E22)

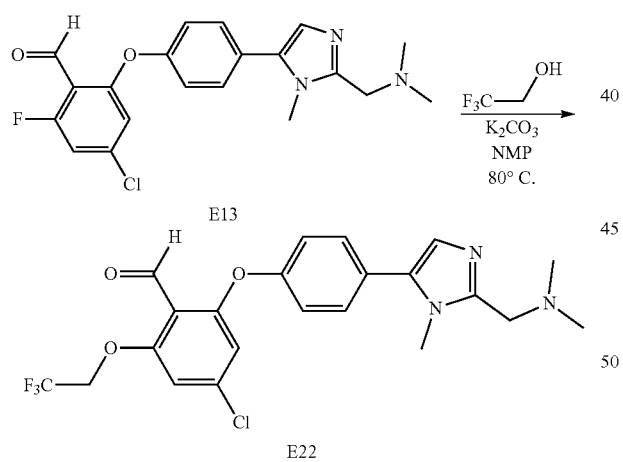

To a mixture of E13 ((1.64 g, 3.81 mmol) and potassium carbonate (2.63 g, 19.03 mmol) in NMP (10 mL) was added 2,2,2-trifluoroethanol (1.25 mL, 17.29 mmol) in one portion. The reaction was heated to 80° C. under an N$_2$ atmosphere overnight, cooled to RT and diluted with EtOAc (150 mL). The organic phase was washed with H$_2$O (1×100 mL, 1×75 mL), saturated aqueous NaHCO$_3$ (50 mL), and brine (50 mL), dried with Na$_2$SO$_4$, filtered, and concentrated in vacuo to provide a dark orange oil. The crude oil was purified by flash column (eluting with 10% MeOH: 90% DCM with 1% TEA) to afford E22 as a tan oil after concentrating the pure fractions (1.02 g, 1.96 mmol, 51.6%).

Example 7.14: Synthesis of 4-Chloro-2-(4-(2-((dimethylamino)methyl)-1-methyl-1H-imidazol-5-yl)-3-fluorophenoxy)benzaldehyde (E23)

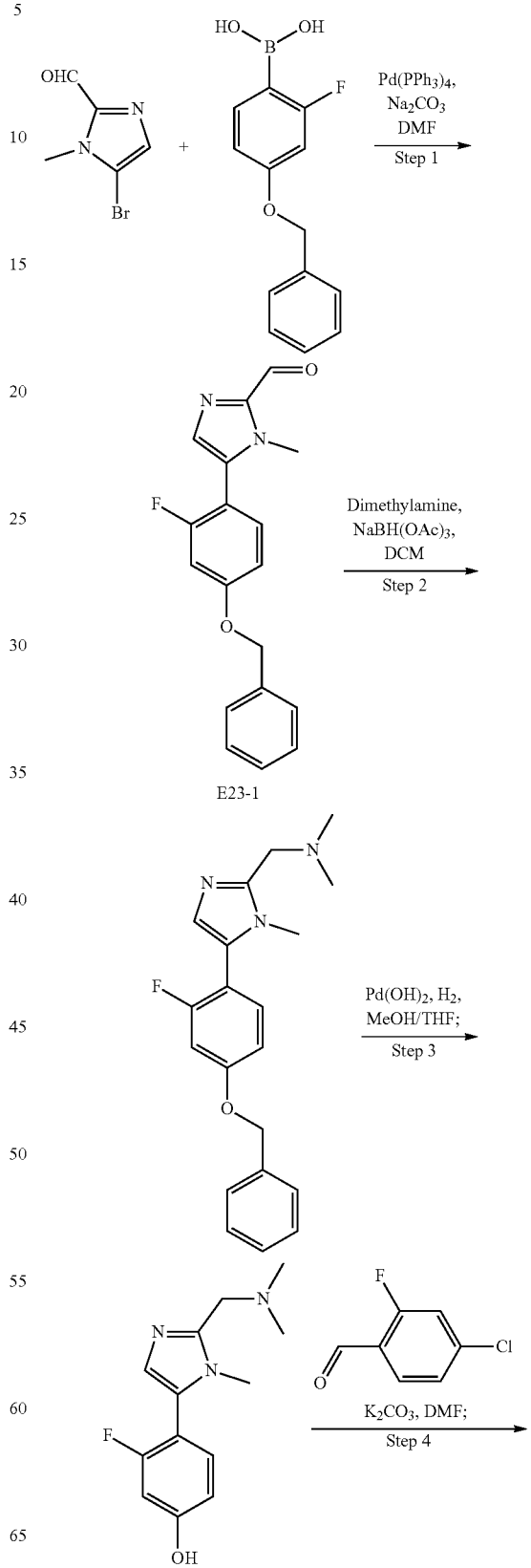

209
-continued

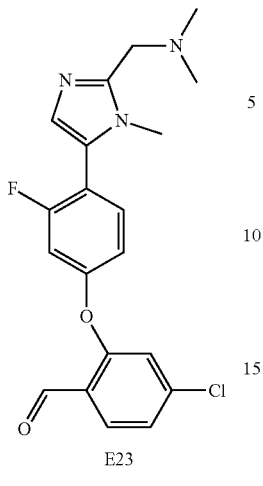

E23

Step 1. 5-(4-(Benzyloxy)-2-fluorophenyl)-1-methyl-1H-imidazole-2-carbaldehyde (E23-1)

The title compound E23-1 was prepared according to the procedure described in Example 7.7, Step 1 for Building block E12 starting from 5-bromo-1-methyl-1H-imidazole-2-carbaldehyde and (4-(benzyloxy)-2-fluorophenyl)boronic acid.

Step 2 to 4. 4-Chloro-2-(4-(2-((dimethylamino)methyl)-1-methyl-1H-imidazol-5-yl)-3-fluorophenoxy)benzaldehyde (E23)

The title compound was prepared according to the procedure described in Example 7.8, Steps 2 to 4 for Building block B14 starting from E23-1.

Example 7.15: Synthesis of 4-Chloro-2-(4-(5-((dimethylamino)methyl)-4-methyl-4H-1,2,4-triazol-3-yl)phenoxy)benzaldehyde (E26)

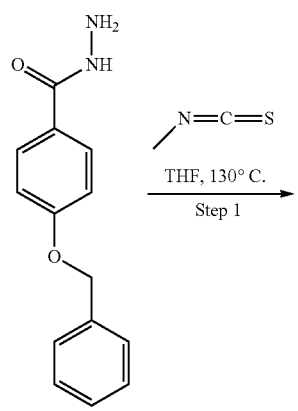

$\xrightarrow{\underset{\text{Step 1}}{\text{THF, 130° C.}}}$ with N=C=S reagent 210
-continued

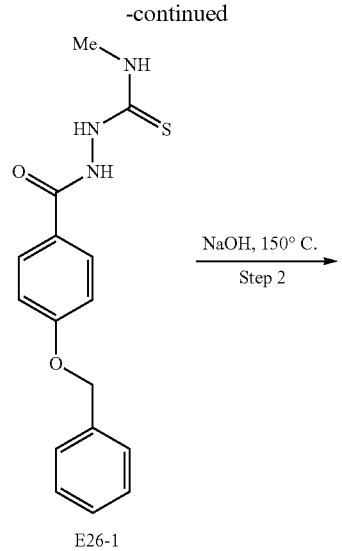

E26-1

$\xrightarrow{\underset{\text{Step 2}}{\text{NaOH, 150° C.}}}$

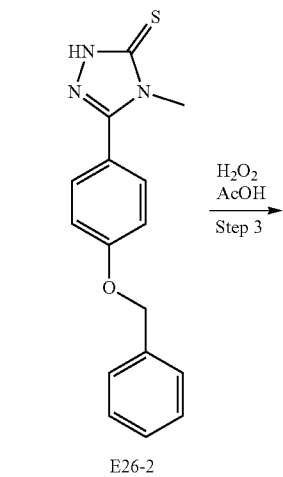

E26-2

$\xrightarrow{\underset{\text{Step 3}}{\substack{\text{H}_2\text{O}_2 \\ \text{AcOH}}}}$

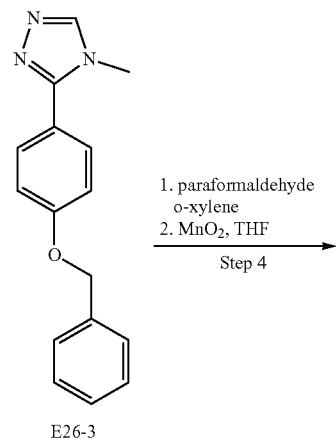

E26-3

$\xrightarrow{\underset{\text{Step 4}}{\substack{\text{1. paraformaldehyde} \\ \text{o-xylene} \\ \text{2. MnO}_2, \text{THF}}}}$

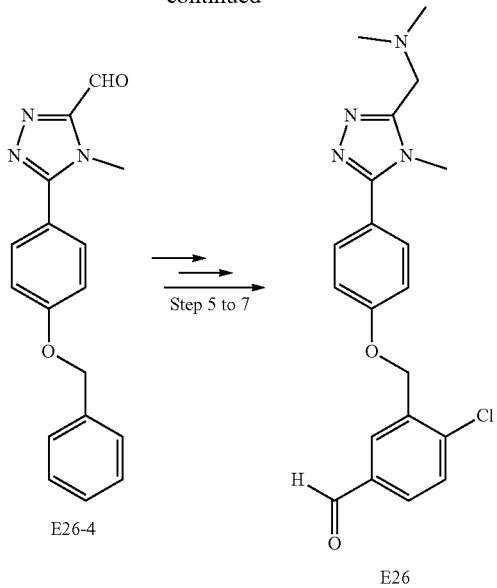

Step 1. 2-(4-(Benzyloxy)benzoyl)N-methylhydrazinecarbothioamide (E26-1)

To a microwave vial containing 4-(benzyloxy)benzohydrazide (556 mg, 2.30 mmol) was added THF and isothiocyanatomethane (185 mg, 2.52 mmol). The resulting mixture was heated gently with heat gun to afford a clear liquid, before being heated to 130° C. in a microwave for 10 min. The resulting white slurry was cooled to RT, filtered, and washed with EtOAc to afford E26-1 as a white solid after drying (656 mg, 91%). The product was carried to the next step without purification.

Step 2. 5-(4-(Benzyloxy)phenyl)-4-methyl-2,4-dihydro-3H-1,2,4-triazole-3-thione (E26-2)

To a microwave vial containing E26-1 (656 mg, 2.08 mmol) was added a solution of NaOH (2 M, 9.26 mL, 18.51 mmol). The resulting mixture was capped, heated to 150° C. in the microwave for 5 min, cooled to RT, neutralized with AcOH, and extracted three times with EtOAc. The combined organic phases washed with brine, dried over sodium sulfate, filtered, and concentrated to afford E26-2 as a crude product (600 mg, 97%). The product was carried to the next step without purification.

Step 3. 3-(4-(Benzyloxy)phenyl)-4-methyl-4H-1,2,4-triazole (E26-3)

To a cooled mixture of E26-2 (600 mg, 2.02 mmol) in DCM (4 mL) and in an ice bath was added a solution of hydrogen peroxide (35%, 0.393 mL, 4.48 mmol) and acetic acid (3 mL, 52.5 mmol) dropwise. The resulting mixture was then warmed to RT and stirred overnight. The reaction Mixture was cooled using an ice bath and NaOH (2 M) was added dropwise until the pH was ~10 to afford a biphasic layer. The separated aqueous phase was extracted twice with DCM The combined organic phases were dried over sodium sulfate, filtered, and concentrated. The crude product was purified by flash column chromatography (eluting with 0-10% DCM/MeOH) to afford E26-3 after concentrating the pure fractions (433 mg, 81%).

Step 4. 5-(4-(Benzyloxy)phenyl)-4-methyl-4H-1,2,4-triazole-3-carbaldehyde (E26-4)

Step 4-1: To a mixture of E26-3 (433 mg, 1.63 mmol) in o-xylene (2 mL) was added paraformaldehyde (250 mg, 8.32 mmol) at RT. The reaction mixture was heated to 125° C. for 3 h. The resulting slurry was cooled to RT, taken up in DCM, filtered through a pad of Celite® and the filtrate was concentrated. The crude product was triturated with MeOH, filtered, and dried to afford the alcohol intermediate as a white solid (447 mg, 93%).

Step 4-2. To a mixture of the alcohol from Step 4-1 (447 mg, 1.51 mmol) in THF (6 mL) was added manganese dioxide (1.49 g, 171 mmol) at RT. The resulting mixture was stirred at RT overnight before being filtered through a pad of Celite® and the filtrate was concentrated to dryness. The crude product was purified by flash column chromatography (eluting with 0-60% DCM/ACN) to afford E26-4 after concentrating the pure fractions (98 mg, 20%) under reduced pressure.

Step 5 to 7. 4-Chloro-2-(4-(5-((dimethylamino)methyl)-4-methyl-4H-1,2,4-triazol-3-yl)phenoxy)benzaldehyde (E26)

The title compound E26 was prepared according to the procedure described in Example 7.8, Steps 2 to 4 for Building block B14 from E26-4.

Example 7.16: Synthesis of tert-Butyl 3-(5-(4-(5-chloro-2-formylphenoxy)phenyl)-1-methyl-1H-imidazol-2-yl)azetidine-1-carboxylate (E27)

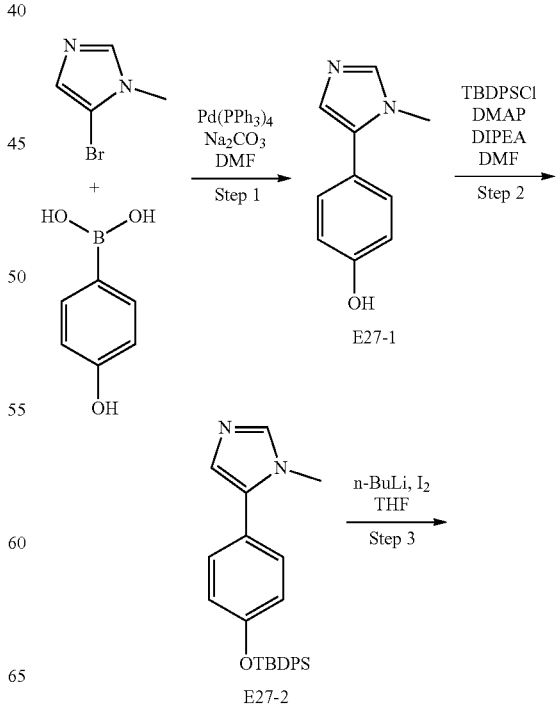

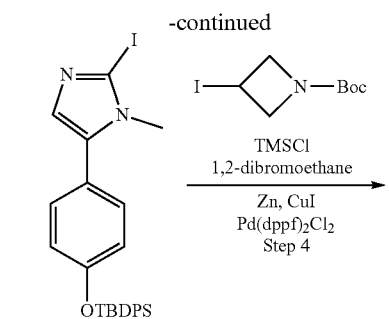

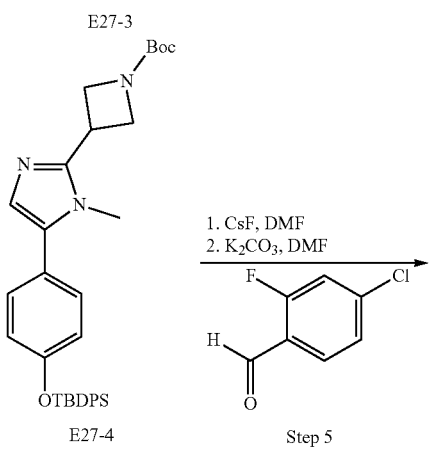

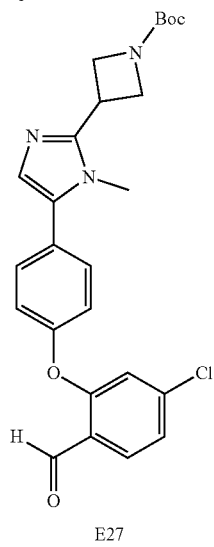

Step 1. 4-(1-Methyl-1H-imidazol-5-yl)phenol (E27-1)

The title compound E27-1 was prepared according to the procedure described in Example 7.7, Step 1 for Building block E12 starting from (4-hydroxyphenyl)boronic acid and 5-bromo-1-methyl-1H-imidazole.

Step 2. 5-(4-((tert-Butyldiphenylsilyl)oxy)phenyl)-1-methyl-1H-imidazole (E27-2)

To a solution of E27-1 (3 g, 17.22 mmol) in DMF (34.4 mL) was added DMAP (0.526 g, 4.31 mmol) and Hunig's base (DIPEA, 9.02 mL, 51.7 mmol), followed by tert-butyldiphenylsilyl chloride (5.31 mL, 20.67 mmol). The resulting mixture was stirred overnight and then diluted with EtOAc and half-saturated sodium bicarbonate solution, and the aqueous phase was extracted with EtOAc (2×). The combined organic phases were washed with half-saturated aqueous solution of sodium bicarbonate solution (2×), water (2×), and brine, dried over sodium sulfate, filtered, and concentrated. The crude product was purified by flash column chromatography on silica gel (eluting impurities first with 100% acetone, then 0-10% MeOH in DCM/MeOH) to provide E27-2 (2 g, 4.85 mmol, 28.1%) after concentrating the pure fractions under reduced pressure.

Step 3. 5-(4-((tert-Butyldiphenylsilyl)oxy)phenyl)-2-iodo-1-methyl-1H-imidazole (E27-3)

To a solution of E27-2 (1.85 g, 4.48 mmol) in THF (44.8 mL) was added n-butyllithium (2.152 mL, 5.38 mmol) dropwise at 0° C. to afford a dark mixture. After stirring for 30 min at 0° C., the reaction mixture was cooled to −78° C. and iodine (1.423 g, 5.60 mmol) in THF (5 mL) was added dropwise. The resulting mixture was stirred at −78° C. for 1 h, quenched by addition of water, and concentrated to remove the bulk of the THF. EtOAc was added. The organic phase was washed with aqueous sodium thiosulfate and brine, dried over sodium sulfate, filtered, and concentrated. Purification by flash column chromatography on silica gel (eluting with 0-100% EtOAc/heptane) provided E27-3 (1.98 g, 3.68 mmol, 82%)

Step 4. tert-Butyl 3-(5-(4-((tert-butyldiphenylsilyl)oxy)phenyl)-1-methyl-1H-imidazol-2-yl)azetidine-1-carboxylate E27-4

To a suspension of zinc powder (1.821 g, 27.9 mmol) in DMA (8 mL) was added TMSCl (0.237 mL, 1.857 mmol) and 1,2-dibromoethane (0.160 mL, 1.857 mmol) and the resulting mixture stirred for 15 min. tert-Butyl 3-iodoazetidine-1-carboxylate (2.58 mL, 14.86 mmol) was then added dropwise as a solution in DMA (4 mL) and the reaction mixture heated to 35° C. with stirring for 1 h. To a mixture of E27-3 (1 g, 1.857 mmol), Pd(dppf)$_2$ (0.152 g, 0.186 mmol), and copper(I) iodide (0.071 g, 0.371 mmol) in DMA (8 mL) under an atmosphere of nitrogen was added to the zincate mixture and the resulting mixture was stirred at 85° C. for 2 h and then at room temp overnight. The reaction mixture was partitioned between EtOAc and H$_2$O. The organic phase was washed with H$_2$O (×3), and the combined aqueous phases were extracted with EtOAc. The combined organic phases were washed with brine, then dried (Na$_2$SO$_4$), filtered, and concentrated in vacuo. The crude product was purified by flash column chromatography on silica gel (eluting with DCM/MeOH, 0-10%) to afford the desired product containing some impurities. The material purified again by flash column chromatography (silica gel column; Heptane/EtOAc 0-100%) to afford E27-4 after concentrating the pure fractions (220 mg, 0.387 mmol, 20.9%).

Step 5. tert-Butyl 3-(5-(4-(5-chloro-2-formylphenoxy)phenyl)-1-methyl-1H-imidazol-2-yl)azetidine-1-carboxylate (E27)

To a mixture of E27-4 (137 mg, 0.241 mmol) and 4-chloro-2-fluorobenzaldehyde (42 mg, 0.265 mmol) in DMF (2.4 mL) was added cesium fluoride (55 mg, 0.362 mmol) and potassium carbonate (50 mg, 0.362 mmol) at RT. The resulting mixture was then heated to 90° C. overnight, cooled to RT, and filtered. The filtrate was taken up in EtOAc and washed with a saturated solution of sodium bicarbonate (×2) and brine, dried over sodium sulfate, filtered, and concentrated. The crude product was combined with another batch of material (total 0.417 mmol) and purified by flash column chromatography on silica gel (eluting with 0-60%

DCM/ACN) to afford E27 after concentrating the pure fractions under reduced pressure (110 mg, 56%).

Example 7.17: Synthesis of 2,4-Difluoro-6-(4-(1-methyl-2-(pyrrolidin-1-ylmethyl)-1H-imidazol-5-yl)phenoxy)benzaldehyde (E29)

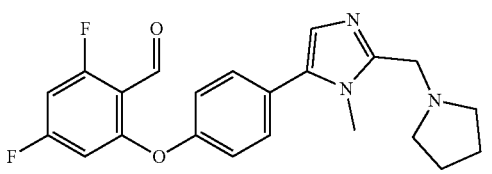

E29

The title compound E29 was prepared according to the procedure described in Example 7.7, Step 2 for Building block E12 starting from the corresponding phenol and 2 equivalents of 2,4,6-trifluorobenzaldehyde. After workup and purification, E29 was isolated as 1:1 mixture of regioisomers containing both the desired product E29 and 2,6-difluoro-4-(4-(1-methyl-2-(pyrrolidin-1-ylmethyl)-1H-imidazol-5-yl)phenoxy)benzaldehyde.

Example 7.18: Synthesis of 4-Chloro-2-(4-(2-((dimethylamino)methyl)-1-ethyl-1H-imidazol-5-yl)phenoxy)-6-fluorobenzaldehyde (E31)

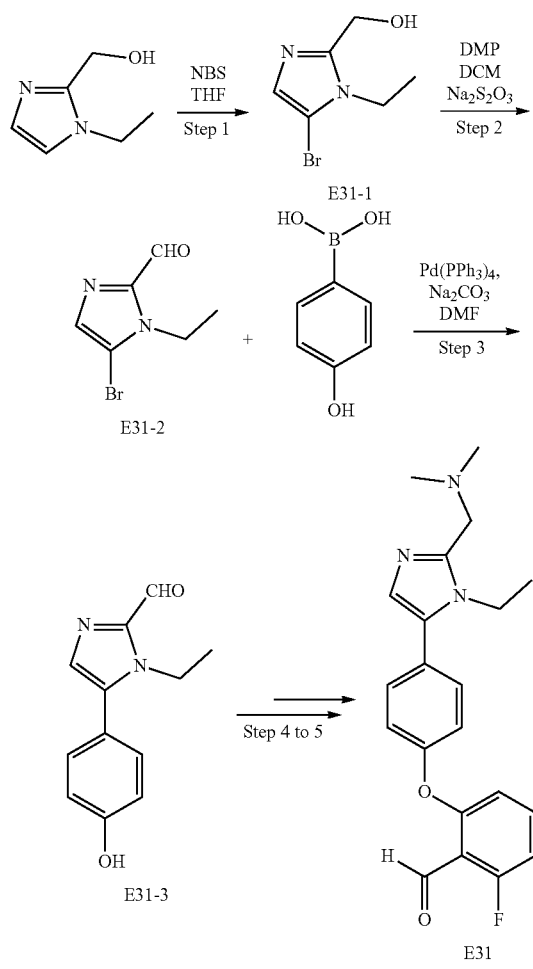

Step 1. (5-Bromo-1-ethyl-1H-imidazol-2-yl)methanol E31-1)

To a mixture of (1-ethyl-1H-imidazol-2-yl)methanol (4 g, 31.7 mmol) in THF (85 mL) was cooled to −20° C. (dry ice in 30% MeOH in water) was added NBS (5.44 g, 30.6 mmol) portion wise over 30 min and the resulting mixture was stirred at −20° C. and slowly warmed to 0 to 5° C. over 4.5 h. The cooling bath was removed. The reaction mixture was stirred at RT overnight and quenched with 60 mL saturated aq. sodium bicarbonate at RT and stirring was continued for 30 min. The mixture was concentrated to remove most of the THF and then extracted with EtOAc (×3). The combined organic phases were washed with a saturated aq.NaHCO$_3$, dried over sodium sulfate, filtered, and concentrated to afford a crude solid which was triturated with EtOAc, filtered, and washed with a small amount of EtOAc to afford E31-1 as a white solid after drying. Additional product was obtained from the filtrate. The filtrate was concentrated under reduced pressure and purified by flash column chromatography on silica gel (eluting with 0-100% DCM/ACN) to afford another batch of product (total 2.5 g of product, 39%)

Step 2. 5-Bromo-1-ethyl-1H-imidazole-2-carbaldehyde (E31-2)

To a mixture of E31-1 (2.18 g, 10.63 mmol) in DCM (42 mL) cooled in an ice bath was added Dess-Martin periodinane (9.02 g, 21.26 mmol) in several portions over 10 min and the resulting mixture was stirred at 0° C. for 30 min, and then gradually warmed to RT and stirred for 3 h. The reaction mixture was quenched with aq. sodium thiosulfate (27.6 mmol) and sodium bicarbonate (52.1 mmol) to afford a gummy mixture suspended in a slightly basic solution. The mixture was filtered, washed thoroughly with DCM to afford a biphasic filtrate. The separated aqueous phase was extracted three times with DCM. The combined organic phases were dried over sodium sulfate, filtered, and concentrated. The crude product was purified by flash column chromatography on silica gel (eluting with 0-35% EtOAc/Heptane) to afford E31-2 as a crystalline solid after concentrating the pure fractions under reduced pressure (1.97 g, 91%).

Step 3. 1-Ethyl-5-(4-hydroxyphenyl)-1H-imidazole-2-carbaldehyde (E31-3)

The title compound was prepared according to the procedure described in Example 7.7, Step 1 for Building block E12 starting from E31-2 and (4-hydroxyphenyl)boronic acid.

Step 4 to 5. 4-Chloro-2-(4-(2-((dimethylamino)methyl)-1-ethyl-1H-imidazol-5-yl)phenoxy)-6-fluorobenzaldehyde (E31)

The title compound was prepared according to the procedure described in Example 7.7, Steps 1 and 2 for Building block E12 starting from E31-3.

Example 7.19: Synthesis of 4-Chloro-2-((5-(2-((dimethylamino)methyl)-1-methyl-1H-imidazol-5-yl)pyridin-2-yl)oxy)benzaldehyde (E34)

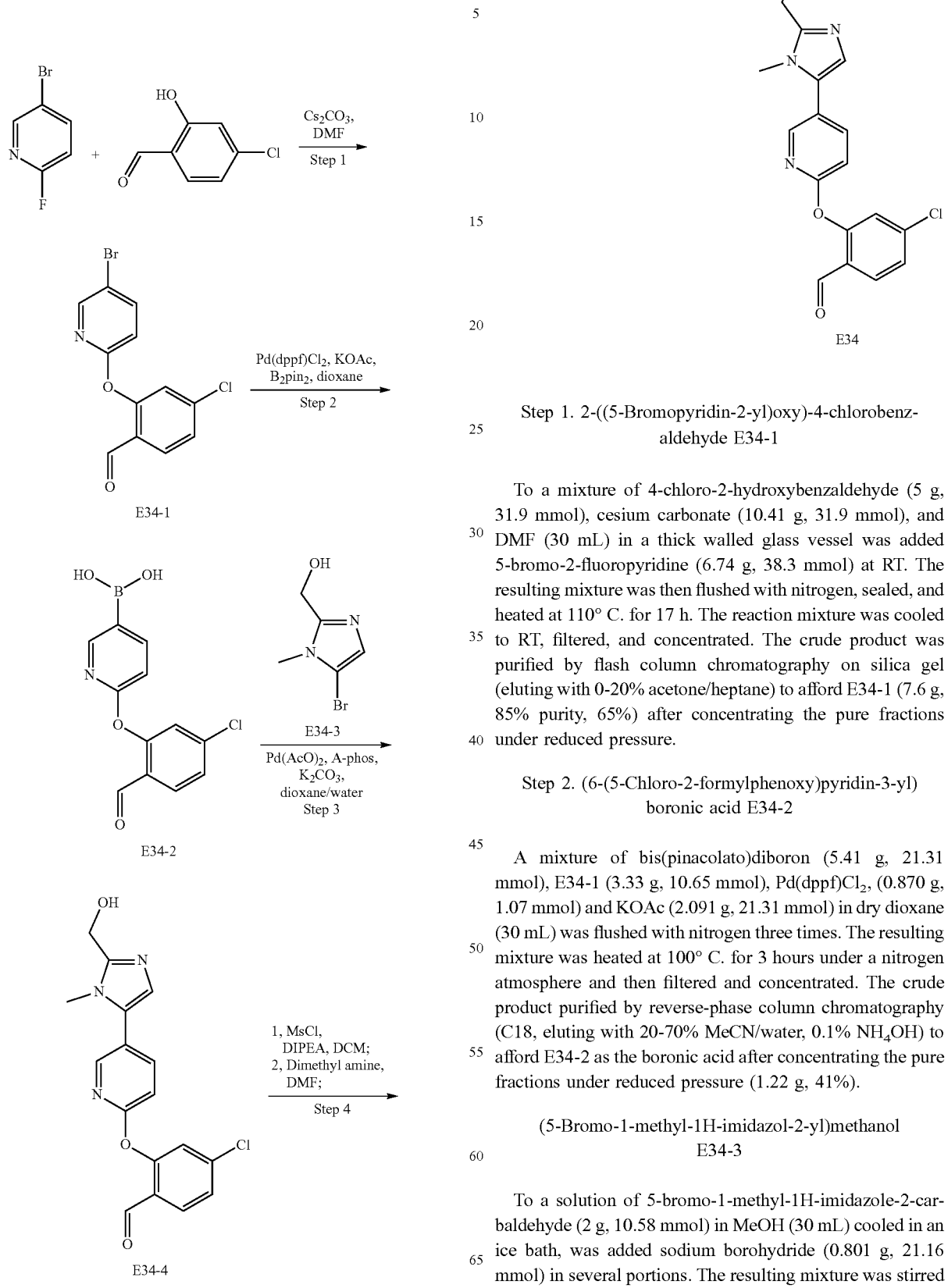

Step 1. 2-((5-Bromopyridin-2-yl)oxy)-4-chlorobenzaldehyde E34-1

To a mixture of 4-chloro-2-hydroxybenzaldehyde (5 g, 31.9 mmol), cesium carbonate (10.41 g, 31.9 mmol), and DMF (30 mL) in a thick walled glass vessel was added 5-bromo-2-fluoropyridine (6.74 g, 38.3 mmol) at RT. The resulting mixture was then flushed with nitrogen, sealed, and heated at 110° C. for 17 h. The reaction mixture was cooled to RT, filtered, and concentrated. The crude product was purified by flash column chromatography on silica gel (eluting with 0-20% acetone/heptane) to afford E34-1 (7.6 g, 85% purity, 65%) after concentrating the pure fractions under reduced pressure.

Step 2. (6-(5-Chloro-2-formylphenoxy)pyridin-3-yl)boronic acid E34-2

A mixture of bis(pinacolato)diboron (5.41 g, 21.31 mmol), E34-1 (3.33 g, 10.65 mmol), Pd(dppf)Cl$_2$, (0.870 g, 1.07 mmol) and KOAc (2.091 g, 21.31 mmol) in dry dioxane (30 mL) was flushed with nitrogen three times. The resulting mixture was heated at 100° C. for 3 hours under a nitrogen atmosphere and then filtered and concentrated. The crude product purified by reverse-phase column chromatography (C18, eluting with 20-70% MeCN/water, 0.1% NH$_4$OH) to afford E34-2 as the boronic acid after concentrating the pure fractions under reduced pressure (1.22 g, 41%).

(5-Bromo-1-methyl-1H-imidazol-2-yl)methanol E34-3

To a solution of 5-bromo-1-methyl-1H-imidazole-2-carbaldehyde (2 g, 10.58 mmol) in MeOH (30 mL) cooled in an ice bath, was added sodium borohydride (0.801 g, 21.16 mmol) in several portions. The resulting mixture was stirred in an ice bath for 60 min and then quenched with water and MeOH at 0° C. and concentrated in vacuo to dryness. The resulting residue was purified by flash chromatography (eluting with 0-40% DCM/MeOH) to afford E34-3 after concentrating the pure fractions under reduced pressure (2 g, quantitative yield).

Step 3. 4-Chloro-2-((5-(2-(hydroxymethyl)-1-methyl-1H-imidazol-5-yl)pyridin-2-yl)oxy)benzaldehyde E34-4

To a mixture in a microwave vial containing E34-3 (0.392 g, 2.054 mmol), E34-2 (0.38 g, 1.370 mmol) and dioxane (6 mL) and flushed with nitrogen was added a pre-mixed solution of Pd(OAc)$_2$ (0.031 g, 0.137 mmol) and (4-(N,N-dimethylamino)phenyl)di-tert-butyl phosphine (APhos, 0.087 g, 0.329 mmol) in 2 mL dioxane (flushed with nitrogen) followed by potassium carbonate (1.2 M aqueous solution, 3.42 mL, 4.11 mmol). The resulting mixture was flushed with nitrogen three times and heated at 120° C. for 16 hours. The reaction mixture was filtered and the filtrate purified by reverse-phase column chromatography (eluting with 50-100% MeCN/water, 0.1% NH$_4$OH) to afford E34-4 after concentrating the pure fractions under reduced pressure (120 mg, 26%).

Step 4. 4-Chloro-2-((5-(2-((dimethylamino)methyl)-1-methyl-1H-imidazol-5-yl)pyridin-2-yl)oxy)benzaldehyde E34

To a solution E34-4 (110 mg, 0.320 mmol) and DIPEA (0.140 mL, 0.800 mmol) in anhydrous DCM (3 mL) at 0° C. was added methanesulfonyl chloride (0.037 mL, 0.480 mmol) and the resulting mixture was stirred at room temperature for 1 hour. Dimethyl amine (130 mg, 1.600 mmol) in DMF (2 mL) was then added and the reaction mixture was stirred at room temperature overnight and then purified directly by reverse-phase column chromatography (eluting with MeCN/water, 0.1% NH$_4$OH) to give E34 after concentrating the pure fractions (50 mg, 42%).

Example 7.20: Synthesis of 4-Chloro-2-(4-(2-((ethyl(1-methylcyclopropyl)amino)methyl)-1-methyl-1H-imidazol-5-yl)phenoxy)-6-fluorobenzaldehyde (E36)

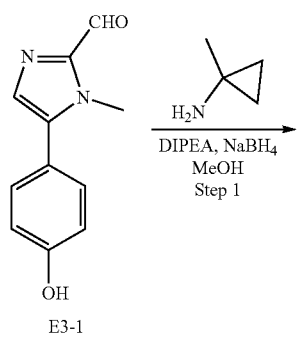

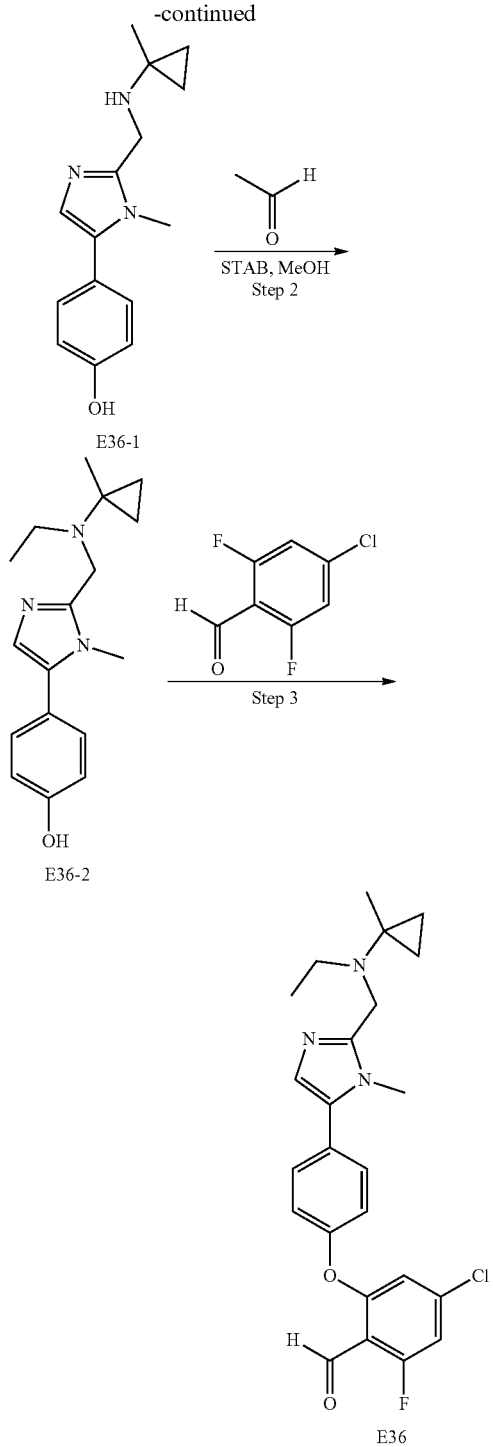

Step 1. 4-(1-Methyl-2-(((1-methylcyclopropyl)amino)methyl)-1H-imidazol-5-yl)phenol E36-1

To a mixture of E3-1 (500 mg, 2.47 mmol), 1-methylcyclopropanamine (266 mg, 2.47 mmol), in MeOH (30 mL) was added DIPEA (0.864 mL, 4.95 mmol). The resulting mixture was stirred at RT for 2 h and then cooled using an ice bath. NaBH$_4$ (131 mg, 3.46 mmol) was added in small portions and the reaction mixture was warmed to RT with stirring for 1 h and then concentrated under reduced pressure. The crude product was taken up in water and extracted twice with EtOAc. The separated organic phase was washed with brine, dried over sodium sulfate, filtered, and concentrated to afford a solid. The solid was taken up in 1:1 ACN/water and then freeze dried to afford E36-1 as a beige solid which was used in the next step without further purification (570 mg, 90%).

Step 2. 4-(2-((Ethyl(1-methylcyclopropyl)amino) methyl)-1-methyl-1H-imidazol-5-yl)phenol (E36-2)

A mixture of acetaldehyde (924 mg, 20.98 mmol) and E36-1 (270 mg, 1.049 mmol) in anhydrous MeOH (5 mL) was stirred at room temperature for 1 hour. Sodium triacetoxyborohydride (1.6 g, 7.34 mmol) was added and stirring was continued for an additional 1 hour. The reaction mixture was concentrated and EtOAc (100 mL) was added. The organic phase was washed with water (2×50 mL), brine (50 mL), dried over sodium sulfate, filtered and concentrated to afford E36-2 (0.30 g, 100% yield) which was carried to the next step without purification.

Step 3. 4-Chloro-2-(4-(2-((ethyl(1-methylcyclopropyl)amino)methyl)-1-methyl-1H-imidazol-5-yl)phenoxy)-6-fluorobenzaldehyde (E36)

The title compound E36 was prepared according to the procedure described in Example 7.7, Step 2 for Building block E12 starting from E36-2 and 4-chloro-2,6-difluorobenzaldehyde.

The following intermediates were in Table 7A prepared according to the procedures described herein above procedures using the appropriate starting materials unless otherwise indicated.

TABLE 7A

| BB No. | Structure/Chemical name |
|---|---|
| E37 | 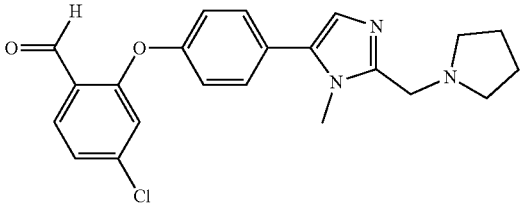 [SMILES: Cn1c(-c2ccc(Oc3cc(Cl)ccc3C=O)cc2)cnc1CN1CCCC1]<br>4-Chloro-2-(4-(1-methyl-2-(pyrrolidin-1-ylmethyl)-1H-imidazol-5-yl)phenoxy)benzaldehyde |
| E38 | 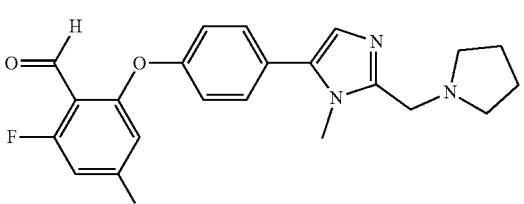<br>4-Chloro-2-((6-(2-((dimethylamino)methyl)-1-methyl-1H-imidazol-5-yl)pyridin-3-yl)oxy)-6-fluorobenzaldehyde |

TABLE 7A-continued

| BB No. | Structure/Chemical name |
|---|---|
| E39 | 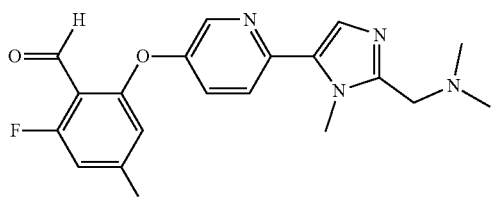<br>4-Chloro-2-((6-(2-((dimethylamino)methyl)-1-methyl-1H-imidazol-5-yl)pyridin-3-yl)oxy)-6-fluorobenzaldehyde |
| E40 | 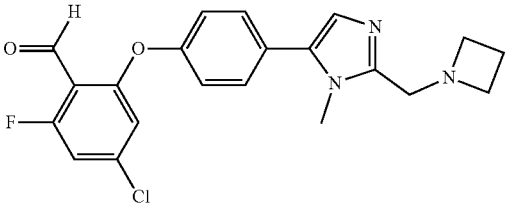 [SMILES: Cn1c(-c2ccc(Oc3cc(Cl)cc(F)c3C=O)cc2)cnc1CN1CCC1]<br>2-(4-(2-(Azetidin-1-ylmethyl)-1-methyl-1H-imidazol-5-yl)phenoxy)-4-chloro-6-fluorobenzaldehyde |
| E41 | 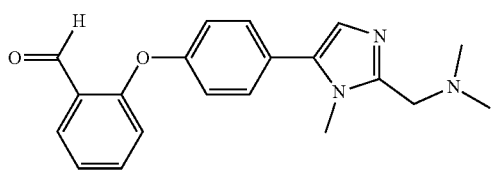 [SMILES: CN(C)Cc1ncc(-c2ccc(Oc3ccccc3C=O)cc2)n1C]<br>2-(4-(2-((Dimethylamino)methyl)-1-methyl-1H-imidazol-5-yl)phenoxy)benzaldehyde |
| E42 | 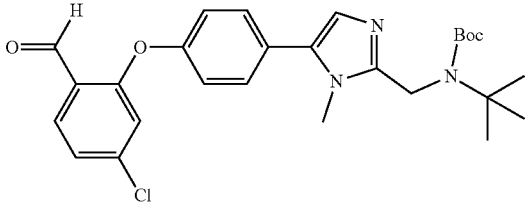 [SMILES: Cn1c(-c2ccc(Oc3cc(Cl)ccc3C=O)cc2)cnc1CN(C(=O)OC(C)(C)C)C(C)(C)C]<br>tert-Butyl((5-(4-(5-chloro-2-formylphenoxy)phenyl)-1-methyl-1H-imidazol-2-yl)methyl)carbamate |
| E43 | 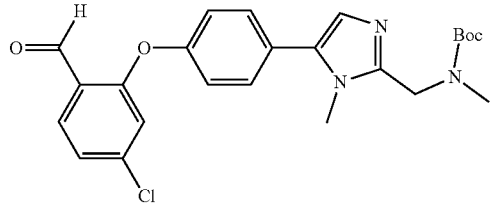 [SMILES: CN(Cc1ncc(-c2ccc(Oc3cc(Cl)ccc3C=O)cc2)n1C)C(=O)OC(C)(C)C]<br>tert-Butyl((5-(4-(5-chloro-2-formylphenoxy)phenyl)-1-methyl-1H-imidazol-2-yl)methyl)(methyl)carbamate |

TABLE 7A-continued

| BB No. | Structure/Chemical name |
|---|---|
| E43 | 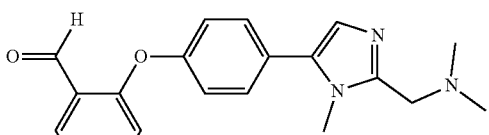<br>2-(4-(2-((Dimethylamino)methyl)-1-methyl-1H-imidazol-5-yl)phenoxy)-4-ethylbenzaldehyde |

Example 8: Miscellaneous Building Blocks and Compounds

The experimental procedures described herein below In Examples 8 and 9 can be used for the synthesis of linear and the corresponding cyclic peptides. The linear peptides can be assembled on solid phase and in solution. The building blocks used for the syntheses are summarized in Examples 1-7 herein above and in Example 8 below.

Example 8.1: Synthesis of tert-butyl (R)-3-((S)-3-((4-chloro-2-(4-(2-((2-(2-ethoxyethoxy)ethoxy)methyl)-1-methyl-1H-imidazol-5-yl)phenoxy)benzyl)-L-alanyl)-2,2-dimethyloxazolidine-4-carboxamido)-3-(4-chlorobenzyl)-piperidine-1-carboxylate trifluoroacetate (104B)

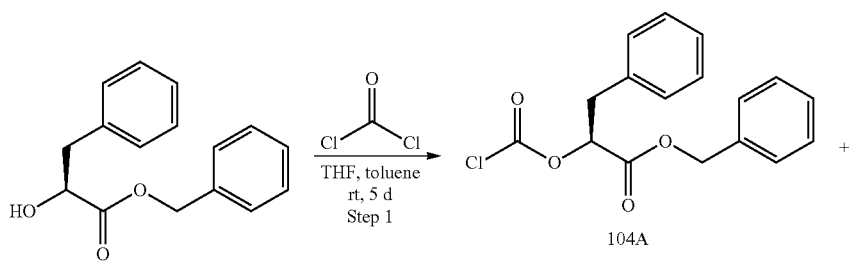

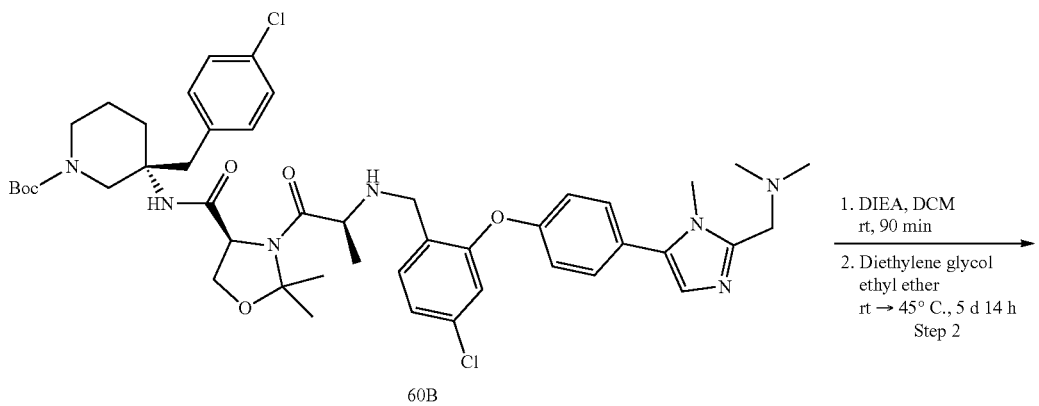

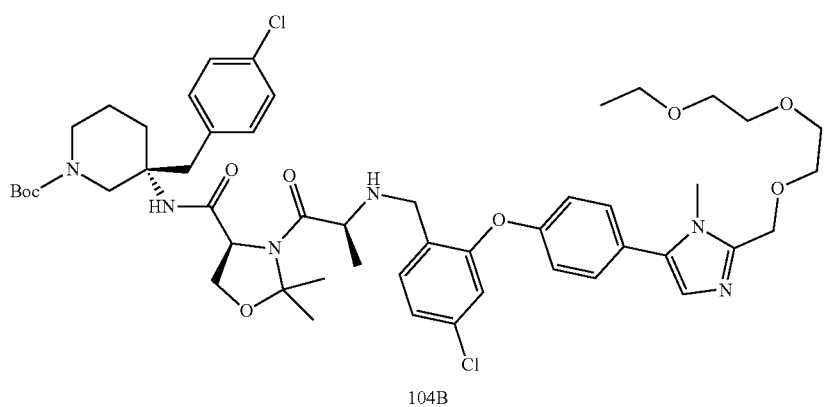

Step 1. (S)-Benzyl 2-((chlorocarbonyl)oxy)-3-phenylpropanoate (104A)

To a solution of (S)-benzyl 2-hydroxy-3-phenylpropanoate (256 mg, 1 mmol) in THF (2 mL) was added to 20% phosgene in toluene (3.00 mL, 5.70 mmol) at 0° C. under an N₂-atmosphere and the resulting mixture was stirred for 26 h and then allowed to warm to rt. Additional 20% phosgene in toluene (1.997 mL, 3.80 mmol) was added and stirring at rt was continued for 3 d 22 h. The reaction mixture was concentrated to dryness in vacuo to afford 104A (297 mg, 0.932 mmol, 93% yield) as a yellowish oil. The crude product was used in the next step without purification.

Step 2. tert-Butyl (R)-3-((S)-3-((4-chloro-2-(4-(2-((2-(2-ethoxyethoxy)ethoxy)methyl)-1-methyl-1H-imidazol-5-yl)phenoxy)benzyl)-L-alanyl)-2,2-dimethyloxazolidine-4-carboxamido)-3-(4-chlorobenzyl)piperidine-1-carboxylate trifluoroacetate (104B)

Step 2-1: To 60B (100 µmol) dissolved in DCM (4 mL) was added DIEA (0.070 mL, 400 µmol) and 104A (49.4 mg, 155 µmol) and the resulting mixture was stirred for 90 min at rt.

Step 2-2: Diethylene glycol ethyl ether (26.8 mg, 200 µmol) was added to the mixture from Step 2-1 and the resulting mixture was stirred for 16 h at rt. Additional diethylene glycol ethyl ether (26.8 mg, 200 µmol) was added and stirring was continued for 23 h at 45° C. Diethylene glycol ethyl ether (215 mg, 1600 µmol) was added and stirring was continued for 3 d 23 h at 45° C. The reaction mixture was then concentrated in vacuo. The crude product was purified by preparative reverse-phase HPLC (eluent A: 0.1% TFA in H₂O; eluent B: ACN). Pure fractions were combined and lyophilized to afford 104B (29 mg, 24.3 µmol, 24% yield) as a white solid. Analytical method 9; $t_R$=4.57 min; [M+H]⁺=965.3.

Example 8.2: Synthesis of tert-butyl (S)-2-amino-4,4-difluorobutanoate trifluoroacetate (58B)

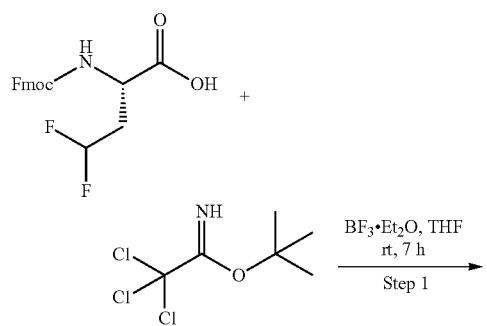

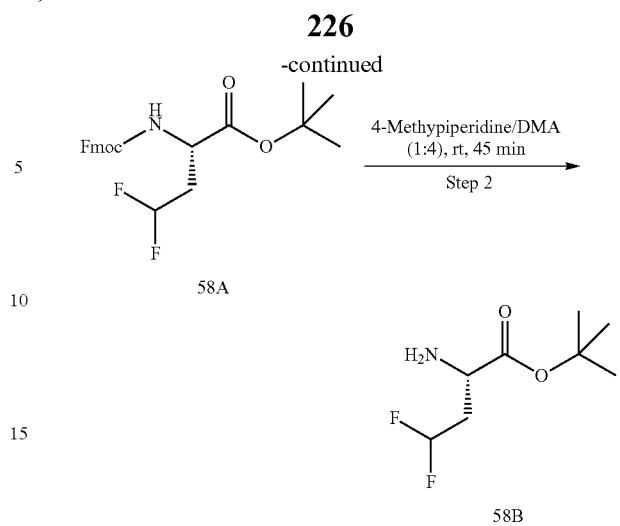

Step 1. tert-Butyl (S)-2-(((((9H-fluoren-9-yl)methoxy)carbonyl)amino)-4,4-difluorobutanoate (58A)

To a solution of (S)-2-(Fmoc-amino)-4,4-difluorobutanoic acid (361 mg, 1 mmol) in THF (10 mL) was added tert-butyl 2,2,2-trichloroacetimidate (0.537 mL, 3.00 mmol) and BF₃·OEt₂ (0.025 mL, 0.200 mmol). The resulting mixture was stirred for 7 h at rt, and then partitioned between EtOAc (60 mL) and 5% aq. NaHCO₃ (20 mL). The organic phase was washed with 5% aq. NaHCO₃ (2×10 mL), 5% aq. KHSO₄ (15 mL) and brine (10 mL), dried over Na₂SO₄, filtered, and concentrated to dryness in vacuo. The crude product was purified by flash silica gel chromatography (eluent A: heptane; eluent B: EtOAc). Pure fractions were combined and concentrated to dryness in vacuo to afford 58A (358 mg, 0.858 mmol, 86% yield) as a white solid. Analytical method 10; $t_R$=1.33 min; [M+Na]+=440.2.

Step 2. tert-Butyl (S)-2-amino-4,4-difluorobutanoate trifluoroacetate (58B)

58A (356 mg, 0.853 mmol) was dissolved in 4-methylpiperidine/DMA (1:4) (5 mL)), stirred at rt for 45 min, and then concentrated to dryness in vacuo. The crude product was purified by reverse-phase flash chromatography (Teledyne ISCO; RediSep Rf Gold C18Aq column 20-40 micron 100 g; eluent A: 0.1% TFA in H₂O; eluent B: 0.1% TFA in ACN). Pure fractions were combined and lyophilized to afford 58B (68.7 mg, 0.222 mmol, 26% yield) as a white solid. Analytical method 10; $t_R$=0.43 min; [M+H]⁺=196.2.

Example 8.3: Synthesis of (2S,5S,8R,12S)-1-(4-chloro-2-(4-(1-methyl-2-(pyrrolidin-1-ylmethyl)-1H-imidazol-5-yl)phenoxy)-benzyl)-8-(4-chlorobenzyl)-12-((R)-2,3-dihydro-1H-inden-1-yl)-5-(hydroxymethyl)-2,7,10-trimethyl-1,4,7,10-tetraazacyclotetradecane-3,6,11,14-tetraone hydrochloride (Compound 86)

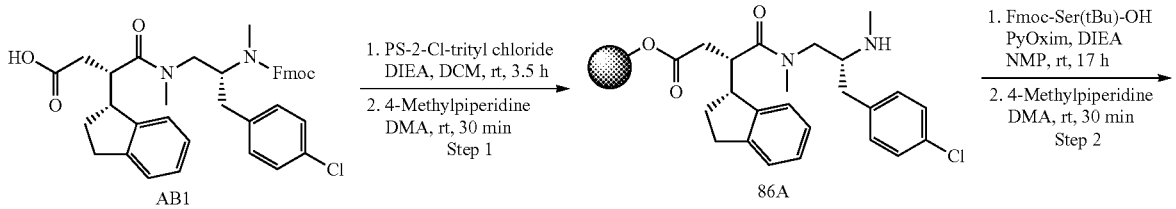

227

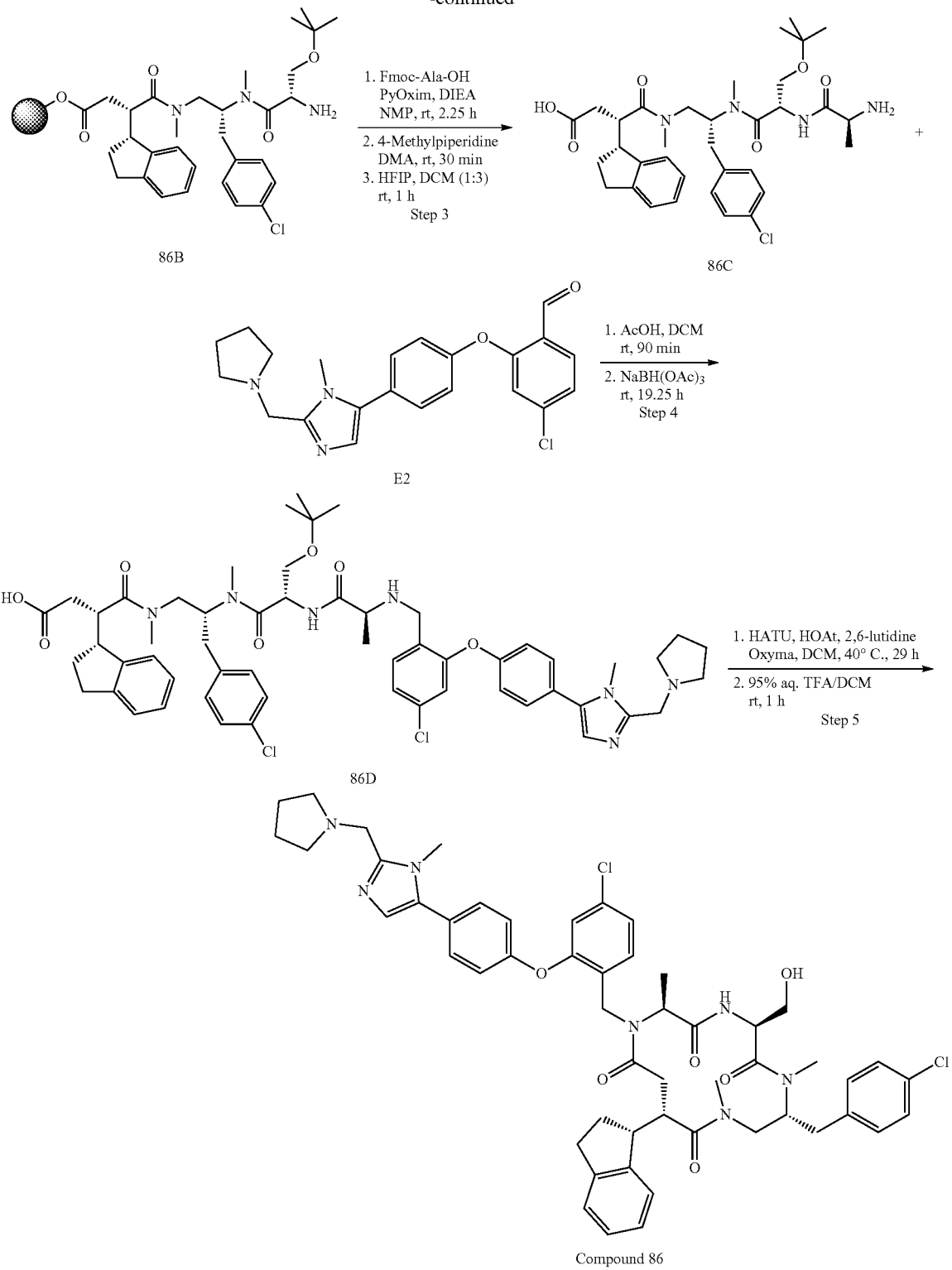

Step 1. PS-2-chlorotrityl (S)-4-(((R)-2-((((9H-fluoren-9-yl)methoxy)carbonyl)(methyl)amino)-3-(4-chloro-phenyl)propyl)(methyl)amino)-3-((R)-2,3-dihydro-1H-inden-1-yl)-4-oxobutanoate (86A)

Step 1-1: PS-2-chlorotrityl chloride (653 mg, 1.044 mmol) was washed thoroughly with DCM. A solution of AB1 (272 mg, 0.418 mmol) dissolved in DCM (10 mL) and DIEA (0.365 mL, 2.088 mmol) was added to the resin and the suspension was shaken at rt for 3.5 h. The resin was then drained and thoroughly washed sequentially with DCM/MeOH/DIPEA (17:2:1), DCM and DMA.

Step 1-2: 4-Methylpiperidine/DMA (1:4) (4 mL) was added to the resin and the resulting suspension was shaken for 10 min at rt, and then drained. This treatment was repeated twice. The resin was washed with DMA (3×) and DCM (3×), and then dried in vacuo to afford 86A (~0.418 mmol).

Step 2. PS-(2-chlorotrityl) (S)-4-(((R)-2-((S)-2-amino-3-(tert-butoxy)-N-methylpropanamido)-3-(4-chloro-phenyl)propyl)(methyl)amino)-3-((R)-2,3-dihydro-1H-inden-1-yl)-4-oxobutanoate (86B)

Step 2-1: 86A (200 µmol) was washed with NMP (3×). To Fmoc-Ser(tBu)—OH (230 mg, 600 µmol) and PyOxim (316 mg, 600 µmol) dissolved in NMP (2 mL) was added DIEA (0.210 mL, 1200 µmol) and the resulting solution was stirred for 2 min at rt, and then added to the resin. The suspension was shaken for 17 h at rt. The resin was drained, then washed with DMA (3×). A solution of Ac$_2$O/pyridine/DMA (1:1:8) (2 mL) was added and the reaction mixture was shaken for 30 min at rt. The resin was drained, then washed with DMA (3×).

Step 2-2: 4-Methylpiperidine/DMA (1:4) (2 mL) was added to the resin. The resulting suspension was shaken for 10 min at rt, and then the resin was drained. This treatment was repeated twice. The resin was washed with DMA (3×) and DCM (3×). 86B was directly carried onto the next step.

Step 3. (S)-4-(((R)-2-((S)-2-((S)-2-Aminopropanamido)-3-(tert-butoxy)-N-methylpropanamido)-3-(4-chloro-phenyl)propyl)(methyl)amino)-3-((R)-2,3-dihydro-1H-inden-1-yl)-4-oxobutanoic acid (86C)

Step 3-1: 86B (200 µmol) was washed with NMP (3×). To Fmoc-Ala-OH (187 mg, 600 µmol) and PyOxim (316 mg, 600 µmol) dissolved in NMP (2 mL) was added DIEA (0.210 mL, 1200 µmol) and the resulting solution was stirred for 2 min at rt, and then added to the resin. The suspension was shaken for 2 h 15 min at rt and the resin was drained, and then washed with DMA (3×). A solution of Ac$_2$O/pyridine/DMA (1:1:8) (2 mL) was added and the reaction was shaken for 30 min at rt. The resin was drained, then washed with DMA (3×).

Step 3-2: 4-Methylpiperidine/DMA (1:4) (2 mL) was added to the resin. The suspension was shaken for 10 min at rt, then the resin was drained. This treatment was repeated twice. The resin was washed with DMA (3×) and DCM (3×).

Step 3-3: HFIP/DCM (1:3) (3 mL) was added to the resin from Step 3-1 and the suspension was shaken for 15 min at rt. The cleavage solution was filtered off and collected.

This procedure was repeated three times. Finally, the resin was washed once with HFIP/DCM (1:3) (1 mL). The combined cleavage and washing solutions were concentrated to dryness in vacuo to afford 86C (~200 µmol) as an orange oil. The crude product was used in the next step without purification. Analytical method 10; $t_R$=0.95; [M+H]$^+$=643.4.

Step 4. (3S,6S,9R,13S)-6-(tert-butoxymethyl)-1-(4-chloro-2-(4-(1-methyl-2-(pyrrolidin-1-ylmethyl)-1H-imidazol-5-yl)phenoxy)phenyl)-9-(4-chlorobenzyl)-13-((R)-2,3-dihydro-1H-inden-1-yl)-3,8,11-trimethyl-4,7,12-trioxo-2,5,8,11-tetraazapentadecan-15-oic acid trifluoroacetate (86D)

86C (200 µmol) and E2 (95 mg, 240 µmol) were dissolved in a mixture of DCM (12 mL) and AcOH (0.046 mL, 800 µmol) and stirred for 90 min at rt. NaBH(OAc)$_3$ (212 mg, 1000 µmol) was added and the resulting mixture was stirred for 19 h 15 min at rt. MeOH (2 mL) was added and the mixture was concentrated to dryness in vacuo. The crude product was purified by preparative reverse-phase HPLC (eluent A: 0.1% TFA in H$_2$O; eluent B: ACN). Pure fractions were combined and lyophilized to afford 86D (127 mg, 93 µmol, 47% yield for 4 steps) as a white solid. Analytical method 9; $t_R$=4.41 min; [M+H]$^+$=1022.4.

Step 5. (2S,5S,8R,12S)-1-(4-chloro-2-(4-(1-methyl-2-(pyrrolidin-1-ylmethyl)-1H-imidazol-5-yl)phenoxy)-benzyl)-8-(4-chlorobenzyl)-12-((R)-2,3-dihydro-1H-inden-1-yl)-5-(hydroxymethyl)-2,7,10-trimethyl-1,4,7,10-tetraazacyclotetradecane-3,6,11,14-tetraone hydrochloride (Compound 86)

Step 5-1: To 86D (127 mg, 0.093 mmol), HATU (141 mg, 0.372 mmol) and HOAt (18.99 mg, 0.140 mmol) was added DCM (93 mL). The resulting mixture was stirred for 5 min at rt, and then 2,6-lutidine (0.325 mL, 2.79 mmol) was added and stirring was continued at 40° C. for 22 h. Additional HATU (70.7 mg, 0.186 mmol) was added and stirring at 40° C. was continued for 3 h. Oxyma Pure (13.22 mg, 0.093 mmol) was added. The reaction mixture was stirred for 4 h at 40° C., and then concentrated to dryness in vacuo. The obtained residue was partitioned between EtOAc (50 mL) and 5% aq. NaHCO$_3$ (5 mL). The organic phase was washed with 5% NaHCO$_3$ (3×5 mL) and brine (5 mL), dried over Na$_2$SO$_4$, filtered, and concentrated to dryness in vacuo. The crude product was used in the next step without purification.

Step 5-2: The residue from Step 5-1: was dissolved in 95% aq. TFA/DCM (1:1) (5 mL) and the resulting solution was stirred for 1 h at rt, and then concentrated to dryness in vacuo. The crude product was purified by preparative reverse-phase HPLC (eluent A: 0.1% TFA in H$_2$O; eluent B: ACN). Pure fractions were combined and lyophilized. The product was dissolved in EtOAc (50 mL) and the organic phase was washed with 5% aq. NaHCO$_3$ (3×5 mL) and brine (5 mL), dried over Na$_2$SO$_4$, filtered, and concentrated to dryness in vacuo. The residue was dissolved in ACN/1H$_2$O (1:1) (20 mL) and 0.1 M aq. HCl (3 mL) was added. After lyophilization Compound 86 (44.3 mg, 0.042 mmol, 45% yield) was obtained as a white solid. Analytical method 9; $t_R$=5.10 min; [M+H]$^+$=948.4

The compounds and intermediates shown in Table 8 were synthesized according to the procedure described in Example 8.3 for Compound 86 from the respective intermediates shown in Table 4, Table 5, Table 6 and Table 7. For several compounds, the final deprotection step was not executed.

TABLE 8
Compounds and intermediates made according to Example 8.3 for Compound 86.
| Cmd No. | Structure | LCMS |
|---|---|---|
| 23 | 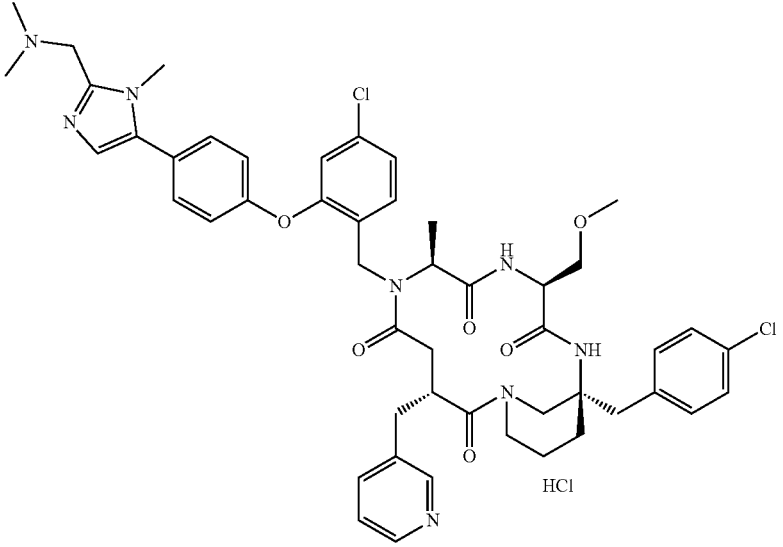 [SMILES: COC[C@@H]1NC(=O)[C@H](C)N(Cc2ccc(Cl)cc2Oc2ccc(-c3cnc(CN(C)C)n3C)cc2)C(=O)C[C@@H](Cc2cccnc2)C(=O)N2CCC[C@@](Cc3ccc(Cl)cc3)(C2)NC1=O ; Cl] | Analytical method 14<br>$t_R$ = 3.27 min<br>$[M + H]^+$ = 923.4 |
| 89 | 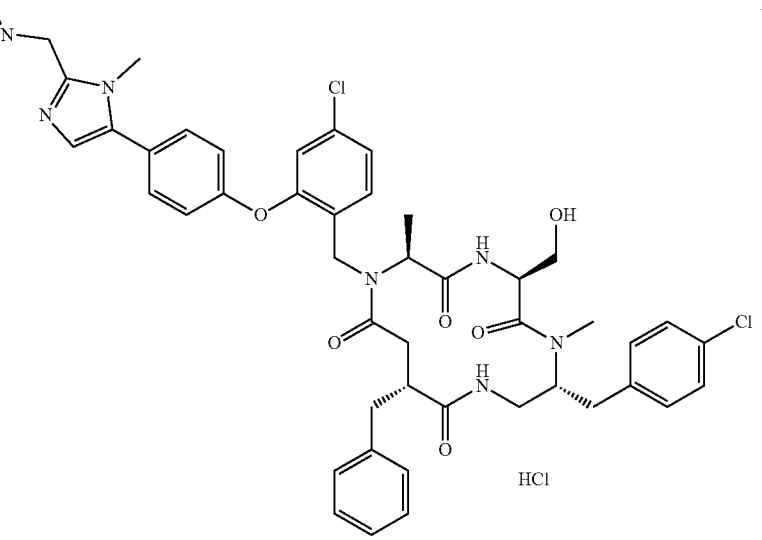 | Analytical method 9<br>$t_R$ = 4.39 min<br>$[M + H]^+$ = 908.3 |

TABLE 8-continued

Compounds and intermediates made according to Example 8.3 for Compound 86.

| Cmd No. | Structure | LCMS |
|---|---|---|
| 91 | 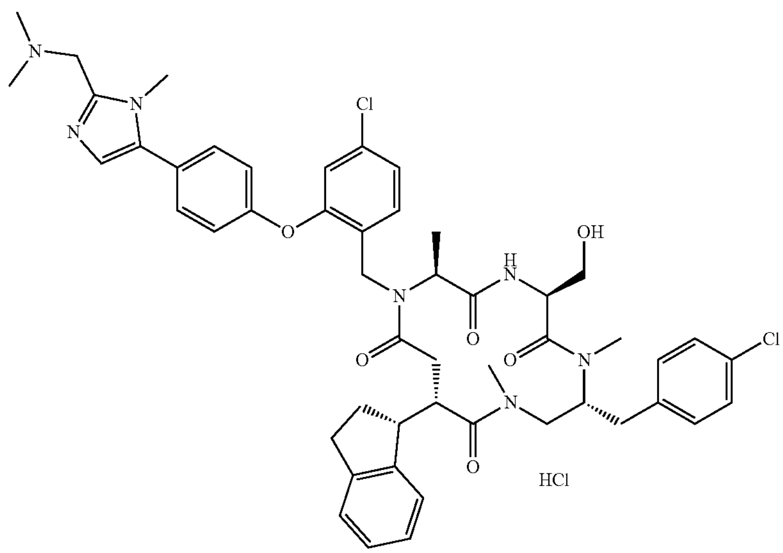 [SMILES: C[C@H]1C(=O)N[C@@H](CO)C(=O)N(C)[C@H](Cc2ccc(Cl)cc2)CN(C)C(=O)[C@H]([C@H]2CCc3ccccc32)CC(=O)N1Cc1ccc(Cl)cc1Oc1ccc(-c2cnc(CN(C)C)n2C)cc1 ; Cl] | Analytical method 9<br>$t_R$ = 5.01 min<br>$[M + H]^+$ = 922.4 |
| 92 | 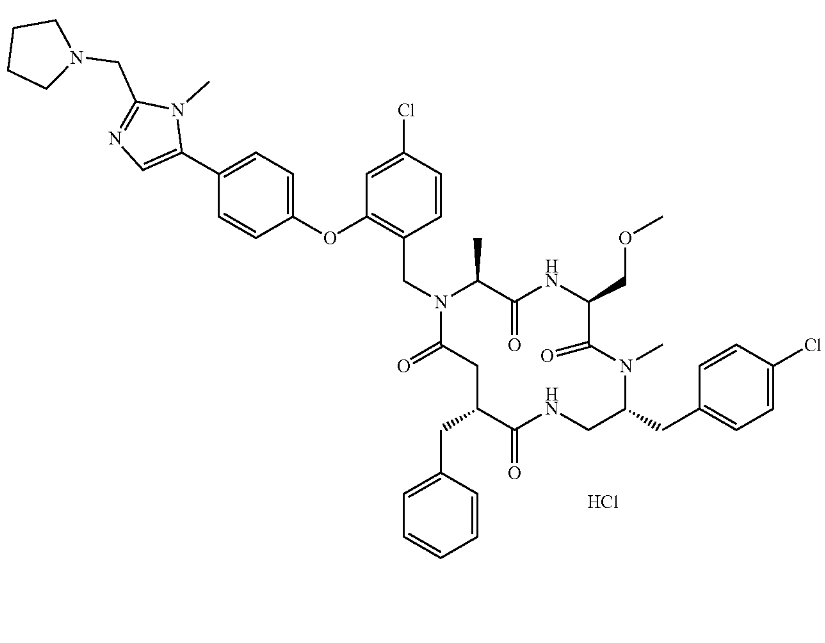 [SMILES: COC[C@@H]1NC(=O)[C@H](C)N(Cc2ccc(Cl)cc2Oc2ccc(-c3cnc(CN4CCCC4)n3C)cc2)C(=O)C[C@@H](Cc2ccccc2)C(=O)NC[C@@H](Cc2ccc(Cl)cc2)N(C)C1=O ; Cl] | Analytical method 9<br>$t_R$ = 4.54 min<br>$[M + H]^+$ = 922.4 |

TABLE 8-continued

Compounds and intermediates made according to Example 8.3 for Compound 86.

| Cmd No. | Structure | LCMS |
|---|---|---|
| 93 | 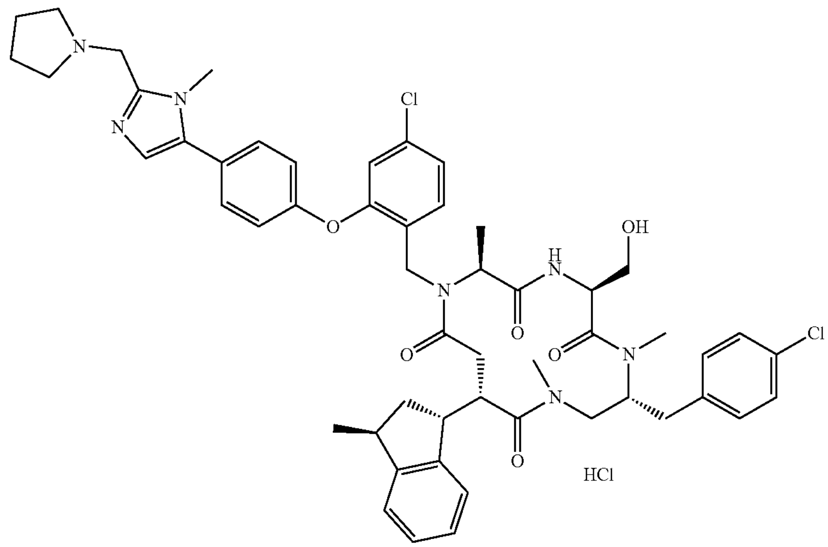 [SMILES: C[C@H]1C[C@H]([C@@H]2CC(=O)N(Cc3ccc(Cl)cc3Oc3ccc(-c4cnc(CN5CCCC5)n4C)cc3)[C@@H](C)C(=O)N[C@@H](CO)C(=O)N(C)[C@H](Cc3ccc(Cl)cc3)CN(C)C2=O)c2ccccc21 ; Cl] | Analytical method 14<br>$t_R$ = 4.68 min<br>$[M + H]^+$ = 962.4 |
| 95 | 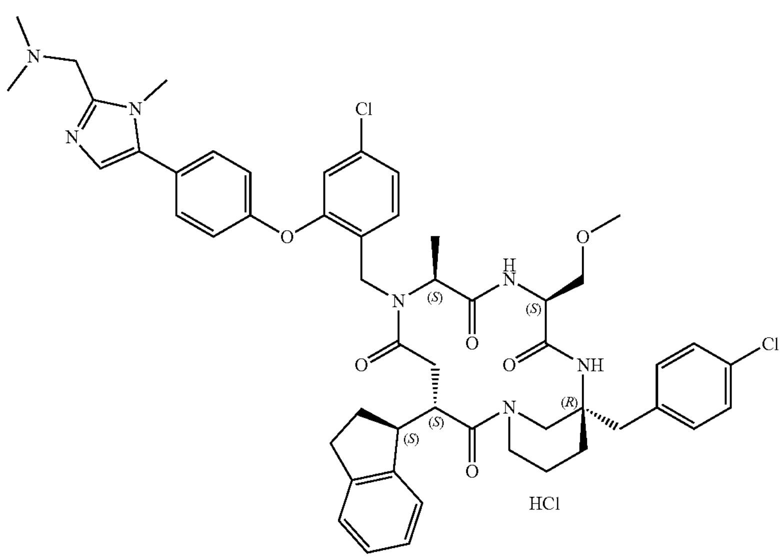 | Analytical method 14<br>$t_R$ = 5.24 min<br>$[M + H]^+$ = 948.4 |

TABLE 8-continued
Compounds and intermediates made according to Example 8.3 for Compound 86.
| Cmd No. | Structure | LCMS |
|---|---|---|
| 101 | 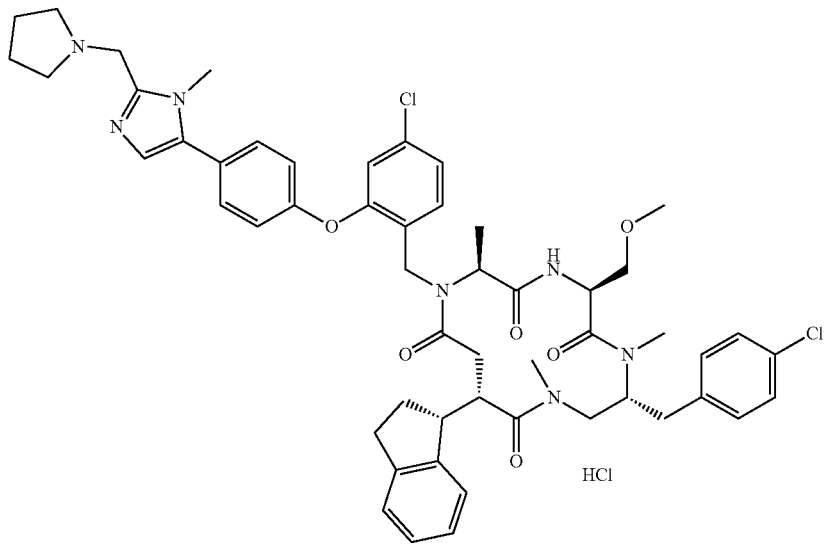 [SMILES: COC[C@@H]1NC(=O)[C@H](C)N(Cc2ccc(Cl)cc2Oc2ccc(-c3cnc(CN4CCCC4)n3C)cc2)C(=O)C[C@@H]([C@H]2CCc3ccccc32)C(=O)N(C)C[C@@H](Cc2ccc(Cl)cc2)N(C)C1=O ; Cl] | Analytical method 9<br>$t_R$ = 5.37 min<br>$[M + H]^+$ = 962.4 |
| 102 | 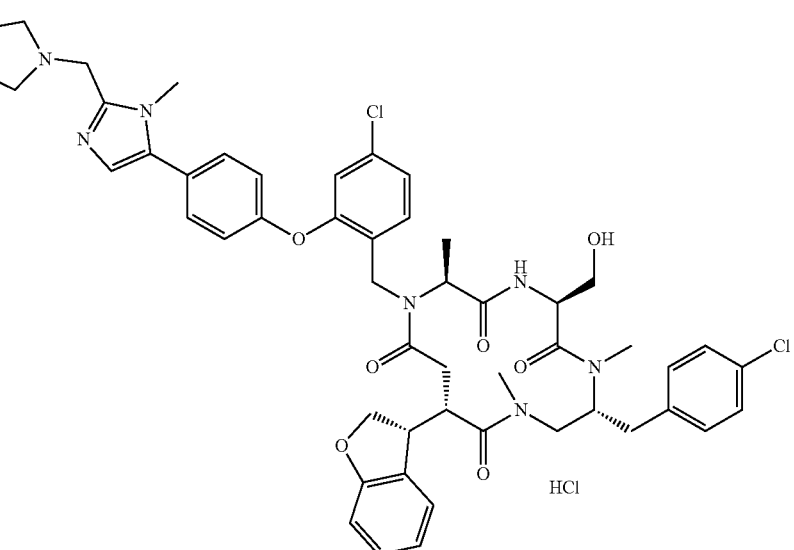 | Analytical method 14<br>$t_R$ = 4.21 min<br>$[M + H]^+$ = 950.4 |

TABLE 8-continued
Compounds and intermediates made according to Example 8.3 for Compound 86.
| Cmd No. | Structure | LCMS |
|---|---|---|
| 103 | 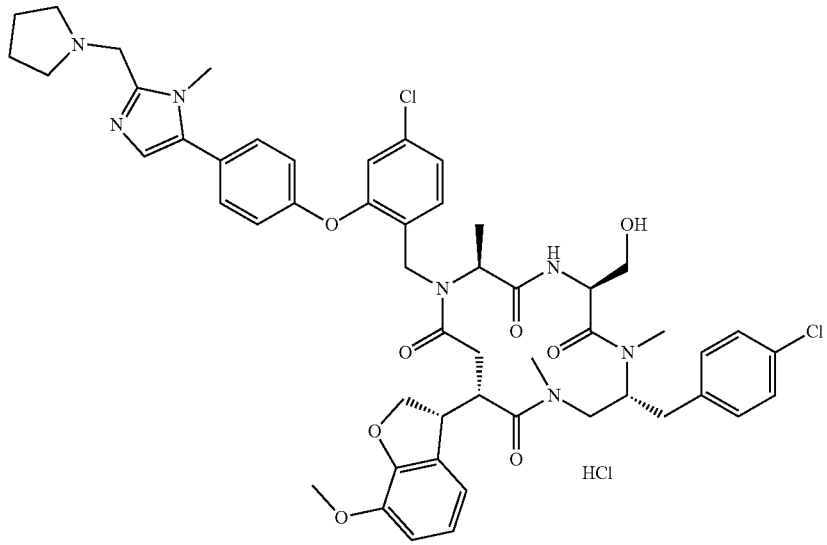 [SMILES: COc1cccc2c1OC[C@@H]2[C@@H]1CC(=O)N(Cc2ccc(Cl)cc2Oc2ccc(-c3cnc(CN4CCCC4)n3C)cc2)[C@@H](C)C(=O)N[C@@H](CO)C(=O)N(C)[C@H](Cc2ccc(Cl)cc2)CN(C)C1=O ; Cl] | Analytical method 9<br>$t_R$ = 4.39 min<br>$[M + H]^+$ = 980.4 |
| 106 | 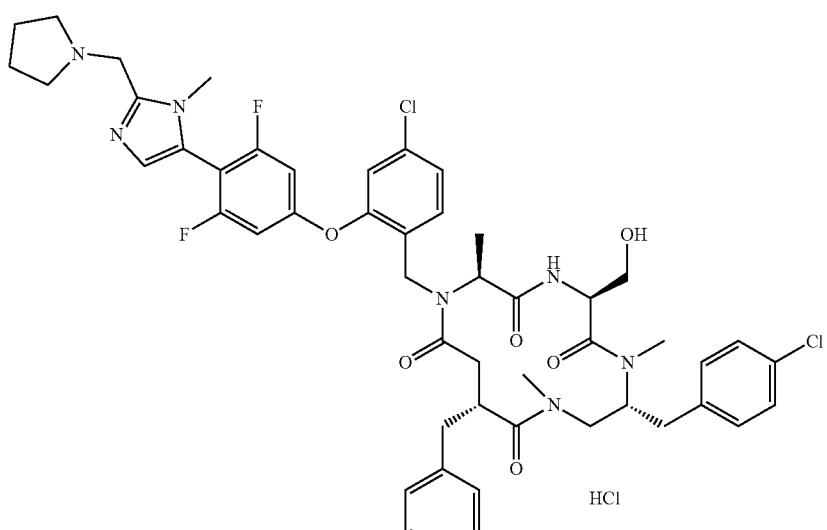 | Analytical method 9<br>$t_R$ = 4.86 min<br>$[M + H]^+$ = 958.4 |

TABLE 8-continued

Compounds and intermediates made according to Example 8.3 for Compound 86.

| Cmd No. | Structure | LCMS |
|---|---|---|
| 107 | 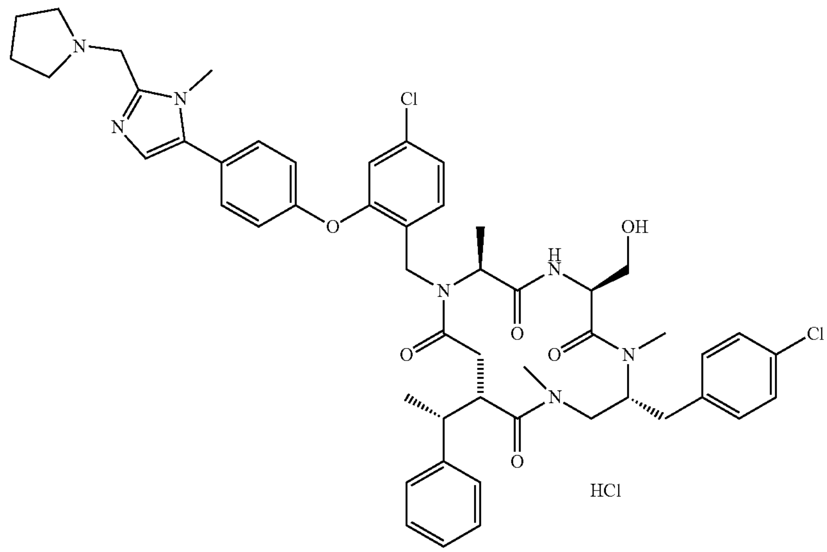 | Analytical method 9<br>$t_R$ = 4.73 min<br>$[M + H]^+$ = 936.4 |
| 108 | 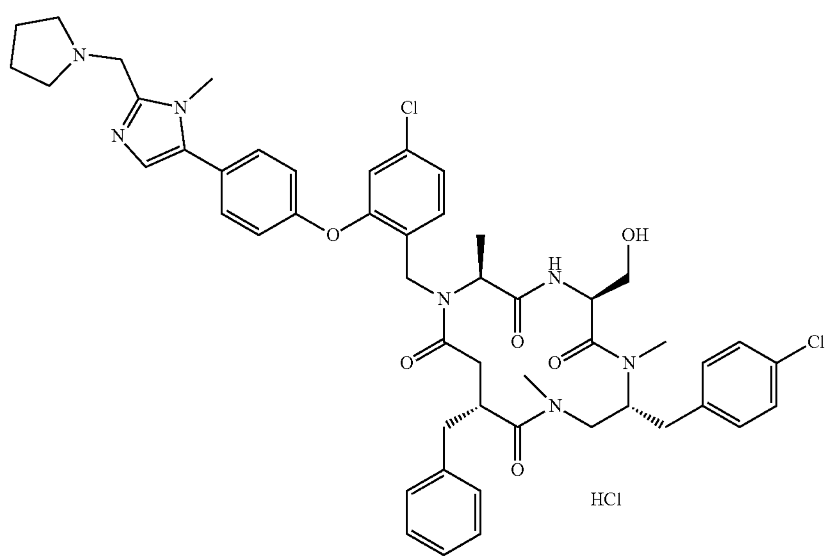 [SMILES: C[C@H]1C(=O)N[C@@H](CO)C(=O)N(C)[C@H](Cc2ccc(Cl)cc2)CN(C)C(=O)[C@H](Cc2ccccc2)CC(=O)N1Cc1ccc(Cl)cc1Oc1ccc(-c2cnc(CN3CCCC3)n2C)cc1 ; Cl] | Analytical method 9<br>$t_R$ = 4.63 min<br>$[M + H]^+$ = 922.4 |

TABLE 8-continued

Compounds and intermediates made according to Example 8.3 for Compound 86.

| Cmd No. | Structure | LCMS |
|---|---|---|
| 110 | 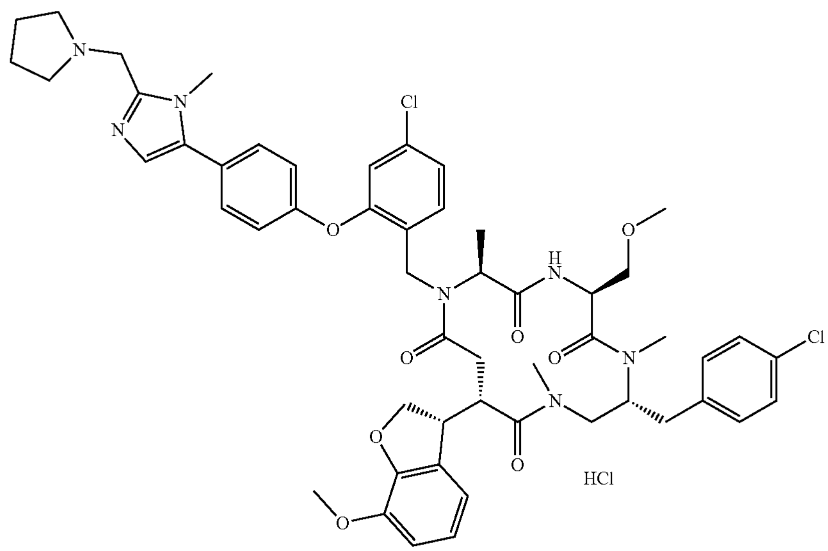 [SMILES: COC[C@@H]1NC(=O)[C@H](C)N(Cc2ccc(Cl)cc2Oc2ccc(-c3cnc(CN4CCCC4)n3C)cc2)C(=O)C[C@@H]([C@H]2COc3c(OC)cccc32)C(=O)N(C)C[C@@H](Cc2ccc(Cl)cc2)N(C)C1=O ; Cl] | Analytical method 9<br>$t_R$ = 4.70 min<br>$[M + H]^+$ = 994.4 |
| 111 | 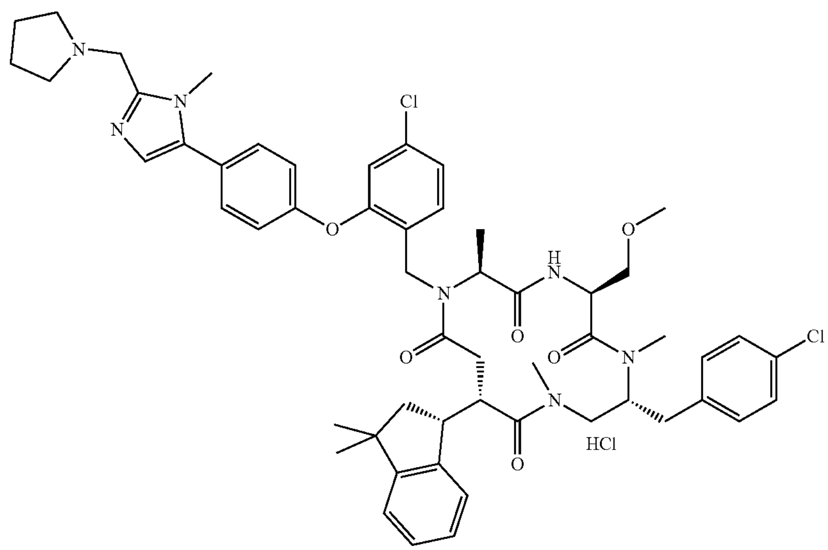 [SMILES: COC[C@@H]1NC(=O)[C@H](C)N(Cc2ccc(Cl)cc2Oc2ccc(-c3cnc(CN4CCCC4)n3C)cc2)C(=O)C[C@@H]([C@H]2CC(C)(C)c3ccccc32)C(=O)N(C)C[C@@H](Cc2ccc(Cl)cc2)N(C)C1=O ; Cl] | Analytical method 9<br>$t_R$ = 5.49 min<br>$[M + H]^+$ = 990.4 |
| 112 | 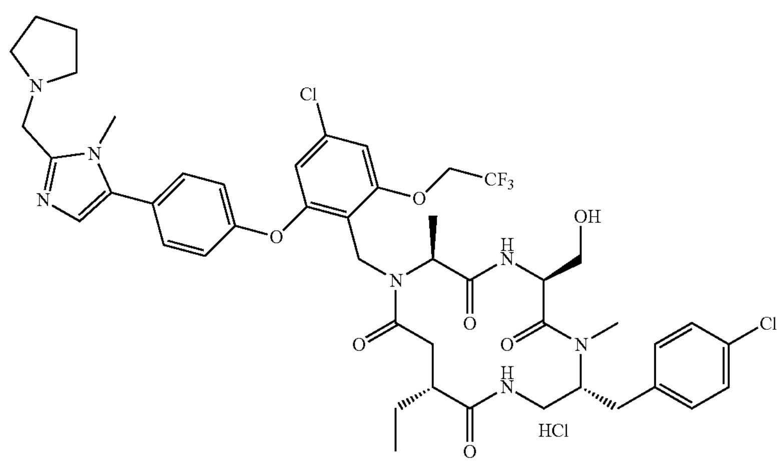 [SMILES: CC[C@@H]1CC(=O)N(Cc2c(OCC(F)(F)F)cc(Cl)cc2Oc2ccc(-c3cnc(CN4CCCC4)n3C)cc2)[C@@H](C)C(=O)N[C@@H](CO)C(=O)N(C)[C@H](Cc2ccc(Cl)cc2)CNC1=O ; Cl] | Analytical method 9<br>$t_R$ = 4.47 min<br>$[M + H]^+$ = 944.3 |

TABLE 8-continued
Compounds and intermediates made according to Example 8.3 for Compound 86.
| Cmd No. | Structure | LCMS |
|---|---|---|
| 113 | 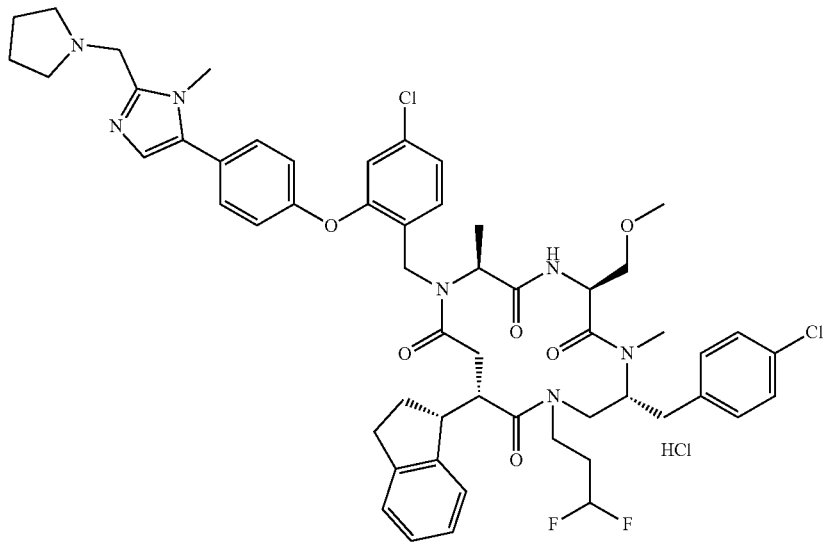 [SMILES: COC[C@@H]1NC(=O)[C@H](C)N(Cc2ccc(Cl)cc2Oc2ccc(-c3cnc(CN4CCCC4)n3C)cc2)C(=O)C[C@@H]([C@H]2CCc3ccccc32)C(=O)N(CCC(F)F)C[C@@H](Cc2ccc(Cl)cc2)N(C)C1=O ; Cl] | Analytical method 9<br>$t_R$ = 5.56 min<br>$[M + H]^+$ = 1026.4 |
| 114 | 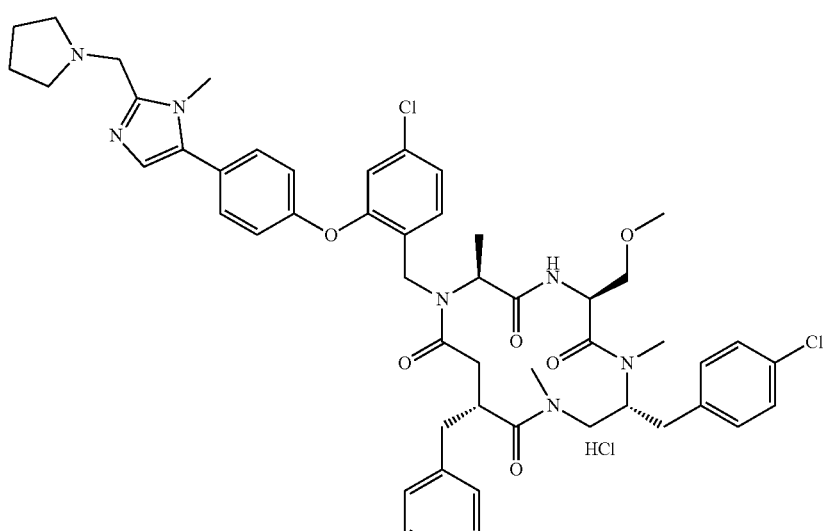 | Analytical method 13<br>$t_R$ = 4.49 min<br>$[M + H]^+$ = 936.4 |

TABLE 8-continued

Compounds and intermediates made according to Example 8.3 for Compound 86.

| Cmd No. | Structure | LCMS |
|---------|-----------|------|
| 115 | 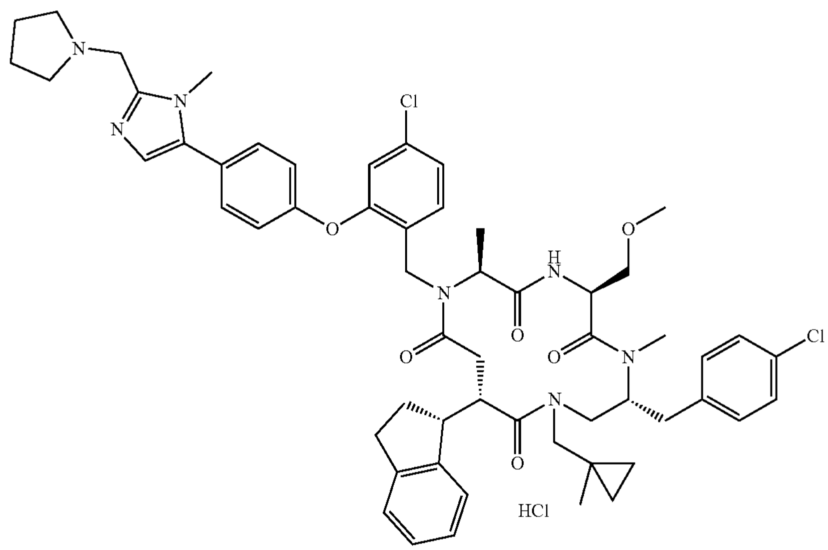 [SMILES: COC[C@@H]1NC(=O)[C@H](C)N(Cc2ccc(Cl)cc2Oc2ccc(-c3cnc(CN4CCCC4)n3C)cc2)C(=O)C[C@@H]([C@H]2CCc3ccccc32)C(=O)N(CC2(C)CC2)C[C@@H](Cc2ccc(Cl)cc2)N(C)C1=O ; Cl] | Analytical method 9<br>$t_R$ = 5.95 min<br>$[M + H]^+$ = 1016.5 |
| 116 | 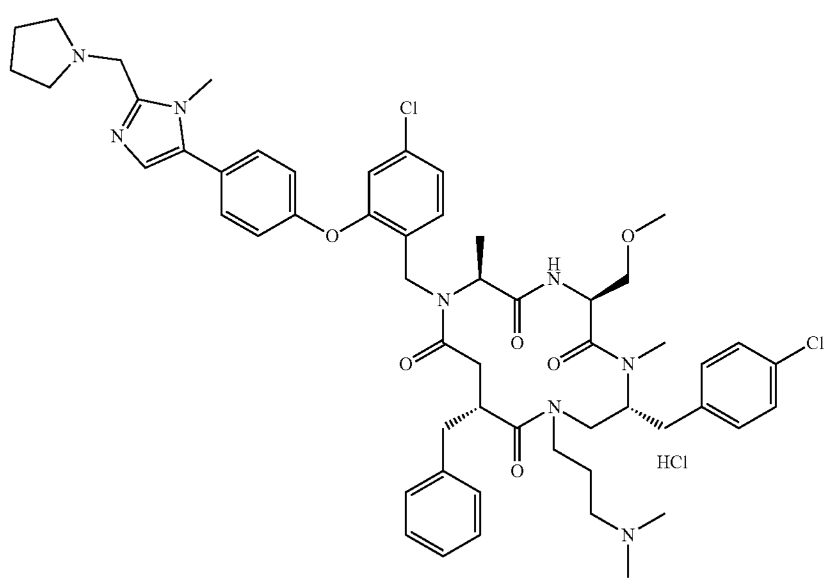 [SMILES: COC[C@@H]1NC(=O)[C@H](C)N(Cc2ccc(Cl)cc2Oc2ccc(-c3cnc(CN4CCCC4)n3C)cc2)C(=O)C[C@@H](Cc2ccccc2)C(=O)N(CCCN(C)C)C[C@@H](Cc2ccc(Cl)cc2)N(C)C1=O ; Cl] | Analytical method 9<br>$t_R$ = 3.75 min<br>$[M + H]^+$ = 1007.5 |

TABLE 8-continued

Compounds and intermediates made according to Example 8.3 for Compound 86.

| Cmd No. | Structure | LCMS |
|---|---|---|
| 117 | 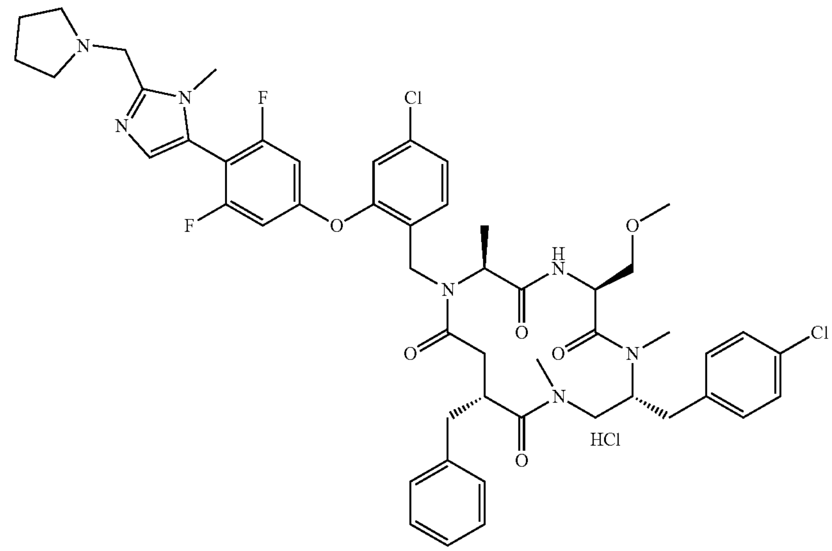 [SMILES: COC[C@@H]1NC(=O)[C@H](C)N(Cc2ccc(Cl)cc2Oc2cc(F)c(-c3cnc(CN4CCCC4)n3C)c(F)c2)C(=O)C[C@@H](Cc2ccccc2)C(=O)N(C)C[C@@H](Cc2ccc(Cl)cc2)N(C)C1=O ; Cl] | Analytical method 13<br>$t_R$ = 4.79 min<br>$[M + H]^+$ = 972.4 |
| 124 | 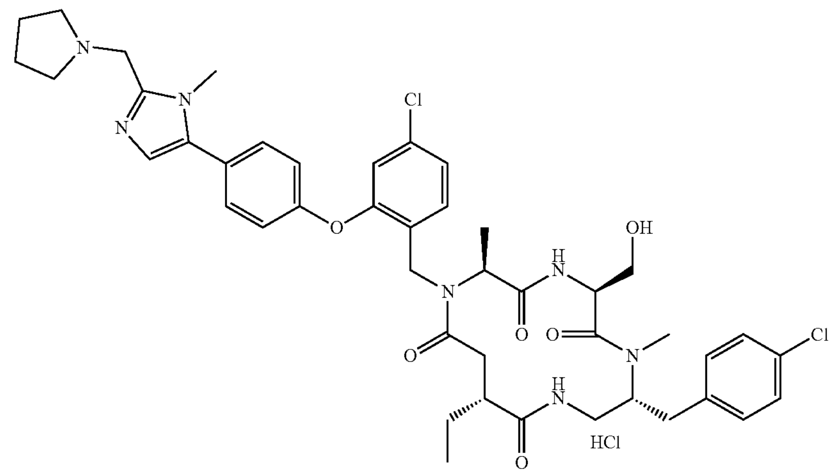 [SMILES: CC[C@@H]1CC(=O)N(Cc2ccc(Cl)cc2Oc2ccc(-c3cnc(CN4CCCC4)n3C)cc2)[C@@H](C)C(=O)N[C@@H](CO)C(=O)N(C)[C@H](Cc2ccc(Cl)cc2)CNC1=O ; Cl] | Analytical method 9<br>$t_R$ = 4.04 min<br>$[M + H]^+$ = 846.3 |
| 125 | 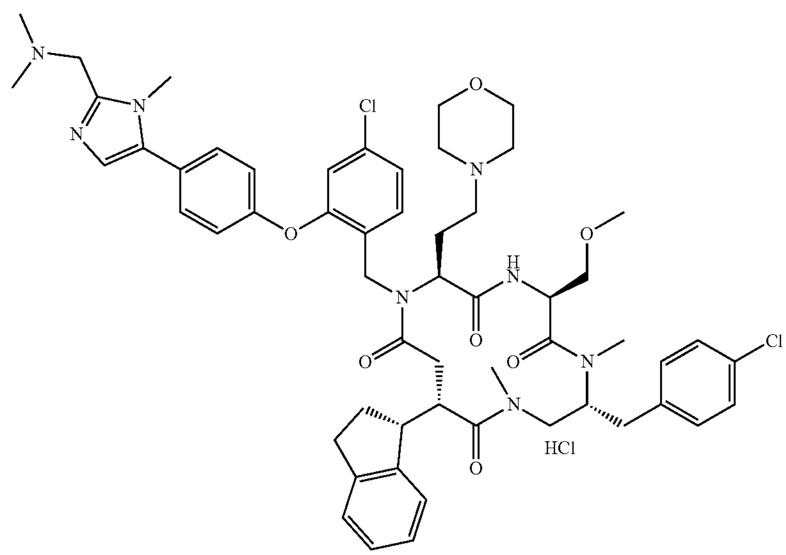 [SMILES: COC[C@@H]1NC(=O)[C@H](CCN2CCOCC2)N(Cc2ccc(Cl)cc2Oc2ccc(-c3cnc(CN(C)C)n3C)cc2)C(=O)C[C@@H]([C@H]2CCc3ccccc32)C(=O)N(C)C[C@@H](Cc2ccc(Cl)cc2)N(C)C1=O ; Cl] | Analytical method 9<br>$t_R$ = 4.26 min<br>$[M + H]^+$ = 1035.4 |

TABLE 8-continued

Compounds and intermediates made according to Example 8.3 for Compound 86.

| Cmd No. | Structure | LCMS |
|---|---|---|
| 127 | 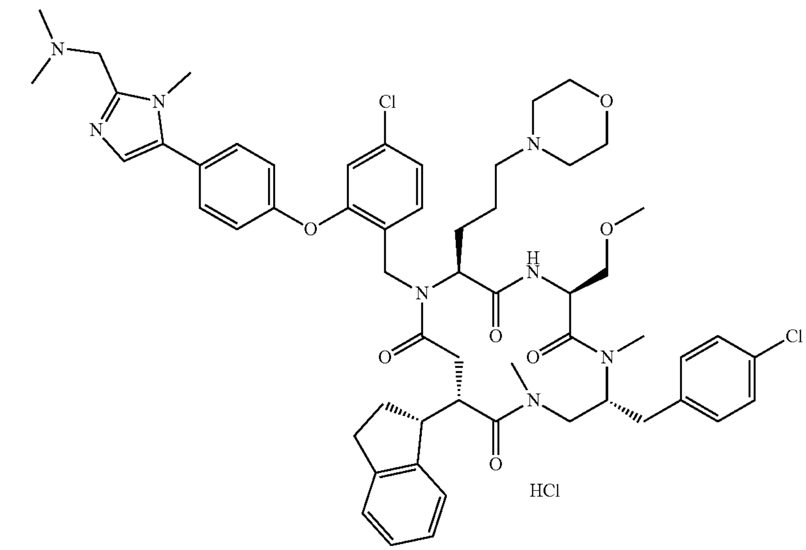 [SMILES: COC[C@@H]1NC(=O)[C@H](CCCN2CCOCC2)N(Cc2ccc(Cl)cc2Oc2ccc(-c3cnc(CN(C)C)n3C)cc2)C(=O)C[C@@H]([C@H]2CCc3ccccc32)C(=O)N(C)C[C@@H](Cc2ccc(Cl)cc2)N(C)C1=O ; Cl] | Analytical method 9<br>$t_R$ = 4.31 min<br>$[M + H]^+$ = 1049.5 |
| 128 | 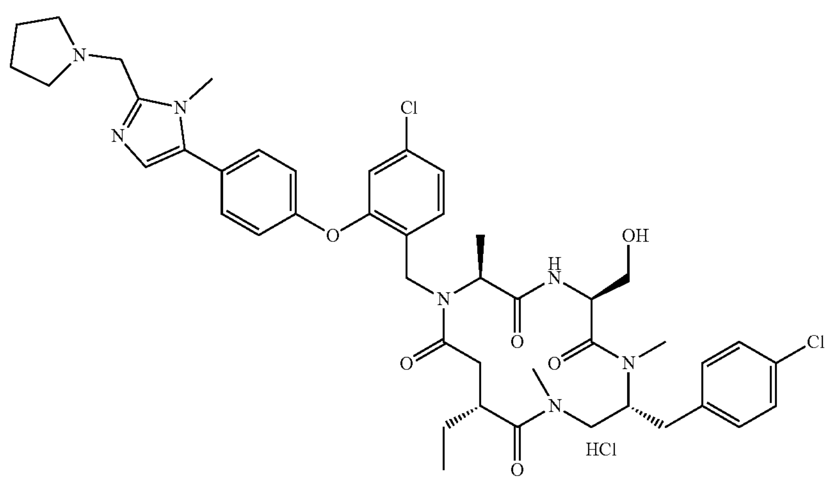 [SMILES: CC[C@@H]1CC(=O)N(Cc2ccc(Cl)cc2Oc2ccc(-c3cnc(CN4CCCC4)n3C)cc2)[C@@H](C)C(=O)N[C@@H](CO)C(=O)N(C)[C@H](Cc2ccc(Cl)cc2)CN(C)C1=O ; Cl] | Analytical method 9<br>$t_R$ = 4.46 min<br>$[M + H]^+$ = 860.3 |
| 131 | 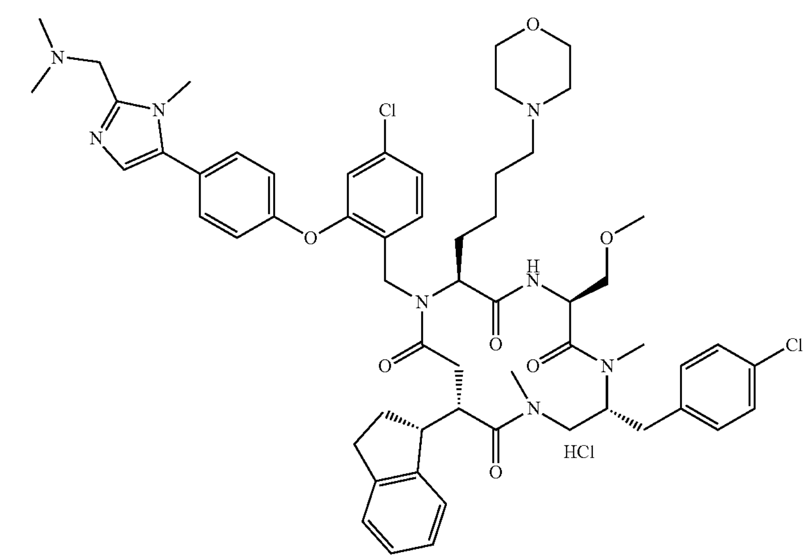 [SMILES: COC[C@@H]1NC(=O)[C@H](CCCCN2CCOCC2)N(Cc2ccc(Cl)cc2Oc2ccc(-c3cnc(CN(C)C)n3C)cc2)C(=O)C[C@@H]([C@H]2CCc3ccccc32)C(=O)N(C)C[C@@H](Cc2ccc(Cl)cc2)N(C)C1=O ; Cl] | Analytical method 9<br>$t_R$ = 4.37 min<br>$[M + H]^+$ = 1063.5 |

TABLE 8-continued

Compounds and intermediates made according to Example 8.3 for Compound 86.

| Cmd No. | Structure | LCMS |
|---|---|---|
| 132A | 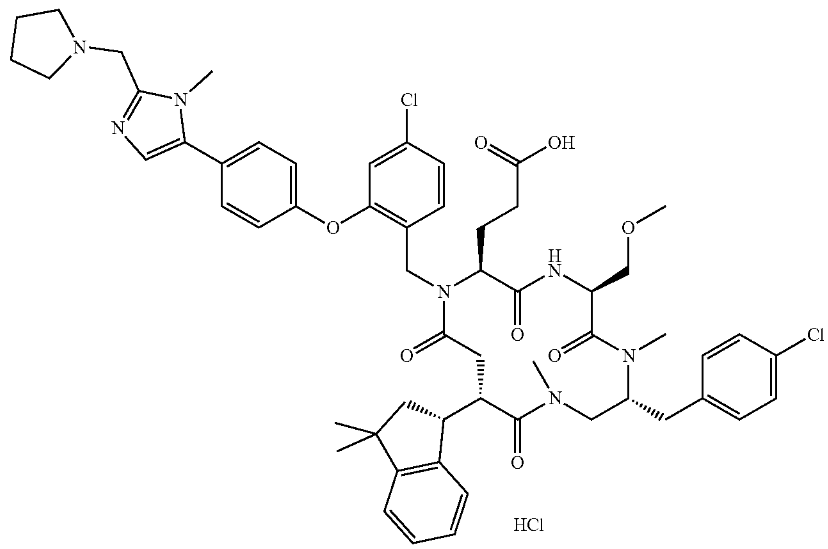 [SMILES: COC[C@@H]1NC(=O)[C@H](CCC(=O)O)N(Cc2ccc(Cl)cc2Oc2ccc(-c3cnc(CN4CCCC4)n3C)cc2)C(=O)C[C@@H]([C@H]2CC(C)(C)c3ccccc32)C(=O)N(C)C[C@@H](Cc2ccc(Cl)cc2)N(C)C1=O ; Cl] | Analytical method 9<br>$t_R$ = 5.28 min<br>$[M + H]^+$ = 1048.4 |
| 134 | 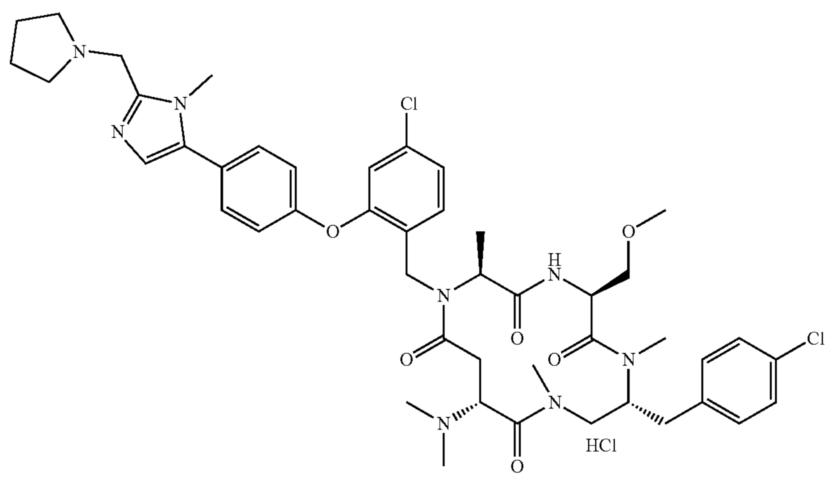 [SMILES: COC[C@@H]1NC(=O)[C@H](C)N(Cc2ccc(Cl)cc2Oc2ccc(-c3cnc(CN4CCCC4)n3C)cc2)C(=O)C[C@@H](N(C)C)C(=O)N(C)C[C@@H](Cc2ccc(Cl)cc2)N(C)C1=O ; Cl] | Analytical method 9<br>$t_R$ = 3.24 min<br>$[M + H]^+$ = 889.4 |
| 135 | 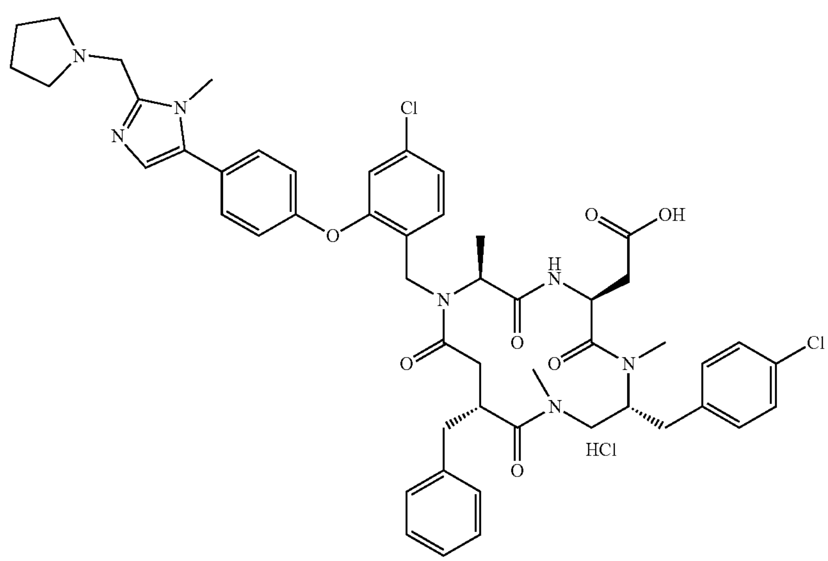 [SMILES: C[C@H]1C(=O)N[C@@H](CC(=O)O)C(=O)N(C)[C@H](Cc2ccc(Cl)cc2)CN(C)C(=O)[C@H](Cc2ccccc2)CC(=O)N1Cc1ccc(Cl)cc1Oc1ccc(-c2cnc(CN3CCCC3)n2C)cc1 ; Cl] | Analytical method 9<br>$t_R$ = 4.83 min<br>$[M + H]^+$ = 950.3 |

Example 8.4: Synthesis of (3R,7S,10S,13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-3-(pyridin-3-ylmethyl)-1,6,9,12-tetraazabicyclo[11.3.1]heptadecane-2,5,8,11-tetraone hydrochloride (Compound 19)
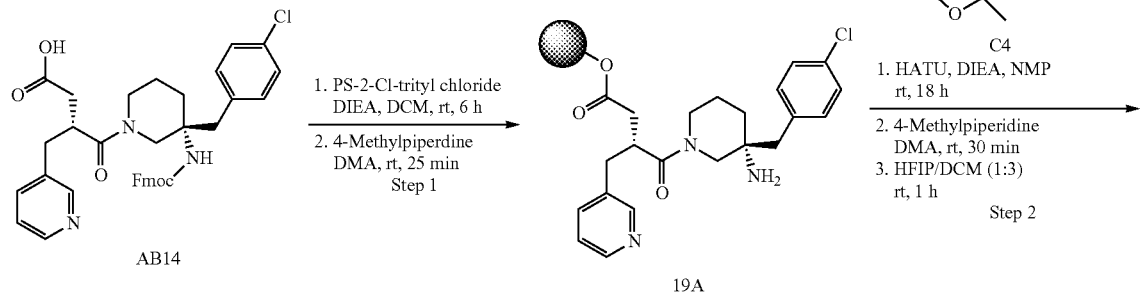
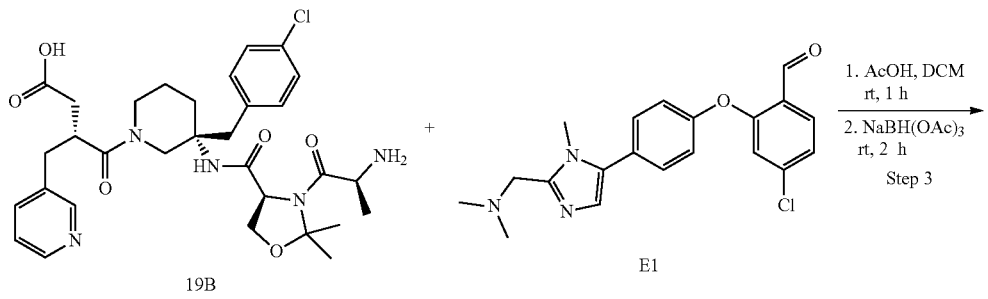
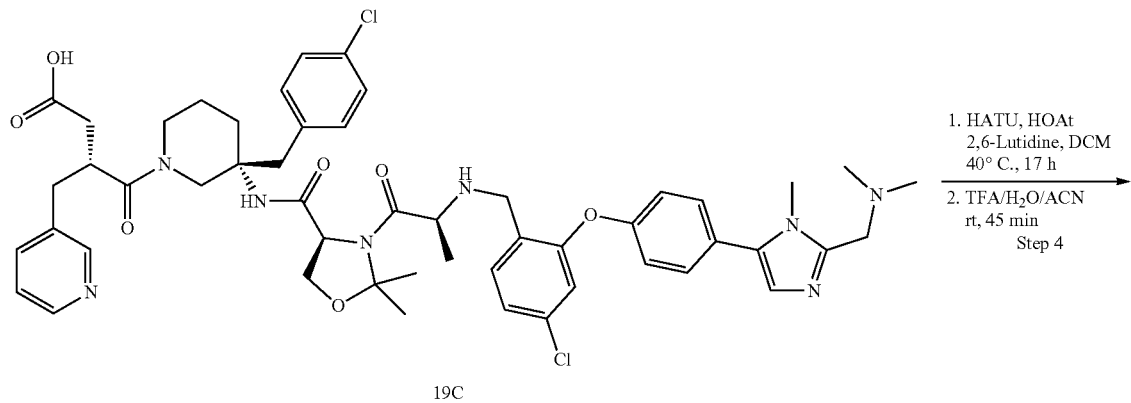

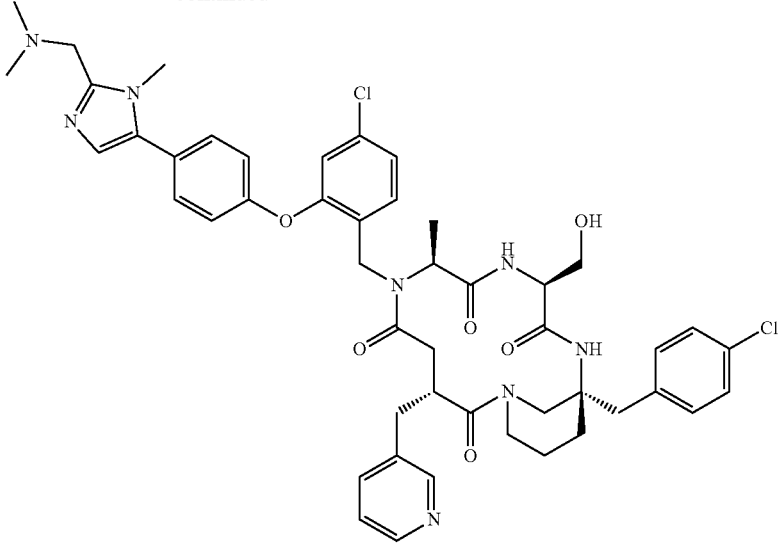

Compound 19

Step 1. PS-2-chlorotrityl (R)-4-((R)-3-amino-3-(4-chlorobenzyl)piperidin-1-yl)-4-oxo-3-(pyridin-3-ylmethyl)-butanoate (19A)

Step 1-1: PS-2-chlorotrityl chloride (653 mg, 1.044 mmol) was washed thoroughly with DCM. AB14 (0.856 g, 1.115 mmol) was dissolved in DCM (25 mL) and DIEA (1.168 ml, 6.69 mmol). The solution was added to the resin and the suspension was shaken at rt for 6 h. The resin was drained and then thoroughly washed sequentially with DCM/MeOH/DIPEA (17:2:1), DCM, DMA, and DCM.

Step 1-2: 4-Methylpiperidine/DMA (1:4) (20 mL) was added to the resin from Step 1-1. The suspension was shaken for 5 min at rt, and then the resin was drained. This treatment was repeated four times. The collected cleavage solutions were used for determination of the loading by UV-spectrometry. The resin was thoroughly washed sequentially with DMA (3×), DCM (3×), DMA (3×), and DCM (3×), and then dried in vacuo to give 19A (817 μmol, 73% yield).

Step 2. (R)-4-((R)-3-((S)-3-(L-Alanyl)-2,2-dimethyloxazolidine-4-carboxamido)-3-(4-chlorobenzyl)piperidin-1-yl)-4-oxo-3-(pyridin-3-ylmethyl)butanoic acid (19B)

Step 2-1: 19A (409 μmol) was washed with NMP (2×10 mL). A solution of Fmoc-Ala-Ser[psi(Me,Me)pro]-OH (C4) (0.323 g, 736 μmol), HATU (0.280 g, 736 μmol) and DIEA (0.157 ml, 899 μmol) in NMP (8 mL) was shaken for 2 min, and then added to the resin. The resulting suspension was shaken for 18 h at rt and the resin was drained. A solution of Fmoc-Ala-Ser[psi(Me,Me)pro]-OH (0.323 g, 736 μmol), HATU (0.280 g, 736 μmol) and DIEA (0.157 mL, 899 μmol) in NMP (8 mL) was shaken for 2 min, and then added to the resin. The resulting suspension was shaken for 18 h at rt. The resin was drained and washed with DMA (3×). A solution of Ac₂O/pyridine/DMA (1:1:8) (15 mL) was added and the reaction was shaken for 15 min at rt. The resin was drained, and then washed with DMA (3×).

Step 2-2: 4-Methylpiperidine/DMA (1:4) (15 mL) was added to the resin from Step 2-1. The resulting suspension was shaken for 10 min at rt, and then the resin was drained. This treatment was repeated twice. The resin was washed with DMA (3×) and DCM (5×).

Step 2-3: HFIP/DCM (1:3) (10 mL) was added to the resin from Step 2-2 and the suspension was shaken for 20 min at rt. The cleavage solution was filtered off and collected. This procedure was repeated two times. Finally, the resin was washed with DCM (2×). The combined cleavage and washing solutions were concentrated to dryness in vacuo and the resulting residue was lyophilized from t-BuOH/H₂O (4:1) to yield 19B (assumed to be 409 μmol) as a yellowish solid. Analytical method 10; $t_R$=0.70; [M+H]⁺=614.3.

Step 3. (R)-4-((R)-3-((S)-3-((4-Chloro-2-(4-(2-((dimethylamino)methyl)-1-methyl-1H-imidazol-5-yl)phenoxy)-benzyl)-L-alanyl)-2,2-dimethyloxazolidine-4-carboxamido)-3-(4-chlorobenzyl)piperidin-1-yl)-4-oxo-3-(pyridin-3-ylmethyl)butanoic acid hydrochloride (19C)

19B (100 μmol) and E1 (44.4 mg, 120 μmol) were dissolved in a mixture of DCM (7 mL) and AcOH (0.023 mL, 400 μmol). The resulting solution was stirred for 1 h at rt, and then NaBH(OAc)₃ (106 mg, 500 μmol) was added. The reaction mixture was stirred for 2 h at rt, and concentrated to dryness in vacuo. The crude product was purified by preparative reverse-phase HPLC (eluent A: 0.01 M HCl in H₂O; eluent B: ACN). Pure fractions were combined and lyophilized to afford 19C (75 mg, 67 μmol, 67% yield for 2 steps). Analytical method 14; $t_R$=2.84 min; [M+H]⁺=967.4.

Step 4. (3R,7S,10S,13R)-6-(4-Chloro-2-(4-(2-((dimethylamino)methyl)-1-methyl-1H-imidazol-5-yl)phenoxy)-benzyl)-13-(4-chlorobenzyl)-10-(hydroxymethyl)-7-methyl-3-(pyridin-3-ylmethyl)-1,6,9,12-tetraazabicyclo-[11.3.1]heptadecane-2,5,8,11-tetraone hydrochloride (Compound 19)

Step 4-1: To a solution of 19C (75 mg, 0.067 mmol) in DCM (67 ml) was added HOAt (13.75 mg, 0.101 mmol), HATU (102 mg, 0.269 mmol) and 2,6-lutidine (0.235 ml, 2.020 mmol). The resulting mixture was stirred for 17 h at 40° C., and then concentrated in vacuo. The residue was partitioned between EtOAc (100 mL) and 5% aq. Na$_2$CO$_3$.

The organic phase was washed with 5% aq. Na$_2$CO$_3$ (5 mL) and brine, dried over Na$_2$SO$_4$, filtered, and concentrated to dryness in vacuo.

Step 4-2: The residue was dissolved in 95% aq. TFA/ACN/H$_2$O (2:5:3) and the resulting solution was stirred at rt for 45 min and then concentrated to dryness in vacuo. The crude product was purified by preparative reverse-phase HPLC (eluent A: 0.01 M HCl in H$_2$O; eluent B: ACN). Pure fractions were combined and lyophilized to afford Compound 19 (34.5 mg, 0.030 mmol, 45% yield) as a white solid. Analytical method 14; t$_R$=2.97 min; [M+H]$^+$=909.4.

The compounds and intermediates shown in Table 9 were synthesized according to the procedure described in Example 8.4 for Compound 19 from the respective intermediates shown in Table 4, Table 5, and Table 7.

TABLE 9

Compounds and intermediates made according to Example 8.4 for Compound 19.

| Cmd No. | Structure | LCMS |
|---|---|---|
| 16 | 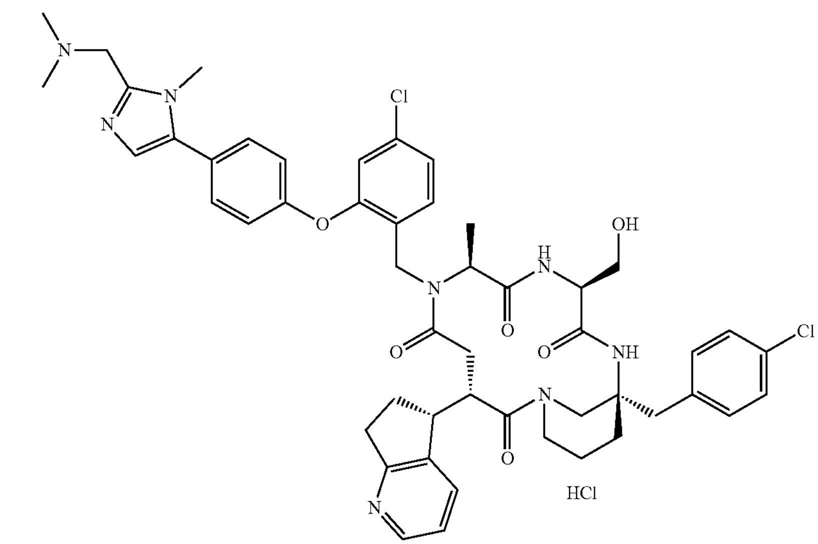 [SMILES: C[C@H]1C(=O)N[C@@H](CO)C(=O)N[C@@]2(Cc3ccc(Cl)cc3)CCCN(C2)C(=O)[C@H]([C@H]2CCc3ncccc32)CC(=O)N1Cc1ccc(Cl)cc1Oc1ccc(-c2cnc(CN(C)C)n2C)cc1 ; Cl] | Analytical method 14<br>t$_R$ = 3.04 min<br>[M + H]$^+$ = 935.4 |
| 47 | 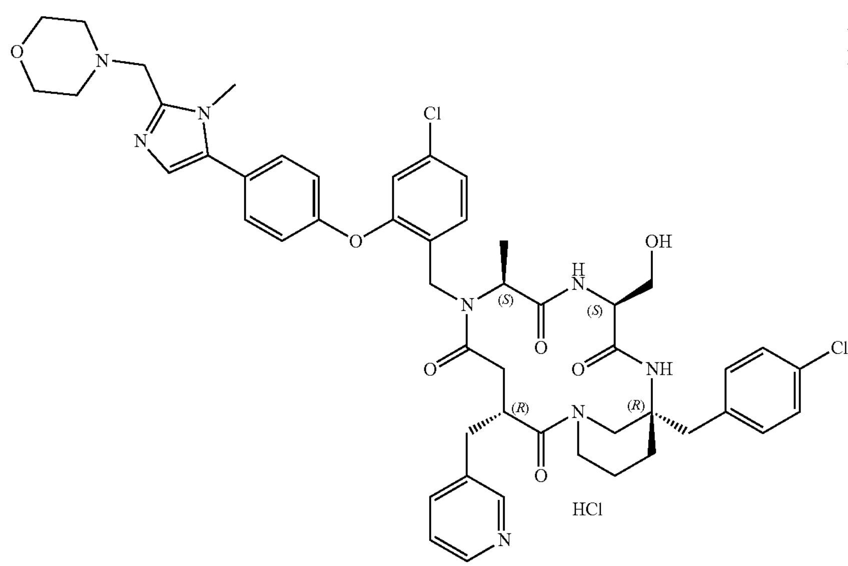 | Analytical method 14<br>t$_R$ = 3.14 min<br>[M + H]$^+$ = 951.4 |

TABLE 9-continued

Compounds and intermediates made according to Example 8.4 for Compound 19.

| Cmd No. | Structure | LCMS |
|---|---|---|
| 70 | 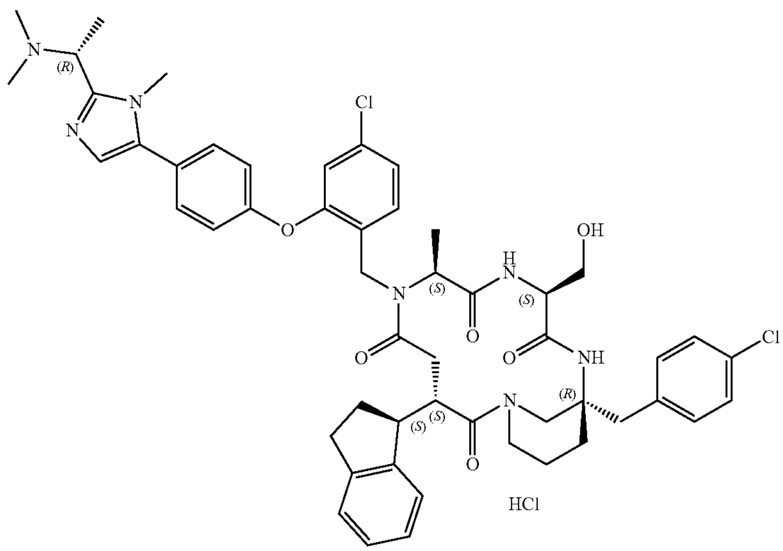 | Analytical method 14<br>$t_R$ = 5.16 min<br>$[M + H]^+$ = 948.3 |
| 74 | 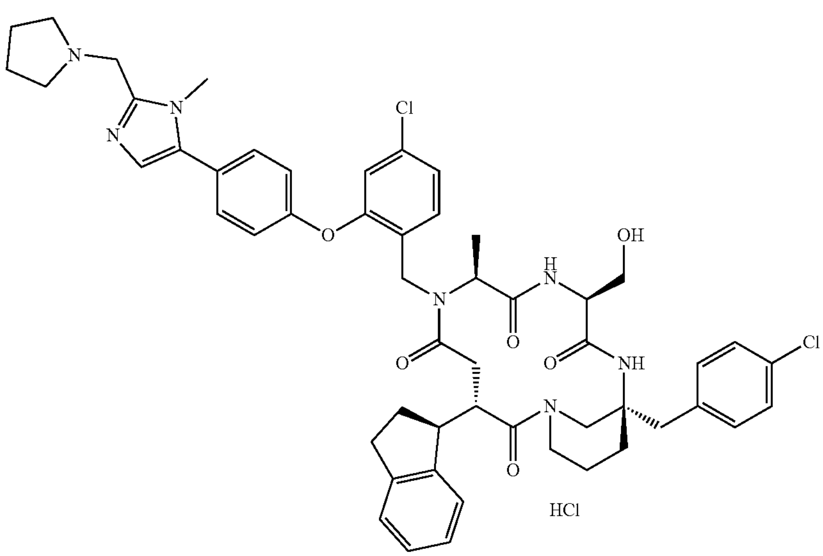 [SMILES: C[C@H]1C(=O)N[C@@H](CO)C(=O)N[C@@]2(Cc3ccc(Cl)cc3)CCCN(C2)C(=O)[C@H]([C@@H]2CCc3ccccc32)CC(=O)N1Cc1ccc(Cl)cc1Oc1ccc(-c2cnc(CN3CCCC3)n2C)cc1 ; Cl] | Analytical method 14<br>$t_R$ = 5.06 min<br>$[M + H]^+$ = 960.3 |

TABLE 9-continued
Compounds and intermediates made according to Example 8.4 for Compound 19.
| Cmd No. | Structure | LCMS |
|---|---|---|
| 77A | 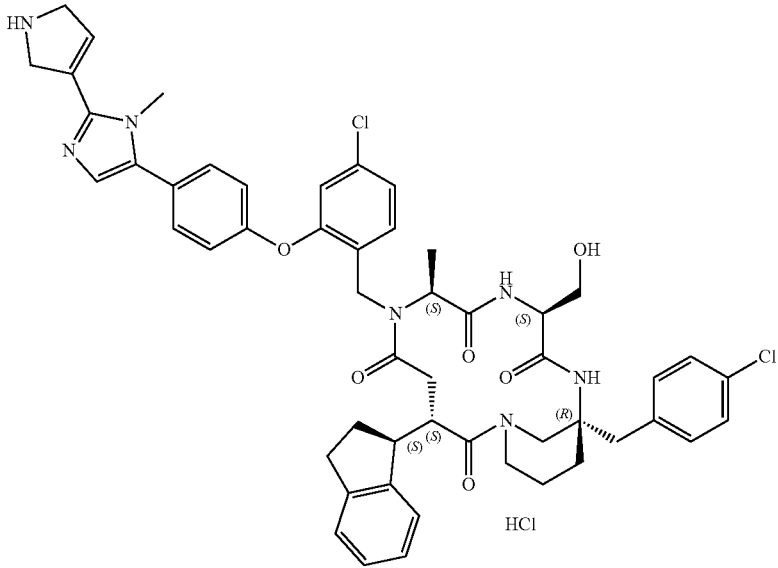 | Analytical method 14<br>$t_R$ = 4.43 min<br>$[M + H]^+$ = 944.4 |
| 81 | 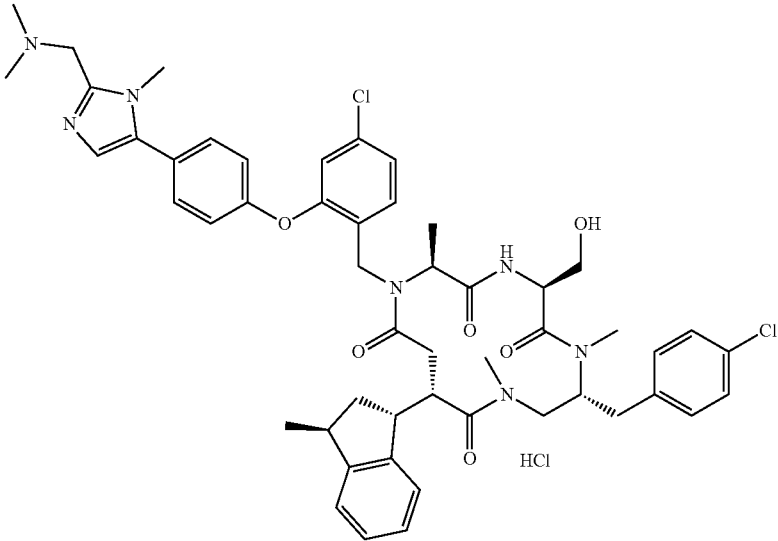 [SMILES: C[C@H]1C[C@H]([C@@H]2CC(=O)N(Cc3ccc(Cl)cc3Oc3ccc(-c4cnc(CN(C)C)n4C)cc3)[C@@H](C)C(=O)N[C@@H](CO)C(=O)N(C)[C@H](Cc3ccc(Cl)cc3)CN(C)C2=O)c2ccccc21 ; Cl] | Analytical method 14<br>$t_R$ = 4.92 min<br>$[M + H]^+$ = 936.4 |

TABLE 9-continued

Compounds and intermediates made according to Example 8.4 for Compound 19.

| Cmd No. | Structure | LCMS |
|---|---|---|
| 84 | 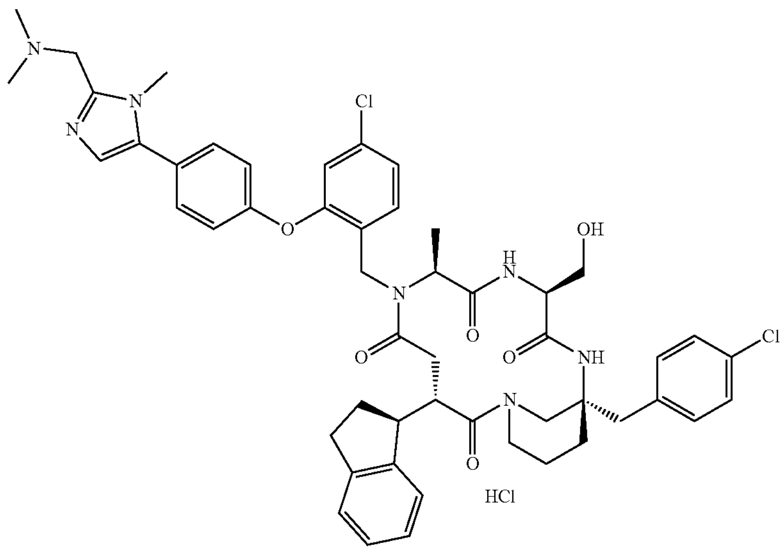 [SMILES: C[C@H]1C(=O)N[C@@H](CO)C(=O)N[C@@]2(Cc3ccc(Cl)cc3)CCCN(C2)C(=O)[C@H]([C@@H]2CCc3ccccc32)CC(=O)N1Cc1ccc(Cl)cc1Oc1ccc(-c2cnc(CN(C)C)n2C)cc1 ; Cl] | Analytical method 14<br>$t_R$ = 5.03 min<br>$[M + H]^+$ = 934.3 |

Example 8.5: Synthesis of (3R,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-7-(2-fluoroethyl)-10-(methoxymethyl)-1,6,9,12-tetraazabicyclo[11.3.1]heptadecane-2,5,8,11-tetraone hydrochloride (Compound 105)

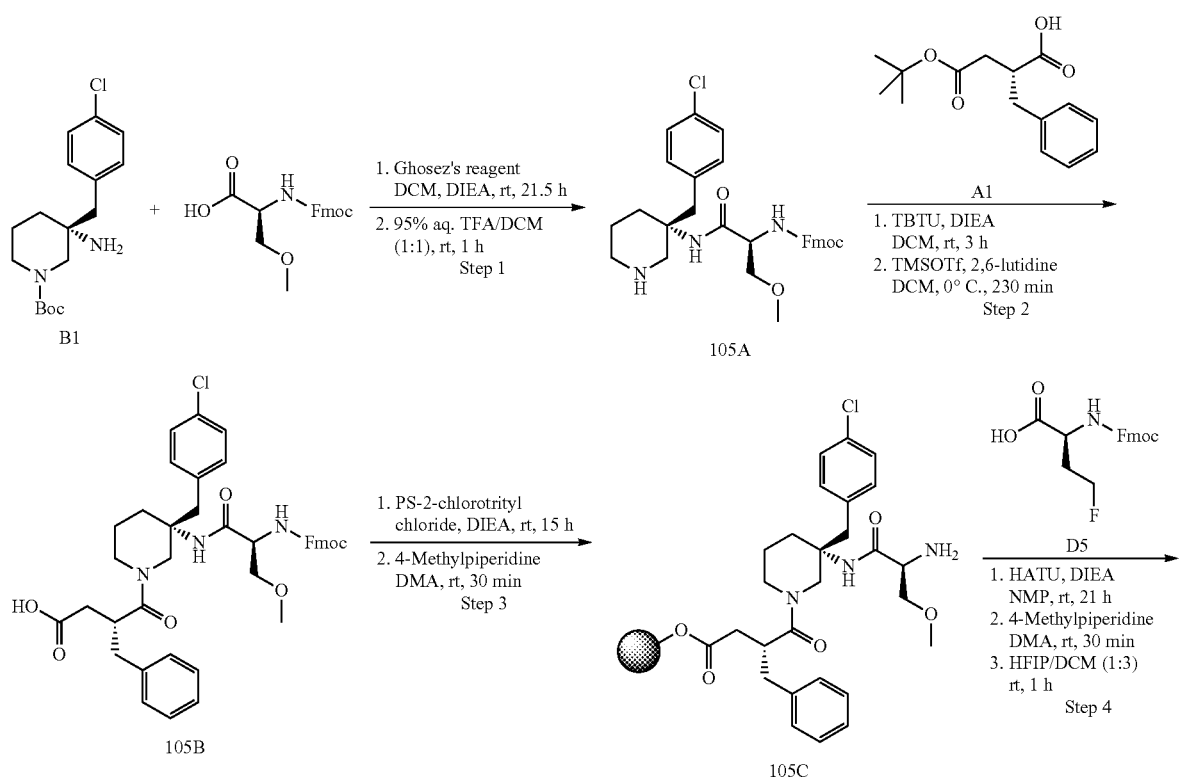

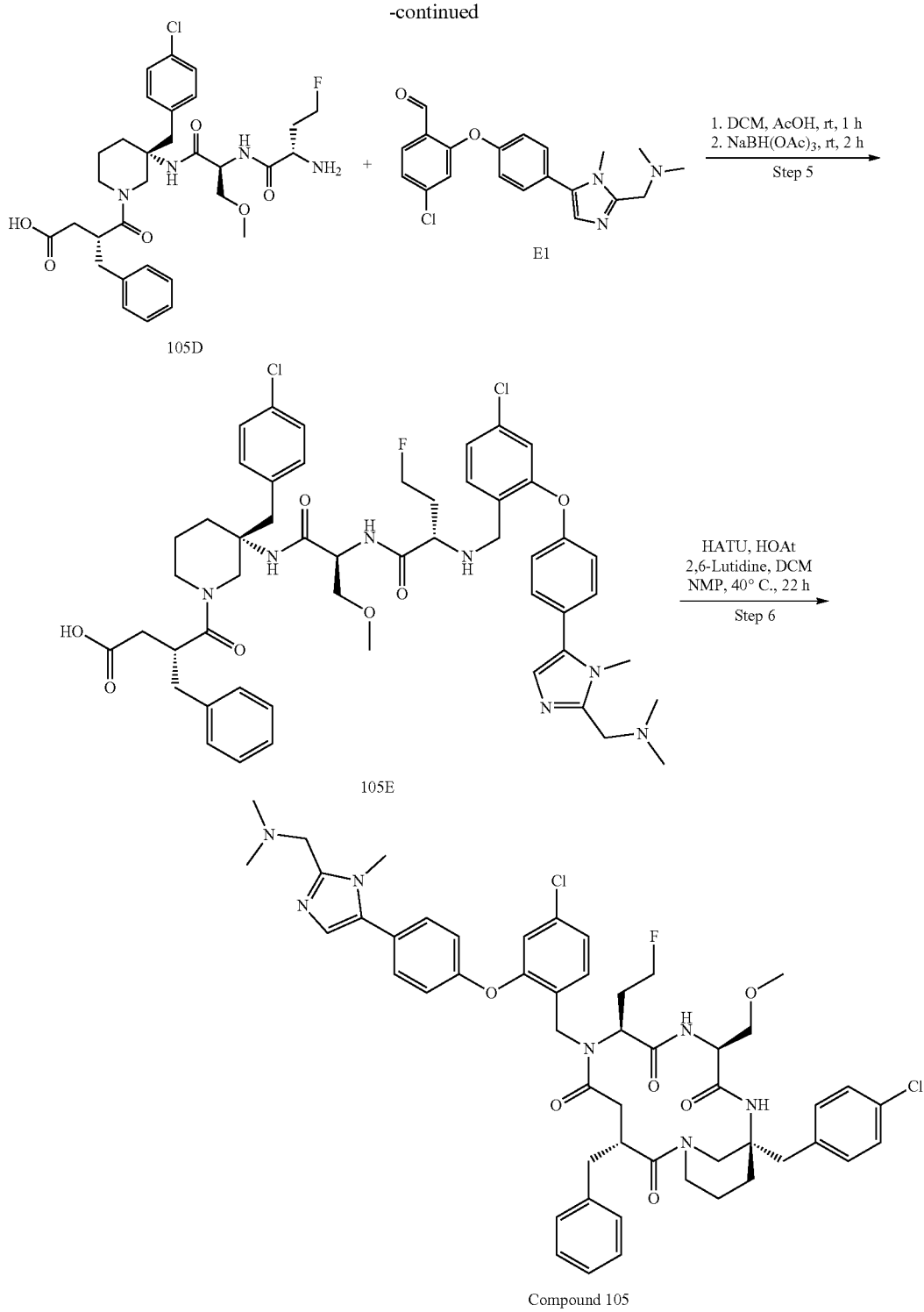

Step 1. (9H-Fluoren-9-yl)methyl ((S)-1-(((R)-3-(4-chlorobenzyl)piperidin-3-yl)amino)-3-methoxy-1-oxopropan-2-yl)carbamate (105A)

Step 1-1: To Fmoc-Ser(Me)-OH (0.683 g, 2.000 mmol) in DCM (10 mL) was added Ghosez's reagent (0.265 mL, 2.000 mmol). The resulting mixture was stirred for 45 min at rt, and then a solution of B1 (0.650 g, 2.00 mmol) and DIEA (0.419 mL, 2.400 mmol) in DCM (5 mL) was added. The reaction mixture was stirred for 5 h 40 min at rt, and then DIEA (0.105 mL, 0.600 mmol) and a solution of Fmoc-Ser(Me)-OH (0.137 g, 0.400 mmol) and Ghosez's reagent (0.053 mL, 0.400 mmol) in DCM (2 mL) (preactivation time: 30 min) were added. The resulting mixture was stirred for 15 h 50 min at rt, and then partitioned between EtOAc (60 mL) and 5% aq. NaHCO₃ (10 mL). The organic phase was washed with 5% NaHCO$_3$ (2×10 mL) and brine (10 mL), dried over Na$_2$SO$_4$, filtered, and concentrated to dryness in vacuo. The crude product was purified by flash silica gel chromatography (eluent A: heptane; eluent B: EtOAc). Pure fractions were combined and concentrated to dryness in vacuo to afford a white foam (1.130 g, 1.743 mmol, 87% yield). Analytical method 10; $t_R$=1.52 min; [M+H]$^+$=648.4.

Step 1-2: The white foam from Step 1-1 (1.743 mmol) was dissolved in 95% aq. TFA/DCM (1:1) (20 mL). The resulting solution was stirred for 1 h at rt, and then concentrated to dryness in vacuo to afford 105A (assumed to be 1.743 mmol) as a white foam. Analytical method 10; $t_R$=0.94 min; [M+H]$^+$=548.4.

Step 2. (R)-4-((R)-3-((S)-2-((((9H-Fluoren-9-yl)methoxy)carbonyl)amino)-3-methoxypropanamido)-3-(4-chlorobenzyl)piperidin-1-yl)-3-benzyl-4-oxobutanoic acid (105B)

Step 2-1: A1 (0.461 g, 1.743 mmol) and TBTU (0.588 g, 1.831 mmol) were dissolved in DCM (10 mL) and DIEA (0.365 mL, 2.092 mmol) and was stirred for 30 min at rt. A solution of 105A (1.743 mmol) in DCM (10 mL) and DIEA (0.761 mL, 4.36 mmol) was then added and the reaction mixture was stirred for 3 h at rt, and then the DCM was removed in vacuo. The resulting residue was partitioned between EtOAc (60 mL) and 5% aq. NaHCO$_3$ (15 mL). The organic phase was washed with 5% aq. NaHCO$_3$ (3×10 mL) and brine (10 mL), dried over Na$_2$SO$_4$, filtered, and concentrated to dryness in vacuo to afford a white foam. Analytical method 10; $t_R$=1.57 min; [M+H]$^+$=794.7.

Step 2-2: To a solution of the white foam from Step 2-1 (1.74 mmol) and 2,6-lutidine (1.623 mL, 13.94 mmol) in DCM (20 mL) at 0° C. was added TMSOTf (1.259 mL, 6.97 mmol) dropwise and the resulting mixture was stirred for 3 h 50 min at 0° C. EtOAc (60 mL) and 5% aq. NaHCO$_3$ (5 mL) were added and the phases were separated. The organic phase was washed with 5% aq. NaHCO$_3$ (3×5 mL), 5% aq. KHSO$_4$ (3×10 mL) and brine (10 mL), dried over Na$_2$SO$_4$, filtered, and concentrated to dryness in vacuo. The resulting residue was dissolved in DCM and the solution was concentrated to dryness in vacuo to afford 105B (assumed to be 1.74 mmol) as a yellowish foam. The crude product was used in the next step without further purification. Analytical method 10; $t_R$=1.41 min; [M+H]$^+$=738.4.

Step 3. PS-2-chlorotrityl (R)-4-((R)-3-((S)-2-amino-3-methoxypropanamido)-3-(4-chlorobenzyl)piperidin-1-yl)-3-benzyl-4-oxobutanoate (105C)

Step 3-1: PS-2-chlorotrityl chloride resin (2.72 g, 4.36 mmol) was washed with DCM (3×). A solution of 105B (1.742 mmol) dissolved in DCM (20 mL) and DIEA (1.825 mL, 10.45 mmol) was added to the resin and the resulting suspension was shaken at rt for 15 h. The resin was drained and then thoroughly washed sequentially with DCM/MeOH/DIPEA (17:2:1) (3×), DCM (3×) and DMA (2×).

Step 3-2: 4-Methylpiperidine/DMA (1:4) (20 mL) was added to the resin from Step 3-1. The resulting suspension was shaken for 10 min at rt, and then the resin was drained. This treatment was repeated twice. The resin was washed with DMA (3×) and DCM (3×) and dried in vacuo to afford 105C (1.32 mmol, 66% yield for 3 steps) (3.65 g; loading determined to be 0.361 mmol/g by UV-spectrometry).

Step 4. (R)-4-((R)-3-((S)-2-((S)-2-Amino-4-fluorobutanamido)-3-methoxypropanamido)-3-(4-chlorobenzyl)piperidin-1-yl)-3-benzyl-4-oxobutanoic acid (105D)

Step 4-1: To a solution of D5 (0.103 g, 300 µmol) in NMP (3 mL) were added HATU (0.114 g, 300 µmol) and DIEA (0.058 ml, 330 µmol). The resulting solution was stirred for 2 min at rt, and then added to the resin 105C (after being washed with NMP (3×)). The resulting suspension was shaken for 21 h at rt. The resin was drained and washed with DMA (3×). A solution of Ac$_2$O/Pyridine/DMA (1:1:8) (3 mL) was added and the reaction mixture was shaken for 15 min at rt. The resin was drained, then washed with DMA (3×).

Step 4-2: 4-Methylpiperidine/DMA (1:4) (3 mL) was added to the resin from Step 4-1. The resulting suspension was shaken for 10 min at rt, and then the resin was drained. This treatment was repeated twice. The resin was washed with DMA (3×) and DCM (3×).

Step 4-3: HFIP/DCM (1:3) (3 mL) was added to the resin from Step 4-2 and the resulting suspension was shaken for 20 min at rt. The cleavage solution was filtered off and collected. This procedure was repeated two times. The resin was then washed with DCM (2×) and the combined cleavage and washing solutions were concentrated to dryness in vacuo. The crude residue was dissolved in DCM and the resulting solution was concentrated to dryness in vacuo. This procedure was repeated three times. After drying using high vacuum, 105D (~100 µmol) was obtained as a colorless oil. The crude product was used in the next step without further purification. Analytical method 10; $t_R$=0.85; [M+H]$^+$=619.5.

Step 5. (R)-3-Benzyl-4-((R)-3-((S)-2-((S)-2-((4-chloro-2-(4-(2-((dimethylamino)methyl)-1-methyl-1H-imidazol-5-yl)phenoxy)benzyl)amino)-4-fluorobutanamido)-3-methoxypropanamido)-3-(4-chlorobenzyl)piperidin-1-yl)-4-oxobutanoic acid hydrochloride (105E)

105D (0.100 mmol) and E1 (44.6 mg, 0.120 mmol) were dissolved in a mixture of DCM (7 mL) and AcOH (0.023 ml, 0.402 mmol). The resulting solution was stirred for 1 h at rt and then NaBH(OAc)$_3$ (106 mg, 0.502 mmol) was added. The reaction mixture was stirred for 2 h at rt, and concentrated to dryness in vacuo. The crude product was purified by preparative reverse-phase HPLC (eluent A: 0.01 M HCl in H$_2$O; eluent B: ACN). Pure fractions were combined and lyophilized to afford 105E (93 mg, 0.086 mmol, 86% yield) as a white solid. Analytical method 10; $t_R$=0.90 min; [M+H]$^+$=972.7.

Step 6. ((3R,7S,10S,13R)-3-Benzyl-6-(4-chloro-2-(4-(2-((dimethylamino)methyl)-1-methyl-1H-imidazol-5-yl)phenoxy)benzyl)-13-(4-chlorobenzyl)-7-(2-fluoroethyl)-10-(methoxymethyl)-1,6,9,12-tetraazabicyclo-[11.3.1]heptadecane-2,5,8,11-tetraone hydrochloride (Compound 105)

To a solution of 105E in DCM (81 mL) and NMP (5 mL) was added HOAt (17.54 mg, 0.129 mmol), HATU (131 mg, 0.344 mmol) and 2,6-lutidine (0.300 ml, 2.58 mmol). The resulting mixture was stirred for 22 h at 40° C., and then concentrated in vacuo. The obtained residue was partitioned between EtOAc (50 mL) and 5% aq. $Na_2CO_3$ (5 mL). The organic phase was washed with 5% aq. $Na_2CO_3$ (3×5 mL) and brine (5 mL), dried over $Na_2SO_4$, filtered, and concentrated to dryness in vacuo. The crude product was purified by preparative reverse-phase HPLC (eluent A: 0.01 M HCl in $H_2O$; eluent B: ACN). Pure fractions were combined and lyophilized to afford Compound 105 (50.5 mg, 0.048 mmol 56% yield) as a white solid. Analytical method 14; $t_R$=5.29 min; $[M+H]^+$=954.4.

The compounds and intermediates shown in Table 10 were synthesized according to the procedure described in Example 8.5 for Compound 105 from the respective intermediates shown in Table 1, Table 3, Table 5, Table 6, and Table 7.

TABLE 10

Compounds and intermediates made according to Example 8.5 for Compound 105.

| Cmd No. | Structure | LCMS |
|---|---|---|
| 59 | 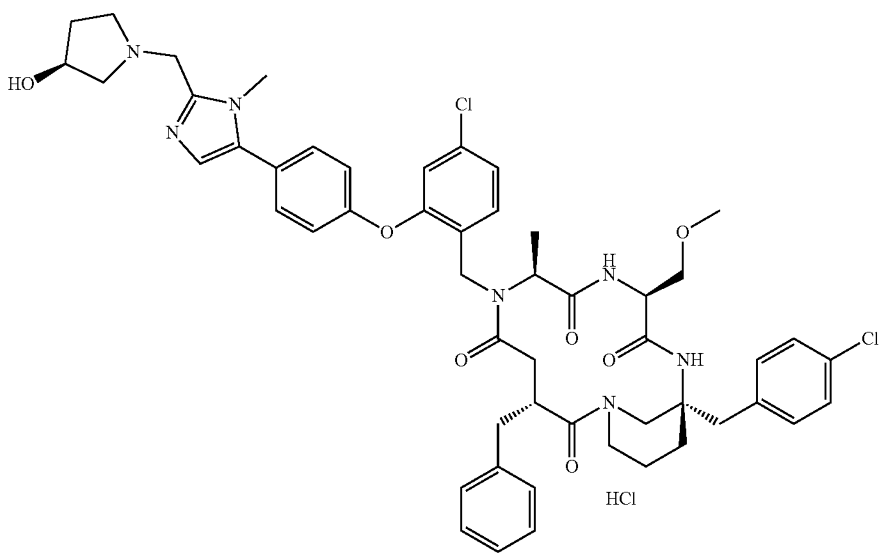 [SMILES: COC[C@@H]1NC(=O)[C@H](C)N(Cc2ccc(Cl)cc2Oc2ccc(-c3cnc(CN4CC[C@H](O)C4)n3C)cc2)C(=O)C[C@@H](Cc2ccccc2)C(=O)N2CCC[C@@](Cc3ccc(Cl)cc3)(C2)NC1=O ; Cl] | Analytical method 14<br>$t_R$ = 5.15 min<br>$[M + H]^+$ = 964.4 |
| 61 | 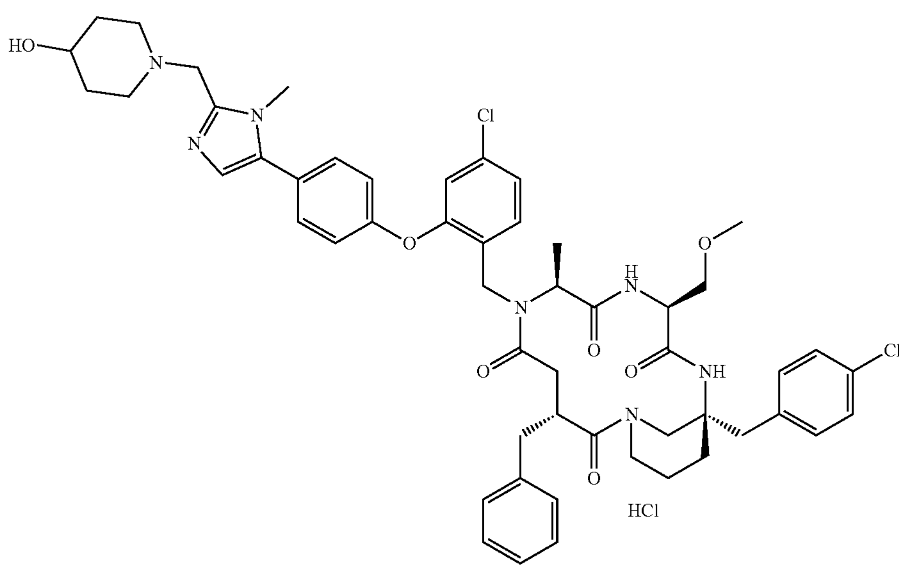 [SMILES: COC[C@@H]1NC(=O)[C@H](C)N(Cc2ccc(Cl)cc2Oc2ccc(-c3cnc(CN4CCC(O)CC4)n3C)cc2)C(=O)C[C@@H](Cc2ccccc2)C(=O)N2CCC[C@@](Cc3ccc(Cl)cc3)(C2)NC1=O ; Cl] | Analytical method 14<br>$t_R$ = 5.00 min<br>$[M + H]^+$ = 978.4 |

TABLE 10-continued
Compounds and intermediates made according to Example 8.5 for Compound 105.
| Cmd No. | Structure | LCMS |
|---|---|---|
| 72 | 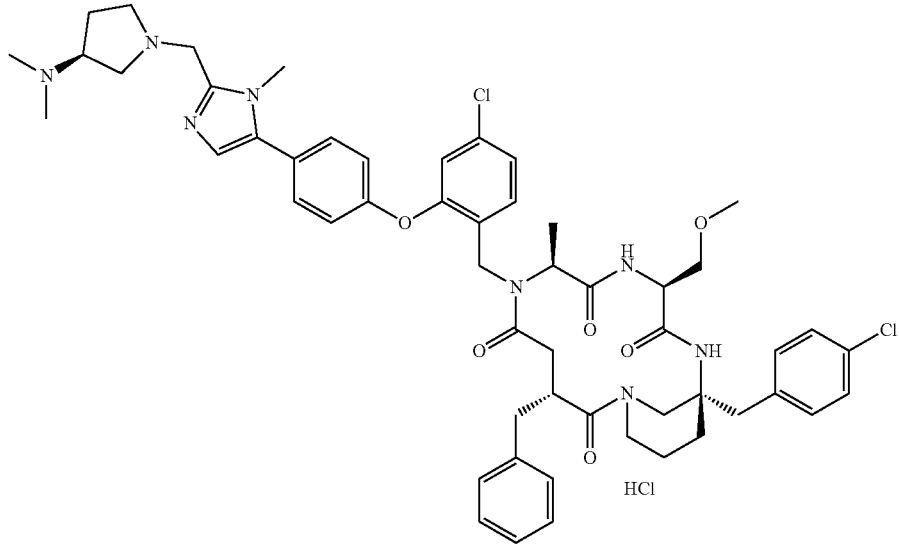 [SMILES: COC[C@@H]1NC(=O)[C@H](C)N(Cc2ccc(Cl)cc2Oc2ccc(-c3cnc(CN4CC[C@H](N(C)C)C4)n3C)cc2)C(=O)C[C@@H](Cc2ccccc2)C(=O)N2CCC[C@@](Cc3ccc(Cl)cc3)(C2)NC1=O ; Cl] | Analytical method 14<br>$t_R$ = 4.57 min<br>$[M + H]^+$ = 991.4 |
| 76 | 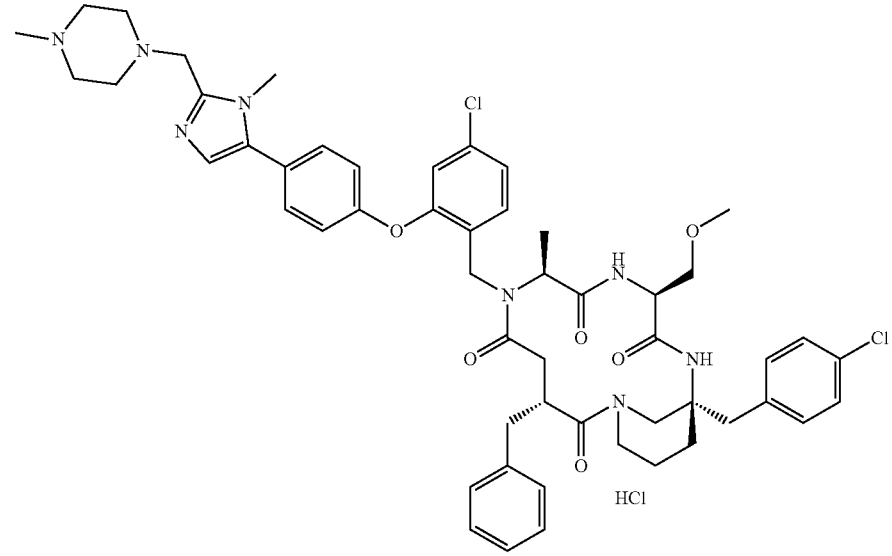 [SMILES: COC[C@@H]1NC(=O)[C@H](C)N(Cc2ccc(Cl)cc2Oc2ccc(-c3cnc(CN4CCN(C)CC4)n3C)cc2)C(=O)C[C@@H](Cc2ccccc2)C(=O)N2CCC[C@@](Cc3ccc(Cl)cc3)(C2)NC1=O ; Cl] | Analytical method 14<br>$t_R$ = 4.54 min<br>$[M + H]^+$ = 977.4 |

Example 8.6: Synthesis of (3R,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7-methyl-1,6,9,12-tetraazabicyclo[11.3.1]heptadecane-2,8,11-trione trifluoroacetate (Compound 120)
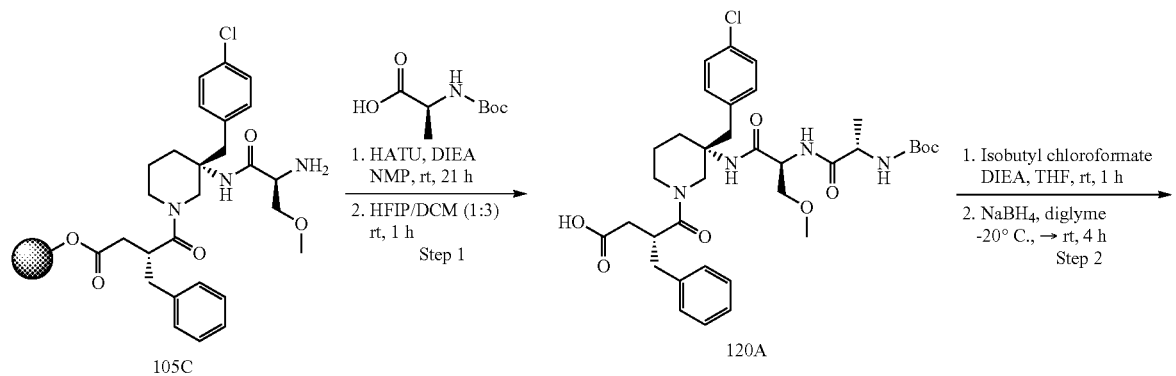
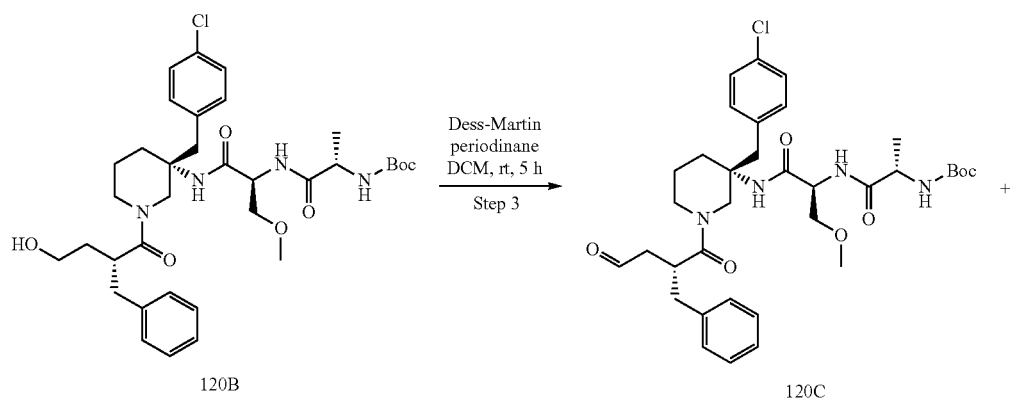
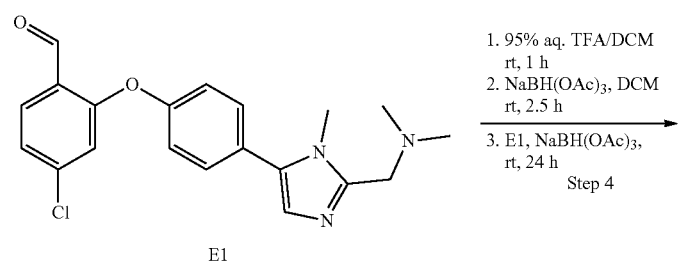

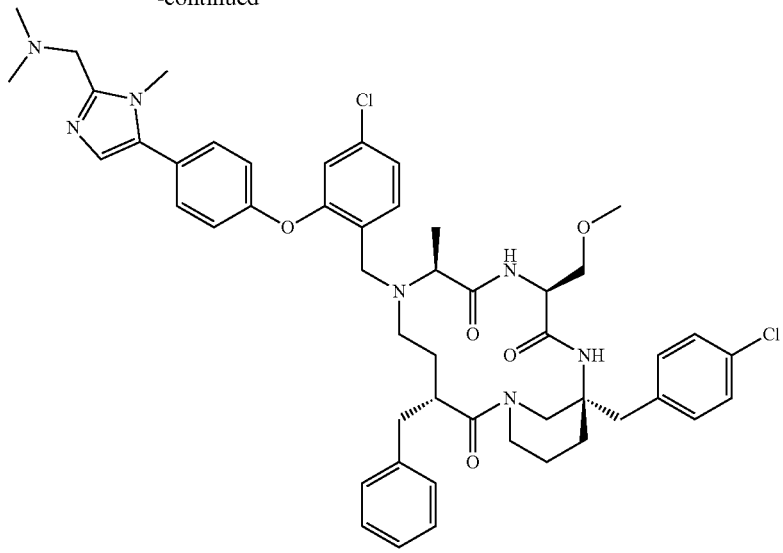

Compound 120

Step 1. (R)-3-Benzyl-4-((R)-3-((S)-2-((S)-2-((tert-butoxycarbonyl)amino)propanamido)-3-methoxy-propan-amido)-3-(4-chlorobenzyl)piperidin-1-yl)-4-oxobutanoic acid (120A)

Step 1-1: To a solution of Boc-Ala-OH (0.057 g, 300 μmol) in NMP (3 mL) was added HATU (0.114 g, 300 μmol) and DIEA (0.058 ml, 330 μmol). The resulting solution was stirred for 2 min at rt and then added to 105C (100 μmol) (see Example 8.5). The resulting suspension was shaken for 21 h at rt. The resin was drained, and then washed with DMA (3×). A solution of $Ac_2O$/Pyridine/DMA (1:1:8) (3 mL) was added and the reaction was shaken for 15 min at rt. The resin was drained and washed with DMA (×3) and DCM (×3).

Step 1-2: HFIP/DCM (1:3) (3 mL) was added to the resin from Step 1-1 and the resulting suspension was shaken for 20 min at rt. The cleavage solution was filtered off and collected. This procedure was repeated two times. The resin was then washed with DCM (2×) and the combined cleavage and washing solutions were concentrated to dryness in vacuo. The crude residue was dissolved in DCM and the resulting solution was concentrated to dryness in vacuo. This procedure was repeated three times. After drying using high vacuum, 120A (~100 μmol) was obtained as a colorless oil. The crude product was used in the next step without purification. Analytical method 10; $t_R$=1.24; [M+H]$^+$=687.4.

Step 2. tert-Butyl ((S)-1-(((S)-1-(((R)-1-((R)-2-ben-zyl-4-hydroxybutanoyl)-3-(4-chlorobenzyl)piperi-din-3-yl)amino)-3-methoxy-1-oxopropan-2-yl)amino)-1-oxopropan-2-yl)carbamate (120B)

To 120A (100 μmol) dissolved in THF (4 mL). DIEA (0.026 mL, 150 μmol) was added isobutyl chloroformate (0.014 mL, 110 μmol) and the resulting mixture was stirred for 35 min at rt. Additional DIEA (0.013 mL, 75 μmol) and isobutyl chloroformate (7.22 μl, 55.0 μmol) were added and the reaction mixture was stirred for 25 min at rt, and then cooled to −20° C. A solution of $NaBH_4$ (7.57 mg, 200 μmol) in diglyme (1 mL) was added and the resulting mixture was stirred for 45 min and then allowed to warm up to rt. Additional $NaBH_4$ (7.57 mg, 200 μmol) in diglyme (1 mL) was added and the reaction mixture was stirred for 45 min at rt. Diglyme (5 mL) and $NaBH_4$ (9.46 mg, 250 μmol) were again added with stirring was continued for 2.5 h at rt. The reaction mixture was partitioned between EtOAc (50 mL) and 5% aq. $NaHCO_3$ (15 mL). The organic phase was washed with 5% aq. $NaHCO_3$ (3×10 mL) and brine (10 mL), dried over $Na_2SO_4$, filtered, and concentrated to dryness in vacuo to afford 120B (assumed to be 100 μmol) as a colorless lacquer. The crude product was used in the next step without purification. Analytical method 10; $t_R$=1.17 min; [M+H]$^+$=673.7.

Step 3. tert-Butyl ((S)-1-(((S)-1-(((R)-1-((R)-2-ben-zyl-4-hydroxybutanoyl)-3-(4-chlorobenzyl)piperi-din-3-yl)amino)-3-methoxy-1-oxopropan-2-yl)amino)-1-oxopropan-2-yl)carbamate (120C)

To a solution of 120B (0.100 mmol) in DCM (10 mL) was added Dess-Martin periodinane (46.5 mg, 0.110 mmol) and the resulting mixture was stirred for 2 h 45 min at rt. Additional Dess-Martin periodinane (23.27 mg, 0.055 mmol) was added and stirring at rt was continued for 2 h 15 min. The reaction was quenched by addition of 5% aq. $NaHCO_3$/20% aq. $Na_2S_2O_3$ (1:1) (20 mL). EtOAc (50 mL) was added and the phases were separated. The organic phase was washed with 5% aq. $NaHCO_3$ (3×10 mL) and brine (10 mL), dried over $Na_2SO_4$, filtered, and concentrated to dryness in vacuo to afford 120C (assumed to be 0.100 mmol) as a yellowish oil. The crude product was used in the next step without purification. Analytical method 10; $t_R$=1.26 min; [M+H]$^+$=671.4.

Step 4. (3R,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7-methyl-1,6,9,12-tetraazabicyclo[11.3.1]hepta-decane-2,8,11-trione trifluoroacetate (Compound 120)

Step 4-1: 120C (100 µmol) was dissolved in 95% aq TFA/DCM (1:1) (10 mL), stirred for 1 h at rt, and then concentrated to dryness in vacuo. The resulting residue was dissolved in toluene and concentrated to dryness. The treatment with toluene was repeated (1×).

Step 4-2: To the residue from Step 4-1 dissolved in DCM (10 mL). AcOH (0.011 mL, 200 µmol) was added NaBH(OAc)$_3$ (42.4 mg, 200 µmol) and the reaction mixture was stirred for 150 min at rt.

Step 4-3: E1 (55.5 mg, 150 µmol) was added to the reaction mixture from Step 4-2 and stirred for 50 min at rt.

Additional NaBH(OAc)$_3$ (42.4 mg, 200 µmol) was added and stirring at rt was continued for 4 h 20 min. M NaBH(OAc)$_3$ (42.4 mg, 200 µmol) was again added and stirring at rt was continued for 18 h 50 min. DCM was removed in vacuo and the product was isolated by preparative reverse-phase HPLC (eluent A: 0.1% TFA in H$_2$O; eluent B: ACN). Fractions containing the product were combined and lyophilized to afford Compound 120 (1.1 mg, 0.572 µmol, 0.6% yield over 4 steps) as a white solid. Analytical method 14; $t_R$=4.13 min, [M+H]+=908.3.

Example 8.7: Synthesis of (3S,7S,10S,13R)-6-(4-chloro-2-(4-(1-methyl-2-(pyrrolidin-1-ylmethyl)-1H-imidazol-5-yl)phenoxy)benzyl)-13-(4-chlorobenzyl)-3-((R)-2,3-dihydro-1H-inden-1-yl)-10-(methoxymethyl)-7-methyl-1,6,9,12-tetraazabicyclo[11.3.1]heptadecane-2,5,8,11-tetraone trifluoroacetate (Compound 96)

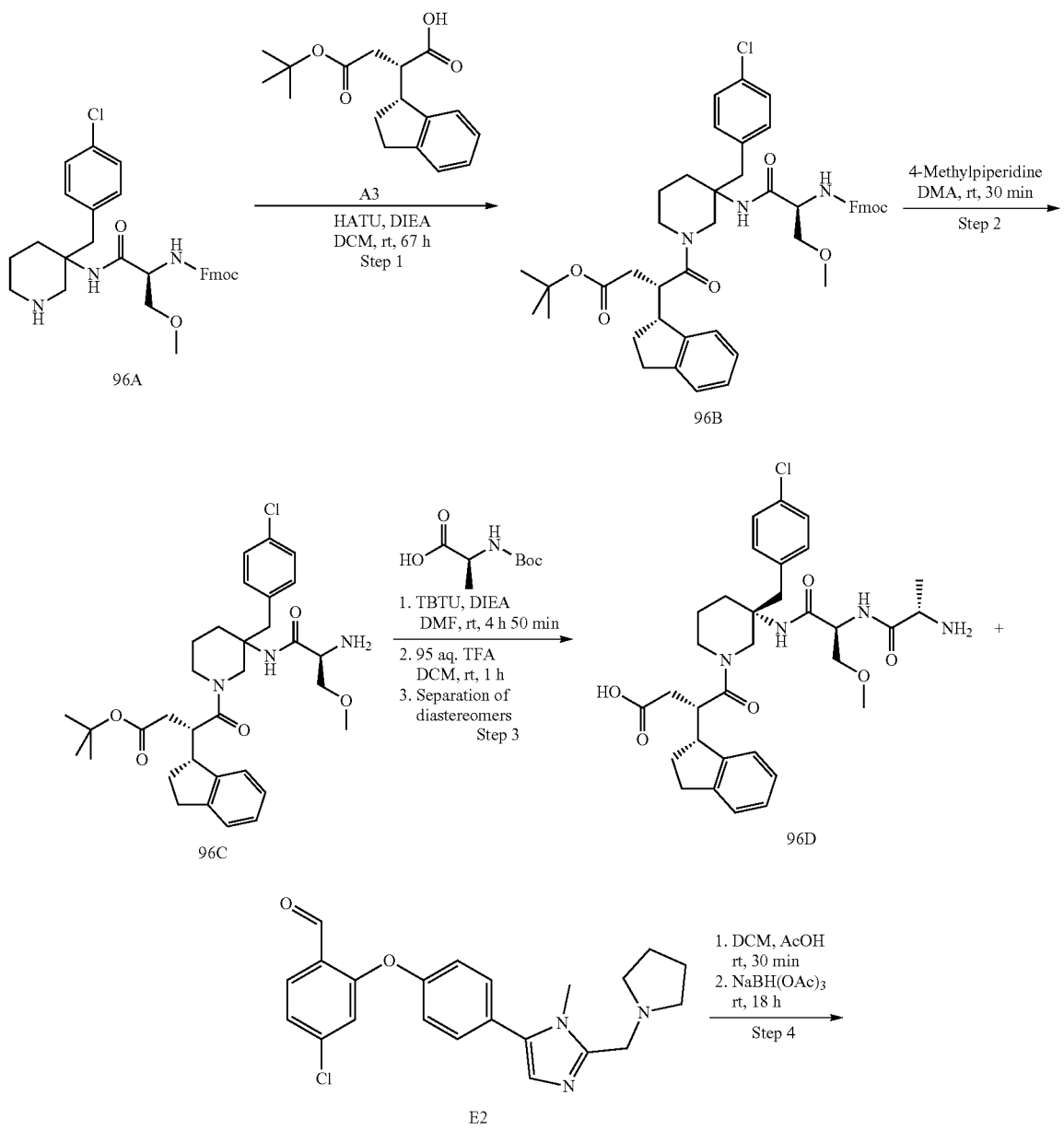

-continued

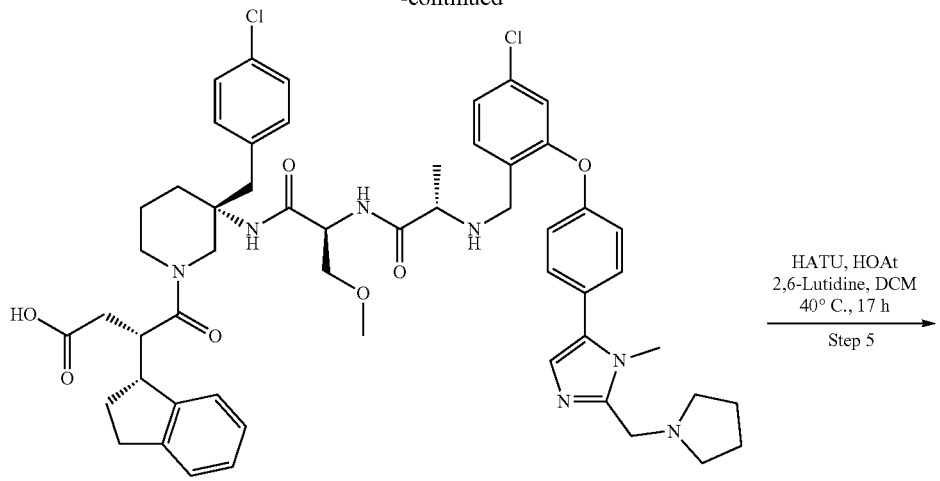

96E

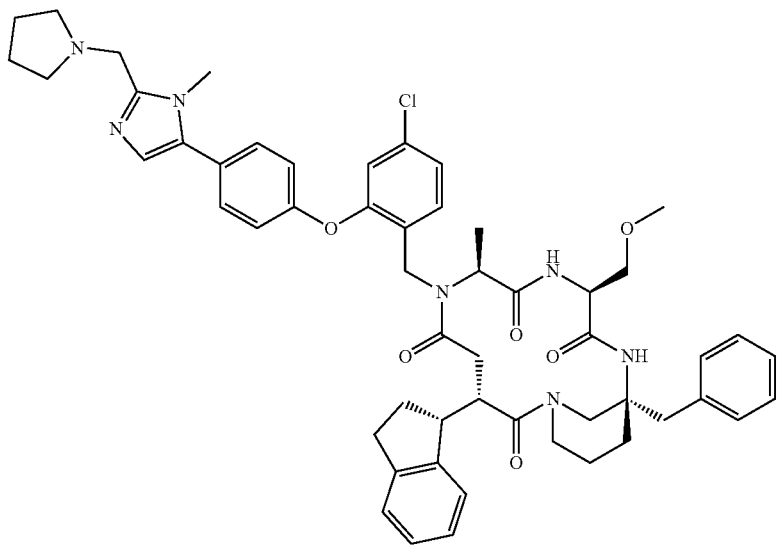

Compound 96

Step 1. tert-Butyl (3S)-4-(3-((S)-2-((((9H-fluoren-9-yl)methoxy)carbonyl)amino)-3-methoxypropanamido)-3-(4-chlorobenzyl)piperidin-1-yl)-3-((R)-2,3-dihydro-1H-inden-1-yl)-4-oxobutanoate (96B)

A3 (87 mg, 0.300 mmol) and HATU (125 mg, 0.330 mmol) were dissolved in DCM (6 mL) and DIEA (0.063 mL, 0.362 mmol). The resulting mixture was stirred for 15 min at rt, and a solution of 96A (0.248 mmol) (96A synthesized according to the procedure described for 105A starting from B8) in DCM (5 mL) and DIEA (0.131 mL, 0.748 mmol) was added. The reaction mixture was stirred for 67 h at rt and then partitioned between EtOAc (50 mL) and 5% aq. NaHCO₃ (10 mL). The organic phase was washed with 5% aq. NaHCO₃ (2×10 mL) and brine (10 mL), dried over Na₂SO₄, filtered, and concentrated to dryness in vacuo to afford 96B (diastereomeric mixture; ~0.248 mmol) as a colorless oil. The crude product was used in the next step without purification. Analytical method 10; $t_R$=1.60 min; [M+H]⁺=820.6.

Step 2. tert-Butyl (3S)-4-(3-((S)-2-amino-3-methoxypropanamido)-3-(4-chlorobenzyl)piperidin-1-yl)-3-((R)-2,3-dihydro-1H-inden-1-yl)-4-oxobutanoate (96C)

96B (0.248 mmol) was dissolved in 4-methylpiperidine/DMA (1:4) (5 mL) and the resulting solution was stirred for 30 min at rt and then concentrated to dryness in vacuo. The crude product was purified by flash silica gel chromatography (eluent A: heptane/DIEA (98:2); eluent 1: EtOAc/DIEA (98:2); eluent B2: EtOAc/MeOH/DIEA (100:5:2)). Pure fractions were combined and concentrated to dryness in vacuo to afford 96C (diastereomeric mixture; 128 mg, 0.214 mmol, 86% yield over 2 steps) as a yellow oil. Analytical method 10; $t_R$=1.16/1.18 min; [M+H]⁺=598.5.

Step 3. (S)-4-((R)-3-((S)-2-((S)-2-Aminopropanamido)-3-methoxypropanamido)-3-(4-chlorobenzyl)piperidin-1-yl)-3-((R)-2,3-dihydro-1H-inden-1-yl)-4-oxobutanoic acid trifluoroacetate (96D)

Step 3-1: To Boc-Ala-OH (44.2 mg, 0.234 mmol) and TBTU (75.0 mg, 0.234 mmol) dissolved in DMF (3 mL) was added DIEA (0.044 mL, 0.255 mmol) was added. The resulting mixture was stirred for 5 min at rt and a solution of 96C (127 mg, 0.212 mmol) in DMF (3 mL) was added. The reaction mixture was then stirred for 4 h 50 min at rt and partitioned between EtOAc (50 mL) and 5% aq. NaHCO₃ (10 mL). The organic phase was washed with 5% aq. NaHCO₃ (3×10 mL) and brine (10 mL), dried over Na₂SO₄, filtered, and concentrated to dryness in vacuo.

Step 3-2: The residue from Step 3-1 was dissolved in 95% aq. TFA/DCM (15 mL), stirred for 1 h at rt, and then concentrated to dryness in vacuo. The diastereomers were separated by preparative reverse-phase HPLC (eluent A: 0.1% TFA in H₂O; eluent B: ACN). Pure fractions were combined and lyophilized to afford 96D (43 mg, 0.059 mmol, 28% yield) as a white solid. Analytical method 10; $t_R$=0.94 min; [M+H]=613.3.

Step 4. ((S)-4-((R)-3-((S)-2-((S)-2-((4-Chloro-2-(4-(1-methyl-2-(pyrrolidin-1-ylmethyl)-1H-imidazol-5-yl)-phenoxy)benzyl)amino)propanamido)-3-methoxypropanamido)-3-(4-chlorobenzyl)piperidin-1-yl)-3-((R)-2,3-dihydro-1H-inden-1-yl)-4-oxobutanoic acid trifluoroacetate (96E)

96D (43 mg, 0.059 mmol) and E2 (30.4 mg, 0.077 mmol) were dissolved in a mixture of DCM (5 mL) and AcOH (0.014 mL, 0.237 mmol). The solution was stirred for 30 min at rt, and then NaBH(OAc)₃ (25.07 mg, 0.118 mmol) was added. The reaction mixture was stirred for 50 min at rt and then additional E2 (11.71 mg, 0.030 mmol) was added. After stirring at rt for 14.5 h more E2 (11.71 mg, 0.030 mmol) was added. The resulting mixture was stirred for 80 min at rt, NaBH(OAc)₃ (25.07 mg, 0.118 mmol) was again added and stirring was continued for 80 min. MeOH (1 mL) was added and the mixture was concentrated to dryness in vacuo. The crude product was purified by preparative reverse-phase HPLC (eluent A: 0.1% TFA in H₂O; eluent B: ACN). Pure fractions were combined and lyophilized to afford 96E (19.4 mg, 0.015 mmol, 25% yield) as an off-white solid. Analytical method 10; $t_R$=1.00 min; [M+H]⁺=992.6.

Step 5. (3S,7S,10S,13R)-6-(4-Chloro-2-(4-(1-methyl-2-(pyrrolidin-1-ylmethyl)-1H-imidazol-5-yl)phenoxy)-benzyl)-13-(4-chlorobenzyl)-3-((R)-2,3-dihydro-1H-inden-1-yl)-10-(methoxymethyl)-7-methyl-1,6,9,12-tetraazabicyclo[11.3.1]heptadecane-2,5,8,11-tetraone trifluoroacetate (Compound 96)

To 96E dissolved in DCM (14.4 mL). HATU (21.87 mg, 0.058 mmol) was added HOAt (2.94 mg, 0.022 mmol) and the resulting mixture was stirred for 5 min at rt. 2,6-Lutidine (0.050 mL, 0.431 mmol) was then added. The reaction mixture was stirred for 17 h at 40° C. and concentrated to dryness in vacuo. The crude product was purified by preparative reverse-phase HPLC (eluent A: 0.1% TFA in H₂O; eluent B: ACN). Pure fractions were combined and lyophilized to afford Compound 96 (8.4 mg, 6.56 μmol, 46% yield) as a white solid. Analytical method 9; $t_R$=5.52 min; [M+H]⁺=974.4.

Example 8.8: Synthesis of (3S,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-1,4,6,9,12-pentaaza-bicyclo[11.3.1]-heptadecane-2,5,8,11-tetraone hydrochloride (Compound 60)

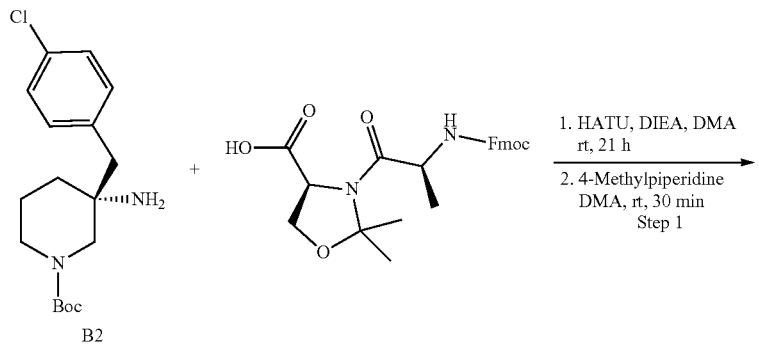

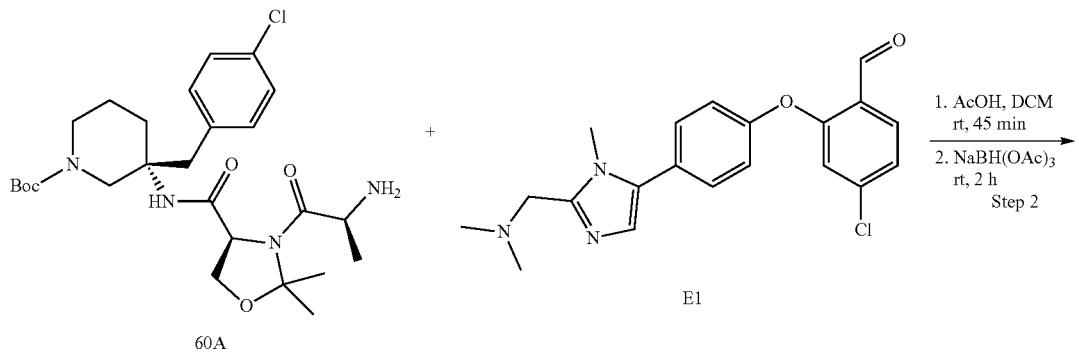

-continued
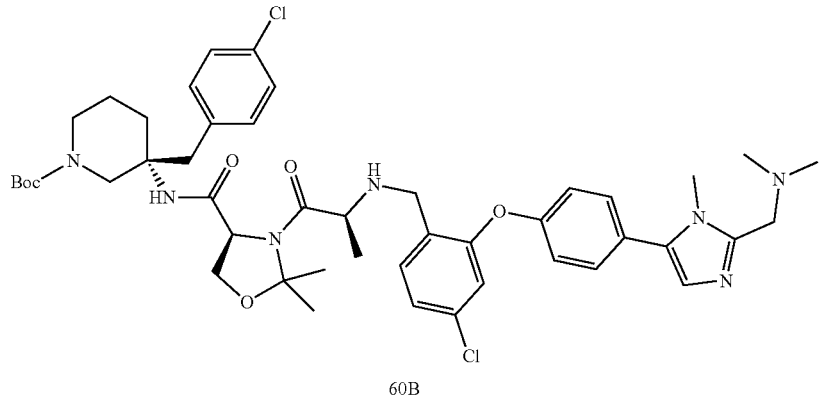
60B
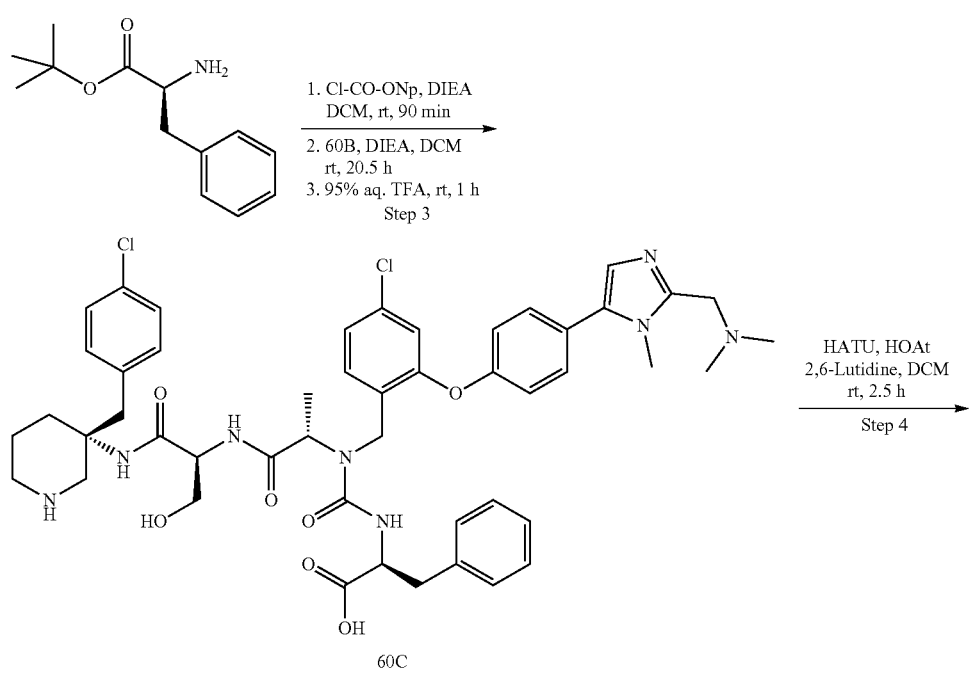
Compound 60

Step 1. (R)-tert-butyl 3-((S)-3-((S)-2-aminopropanoyl)-2,2-dimethyloxazolidine-4-carboxamido)-3-(4-chloro-benzyl)piperidine-1-carboxylate (60A)

Step 1-1: To a solution of Fmoc-Ala-Ser[psi(Me,Me)pro]-OH (438 mg, 1000 μmol) and HATU (399 mg, 1050 μmol) in DMA (5 mL) was added DIEA (0.227 mL, 1300 μmol). The resulting solution was stirred for 2 min at rt, and then added to a solution of B2 (325 mg, 1000 μmol) in DMA (5 mL). The reaction mixture was stirred for 4 h 40 min at rt. Additional Fmoc-Ala-Ser[psi(Me,Me)pro]-OH (132 mg, 300 μmol), HATU (133 mg, 350 μmol) and DIEA (0.070 mL, 400 μmol) in DMA (1 mL) (preactivation time: 2 min) were added and stirring at rt was continued for 16 h 20 min. The reaction mixture was partitioned between EtOAc (70 mL) and 5% aq. NaHCO$_3$ (15 mL). The organic phase was washed with 5% aq. NaHCO$_3$ (3×10 mL) and brine (10 mL), dried over Na$_2$SO$_4$, filtered, and concentrated to dryness in vacuo.

Step 1-2. The residue from Step 1-1 was dissolved in DMA/4-methylpiperidine (4:1) (10 mL), stirred for 30 min at rt, and then concentrated to dryness in vacuo. The crude product was purified by flash silica gel chromatography (eluent A: EtOAc/DIEA (98:2); eluent B: EtOAc/MeOH/DIEA (90:10:2)). Pure fractions were combined and concentrated to dryness in vacuo to afford 60A (465 mg, 889 μmol, 89% yield) as a white solid. Analytical method 10; $t_R$=0.86 min; [M+H]$^+$=523.3.

Step 2. (R)-tert-butyl 3-((S)-3-((S)-2-((4-chloro-2-(4-(2-((dimethylamino)methyl)-1-methyl-1H-imidazol-5-yl)phenoxy)benzyl)amino)propanoyl)-2,2-dimethyloxazolidine-4-carboxamido)-3-(4-chlorobenzyl)piperidine-1-carboxylate (60B)

60A (465 mg, 0.889 mmol) and E1 (362 mg, 0.978 mmol) were dissolved in a mixture of DCM (10 mL) and AcOH (0.204 mL, 3.56 mmol) and stirred for 45 min at rt. NaBH(OAc)$_3$ (942 mg, 4.44 mmol) was added and the reaction mixture was stirred for 2 h at rt and then partitioned between EtOAc (70 mL) and 5% aq. Na$_2$CO$_3$ (20 mL). The organic phase was washed with 5% aq. Na$_2$CO$_3$ (3×10 mL) and brine (10 mL), dried over Na$_2$SO$_4$, filtered, and concentrated to dryness in vacuo to afford 60B (assumed to be 0.889 mmol) as a light beige foam. The crude product was used in the next step without purification. Analytical method 10; $t_R$=0.86 min; [M+H]$^+$=876.6.

Step 3. (S)-2-(3-(4-chloro-2-(4-(2-((dimethylamino)methyl)-1-methyl-1H-imidazol-5-yl)phenoxy)benzyl)-3-((S)-1-(((S)-1-(((R)-3-(4-chlorobenzyl)piperidin-3-yl)amino)-3-hydroxy-1-oxopropan-2-yl)amino)-1-oxopropan-2-yl)ureido)-3-phenylpropanoic acid hydrochloride (60C)

Step 3-1. (S)-tert-Butyl 2-amino-3-phenylpropanoate HCl (38.7 mg, 150 μmol) was dissolved in DCM (2 mL) and DIEA (0.052 mL, 300 μmol). 4-Nitrophenyl chloroformate (30.2 mg, 150 μmol) was added and the reaction mixture was stirred for 90 min at rt.

Step 3-2. A solution of 60B (100 μmol) in DCM (2 mL) and DIEA (0.026 mL, 150 μmol) was added to the mixture from Step 3-1. The resulting mixture was stirred for 20.5 h at rt and partitioned between EtOAc (40 mL) and 5% aq. NaHCO$_3$ (7 mL). The organic phase was washed with 5% aq. NaHCO$_3$ (4×7 mL) and brine (5 mL), dried over Na$_2$SO$_4$, filtered, and concentrated to dryness in vacuo.

Step 3-3. The residue from Step 3-2 was dissolved in 95% aq. TFA (5 mL), stirred for 1 h at rt, and then concentrated to dryness in vacuo. The crude product was purified by preparative reverse-phase HPLC (eluent A: 0.01 M HCl in H$_2$O; eluent B: ACN). Pure fractions were combined and lyophilized to afford 60C (52 mg, 50.1 μmol, 50% yield for 2 steps) as a white solid. Analytical method 14; $t_R$=3.43 min; [M+H]$^+$=927.3.

Step 4. (3S,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-1,4,6,9,12-pentaazabicyclo[11.3.1]-heptadecane-2,5,8,11-tetraone hydrochloride (Compound 60)

To 60C (52 mg, 0.050 mmol) dissolved DCM (50 mL) was added HATU (76 mg, 0.201 mmol) and HOAt (10.23 mg, 0.075 mmol). After stirring for 10 min at rt, 2,6-lutidine (0.175 mL, 1.504 mmol) was added and reaction mixture was stirred for 2.5 h at rt and then concentrated to dryness in vacuo. The residue was partitioned between EtOAc (40 mL) and 5% aq. NaHCO$_3$ (5 mL). The organic phase was washed with 5% aq. NaHCO$_3$ (3×5 mL) and brine (5 mL), dried over Na$_2$SO$_4$, filtered, and concentrated to dryness in vacuo. The crude product was purified by preparative reverse-phase HPLC (eluent A: 0.01 M HCl in H$_2$O; eluent B: ACN). Pure fractions were combined and lyophilized to afford Compound 60 (27.1 mg, 0.027 mmol, 55% yield) as a white solid. Analytical method 14; $t_R$=4.49 min; [M+H]$^+$=909.3.

The compounds and intermediates shown in Table 11 were synthesized according to the procedure described in Example 8.8 for Compound 60.

Table 11: Compounds and intermediates made according to Example 8.8 for Compound 60. Compound 104 was synthesized according to the procedure described for Compound 60 in Example 8.8 starting from 104B.

| Cmd No. | Structure | Synthesis procedure/ LCMS |
|---|---|---|
| 58 | 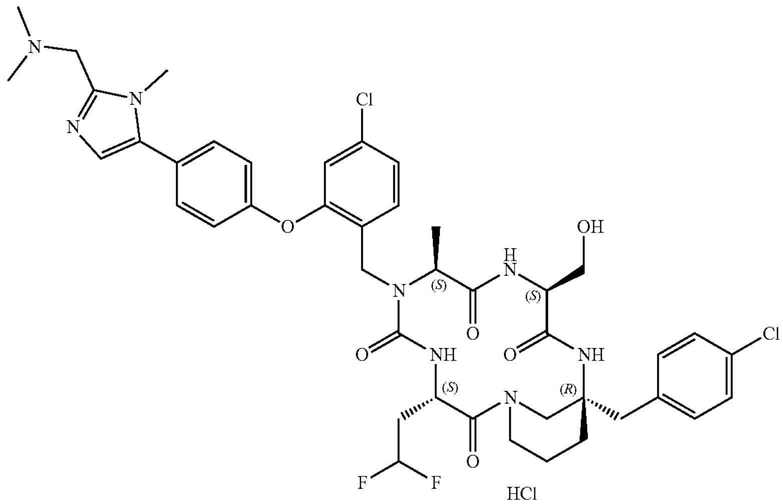 | Starting from 60B and 58B/Analytical method 9<br>$t_R$ = 4.06 min<br>$[M + H]^+$ = 883.3 |
| 67 | 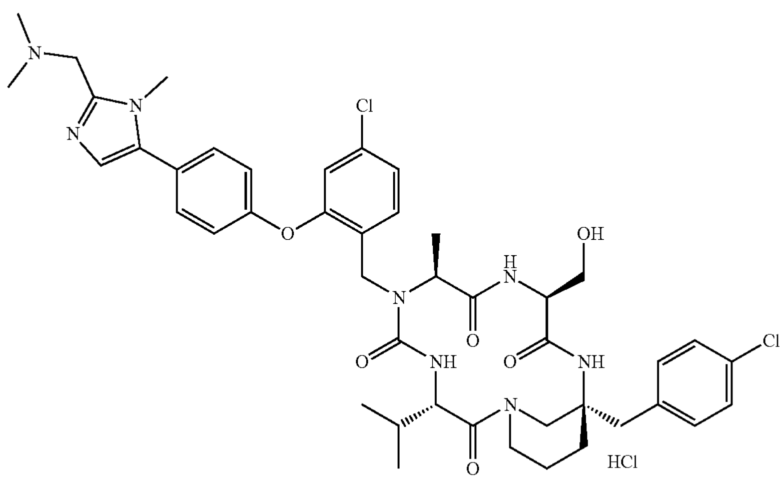 [SMILES: CC(C)[C@@H]1NC(=O)N(Cc2ccc(Cl)cc2Oc2ccc(-c3cnc(CN(C)C)n3C)cc2)[C@@H](C)C(=O)N[C@@H](CO)C(=O)N[C@@]2(Cc3ccc(Cl)cc3)CCCN(C2)C1=O ; Cl] | Starting from 60B and H-Val-OtBu/Analytical method 14<br>$t_R$ = 4.22 min<br>$[M + H]^+$ = 861.3 |
| 104 | 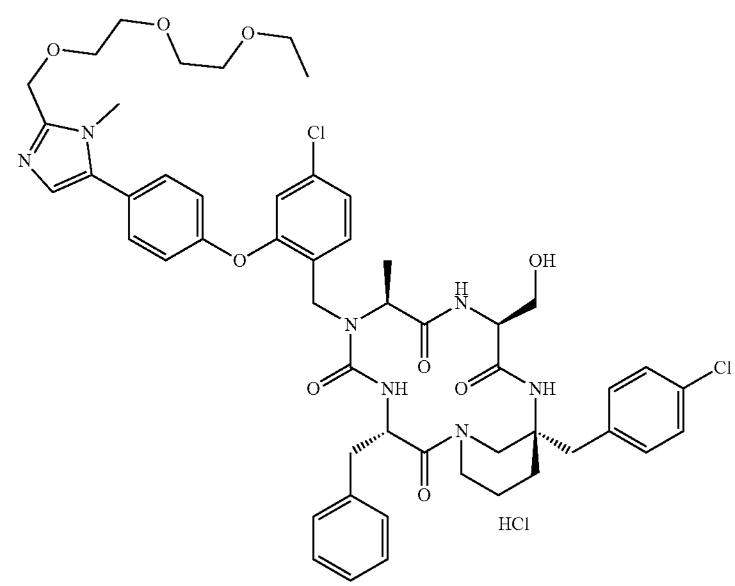 [SMILES: CCOCCOCCOCc1ncc(-c2ccc(Oc3cc(Cl)ccc3CN3C(=O)N[C@@H](Cc4ccccc4)C(=O)N4CCC[C@@](Cc5ccc(Cl)cc5)(C4)NC(=O)[C@H](CO)NC(=O)[C@@H]3C)cc2)n1C ; Cl] | Starting from 104B (Example 8.1)/Analytical method 14<br>$t_R$ = 4.83 min<br>$[M + H]^+$ = 998.3 |

Example 8.9: Synthesis of (3S,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-4-oxa-1,6,9,12-tetraazabicyclo[11.3.1]heptadecane-2,5,8,11-tetraone hydrochloride (Compound 78)
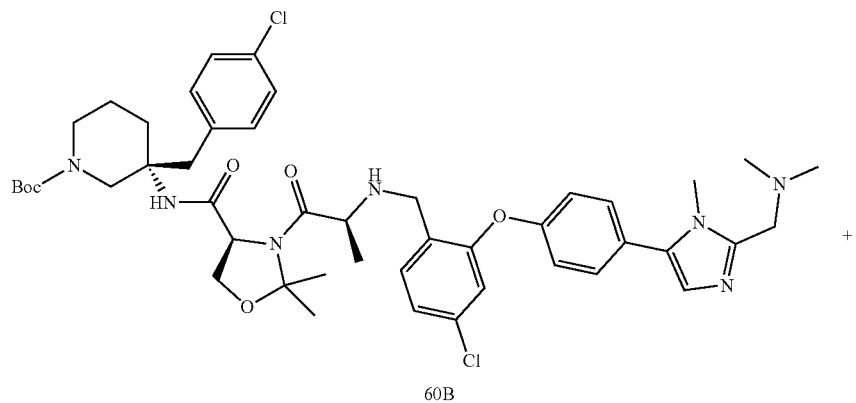
60B
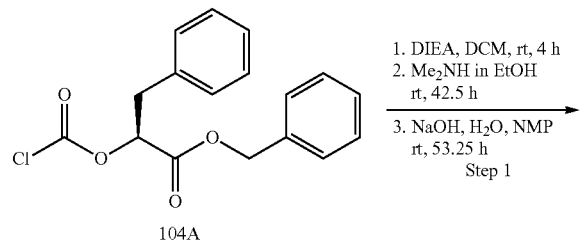
104A
1. DIEA, DCM, rt, 4 h
2. Me₂NH in EtOH
   rt, 42.5 h
3. NaOH, H₂O, NMP
   rt, 53.25 h
   Step 1
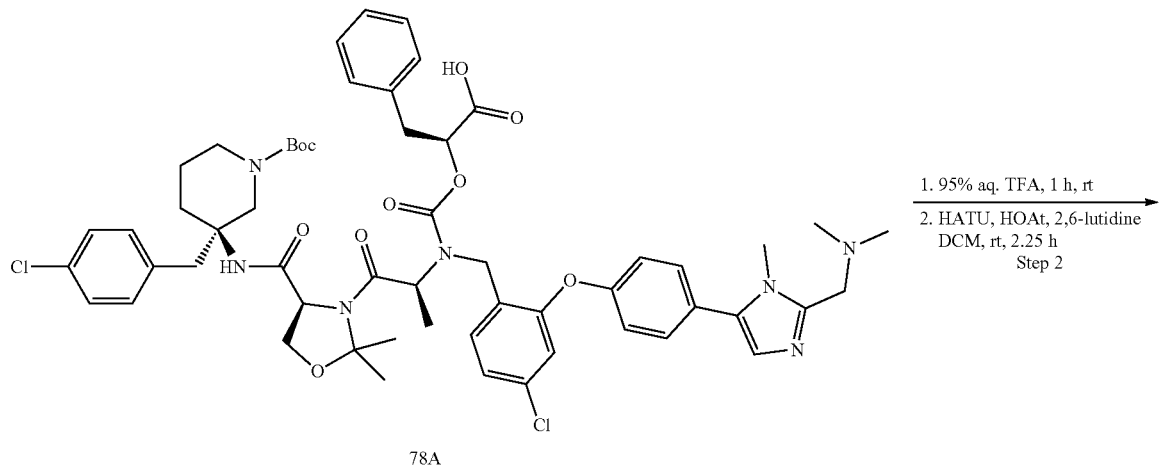
78A
1. 95% aq. TFA, 1 h, rt
2. HATU, HOAt, 2,6-lutidine
   DCM, rt, 2.25 h
   Step 2

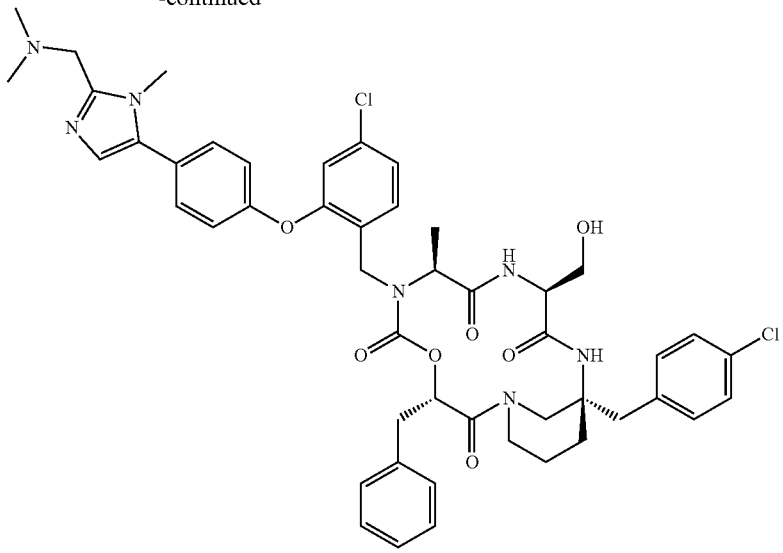

Compound 78

Step 1. (S)-2-((((S)-1-((S)-4-(((R)-1-(tert-butoxycarbonyl)-3-(4-chlorobenzyl)piperidin-3-yl)carbamoyl)-2,2-dimethyloxazolidin-3-yl)-1-oxopropan-2-yl)(4-chloro-2-(4-(2-((dimethylamino)methyl)-1-methyl-1H-imidazol-5-yl)phenoxy)benzyl)carbamoyl)oxy)-3-phenylpropanoic acid trifluoroacetate (78A)

Step 1-1: To 60B (100 μmol) dissolved in DCM (1 mL) was added a solution of 104A (159 mg, 500 μmol) in DCM (1 mL) and DIEA. The resulting mixture was stirred for 4 h at rt.

Step 1-2: 33% Me$_2$NH in EtOH (0.143 mL, 800 μmol) was added to the mixture from Step 1-1 stirring was continued for 42.5 h at rt. The reaction mixture was concentrated in vacuo and the residue was partitioned between EtOAc (40 mL) and 5% aq. NaHCO$_3$ (5 mL). The organic phase was washed with 5% aq. NaHCO$_3$ (2×5 mL) and brine (5 mL), dried over Na$_2$SO$_4$, filtered, and concentrated to dryness in vacuo.

Step 1-3: To the residue from Step 1-2 dissolved in NMP (6 mL) and H$_2$O (0.9 mL) was added 4 M NaOH (0.100 mL, 400 μmol) and the resulting mixture was stirred for 4 h 45 min at rt. Additional H$_2$O (1.9 mL) and 4 M NaOH (0.100 mL, 400 μmol) were added and stirring was continued for 17 h. 1 M NaOH (0.500 mL, 500 μmol) was again added and the reaction mixture was stirred for 22.5 h at rt. Additional 1 M NaOH (0.500 mL, 500 μmol) was added and the reaction mixture was stirred for 9 h at rt, quenched by addition of AcOH (0.1 mL), and concentrated in vacuo. The crude product was purified by preparative reverse-phase HPLC (eluent A: 0.1% TFA in H$_2$O; eluent B: ACN). Pure fractions were combined and lyophilized to afford 78A (38.9 mg, 30.0 μmol, 30% yield) as a white solid. Analytical method 9; t$_R$=5.81 min; [M+H]$^+$=1068.4.

Step 2. (3S,7S,10S,13R)-3-benzyl-6-(4-chloro-2-(4-(2-((dimethylamino)methyl)-1-methyl-1H-imidazol-5-yl)-phenoxy)benzyl)-13-(4-chlorobenzyl)-10-(hydroxymethyl)-7-methyl-4-oxa-1,6,9,12-tetraazabicyclo[11.3.1]-heptadecane-2,5,8,11-tetraone hydrochloride (Compound 78)

Step 2-1: 78A (38.9 mg, 0.030 mmol) was dissolved in 95% aq. TFA (5 mL), stirred for 1 h at rt, and then concentrated to dryness in vacuo.

Step 2-2: To the residue from Step 2-1 dissolved in DCM (30 mL) was added HOAt (6.12 mg, 0.045 mmol) and HATU (45.6 mg, 0.120 mmol) and the resulting mixture was stirred for 5 min at rt. 2,6-lutidine (0.105 mL, 0.900 mmol) was added and the reaction mixture was stirred for 2 h 15 min at rt and then concentrated to dryness in vacuo. The obtained residue was partitioned between EtOAc (40 mL) and 5% aq. NaHCO$_3$ (10 mL). The organic phase was washed with 5% aq. NaHCO$_3$ (2×10 mL) and brine (10 mL), dried over Na$_2$SO$_4$, filtered, and concentrated to dryness in vacuo. The crude product was purified by preparative reverse-phase HPLC (eluent A: 0.01 M HCl in H$_2$O; eluent B: ACN). Pure fractions were combined and lyophilized to afford Compound 78 (11.3 mg, 0.011 mmol, 38% yield) as a white solid. Analytical method 9; t$_R$=4.71 min; [M+H]$^+$=910.3.

Example 8.10: Synthesis of ((3S,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7-methyl-4-oxa-1,6,9,12-tetraazabicyclo[11.3.1]heptadecane-2,5,8,11-tetraone hydrochloride (Compound 156)
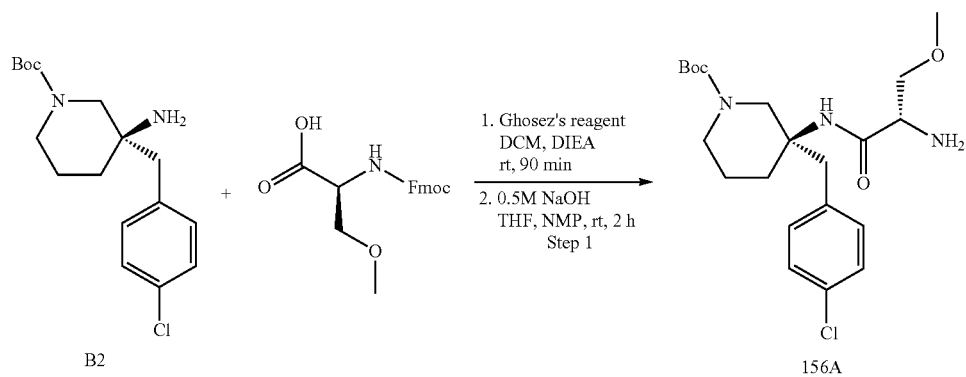
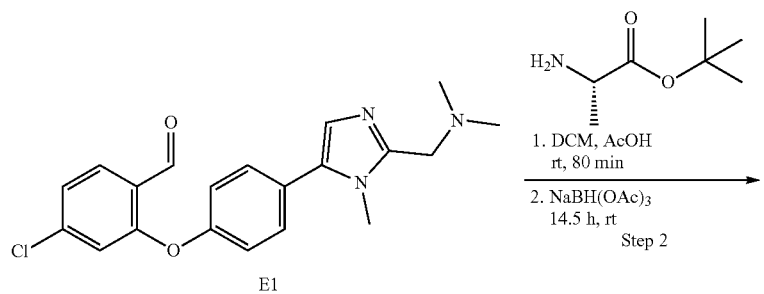
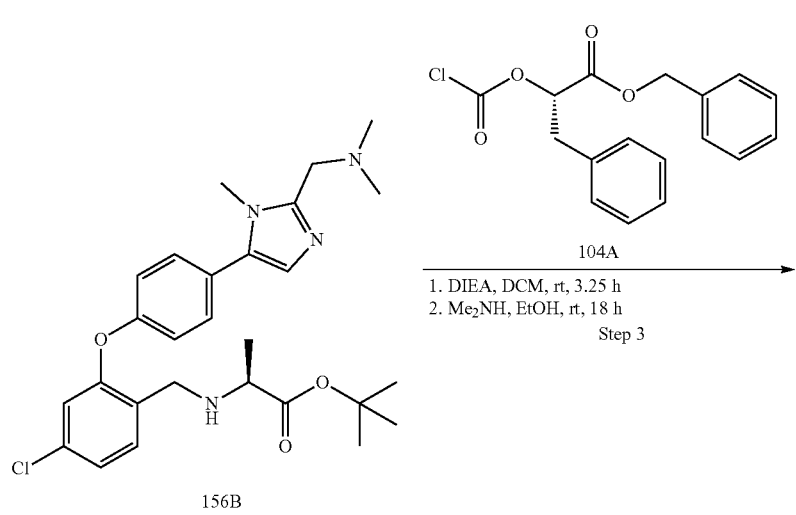

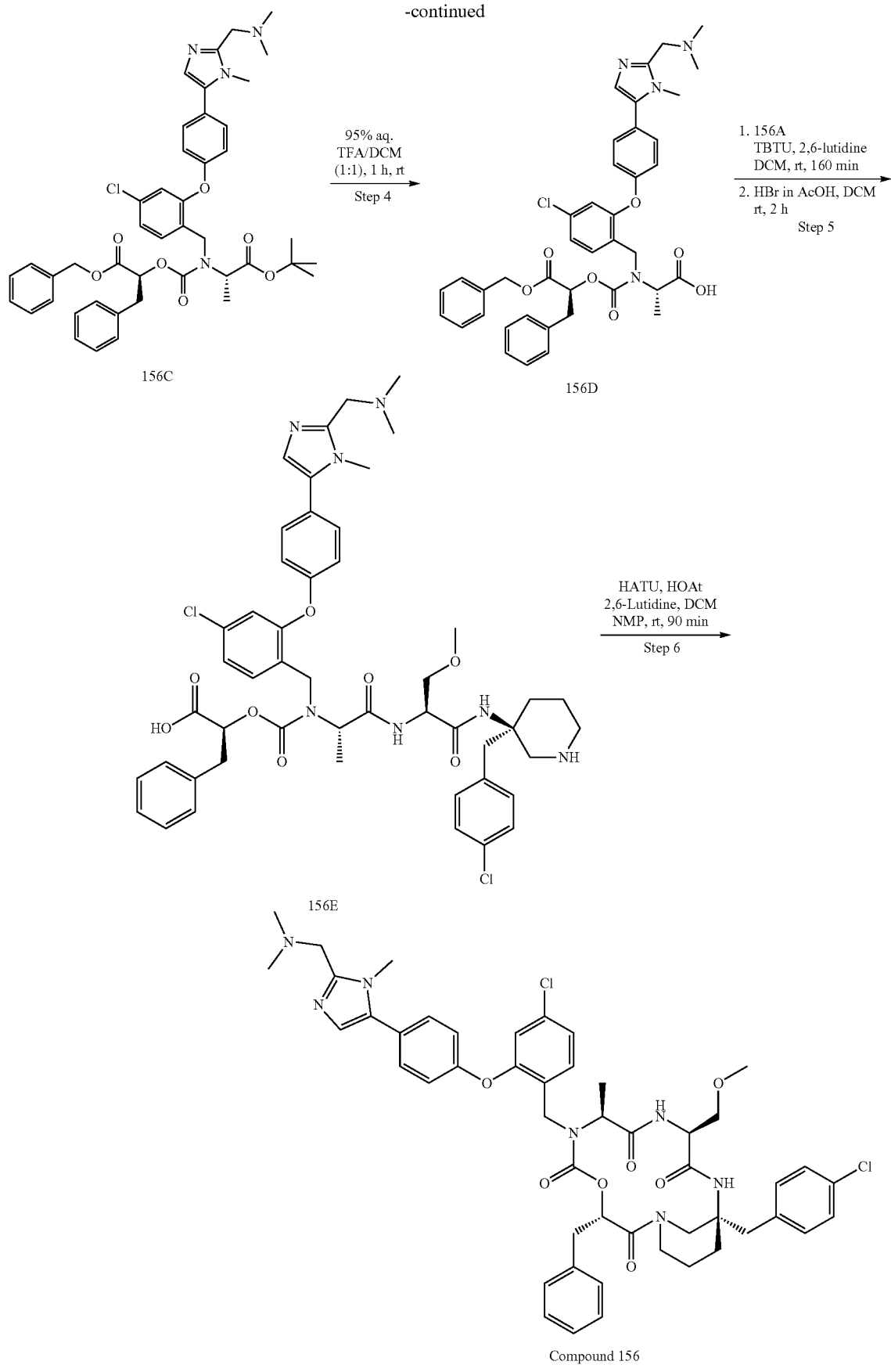

Step 1. tert-Butyl (R)-3-((S)-2-amino-3-methoxypropanamido)-3-(4-chlorobenzyl)piperidine-1-carboxylate (156A)

Step 1-1. To Fmoc-Ser(Me)-OH (246 mg, 720 µmol) in DCM (3 mL) was added Ghosez's reagent (0.095 mL, 720 µmol). The resulting mixture was stirred for 45 min at rt, and then a solution of B2 (195 mg, 600 µmol) and DIEA (0.157 mL, 900 µmol) in DCM (2 mL) was added. The reaction mixture was stirred for 90 min at rt and DCM was removed in vacuo.

Step 1-2. To the residue from Step 1-1 was dissolved in THF (5 mL) and NMP (4 mL) was added 0.5 M aq. NaOH (3.6 mL, 1800 µmol) and the resulting mixture was stirred for 2 h at rt. The THF was removed in vacuo and the residue was partitioned between EtOAc (50 mL) and 5% aq. $Na_2CO_3$ (5 mL). The organic phase was washed with 5% aq. $Na_2CO_3$ (2×5 mL) and brine (10 mL), dried over $Na_2SO_4$, filtered, and concentrated to dryness in vacuo. The crude product was purified by flash silica gel chromatography (eluent A: EtOAc/DIEA (98:2); eluent B: EtOAc/MeOH/DIEA (85:15:2)). Pure fractions were combined and concentrated to dryness in vacuo to afford 156A (~600 µmol) as a yellow oil. The product was used in the next step without further purification. Analytical method 10; $t_R$=0.77 min; $[M+H]^+$=426.3.

Step 2. tert-Butyl (4-chloro-2-(4-(2-((dimethylamino)methyl)-1-methyl-1H-imidazol-5-yl)phenoxy)benzyl)-L-alaninate (156B)

To E1 (534 mg, 1.444 mmol) and (S)-tert-butyl 2-aminopropanoate HCl (393 mg, 2.166 mmol) was added a mixture of DCM (20 mL) and AcOH (0.331 mL, 5.78 mmol). The resulting solution was stirred for 80 min at rt and then $NaBH(OAc)_3$ (1530 mg, 7.22 mmol) was added. The reaction was stirred for 14.5 h at rt, the DCM was removed and the residue was partitioned between EtOAc (50 ml) and 5% aq. $Na_2CO_3$ (30 mL). The organic phase was washed with 5% aq. $Na_2CO_3$ (3×10 mL) and brine (10 mL), dried over $Na_2SO_4$, filtered, and concentrated to dryness in vacuo. The crude product was purified by flash silica gel chromatography (eluent A: EtOAc/DIEA (98:2); eluent B: EtOAc/MeOH/DIEA (90:10:2)). Pure fractions were combined and concentrated to dryness in vacuo to afford 156B (347 mg, 0.695 mmol, 48% yield) as a yellow oil. Analytical method 10; $t_R$=0.59 min, $[M+H]^+$=499.5.

Step 3. Benzyl (S)-2-((((S)-1-(tert-butoxy)-1-oxopropan-2-yl)(4-chloro-2-(4-(2-((dimethylamino)methyl)-1-methyl-1H-imidazol-5-yl)phenoxy)benzyl)carbamoyl)oxy)-3-phenylpropanoate (156C)

Step 3-1: To a solution of 156B (278 mg, 0.557 mmol) in DCM (5 mL) and DIEA (0.389 mL, 2.228 mmol) was added a solution of 104A (408 mg, 1.281 mmol; see Example 8.9) in DCM (4 mL). The reaction mixture was stirred for 1 h 45 min at rt, additional 104A (98 mg, 0.306 mmol) in DCM (1 mL) was added and stirring was continued for 90 min.

Step 3-2: 33% Dimethylamine in EtOH (0.796 mL, 4.46 mmol) was added to the mixture from Step 3-1. The resulting mixture was stirred for 18 h at rt and then concentrated to dryness in vacuo. The crude product was purified by flash silica gel chromatography (eluent A: EtOAc/DIEA (98:2); eluent B: EtOAc/MeOH/DIEA (90:10:2)). Pure fractions were combined and concentrated to dryness in vacuo to afford 156C (362 mg, 0.463 mmol, 83% yield) as a yellow oil. Analytical method 10; $t_R$=1.13 min; $[M+H]^+$=781.5.

Step 4. Benzyl (S)-2-((((S)-1-(tert-butoxy)-1-oxopropan-2-yl)(4-chloro-2-(4-(2-((dimethylamino)methyl)-1-methyl-1H-imidazol-5-yl)phenoxy)benzyl)carbamoyl)oxy)-3-phenylpropanoate (156D)

156C (362 mg, 0.463 mmol) was dissolved in 95% aq. TFA/DCM (1:1) (10 mL). The reaction mixture was stirred for 1 h at rt and then concentrated to dryness in vacuo to afford 156D (assumed to be 0.463 mmol) as yellow oil which was used in the next step without purification. Analytical method 10; $t_R$=0.95 min; $[M+H]^+$=725.4.

Step 5. (4S,7S,11S)-11-benzyl-8-(4-chloro-2-(4-(2-((dimethylamino)methyl)-1-methyl-1H-imidazol-5-yl)phen-oxy)benzyl)-4-(((R)-3-(4-chlorobenzyl)piperidin-3-yl)carbamoyl)-7-methyl-6,9-dioxo-2,10-dioxa-5,8-diazadodecan-12-oic acid hydrochloride (156E)

Step 5-1: To 156D (463 µmol) and TBTU (223 mg, 695 µmol) was added DCM (10 mL) and 2,6-lutidine (1.079 mL, 9260 µmol). The resulting mixture was stirred for 5 min at rt and then a solution of 156A (230 mg, 486 µmol) in DCM (10 mL) was added. The reaction mixture was stirred for 160 min at rt and the DCM was removed in vacuo. The residue was partitioned between EtOAc (50 mL) and 5% aq. $NaHCO_3$ (10 mL). The organic phase was washed with 5% aq. $NaHCO_3$ (3×10 mL) and brine (10 mL), dried over $Na_2SO_4$, filtered, and concentrated to dryness in vacuo to afford a yellow oil. Analytical method 10; $t_R$=1.24 min; $[M+H]^+$=1132.3.

Step 5-2: The residue from Step 5-1 (448 mg, 0.395 mmol) was slowly dissolved in 33% wt HBr in AcOH (20 mL) and DCM (10 mL). The resulting mixture was stirred for 2 h at rt, then concentrated to dryness in vacuo. The crude product was purified by preparative reverse-phase HPLC (eluent A: 0.01 M HCl in $H_2O$; eluent B: ACN). After lyophilization, 156E-Batch 1 (89.8 mg, 0.085 mmol, 18% yield for Step 5 and Step 6) was obtained as a white solid and 156E-Batch 2 (63.4 mg, 0.060 mmol, 13% yield for Step 5 and Step 6) as an off-white solid. Analytical method 14; $t_R$=4.02 min; $[M+H]^+$=942.3.

Step 6. (3S,7S,10S,13R)-3-benzyl-6-(4-chloro-2-(4-(2-((dimethylamino)methyl)-1-methyl-1H-imidazol-5-yl)-phenoxy)benzyl)-13-(4-chlorobenzyl)-10-(methoxymethyl)-7-methyl-4-oxa-1,6,9,12-tetraazabicyclo[11.3.1]heptadecane-2,5,8,11-tetraone hydrochloride (Compound 156)

The cyclization of 156E was done in two portions. Portion 1: To a solution of 156E-Batch 1 (89.4 mg, 0.085 mmol) in DCM/NMP (14:3) (85 mL) was added HOAt (52.0 mg, 0.382 mmol) and HATU (129 mg, 0.340 mmol). The resulting mixture was stirred for 5 min at rt, and then 2,6-lutidine (0.297 mL, 2.55 mmol) was added. The reaction mixture was stirred for 90 min at rt, and then concentrated to dryness in vacuo. The residue was partitioned between EtOAc (50 mL) and 5% aq. $NaHCO_3$ (10 mL). The organic phase was washed with 5% aq. $NaHCO_3$ (2×10 mL) and brine, dried over $Na_2SO_4$, filtered, and concentrated to dryness in vacuo.

Portion 2: To a solution of 156E-Batch 2 (63.0 mg, 0.060 mmol) in DCM/NMP (53:10) (63 mL) was added HOAt (36.7 mg, 0.269 mmol) and HATU (91 mg, 0.239 mmol). The resulting mixture was stirred for 5 min at rt and then 2,6-lutidine (0.209 mL, 1.796 mmol) was added. The reaction mixture was stirred for 90 min at rt and concentrated to dryness in vacuo. The residue was partitioned between EtOAc (50 mL) and 5% aq. $NaHCO_3$ (10 mL). The organic phase was washed with 5% aq. $NaHCO_3$ (2×10 mL) and brine, dried over $Na_2SO_4$, filtered, and concentrated to dryness in vacuo.

The crude product was purified by preparative reverse-phase HPLC (eluent A: 0.01 M HCl in $H_2O$; eluent B: ACN). Pure fractions were combined and lyophilized to afford Compound 156 (55.6 mg, 0.055 mmol, 38% yield) as a white solid. Analytical method 14; $t_R$=5.23 min; $[M+H]^+$=924.3.

Example 8.11: Synthesis of (3R,7S,10S,13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-3-isopropyl-7-methyl-1,6,9,12-tetraazabicyclo[11.3.1]heptadecane-2,5,8,11-tetraone hydrochloride (Compound 133)
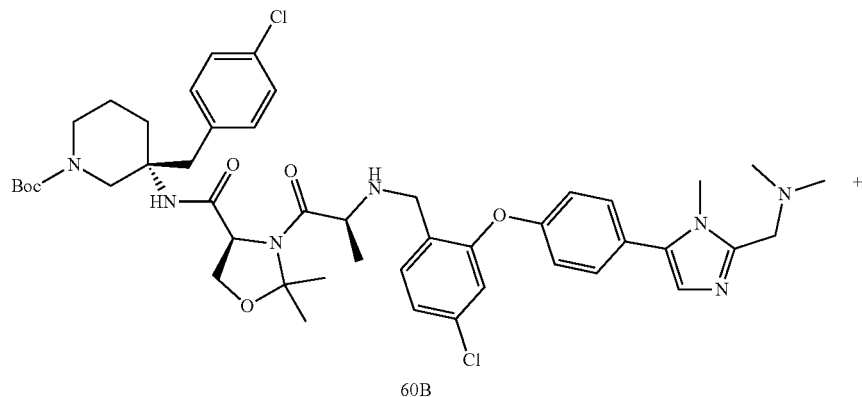
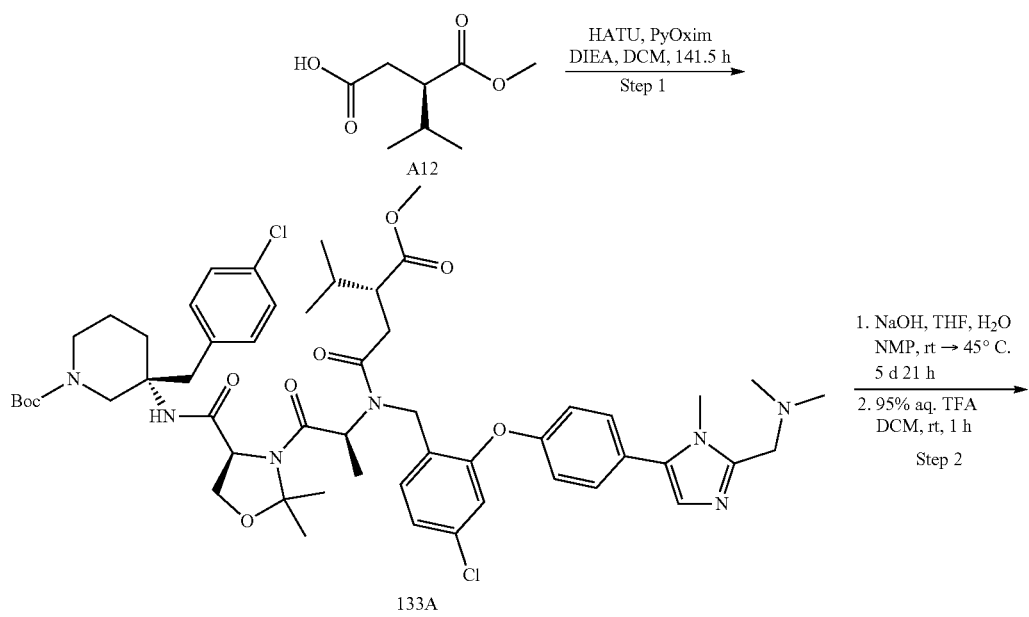

-continued

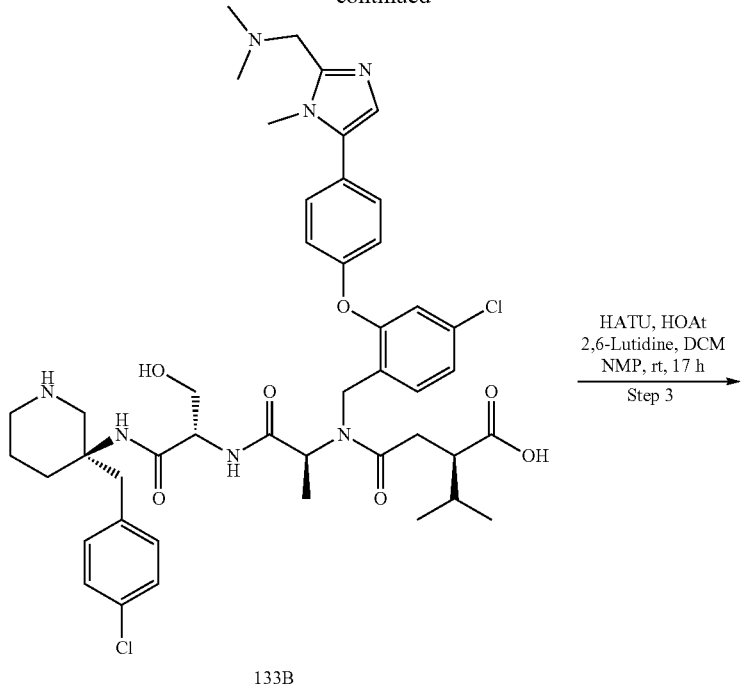

133B

HATU, HOAt
2,6-Lutidine, DCM
NMP, rt, 17 h
─────────→
Step 3

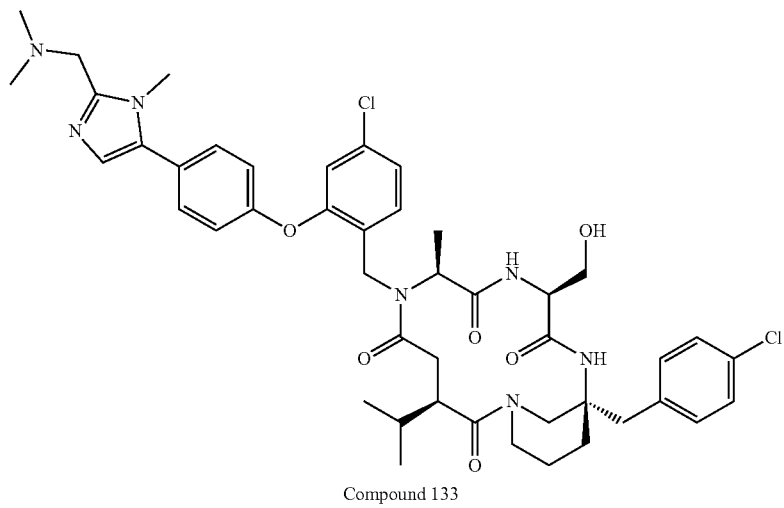

Compound 133

Step 1. tert-Butyl (R)-3-((S)-3-(N-(4-chloro-2-(4-(2-((dimethylamino)methyl)-1-methyl-1H-imidazol-5-yl)-phenoxy)benzyl)-N—((R)-3-(methoxycarbonyl)-4-methylpentanoyl)-L-alanyl)-2,2-dimethyloxazolidine-4-carboxamido)-3-(4-chlorobenzyl)piperidine-1-carboxylate (133A)

(R)-3-(methoxycarbonyl)-4-methylpentanoic acid (A12, 20.90 mg, 120 μmol) and HATU (45.6 mg, 120 μmol) were dissolved in DCM (1 mL) and DIEA (0.026 mL, 150 μmol) and stirred for 30 min at rt. A solution of 60B (100 μmol) in DCM (3 mL) was then added and the resulting mixture was stirred for 2 h at rt and then for 2 h at 40° C. Additional DIEA (0.026 mL, 150 μmol) was added and stirring at 40° C. was continued for 17.5 h. A solution of (R)-3-(methoxy-carbonyl)-4-methylpentanoic acid (20.90 mg, 120 μmol) and PyOxim (68.6 mg, 130 μmol) in DCM (1 mL) and DIEA (0.026 mL, 150 μmol) was added (preactivation time 2 min) and the reaction mixture was stirred for 32 h at rt. Additional solution of (R)-3-(methoxycarbonyl)-4-methylpentanoic acid (41.8 mg, 240 μmol) and HATU (91 mg, 240 μmol) in DCM (1 mL) and DIEA (0.052 mL, 300 μmol) was added (preactivation time 20 min) stirring was continued for 88 h at rt. The reaction mixture was partitioned between EtOAc (50 mL) and 5% aq. $Na_2CO_3$ (10 mL). The organic phase was washed with 5% aq. $Na_2CO_3$ (3×10 mL) and brine (10 mL), dried over $Na_2SO_4$, filtered, and concentrated to dryness in vacuo to afford 133A (~100 μmol) as a brown oil which was used in the next step without purification. Analytical method 10; $t_R$=1.20 min; [M+H]$^+$=1032.5.

Step 2. (S)-4-((4-Chloro-2-(4-(2-((dimethylamino)methyl)-1-methyl-1H-imidazol-5-yl)phenoxy)benzyl)((S)-1-(((S)-1-(((R)-3-(4-chlorobenzyl)piperidin-3-yl)amino)-3-hydroxy-1-oxopropan-2-yl)amino)-1-oxopropan-2-yl)amino)-2-isopropyl-4-oxobutanoic acid hydrochloride (133B)

Step 2-1: To 133A (0.100 mmol) dissolved in THF (5 mL) was added 0.25 M aq. NaOH (2.000 mL, 500 µmol) and the resulting mixture was stirred for 90 min at rt. Additional 0.25 M aq. NaOH (2.000 mL, 500 µmol) was added and stirring was continued for 2 h at rt. 2 M aq. NaOH (0.500 mL, 1000 µmol) was again added and the reaction mixture was stirred for 2 h at rt. Additional 2 M aq. NaOH (0.500 mL, 1000 µmol) and NMP (2 mL) was added and stirring was continued for 16 h at rt and then for 4 d 23.5 h at 45° C. The reaction mixture was quenched with AcOH (0.115 mL, 2.001 mmol) and the THF was removed in vacuo. The residue was partitioned between EtOAc (50 mL) and H$_2$O (5 mL). The organic phase was washed with 5% NaHCO$_3$ (5 mL) and brine (5 mL), dried over Na$_2$SO$_4$, filtered, and concentrated to dryness in vacuo.

Step 2-2: The residue from Step 2-1 was dissolved in 95% aq. TFA (7 mL) and DCM (3 mL), stirred for 1 h at rt, and then concentrated to dryness in vacuo. The crude product was purified by preparative reverse-phase HPLC (eluent A: 0.01 M HCl in H$_2$O; eluent B: ACN). Pure fractions were combined and lyophilized to afford 133B (16 mg, 0.016 mmol, 16% yield for 2 steps) as a white solid. Analytical method 14; $t_R$=3.37 min; [M+H]$^+$=878.4.

Step 3. (3R,7S,10S,13R)-6-(4-chloro-2-(4-(2-((dimethylamino)methyl)-1-methyl-1H-imidazol-5-yl)phenoxy)-benzyl)-13-(4-chlorobenzyl)-10-(hydroxymethyl)-3-isopropyl-7-methyl-1,6,9,12-tetraazabicyclo[11.3.1]-heptadecane-2,5,8,11-tetraone hydrochloride (Compound 133)

To 133B (16 mg, 0.016 mmol) in DCM/NMP (3:1) (16 mL) was added HATU (24.62 mg, 0.065 mmol) and HOAt (3.31 mg, 0.024 mmol). The resulting mixture was stirred for 10 min at rt and then 2,6-lutidine (0.057 mL, 0.486 mmol) was added. The reaction mixture was stirred for 15 h at rt, additional HATU (6.16 mg, 0.016 mmol) was added and stirring was continued for 2 h. The reaction mixture was concentrated in vacuo. The crude product was purified by preparative reverse-phase HPLC (eluent A: 0.01 M HCl in H$_2$O; eluent B: ACN). Pure fractions were combined and lyophilized to afford Compound 133 (9.1 mg, 9.55 µmol, 59% yield) as a white solid. Analytical method 9; $t_R$=4.63 min; [M+H]$^+$=860.4.

Example 8.12: Synthesis of (3S,7S,10S,13R)-6-(4-chloro-2-(4-(1-methyl-2-(pyrrolidin-1-ylmethyl)-1H-imidazol-5-yl)phenoxy)benzyl)-13-(4-chlorobenzyl)-3-((R)-2,3-dihydro-1H-inden-1-yl)-10-(hydroxymethyl)-7-methyl-1,6,9,12-tetraazabicyclo[11.3.1]heptadecane-2,5,8,11-tetraone hydrochloride (Compound 68)

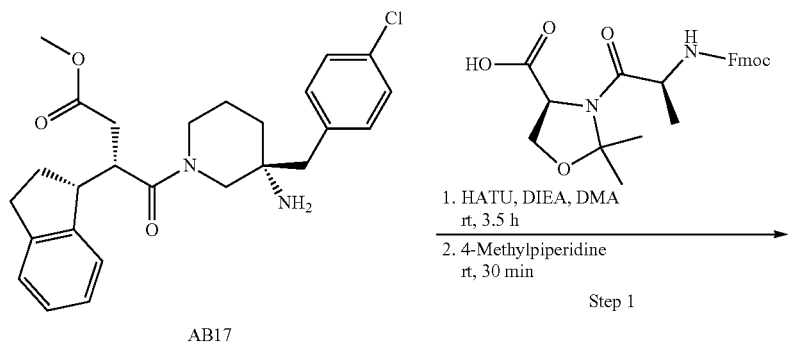

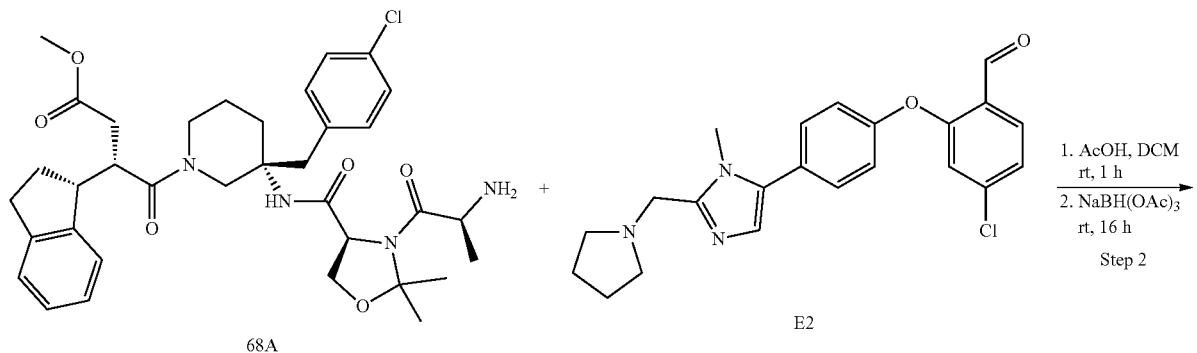

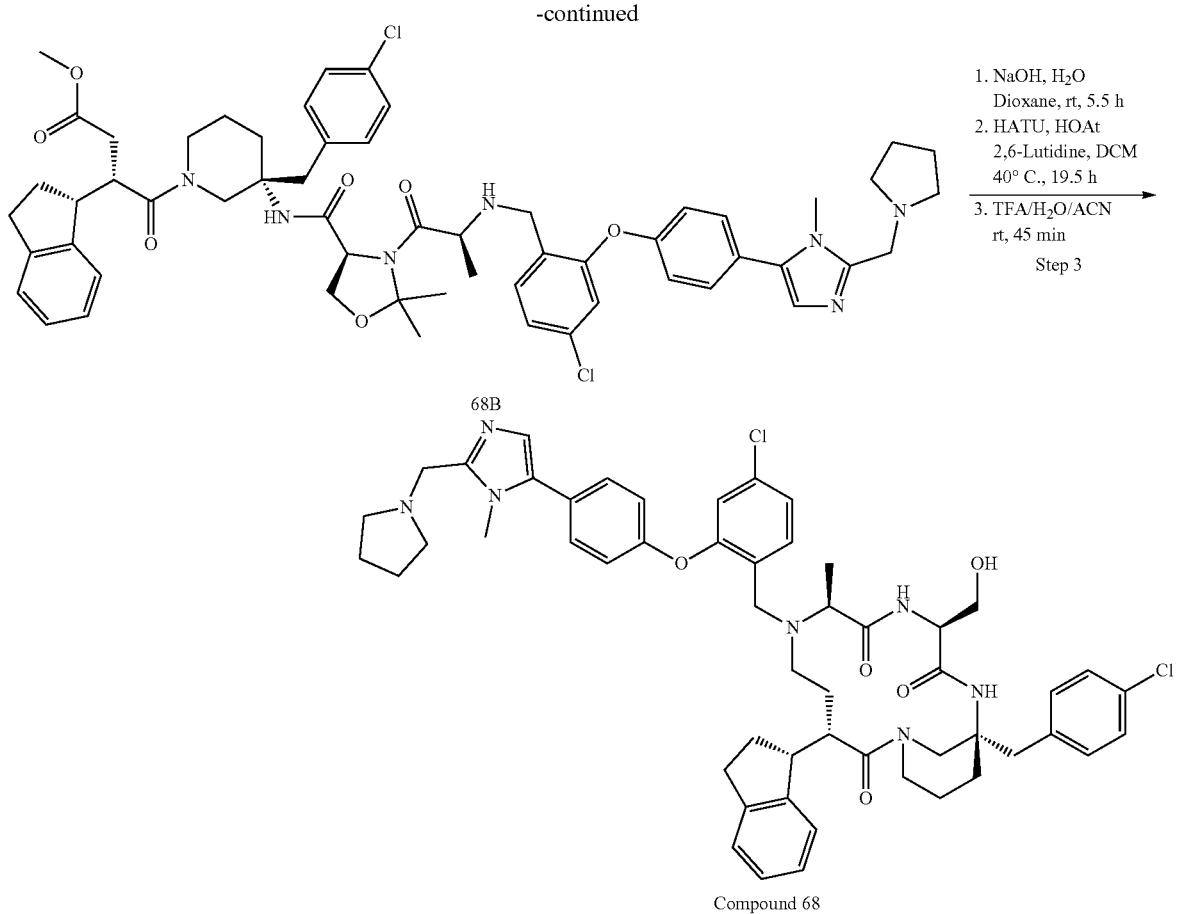

Compound 68

Step 1. Methyl (S)-4-((R)-3-((S)-3-(L-alanyl)-2,2-dimethyloxazolidine-4-carboxamido)-3-(4-chlorobenzyl)-piperidin-1-yl)-3-((R)-2,3-dihydro-1H-inden-1-yl)-4-oxobutanoate trifluoroacetate (68A)

Step 1-1: To a solution of Fmoc-Ala-Ser[psi(Me,Me)pro]-OH (119 mg, 0.270 mmol) and HATU (103 mg, 0.270 mmol) in DMA (2 mL) was added DIEA (0.061 mL, 0.351 mmol). The resulting solution was stirred for 2 min at rt and then a solution of AB17 (123 mg, 0.270 mmol) in DMA (3 mL) was added. The reaction mixture was stirred for 3.5 h at rt.

Step 1-2: 4-Methylpiperidine (1 mL) was added to the mixture of Step 1-1. The reaction mixture was stirred for 30 min at rt and then quenched by addition of AcOH (1.5 mL) and H$_2$O (2 mL). The resulting solution was directly subjected to preparative reverse-phase HPLC (eluent A: 0.1% TFA in H$_2$O; eluent B: ACN). Pure fraction were combined and lyophilized to afford 68A (120.6 mg, 0.157 mmol, 58.1% yield) as a white solid. Analytical method 10; $t_R$=1.11; [M+H]+=653.2.

Step 2. Methyl (S)-4-((R)-3-((S)-3-((4-chloro-2-(4-(1-methyl-2-(pyrrolidin-1-ylmethyl)-1H-imidazol-5-yl)phenoxy)benzyl)-L-alanyl)-2,2-dimethyloxazolidine-4-carboxamido)-3-(4-chlorobenzyl)piperidin-1-yl)-3-((R)-2,3-dihydro-1H-inden-1-yl)-4-oxobutanoate (68B)

68A (120.0 mg, 0.156 mmol) and E2 (74.3 mg, 0.188 mmol) were dissolved in a mixture of DCM (8 mL) and AcOH (0.036 mL, 0.626 mmol) and stirred for 1 h at rt. NaBH(OAc)$_3$ (166 mg, 0.782 mmol) was added and the reaction mixture was stirred for 16 h at rt and then concentrated to dryness in vacuo. The resulting residue was partitioned between EtOAc (50 mL) and 5% aq. Na$_2$CO$_3$ (10 mL). The organic phase was washed with 5% aq. Na$_2$CO$_3$ (3×10 mL) and brine (10 mL), dried over Na$_2$SO$_4$, filtered, and concentrated to dryness in vacuo to afford 68B (159 mg, 0.154 mmol, 98% yield) as a beige foam. The product was used in the next step without purification. Analytical method 10; $t_R$=1.11 min; [M+H]$^+$=1032.3.

Step 3. (3S,7S,10S,13R)-6-(4-Chloro-2-(4-(1-methyl-2-(pyrrolidin-1-ylmethyl)-1H-imidazol-5-yl)phenoxy)-benzyl)-13-(4-chlorobenzyl)-3-((R)-2,3-dihydro-1H-inden-1-yl)-10-(hydroxymethyl)-7-methyl-1,6,9,12-tetraazabicyclo[11.3.1]heptadecane-2,5,8,11-tetraone hydrochloride (Compound 68)

Step 3-1: To 68B (159 mg, 0.154 mmol) dissolved in dioxane (8 mL) and H$_2$O (2 mL) was added 1 M aq. NaOH (0.616 mL, 0.616 mmol). The resulting mixture was stirred for 5.5 h at rt and then quenched by the addition of a solution of 1 M aq. HCl (0.462 mL, 0.462 mmol) in H$_2$O (0.92 mL). The reaction mixture was concentrated to dryness in vacuo to afford a beige solid. Analytical method 10; $t_R$=1.05 min; [M+H]=1018.3.

Step 3-2: To a solution of the residue of Step 3-1 (154 μmol) in DCM (154 mL) was added HOAt (21.0 mg, 154

µmol) and HATU (234 mg, 616 µmol) and the resulting mixture was stirred for 5 min at rt. 2,6-lutidine (0.538 mL, 4620 µmol) was added and the reaction mixture was stirred for 19.5 h at 40° C. and then concentrated to dryness in vacuo. The residue was partitioned between EtOAc (50 mL) and 5% aq. NaHCO$_3$ (10 mL). The organic phase was washed with 5% aq. NaHCO$_3$ (2×10 mL) and brine (10 mL), dried over Na$_2$SO$_4$, filtered, and concentrated to dryness in vacuo.

Step 3-3: The residue from Step 3-2 was dissolved in ACN/H$_2$O (5:3) (8 mL) and 95% aq.

TFA (2 mL) was added. The reaction was stirred for 45 min at rt, then concentrated to dryness in vacuo. The product was purified by preparative reversed-phase HPLC (eluent A: 0.1% TFA in H$_2$O; eluent B: ACN). Pure fractions were combined and lyophilized. The product (TFA salt) was dissolved in EtOAc (100 mL) and the organic phase was washed with 5% aq. NaHCO$_3$ (3×5 mL) and brine (5 mL), dried over Na$_2$SO$_4$, filtered, and concentrated to dryness in vacuo. The residue was dissolved in ACN/H$_2$O (1:1) (40 mL) and 0.1 M aq. HCl (4.5 mL) was added. After lyophilization Compound 68 (40.6 mg, 38.1 µmol, 25% yield) was obtained as a white solid. Analytical method 9; $t_R$=5.02 min; [M+H]$^+$=960.3.

Example 8.13: Synthesis of (2S,3S)-2-(((Allyloxy) carbonyl)amino)-3-(tert-butoxy)butanoic acid (Intermediate O)

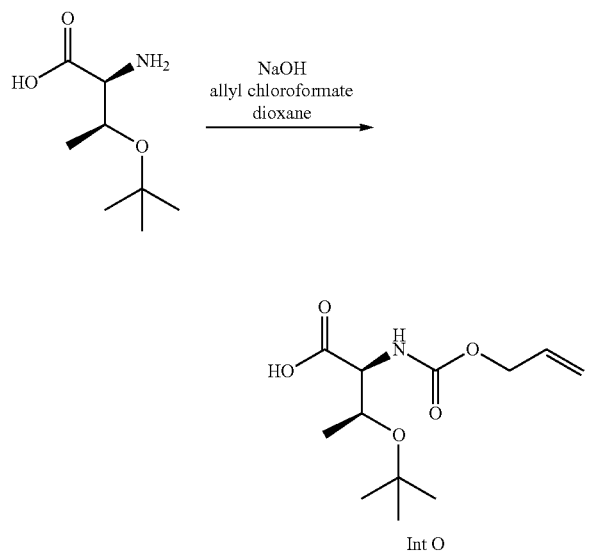

To a round bottom flask containing O-tert-butyl-L-allothreonine (2.3 g, 13.13 mmol) in NaOH (26.9 mL, 26.9 mmol) and cooled in an ice bath was added allyl chloroformate (1.54 mL, 14.44 mmol) in dioxane (15 mL) dropwise via addition funnel. Additional 1 N NaOH was then added until the pH was about 9-10. The resulting mixture was warmed to RT and allowed to stir for 2 h to complete the reaction. The reaction mixture was transferred to a separatory funnel and washed twice with ether. The aqueous phase was collected, acidified to pH ~2, and extracted twice with EtOAc. The combined organic phases were washed with brine, dried over Na$_2$SO$_4$, filtered, and concentrated to afford Intermediate O (Int O) as an oil after drying (3 g, 88% yield). $^1$H NMR (400 MHz, dichloromethane-d$_2$) δ ppm 1.16-1.35 (m, 12H) 3.70 (s, 2H) 3.98-4.09 (m, 1H) 4.35 (dd, J=8.31, 4.89 Hz, 1H) 4.61 (d, J=5.38 Hz, 2H) 5.25 (dq, J=10.51, 1.39 Hz, 1H) 5.30-5.56 (m, 1H) 5.86-6.08 (m, 1H). The product was used in the next step without further purification.

Example 8.14: Synthesis of N-(((9H-Fluoren-9-yl) methoxy)carbonyl)-O-(difluoromethyl)-L-serine (Intermediate P)

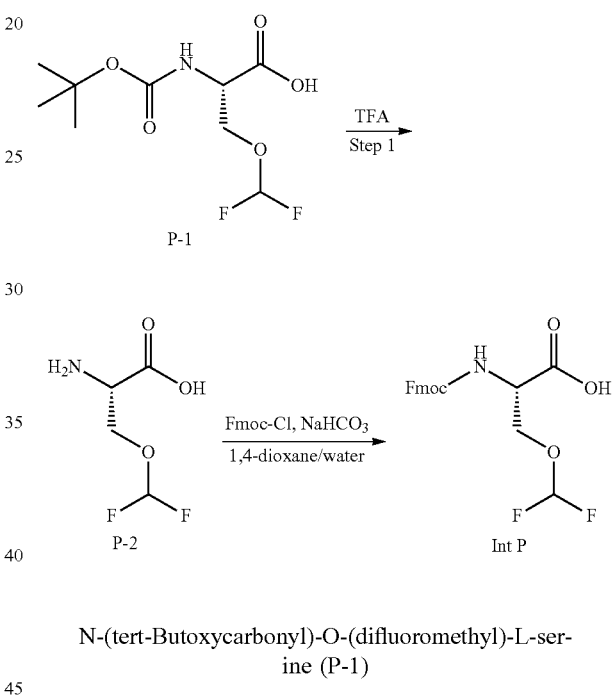

N-(tert-Butoxycarbonyl)-O-(difluoromethyl)-L-serine (P-1)

The title compound was prepared according to described in the literature example described in patent US2015/218212 A1, 2015.

Step 1. O-(Difluoromethyl)-L-serine (P-2)

To a solution of P-1 (1.56 g, 6.11 mmol) in anhydrous DCM (Volume: 20 mL) was added TFA (7.06 mL, 92 mmol). The resulting mixture was stirred at RT overnight and then concentrated under reduced pressure. The obtained residue was diluted with toluene (10 mL) and concentrated under reduced pressure. This process was repeated twice more to afford P-2 (0.948 g, 100%), which was used in the nest step without further purification. MS [M+H]=156.0.

Step 2. N-(((9H-Fluoren-9-yl)methoxy)carbonyl)-O-(difluoromethyl)-L-serine (Intermediate P)

P-2 (0.948 g, 6.11 mmol) was dissolved in a mixture of dioxane (40 mL) and water (20 mL) and was cooled to 0° C.

Sodium bicarbonate (30.8 g, 36.7 mmol) was added, followed by Fmoc-Cl (1.739 g, 6.72 mmol) a min later. The resulting mixture was stirred at 0° C. for 1 h, and then at room temperature for overnight. EtOAc was added and the reaction mixture was washed with H₂O, 1 N HCl, and brine. The organic phase was dried over Na₂SO₄, filtered, and concentrated. The crude product was purified by flash column chromatography on silica gel (eluting with 0-100% EtOAc/heptane) to give Int P as a white solid (1.6 g, 4.24 mmol, 69.4%) after drying under high vacuum. MS [M+H]=378.1.

Example 8.14: Synthesis of (4-Chloro-2-(4-(2-((dimethylamino)methyl)-1-methyl-1H-imidazol-5-yl)phenoxy)benzyl)-L-alanine (DE1)

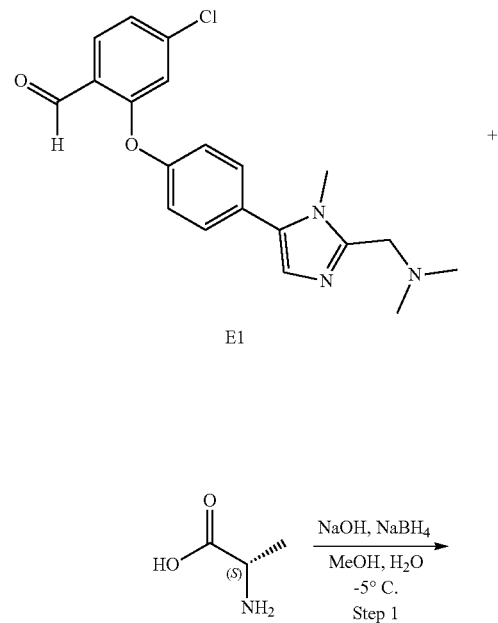

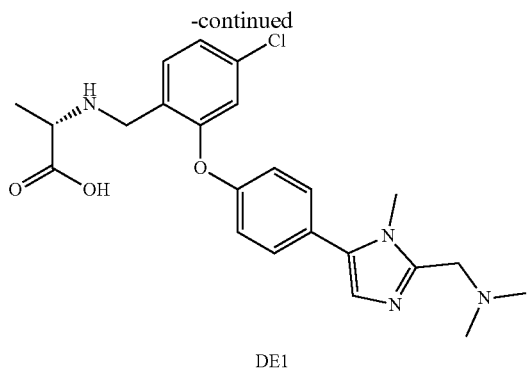

To a suspension of L-alanine (257 mg, 2.88 mmol) in MeOH (4 mL) and water (0.4 mL) at RT was added NaOH (115 mg, 2.88 mmol). The resulting mixture was allowed to stir for 30 min at RT and then E1 (1.02 g, 2.74 mmol) was added. The reaction mixture was cooled to −5° C. and allowed to stir for 1 h. NaBH₄ (42 mg, 1.1 mmol) was added in portions maintaining the internal reaction temperature below 0° C. The reaction mixture was stirred at 0° C. for 1 h, then quenched by adding water dropwise until gas evolution stopped, concentrated under reduced pressure. The aqueous residue was extracted with EtOAc (2×50 mL). The separated aqueous phase was loaded onto a pad of Dowex®. The pad was eluted with water, followed by 2 M NH₄OH in water. The combined aqueous filtrates were lyophilized to provide a white solid which was then dissolved in water. The aqueous phase was acidified to pH 7, extracted with 20% IPA in CHCl₃ (100 mL) several times, diluted with brine, and back-extracted with a solution of 20% IPA in CHCl₃. The combined organic phases were dried over Na₂SO₄, filtered, and concentrated to yield DE1 as a white solid (510 mg, 42%) which was used in the next step without further purification. Analytical method 7: $t_R$=0.49 min; MS [M+H]⁺=443.3.

The following intermediates in Table 12 were made according to the procedure described in Example 8.14 for DE1.

TABLE 12

| BB No. | Structure | Chemical Name |
|---|---|---|
| DE2 | (structure shown) | (4-Chloro-2-(4-(2-((dimethylamino)methyl)-1-methyl-1H-imidazol-5-yl)phenoxy)-6-fluorobenzyl)-L-alanine |

TABLE 12-continued

| BB No. | Structure | Chemical Name |
|---|---|---|
| DE3 | 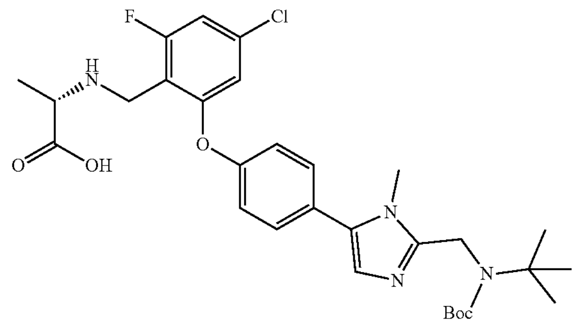 [SMILES: C[C@H](NCc1c(F)cc(Cl)cc1Oc1ccc(-c2cnc(CN(C(=O)OC(C)(C)C)C(C)(C)C)n2C)cc1)C(=O)O] | (2-(4-(2-(((tert-butoxycarbonyl)(tert-butyl)amino)methyl)-1-methyl-1H-imidazol-5-yl)phenoxy)-4-chloro-6-fluorobenzyl)-L-alanine |
| DE4 | 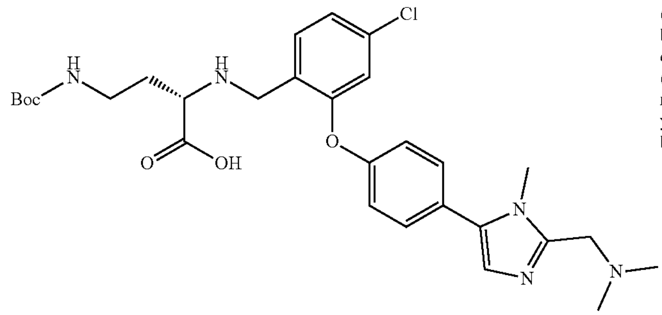 [SMILES: CN(C)Cc1ncc(-c2ccc(Oc3cc(Cl)ccc3CN[C@@H](CCNC(=O)OC(C)(C)C)C(=O)O)cc2)n1C] | (S)-4-((tert-butoxycarbonyl)amino)-2-((4-chloro-2-(4-(2-((dimethylamino)methyl)-1-methyl-1H-imidazol-5-yl)phenoxy)benzyl)amino)butanoic acid |

Example 8.15: Synthesis of (S)-3-((Allyloxy)carbonyl)-2,2-dimethyloxazolidine-4-carboxylic acid (Intermediate E)

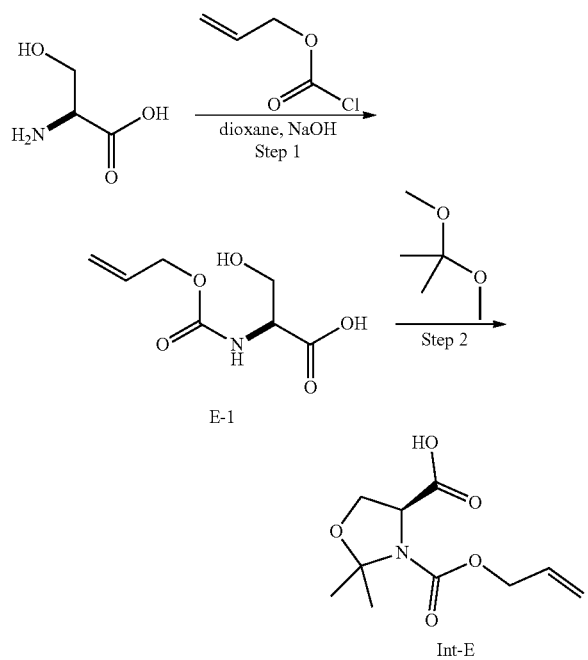

Step 1. (S)-2-(((Allyloxy)carbonyl)amino)-3-hydroxypropanoic acid (E-1)

To a round bottom flask containing L-serine (20.14 g, 192 mmol) was added NaOH (1 M, 393 mL, 393 mmol). The resulting mixture was cooled using an ice bath and allyl chloroformate (24.5 mL, 230 mmol) in dioxane (151 mL) was added dropwise via addition funnel. Additional NaOH (1 M) was added until the pH was about pH=9-10. The reaction mixture was warmed to RT, stirred overnight, transferred to a separatory funnel, and extracted twice with ether. The aqueous phase was acidified to pH 2.5 and extracted three times with EtOAc. The combined organic phases were dried over $Na_2SO_4$, filtered, and concentrated to afford 21 g of the desired product. Additional product was recovered from the water phase by adding brine and extracting twice with EtOAc. The combined organic phases were dried over $Na_2SO_4$, filtered, and concentrated to afford another 6 g of E-1 (75%) which was used in the next step without purification.

Step 2. (S)-3-((Allyloxy)carbonyl)-2,2-dimethyloxazolidine-4-carboxylic acid (Intermediate E)

To a round bottom flask containing E-1 (21 g, 111 mmol) in DCM (129 mL) was added p-TsOH (2.11 g, 11.10 mmol) and dimethoxy propane (93 g, 890 mmol). The resulting mixture was heated to reflux and stirred at reflux for 2 h. The heat source was removed and the reaction mixture was allowed to stir at RT overnight, concentrated under reduced pressure, and taken up in EtOAc. The organic phase was washed with saturated aq. $Na_2CO_3$. The separated aqueous phase was acidified to pH ~2 with 6 N HCl. The aqueous phase was extracted twice with EtOAc. The combined organic phases were washed with water and brine, dried over $Na_2SO_4$, filtered, and concentrated to afford Int-E (6 g, 26.2 mmol). The product was used in the next step without purification.

Example 8.16: Synthesis of (R)-tert-Butyl 3-((S)-2-amino-3-methoxy-N-methylpropanamido)-3-(4-chlorobenzyl)piperidine-1-carboxylate (intermediate F)

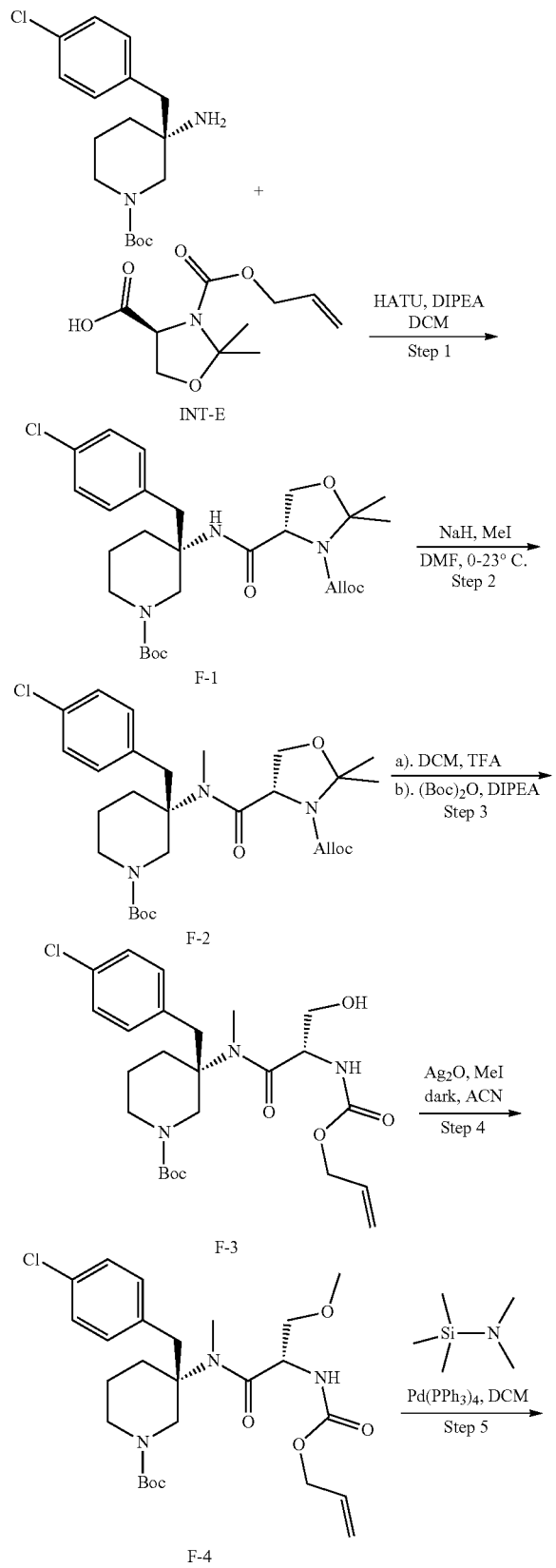

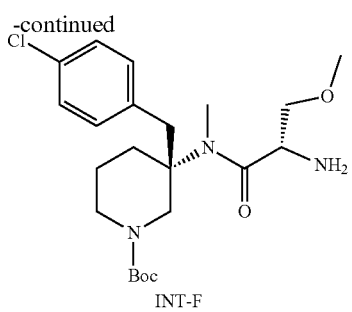

INT-F

Step 1. (S)-Allyl 4-(((R)-1-(tert-butoxycarbonyl)-3-(4-chlorobenzyl)piperidin-3-yl)carbamoyl)-2,2-dimethyloxazolidine-3-carboxylate (F-1)

To a suspension of B2 (4.96 g, 15.27 mmol) in DCM (100 mL) was added DIPEA (6.38 mL, 45.8 mmol) and INT-E (3.5 g, 15.27 mmol). The resulting mixture was cooled to 0° C. and HATU (6.39 g, 16.80 mmol) was added. The cooling bath was removed and the resulting solution was stirred at RT overnight, diluted with DCM (100 mL), and washed twice with a 5% aqueous solution of NaHCO$_3$ and brine. The organic phase was dried over sodium sulfate, filtered, and concentrated under reduced pressure. The resulting oil was purified by flash column chromatography on silica gel (eluting with 0-60% EtOAc in heptane) to afford F-1 (6.1 g, 11.38 mmol, 74.5%) as a white foam. Analytical method 5: $t_R$=1.28 min; MS [M+H]$^+$=536.3.

Step 2. (S)-Allyl 4-(((R)-1-(tert-butoxycarbonyl)-3-(4-chlorobenzyl)piperidin-3-yl)(methyl)carbamoyl)-2,2-dimethyloxazolidine-3-carboxylate (F-2)

To a solution of F-1 (6.1 g, 11.38 mmol) in anhydrous DMF (50 mL) at 0° C. under an atmosphere of nitrogen was added NaH (1.00 g, 25.03 mmol) in portions over 20 min. The resulting mixture was stirred at 0° C. for 2 h (turned light brown), and MeI (2.85 mL, 45.5 mmol) was added and stirring was continued at 0° C. for 6.5 h. Once LCMS showed complete consumption of starting material, the reaction mixture was quenched with saturated aq. NaHCO$_3$. The resulting yellow precipitate was collected by vacuum filtration and redissolved in EtOAc. The organic phase was washed with water, dried over sodium sulfate, filtered, and concentrated to afford F-2 (6.37 g, 11.58 mmol, quantitative) as a yellow foam. Analytical method 5: $t_R$=1.12 min; MS [M+H]$^+$=550.0.

Step 3. (R)-tert-Butyl 3-((S)-2-(((allyloxy)carbonyl)amino)-3-hydroxy-N-methylpropanamido)-3-(4-chlorobenzyl)piperidine-1-carboxylate, Allyl ((S)-1-(((R)-3-(4-chlorobenzyl)piperidin-3-yl)(methyl)amino)-3-hydroxy-1-oxopropan-2-yl)carbamate (F-3)

To a solution of F-2 (1 g, 1.818 mmol) in DCM (25 mL) was added dropwise 0.2 M TFA in DCM (136 mL, 27.3 mmol). After stirring for 1 h at RT, additional DCM (100 mL) was added and the resulting mixture was stirred overnight. The reaction mixture was quenched and washed with saturated aq. NaHCO$_3$. The organic phase was dried over sodium sulfate, filtered, and concentrated to about 50 mL under reduced pressure.

To the above solution was added TEA (0.507 mL, 3.64 mmol) and (Boc)₂O (0.211 mL, 0.909 mmol). The resulting mixture was stirred at RT for 1.5 h., diluted with 100 mL of EtOAc and washed with 50 mL of saturated aq. NaHCO₃ solution. The organic phase was dried over sodium sulfate, filtered, and concentrated. The crude material was purified by flash column chromatography on silica gel (eluting with 0-100% EtOAc and hexanes) to afford F-3 (615 mg, 1.206 mmol, 66.3%) as a white foam. Analytical method 5: $t_R$=1.13 min; MS [M+H]⁺=510.4.

Step 4. (R)-tert-Butyl 3-((S)-2-(((allyloxy)carbonyl)amino)-3-methoxy-N-methylpropanamido)-3-(4-chlorobenzyl)piperidine-1-carboxylate (F-4)

To a solution of F-3 (615 mg, 1.206 mmol) in anhydrous ACN (10 mL) was added Ag₂O (1397 mg, 6.03 mmol) and MeI (0.754 mL, 12.06 mmol). The reaction was stirred at RT under an atmosphere of nitrogen in the dark overnight (16 h). LCMS showed that the desired product as a major product. The reaction mixture was filtered through a pad of Celite® and the filtrate concentrated under reduced pressure to afford F-4 as a white foam (591 mg, 1.128 mmol, 94%). Analytical method 5: $t_R$=1.23 min; MS [M+H]⁺=524.0.

Step 5. (R)-tert-Butyl 3-((S)-2-amino-3-methoxy-N-methylpropanamido)-3-(4-chlorobenzyl)piperidine-1-carboxylate (Intermediate F)

To a solution of F-4 (591 mg, 1.128 mmol) and N,N,1,1,1-pentamethylsilanamine (793 mg, 6.77 mmol) in DCM (20 mL) was added tetrakis(triphenylphosphine) palladium (0) (65.2 mg, 0.056 mmol) and the resulting mixture was stirred at RT for 2 h. The reaction mixture was then evaporated to dryness. The resulting oil Int-F was used in the next step without further purification. Analytical method 5: $t_R$=1.07 min; MS [M+H]⁺=440.2.

Example 8.17: Synthesis of (R)-tert-Butyl 3-((S)-2-amino-3-hydroxy-N-methylpropanamido)-3-(4-chlorobenzyl)piperidine-1-carboxylate (Intermediate G)

To a flask containing F-2 (2.1 g, 3.82 mmol) and N,N-dimethyltrimethyisilylamine (2.69 g, 22.91 mmol) was added DCM (10 mL), followed by Pd(PPh₃)₄ (0.221 g, 0.191 mmol). The resulting mixture was bubbled with N₂ for 5 min and then stirred at RT under a N₂ atmosphere for 90 min. Water (0.2 mL) was added and the reaction mixture was concentrated under reduced pressure to afford the desired product Int G as the major product by LC/MS. The material was used in the next step without purification.

Alternatively, Int-G can be prepared as shown below starting from B2 as shown in the scheme below.

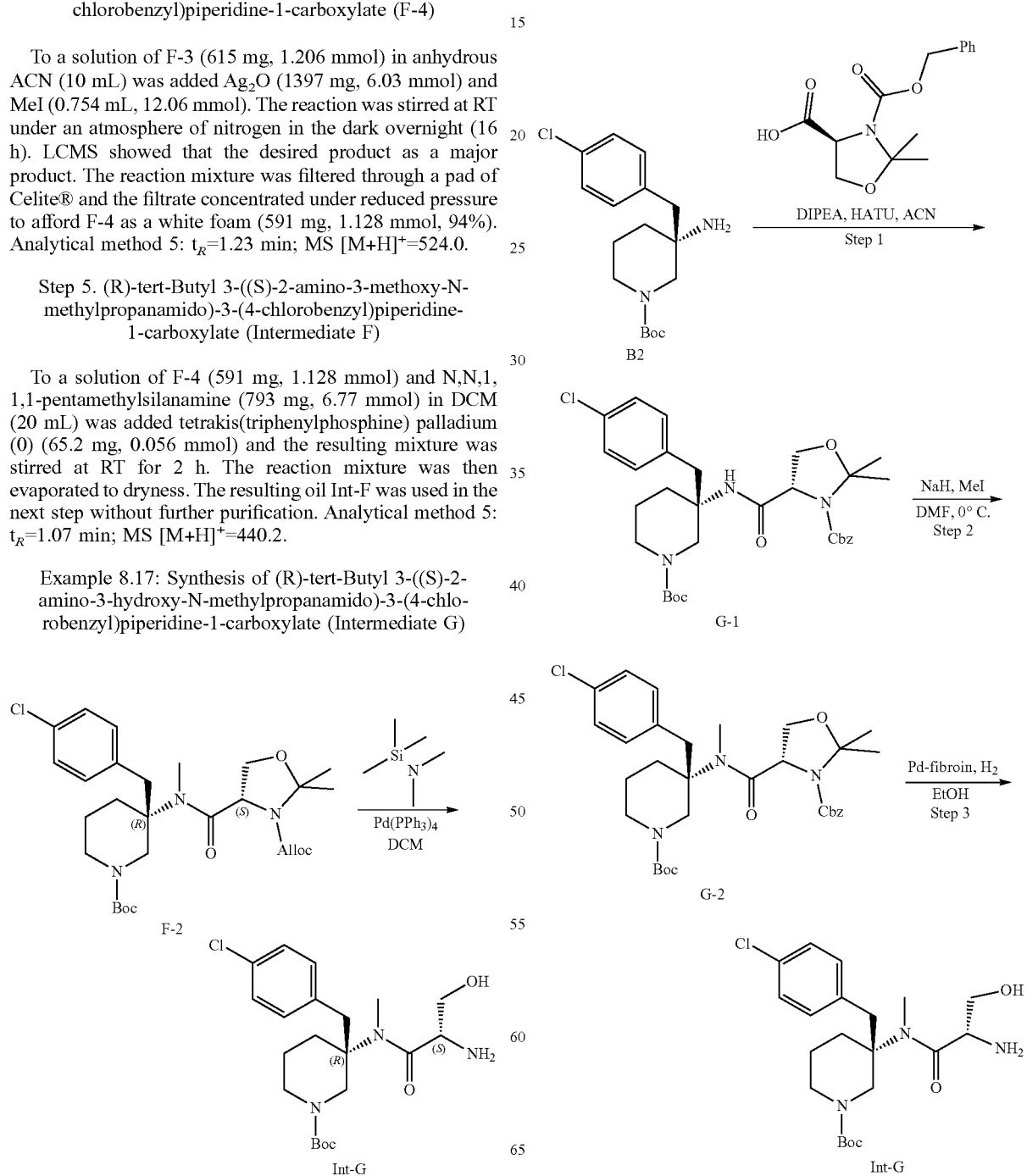

Step 1. (S)-Benzyl 4-(((R)-1-(tert-butoxycarbonyl)-3-(4-chlorobenzyl)piperidin-3-yl)carbamoyl)-2,2-dimethyloxazolidine-3-carboxylate (G-1)

To a solution of intermediate B2 (524 mg, 1.613 mmol) in anhydrous ACN (5 mL) was added DIPEA (0.563 mL, 3.23 mmol) and (S)-3-((benzyloxy)carbonyl)-2,2-dimethyloxazolidine-4-carboxylic acid (496 mg, 1.774 mmol), followed by addition of HATU (675 mg, 1.774 mmol). The resulting mixture was stirred at RT overnight and then concentrated. The crude material was purified by ISCO flash column chromatography on silica gel (eluting with 0-50% EtOAc in heptane) to afford G-1 (817 mg, 1.394 mmol, 86%) as a white foam. Analytical method 5: $t_R$=1.34 min; MS [M+H]$^+$−100=486.3. TLC: Rf=0.53; 1:1 EtOAc/Heptane.

Step 2. Benzyl 4-(((R)-1-(tert-butoxycarbonyl)-3-(4-chlorobenzyl)piperidin-3-yl)(methyl)carbamoyl)-2,2-dimethyloxazolidine-3-carboxylate (G-2)

To a solution of G-1 (560 mg, 0.955 mmol) in anhydrous DMF (15 mL) at 0° C. under an atmosphere of nitrogen was added 60% (in mineral oil) NaH (76 mg, 1.911 mmol). The resulting mixture was stirred at 0° C. for 30 min and MeI (0.179 mL, 2.87 mmol) was added. The reaction mixture was stirred at 0° C. for 60 min. LCMS showed starting material still present. An additional 1.0 eq of NaH was added and stirring was continued for an additional 30 min. Additional MeI was added and the reaction mixture was stirred for another 30 min and then quenched with saturated aq. NaHCO$_3$ and water. The resulting white precipitate was collected by vacuum filtration and redissolved in EtOAc. The organic phase was dried over sodium sulfate, filtered, and concentrated under reduced pressure to afford G-2 (500 mg, 0.833 mmol, 87%) which was used in the next step without further purification. Analytical method 5: $t_R$=1.36 min; MS [M+H]$^+$=600.4.

Step 3. (3R)-tert-Butyl 3-(2-amino-3-hydroxy-N-methylpropanamido)-3-(4-chlorobenzyl)piperidine-1-carboxylate (Int-G)

To a mixture of G-2 (660 mg, 1.100 mmol) in EtOH (100 mL) was added Pd-fibroin (731 mg, 0.110 mmol) under a nitrogen atmosphere. The resulting mixture was fitted with a hydrogen balloon and stirred at RT for 5 h. Another 731 mg of Pd-fibroin was added and the reaction mixture was stirred overnight. The hydrogen balloon was disconnected and the reaction vial was flushed with nitrogen three times before being exposed to air. The reaction mixture was filtered through a pad of pre-wetted (with DCM) Celite® and washed with additional DCM. The filtrate was concentrated under reduced pressure to afford a crude product, which was purified by reverse-phase column chromatography (eluting with 0-100% ACN water containing 0.1% NH$_4$OH) to afford Int-G (57 mg, 0.134 mmol, 12.2%). Analytical method 5: $t_R$=0.97 min; MS [M+H]$^+$=426.4.

Example 8.18: Synthesis of N-(tert-butoxycarbonyl)-N-(4-chloro-2-(4-(2-((dimethylamino)methyl)-1-methyl-1H-imidazol-5-yl)phenoxy)-6-fluorobenzyl)-L-alanine (Intermediate H)

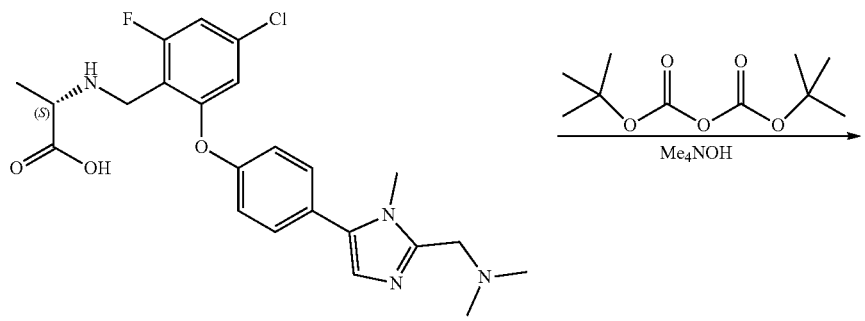

DE2

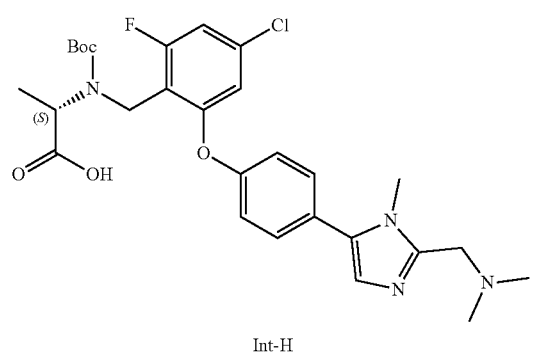

Int-H

To a slurry containing DE2 (12.85 g, 27.9 mmol) in ACN (232 mL) was added tetramethylammonium hydroxide pentahydrate (2.54 g, 27.9 mmol) at RT. The resulting slurry was stirred for 20 min and Boc anhydride (9.13 g, 41.8 mmol) was added. The reaction mixture was stirred overnight, then quenched with water, and concentrated under reduced pressure to remove excess ACN. The pH of the resulting aqueous phase was adjusted to pH ~5.5 with 1 N HCl and extracted twice with 2-methyltetrahydrofuran. The organic phases were combined and dried over sodium sulfate, filtered, and concentrated to afford Int-H after drying under high vacuum (12.92 g, 83%).

Example 8.19: Synthesis of tert-Butyl (S)-3-((R)-3-((S)-2-((S)-2-aminopropanamido)-3-methoxypropanamido)-3-(4-chlorobenzyl) piperidine-1-carbonyl)-5,5,5-trifluoropentanoate (Intermediate K)

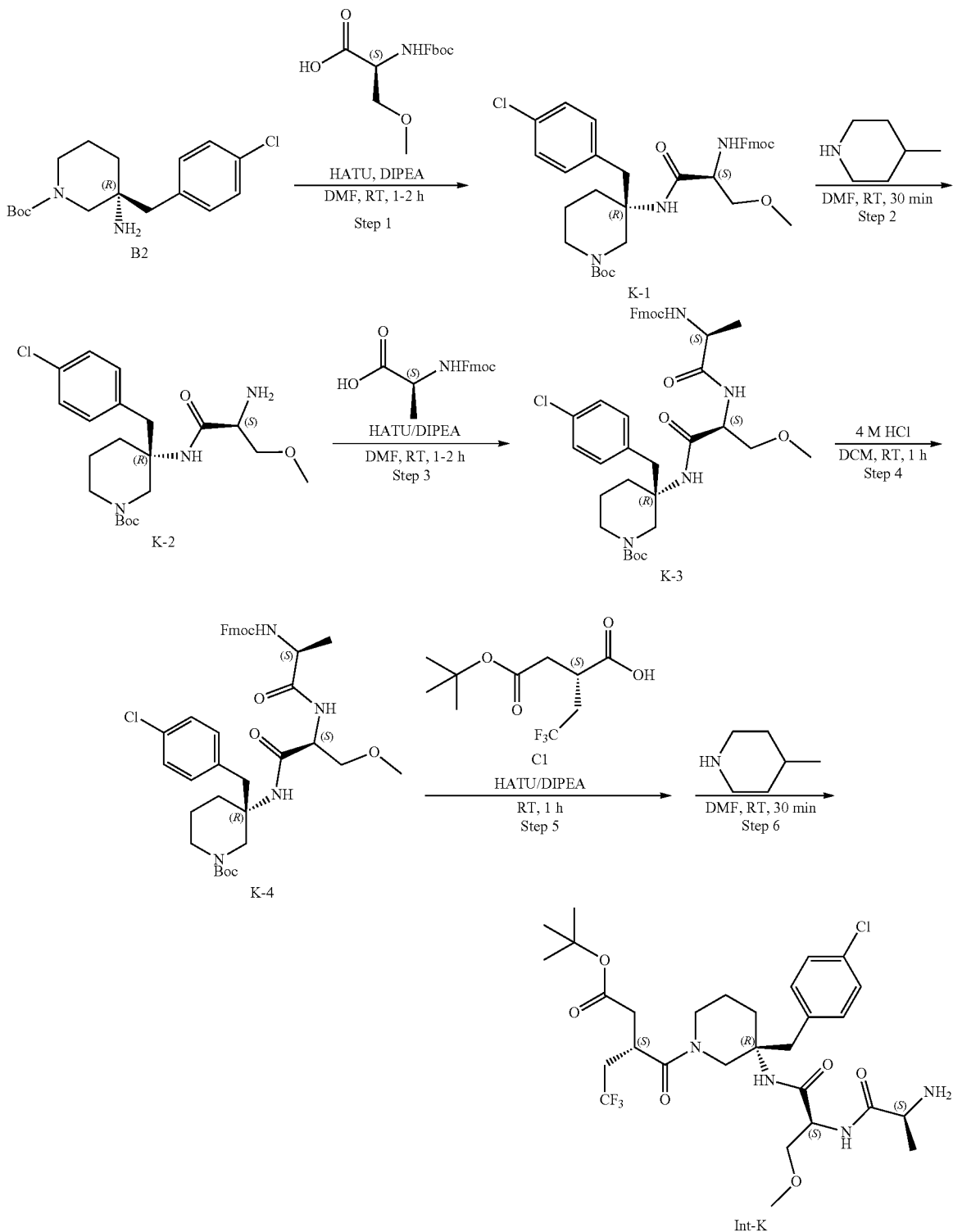

Step 1. tert-Butyl (R)-3-((S)-2-((((9H-fluoren-9-yl)methoxy)carbonyl)amino)-3-methoxypropanamido)-3-(4-chlorobenzyl)piperidine-1-carboxylate (K-1)

To a solution of Fmoc-Ser(OMe)-OH (2.84 g, 8.31 mmol, 1.08 eq) in DMF (25 mL) was added HATU (3.16 g, 8.31 mmol, 1.08 eq) and DIPEA (2.69 mL, 15.39 mmol). The resulting mixture was stirred for 2 min and a solution of B2 (2.5 g, 7.70 mmol) in DMF (10 mL) was then added in one portion. The reaction mixture was stirred at RT and then diluted with EtOAc. The organic phase was washed twice with a 5% aqueous solution of NaHCO$_3$ and brine, dried over Na$_2$SO$_4$, filtered, and concentrated to give K-1 (5.66 g) as light yellow foam which was used in next step without further purification. Analytical method 7: $t_R$=1.39 min; MS [M+Na]$^+$=670.2.

Step 2. tert-Butyl (R)-3-((S)-2-amino-3-methoxypropanamido)-3-(4-chlorobenzyl)piperidine-1-carboxylate (K-2)

To a solution of K-1 (5.66 g, 7.68 mmol) in DMF (40 mL) was added 4-methylpiperidine (10 mL, 85 mmol). The reaction mixture was stirred for 30 min at RT and then concentrated to dryness. The residue was diluted with EtOAc. The organic phase was washed with H$_2$O and brine, dried over Na$_2$SO$_4$, filtered, and concentrated to give K-2 (6.42 g) as a light yellow solid which was used in next step without further purification. Analytical method 5: $t_R$=1.09 min; MS [M+H]$^+$=426.3.

Step 3. tert-Butyl (R)-3-((S)-2-((S)-2-((((9H-fluoren-9-yl)methoxy)carbonyl)amino)propanamido)-3-methoxypropanamido)-3-(4-chlorobenzyl)piperidine-1-carboxylate (K-3)

To a solution of Fmoc-Ala-OH (4.79 g, 15.37 mmol) in DMF (45 mL) was added HATU (5.85 g, 15.37 mmol) and DIPEA (6 mL, 34.4 mmol). The resulting mixture was stirred for 2 min and a solution of K-2 (6.42 g, 7.69 mmol) in DMF (15 mL) was then added in one portion. The reaction mixture was stirred at RT and then diluted with EtOAc. The organic phase was washed twice with a 5% aqueous solution of NaHCO$_3$ and brine, dried over Na$_2$SO$_4$, filtered, and concentrated. The crude product was purified by flash column chromatography on silica gel (eluting with 0-100% EtOAc/heptane) to give K-3 (1.69 g, 30.6%) as a yellow foam. Analytical method 5: $t_R$=1.34 min; MS [M+H]$^+$=719.5.

Step 4. (9H-Fluoren-9-yl)methyl ((S)-1-(((S)-1-(((R)-3-(4-chlorobenzyl)piperidin-3-yl)amino)-3-methoxy-1-oxopropan-2-yl)amino)-1-oxopropan-2-yl)carbamate (K-4)

To a solution of K-3 (1.69 g, 2.35 mmol) in DCM (5 mL) was added HCl in dioxane (12 mL, 48.0 mmol) dropwise. The resulting mixture was stirred at RT for 1 h and then concentrated to give K-4 (1.8 g) as yellow foam which was used directly in next step without further purification. Analytical method 5: $t_R$=1.18 min; MS [M+H]$^+$=619.3.

Step 5 & 6. tert-Butyl (S)-3-((R)-3-((S)-2-((S)-2-aminopropanamido)-3-methoxypropanamido)-3-(4-chlorobenzyl) piperidine-1-carbonyl)-5,5,5-trifluoropentanoate (Intermediate K)

To a solution of A14 (0.72 g, 2.81 mmol, 1.2 eq) in DMF (10 mL) was added HATU (1.077 g, 2.83 mmol) and DIPEA (2.06 mL, 11.81 mmol). The resulting mixture was stirred for 2 min and then a solution of K-4 (1.8 g, 2.36 mmol) in DMF (5 mL) was in one portion. The reaction mixture was stirred at RT for 1 h and then 4-methylpiperidine (4.5 mL, 38.1 mmol, 16 eq) was added in one portion. The reaction mixture was stirred for 30 min at RT and then concentrated to dryness. The crude product was purified by reverse phase column chromatography (eluting with 0-100% ACN/H$_2$O with 0.1% NH$_4$OH) to afford Int-K as off-white foam. Analytical method 4: $t_R$=1.88 min; MS [M+H]$^+$=635.4.

Example 8.20: Synthesis of (R)-Methyl 4-((R)-3-((S)-3-((S)-2-aminopropanoyl)-2,2-dimethyloxazolidine-4-carboxamido)-3-(4-chlorobenzyl)piperidin-1-yl)-3-benzyl-4-oxobutanoate trifluoroacetic acid salt (Intermediate M)

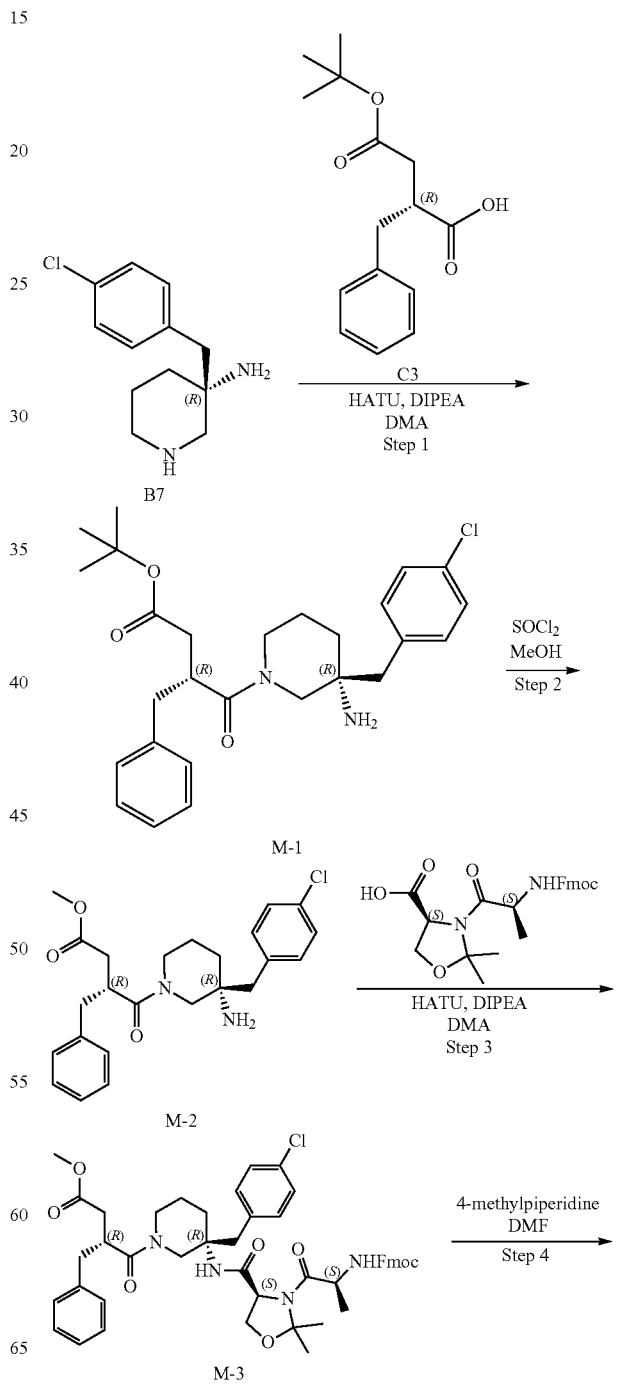

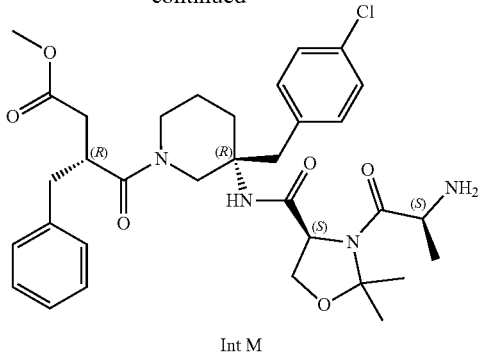

Int M

Step 1. (R)-tert-Butyl 4-((R)-3-amino-3(4-chlorobenzyl)piperidin-1-yl)-3-benzyl-4-oxobutanoate (M-1)

To a vial containing C3 (244 mg, 0.924 mmol) n DMA (4 mL) at room temperature was added DIPEA (0.323 mL, 1.848 mmol) and HATU (358 mg, 0.942 mmol) in several portions. Once the addition was complete, the resulting mixture was stirred at room temperature for another 15 mi and then added dropwise to another vial containing B7 (275 mg, 0924 mmol) in DMA (1.5 mL) and DIPEA (0.807 mL, 4.62 mmol). The reaction mixture was stirred at room temperature overnight, then transferred to a separatory funnel, diluted with EtOAc, and washed with saturated aq. sodium bicarbonate and brine (×3). The organic phase was dried over sodium sulfate, filtered, and concentrated to afford M-1 (435 mg, quantitative yield), which was carried to the next step without purification.

Step 2. (R)-Methyl 4-((R)-3-amino-3-(4-chlorobenzyl)piperidin-1-yl)-3-benzyl-4-oxobutanoate (M-2)

To a round bottom flask containing M-1 (435 mg, 0.924 mmol) in anhydrous methanol (18 mL) and cooled in an ice bath was added thionyl chloride (1.35 mL, 18.47 mmol) dropwise. When the addition was complete, the resulting mixture was warmed to room temperature gradually and then stirred overnight to complete the reaction. The reaction mixture was concentrated to dryness under reduced pressure with heating in a water bath at 30° C. The crude oil was dissolved in EtOAc, washed with a half-saturated aqueous solution of sodium bicarbonate, and then washed with brine. The separated organic phase was dried over sodium sulfate, filtered, and concentrated to afford M-2 (408 mg, quantitative yield), which was carried to the next step without purification.

Step 3. (R)-Methyl 4-((R)-3-((S)-3-((S)-2-((((9H-fluoren-9-yl)methoxy)carbonyl)amino)propanoyl)-2,2-dimethyloxazolidine-4-carboxamido)-3-(4-chlorobenzyl)piperidin-1-yl)-3-benzyl-4-oxobutanoate (M3)

To a vial containing M-2 (408 mg, 0.951 mmol) and (S)-3-((S)-2-((((9H-fluoren-9-yl)methoxy)carbonyl)amino) propanoyl)-2,2-dimethyloxazolidine-4-carboxylic acid (417 mg, 0.951 mg) was added DMA (4.7 mL) and DIPEA (0.249 mL, 1.427 mmol) with stirring. HATU (362 mg, 0.951 mmol) was then added in one portion and the resulting mixture was stirred at room temperature overnight to complete the reaction. EtOAc was added and the reaction mixture was transferred to a separatory funnel and washed with a half-saturated solution of sodium bicarbonate. The organic phase was washed three times with brine, dried over sodium sulfate, filtered, and concentrated. The crude product was purified by flash column chromatography on silica gel (eluting with 0-55% DCM/EtOAc) to afford M-3 (660 mg, 82%) after concentrating the pure fractions under reduced pressure.

Step 4. (R)-Methyl 4-((R)-3-((S)-3-((S)-2-amino-propanoyl)-2,2-dimethyloxazolidine-4-carboxamido)-3-(4-chlorobenzyl)piperidin-1-yl)-3-benzyl-4-oxobutanoate trifluoroacetic acid salt (Intermediate M)

To a round bottom flask containing M-3 (660 mg, 0.777 mmol) in DMF (5 mL) was added 4-methylpiperidine (2.75 mL, 23.31 mmol) at room temperature and the resulting mixture was stirred for 35 min. The resulting white slurry was cooled in an ice bath and quenched with acetic acid (1.56 mL, 27.2 mmol) dropwise. Water (0.5 mL) was then added and the slurry was filtered and the filtrate was purified by reverse-phase column chromatography on a C18 column (eluting with 30-70% water/ACN, 0.1% TFA) in three injections. After freeze drying, the pure fractions afforded Int M as a white powder (576 mg, quantitative yield)

The following intermediate in Table 13 was prepared according to the procedure described for 8.20 for Intermediate M.

TABLE 13

| BB No. | Structure | Chemical Name |
|---|---|---|
| M2 | 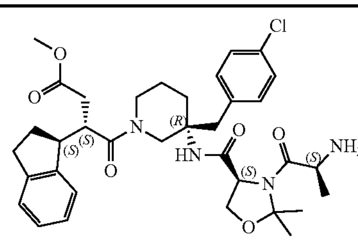 | Methyl (S)-4-((R)-3-((S)-3-(L-alanyl)-2,2-dimethyl-oxazolidine-4-carboxamido)-3-(4-chlorobenzyl)piperidin-1-yl)-3-((S)-2,3-dihydro-1H-inden-1-yl)-4-oxobutanoate |

Example 8.21:Synthesis of (3S,7S,10S,13R)-6-(4-Chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-3-(2,2,2-trifluoroethyl)-1,6,9,12-tetraazabicyclo[11.3.1]heptadecane-2,5,8,11-tetraone (Compound 83)

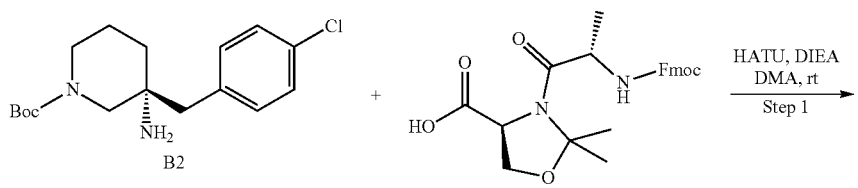

-continued
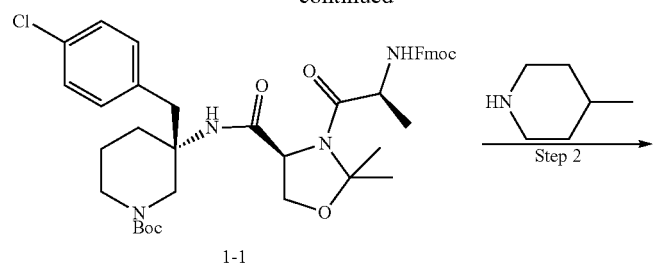
1-1
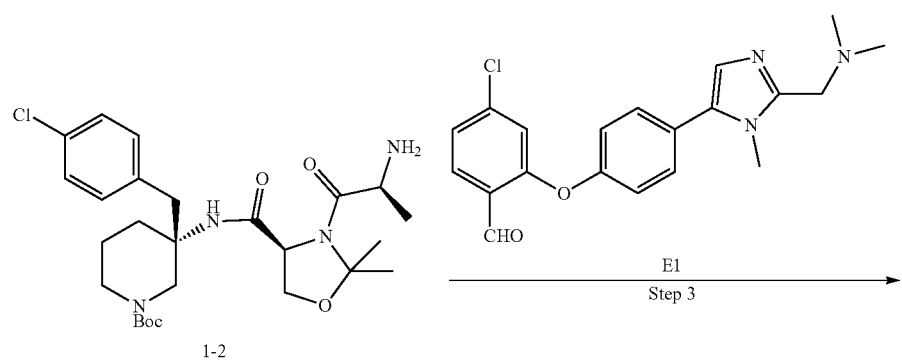
1-2
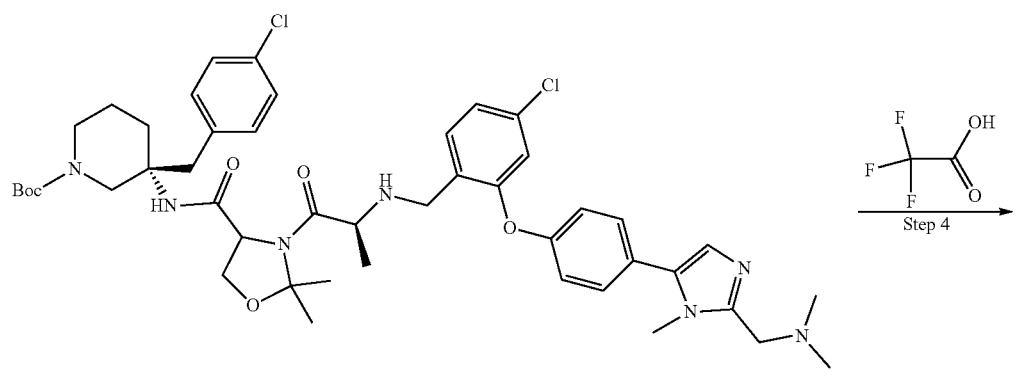
1-3
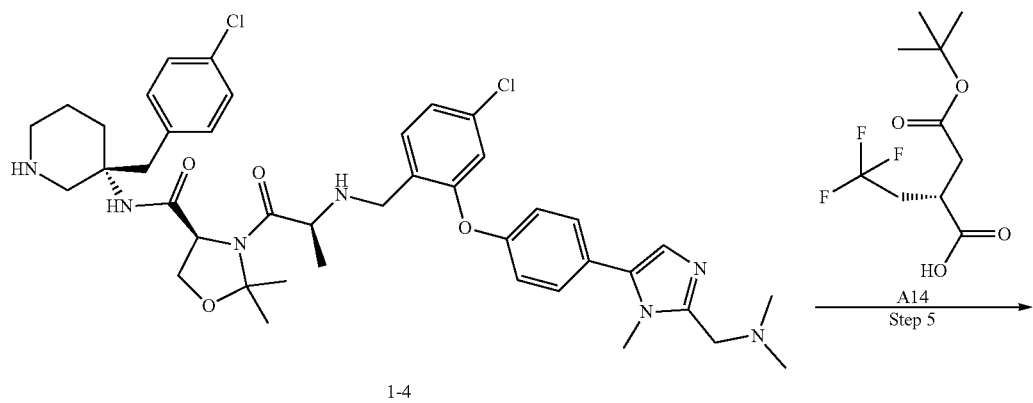
1-4

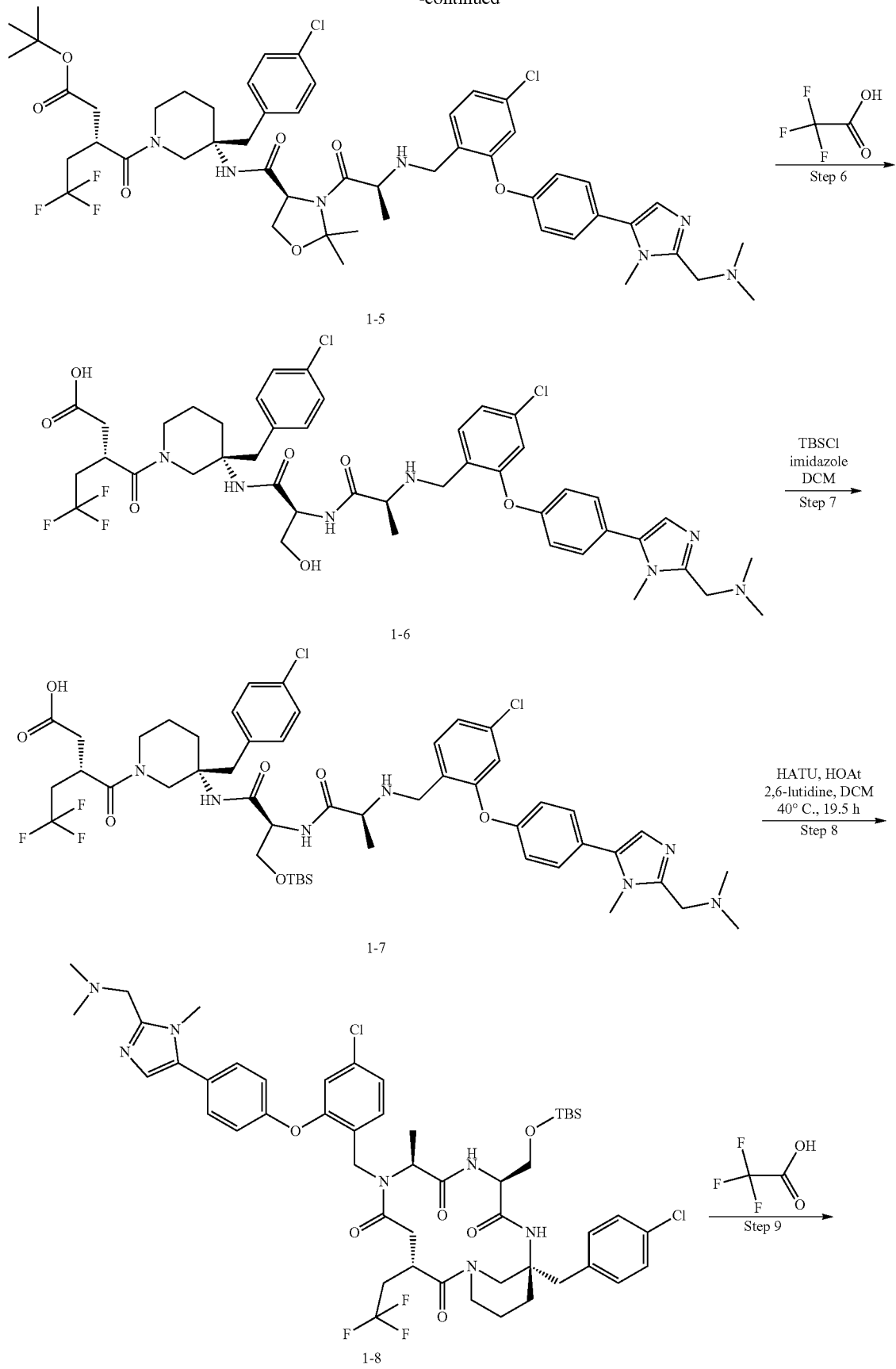

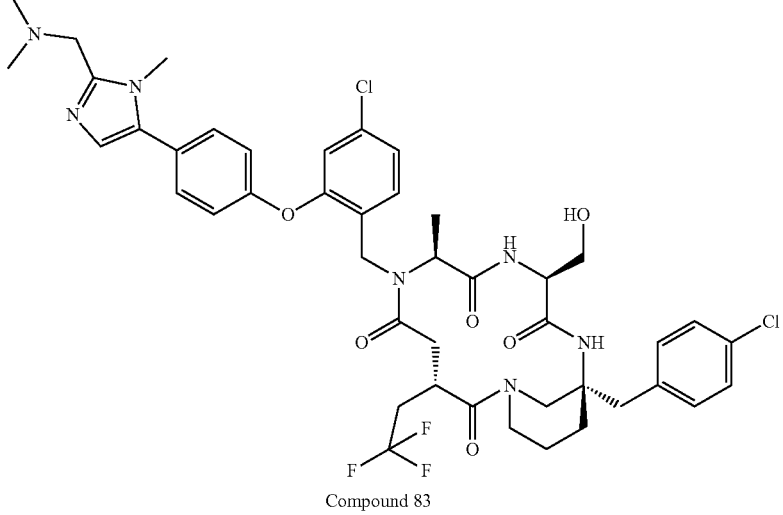

Compound 83

Step 1 to 2. (R)-tert-Butyl 3-((S)-3-((S)-2-amino-propanoyl)-2,2-dimethyloxazolidine-4-carbox-amido)-3-(4-chlorobenzyl)piperidine-I-carboxylate (1-2)

To a solution of B32 (2.5 g, 7.70 mmol) and Fmoc-Ala-Ser[psi(Me,Me)pro]-OH (3.64 g, 8.31 mmol) in DMF (30.8 ml) was added DIEA (2.69 ml, 15.39 mmol), followed by HATU (3.16 g, 8.31 mmol) as a solid in one portion. The resulting clear yellow mixture was stirred overnight.

To reaction mixture containing the desire intermediate 1-1 was added 4-methyl piperidine (3.63 ml, 30.8 mmol) and stirring was continued for 3 hr at RT. Methanol was added and the reaction mixture was concentrated under reduced pressure (in 50° C.) to remove DMF. The obtained solid was then taken up in large amount of EtOAc and washed twice with half-saturated sodium bicarbonate solution, and brine. The combined organic phases were dried over sodium sulfate, filtered, and concentrated to afford 1-2 as a white solid (3.5 g, ~90% yield; contains some Fmoc adduct), which was carried to the next step without purification. Analytical Method 5, $t_R$=1.07 min., $[M+H]^+$=523.2.

Step 3. (R)-tert-Butyl 3-((S)-3-((S)-2-((4-chloro-2-(4-(2-((dimethylamino)methyl-1-methyl-1H-imidazol-5-yl)phenoxy)benzyl)amino)propanoyl)-2,2-dimethyloxazolidine-4-carboxamido)~3~(4~chlorobenzyl)piperidine-1-carboxylate (1-3)

To a round bottom flask containing 1-2 (3.5 g, 6.69 mmol) and E1 (2.72 g, 7.36 mmol) dissolved in DCM (268 ml) was added acetic acid (1.532 ml, 26.8 mmol). The resulting mixture was stirred for 1 h at rt and then sodium triacetoxyborohydride (7.09 g, 33.5 mmol) was added as a solid in two portions. The reaction mixture was stirred for overnight at room temperature and then concentrated. The obtained residue was diluted with EtOAc and water. The organic phase was washed twice with saturated NaHCO₃ twice and brine, dried over Na₂SO₄, filtered, and concentrated. The residue was purified by flash column chromatography on silica gel (eluting with 0-10% DCM/MeOH) to provide 1-3 (4.4 g, 5.02 mmol, 75.0% yield) as an off-white solid. Analytical Method 5, $t_R$=1.33 min., $[M+H]^+$=876.2

Step 4. (S)-3-((S)-2-((4-Chloro-2-(4-(2-((dimethylamino)methyl)-1-methyl-1H-imidazol-5-yl)phenoxy)benzyl)amino)propanoyl)-N—((R)-3-(4-chlorobenzyl)piperidin-3-yl)-2,2-dimethyloxazolidine-4-carboxamide (1-4)

To a round bottom flask containing 1-3 (4.4 g, 5.02 mmol) in ACN (60 ml) and water (5 ml) cooled in an ice bath was added TFA (30.9 ml, 401 mmol) dropwise over two minutes. The ice bath was removed and stirring continued at rt for 45 min. Additional TFA was added (ca. 10 mL), and the reaction mixture was stirred at room temp for 2.5 hr and then concentrated under reduced pressure to remove most of the solvent. The obtained residue was carefully treated with saturated sodium bicarbonate solution and then NaOH (1 N) with stirring until the aqueous solution pH was 8. The resulting mixture was extracted with EtOAc twice, and the combined organic phases were washed with brine, then dried over sodium sulfate, filtered, and concentrated to provide 1-4 (2.5 g, 3.22 mmol, 64.1% yield) as an off-white foam. The material was carried to the next step without purification. Analytical Method 5, $t_R$=1.17 min., $[M+H]^+$=776.1

Step 5. tert-Butyl (S)-3-((R)-3-((S)-3-((4-chloro-2-(4-(2-((dimethylamino)methyl)-1-methyl-1H-imidazol-5-yl)phenoxy)benzyl)-L-alanyl)-2,2-dimethyloxazolidine-4-carboxamido)-3-(4-chlorobenzyl)piperidine-1-carbonyl)-5,5,5-trifluoropentanoate (1-5)

To a solution of A14 (120 mg, 0.468 mmol) in DMF (2 mL) was added DIPEA (0.20 mL, 1.16 mmol) and HATU (184 mg, 0.483 mmol). The resulting mixture was stirred at rt for 5 min before being added into a solution of 1-4 (300 mg, 0.386 mmol) in DMF (2 mL). The reaction mixture was stirred for another 1 h, then quenched with a 5% solution of NaHCO₃ and extracted with EtOAc. The organic phase was washed with a 5% NaHCO₃ solution and brine, dried over sodium sulfate, filtered, and concentrated to afford 1-5 (450 mg) as a brown oil. The crude product was used directly in next step without further purification. Analytical Method 5, $t_R$=1.37 min., $[M+H]^+$=1014.3.

Step 6. (S)-3-((R)-3-((S)-2-((S)-2-((4-Chloro-2-(4-(2-((dimethylamino)methyl)-1-methyl-1H-imidazol-5-yl)phenoxy)benzyl)amino)propanamido)-3-hydroxypropanamido)-3-(4-chlorobenzyl)piperidine-1-carbonyl)-5,5,5-trifluoropentanoic acid (1-6)

To a solution of 1-5 (450 mg, 0.443 mmol) in DCM (3 mL) was added TFA (3 mL, 38.9 mmol) dropwise at 0° C. The resulting mixture was stirred for 2 h at RT and then H$_2$O (3 mL) and ACN (3 mL) were added and stirring was continued for another 1-2 h. The reaction mixture was concentrated down, diluted with DCM, the pH was adjusted to pH=7-8 with saturated aq. NaHCO$_3$/Na$_2$CO$_3$. The organic phase was separated, dried over sodium sulfate, filtered, and concentrated to give 1-6 (289 mg, 71% yield) as a light yellow oil, which was used directly in next step without further purification. Analytical Method 5, $t_R$=0.83 min., [M+H]$^+$=918.1.

Step 7. (S)-3-((R)-3-((S)-3-((tert-Butyldimethylsilyl)oxy)-2-((S)-2-((4-chloro-2-(4-(2-((dimethylamino)methyl)-1-methyl-1H-imidazol-5-yl)phenoxy)benzyl)amino)propanamido)propanamido)-3-(4-chlorobenzyl)piperidine-1-carbonyl)-5,5,5-trifluoropentanoic acid (1-7)

To a solution of 1-6 (289 mg, 0.315 mmol) in DCM (10 mL) was added imidazole (139 mg, 2.042 mmol) and TBSCl (233 mg, 1.546 mmol). The resulting mixture was stirred at RT for 3 h and then washed with water. The organic phase was dried over sodium sulfate, filtered, and concentrated. The crude product was purified on a basic reverse-phase column chromatography (eluting with 5-100% water/ACN containing 0.1% NH$_4$OH) to give 1-7 (132 mg, 40.6%) as a white solid after freeze drying the pure fractions. Analytical Method 5, $t_R$=1.10 min., [M+H]$^+$=1032.3.

Step 8. (3S,7S,10S,13R)-10-(((tert-Butyldimethylsilyl)oxy)methyl)-6-(4-chloro-2-(4-(2-((dimethylamino)methyl)-1-methyl-1H-imidazol-5-yl)phenoxy)benzyl)-13-(4-chlorobenzyl)-7-methyl-3-(2,2,2-trifluoroethyl)-1,6,9,12-tetraazabicyclo[11.3.1]heptadecane-2,5,8,11-tetraone (1-8)

To a solution of 1-7 (132 mg, 0.128 mmol) in DCM (100 mL) was added HOAt (17.39 mg, 0.128 mmol), HATU (194 mg, 0.511 mmol) and 2,6-lutidine (0.35 mL, 3.01 mmol). The resulting mixture was refluxed at 48° C. overnight and then concentrated to dryness. The obtained residue was partitioned between EtOAc and 5% aq. NaHCO$_3$. The organic phase was washed with brine, dried over Na$_2$SO$_4$, filtered, and concentrated to afford 1-8 (200 mg, crude) as a brown oil. This crude product was used directly in next step without further purification. Analytical Method 5, $t_R$=1.49 min., [M+H]$^+$=1014.4.

Step 9. (3S,7S,10S,13R)-6-(4-Chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-3-(2,2,2-trifluoroethyl)-1,6,9,12-tetraazabicyclo[11.3.1]heptadecane-2,5,8,11-tetraone (Compound 83)

To a solution of 1-8 (200 mg, 0.197 mmol) in DCM (2 mL) was added TFA (2 mL, 26.0 mmol) dropwise. The resulting mixture was stirred at RT for 1 h and then concentrated to dryness. The residue was dissolved in DCM and washed with saturated aq. NaHCO$_3$. The organic phase was separated and concentrated to dryness. The crude product was purified on reverse-phase column chromatography (eluting with 10-100% water/ACN containing 0.1% NH$_4$OH) to give Compound 83 (46 mg, 25%) as a white solid after freeze drying the pure fractions. Analytical Method 3, $t_R$=1.06 min. [M+H]$^+$=900.3.

The compounds in Table 14 were synthesized according to the procedure described in Example 8.21 for Compound 83 from the respective intermediates shown in Tables 1-7 and described above in Example 8.

TABLE 14

| Cmd No. | Structure | LCMS |
|---|---|---|
| 42 | 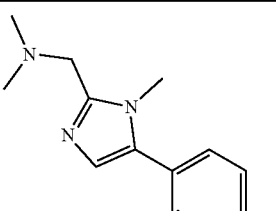 | Analytical Method 10<br>$t_R$ = 2.87 min.<br>[M + H]$^+$ = 872.7 |

TABLE 14-continued
| Cmd No. | Structure | LCMS |
|---|---|---|
| 46 | 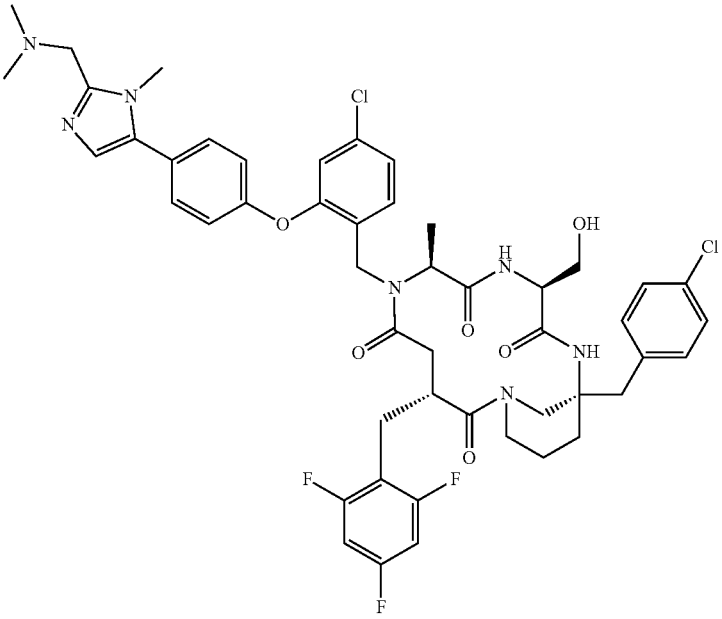 [SMILES: C[C@H]1C(=O)N[C@@H](CO)C(=O)N[C@@]2(Cc3ccc(Cl)cc3)CCCN(C2)C(=O)[C@H](Cc2c(F)cc(F)cc2F)CC(=O)N1Cc1ccc(Cl)cc1Oc1ccc(-c2cnc(CN(C)C)n2C)cc1] | Analytical Method 2<br>$t_R$ = 2.69 min.<br>$[M + H]^+$ = 962.3 |
| 62 | 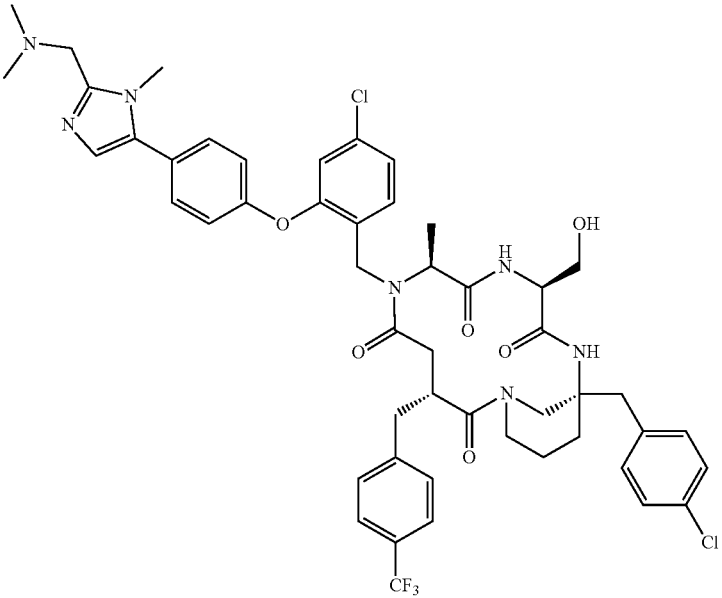 [SMILES: C[C@H]1C(=O)N[C@@H](CO)C(=O)N[C@@]2(Cc3ccc(Cl)cc3)CCCN(C2)C(=O)[C@H](Cc2ccc(C(F)(F)F)cc2)CC(=O)N1Cc1ccc(Cl)cc1Oc1ccc(-c2cnc(CN(C)C)n2C)cc1] | Analytical Method 3<br>$t_R$ = 1.17 min.<br>$[M + H]^+$ = 976.4 |

TABLE 14-continued

| Cmd No. | Structure | LCMS |
|---|---|---|
| 144 | 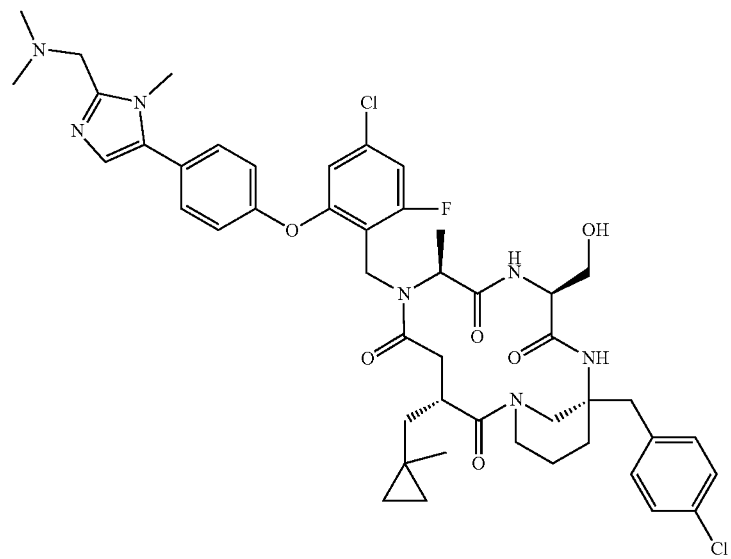 [SMILES: C[C@H]1C(=O)N[C@@H](CO)C(=O)N[C@@]2(Cc3ccc(Cl)cc3)CCCN(C2)C(=O)[C@H](CC2(C)CC2)CC(=O)N1Cc1c(F)cc(Cl)cc1Oc1ccc(-c2cnc(CN(C)C)n2C)cc1] | Analytical Method 3<br>$t_R$ = 1.12 min.<br>$[M + H]^+$ = 904.38 |
| 146 | 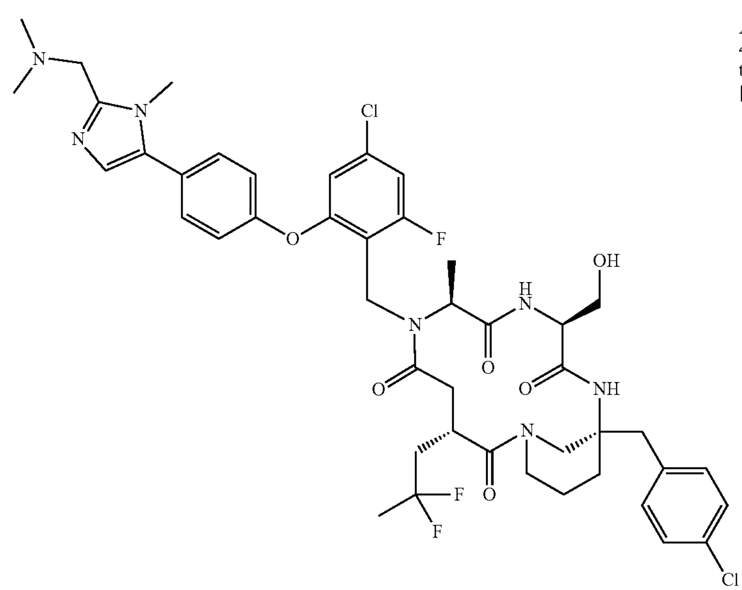 [SMILES: C[C@H]1C(=O)N[C@@H](CO)C(=O)N[C@@]2(Cc3ccc(Cl)cc3)CCCN(C2)C(=O)[C@H](CC(C)(F)F)CC(=O)N1Cc1c(F)cc(Cl)cc1Oc1ccc(-c2cnc(CN(C)C)n2C)cc1] | Analytical Method 4<br>$t_R$ = 1.99 min.<br>$[M + H]^+$ = 914.3 |

Example 8.22:Synthesis of (3S,7S,10S,13R)-6-(4-Chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-3-(2,2,2-trifluoroethyl)-1,6,9,12-tetraazabicyclo[11.3.1]heptadecane-2,5,8,11-tetraone (Compound 82)
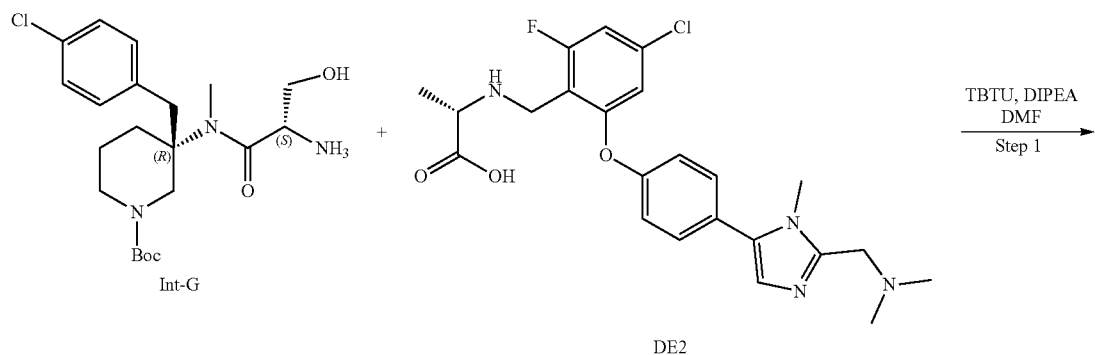
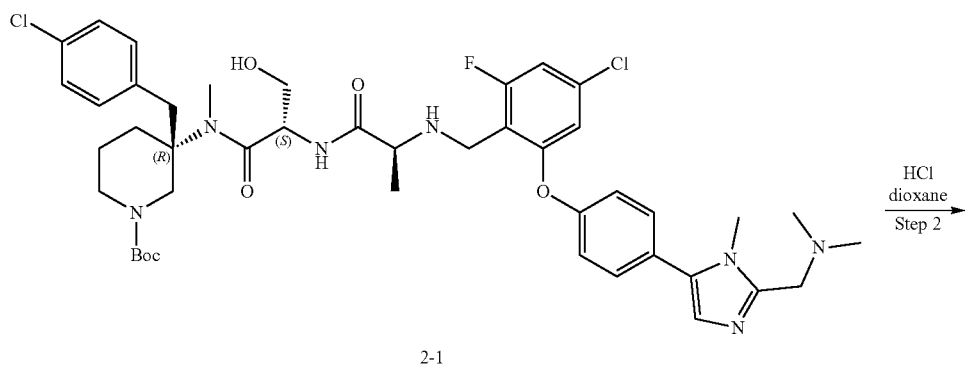
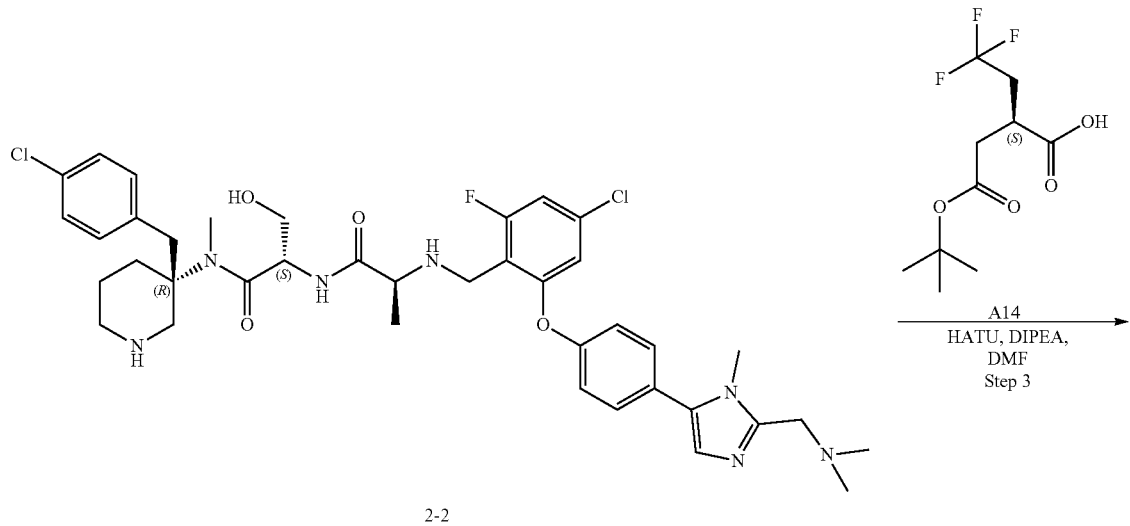

-continued
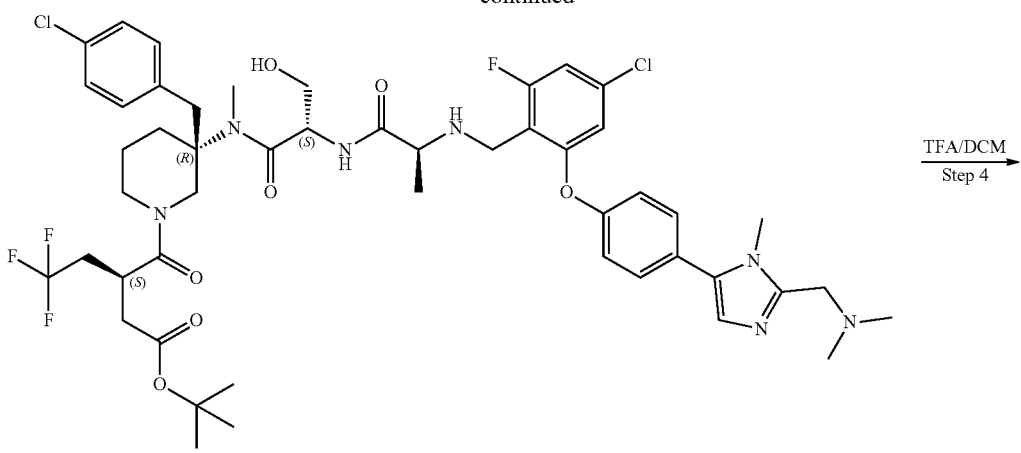
2-3
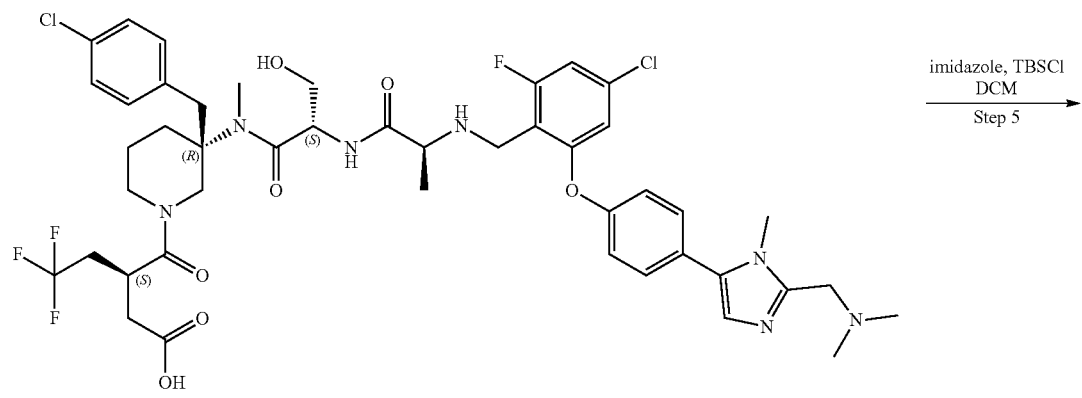
2-4
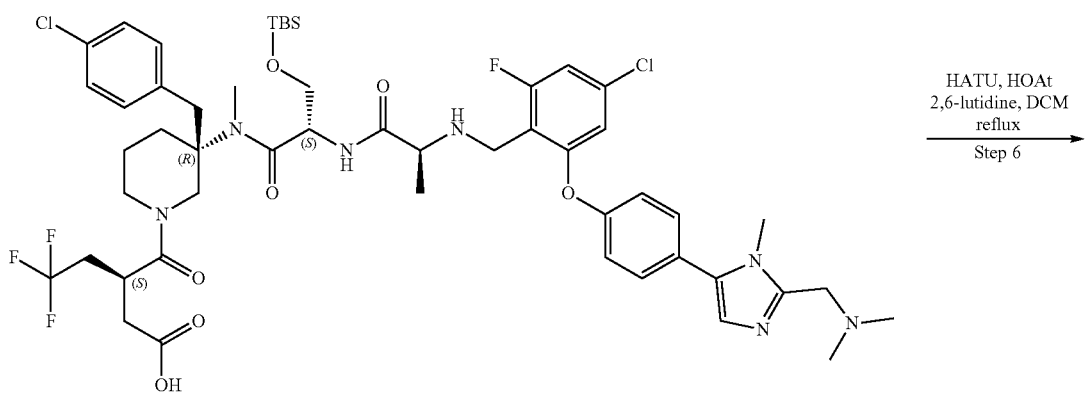
2-5

-continued

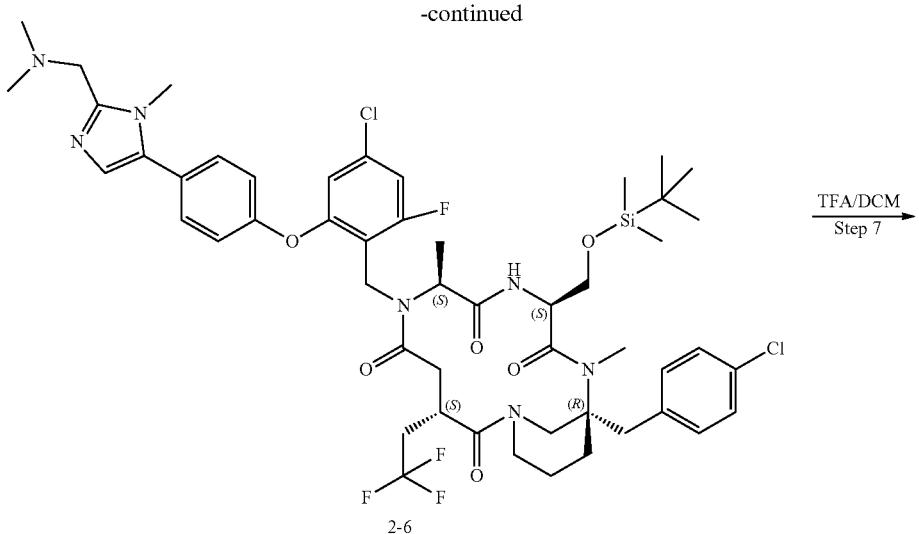

2-6

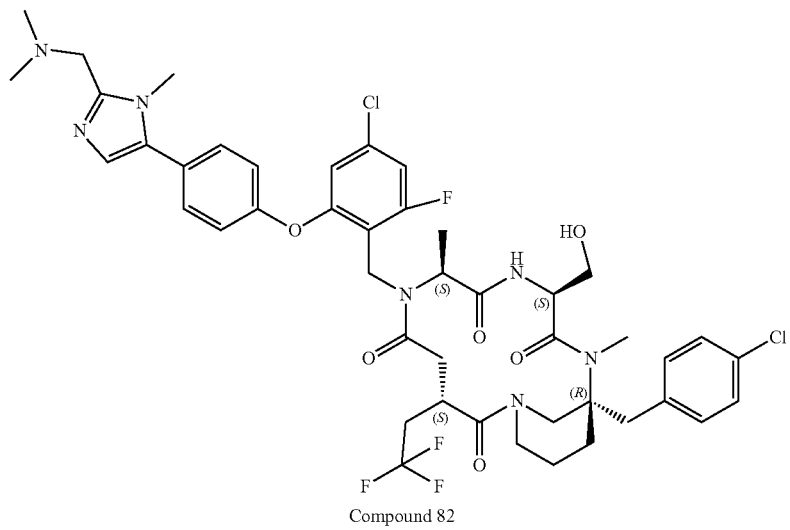

Compound 82

Step 1. (R)-tert-Butyl 3-((S)-2-((S)-2-((4-chloro-2-(4-(2-((dimethylamino)methyl)-1-methyl-1H-imidazol-5-yl)phenoxy)-6-fluorobenzyl)amino)propanamido)-3-hydroxy-N-methylpropanamido)-3-(4-chlorobenzyl)piperidine-1-carboxylate (2-1)

To a solution of Int G (1.003 g, 2.12 mmol) and DE2 (0.977 g, 2.120 mmol) in DMF (10 mL) was added DIPEA (1.481 mL, 8.48 mmol) and the resulting mixture was stirred for 5 min at RT. TBTU (0.681 g, 2.120 mmol) was added stirring was continued for 16 h at RT. The reaction mixture was partitioned between EtOAc (200 mL) and 5% aq. NaHCO$_3$ (15 mL). The organic phase was washed with 5% NaHCO$_3$ (3×10 mL) and brine (10 mL), dried over Na$_2$SO$_4$, filtered, and concentrated. The crude product was purified by flash column chromatography on silica gel (eluting with 0-15% DCM/MeOH with 0.2 TEA modifier), to afford 2-1 (1.20 g, 1.312 mmol, 61.9% yield) as a light yellow solid. Analytical Method 5, $t_R$=1.30 min, [M+H]$^+$=868.6.

Step 2. (S)-2-((S)-2-((4-Chloro-2-(4-(2-((dimethylamino)methyl)-1-methyl-1H-imidazol-5-yl)phenoxy)-6-fluorobenzyl)amino)propanamido)-N—((R)-3-(4-chlorobenzyl)piperidin-3-yl)-3-hydroxy-N-methylpropanamide (2-2)

To a solution 2-1 (300 mg, 0.345 mmol) in dioxane (4 ml) at 0° C. was added HCl in dioxane (4 N, 1.73 ml, 6.91 mmol) dropwise. The resulting mixture was warmed and stirred at RT overnight to afford a white slurry. The reaction mixture was concentrated and dried under high vacuum to afford 2-2 as an off-white solid. The material was used in the next step without purification (303 mg, quantitative yield). Analytical Method 5, $t_R$=1.13 min, [M+H]$^+$=768.5.

Step 3. (S)-tert-Butyl 3-((R)-3-((S)-2-((S)-2-((4-chloro-2-(4-(2-((dimethylamino)methyl)-1-methyl-1H-imidazol-5-yl)phenoxy)-6-fluorobenzyl)amino)propanamido)-3-hydroxy-N-methylpropanamido)-3-(4-chlorobenzyl)piperidine-1-carbonyl)-5,5,5-trifluoropentanoate (2-3)

To a solution of 2-2 (303 mg, 0.328 mmol) and A14 (88 mg, 0.344 mmol) in DMF (3 mL) was added DIPEA (0.23 mL, 1.31 mmol) and the resulting mixture was stirred for 5 min at rt to make sure all solids were dissolved. HATU (131 mg, 0.344 mmol) was added and stirring was continued for 16 h at RT. The reaction mixture was taken up in EtOAc and washed with a saturated NaHCO$_3$ solution and brine. The organic phase dried over Na$_2$SO$_4$, filtered, and concentrated. The crude product was purified by flash column chromatography on silica gel (eluting with 0-15% DCM/MeOH with 1% TEA), to afford 2-3 (220 mg, 0.208 mmol, 63.3% yield) after concentrating the pure fractions. Analytical Method 5, $t_R$=1.32 min, MS [M+H]+=1006.7.

Step 4. (S)-3-((R)-3-((S)-2-((S)-2-((4-Chloro-2-(4-(2-((dimethylamino)methyl)-1-methyl-1H-imidazol-5-yl)phenoxy)-6-fluorobenzyl)amino)propanamido)-3-hydroxy-N-methylpropanamido)-3-(4-chlorobenzyl)piperidine-1-carbonyl)-5,5,5-trifluoropentanoic acid (2-4)

To a solution of 2-3 (220 mg, 0.218 mmol) in DCM (10 mL) was added TFA (1 mL, 12.98 mmol) was added at 0° C. and the resulting mixture was gradually warmed to RT and stirred overnight. The reaction mixture was concentrated under reduced pressure to dryness and dried under high vac. The crude product was purified by reverse-phase column chromatography (eluting with 10-80% water/ACN with 0.1% NH$_4$OH) to afford the desired product. The fractions were collected and concentrated in vacuo to remove ACN and afford a mostly aq. residue, which was then extracted with DCM (×4). The organic phases were dried over MgSO$_4$, filtered, and concentrated in vacuo to yield 2-4 (132 mg, 0.139 mmol, 63.5% yield) as a white solid. Analytical Method 5, $t_R$=0.85 min, [M+H]$^+$=950.6.

Step 5. (S)-3-((R)-3-((S)-3-((tert-Butyldimethylsilyl)oxy)-2-((S)-2-((4-chloro-2-(4-(2-((dimethylamino)methyl)-1-methyl-1H-imidazol-5-yl)phenoxy)-6-fluorobenzyl)amino)propanamido)-N-methylpropanamido)-3-(4-chlorobenzyl)piperidine-1-carbonyl)-5,5,5-trifluoropentanoic acid (2-5)

To a solution of 2-4 (132 mg, 0.139 mmol) and imidazole (28.4 mg, 0.416 mmol) in DCM (15 mL) at 0° C. was added TBSCl (62.8 mg, 0.416 mmol) dropwise. The resulting mixture was warmed to RT and stirred for overnight. Additional TBSCl (630 mg) and imidazole (280 mg) were added and stirring was continued for 5 hr. The reaction mixture was quenched with water (100 ml), and the organic phase was collected, dried over sodium sulfate, filtered, and concentrated. The crude product was purified by basic reverse-phase column chromatography (eluting with 0-100% water/ACN with 0.1% NH$_4$OH) to afford 2-5 after freeze drying the fractions containing pure product (95 mg, 0.085 mmol, 61.0% yield). Analytical Method 5, $t_R$=1.43 min, [M+H]$^+$=1064.4.

Step 6. (3S,7S,10S,13R)-10-(((tert-Butyldimethylsiyl)oxy)methyl)-6-(4-chloro-2-(4-(2-((dimethylamino)methyl)-1-methyl-1H-imidazol-5-yl)phenoxy)-6-fluorobenzyl)-13-(4-chlorobenzyl)-7,12-dimethyl-3-(2,2,2-trifluoroethyl)-1,6,9,12-tetraazabicyclo[11.3.1]heptadecane-2,5,8,11-tetraone (2-6)

To a solution of 2-5 (95 mg, 0.09 mmol) in DCM (100 mL) was added 2,6-lutidine (0.21 mL, 1.78 mmol), HOAt (12.1 mg, 0.09 mmol) and HATU (136 mg, 0.36 mmol) and the resulting mixture was heated at 40° C. in a heating bath for 16 hr. The reaction mixture was cooled to RT and washed with NaHCO$_3$ and brine. The organic phase was dried over Na$_2$SO$_4$, filtered, and concentrated to afford 2-6 as a crude oil (142 mg). The material was taken to the next step without purification. Analytical Method 5, $t_R$=1.56 min, [M+H]$^+$=1046.4.

Step 7. (3S,7S,10S,13R)-6-(4-Chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-3-(2,2,2-trifluoroethyl)-1,6,9,12-tetraazabicyclo[11.3.1]heptadecane-2,5,8,11-tetraone (Compound 82)

To a solution of 2-6 (142 mg, 0.136 mmol) in DCM (Volume: 2 mL) at 0° C. was added TFA (2 mL, 26.0 mmol) dropwise and the resulting mixture was stirred at RT for 2 h. The reaction mixture was concentrated to dryness and the residue taken up in DCM. The organic phase was washed with a saturated solution of NaHCO$_3$, filtered, and concentrated. The crude product was purified by reverse-phase column chromatography (eluting with 10-100% water/ACN with 0.1% NH$_4$OH) to afford the desired product after freeze drying. The material was then purified again using basic HPLC, the pure fractions were collected and freeze dried to afford Compound 82 as a white solid (20 mg, 0.021 mmol, 15.49% yield). Analytical Method 7, $t_R$=0.93 min., [M+H]$^+$=932.2.

The compounds in Table 15 were synthesized according to the procedure described in Example 8.22 for Compound 82 from the respective intermediates shown in Tables 1-7 and described above in Example 8.

TABLE 15
| Cmd No. | Structure | LCMS |
|---|---|---|
| 20 | 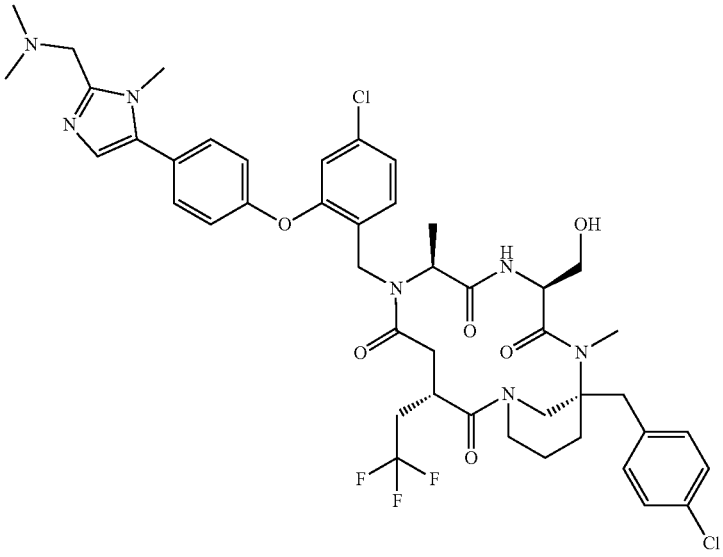 [SMILES: C[C@H]1C(=O)N[C@@H](CO)C(=O)N(C)[C@@]2(Cc3ccc(Cl)cc3)CCCN(C2)C(=O)[C@H](CC(F)(F)F)CC(=O)N1Cc1ccc(Cl)cc1Oc1ccc(-c2cnc(CN(C)C)n2C)cc1] | Analytical Method 7<br>$t_R$ = 1.00 min.<br>$[M + H]^+$ = 914.5 |
| 37 | 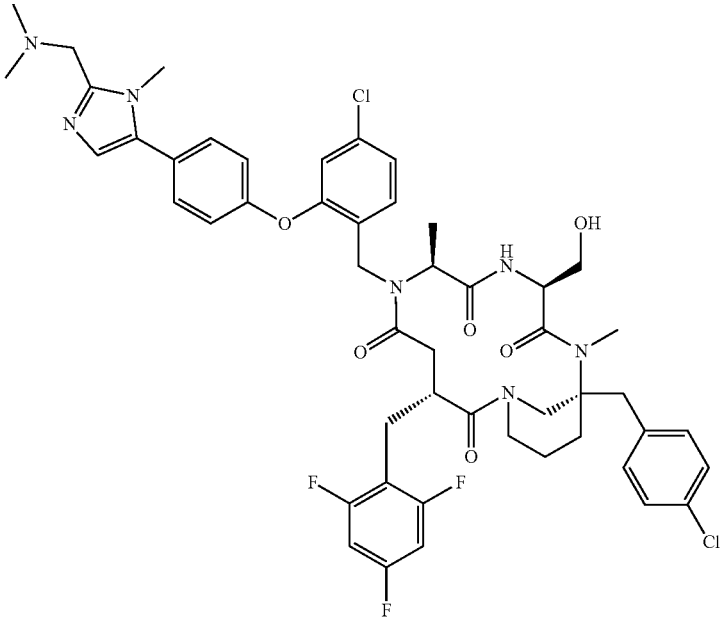 [SMILES: C[C@H]1C(=O)N[C@@H](CO)C(=O)N(C)[C@@]2(Cc3ccc(Cl)cc3)CCCN(C2)C(=O)[C@H](Cc2c(F)cc(F)cc2F)CC(=O)N1Cc1ccc(Cl)cc1Oc1ccc(-c2cnc(CN(C)C)n2C)cc1] | Analytical Method 7<br>$t_R$ = 1.02 min.<br>$[M + H]^+$ = 976.5 |

TABLE 15-continued

| Cmd No. | Structure | LCMS |
|---|---|---|
| 53 | 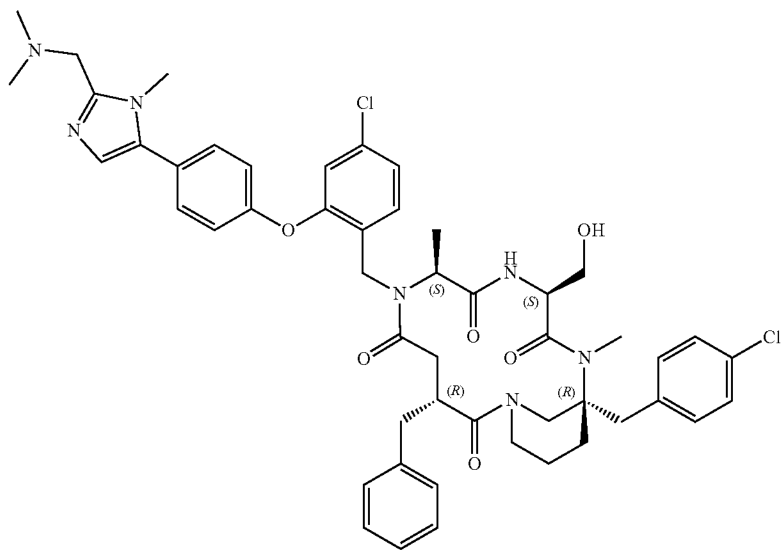 | Analytical Method 3<br>$t_R$ = 1.12 min.<br>$[M + H]^+$ = 922.38 |
| 79 | 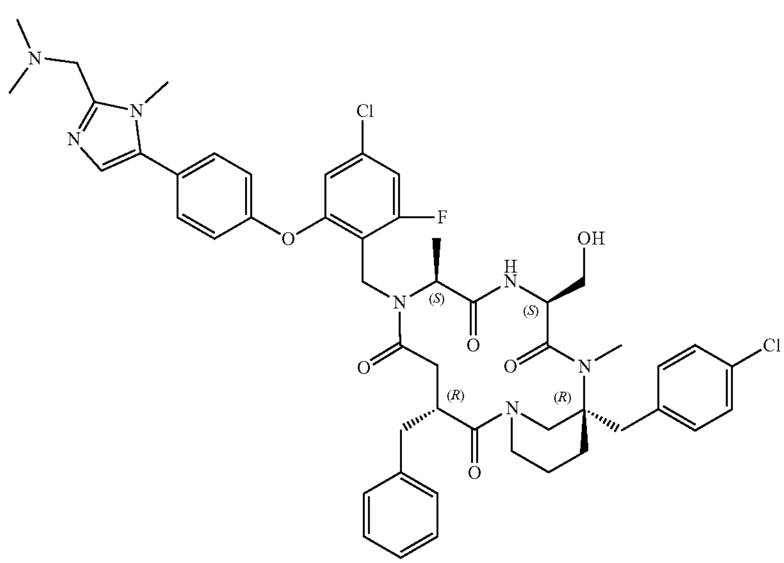 | Analytical Method 2<br>$t_R$ = 3.02 min.<br>$[M + H]^+$ = 940.7 |

TABLE 15-continued

| Cmd No. | Structure | LCMS |
|---|---|---|
| 151 | 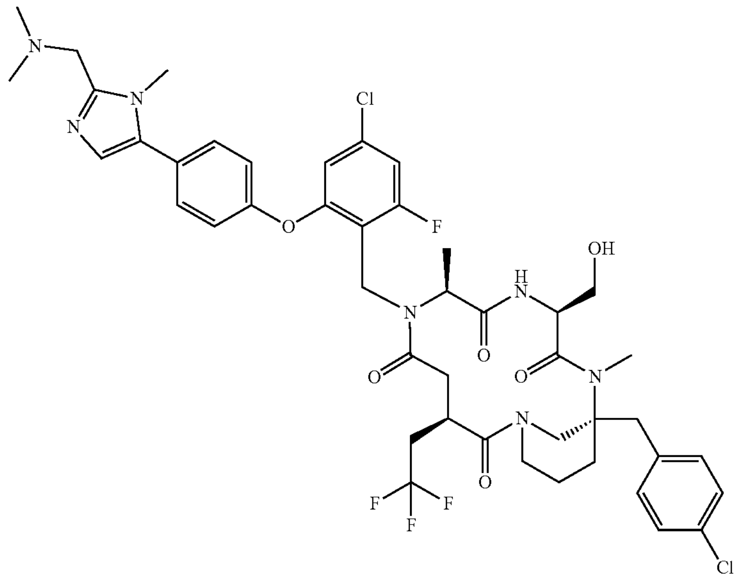 [SMILES: C[C@H]1C(=O)N[C@@H](CO)C(=O)N(C)[C@@]2(Cc3ccc(Cl)cc3)CCCN(C2)C(=O)[C@@H](CC(F)(F)F)CC(=O)N1Cc1c(F)cc(Cl)cc1Oc1ccc(-c2cnc(CN(C)C)n2C)cc1] | Analytical Method 3<br>$t_R$ = 1.08 min.<br>$[M + H]^+$ = 932.3 |
| 164 | 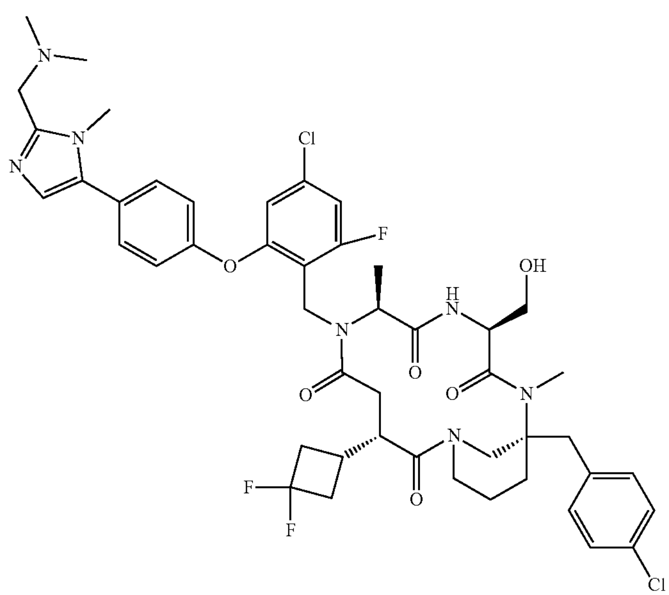 [SMILES: C[C@H]1C(=O)N[C@@H](CO)C(=O)N(C)[C@@]2(Cc3ccc(Cl)cc3)CCCN(C2)C(=O)[C@H](C2CC(F)(F)C2)CC(=O)N1Cc1c(F)cc(Cl)cc1Oc1ccc(-c2cnc(CN(C)C)n2C)cc1] | Analytical Method 2<br>$t_R$ = 2.86 min.<br>$[M + H]^+$ = 942.5 |

Example 8.23: Synthesis of (3S,7S,10S,13R)-6-(4-Chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone (Compound 22)
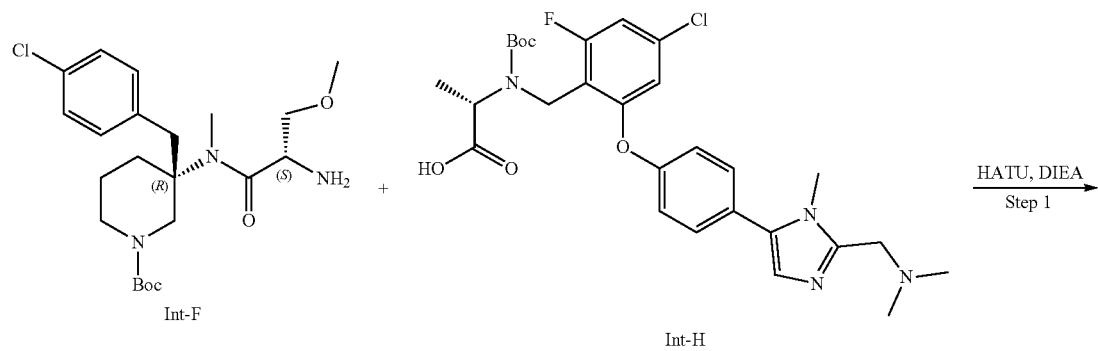
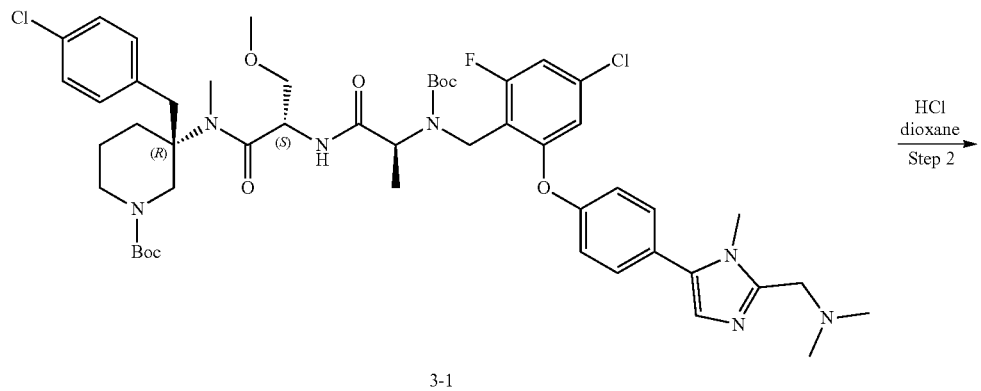
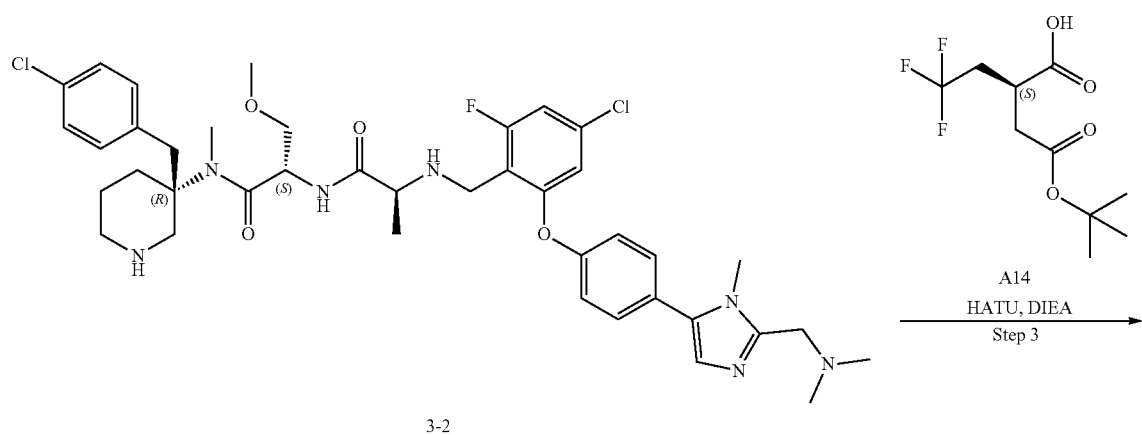

-continued

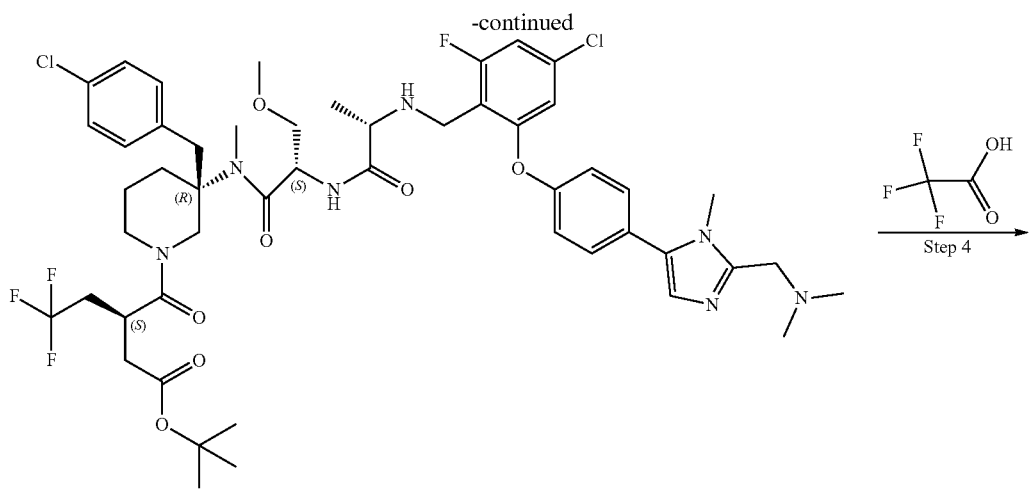

3-3

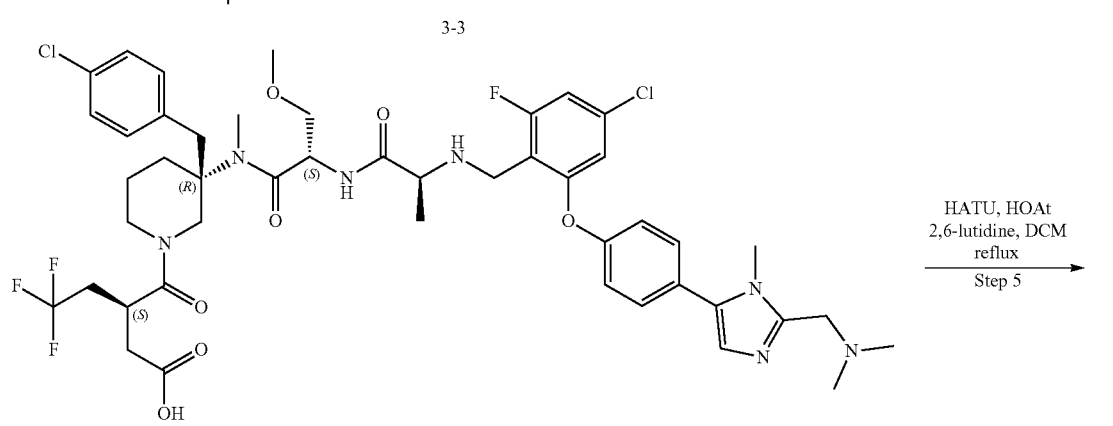

3-4

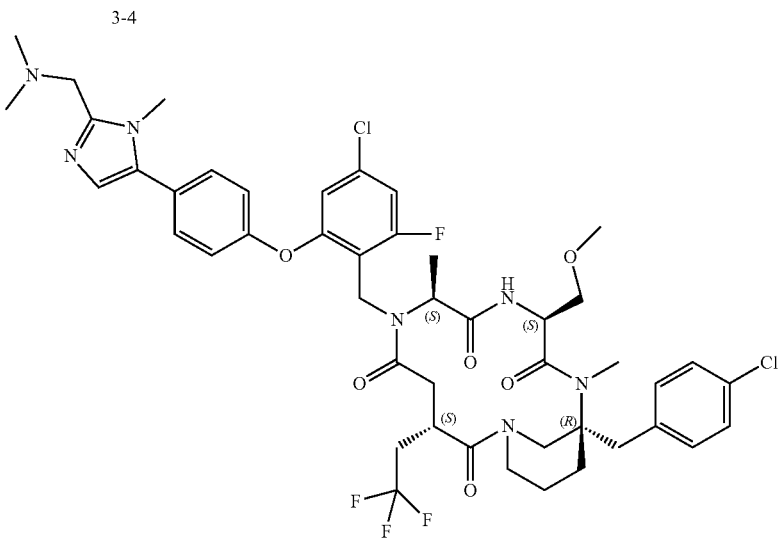

Compound 22

Step 1. (R)-tert-Butyl 3-((S)-2-((S)-2-((tert-butoxy-carbonyl)(4-chloro-2-(4-(2-((dimethylamino)methyl)-1-methyl-1H-imidazol-5-yl)phenoxy)-6-fluorobenzyl)amino)propanamido)-3-methoxy-N-methylpropanamido)-3-(4-chlorobenzyl)piperidine-1-carboxylate (3-1)

To a solution of Int H (0.80 g, 1.45 mmol) and Intermediate F (0.86 g, 1.46 mmol) in ACN (20 mL) was added DIPEA (0.51 mL, 2.89 mmol) and HATU (0.58 g, 1.52 mmol) and the resulting mixture was stirred at RT for 0.5 hr. The reaction mixture was diluted with 20 mL of saturated NaHCO$_3$ and 20 mL of water, and extracted with EtOAc. The organic phases were washed with a 5% NaHCO$_3$ solution and brine, dried over sodium sulfate, filtered, and concentrated. The crude product was purified by flash column chromatography on silica gel (eluting with 0-15% DCM/MeOH with 0.2% TEA) to afford 3-1 as a yellow foam after concentrating the pure fractions (1.36 g, 86% yield). Analytical Method 5, t$_R$=1.47 min, [M+H]$^+$=982.8.

Step 2.: (S)-2-((S)-2-((4-chloro-2-(4-(2-((dimethyl-amino)methyl)-1-methyl-1H-imidazol-5-yl)phenoxy)-6-fluorobenzyl)amino)propanamido)-N—((R)-3-(4-chlorobenzyl)piperidin-3-yl)-3-methoxy-N-methylpropanamide (3-2)

To a solution of 3-1 (1.36 g, 1.25 mmol) in anhydrous dioxane (6 mL) and cooled in an ice bath was added cold HCl in dioxane (4N, 6 mL, 24.0 mmol). The cooling bath was removed and the resulting mixture was stirred at RT for 16 h. The reaction mixture was concentrated in vacuo to afford a crude residue, which was taken up in toluene and concentrated again (repeat) to afford 3-2 as a yellow solid (1.23 g, ~quantitative yield). The material was used in the next step without further purification. Analytical Method 5, $t_R$=1.27 min, $[M+H]^+$=782.5.

Step 3. (S)-tert-Butyl 3-((R)-3-((S)-2-((S)-2-((4-chloro-2-(4-(2-((dimethylamino)methyl)-1-methyl-1H-imidazol-5-yl)phenoxy)-6-fluorobenzyl)amino)propanamido)-3-methoxy-N-methylpropanamido)-3-(4-chlorobenzyl)piperidine-1-carbonyl)-5,5,5-trifluoropentanoate (3-3)

To a solution of 3-2 (0.71 g, 0.80 mmol) in 10 mL of ACN was added DIPEA (0.56 mL, 3.18 mmol) and A14 (0.20 g, 0.80 mmol), followed by HATU (0.30 g, 0.80 mmol). The resulting mixture was stirred for 1 h, quenched with 20 ml of 5% NaHCO$_3$, and extracted with EtOAc. The combined organic phases were washed with 5% NaHCO$_3$, brine, dried over sodium sulfate, filtered, and concentrated to afford 3-3 as a yellow solid (550 mg, 61% yield). The material was used in the next step without further purification. Analytical Method 4, $t_R$=1.79 min, $[M+H]^+$=1020.6.

Step 4.: (S)-3-((R)-3-((S)-2-((S)-2-((4-chloro-2-(4-(2-((dimethylamino)methyl)-1-methyl-1H-imidazol-5-yl)phenoxy)-6-fluorobenzyl)amino)propanamido)-3-methoxy-N-methylpropanamido)-3-(4-chlorobenzyl)piperidine-1-carbonyl)-5,5,5-trifluoropentanoic acid (3-4)

To a solution of 3-3 (550 mg, 0.46 mmol) in DCM (3 mL) was added TFA (5 mL, 64.9 mmol) at 0° C. The cooling bath was removed and the resulting mixture was stirred at RT for 1 h. The reaction mixture was concentrated in vacuo (added toluene as azeotrope to aid TFA removal) and the crude product was purified by reverse-phase column chromatography (eluting with 0-50% water/ACN with 0.1% NH$_4$OH) to afford 3-4 as a white fluffy power after lyophilization (138 mg, 30% yield). Analytical Method 5, $t_R$=0.85 min, $[M+H]^+$=964.6.

Step 5. (3S,7S,10S,13R)-6-(4-Chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone (Example 22)

To a solution of 3-4 (138 mg, 0.14 mmol) in anhydrous DCM (100 mL) was added 2,6-lutidine (0.25 mL, 2.10 mmol), HOAt (20.0 mg, 0.14 mmol), and HATU (277 mg, 0.56 mmol).

The resulting mixture was refluxed for overnight at 48° C. using a heating bath. The reaction mixture was then concentrated to dryness in vacuo and partitioned between EtOAc (100 mL) and 5% aq. NaHCO$_3$ (30 mL). The organic phase was washed with 5% aq. NaHCO$_3$ (2×30 mL) and brine (30 mL), dried over Na$_2$SO$_4$, filtered, and concentrated. The crude oil was diluted with ACN and purified by ISCO on C18 100 g column, eluting with 0-100% ACN in water (0.1% TFA as the modifier) to afford Compound 22 as a white solid after lyophilization (76 mg, 56% yield). Analytical Method 3, $t_R$=1.13 min., $[M+H]^+$=946.35.

The compounds in Table 16 were synthesized according to the procedure described in Example 8.23 for Compound 22 from the respective intermediates shown in Tables 1-7 and described above in Example 8.

TABLE 16

| Cmd No. | Structure | LCMS |
|---|---|---|
| 9 | 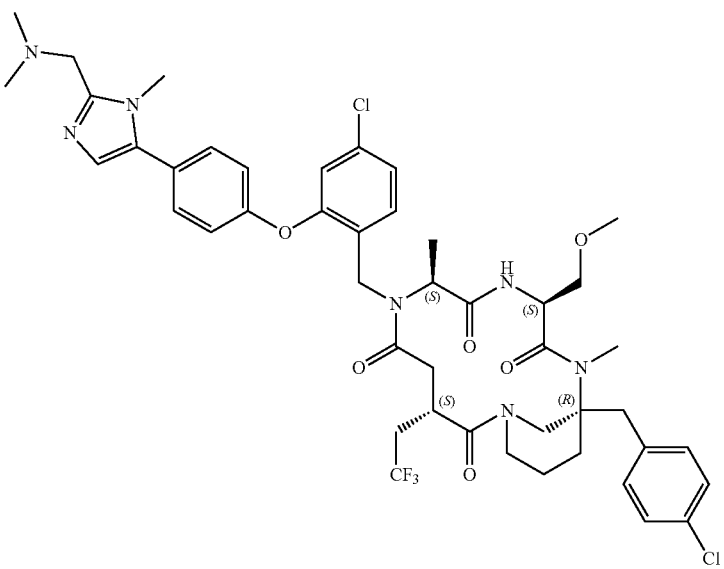 | Analytical Method 3<br>$t_R$ = 1.13 min.<br>$[M + H]^+$ = 928.35 |

TABLE 16-continued

| Cmd No. | Structure | LCMS |
|---|---|---|
| 12 | 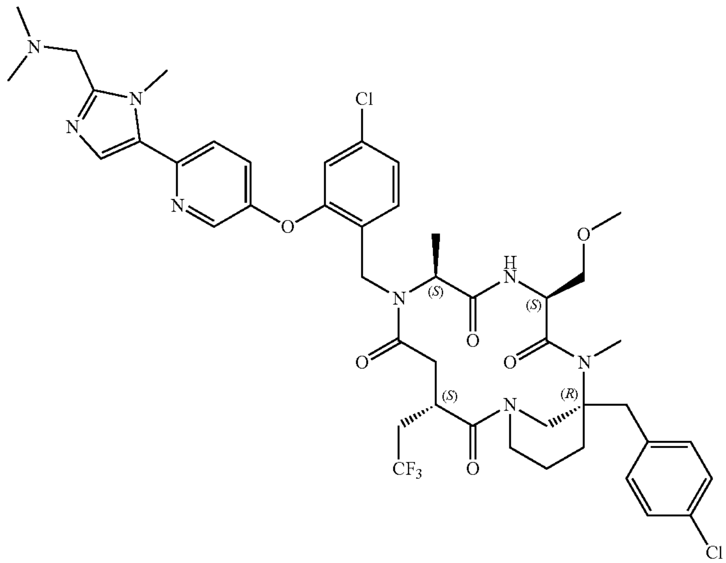 | Analytical Method 3<br>$t_R$ = 1.12 min.<br>$[M + H]^+$ = 929.35 |
| 140 | 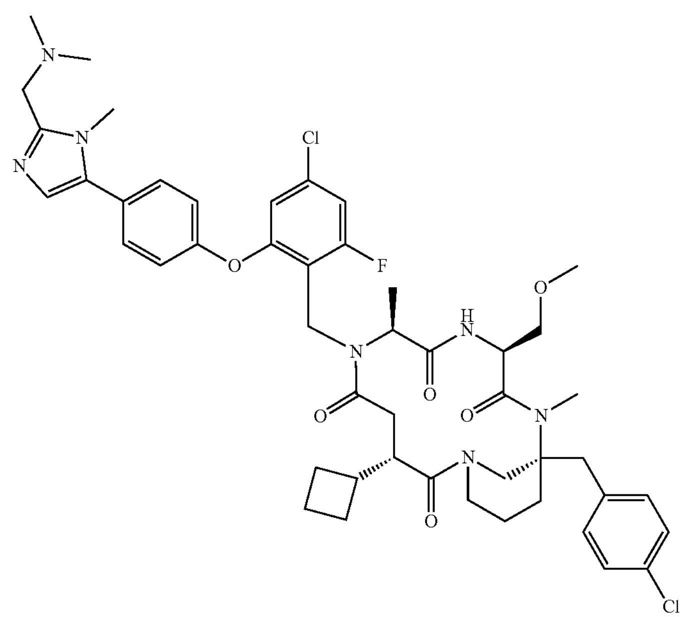 [SMILES: COC[C@@H]1NC(=O)[C@H](C)N(Cc2c(F)cc(Cl)cc2Oc2ccc(-c3cnc(CN(C)C)n3C)cc2)C(=O)C[C@@H](C2CCC2)C(=O)N2CCC[C@@](Cc3ccc(Cl)cc3)(C2)N(C)C1=O] | Analytical Method 4<br>$t_R$ = 2.27 min.<br>$[M + H]^+$ = 918.5 |

TABLE 16-continued
| Cmd No. | Structure | LCMS |
|---|---|---|
| 159 | 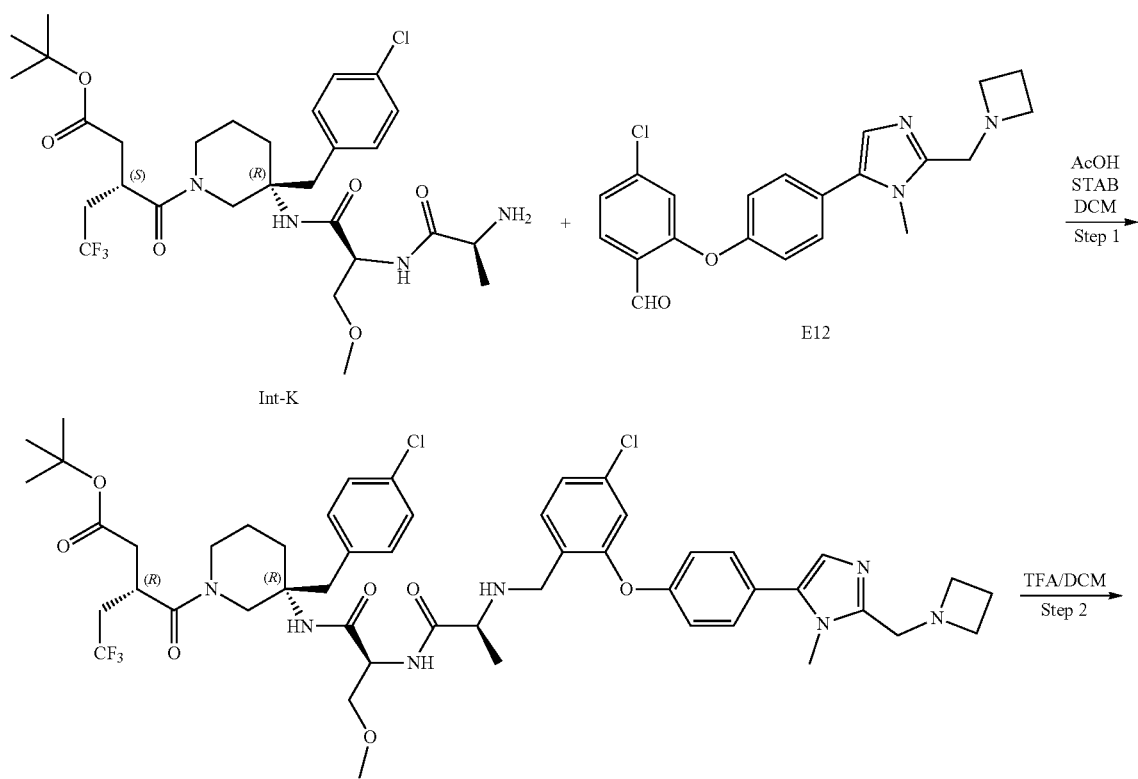 | Analytical Method 3<br>$t_R$ = 1.19 min.<br>[M + H]$^+$ = 954.39 |
Example 8.24: Synthesis of (3S,7S,10S,13R)-6-(2-(4-(2-(Azetidin-1-ylmethyl)-1-methyl-1H-imidazol-5-yl)phenoxy)-4-chlorobenzyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone (Compound 33)

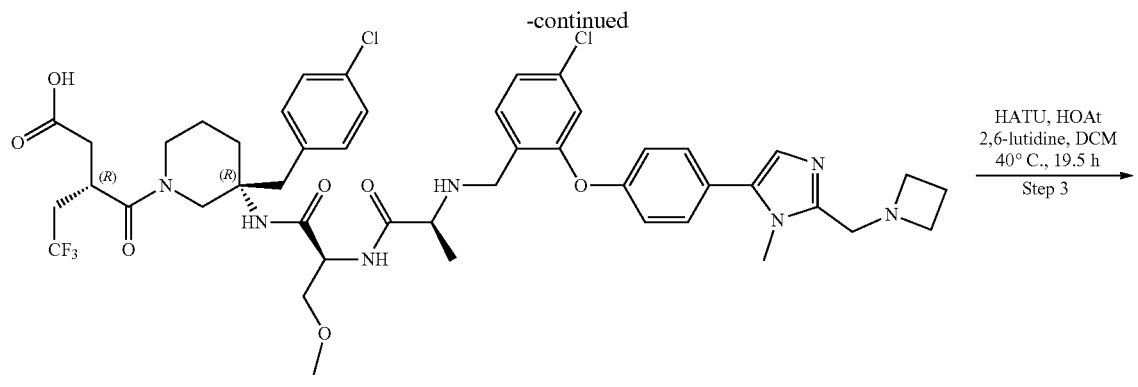

4-2

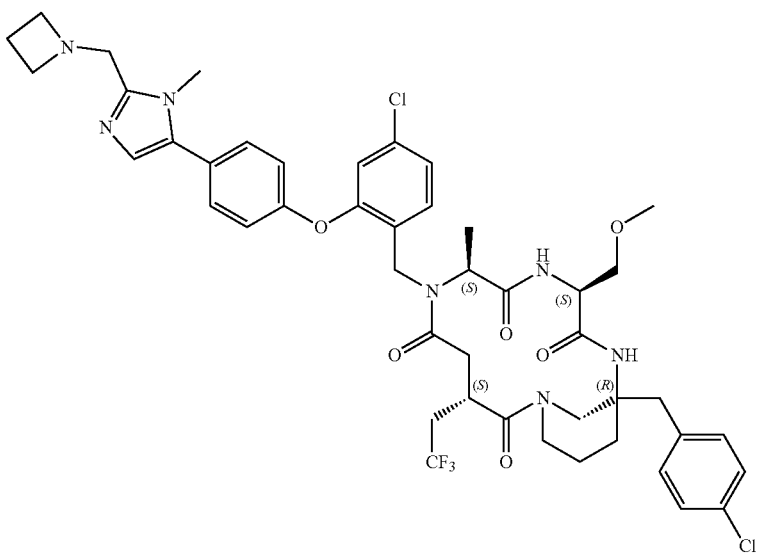

Compound 33

Step 1. (S)-tert-Butyl 3-((R)-3-((S)-2-((S)-2-((2-(4-(2-(azetidin-1-ylmethyl)-1-methyl-1H-imidazol-5-yl)phenoxy)-4-chlorobenzyl)amino)propanamido)-3-methoxypropanamido)-3-(4-chlorobenzyl)piperidine-1-carbonyl)-5,5,5-trifluoropentanoate (4-1)

To a solution of Intermediate K (250 mg, 0.39 mmol) and E12 (150 mg, 0.39 mmol) in DCM (20 mL) was added acetic acid (0.09 mL, 1.58 mmol) at room temperature and the resulting mixture was stirred for 1 h. Sodium triacetoxyborohydride (417 mg, 1.97 mmol) was added in one portion and stirring was continued at room temperature for overnight. The reaction mixture was quenched with methanol and concentrated under reduced pressure. The resulting residue was taken up in EtOAc and washed twice with a half saturated solution of sodium carbonate and brine. The organic phase was dried over sodium sulfate, filtered, and concentrated. Flash column chromatography on silica gel (eluting with 0-20% MeOH in DCM) afforded 4-1 (293 mg, 74% yield) after concentrating the pure fractions. MS [M+H]$^+$=1000.5

Step 2. (S)-3-((R)-3-((S)-2-((S)-2-((2-(4-(2-(Azetidin-1-ylmethyl)-1-methyl-1H-imidazol-5-yl)phenoxy)-4-chlorobenzyl)amino)propanamido)-3-methoxypropanamido)-3-(4-chlorobenzyl)piperidine-1-carbonyl)-5,5,5-trifluoropentanoic acid (4-2)

To a solution of 4-1 (293 mg, 0.29 mmol) in DCM (2.5 mL) and cooled in an ice bath was added trifluoroacetic acid (2 ml, 26.1 mmol) dropwise. The resulting mixture was warmed to room temperature gradually and stirred for 40 min. The reaction mixture was cooled in an ice bath and then quenched by adding a chilled saturated solution of sodium bicarbonate (26 mL) dropwise. Additional DCM was added and the mixture was warmed to room temperature gradually and stirring was continued for 1 hour. The biphasic mixture was passed through a phase separator and the organic phase dried over sodium sulfate, filtered, and concentrated to afford 4-2 as a crude product (277 mg, assume quantitative yield). The crude material was used immediately in the next step without purification. MS [M+H]$^+$=944.6

Step 3. (3S,7S,10S,13R)-6-(2-(4-(2-(Azetidin-1-ylmethyl)-1-methyl-1H-imidazol-5-yl)phenoxy)-4-chlorobenzyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone (Compound 33)

To a solution of 4-2 (277 mg, 0.29 mmol) in anhydrous DCM (250 mL) was added 2,6-lutidine (1.02 mL, 8.79 mmol), HOAt (40 mg, 0.29 mmol), and HATU (446 mg, 1.173 mmol). The resulting mixture was heated to 45° C. overnight. The reaction mixture was cooled and filtered, and the filtrate concentrated to dryness under reduced pressure. The obtained residue was taken up in DCM and the organic phase was washed with a solution of half-saturated sodium bicarbonate. The organic phase was then dried over sodium sulfate, filtered, and concentrated.

The crude product was purified by flash column chromatography on silica gel (eluting with 0-20% MeOH in DCM, product eluted out ~15% MeOH) to afford the desired product after concentrating the pure fractions. The product was taken up in 1:1 ACN/water and freeze dried to afford Compound 33 as a white powder. Analytical Method 3, $t_R$=1.12 min., [M+H]$^+$=926.3.

The compounds in Table 17 were synthesized according to the procedure described in Example 8.24 for Compound 33 from the respective intermediates shown in Tables 1-7 and described above in Example 8.

TABLE 17

| Cmd No. | Structure | LCMS |
|---|---|---|
| 2 | 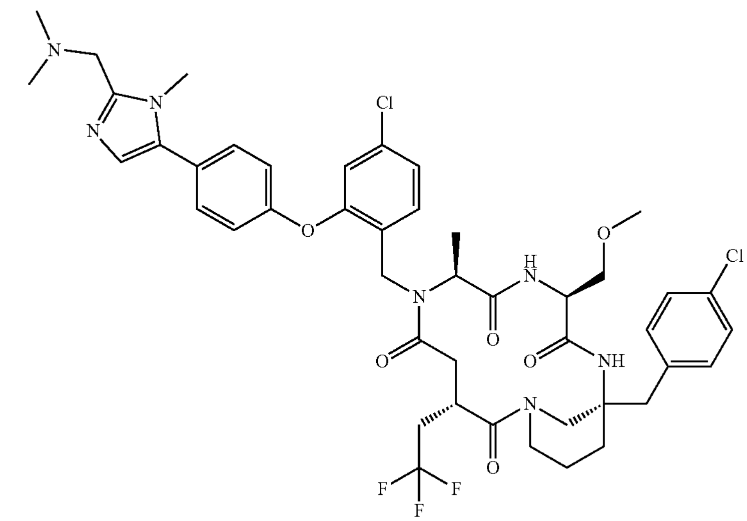 [SMILES: COC[C@@H]1NC(=O)[C@H](C)N(Cc2ccc(Cl)cc2Oc2ccc(-c3cnc(CN(C)C)n3C)cc2)C(=O)C[C@@H](CC(F)(F)F)C(=O)N2CCC[C@@](Cc3ccc(Cl)cc3)(C2)NC1=O] | Analytical Method 2<br>$t_R$ = 3.00 min.<br>[M + H]$^+$ = 914.0 |
| 6 | 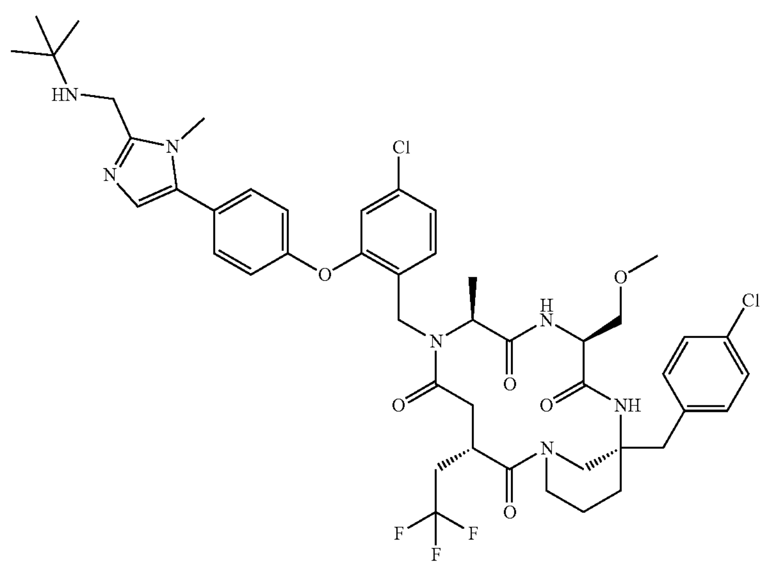 [SMILES: COC[C@@H]1NC(=O)[C@H](C)N(Cc2ccc(Cl)cc2Oc2ccc(-c3cnc(CNC(C)(C)C)n3C)cc2)C(=O)C[C@@H](CC(F)(F)F)C(=O)N2CCC[C@@](Cc3ccc(Cl)cc3)(C2)NC1=O] | Analytical Method 2<br>$t_R$ = 3.16 min.<br>[M + H]$^+$ = 942.6 |

TABLE 17-continued

| Cmd No. | Structure | LCMS |
|---|---|---|
| 8 | 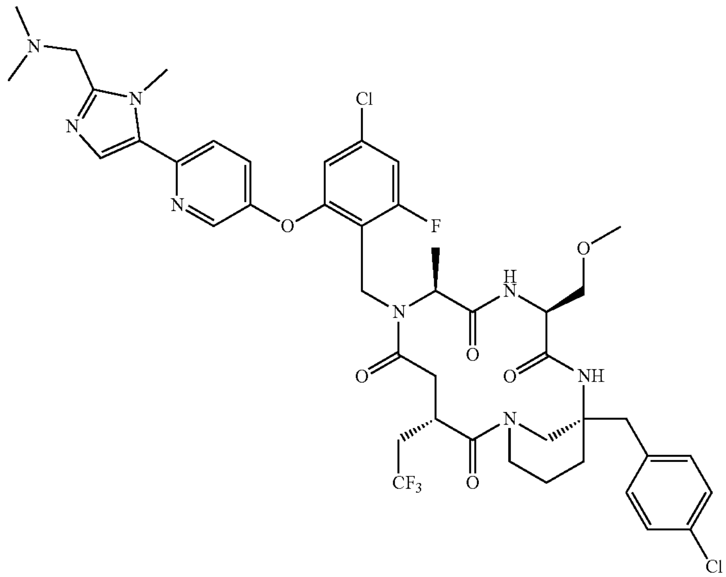 [SMILES: COC[C@@H]1NC(=O)[C@H](C)N(Cc2c(F)cc(Cl)cc2Oc2ccc(-c3cnc(CN(C)C)n3C)nc2)C(=O)C[C@@H](CC(F)(F)F)C(=O)N2CCC[C@@](Cc3ccc(Cl)cc3)(C2)NC1=O] | Analytical Method 3<br>$t_R$ = 1.12 min.<br>$[M + H]^+$ = 933.3 |
| 29 | 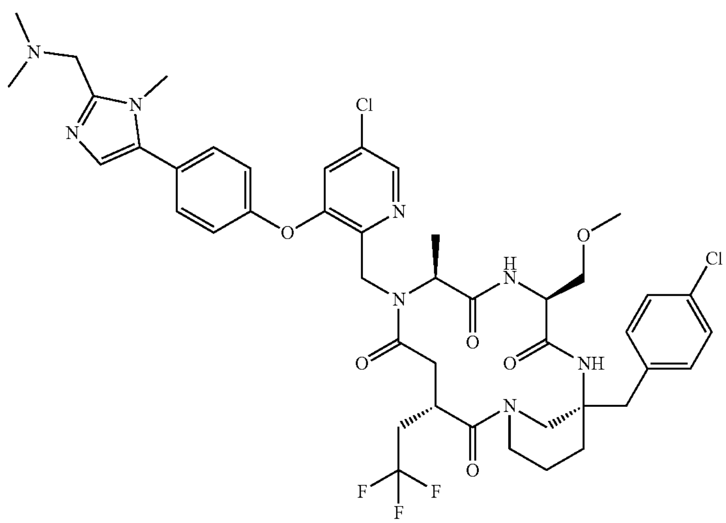 [SMILES: COC[C@@H]1NC(=O)[C@H](C)N(Cc2ncc(Cl)cc2Oc2ccc(-c3cnc(CN(C)C)n3C)cc2)C(=O)C[C@@H](CC(F)(F)F)C(=O)N2CCC[C@@](Cc3ccc(Cl)cc3)(C2)NC1=O] | Analytical Method 2<br>$t_R$ = 2.88 min.<br>$[M + H]^+$ = 915.2 |
| 36 | 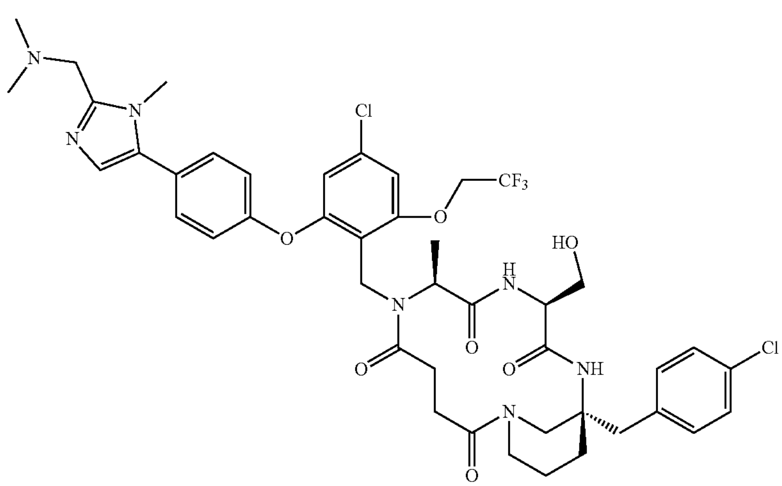 [SMILES: C[C@H]1C(=O)N[C@@H](CO)C(=O)N[C@@]2(Cc3ccc(Cl)cc3)CCCN(C2)C(=O)CCC(=O)N1Cc1c(OCC(F)(F)F)cc(Cl)cc1Oc1ccc(-c2cnc(CN(C)C)n2C)cc1] | Analytical Method 3<br>$t_R$ = 1.01 min.<br>$[M + H]^+$ = 916.32 |

TABLE 17-continued

| Cmd No. | Structure | LCMS |
|---|---|---|
| 39 | 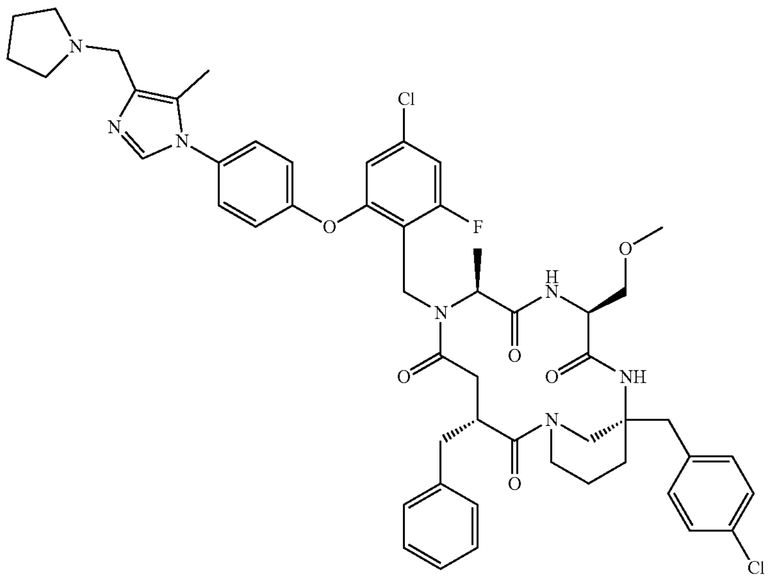 [SMILES: COC[C@@H]1NC(=O)[C@H](C)N(Cc2c(F)cc(Cl)cc2Oc2ccc(-n3cnc(CN4CCCC4)c3C)cc2)C(=O)C[C@@H](Cc2ccccc2)C(=O)N2CCC[C@@](Cc3ccc(Cl)cc3)(C2)NC1=O] | Analytical Method 3<br>$t_R$ = 1.17 min.<br>$[M + H]^+$ = 966.4 |
| 52 | 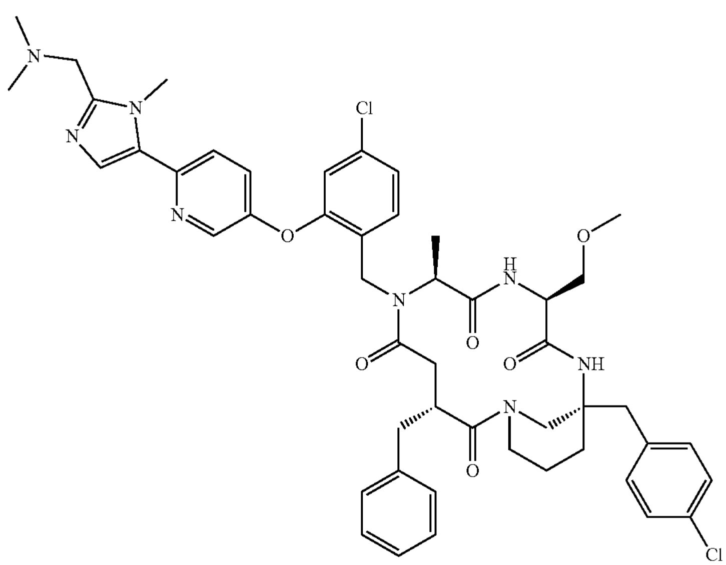 [SMILES: COC[C@@H]1NC(=O)[C@H](C)N(Cc2ccc(Cl)cc2Oc2ccc(-c3cnc(CN(C)C)n3C)nc2)C(=O)C[C@@H](Cc2ccccc2)C(=O)N2CCC[C@@](Cc3ccc(Cl)cc3)(C2)NC1=O] | Analytical Method 2<br>$t_R$ = 3.06 min.<br>$[M + H]^+$ = 923.3 |

| Cmd No. | Structure | LCMS |
|---|---|---|
| 63 | 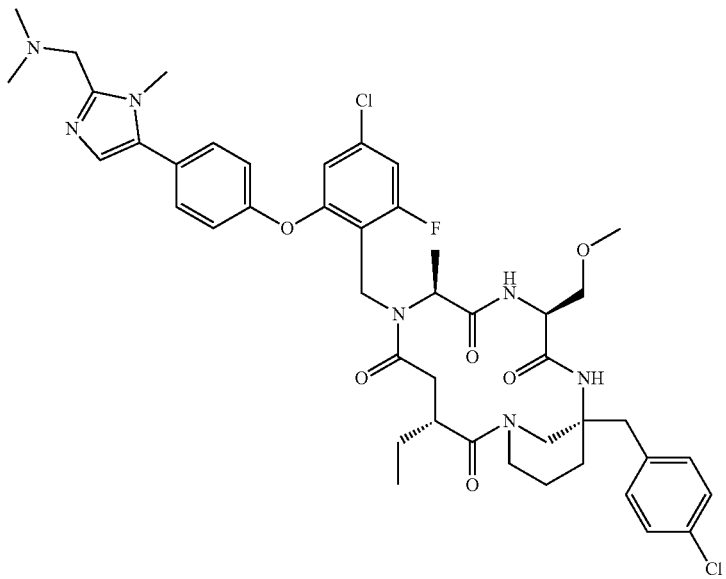 [SMILES: CC[C@@H]1CC(=O)N(Cc2c(F)cc(Cl)cc2Oc2ccc(-c3cnc(CN(C)C)n3C)cc2)[C@@H](C)C(=O)N[C@@H](COC)C(=O)N[C@@]2(Cc3ccc(Cl)cc3)CCCN(C2)C1=O] | Analytical Method 2<br>$t_R$ = 1.22 min.<br>$[M + H]^+$ = 878.5 |
| 122 | 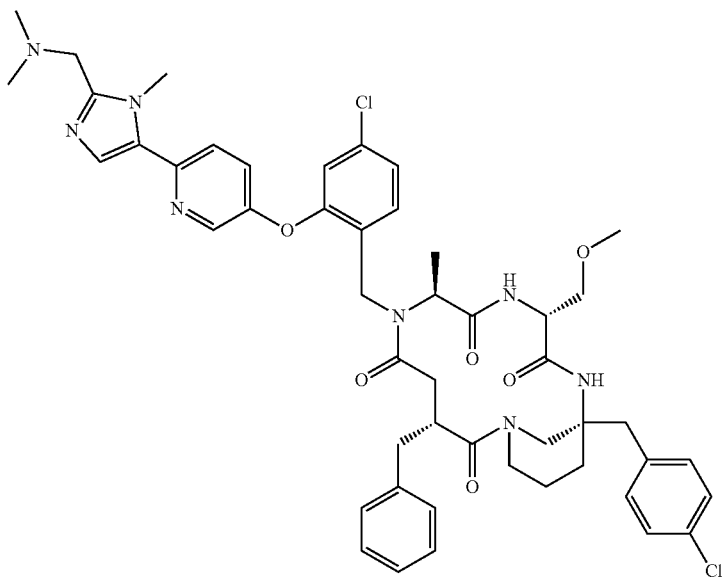 [SMILES: COC[C@H]1NC(=O)[C@H](C)N(Cc2ccc(Cl)cc2Oc2ccc(-c3cnc(CN(C)C)n3C)nc2)C(=O)C[C@@H](Cc2ccccc2)C(=O)N2CCC[C@@](Cc3ccc(Cl)cc3)(C2)NC1=O] | Analytical Method 2<br>$t_R$ = 2.99 min.<br>$[M + H]^+$ = 923.7 |

373
374

TABLE 17-continued

| Cmd No. | Structure | LCMS |
|---|---|---|
| 138 | 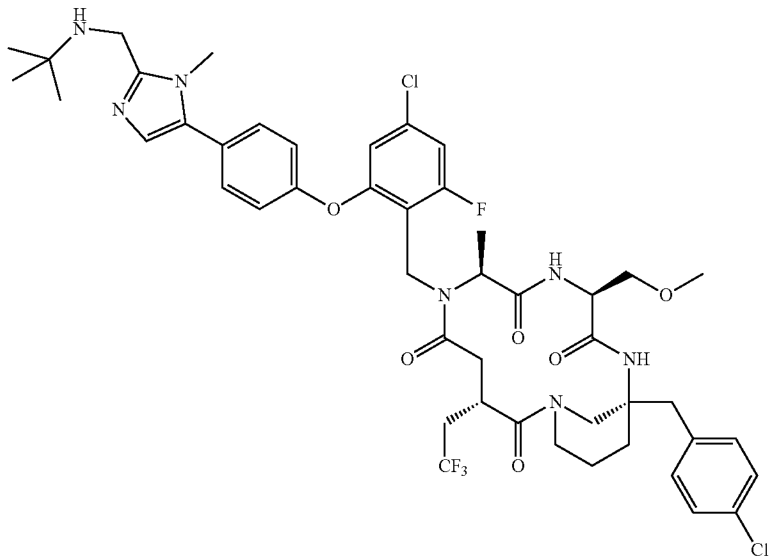 [SMILES: COC[C@@H]1NC(=O)[C@H](C)N(Cc2c(F)cc(Cl)cc2Oc2ccc(-c3cnc(CNC(C)(C)C)n3C)cc2)C(=O)C[C@@H](CC(F)(F)F)C(=O)N2CCC[C@@](Cc3ccc(Cl)cc3)(C2)NC1=O] | Analytical Method 3<br>$t_R$ = 1.14 min.<br>[M + H]$^+$ = 960.4 |
| 142 | 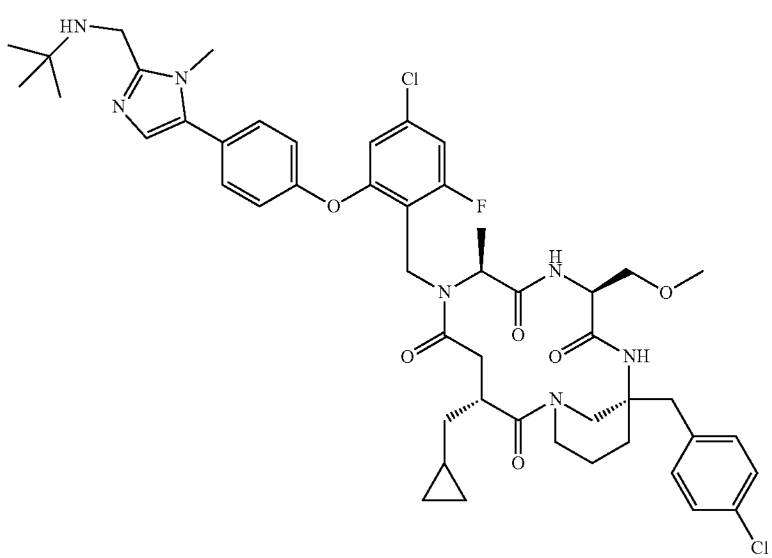 [SMILES: COC[C@@H]1NC(=O)[C@H](C)N(Cc2c(F)cc(Cl)cc2Oc2ccc(-c3cnc(CNC(C)(C)C)n3C)cc2)C(=O)C[C@@H](CC2CC2)C(=O)N2CCC[C@@](Cc3ccc(Cl)cc3)(C2)NC1=O] | Analytical Method 3<br>$t_R$ = 1.19 min.<br>[M + H]$^+$ = 932.4 |

| Cmd No. | Structure | LCMS |
|---|---|---|
| 149 | 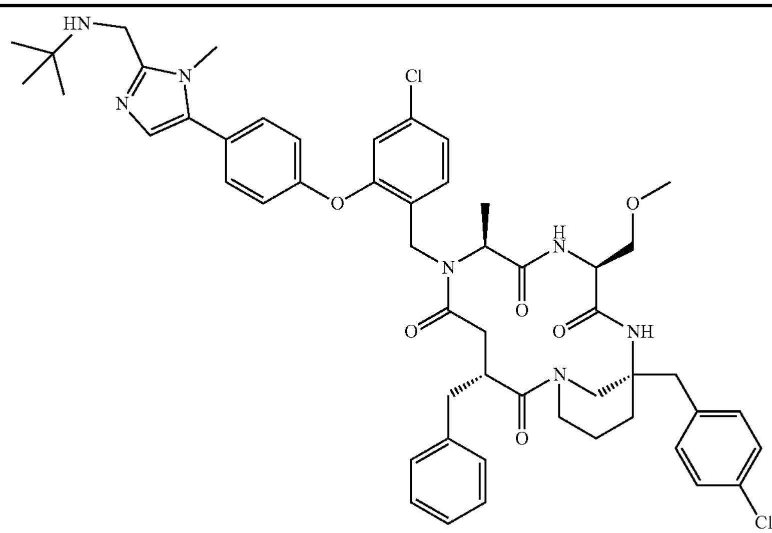 | Analytical Method 3<br>$t_R$ = 1.16 min.<br>$[M + H]^+$ = 950.4 |

Example 8.25: Synthesis of (3R,7S,10S,13R)-3-Benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-1,6,9,12-tetraazabicyclo[11.3.1]heptadecane-2,5,8,11-tetraone (Compound 50)

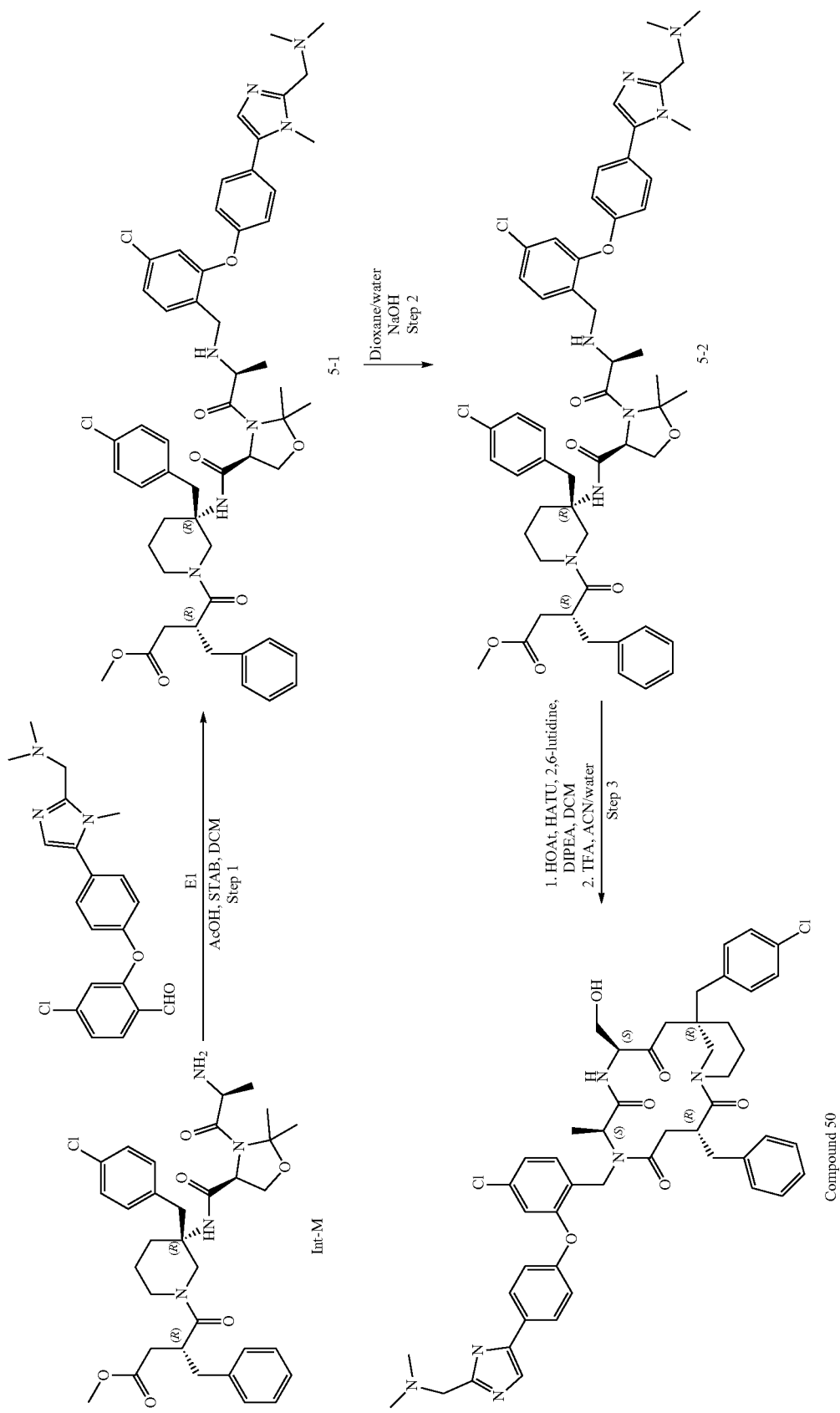

Step 1. (R)-Methyl 3-benzyl-4-((R)-3-((S)-3-((S)-2-((4-chloro-2-(4-(2-((dimethylamino)methyl)-1-methyl-1H-imidazol-5-yl)phenoxy)benzyl)amino)propanoyl)-2,2-dimethyloxazolidine-4-carboxamido)-3-(4-chlorobenzyl)piperidin-1-yl)-4-oxobutanoate (5-1)

The title compound 5-1 was prepared according to the procedure described for Example 8, Step 1 starting from Int M (200 mg, 0.27 mmol) and E1 (100 mg, 0.27 mmol). After workup and purification, the product 5-1 was obtained (213 mg, 72% yield). MS [M+H]$^+$=982.8.

Step 2. (R)-3-benzyl-4-((R)-3-((S)-3-((S)-2-((4-chloro-2-(4-(2-((dimethylamino)methyl)-1-methyl-1H-imidazol-5-yl)phenoxy)benzyl)amino)propanoyl)-2,2-dimethyloxazolidine-4-carboxamido)-3-(4-chlorobenzyl)piperidin-1-yl)-4-oxobutanoic acid (5-2)

To a round bottom flask containing 5-1 (213 mg, 0.22 mmol) in dioxane (10 mL) and water (2.5 mL) was added sodium hydroxide (1M, 0.87 mL, 0.87 mmol) dropwise. The resulting mixture was stirred at room temperature for 2 h, cooled in an ice bath, and quenched with HCl (1M, 0.65 mL, 0.65 mmol) in water (1.4 mL), The reaction mixture was warmed to room temperature, stirred for 15 min, and then subsequently freeze dried to afford example 5-2 as an off white powder (210 mg, quantitative). The material was used in the next step without purification. MS [M+H]$^+$=965.8.

Step 3. (3R,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-1,6,9,12-tetraazabicyclo[11.3.1]heptadecane-2,5,8,11-tetraone (Compound 50)

To a solution of 5-2 (210 mg, 0.22 mmol) in anhydrous DCM (210 mL) was added 2,6-lutidine (0.76 mL, 6.52 mmol), HOAt (30 mg, 0.22 mmol), and HATU (330 mg, 0.87 mmol). The resulting mixture was heated to 45° C. overnight. The resulting cloudy mixture was cooled and filtered, and the filtrate was concentrated to dryness under reduced pressure. The residue was taken up in DCM and washed with a solution of half-saturated sodium bicarbonate. The organic phase was then dried over sodium sulfate, filtered, and concentrated. The crude product was purified by flash column chromatography on silica gel (eluting with 0-20% MeOH in DCM, product eluted out ~10% MeOH) to afford the cyclized intermediate which was used directly in the next step (142 mg, 69% yield). MS [M+H]$^+$=948.5.

To a vial containing the cyclized intermediate (142 mg, 0.15 mmol) in ACN (5 mL) and water (3 mL) and cooled in an ice bath was added trifluoroacetic acid (1.44 mL, 18.70 mmol) dropwise. The resulting mixture was warmed to room temperature and stirred for ~1 h. The reaction mixture was then diluted with a 1:1 mixture of ACN/water and freeze dried. The crude solid was taken up in EtOAc, a half-saturated solution of sodium bicarbonate was added and the resulting mixture was stirred vigorously for 15 min to afford a biphasic mixture. The aqueous phase was drained off and the organic phase was washed with saturated aq. sodium bicarbonate (×2) and brine (×2), dried over sodium sulfate, filtered, and concentrated. The crude residue was taken up in 1:1 ACN/water and freeze dried to afford Compound 50 as a white powder (123 mg, 86% yield). Analytical Method 3, $t_R$=1.07 min., [M+H]$^+$=908.4

The compounds in Table 18 were synthesized according to the procedure described in Example 8.25 for Compound 50 from the respective intermediates shown in Tables 1-7 and described above in Example 8.

TABLE 18

| Cmd No. | Structure | LCMS |
|---|---|---|
| 5 | 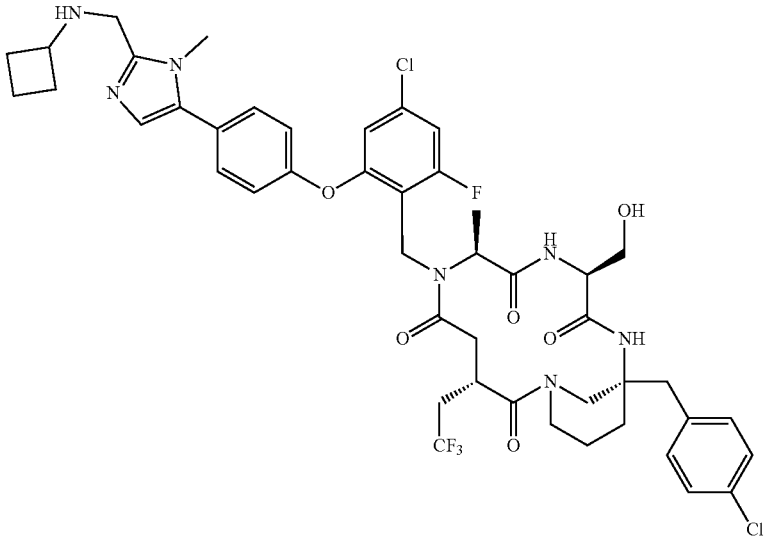 [SMILES: C[C@H]1C(=O)N[C@@H](CO)C(=O)N[C@@]2(Cc3ccc(Cl)cc3)CCCN(C2)C(=O)[C@H](CC(F)(F)F)CC(=O)N1Cc1c(F)cc(Cl)cc1Oc1ccc(-c2cnc(CNC3CCC3)n2C)cc1] | Analytical Method 3<br>$t_R$ = 1.03 min.<br>[M + H]$^+$ = 944.35 |

TABLE 18-continued
| Cmd No. | Structure | LCMS |
|---|---|---|
| 7 | 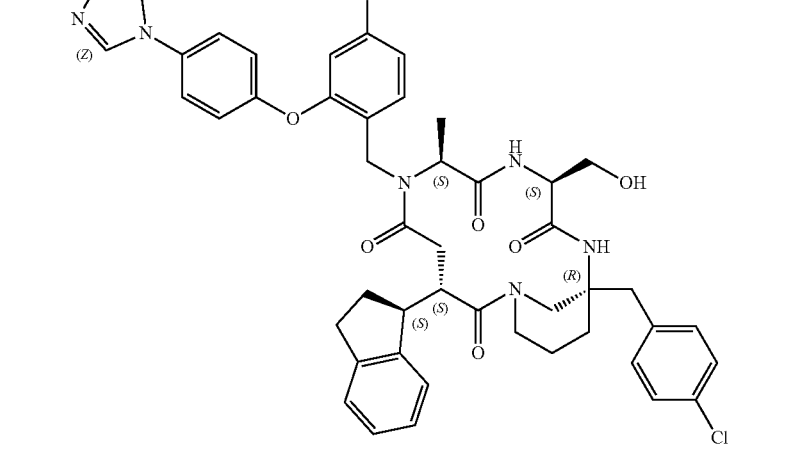 | Analytical Method 3<br>$t_R$ = 1.10 min.<br>$[M + H]^+$ = 934.4 |
| 10 | 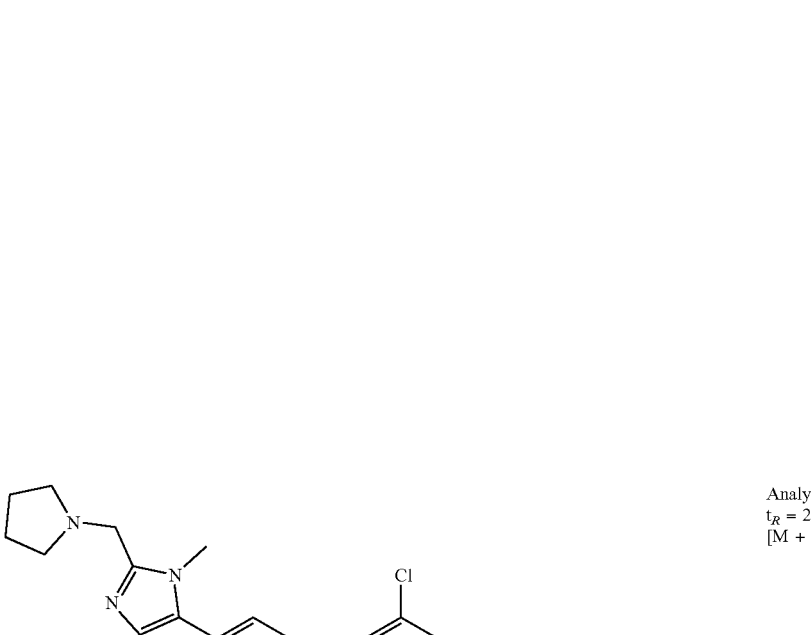 | Analytical Method 2<br>$t_R$ = 2.07 min.<br>$[M + H]^+$ = 916.5 |

TABLE 18-continued
| Cmd No. | Structure | LCMS |
|---|---|---|
| 11 | 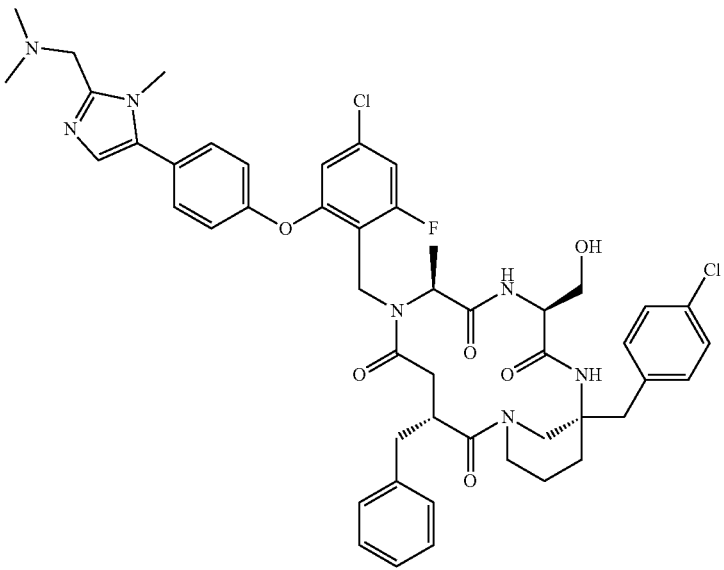 [SMILES: C[C@H]1C(=O)N[C@@H](CO)C(=O)N[C@@]2(Cc3ccc(Cl)cc3)CCCN(C2)C(=O)[C@H](Cc2ccccc2)CC(=O)N1Cc1c(F)cc(Cl)cc1Oc1ccc(-c2cnc(CN(C)C)n2C)cc1] | Analytical Method 2<br>$t_R$ = 2.97 min.<br>$[M + H]^+$ = 926.6 |
| 15 | 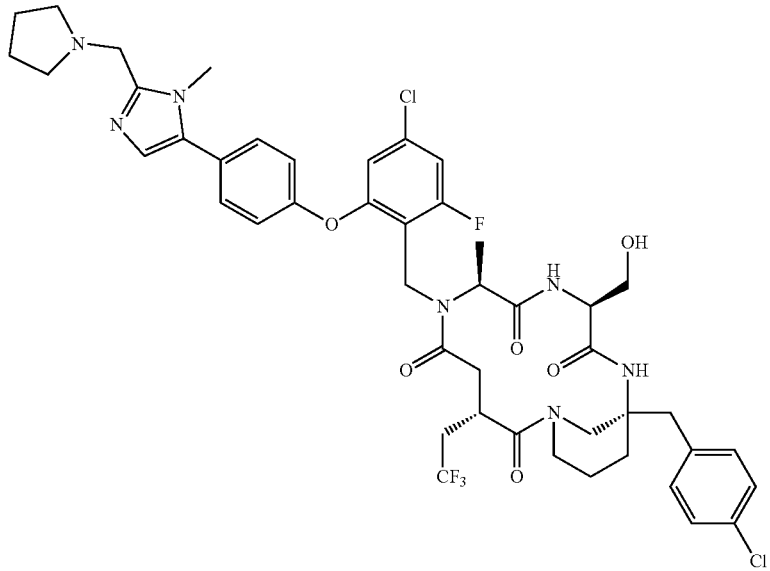 [SMILES: C[C@H]1C(=O)N[C@@H](CO)C(=O)N[C@@]2(Cc3ccc(Cl)cc3)CCCN(C2)C(=O)[C@H](CC(F)(F)F)CC(=O)N1Cc1c(F)cc(Cl)cc1Oc1ccc(-c2cnc(CN3CCCC3)n2C)cc1] | Analytical Method 3<br>$t_R$ = 1.10 min.<br>$[M + H]^+$ = 944.3 |

TABLE 18-continued

| Cmd No. | Structure | LCMS |
|---|---|---|
| 25 | 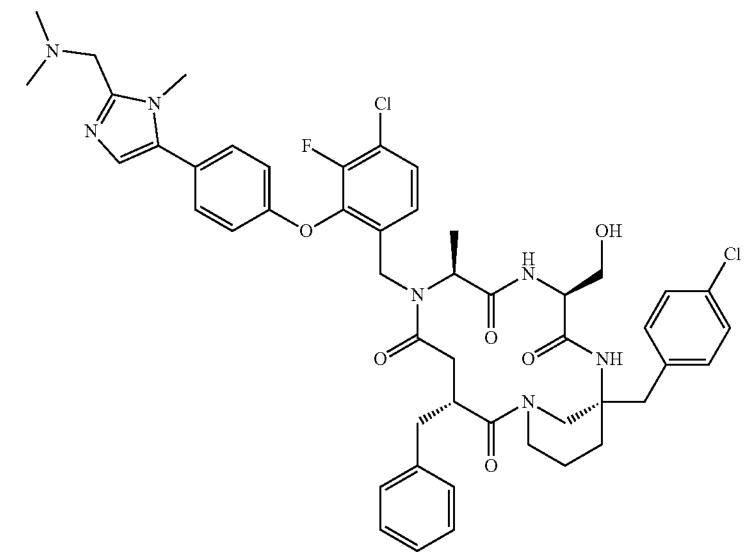 [SMILES: C[C@H]1C(=O)N[C@@H](CO)C(=O)N[C@@]2(Cc3ccc(Cl)cc3)CCCN(C2)C(=O)[C@H](Cc2ccccc2)CC(=O)N1Cc1ccc(Cl)c(F)c1Oc1ccc(-c2cnc(CN(C)C)n2C)cc1] | Analytical Method 2<br>$t_R$ = 2.94 min.<br>$[M + H]^+$ = 926.4 |
| 26 | 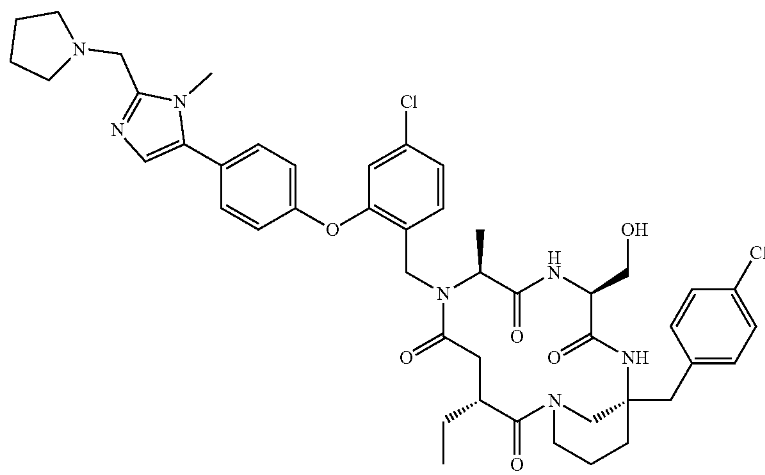 [SMILES: CC[C@@H]1CC(=O)N(Cc2ccc(Cl)cc2Oc2ccc(-c3cnc(CN4CCCC4)n3C)cc2)[C@@H](C)C(=O)N[C@@H](CO)C(=O)N[C@@]2(Cc3ccc(Cl)cc3)CCCN(C2)C1=O] | Analytical Method 2<br>$t_R$ = 2.96 min.<br>$[M + H]^+$ = 872.5 |
| 28 | 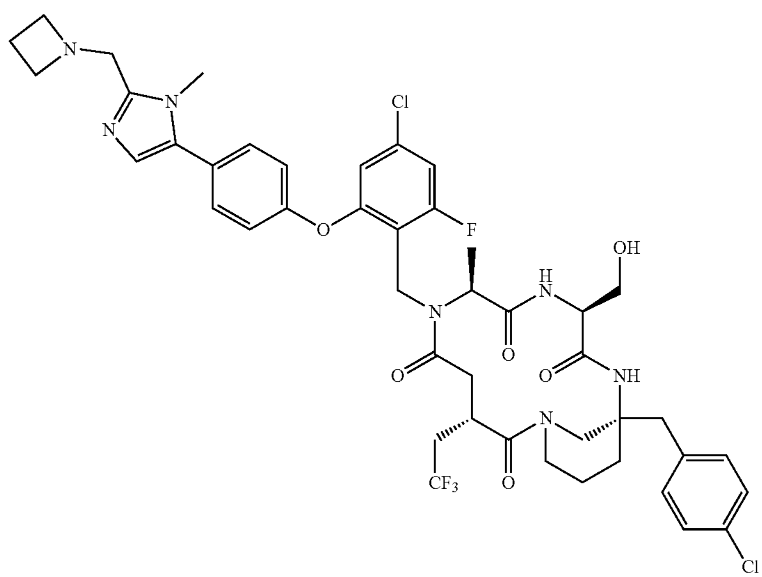 [SMILES: C[C@H]1C(=O)N[C@@H](CO)C(=O)N[C@@]2(Cc3ccc(Cl)cc3)CCCN(C2)C(=O)[C@H](CC(F)(F)F)CC(=O)N1Cc1c(F)cc(Cl)cc1Oc1ccc(-c2cnc(CN3CCC3)n2C)cc1] | Analytical Method 3<br>$t_R$ = 1.09 min.<br>$[M + H]^+$ = 930.3 |

TABLE 18-continued
| Cmd No. | Structure | LCMS |
|---|---|---|
| 34 | 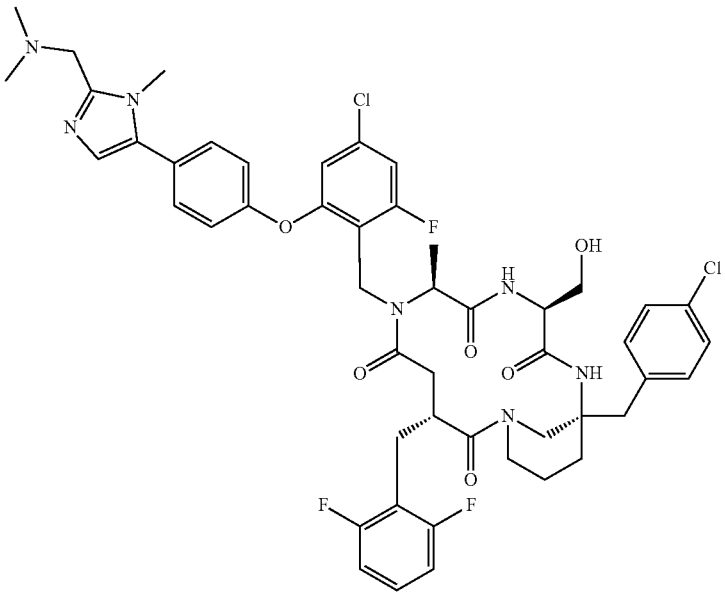 [SMILES: C[C@H]1C(=O)N[C@@H](CO)C(=O)N[C@@]2(Cc3ccc(Cl)cc3)CCCN(C2)C(=O)[C@H](Cc2c(F)cccc2F)CC(=O)N1Cc1c(F)cc(Cl)cc1Oc1ccc(-c2cnc(CN(C)C)n2C)cc1] | Analytical Method 2<br>$t_R$ = 2.96 min.<br>$[M + H]^+$ = 962.6 |
| 41 | 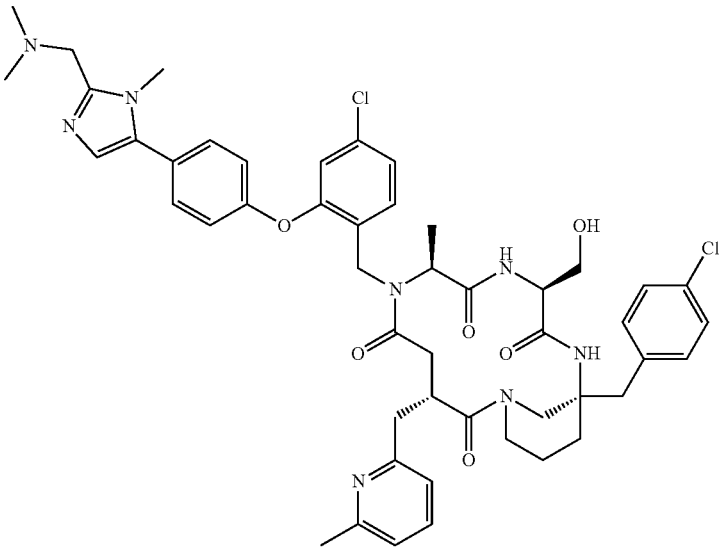 [SMILES: Cc1cccc(C[C@@H]2CC(=O)N(Cc3ccc(Cl)cc3Oc3ccc(-c4cnc(CN(C)C)n4C)cc3)[C@@H](C)C(=O)N[C@@H](CO)C(=O)N[C@@]3(Cc4ccc(Cl)cc4)CCCN(C3)C2=O)n1] | Analytical Method 2<br>$t_R$ = 2.65 min.<br>$[M + H]^+$ = 923.5 |

TABLE 18-continued
| Cmd No. | Structure | LCMS |
|---|---|---|
| 43 | 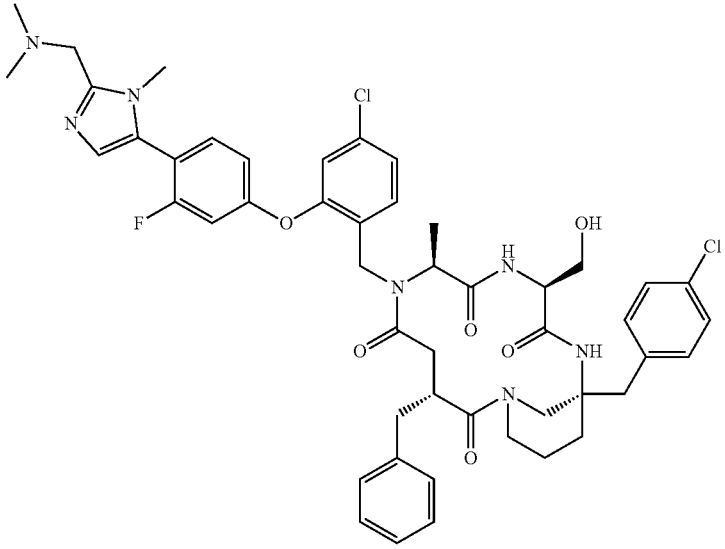 [SMILES: C[C@H]1C(=O)N[C@@H](CO)C(=O)N[C@@]2(Cc3ccc(Cl)cc3)CCCN(C2)C(=O)[C@H](Cc2ccccc2)CC(=O)N1Cc1ccc(Cl)cc1Oc1ccc(-c2cnc(CN(C)C)n2C)c(F)c1] | Analytical Method 2<br>$t_R$ = 2.97 min.<br>$[M + H]^+$ = 926.6 |
| 48 | 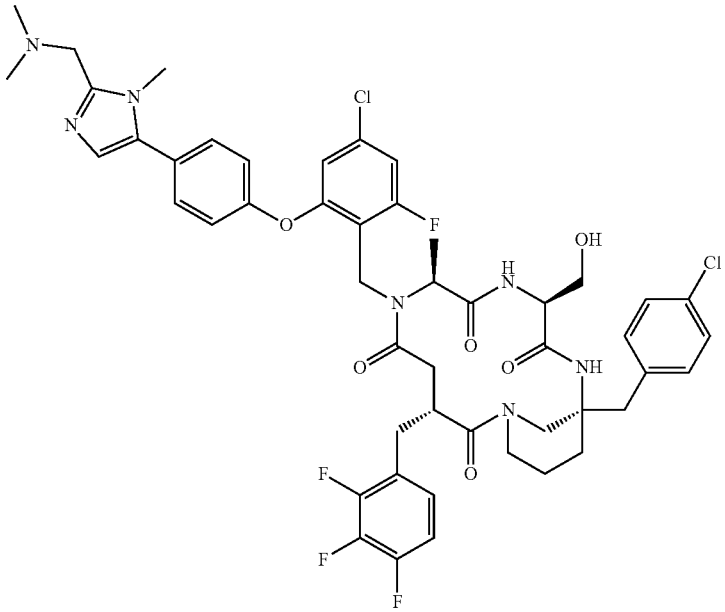 [SMILES: C[C@H]1C(=O)N[C@@H](CO)C(=O)N[C@@]2(Cc3ccc(Cl)cc3)CCCN(C2)C(=O)[C@H](Cc2ccc(F)c(F)c2F)CC(=O)N1Cc1c(F)cc(Cl)cc1Oc1ccc(-c2cnc(CN(C)C)n2C)cc1] | Analytical Method 2<br>$t_R$ = 3.00 min.<br>$[M + H]^+$ = 980.5 |

TABLE 18-continued
| Cmd No. | Structure | LCMS |
|---|---|---|
| 49 | 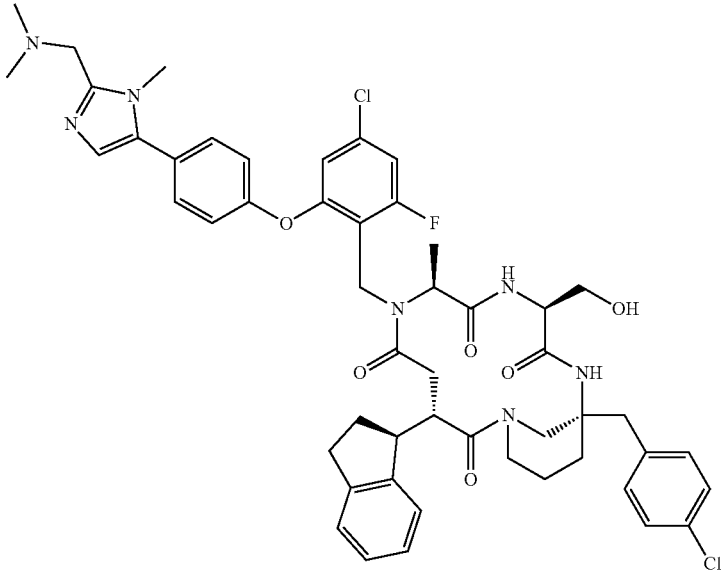 [SMILES: C[C@H]1C(=O)N[C@@H](CO)C(=O)N[C@@]2(Cc3ccc(Cl)cc3)CCCN(C2)C(=O)[C@H]([C@@H]2CCc3ccccc32)CC(=O)N1Cc1c(F)cc(Cl)cc1Oc1ccc(-c2cnc(CN(C)C)n2C)cc1] | Analytical Method 3<br>$t_R$ = 1.12 min.<br>$[M + H]^+$ = 952.4 |
| 51 | 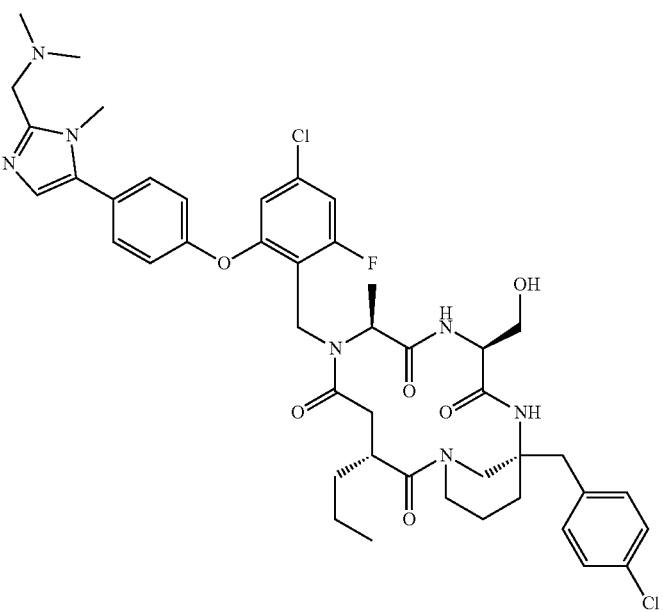 [SMILES: CCC[C@@H]1CC(=O)N(Cc2c(F)cc(Cl)cc2Oc2ccc(-c3cnc(CN(C)C)n3C)cc2)[C@@H](C)C(=O)N[C@@H](CO)C(=O)N[C@@]2(Cc3ccc(Cl)cc3)CCCN(C2)C1=O] | Analytical Method 2<br>$t_R$ = 2.91 min.<br>$[M + H]^+$ = 878.4 |

TABLE 18-continued

| Cmd No. | Structure | LCMS |
| --- | --- | --- |
| 54 | 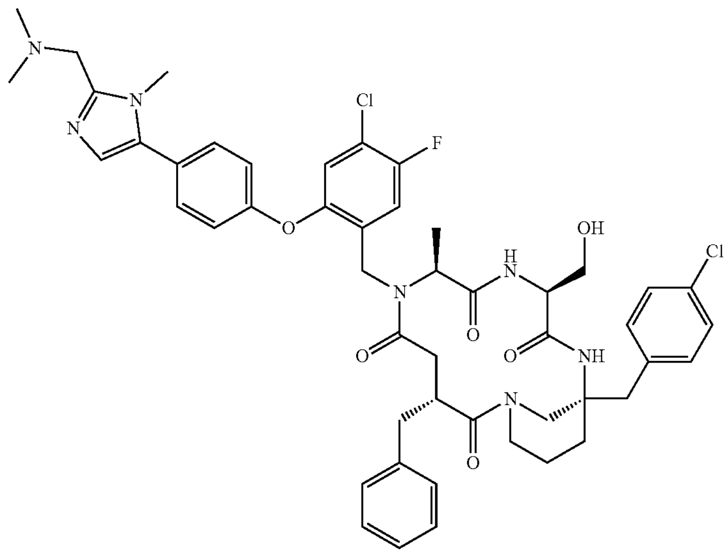 [SMILES: C[C@H]1C(=O)N[C@@H](CO)C(=O)N[C@@]2(Cc3ccc(Cl)cc3)CCCN(C2)C(=O)[C@H](Cc2ccccc2)CC(=O)N1Cc1cc(F)c(Cl)cc1Oc1ccc(-c2cnc(CN(C)C)n2C)cc1] | Analytical Method 2<br>$t_R$ = 2.97 min.<br>Analytical Method 2<br>$[M + H]^+$ = 926.3 |
| 56 | 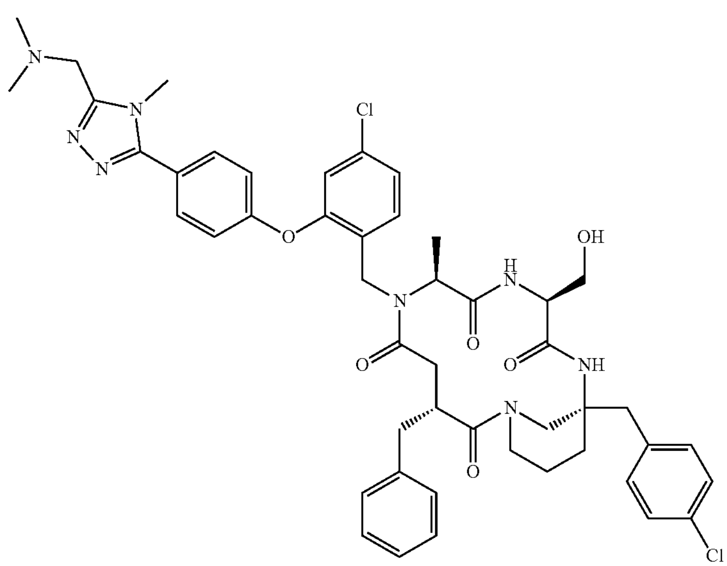 | Analytical Method 3<br>$t_R$ = 1.07 min<br>$[M + H]^+$ = 909.4 |

TABLE 18-continued

| Cmd No. | Structure | LCMS |
|---|---|---|
| 69 | 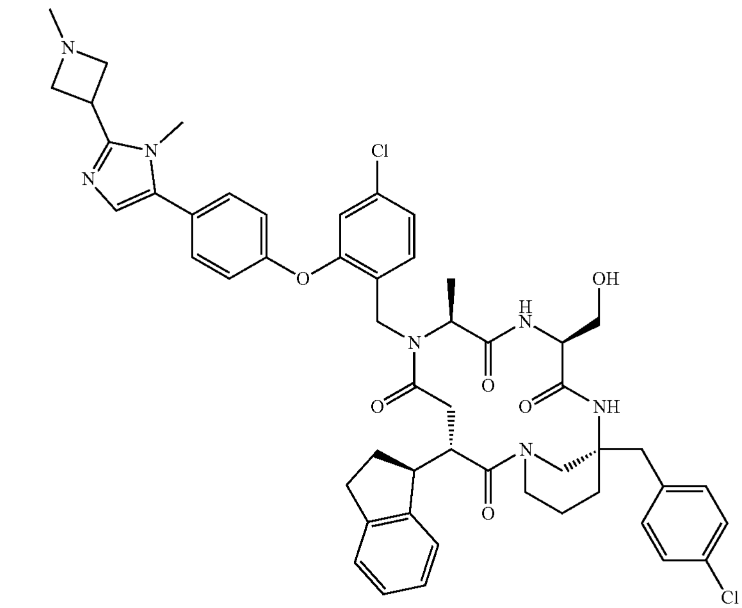 [SMILES: C[C@H]1C(=O)N[C@@H](CO)C(=O)N[C@@]2(Cc3ccc(Cl)cc3)CCCN(C2)C(=O)[C@H]([C@@H]2CCc3ccccc32)CC(=O)N1Cc1ccc(Cl)cc1Oc1ccc(-c2cnc(C3CN(C)C3)n2C)cc1] | Analytical Method 3<br>$t_R$ = 1.07 min.<br>[M + H]$^+$ = 946.4 |
| 75 | 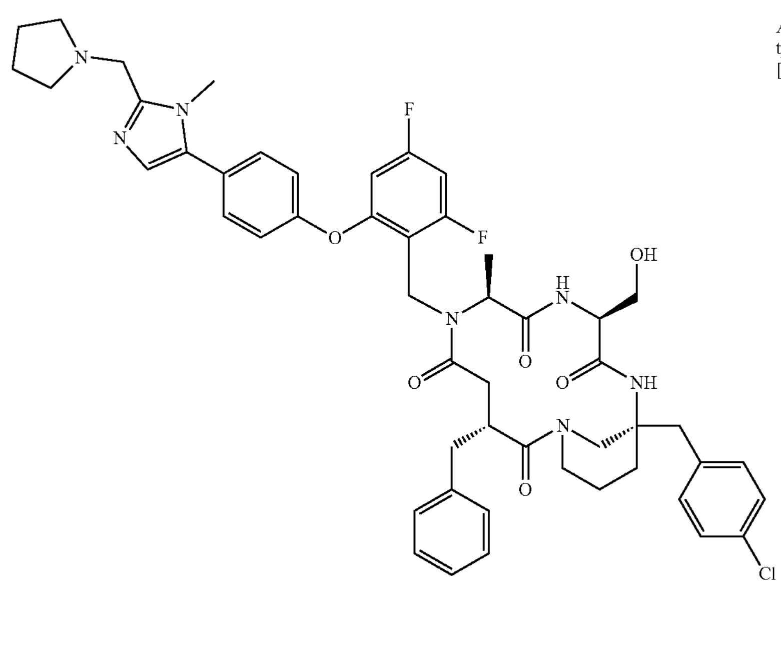 [SMILES: C[C@H]1C(=O)N[C@@H](CO)C(=O)N[C@@]2(Cc3ccc(Cl)cc3)CCCN(C2)C(=O)[C@H](Cc2ccccc2)CC(=O)N1Cc1c(F)cc(F)cc1Oc1ccc(-c2cnc(CN3CCCC3)n2C)cc1] | Analytical Method 3<br>$t_R$ = 1.11 min.<br>[M + H]$^+$ = 936.4 |

TABLE 18-continued

| Cmd No. | Structure | LCMS |
|---|---|---|
| 80 | 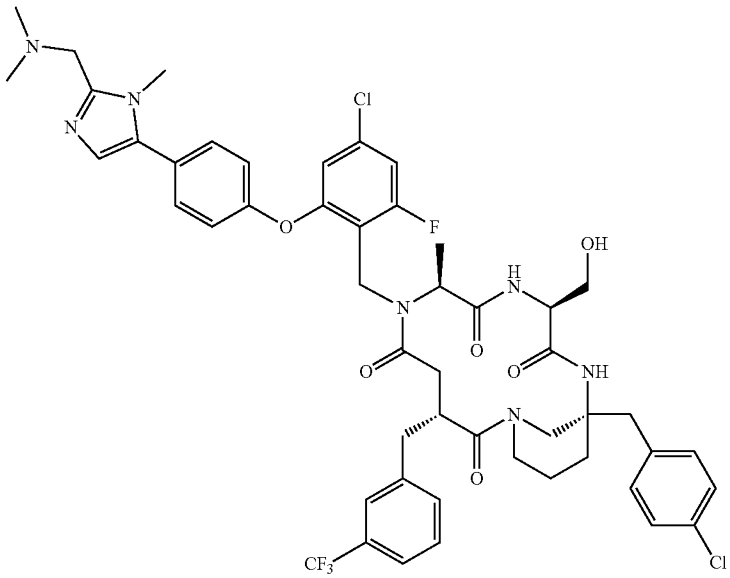 [SMILES: C[C@H]1C(=O)N[C@@H](CO)C(=O)N[C@@]2(Cc3ccc(Cl)cc3)CCCN(C2)C(=O)[C@H](Cc2cccc(C(F)(F)F)c2)CC(=O)N1Cc1c(F)cc(Cl)cc1Oc1ccc(-c2cnc(CN(C)C)n2C)cc1] | Analytical Method 3<br>$t_R$ = 1.15 min.<br>[M + H]$^+$ = 994.3 |
| 87 | 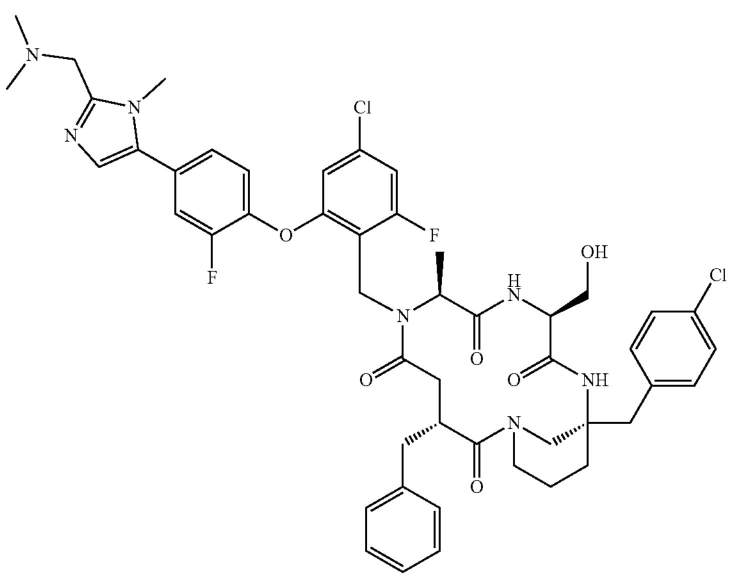 [SMILES: C[C@H]1C(=O)N[C@@H](CO)C(=O)N[C@@]2(Cc3ccc(Cl)cc3)CCCN(C2)C(=O)[C@H](Cc2ccccc2)CC(=O)N1Cc1c(F)cc(Cl)cc1Oc1ccc(-c2cnc(CN(C)C)n2C)cc1F] | Analytical Method 2<br>$t_R$ = 2.93 min.<br>[M + H]$^+$ = 944.6 |

TABLE 18-continued
| Cmd No. | Structure | LCMS |
|---|---|---|
| 88 | 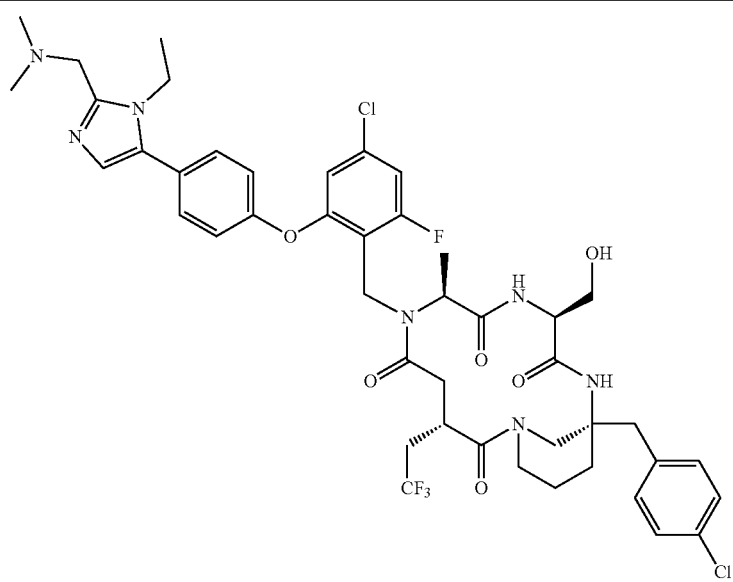 | Analytical Method 2<br>$t_R$ = 2.93 min.<br>$[M + H]^+$ = 932.6 |
| 98 | 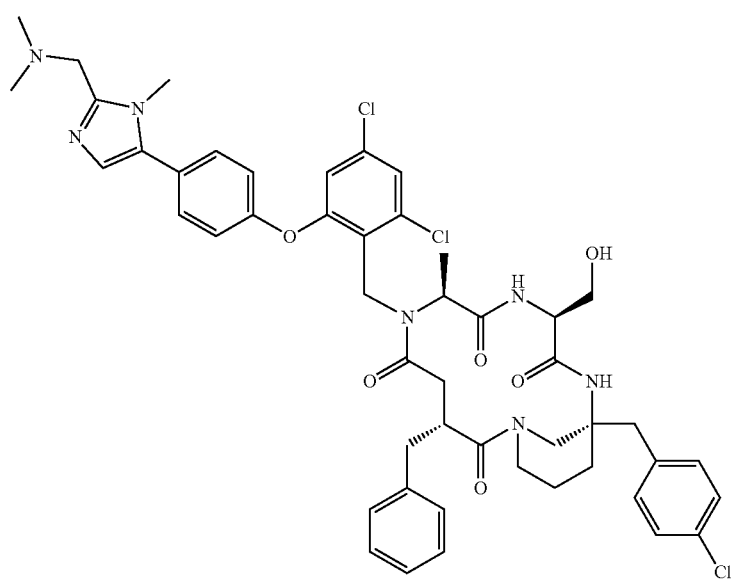 [SMILES: C[C@H]1C(=O)N[C@@H](CO)C(=O)N[C@@]2(Cc3ccc(Cl)cc3)CCCN(C2)C(=O)[C@H](Cc2ccccc2)CC(=O)N1Cc1c(Cl)cc(Cl)cc1Oc1ccc(-c2cnc(CN(C)C)n2C)cc1] | Analytical Method 2<br>$t_R$ = 3.02 min.<br>$[M + H]^+$ = 942.5 |

401
TABLE 18-continued
| Cmd No. | Structure | LCMS |
| --- | --- | --- |
| 145 | 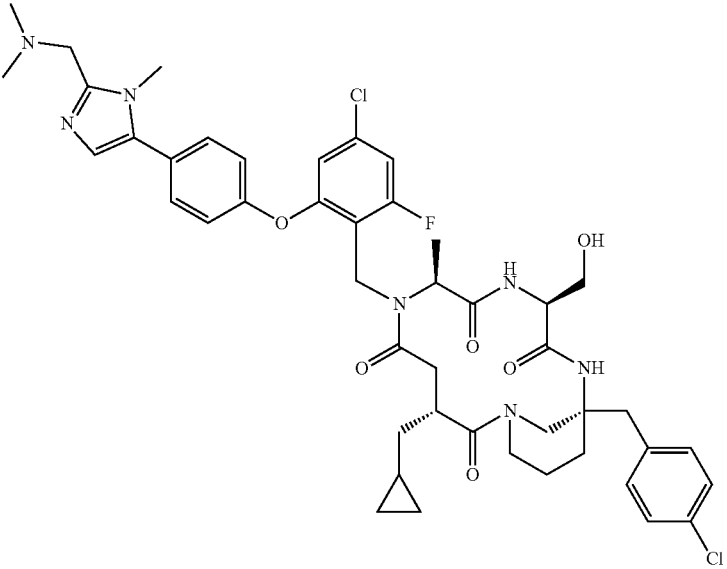 [SMILES: C[C@H]1C(=O)N[C@@H](CO)C(=O)N[C@@]2(Cc3ccc(Cl)cc3)CCCN(C2)C(=O)[C@H](CC2CC2)CC(=O)N1Cc1c(F)cc(Cl)cc1Oc1ccc(-c2cnc(CN(C)C)n2C)cc1] | Analytical Method 3<br>$t_R$ = 1.09 min.<br>$[M + H]^+$ = 890.4 |
| 148 | 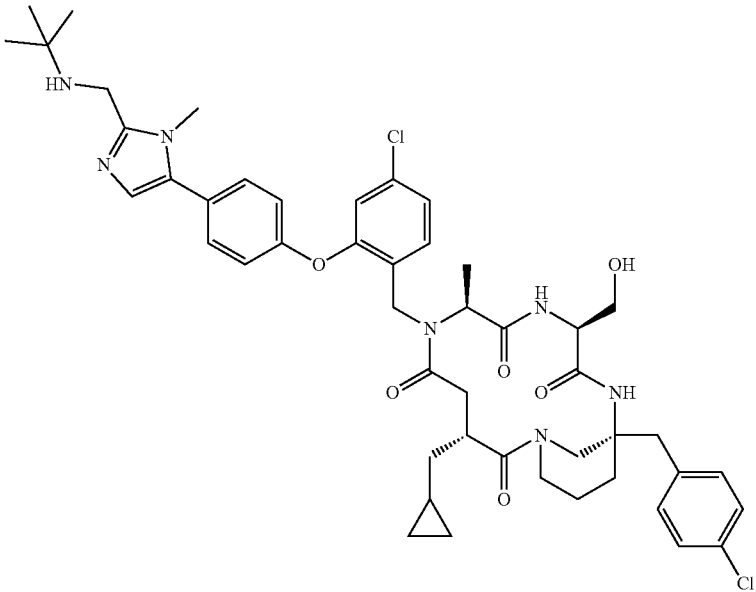 [SMILES: C[C@H]1C(=O)N[C@@H](CO)C(=O)N[C@@]2(Cc3ccc(Cl)cc3)CCCN(C2)C(=O)[C@H](CC2CC2)CC(=O)N1Cc1ccc(Cl)cc1Oc1ccc(-c2cnc(CNC(C)(C)C)n2C)cc1] | Analytical Method 4<br>$t_R$ = 2.13 min.<br>$[M + H]^+$ = 900.5 |

TABLE 18-continued

| Cmd No. | Structure | LCMS |
|---|---|---|
| 150 | 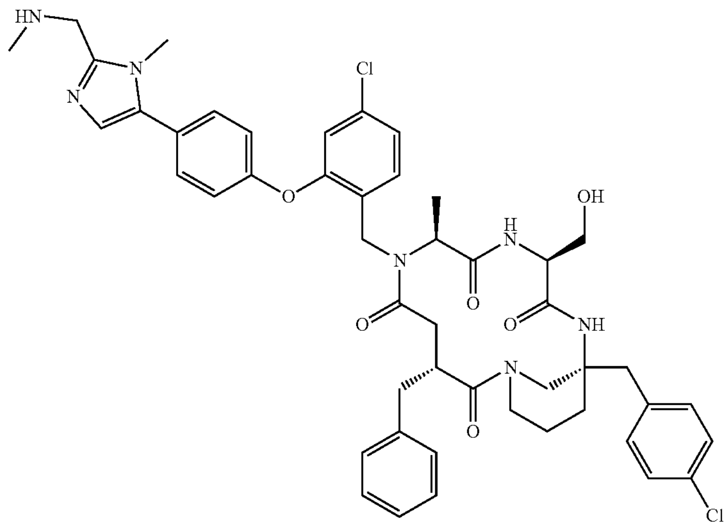 [SMILES: CNCc1ncc(-c2ccc(Oc3cc(Cl)ccc3CN3C(=O)C[C@@H](Cc4ccccc4)C(=O)N4CCC[C@@](Cc5ccc(Cl)cc5)(C4)NC(=O)[C@H](CO)NC(=O)[C@@H]3C)cc2)n1C] | Analytical Method 3<br>$t_R$ = 1.07 min<br>$[M + H]^+$ = 894.4 |
| 152 | 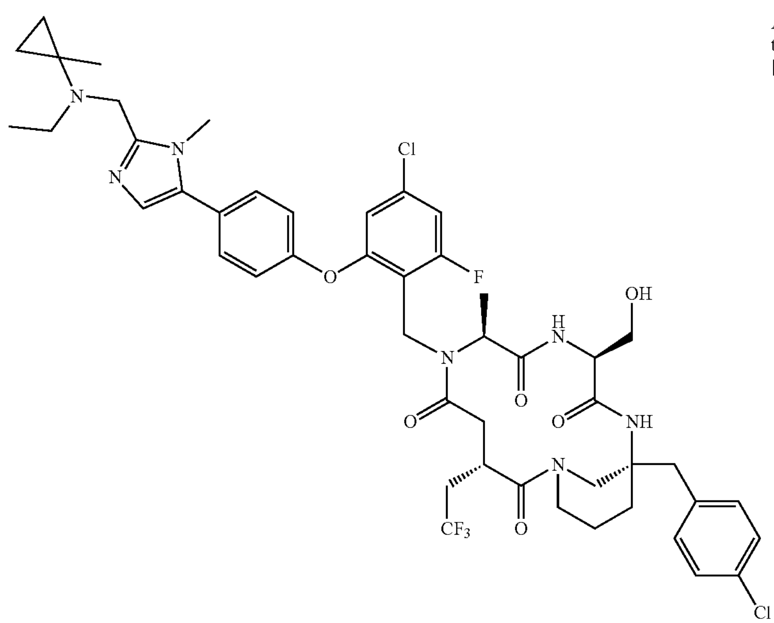 [SMILES: CCN(Cc1ncc(-c2ccc(Oc3cc(Cl)cc(F)c3CN3C(=O)C[C@@H](CC(F)(F)F)C(=O)N4CCC[C@@](Cc5ccc(Cl)cc5)(C4)NC(=O)[C@H](CO)NC(=O)[C@@H]3C)cc2)n1C)C1(C)CC1] | Analytical Method 3<br>$t_R$ = 1.22 min.<br>$[M + H]^+$ = 972.4 |
| 153 | 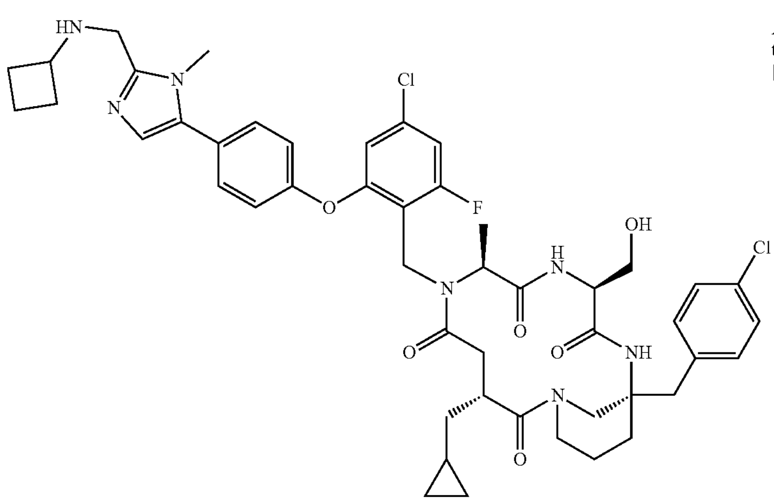 [SMILES: C[C@H]1C(=O)N[C@@H](CO)C(=O)N[C@@]2(Cc3ccc(Cl)cc3)CCCN(C2)C(=O)[C@H](CC2CC2)CC(=O)N1Cc1c(F)cc(Cl)cc1Oc1ccc(-c2cnc(CNC3CCC3)n2C)cc1] | Analytical Method 3<br>$t_R$ = 1.09 min.<br>$[M + H]^+$ = 916.4 |

TABLE 18-continued
| Cmd No. | Structure | LCMS |
|---|---|---|
| 154 | 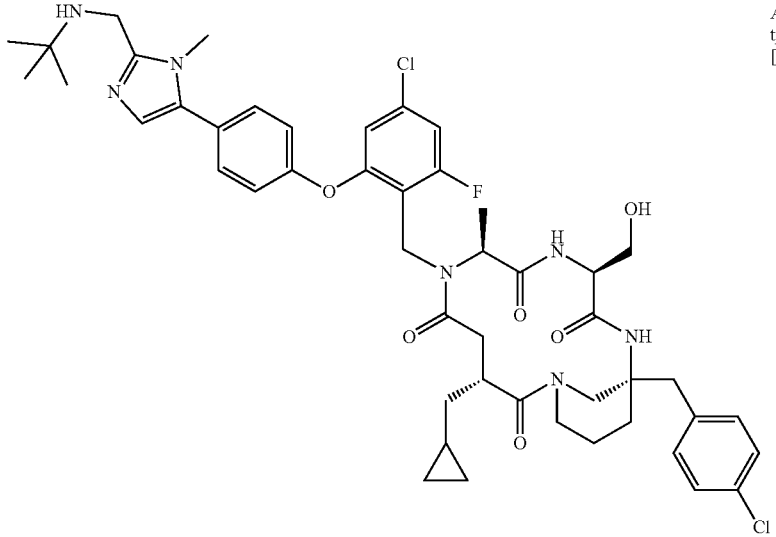 | Analytical Method 3<br>$t_R$ = 1.09 min.<br>$[M + H]^+$ = 918.4 |
| 155 | 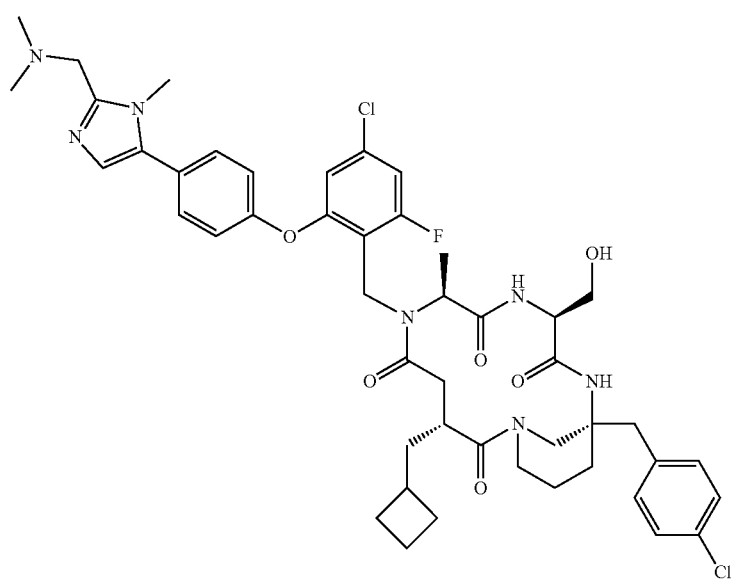 [SMILES: C[C@H]1C(=O)N[C@@H](CO)C(=O)N[C@@]2(Cc3ccc(Cl)cc3)CCCN(C2)C(=O)[C@H](CC2CCC2)CC(=O)N1Cc1c(F)cc(Cl)cc1Oc1ccc(-c2cnc(CN(C)C)n2C)cc1] | Analytical Method 3<br>$t_R$ = 1.15 min. MS<br>$[M + H]^+$ = 904.4 |

TABLE 18-continued
| Cmd No. | Structure | LCMS |
|---|---|---|
| 161 | 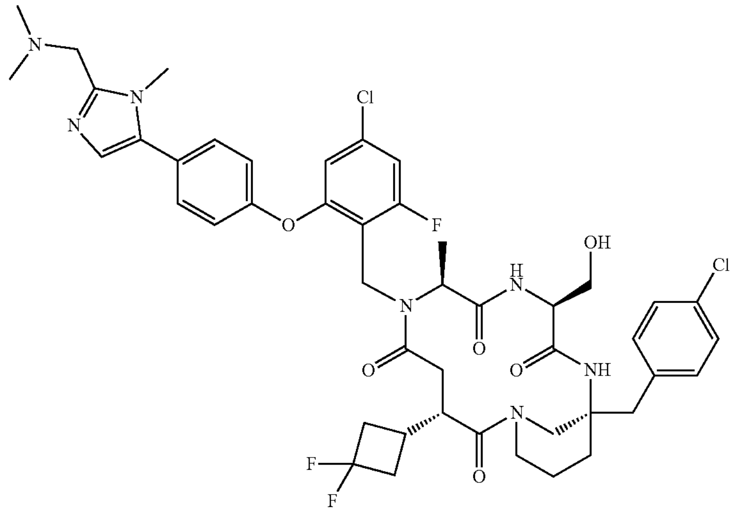 [SMILES: C[C@H]1C(=O)N[C@@H](CO)C(=O)N[C@@]2(Cc3ccc(Cl)cc3)CCCN(C2)C(=O)[C@H](C2CC(F)(F)C2)CC(=O)N1Cc1c(F)cc(Cl)cc1Oc1ccc(-c2cnc(CN(C)C)n2C)cc1] | Analytical Method 4<br>$t_R$ = 1.99 min.<br>$[M + H]^+$ = 926.2 |
Example 8.26: Synthesis of (3S,7S,10S,13R)-13-(4-chlorobenzyl)-3-((S)-2,3-dihydro-1H-inden-1-yl)-6-(2-(4-(2-((dimethylamino) methyl)-1-methyl-1H-imidazol-5-yl)phenoxy)benzyl)-10-(hydroxymethyl)-7-methyl-1,6,9,12-tetraazabicyclo [11.3.1] heptadecane-2,5,8,11-tetraone (Compound 55)
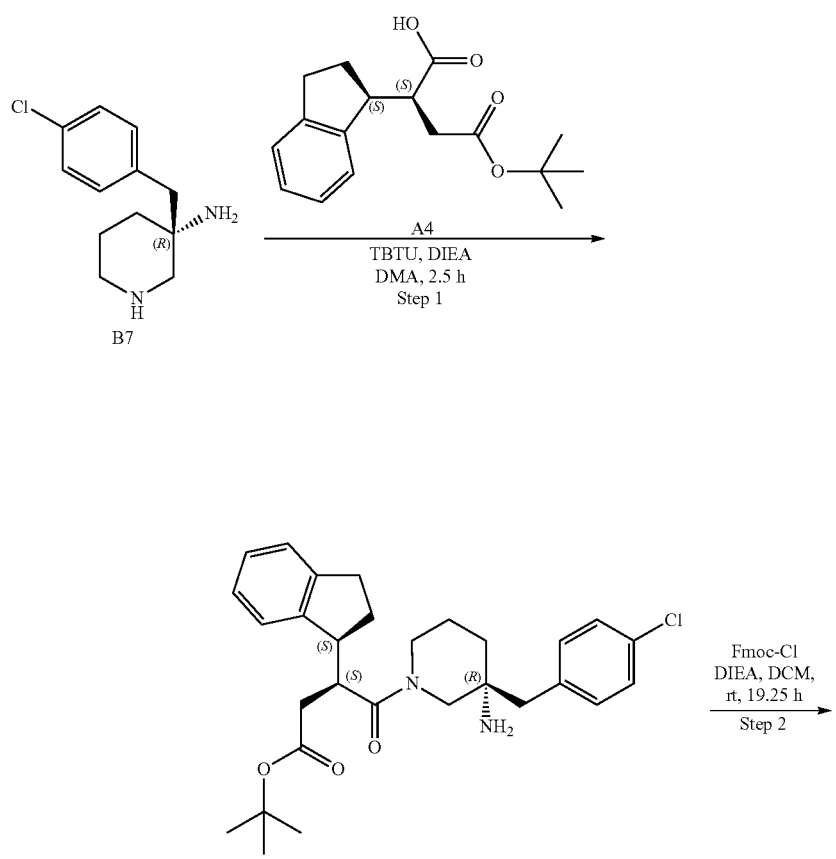
6-1

-continued
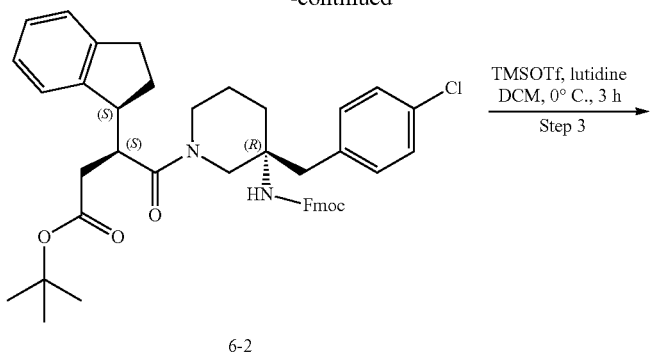
6-2
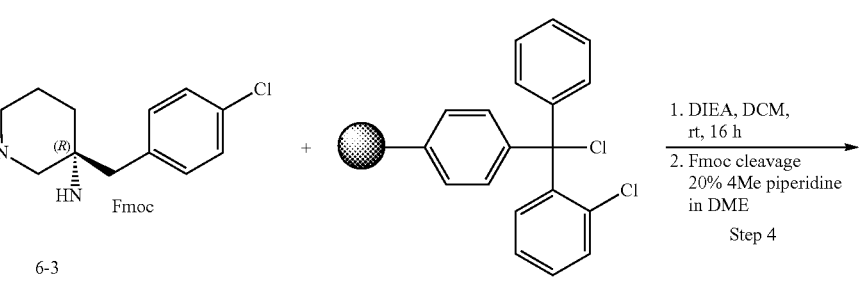
6-3
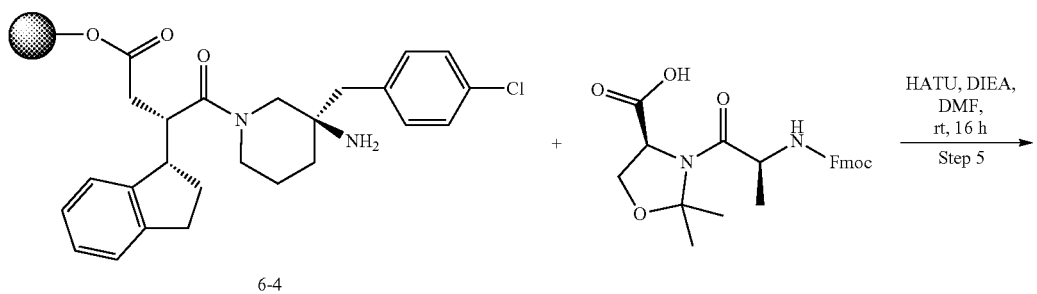
6-4
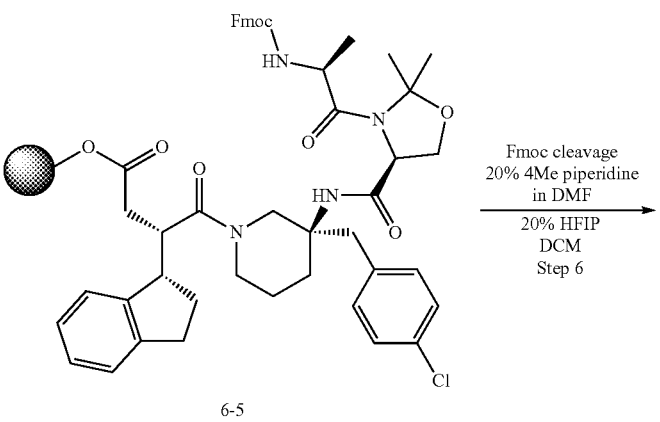
6-5

-continued
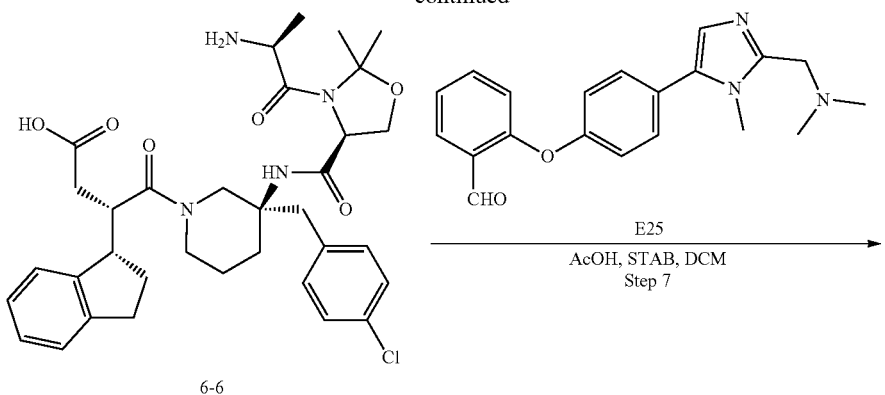
6-6
E25
AcOH, STAB, DCM
Step 7
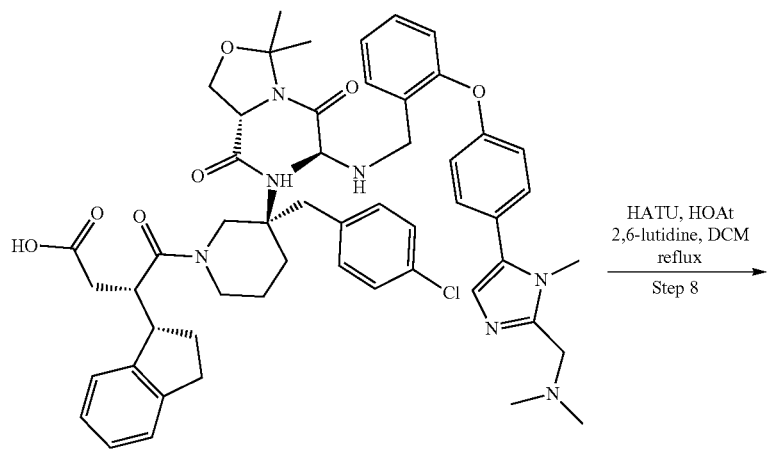
6-7
HATU, HOAt
2,6-lutidine, DCM
reflux
Step 8
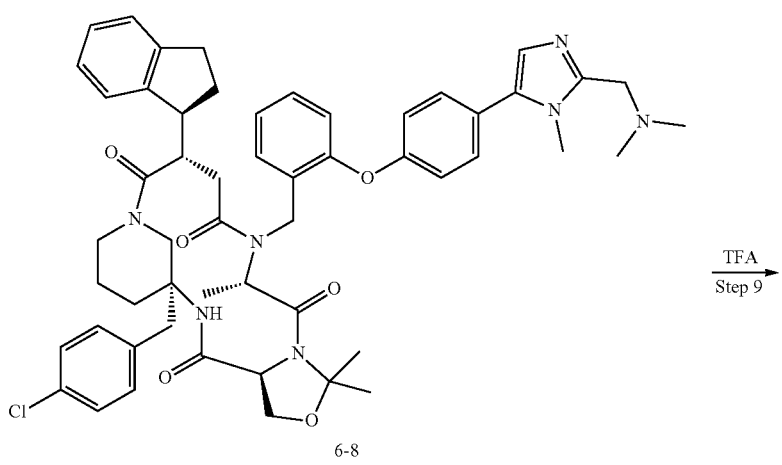
6-8
TFA
Step 9

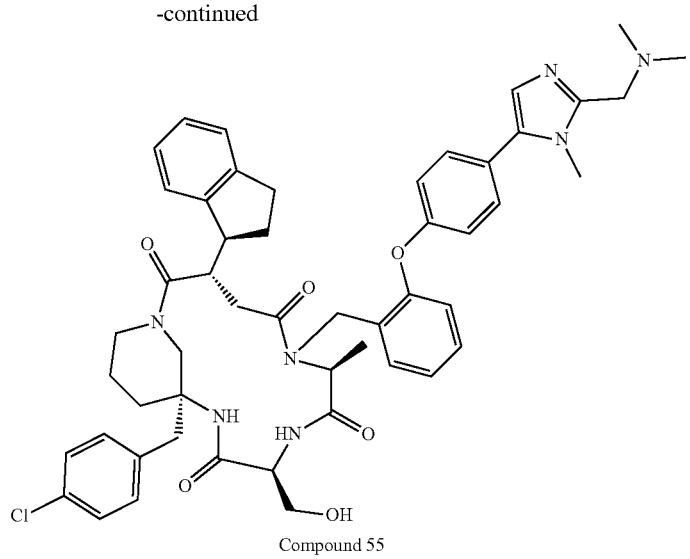

Compound 55

Step 1. (S)-tert-butyl 4-((R)-3-amino-3-(4-chlorobenzyl)piperidin-1-yl)-3-((S)-2,3-dihydro-1H-inden-1-yl)-4-oxobutanoate (6-1)

To a solution of A4 (1.376 g, 4.74 mmol) and TBTU (1.522 g, 4.74 mmol) in DMA (10 mL) was added DIEA (1.08 mL, 6.16 mmol). The resulting mixture was stirred for 5 min. at RT, and then added to a solution of B7 (1.41 g, 4.74 mmol) in DMA (10 mL) and DIEA (3.31 mL, 18.96 mmol). The reaction mixture was stirred for 2.5 h at RT, the solvent was removed in vacuo and the resulting residue was partitioned between EtOAc (100 mL) and 1M aq. NaHCO$_3$ (40 mL). The organic phase was washed with 1M NaHCO$_3$ (2×15 mL) and brine (15 mL), dried over Na$_2$SO$_4$, filtered, and concentrated to dryness to afford 6-1 (2.4 g, 3.86 mmol, 81% yield) as a yellow solid. The product was used in the next step without purification. Analytical Method 5, $t_R$=1.30 min., [M+H]$^+$=497.4.

Step 2. (S)-tert-Butyl 4-((R)-3-((((9H-fluoren-9-yl)methoxy)carbonyl)amino)-3-(4-chlorobenzyl) piperidin-1-yl)-3-((S)-2,3-dihydro-1H-inden-1-yl)-4-oxobutanoate (6-2)

To 6-1 (2.4 g, 4.83 mmol) dissolved in DCM (20 mL) was added DIPEA (1.69 mL, 9.66 mmol) and a solution of Fmoc-Cl (1.25 g, 4.83 mmol) in DCM (10 mL) and the resulting mixture was stirred overnight at RT. The reaction mixture was concentrated in vacuo and the residue was partitioned between EtOAc (70 mL) and 1M NaHCO$_3$ (50 mL). The organic phase was washed with 1M NaHCO$_3$ (50 mL), water (100 mL) and brine (100 mL), dried over Na$_2$SO$_4$, filtered, and concentrated to dryness. The crude product was purified by flash column chromatography on silica gel (eluting with 0-40% EtOAc/heptane) to afford 6-2 as a white foam after concentrating the pure fractions (2.2 g, 2.91 mmol, 60.2% yield). Analytical Method 5, $t_R$=1.56 min., [M+H]$^+$=718.7.

Step 3. (S)-4-((R)-3-((((9H-Fluoren-9-yl)methoxy)carbonyl)amino)-3-(4-chlorobenzyl)piperidin-1-yl)-3-((S)-2,3-dihydro-1H-inden-1-yl)-4-oxobutanoic acid (6-3)

To a solution of 6-2 (2.2 g, 3.06 mmol) and lutidine (3.56 mL, 30.6 mmol) in DCM (50 mL) at 0° C. was added trimethylsilyl trifluoromethanesulfonate (2.76 mL, 15.29 mmol) dropwise. The resulting mixture was stirred for 3 h at 0° C. DCM (100 mL) and 5% aq. KHSO$_4$ (50 mL) were then added and the phases were separated. The organic phase was washed with 5% aq. KHSO$_4$ (3×30 mL) and brine (30 mL), dried over Na$_2$SO$_4$, filtered, and concentrated to dryness in vacuo to yield 6-3 as an off-white solid (2.2 g, 3.32 mmol, ~quantitative yield). Analytical Method 5, $t_R$=0.92 min., [M+H]$^+$=662.7. The product was used in the next step without further purification.

Step 4. Resin loaded (S)-4-((R)-3-((((9H-fluoren-9-yl)methoxy)carbonyl)amino)-3-(4-chlorobenzyl)piperidin-1-yl)-3-((S)-2,3-dihydro-1H-inden-1-yl)-4-oxobutanoic acid (6-4)

Step 4-1: To 6-3 (2.2 g, 3.32 mmol) dissolved in DCM (65 mL) was added DIPEA (3.48 ml, 19.90 mmol). The resulting mixture was added to a glass tube containing pre-washed 2-Chlorotrityl chloride resin (6.22 g, 9.95 mmol) and shaken at RT for 16 h. The reaction solution was drained and the resin was washed with DCM (3×40 ml) and DMA (2×40 ml). Finally, the resin was taken up in a mixture of DCM/MeOH (50 mL/20 mL) and shaken for 30 min. The resulting mixture was drained and the resin was filtered and washed with DMF (2×40 mL) and DCM (2×40 mL).

Step 4-2: To a glass tube containing the resin from Step 4-1 was added a solution of 20% 4-Me-piperidine in DMF (100 mL) and the resulting mixture was shaken at RT for 2 h. The mixture was filtered, washed with DMF (100 mL×2) and DCM (100 mL×2) and dried under vacuum to afford the 6-4 (6.3 g, crude). Small amount of resin cleaved with TFA to determine purity. Analytical Method 7, $t_R$=0.81 min., [M+H]$^+$=441.4.

Step 5. Resin loaded (S)-4-((R)-3-((S)-3-((((9H-fluoren-9-yl)methoxy)carbonyl)-L-alanyl)-2,2-dimethyloxazolidine-4-carboxamido)-3-(4-chlorobenzyl)piperidin-1-yl)-3-((S)-2,3-dihydro-1H-inden-1-yl)-4-oxobutanoic acid (6-5)

To 6-4 (4 g, 8.79 mmol) in a 40 mL falcon tube was added a pre-mixed solution of Fmoc-Ala-Ser[Psi-Pro]-OH (5.78 g, 13.19 mmol), DIPEA (6.14 mL, 35.2 mmol) and HATU (5.01 g, 13.19 mmol) in DMF (30 mL) and the tube was shaken at RT overnight. The resin was then filtered and washed with DMF (100 mL×2), followed by DCM (100 mL×2) to afford 6-5 (1.33 g, crude). Analytical Method 7, $t_R$=1.33 mins; [M+H]$^+$=821.3 (unprotected serine mass).

Step 6. (S)-4-((R)-3-((S)-3-((S)-2-Aminopropanoyl)-2,2-dimethyloxazolidine-4-carboxamido)-3-(4-chlorobenzyl)piperidin-1-yl)-3-((S)-2,3-dihydro-1H-inden-1-yl)-4-oxobutanoic acid (6-6)

6-5 (1.33 g, 1.52 mmol) in a 100 mL glass tube was added 20% 4-Me-piperidine in DMF (50 mL) and the tube was shaken at RT for 2 h. The resin was then filtered and washed with DMF (50 mL×2), followed by DCM (50 mL×2). The resulting resin was placed back in a glass tube, and a solution of 20% HFIP in DCM (50 mL) was added. The mixture was shaken at RT for 20 min. and the solution was drained off and collected. This step was repeated a total of three times and the collected solution was concentrated in vacuo to afford a crude solid. (~1.6 g). The crude material was then purified on reverse-phase column chromatography (eluting with 0-60% water/ACN with 0.1% NH$_4$OH) to yield 6-6 as a white solid after freeze drying the pure fractions (800 mg, 0.88 mmol, 57.6% yield). Analytical Method 5, $t_R$=0.72 min., [M+H]+=639.3.

Step 7. (S)-4-((R)-3-(4-Chlorobenzyl)-3-((S)-3-((S)-2-((2-(4-(2-((dimethylamino)methyl)-1-methyl-1H-imidazol-5-yl)phenoxy)benzyl)amino)propanoyl)-2,2-dimethyloxazolidine-4-carboxamido)piperidin-1-yl)-3-((S)-2,3-dihydro-1H-inden-1-yl)-4-oxobutanoic acid (6-7)

To Intermediate 6-6 (100 mg, 0.156 mmol) dissolved in DCM (2 mL) and NMP (1 mL) was added Intermediate E25 (52.5 mg, 0.16 mmol), followed by acetic acid (45 uL, 0.78 mmol) and resulting mixture was stirred at RT for 1.5 h. Sodium triacetoxyborohydride (166 mg, 0.782 mmol) was then added and stirring was continued for 16 hr at RT. The reaction mixture was quenched with MeOH/water (1 mL) and stirred until gas evolution ceased. The mixture was concentrated and purified directly via reverse-phase column chromatography (eluting with water/ACN with 0.1% NH$_4$OH) to afford 6-7 as a white solid after freeze drying the pure fractions (105 mg, 70%). Analytical Method 2, $t_R$=1.94 min., [M+H]$^+$=958.5.

Step 8. (3S,7S,10S,13R)-13-(4-Chlorobenzyl)-3-((S)-2,3-dihydro-1H-inden-1-yl)-6-(2-(4-(2-((dimethylamino)methyl)-1-methyl-1H-imidazol-5-yl)phenoxy)benzyl)-10-(hydroxymethyl)-7-methyl-1,6,9,12-tetraazabicyclo[11.3.1]heptadecane-2,5,8,11-tetraone (6-8)

To 6-7 (105 mg, 0.110 mmol) dissolved in DCM (150 mL) was added HATU (167 mg, 0.438 mmol), 2,6-lutidine (0.38 mL, 3.29 mmol) and HOAt (15 mg, 0.11 mmol) and the resulting mixture was stirred at 45° C. overnight. The reaction mixture was then concentrated to dryness and partitioned between EtOAc (100 mL) and 5% aq. NaHCO$_3$ (100 mL). The organic phase was washed with 5% aq. NaHCO$_3$ (2×50 mL) and brine (50 mL), dried over Na$_2$SO$_4$, filtered, and concentrated to dryness to afford 6-8 (103 mg, crude). The material was used in the next step without purification. Analytical Method 2: $t_R$=3.18 min., [M+H]$^+$=940.7.

Step 9. (3S,7S,10S,13R)-13-(4-chlorobenzyl)-3-((S)-2,3-dihydro-1H-inden-1-yl)-6-(2-(4-(2-((dimethylamino)methyl)-1-methyl-1H-imidazol-5-yl)phenoxy)benzyl)-10-(hydroxymethyl)-7-methyl-1,6,9,12-tetraazabicyclo[11.3.1]heptadecane-2,5,8,11-tetraone (Compound 55)

6-8 (103 mg, 0.11 mmol) was dissolved in a mixture of ACN/H$_2$O (5:3) (8 mL) and cooled in an ice bath. TFA (1.02 mL, 13.2 mmol) (pre-chilled) was added dropwise, the ice bath was removed, and the resulting mixture was stirred at RT for 75 min. Saturated aqueous NaHCO$_3$ was added and the cloudy mixture were extracted with EtOAc (×2). The combined organic phases were washed with brine, dried over sodium sulfate, filtered, and concentrated. The resulting crude oil was purified by reverse-phase column chromatography (eluting with MeCN/water with 0.1% NH$_4$OH) to afford Compound 55 as a white solid (23 mg, 0.02 mmol, 22.1% yield). Analytical Method 7, $t_R$=1.09 min., [M+H]$^+$=900.5.

The compounds in Table 19 were synthesized according to the procedure described in Example 8.26 for Compound 55 from the respective intermediates shown in Tables 1-7 and described above in Example 8.

TABLE 19

| Cmd No. | Structure | LCMS |
|---|---|---|
| 31 | 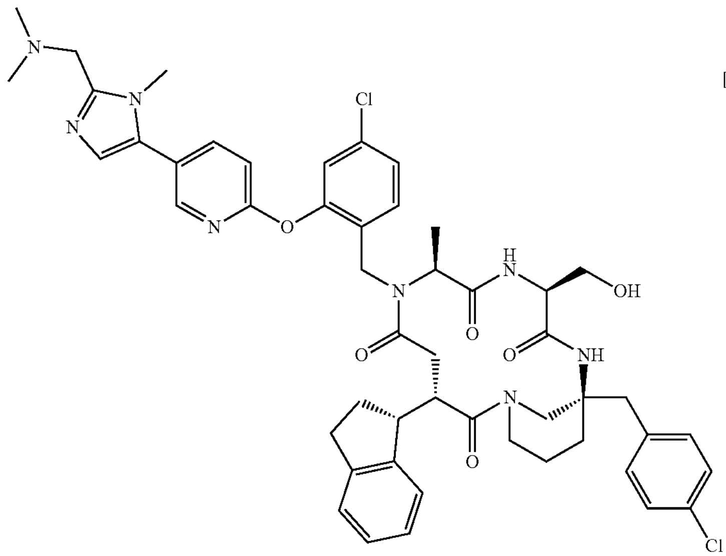 [SMILES: C[C@H]1C(=O)N[C@@H](CO)C(=O)N[C@@]2(Cc3ccc(Cl)cc3)CCCN(C2)C(=O)[C@H]([C@H]2CCc3ccccc32)CC(=O)N1Cc1ccc(Cl)cc1Oc1ccc(-c2cnc(CN(C)C)n2C)cn1] | Analytical Method 2<br>$t_R$ = 2.96 min.<br>$[M + H]^+$ = 935.5 |
| 73 | 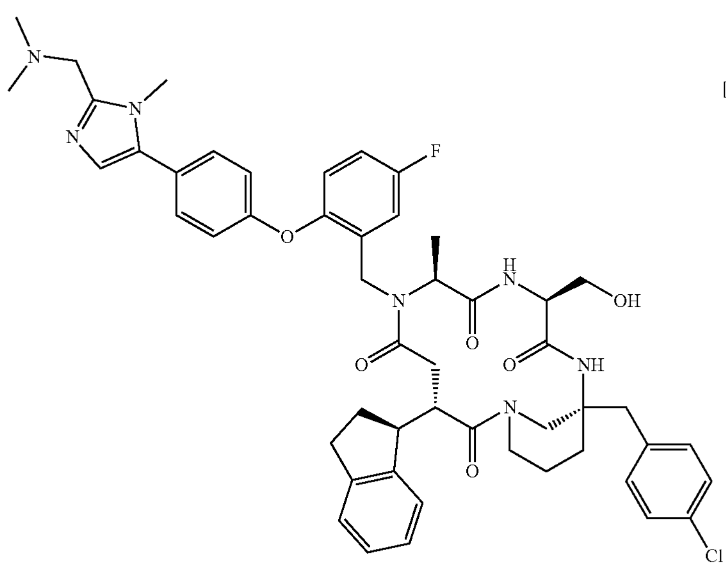 [SMILES: C[C@H]1C(=O)N[C@@H](CO)C(=O)N[C@@]2(Cc3ccc(Cl)cc3)CCCN(C2)C(=O)[C@H]([C@@H]2CCc3ccccc32)CC(=O)N1Cc1cc(F)ccc1Oc1ccc(-c2cnc(CN(C)C)n2C)cc1] | Analytical Method 7<br>$t_R$ = 1.02 min.<br>$[M + H]^+$ = 918.5 |

TABLE 19-continued
| Cmd No. | Structure | LCMS |
|---|---|---|
| 90 | 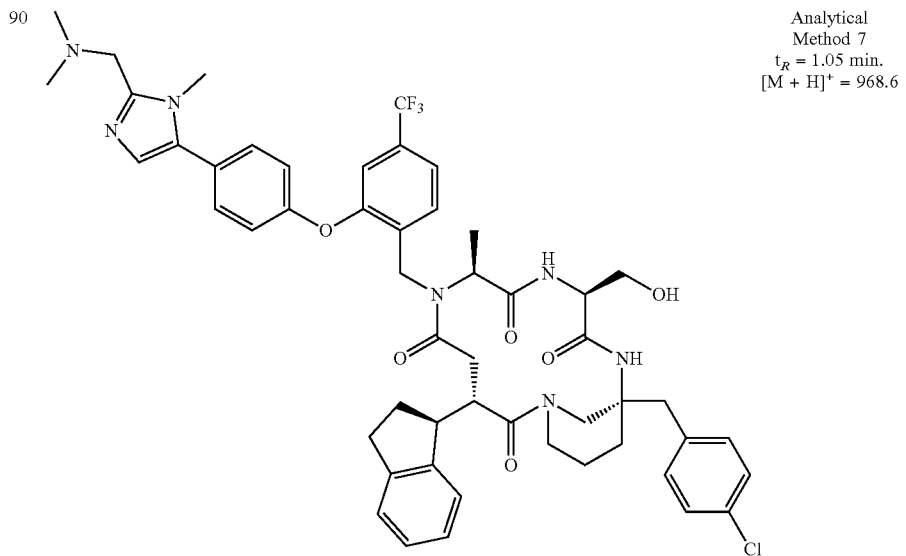 | Analytical Method 7<br>$t_R$ = 1.05 min.<br>$[M + H]^+$ = 968.6 |
| 100 | 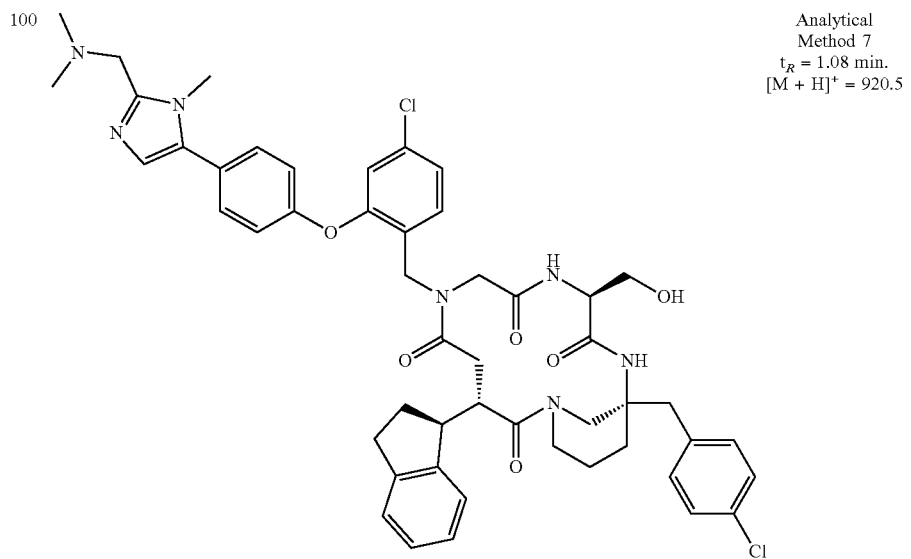 | Analytical Method 7<br>$t_R$ = 1.08 min.<br>$[M + H]^+$ = 920.5 |

TABLE 19-continued
| Cmd No. | Structure | LCMS |
|---|---|---|
| 123 | 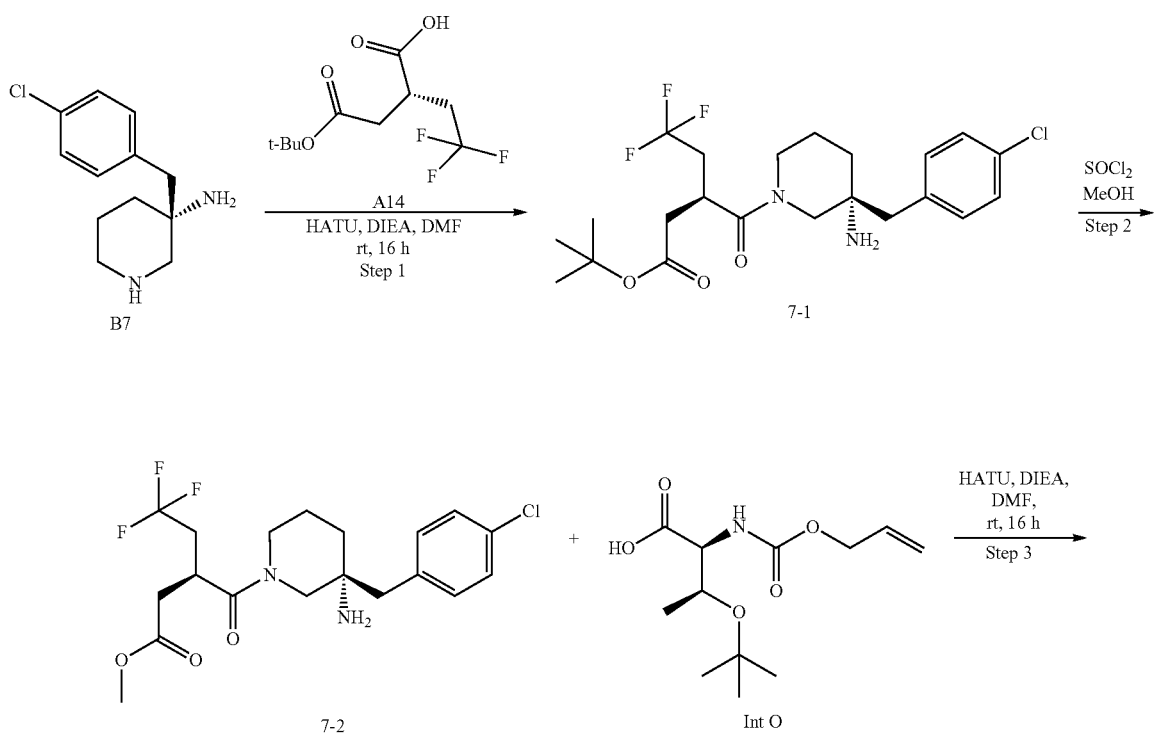 | Analytical Method 7 $t_R$ = 1.11 min. [M + H]$^+$ = 918.5 |
Example 8.27: Synthesis of (3S,7S,10S,13R)-6-(4-chloro-2-(4-(2-((dimethylamino)methyl)-1-methyl-1H-imidazol-5-yl)phenoxy)benzyl)-13-(4-chlorobenzyl)-10-((S)-1-hydroxyethyl)-7-methyl-3-(2,2,2-trifluoroethyl)-1,6,9,12-tetraazabicyclo[11.3.1]heptadecane-2,5,8,11-tetraone (Compound 64)

-continued
423 424
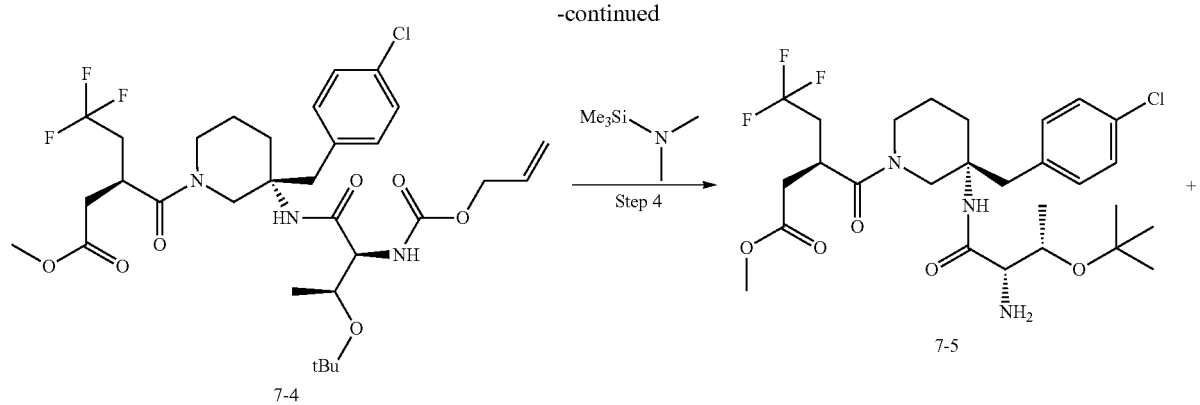
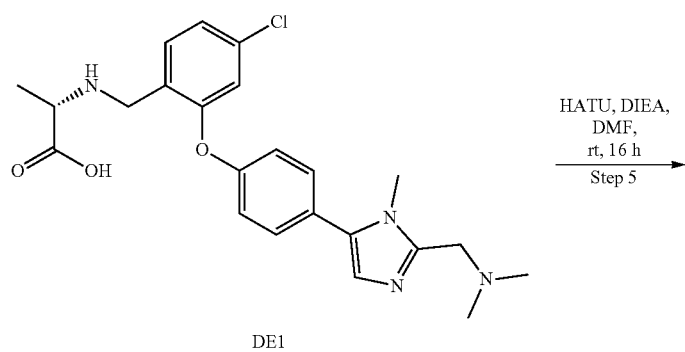
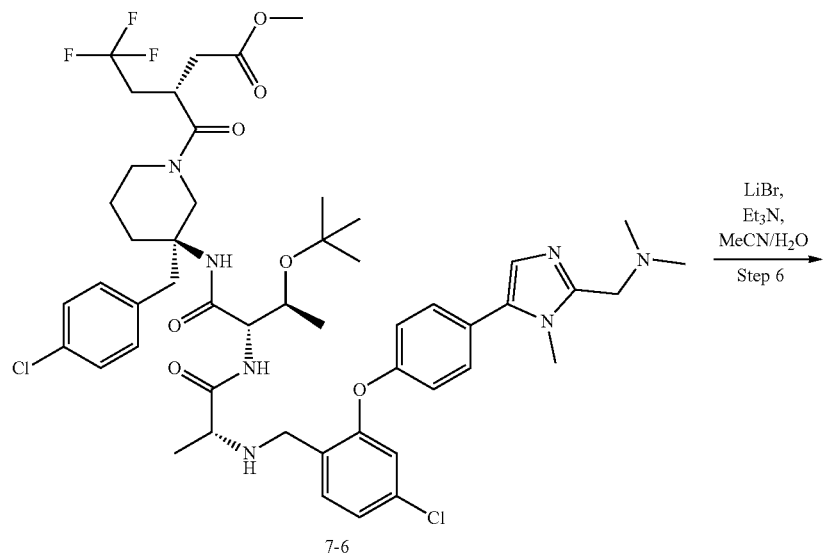

-continued
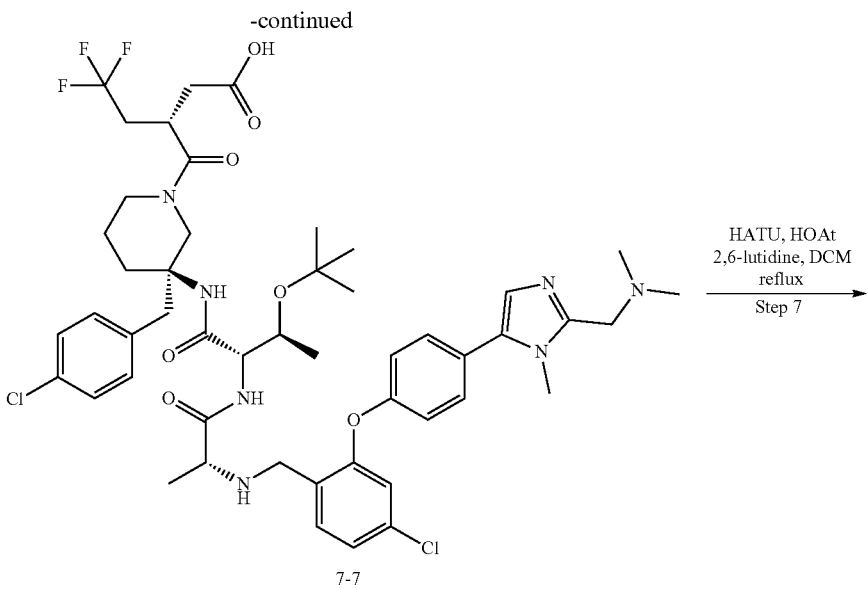
7-7
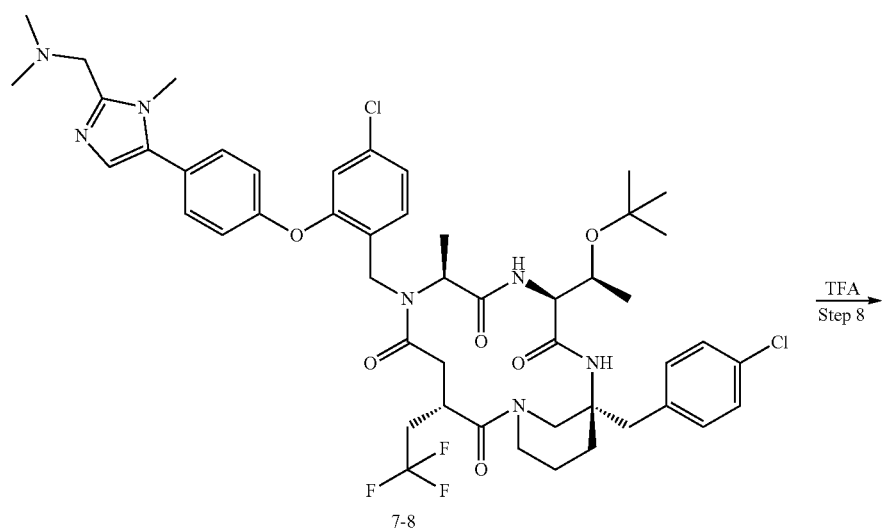
7-8
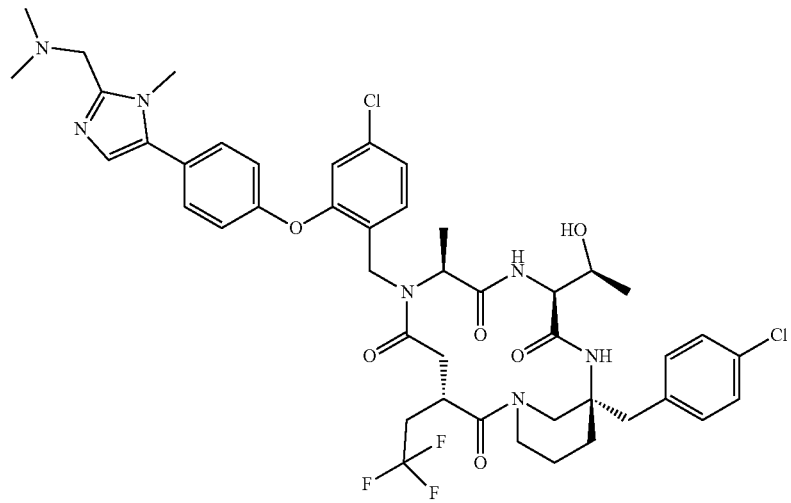
Compound 64

Step 1. (S)-tert-Butyl 3-((R)-3-amino-3-(4-chlorobenzyl)piperidine-1-carbonyl)-5,5,5-trifluoropentanoate (7-1)

To a solution of intermediate A14 (2.58 g, 10.1 mmol) and DIPEA (4.40 mL, 25.2 mmol) in DMF (10 mL) was added HATU (3.83 g, 10.1 mmol) in 2 portions over 5 min. The resulting mixture was stirred for 5 min and then added to an ice-cooled solution of intermediate B7 (3 g, 10.08 mmol) and DIPEA (8.80 mL, 50.4 mmol) in DMF (20 mL). The reaction mixture was allowed to warm to room temperature, stirred for 90 min and then partitioned between EtOAc and saturated aq. sodium bicarbonate solution. The aqueous phase was extracted with EtOAc (×2) and the combined organic phases was washed with saturated sodium bicarbonate solution, water (×3), and brine, dried over sodium sulfate, filtered and concentrated to provide 7-1 (1.63 g, 3.52 mmol, 34.9% yield) as an orange-brown oil. Analytical Method 5, $t_R$=1.18 min., [M+H]$^+$=463.7. The product was used in the next step without purification.

Step 2. (S)-Methyl 3-((R)-3-amino-3-(4-chlorobenzyl)piperidine-I-carbonyl)-5,5,5-trifluoropentanoate (7-2)

A solution of 7-1 (1.63 g, 3.52 mmol) in anhydrous MeOH (15 mL) was cooled in an ice bath. SOCl$_2$ (2.57 mL, 35.2 mmol) was added dropwise to the solution. After the addition, the ice bath was allowed to expire and stirring was continued at 45° C. for 4 h. The reaction mixture was then cooled back down to RT and concentrated to yield 7-2 (1.48 g), which was used in the next step without purification. Analytical Method 5, $t_R$=1.01 min., [M+H]$^+$=421.3.

Step 3. (S)-Methyl-3-((R)-3-((2S,3S)-2-(((allyloxy)carbonyl)amino)-3-(tert-butoxy)butanamido)-3-(4-chlorobenzyl)piperidine-1-carbonyl)-5,5,5-trifluoropentanoate (7-4)

To a solution of Int O (457 mg, 1.76 mmol) in DMF (10 mL) was added HATU (736 mg, 1.94 mmol) and DIPEA (1.85 mL, 10.6 mmol). The resulting mixture was stirred for 2 min and 7-2 (741 mg, 1.76 mmol) in DMF (5 mL) was added in one portion. The reaction mixture was stirred overnight and then diluted with EtOAc and washed with 5% NaHCO$_3$ (twice), then brine. The organic phase was dried over Na$_2$SO$_4$, filtered, and concentrated to afford 7-4 as a brown oil (1.1 g, 1.66 mmol, 94% yield). The product was used in the next step without purification. Analytical Method 5, $t_R$=1.27 min., [M+H]$^+$=662.4.

Step 4. (S)-Methyl 3-((R)-3-((2S,3S)-2-amino-3-(tert-butoxy)butanamido)-3-(4-chlorobenzyl) piperidine-1-carbonyl)-5,5,5-trifluoropentanoate (7-5)

A solution of 7-4 (1.1 g, 1.66 mmol) in DCM (30 mL) and N,N,1,1,1-pentamethylsilanamine (2.66 mL, 16.6 mmol) was degassed by bubbling in N$_2$ gas through the solution for 10 min. Pd(PPh$_3$)$_4$ (0.10 g, 0.08 mmol) was added and the resulting mixture was allowed to stir for 20 min. The reaction mixture was then quenched with water and allowed to stir for 5 min. The phases were separated and the aqueous phase was extracted with DCM. The combined organic phases were dried over Na$_2$SO$_4$, filtered, and concentrated to yield 7-5 as a crude oil (960 mg). The product was used in the next step without purification. Analytical Method 5, $t_R$=1.23 min., [M+H]$^+$=578.0.

Step 5. (S)-Methyl 3-((R)-3-((2S,3S)-3-(tert-butoxy)-2-((R)-2-((4-chloro-2-(4-(2-((dimethylamino)methyl)-1-methyl-1H-imidazol-5-yl)phenoxy)benzyl) amino)propanamido)butanamido)-3-(4-chlorobenzyl)piperidine-1-carbonyl)-5,5,5-trifluoropentanoate (7-6)

To a mixture of DE1 (0.74 g, 1.66 mmol) and 7-5 (0.96 g, 1.66 mmol) in acetonitrile (20 mL) was added DIPEA (0.87 mL, 4.98 mmol), followed by TBTU (0.53 g, 1.66 mmol). The resulting mixture was allowed to stir for 45 min. and then quenched with saturated aq. NaHCO$_3$ (50 mL). The mixture was concentrated to remove most of the ACN and taken up in EtOAc (100 mL). The phases were separated and the aqueous phase was back extracted with EtOAc (×2). The combined organic phases were washed with brine, dried over Na$_2$SO$_4$, filtered, and concentrated in vacuo. The crude residue was purified via normal phase flash column chromatography on silica gel (eluting with 0-10% DCM/MeOH) to yield 7-6 as a white solid (1.09 g, 1.09 mmol, 65.4% yield). Analytical Method 5, $t_R$=1.40 min., [M+H]$^+$=1002.6.

Step 6. (S)-3-((R)-3-((2S,3S)-3-(tert-Butoxy)-2-((R)-2-((4-chloro-2-(4-(2-((dimethylamino) methyl)-1-methyl-1H-imidazol-5-yl)phenoxy)benzyl)amino)propanamido)butanamido)-3-(4-chlorobenzyl) piperidine-1-carbonyl)-5,5,5-trifluoropentanoic acid (7-7)

To a solution of 7-6 (1.09 g, 1.09 mmol) in ACN (7.4 mL) and water (0.4 mL) was added triethylamine (1.52 ml, 10.9 mmol), followed by LiBr (1.89 g, 21.7 mmol). The resulting mixture was heated to 45° C. and allowed to stir for 30 min. The reaction mixture was then cooled to RT and concentrated in vacuo. The residue was partitioned in EtOAc/water and the phases were separated. The aqueous phase was acidified with 0.5 N HCl to a pH of ~6. The aqueous was extracted again. The combined organic phases were washed with brine, dried over Na$_2$SO$_4$, filtered, and concentrated to afford 7-7 as a yellow gummy solid (980 mg, 0.99 mmol, 91% yield). The product was used in the next step without purification. Analytical Method 5, $t_R$=0.95 min., [M+H]$^+$=988.6.

Step 7. (3S,7S,10S,13R)-10-((S)-1-(tert-Butoxy)ethyl)-6-(4-chloro-2-(4-(2-((dimethylamino)methyl)-1-methyl-1H-imidazol-5-yl)phenoxy)benzyl)-13-(4-chlorobenzyl)-7-methyl-3-(2,2,2-trifluoroethyl)-1,6,9,12-tetraazabicyclo[11.3.1]heptadecane-2,5,8,11-tetraone (7-8)

To a solution of 7-7 (980 mg, 0.99 mmol) in DCM (900 mL) was added 2,6-lutidine (2.31 mL, 19.8 mmol), HOAt (135 mg, 0.99 mmol) and HATU (1.51 g, 3.96 mmol) and the resulting mixture was heated at 40° C. (heating bath) overnight. The reaction mixture was cooled RT and washed with NaHCO$_3$, and brine. The organic phase was dried over Na$_2$SO$_4$, filtered, and concentrated to afford 7-8 as a crude oil (1 g). The product was used in the next step without purification. Analytical Method 5, $t_R$=1.41 min., [M+H]$^+$=970.7.

Step 8. (3S,7S,10S,13R)-6-(4-Chloro-2-(4-(2-((dimethylamino)methyl)-1-methyl-1H-imidazol-5-yl)phenoxy)benzyl)-13-(4-chlorobenzyl)-10-((S)-1-hydroxyethyl)-7-methyl-3-(2,2,2-trifluoroethyl)-1,6,9,12-tetraazabicyclo[11.3.1]heptadecane-2,5,8,11-tetraone (Compound 64)

To a mixture of 7-8 (1 g, 1.03 mmol) in DCM (2.6 mL) at 0° C. was added TFA (3.17 ml, 41.2 mmol) dropwise. The resulting mixture was allowed to stir for 4 h and then concentrated in vacuo and purified via reverse-phase column chromatography (eluting with 45-80% water/ACN with 0.1% NH$_4$OH) to yield Compound 64 as a white solid after concentrating the pure fractions (180 mg, 0.187 mmol, 18.2% yield). Analytical Method 7, t$_R$=1.02 min., [M+H]$^+$=914.3.

The compounds in Table 20 were synthesized according to the procedure described in Example 8.27 for Compound 64 from the respective intermediates shown in Tables 1-7 and described above in Example 8.

TABLE 20

| Cmd No. | Structure | LCMS |
|---|---|---|
| 97 | 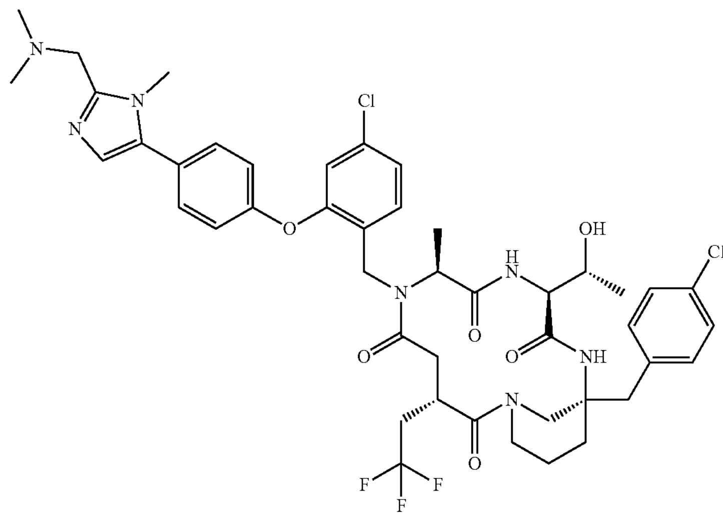 [SMILES: C[C@@H](O)[C@@H]1NC(=O)[C@H](C)N(Cc2ccc(Cl)cc2Oc2ccc(-c3cnc(CN(C)C)n3C)cc2)C(=O)C[C@@H](CC(F)(F)F)C(=O)N2CCC[C@@](Cc3ccc(Cl)cc3)(C2)NC1=O] | Analytical Method 7 t$_R$ = 0.96 min. [M + H]$^+$ = 914.4 |
| 109 | 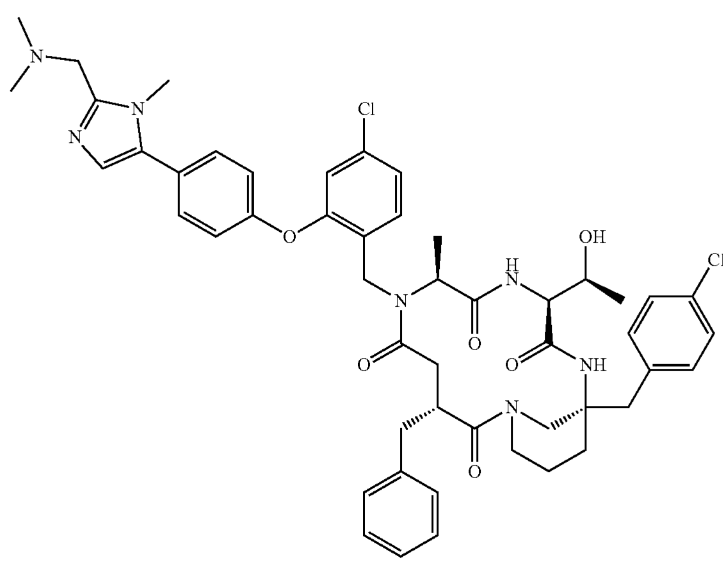 [SMILES: C[C@H](O)[C@@H]1NC(=O)[C@H](C)N(Cc2ccc(Cl)cc2Oc2ccc(-c3cnc(CN(C)C)n3C)cc2)C(=O)C[C@@H](Cc2ccccc2)C(=O)N2CCC[C@@](Cc3ccc(Cl)cc3)(C2)NC1=O] | Analytical Method 7 t$_R$ = 1.00 min. [M + H]$^+$ = 922.5 |

TABLE 20-continued
| Cmd No. | Structure | LCMS |
|---|---|---|
| 147 | 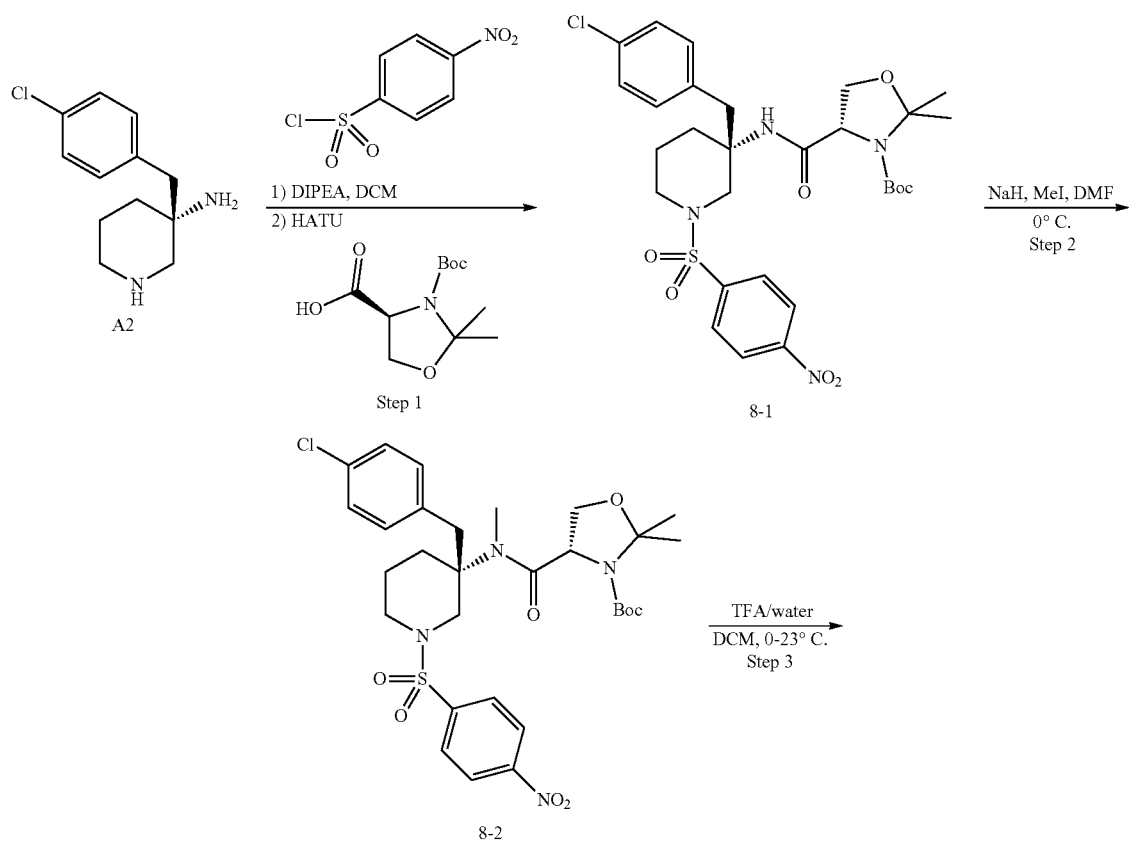 | Analytical Method 4<br>$t_R$ = 2.07 min.<br>$[M + H]^+$ = 928.4 |
Example 8.28: Synthesis of (3R,7S,10S,13R)-6-(4-Chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-3-(pyridin-2-ylmethyl)-1,6,9,12-tetraazabicyclo[11.3.1]heptadecane-2,5,8,11-tetraone (Compound 32)

433
434
-continued
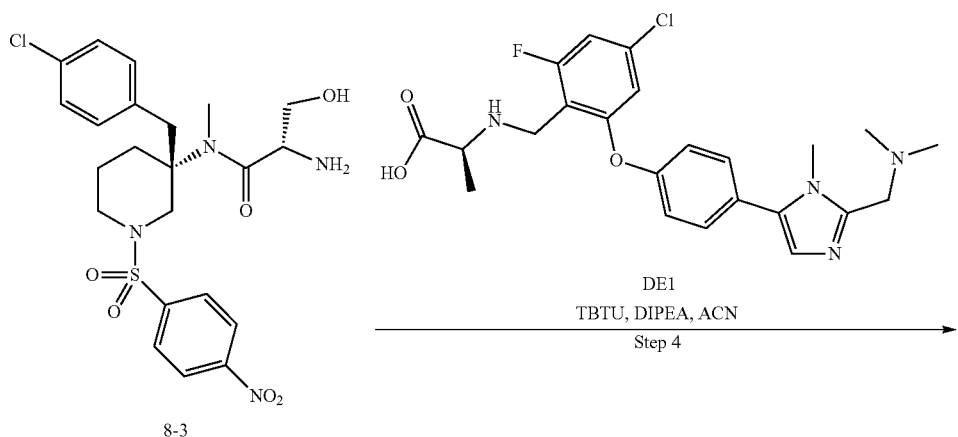
8-3
DE1
TBTU, DIPEA, ACN
―――――――――――→
Step 4
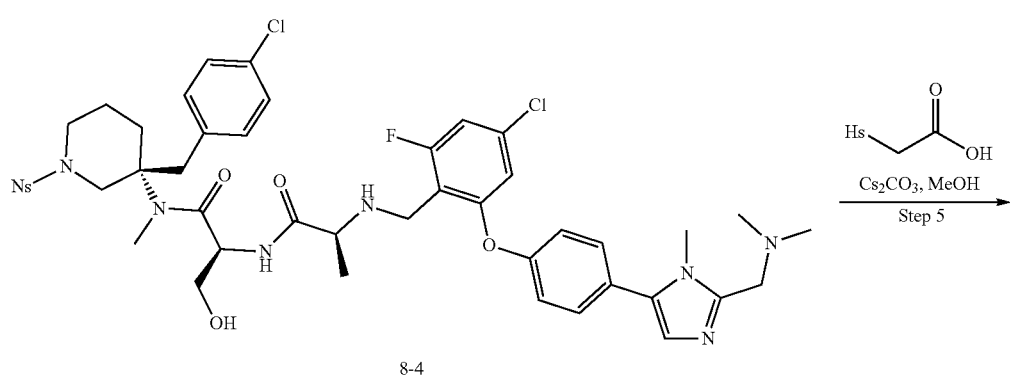
8-4
Cs₂CO₃, MeOH
―――――――→
Step 5
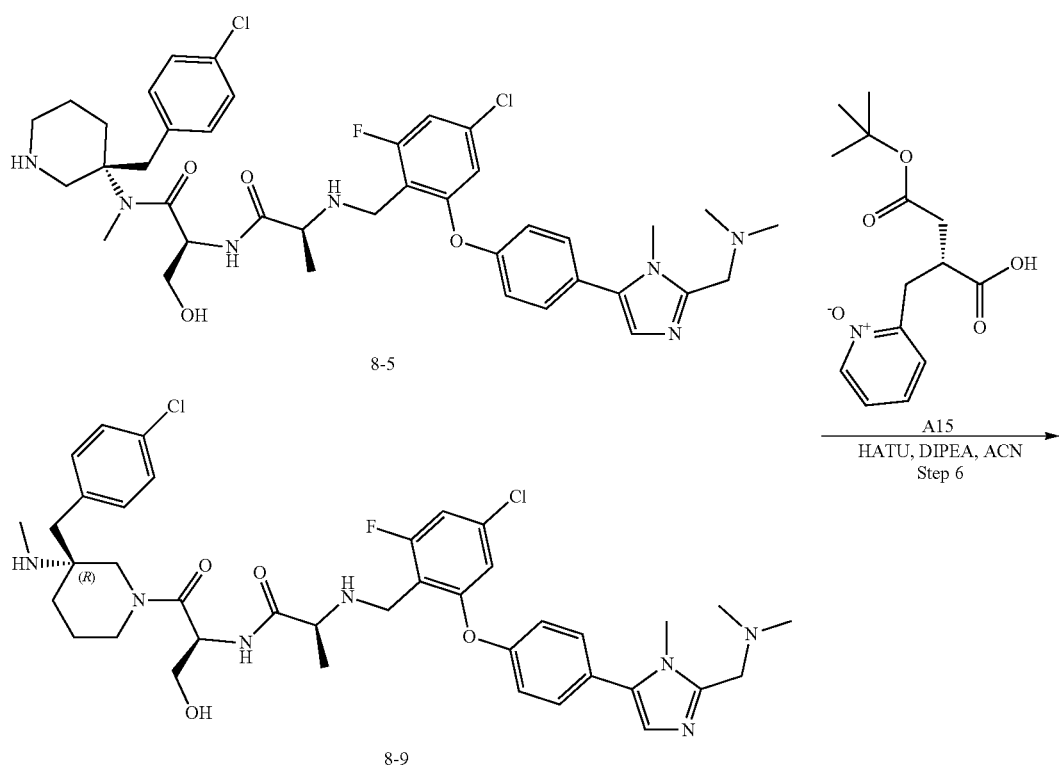
8-5
A15
HATU, DIPEA, ACN
―――――――――→
Step 6
8-9

-continued
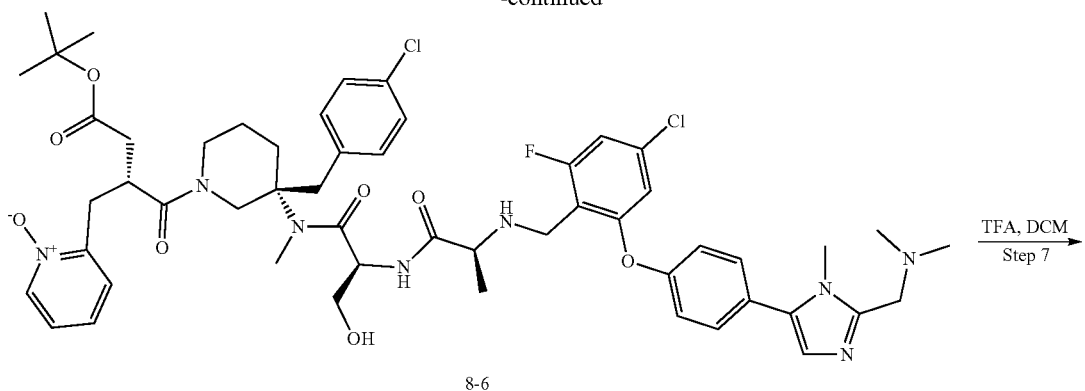
8-6
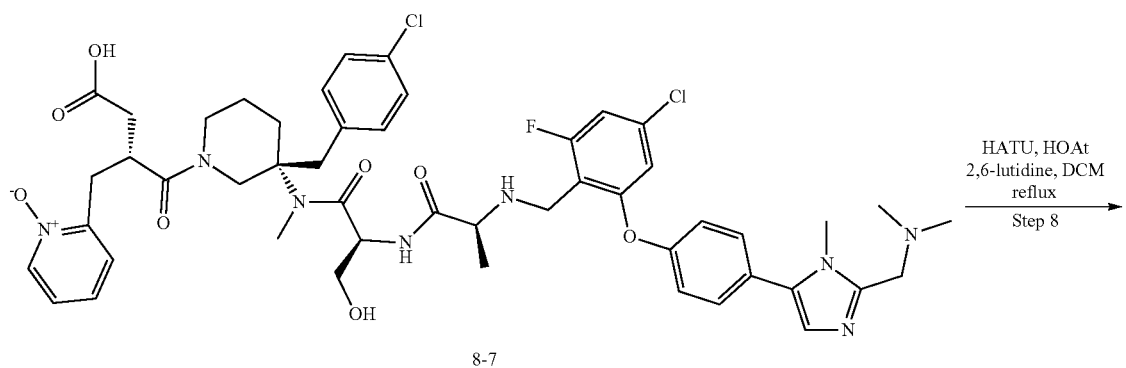
8-7
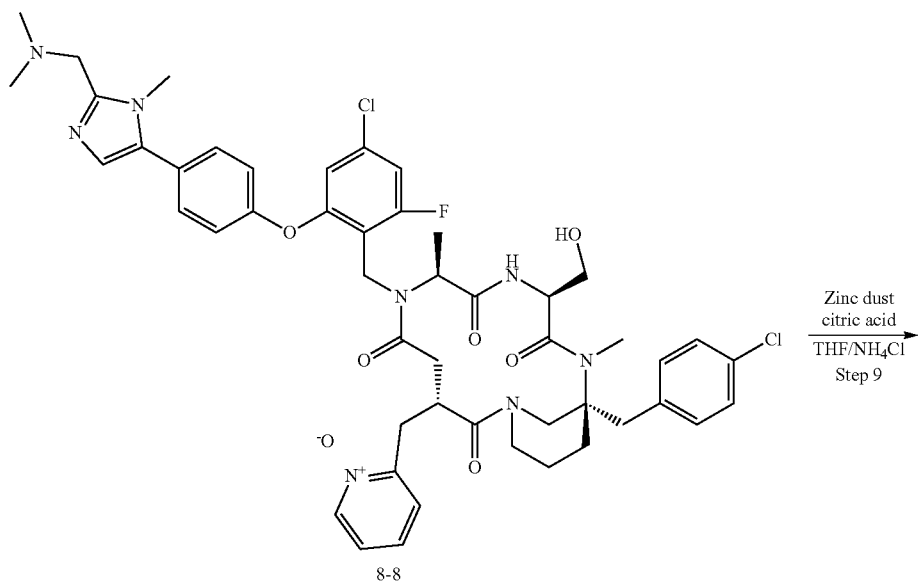
8-8

-continued

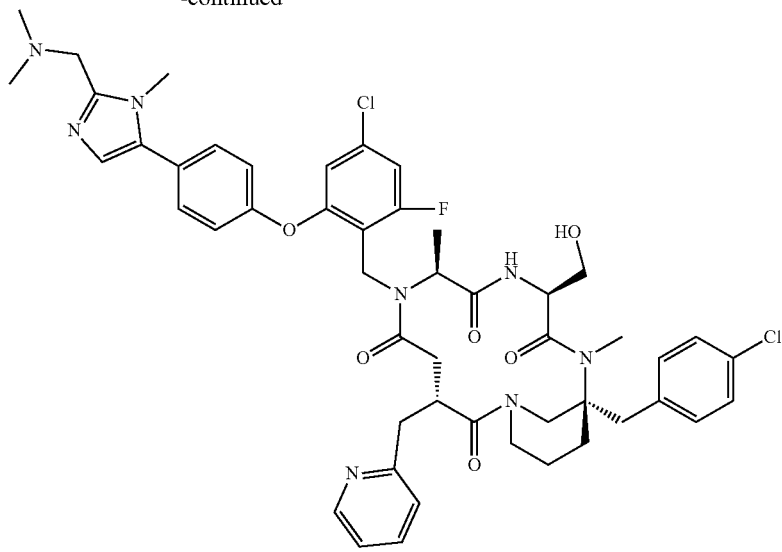

Compound 32

Step 1. (R)-3-(4-Chlorobenzyl)-1-((4-nitrophenyl)sulfonyl)piperidin-3-amine, (S)-tert-butyl 4-(((R)-3-(4-chlorobenzyl)-1-((4-nitrophenyl)sulfonyl)piperidin-3-yl)carbamoyl)-2,2-dimethyloxazolidine-3-carboxylate (8-1)

To a suspension of B7 (370 mg, 1.24 mmol) in DCM (10 mL) was added TEA (1.73 mL, 12.4 mmol), and Nosyl chloride (275 mg, 1.24 mmol). The resulting solution was stirred at RT for 10 min and (S)-3-(tert-butoxycarbonyl)-2,2-dimethyloxazolidine-4-carboxylic acid (335 mg, 1.37 mmol) and HATU (520 mg, 1.37 mmol) were then added. The reaction mixture was stirred at RT for 2 h and then additional (S)-3-(tert-butoxycarbonyl)-2,2-dimethyloxazolidine-4-carboxylic acid (0.5 eq) and HATU (0.5 eq) were added. The mixture was diluted with EtOAc (50 mL) and washed with 2×50 ml of 5% NaHCO$_3$ solution and brine. The organic phase was dried over sodium sulfate, filtered, and concentrated to afford a crude oil. The material was purified by flash column chromatography on silica gel (eluting with 0-100% EtOAc/Heptane) to afford 8-1 (810 mg, 1.27 mmol) as a white foam. Analytical Method 5, $t_R$=1.30 min., [M+H]$^+$−100=537.2.

Step 2. (S)-tert-Butyl 4-(((R)-3-(4-chlorobenzyl)-1-((4-nitrophenyl)sulfonyl)piperidin-3-yl)(methyl)carbamoyl)-2,2-dimethyloxazolidine-3-carboxylate (8-2)

To a solution of 8-1 (780 mg, 1.22 mmol) in anhydrous DMF (10 mL) at 0° C. under a nitrogen atmosphere was added NaH (60% in mineral oil, 112 mg, 2.80 mmol). The resulting mixture was stirred at 0° C. for 60 min. MeI (0.31 mL, 4.90 mmol) was added and stirring was continued at 0° C. for 1.5 h. The reaction mixture was quenched by saturated NaHCO$_3$ and water to afford a slurry. The gray precipitates were collected by vacuum filtration and re-dissolved in EtOAc. The organic phase was washed with water and brine, dried over sodium sulfate, filtered, and concentrated to afford 8-2 (690 mg, 1.06 mmol, 87% yield) as a yellow foam. The product was used in the next step without further purification. Analytical Method 5, $t_R$=1.34 min., MS [M+H−100]$^+$=551.1.

Step 3. (S)-2-Amino-N—((R)-3-(4-chlorobenzyl)-1-((4-nitrophenyl)sulfonyl)piperidin-3-yl)-3-hydroxy-N-methylpropanamide (8-3)

To a solution of 8-2 (680 mg, 1.04 mmol) in DCM (10 mL) was added TFA (5 mL, 64.9 mmol) at 0° C. The ice bath was removed and the mixture was stirred at RT for 1 h. Water (0.06 mL, 3.13 mmol) was added and stirring was continued for 1 additional hour. The reaction mixture was concentrated to remove the excess TFA. The resulting crude oil was diluted with 15 mL of 2N Na$_2$CO$_3$ and extracted with 2×20 mL of DCM. The combined organic phases were washed with saturated NaHCO$_3$, dried over sodium sulfate, filtered, and concentrated to afford 8-3 (534 mg, 1.04 mmol, 100% yield) as yellow foam. The product was used in the next step without further purification. Analytical Method 5, $t_R$=0.96 min., [M+H]$^+$=511.2.

Step 4. (S)-2-((S)-2-((4-Chloro-2-(4-(2-((dimethylamino)methyl)-1-methyl-1H-imidazol-5-yl)phenoxy)-6-fluorobenzyl)amino)propanamido)-N—((R)-3-(4-chlorobenzyl)-1-((4-nitrophenyl)sulfonyl)piperidin-3-yl)-3-hydroxy-N-methylpropanamide (8-4)

To a suspension of 8-3 (482 mg, 1.05 mmol) in ACN (15 mL) was added DIPEA (0.55 mL, 3.14 mmol) and TBTU (336 mg, 1.05 mmol). The resulting mixture was stirred at RT for 2 min and then a solution of DE1 (534 mg, 1.05 mmol, in 10 mL ACN) was added. The reaction mixture was stirred for 1 h and then a solution of saturated NaHCO$_3$ and water (50 mL of each) were added. The mixture was then extracted with 2×50 mL of DCM. The combined organics were washed with brine, dried over sodium sulfate, filtered, and concentrated to afford 13-4 (1.06 g, 0.83 mmol, 79% yield) as yellow foam. The product was used directly in the next step without further purification. Analytical Method 5, $t_R$=1.22 min., [M+H]$^+$=953.5.

Step 5. (S)-2-((S)-2-((4-Chloro-2-(4-(2-((dimethylamino)methyl)-1-methyl-1H-imidazol-5-yl)phenoxy)-6-fluorobenzyl)amino)propanamido)-N—((R)-3-(4-chlorobenzyl)piperidin-3-yl)-3-hydroxy-N-methylpropanamide (8-5)

To a solution of 8-4 (482 mg, 0.51 mmol) in MeOH (25 mL) was added mercaptoacetic acid (0.14 mL, 2.02 mmol)

and Cs$_2$CO$_3$ (1.15 g, 3.54 mmol). The resulting mixture was stirred at RT for 3.5 h, diluted with 150 ml of water and extracted with 2×100 mL of DCM (a small amount of brine might be required to assist the partition). The combined organic phases were dried over sodium sulfate, filtered, and concentrated to afford 8-5 (388 mg, 0.505 mmol, ~ quantitative yield) as a yellow foam (Analytical Method 5, t$_R$=1.15 min; [M+H]$^+$=768.3.) containing ~10% of 8-9 (Analytical Method 5, t$_R$=1.23 min). The product was used directly in the next step without further purification.

Step 6. 2-((R)-4-(tert-Butoxy)-2-((R)-3-((S)-2-((S)-2-((4-chloro-2-(4-(2-((dimethylamino)methyl)-1-methyl-1H-imidazol-5-yl)phenoxy)-6-fluorobenzyl)amino)propanamido)-3-hydroxy-N-methylpropanamido)-3-(4-chlorobenzyl)piperidine-1-carbonyl)-4-oxobutyl)pyridine 1-oxide (8-6)

To a solution of A15 (135 mg, 0.48 mmol) in 5 mL of ACN was added DIPEA (0.34 mL, 1.92 mmol) and HATU (183 mg, 0.48 mmol). The resulting mixture was stirred at RT for 5 min. before being added into a solution of 8-5 (369 mg, 0.48 mmol) in 6 mL of ACN. The reaction was continued for 30 min. before being quenched with 50 mL of 5% NaHCO$_3$. The mixture was extracted with 2×50 mL of EtOAc. The combined EtOAc phases were washed with brine and dried over sodium sulfate, filtered, and concentrated to afford 8-6 (495 mg, 0.480 mmol, assume quantitative yield) as a yellow solid which was used in the next step without further purification. Analytical Method 5, t$_R$=1.15 min., [M+H]$^+$=1031.8.

Step 7. 2-((R)-2-(Carboxymethyl)-3-((R)-3-((S)-2-((S)-2-((4-chloro-2-(4-(2-((dimethylamino)methyl)-1-methyl-1H-imidazol-5-yl)phenoxy)-6-fluorobenzyl)amino)propanamido)-3-hydroxy-N-methylpropanamido)-3-(4-chlorobenzyl)piperidin-1-yl)-3-oxopropyl)pyridine 1-oxide (8-7)

To a solution of 8-6 (495 mg, 0.480 mmol) in DCM (5 mL) was added TFA (5 mL, 64.9 mmol). The resulting mixture was stirred at RT for 1.5 h and then concentrated. The crude product taken up in DMSO, and directly purified by reverse-phase column chromatography (eluting with 0-50% water/ACN containing 0.1% NH$_4$OH) to afford 8-7 (125 mg, 0.11 mmol, 23% yield) after freeze drying the pure fractions. Analytical Method 5, t$_R$=0.78 min., [M+H]$^+$=975.3.

Step 8. 2-(((3R,7S,10S,13R)-6-(4-Chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-2,5,8,11-tetraoxo-1,6,9,12-tetraazabicyclo[11.3.1]heptadecan-3-yl)methyl)pyridine 1-oxide (8-8)

To a solution of 8-7 (125 mg, 0.13 mmol) in DCM (120 mL) was added 2,6-lutidine (0.45 mL, 3.84 mmol), HOAt (17.4 mg, 0.13 mmol), and HATU (195 mg, 0.51 mmol). The resulting mixture was refluxed for 4 h in a 48° C. heating bath, cooled back down to RT, and then concentrated. The crude residue was partitioned between EtOAc (50 mL) and 5% aq. NaHCO$_3$ (50 mL). The organic phase was washed with 5% aq. NaHCO$_3$ (2×50 mL) and brine (50 mL), dried over Na$_2$SO$_4$, filtered and concentrated to dryness to afford 8-8 (123 mg, 0.13 mmol, assume quantitative yield). The product was used in the next step without further purification. Analytical Method 5, t$_R$=0.96 min., [M+H]$^+$=957.4.

Step 9. (3R,7S,10S,13R)-6-(4-Chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-3-(pyridin-2-ylmethyl)-1,6,9,12-tetraazabicyclo[11.3.1]heptadecane-2,5,8,11-tetraone (Compound 32)

To a solution of 8-8 (123 mg, 0.13 mmol) in THF (15 mL) was added a saturated solution of NH$_4$Cl (5 mL), zinc dust (537 mg, 8.22 mmol) and citric acid (444 mg, 2.31 mmol). The resulting mixture was stirred at RT for 30 min to afford a biphasic mixture. The organic phase was collected and the aqueous phase was extracted with DCM. The combined organic phases were concentrated and the obtained residue was taken up in DCM, washed with 5% NaHCO$_3$ solution, dried over sodium sulfate, filtered and concentrated. The crude product was taken up in DMSO and purified by HPLC (0.1% NH$_4$OH as buffer) to afford Compound 32 (20 mg, 0.02 mmol, 16% yield) after freeze drying the pure fractions. Analytical Method 2, t$_R$=2.59 min, [M+H]$^+$=941.5.

Example 8.29: Synthesis of (3R,7S,10S,13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-3-((6-methylpyridin-2-yl)methyl)-1,6,9,12-tetraazabicyclo[11.3.1]heptadecane-2,5,8,11-tetraone (Compound 13)

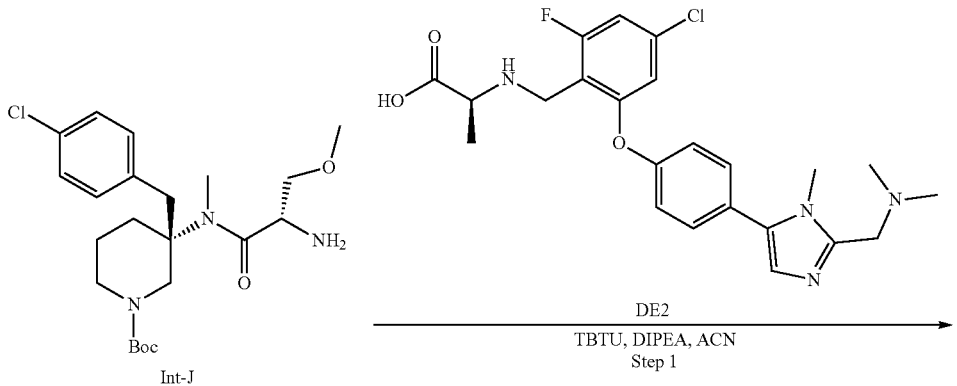

-continued
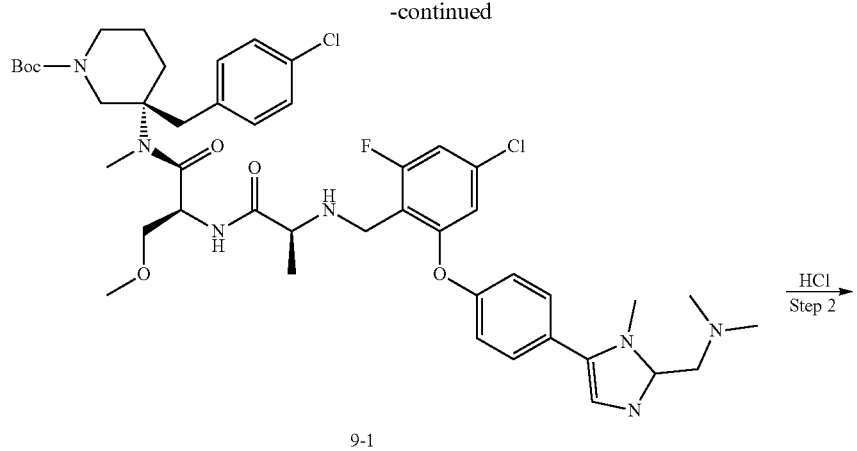
9-1
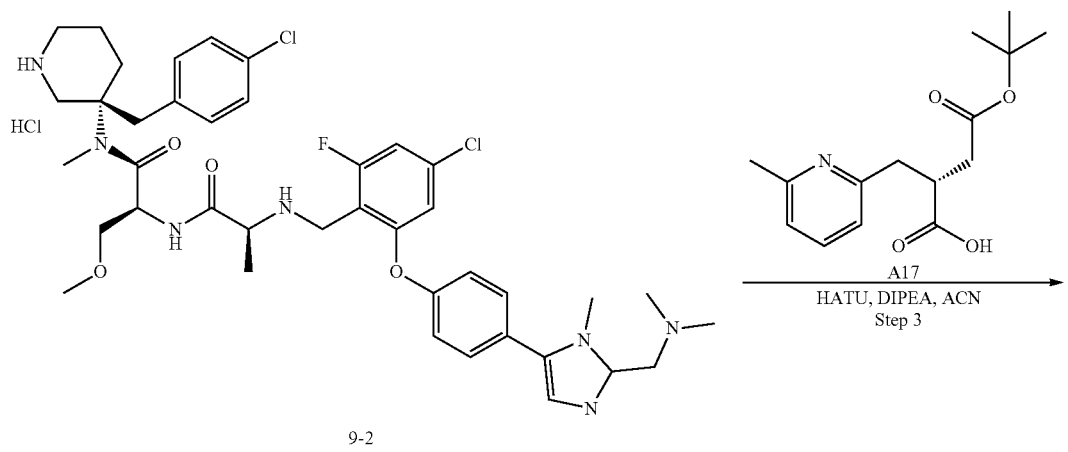
9-2
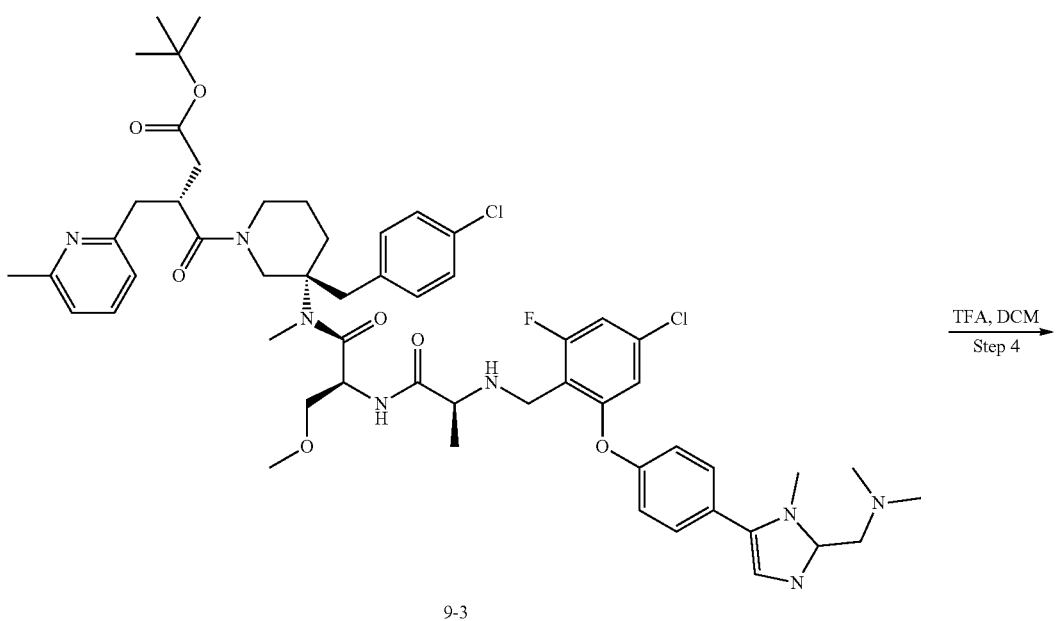
9-3

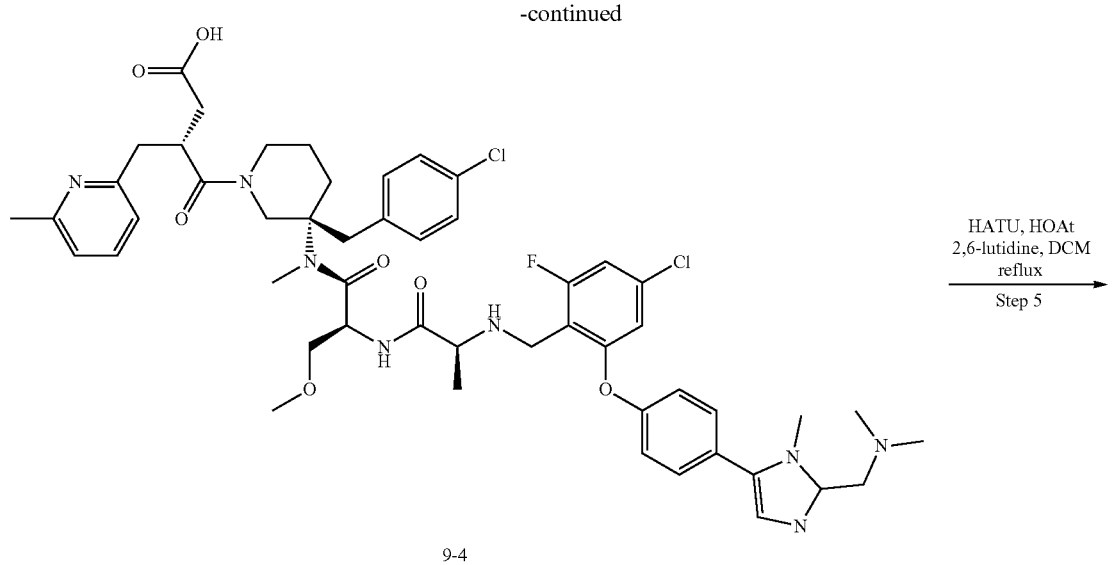

9-4

HATU, HOAt
2,6-lutidine, DCM
reflux
―――――――→
Step 5

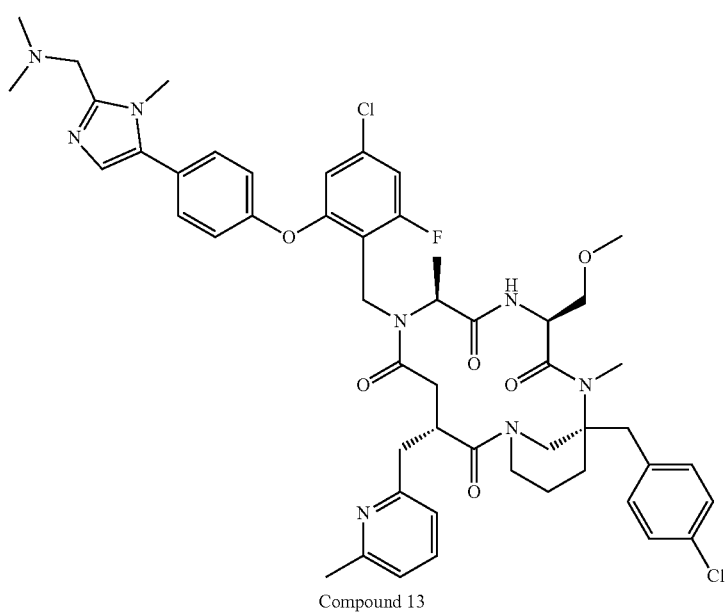

Compound 13

Step 1. (R)-tert-Butyl 3-((S)-2-((S)-2-((4-chloro-2-(4-(2-((dimethylamino)methyl)-1-methyl-1H-imidazol-5-yl)phenoxy)-6-fluorobenzyl)amino)propanamido)-3-methoxy-N-methylpropanamido)-3-(4-chlorobenzyl)piperidine-1-carboxylate (9-1)

To a solution of Intermediate J (0.50 g, 1.13 mmol) and DE2 (0.57 g, 1.24 mmol) in ACN (25 mL) was added DIPEA (0.59 mL, 3.38 mmol) and TBTU (0.40 g, 1.24 mmol). The resulting mixture was stirred at RT for 0.5 h, diluted with a half saturated solution of NaHCO$_3$ (100 mL), and extracted with 100 mL of EtOAc. The organic phase was washed with 5% NaHCO$_3$ and brine, dried over sodium sulfate, filtered and concentrated to afford 9-1 (1 g, quantitative yield) as a yellow foam. Analytical Method 5, $t_R$=1.33 min., [M+H]$^+$=882.7. The material was used in the next step without purification.

Step 2. (S)-2-((S)-2-((4-chloro-2-(4-(2-((dimethylamino)methyl)-1-methyl-1H-imidazol-5-yl)phenoxy)-6-fluorobenzyl)amino)propanamido)-N—((R)-3-(4-chlorobenzyl)piperidin-3-yl)-3-methoxy-N-methylpropanamide hydrochloride (9-2)

To a chilled mixture of 9-1 (1 g, 1.13 mmol) in anhydrous methanol (11 mL) and in an ice bath was added cold HCl in dioxane (4 N, 11.3 mL, 45.1 mmol). The ice bath was removed and resulting mixture was warmed to RT slowly and stirred for 1.5 h. Additional methanol (11 mL) and HCl (20 eq., 4N in dioxane) were added and stirring was continued at RT for 1 h. The reaction mixture was concentrated under reduced pressure, toluene was added, and the mixture was concentrated again. This step was repeated three times to afford 9-2 as a yellow solid (0.97 g, ~quantitative yield). Analytical Method 5, $t_R$=1.17 min., [M+H]$^+$=782.4. The material was used in the next step without purification.

Step 3. (R)-tert-Butyl 4-((R)-3-((S)-2-((S)-2-((4-chloro-2-(4-(2-((dimethylamino)methyl)-1-methyl-1H-imidazol-5-yl)phenoxy)-6-fluorobenzyl)amino)propanamido)-3-methoxy-N-methylpropanamido)-3-(4-chlorobenzyl)piperidin-1-yl)-3-((6-methylpyridin-2-yl)methyl)-4-oxobutanoate (9-3)

To a solution of 9-2 (0.48 g, 0.56 mmol) in 10 mL of ACN was added DIPEA (0.30 mL, 1.69 mmol) and intermediate A17 (0.19 g, 0.68 mmol). The resulting mixture was stirred at RT and HATU (0.26 g, 0.68 mmol) was added. The reaction mixture was stirred for 1 h, quenched with 50 mL of 5% NaHCO$_3$ solution, and extracted with 2×50 mL of EtOAc. The combined organic phases were washed with 5% NaHCO$_3$ solution and brine. The mixture was dried over sodium sulfate, filtered, and concentrated to afford 9-3 as a yellow solid (0.589 g, 0.56 mmol, assume quantitative yield). The crude product was used in the next step without purification. Analytical Method 5, $t_R$=1.34 min., [M+H]$^+$=1043.7.

Step 4. (R)-4-((R)-3-((S)-2-((S)-2-((4-chloro-2-(4-(2-((dimethylamino)methyl)-1-methyl-1H-imidazol-5-yl)phenoxy)-6-fluorobenzyl)amino)propanamido)-3-methoxy-N-methylpropanamido)-3-(4-chlorobenzyl)piperidin-1-yl)-3-((6-methylpyridin-2-yl)methyl)-4-oxobutanoic acid (9-4)

To a solution of 9-3 (589 mg, 0.56 mmol) in DCM (5 mL) was added TFA (5 mL, 64.9 mmol) at 0° C. The cooling bath was removed and the resulting mixture was stirred at RT for 1 h and then concentrated under reduced pressure. Toluene was added and the mixture was again concentrated (repeat step one more time) to remove the excess TFA. The crude material was then purified by reverse-phase column chromatography (eluting with 0-50% water/ACN with 0.1% NH$_4$OH) to afford 9-4 (153 mg, 0.16 mmol, 28% yield) as a white powder after freeze drying the pure fractions. Analytical Method 5, $t_R$=0.82 min., [M+H]$^+$=987.3.

Step 5. (3R,7S,10S,13R)-6-(4-Chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-3-((6-methylpyridin-2-yl)methyl)-1,6,9,12-tetraazabicyclo[11.3.1]heptadecane-2,5,8,11-tetraone (Compound 13)

To a solution of 9-4 (153 mg, 0.16 mmol) in anhydrous DCM (100 mL) was added 2,6-lutidine (0.54 mL, 4.65 mmol), HOAt (21 mg, 0.16 mmol), and HATU (236 mg, 0.62 mmol). The resulting mixture was heated to reflux overnight in a 48° C. heating bath, then cooled to RT and concentrated to dryness. The obtained residue was partitioned between EtOAc (50 mL) and 5% aq. NaHCO$_3$ (50 mL). The organic phase was collected, washed with 5% aq. NaHCO$_3$ (2×50 mL) and brine (50 mL), dried over Na$_2$SO$_4$, filtered, and concentrated. The crude oil was taken up in ACN and purified by HPLC (eluting with 0-100% water/ACN) to afford Compound 13 (52 mg, 0.05 mmol, 33% yield) after freeze drying the pure fractions. Analytical Method 2, $t_R$=2.89 min., [M+H]$^+$=969.7.

The compounds in Table 21 were synthesized according to the procedure described in Example 8.29 for Compound 13 from the respective intermediates shown in Tables 1-7 and described above in Example 8.

TABLE 21

| Cmd No. | Structure | LCMS |
|---|---|---|
| 38 | 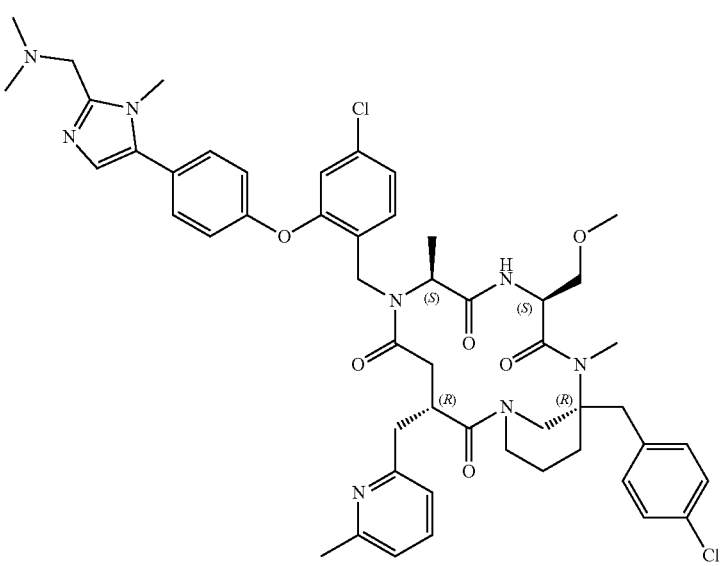 | Analytical Method 2<br>$t_R$ = 22.90 min.<br>[M + H]$^+$ = 951.2 |

| Cmd No. | Structure | LCMS |
|---|---|---|
| 65 | 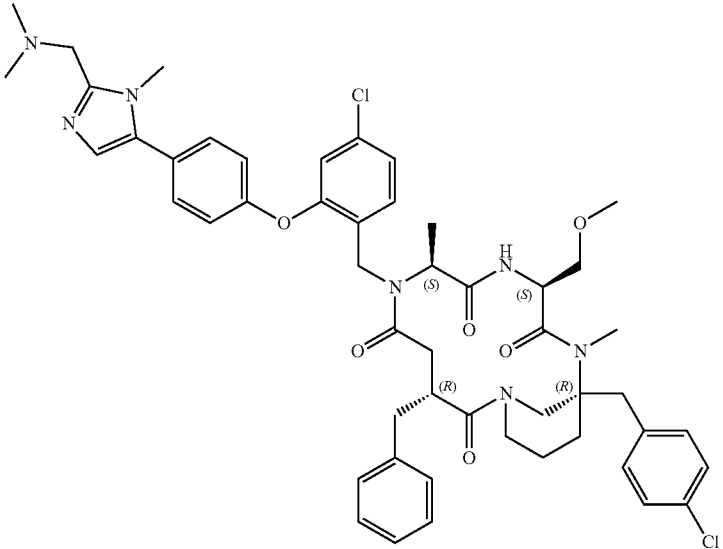 | Analytical Method 2<br>$t_R$ = 23.20 min.<br>$[M + H]^+$ = 936.1 |
| 158 | 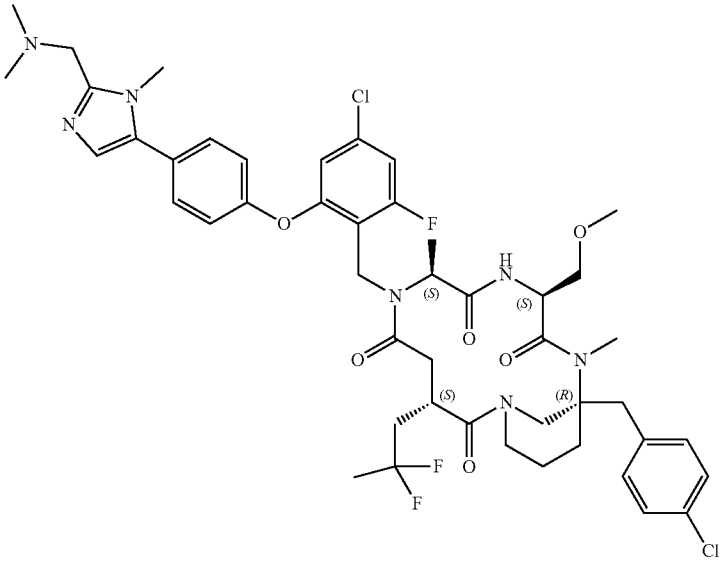 | Analytical Method 4<br>$t_R$ = 22.14 min.<br>$[M + H]^+$ = 942.5 |

Example 8.30: Synthesis of (3R,7S,10S,13R)-6-(4-Chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-3-(pyridin-2-ylmethyl)-1,6,9,12-tetraazabicyclo[11.3.1]heptadecane-2,5,8,11-tetraone (Compound 57)
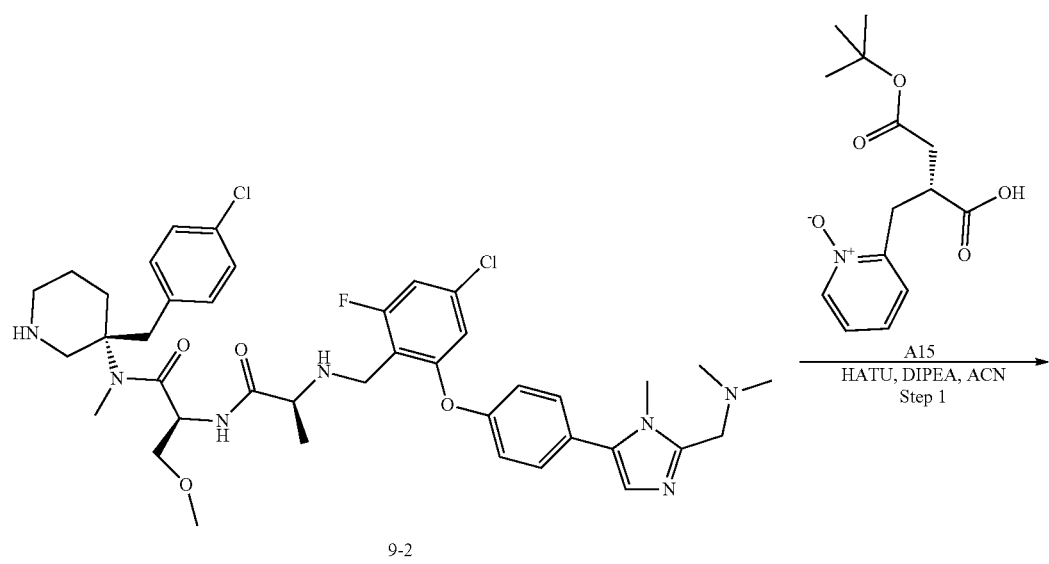
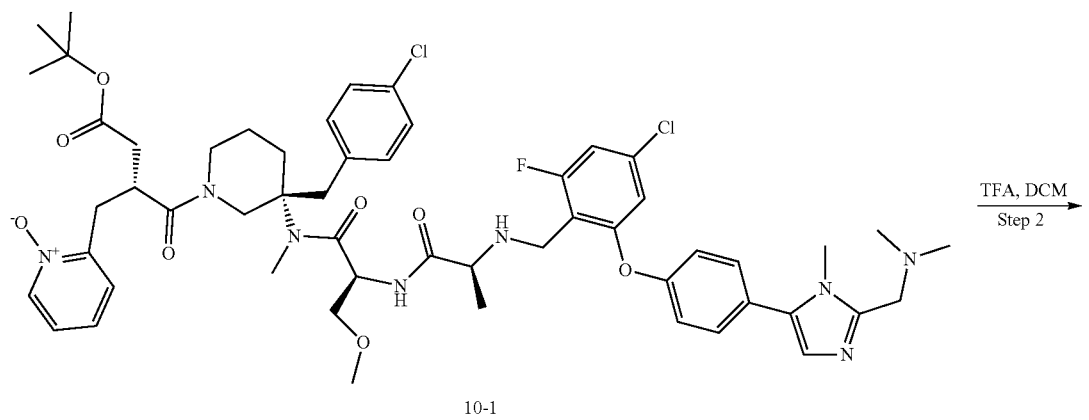
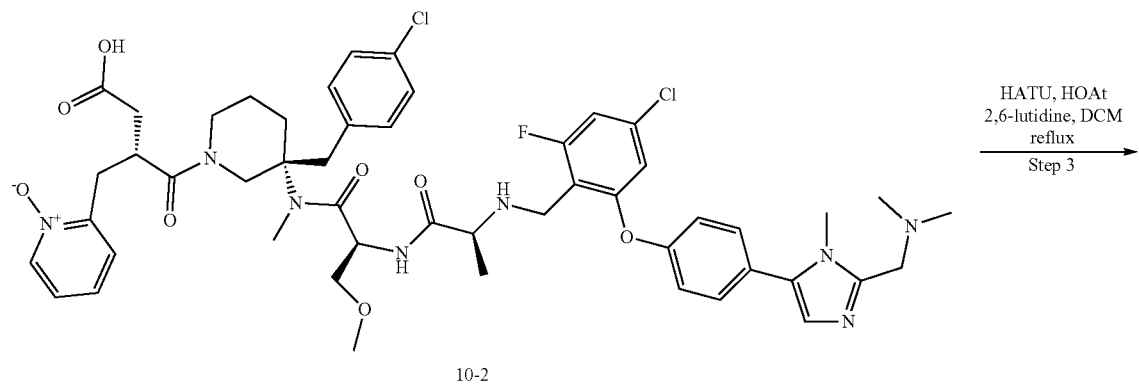

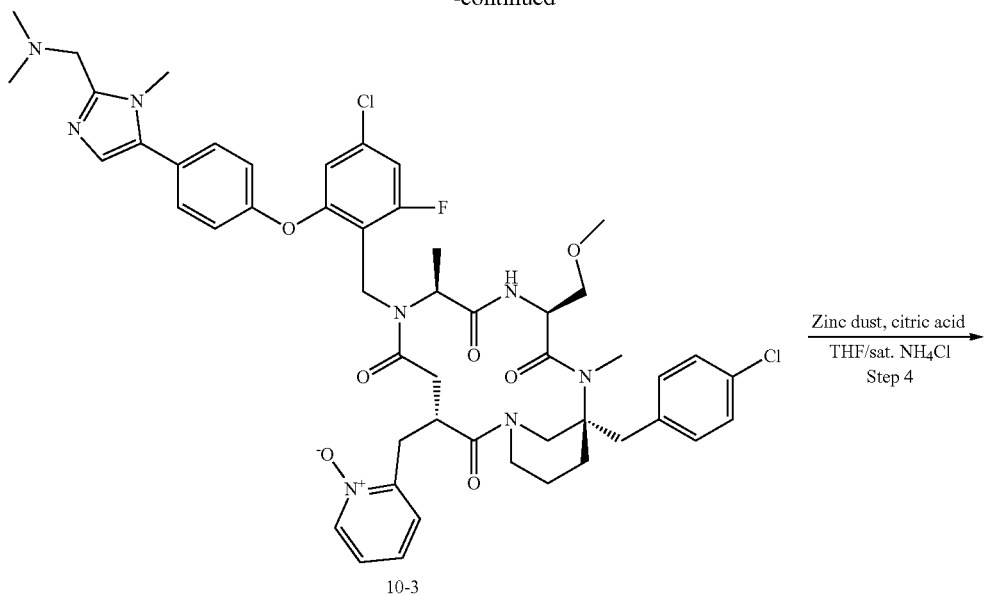

10-3

Zinc dust, citric acid
⟶
THF/sat. NH₄Cl
Step 4

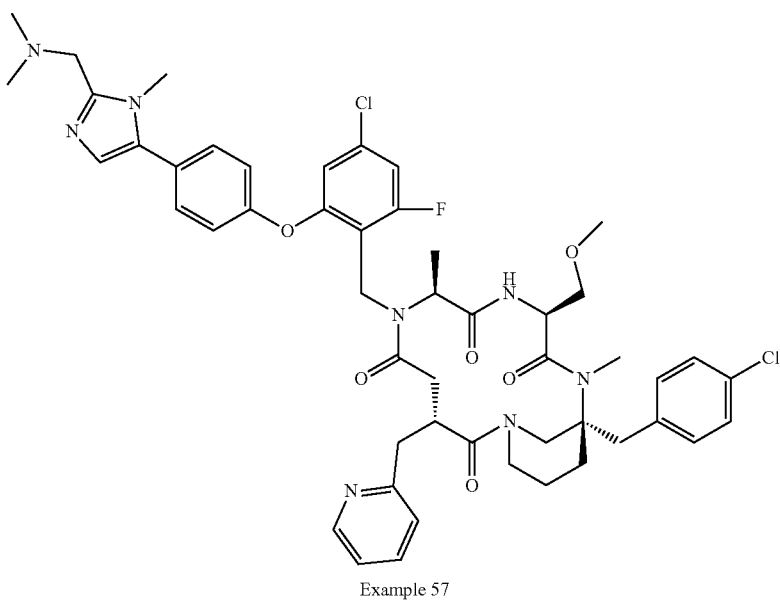

Example 57

Step 1. 2-((R)-4-(tert-Butoxy)-2-((R)-3-((S)-2-((S)-2-((4-chloro-2-(4-(2-((dimethylamino)methyl)-1-methyl-1H-imidazol-5-yl)phenoxy)-6-fluorobenzyl)amino)propanamido)-3-methoxy-N-methylpropanamido)-3-(4-chlorobenzyl)piperidine-1-carbonyl)-4-oxobutyl)pyridine-1-oxide (10-1)

To a solution of A15 (40 mg, 0.143 mmol) in 2 mL of ACN was added DIPEA (0.08 mL, 0.48 mmol) and HATU (54 mg, 0.14 mmol)). The resulting mixture was stirred at RT for 5 min and a solution of 9-2 (93 mg, 0.12 mmol) in 2 ml of ACN was then added. The reaction mixture was stirred for overnight, quenched with 15 ml of 5% NaHCO₃, and extracted with EtOAc. The combined organic phases were washed with a solution of 5% NaHCO₃ and brine, dried over sodium sulfate, filtered and concentrated to afford 10-1 (124 mg, 0.12 mmol, ~quantitative yield) as a yellow solid. The crude product was used in the next step without further purification. Analytical Method 5, $t_R$=1.20 min., [M+H]⁺=1045.5.

Step 2. 2-((R)-2-(Carboxymethyl)-3-((R)-3-((S)-2-((S)-2-((4-chloro-2-(4-(2-((dimethylamino)methyl)-1-methyl-1H-imidazol-5-yl)phenoxy)-6-fluorobenzyl)amino)propanamido)-3-methoxy-N-methylpropanamido)-3-(4-chlorobenzyl)piperidin-1-yl)-3-oxopropyl)pyridine-1-oxide (10-2)

To a solution of 10-1 (124 mg, 0.12 mmol) in DCM (2 mL) was added TFA (2 mL, 26.1 mmol) and the resulting mixture was stirred at RT for 4 h. The reaction mixture was then concentrated and the crude material purified by reverse-phase column chromatography (eluting with 0-100% water/ACN with 0.1% NH$_4$OH) to afford 10-2 (26 mg, 0.03 mmol, 22% yield) after freeze drying the pure fractions. Analytical Method 5, $t_R$=0.77 min., [M+H]$^+$=989.6.

Step 3. 2-(((3R,7S,10S,13R)-6-(4-Chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-2,5,8,11-tetraoxo-1,6,9,12-tetraazabicyclo[11.3.1]heptadecan-3-yl)methyl)pyridine-1-oxide (10-3)

To a solution of 10-2 (26 mg, 0.03 mmol) in DCM (20 mL) was added 2,6-lutidine (0.09 mL, 0.79 mmol), HOAt (4 mg, 0.03 mmol), and HATU (40 mg, 0.11 mmol). The resulting mixture was heated to reflux for 1.5 h in a 48° C. heating bath and then cooled down to RT and concentrated. The residue was partitioned between EtOAc and 5% aq. NaHCO$_3$ solution. The organic phase was washed with 5% aq. NaHCO$_3$ (2×15 mL) and brine (15 mL), dried over Na$_2$SO$_4$, filtered, and concentrated to afford 10-3 (25 mg, 0.03 mmol, ~quantitative yield) which was used in the next step without further purification. Analytical Method 5, $t_R$=1.07 min., [M+H]$^+$=971.4.

Step 4. (3R,7S,10S,13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(methoxymethyl)-7,12-dimethyl-3-(pyridin-2-ylmethyl)-1,6,9,12-tetraazabicyclo[11.3.1]heptadecane-2,5,8,11-tetraone (Compound 57)

To a solution of 10-3 (25 mg, 0.03 mmol) in THF (5 mL) was added saturated NH$_4$Cl solution (1.7 mL), zinc (109 mg, 1.66 mmol) and citric acid (90 mg, 0.47 mmol). The resulting mixture was stirred at RT for 30 min to afford a biphasic mixture. The organic phase was collected and the aqueous phase was extracted with DCM. The combined organic phases were concentrated and the obtained residue was taken up in DCM, washed with 5% NaHCO$_3$ solution, dried over sodium sulfate, and concentrated. The crude product was taken up in DMSO and purified by HPLC (eluting with 0-100% water/ACN with 0.1% NH$_4$OH) to afford Compound 57 (12 mg, 0.01 mmol, 48% yield). Analytical Method 2, $t_R$=2.77 min., [M+H]+=955.4.

The compound in Table 22 was synthesized according to the procedure described in Example 8.30 for Compound 57 from the respective intermediates shown in Tables 1-7 and described above in Example 8.

TABLE 22

| Cmd No. | Structure | LCMS |
|---|---|---|
| 3 | 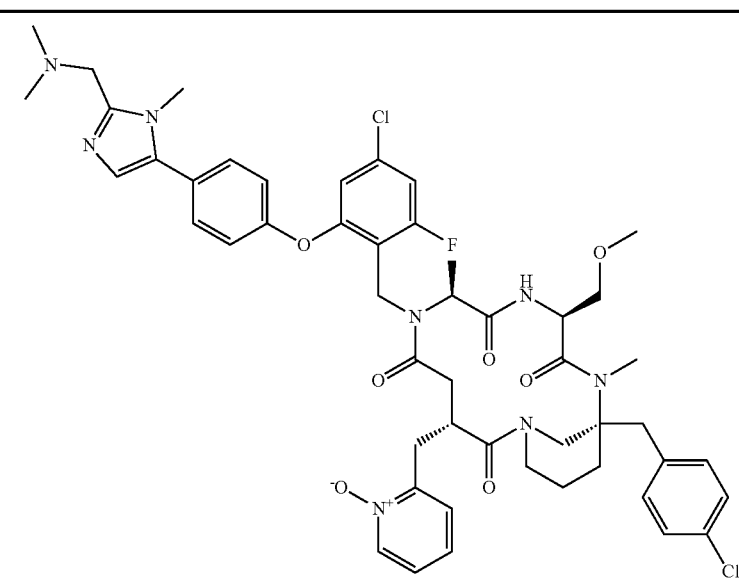 | Analytical Method 2<br>$t_R$ = 2.43 min.<br>[M + H]$^+$ = 971.7 |

Example 8.31: Synthesis of (3R,7S,10S,13R)-6-(4-Chloro-2-((6-(2-((dimethylamino)methyl)-1-methyl-1H-imidazol-5-yl)pyridin-3-yl)oxy)benzyl)-13-(4-chlorobenzyl)-10-(methoxymethyl)-7,12-dimethyl-3-(pyridin-2-ylmethyl)-1,6,9,12-tetraazabicyclo[11.3.1]heptadecane-2,5,8,11-tetraone (Compound 94)
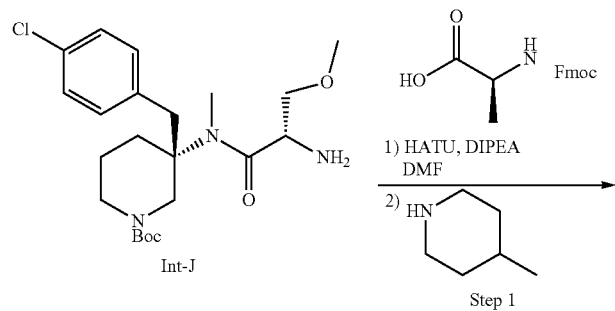
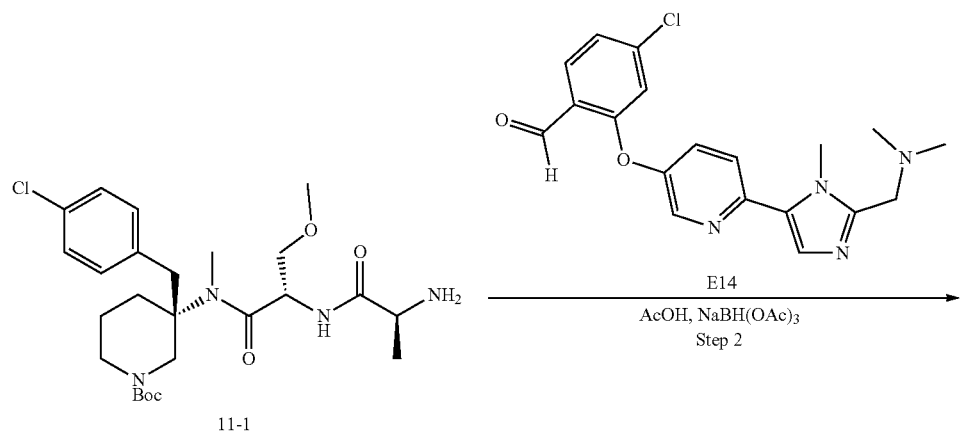
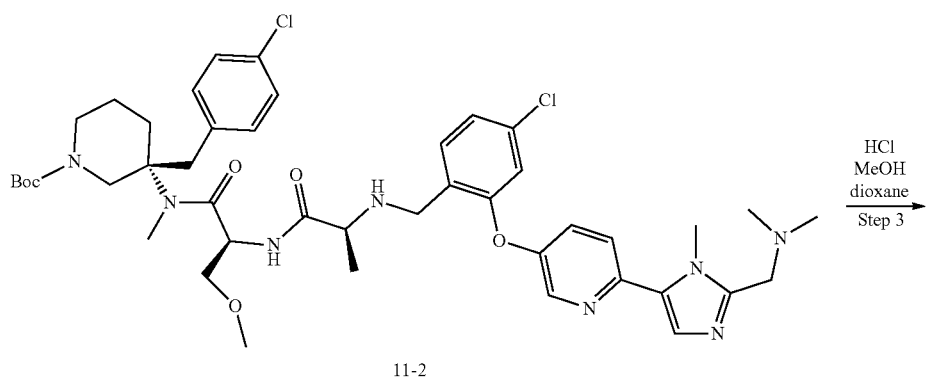

-continued
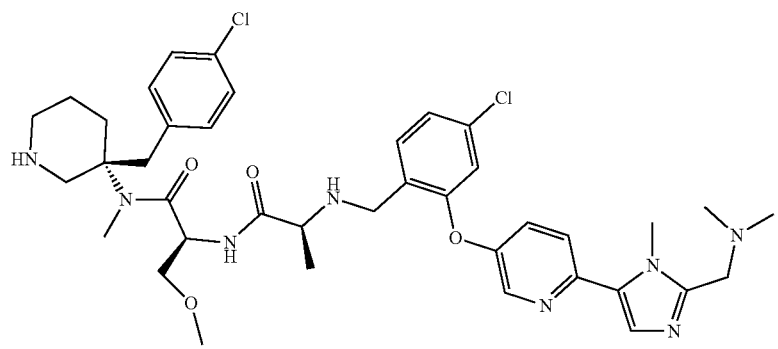
11-3
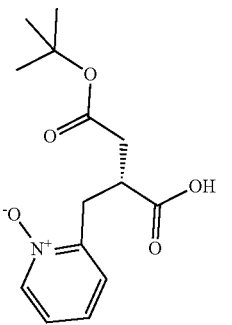
A15
HATU, DIPEA, ACN
Step 4
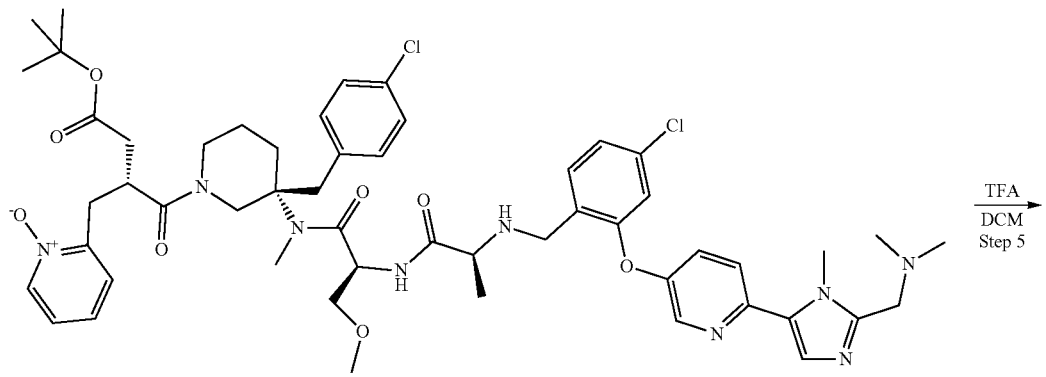
11-4
TFA
DCM
Step 5
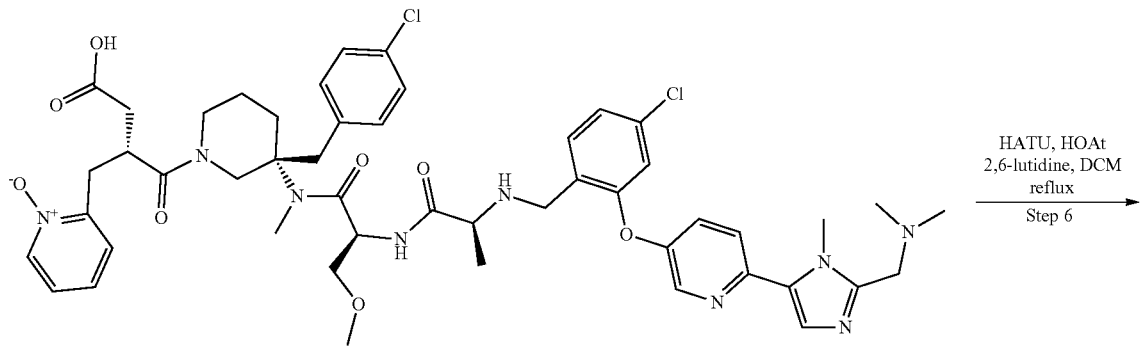
11-5
HATU, HOAt
2,6-lutidine, DCM
reflux
Step 6

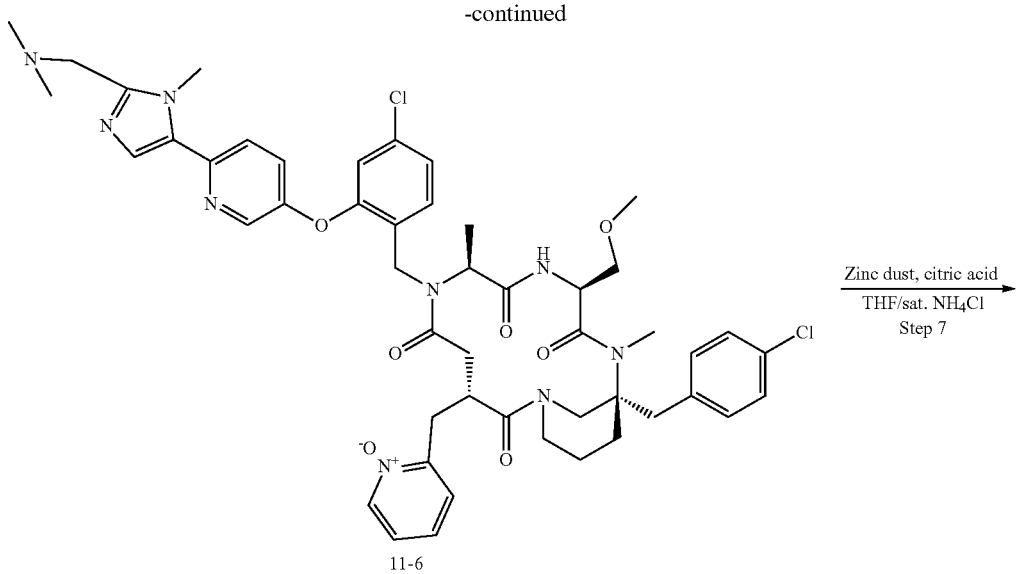

11-6

Zinc dust, citric acid
THF/sat. NH₄Cl
Step 7

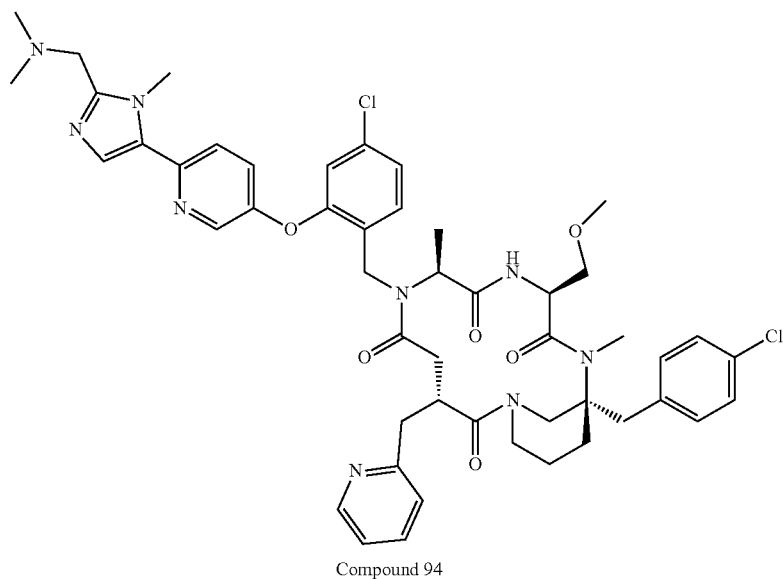

Compound 94

Step 1. (R)-tert-Butyl 3-((S)-2-((S)-2-((((9H-fluoren-9-yl)methoxy)carbonyl)amino)propanamido)-3-methoxy-N-methylpropanamido)-3-(4-chlorobenzyl)piperidine-1-carboxylate (11-1)

Step 1-1: To a solution of Intermediate J (252 mg, 0.57 mmol) in DMF was added DIPEA (0.2 mL, 1.14 mmol), Fmoc-Ala-OH (187 mg, 0.60 mmol), and HATU (228 mg, 0.60 mmol). The resulting mixture was stirred at RT for overnight.

Step 1-2: 4-Methylpiperidine (1.35 mL, 11.4 mmol) was then added and stirring was continued for 1 h to complete the de-protection step. The resulting mixture was diluted with 50 mL of EtOAc and washed with 5% NaHCO₃ (3×50 mL). The combined organic phases were dried with sodium sulfate, filtered, and concentrated. The crude product was taken up in a mixture of DMSO/ACN and purified by reverse-phase column chromatography (eluting with 0-100% water/ACN with 0.1% NH₄OH) to afford 11-1 (170 mg, 0.27 mmol, 47% yield) after freeze drying the pure fractions. Analytical Method 5, $t_R$=1.04 min., [M+H]⁺=511.1.

Step 2. (R)-tert-Butyl 3-((S)-2-((S)-2-((4-chloro-2-((6-(2-((dimethylamino)methyl)-1-methyl-1H-imidazol-5-yl)pyridin-3-yl)oxy)benzyl)amino)propanamido)-3-methoxy-N-methylpropanamido)-3-(4-chlorobenzyl)piperidine-1-carboxylate (11-2)

To a mixture of 11-1 (170 mg, 0.33 mmol) and E14 (173 mg, 0.47 mmol) in DCM (5 mL) was added AcOH (0.08 mL, 1.33 mmol) and the resulting mixture was stirred at RT for 1 h. Sodium triacetoxyborohydride (282 mg, 1.33 mmol) was added and stirring was continued for 1.5 h. EtOAc was added and the organic phase was washed with 3×50 mL of 5% NaHCO$_3$ and brine, dried over Na$_2$SO$_4$, filtered, concentrated to afford 11-2 as a yellow oil (288 mg, 0.33 mmol, ~quantitative yield). The crude product was used in the next step without purification. Analytical Method 5, $t_R$=1.30 min., [M+H]$^+$=865.3.

Step 3. (S)-2-((S)-2-((4-Chloro-2-((6-(2-((dimethylamino)methyl)-1-methyl-1H-imidazol-5-yl)pyridin-3-yl)oxy)benzyl)amino)propanamido)-N—((R)-3-(4-chlorobenzyl)piperidin-3-yl)-3-methoxy-N-methylpropanamide (11-3)

To a solution of 11-2 (288 mg, 0.33 mmol) in anhydrous methanol (5 mL) was added cold HCl in dioxane (5 mL, 20.0 mmol). The resulting mixture was stirred at RT for 4 h and then concentrated. The obtained crude residue which was taken up in toluene and concentrated quantitative yield). The product was used in the next step without purification. Analytical Method 5, $t_R$=1.10 min., [M+H]$^+$=765.5.

Step 4. 2-((R)-4-(tert-Butoxy)-2-((R)-3-((S)-2-((S)-2-((4-chloro-2-((6-(2-((dimethylamino)methyl)-1-methyl-1H-imidazol-5-yl)pyridin-3-yl)oxy)benzyl)amino)propanamido)-3-methoxy-N-methylpropanamido)-3-(4-chlorobenzyl)piperidine-1-carbonyl)-4-oxobutyl)pyridine 1-oxide (11-4)

To a solution of 11-3 (279 mg, 0.33 mmol) in 10 mL of ACN was added DIPEA (0.17 mL, 1.0 mmol), A15 (140 mg, 0.50 mmol), and HATU (164 mg, 0.43 mmol)). The resulting mixture was stirred at RT for 2 h and then quenched with 50 mL of 5% NaHCO$_3$ and extracted with 2×50 mL of EtOAc. The combined organic phases were washed with 5% NaHCO$_3$ and brine, dried over sodium sulfate, filtered, and concentrated to afford 11-4 as a yellow oil (342 mg, 0.33 mmol, ~quantitative yield). The product was used in the next step without further purification. Analytical Method 5, $t_R$=1.13 min., [M+H]$^+$=1028.7.

Step 5. 2-((R)-2-(Carboxymethyl)-3-((R)-3-((S)-2-((S)-2-((4-chloro-2-((6-(2-((dimethylamino)methyl)-1-methyl-1H-imidazol-5-yl)pyridin-3-yl)oxy)benzyl)amino)propanamido)-3-methoxy-N-methylpropanamido)-3-(4-chlorobenzyl)piperidin-1-yl)-3-oxopropyl)pyridine 1-oxide (11-5)

To a solution of 11-4 (342 mg, 0.33 mmol) in DCM (5 mL) was added TFA (5 mL, 64.9 mmol) and the resulting mixture was stirred at RT for 1 h. The reaction mixture was concentrated to afford a crude residue which was taken up in toluene and concentrated again. This was repeated once more. The crude product was purified by reverse-phase column chromatography (eluting with 0-50% water/ACN with 0.1% NH$_4$OH) to afford 11-5 (135 mg, 0.14 mmol, 38% yield) as a white fluffy power after freeze drying the pure fractions. Analytical Method 5, $t_R$=0.76 min., [M+H]$^+$=972.3.

Step 6. 2-(((3R,7S,10S,13R)-6-(4-Chloro-2-((6-(2-((dimethylamino)methyl)-1-methyl-1H-imidazol-5-yl)pyridin-3-yl)oxy)benzyl)-13-(4-chlorobenzyl)-10-(methoxymethyl)-7,12-dimethyl-2,5,8,11-tetraoxo-1,6,9,12-tetraazabicyclo[11.3.1]heptadecan-3-yl)methyl)pyridine 1-oxide (11-6)

To a solution of 11-5 (135 mg, 0.14 mmol) in anhydrous DCM (100 mL) was added 2,6-lutidine (0.49 mL, 4.16 mmol), HOAt (19 mg, 0.14 mmol), and HATU (211 mg, 0.56 mmol). The resulting mixture was refluxed overnight in a 48° C. heating bath, then to RT and concentrated to dryness. The obtained residue was partitioned between EtOAc (50 mL) and 5% aq. NaHCO$_3$ (50 mL). The organic phase was washed with 5% aq. NaHCO$_3$ (2×50 mL) and brine (50 mL), dried over Na$_2$SO$_4$, filtered, and concentrated to dryness to afford 11-6 (133 mg, 0.14 mmol, ~quantitative yield). The product was used in the next step without further purification. Analytical Method 5, $t_R$=1.02 min., [M+H]+/2=477.8.

Step 7. (3R,7S,10S,13R)-6-(4-Chloro-2-((6-(2-((dimethylamino)methyl)-1-methyl-1H-imidazol-5-yl)pyridin-3-yl)oxy)benzyl)-13-(4-chlorobenzyl)-10-(methoxymethyl)-7,12-dimethyl-3-(pyridin-2-ylmethyl)-1,6,9,12-tetraazabicyclo[11.3.1]heptadecane-2,5,8,11-tetraone (Compound 94)

To a solution of 11-6 (133 mg, 0.14 mmol) in THF (10 mL) was added saturated NH$_4$Cl (3.34 mL), zinc dust (583 mg, 8.91 mmol), and citric acid (482 mg, 2.51 mmol). The resulting was stirred at RT for 90 min to afford a biphasic mixture. The organic phase was separated and the remaining aqueous phase was washed with DCM. The combined organic phases were concentrated and the residue was taken up in DCM, and washed with 5% NaHCO$_3$. The organic phase was dried over sodium sulfate, filtered, and concentrated. The crude product was taken up in ACN and purified by reverse-phase column chromatography (eluting with 0-100% water/ACN with 0.1% NH$_4$OH) to afford Compound 94 (51 mg, 0.05 mmol, 37% yield) after concentrating the pure fractions. Analytical Method 2, $t_R$=2.66 min., [M+H]$^+$=938.4.

The compounds in Table 23 were synthesized according to the procedure described in Example 8.31 for Compound 94 from the respective intermediates shown in Tables 1-7 and described above in Example 8. Compound 174 was made according to Example 8.31, Steps 2-7.

TABLE 23
| Cmd No. | Structure | LCMS |
|---|---|---|
| 14 | 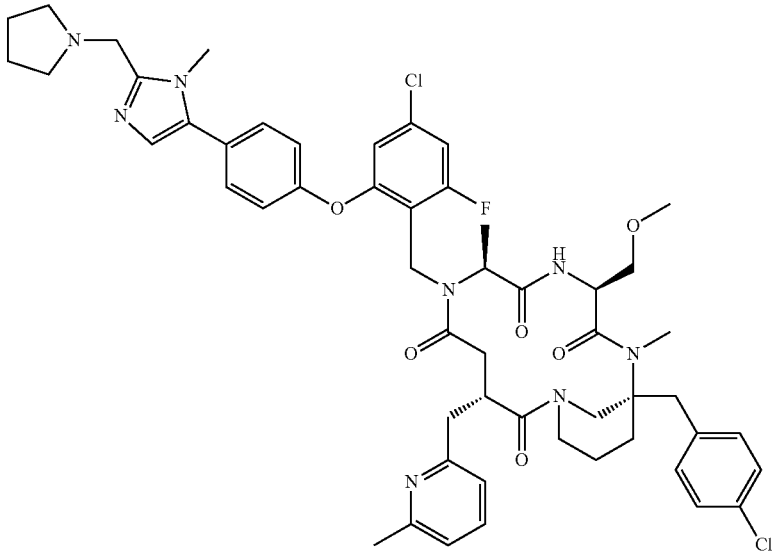 [SMILES: COC[C@@H]1NC(=O)[C@H](C)N(Cc2c(F)cc(Cl)cc2Oc2ccc(-c3cnc(CN4CCCC4)n3C)cc2)C(=O)C[C@@H](Cc2cccc(C)n2)C(=O)N2CCC[C@@](Cc3ccc(Cl)cc3)(C2)N(C)C1=O] | Analytical Method 2<br>$t_R$ = 3.06 min.<br>$[M + H]^+$ = 995.1 |
| 24 | 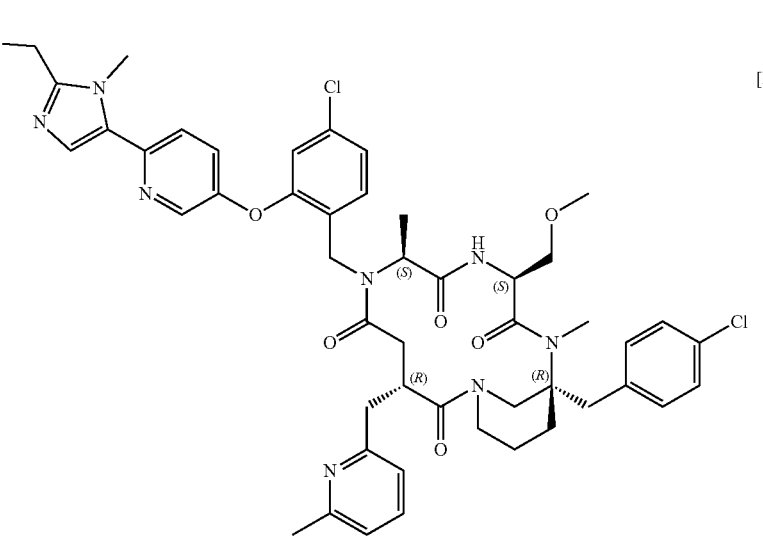 | Analytical Method 2<br>$t_R$ = 2.79 min.<br>$[M + H]^+$ = 952.5 |

TABLE 23-continued

| Cmd No. | Structure | LCMS |
|---|---|---|
| 171 | 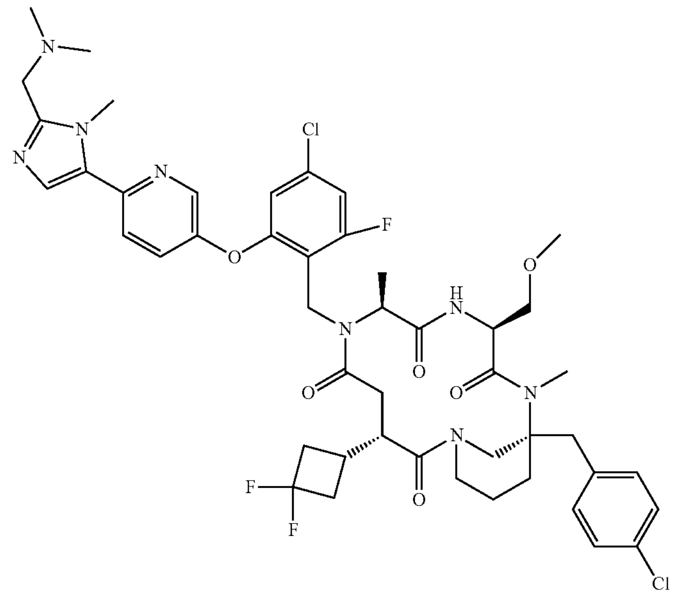 [SMILES: COC[C@@H]1NC(=O)[C@H](C)N(Cc2c(F)cc(Cl)cc2Oc2ccc(-c3cnc(CN(C)C)n3C)nc2)C(=O)C[C@@H](C2CC(F)(F)C2)C(=O)N2CCC[C@@](Cc3ccc(Cl)cc3)(C2)N(C)C1=O] | Analytical Method 2<br>$t_R$ = 2.88 min.<br>[M + H]$^+$ 955.6 |
| 174 | 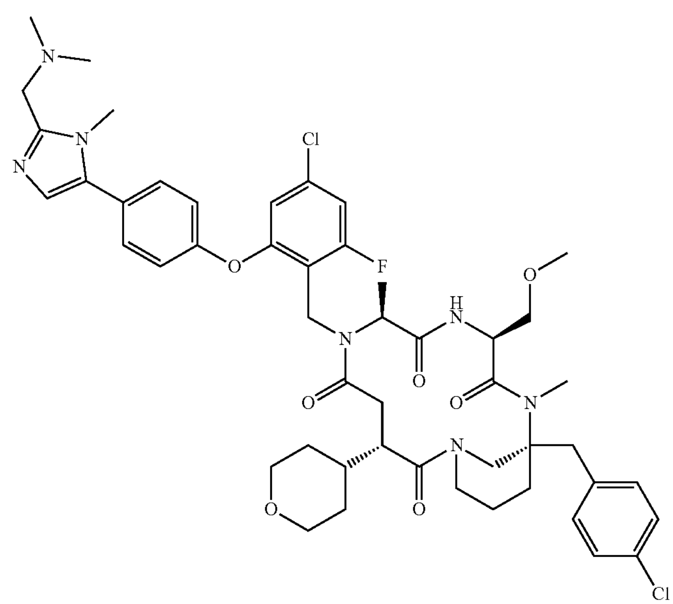 [SMILES: COC[C@@H]1NC(=O)[C@H](C)N(Cc2c(F)cc(Cl)cc2Oc2ccc(-c3cnc(CN(C)C)n3C)cc2)C(=O)C[C@@H](C2CCOCC2)C(=O)N2CCC[C@@](Cc3ccc(Cl)cc3)(C2)N(C)C1=O] | Analytical Method 2<br>$t_R$ = 2.79 min.<br>[M + H]$^+$ 949.1 |

| Cmd No. | Structure | LCMS |
|---|---|---|
| 175 | 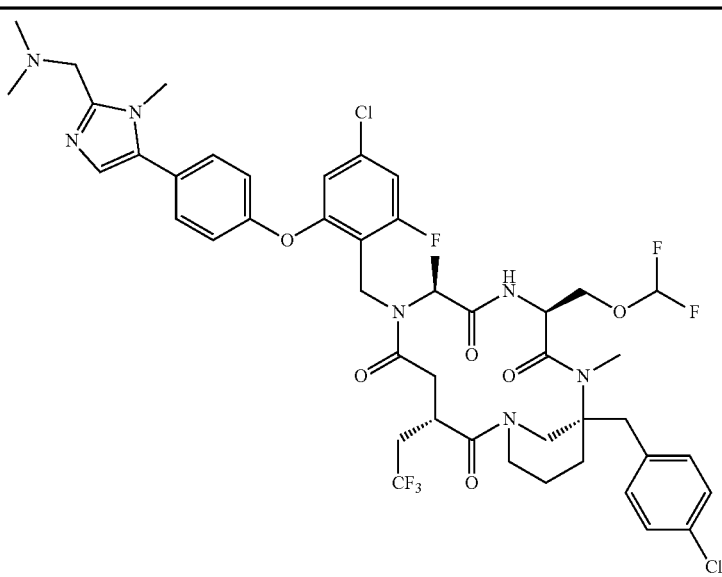 | Analytical Method 3<br>$t_R$ = 1.19 min.<br>$[M + H]^+$ 982.3;<br>Starting from Intermediate L |
Example 8.32: Synthesis of (3R,7S,10S,13R)-6-(4-Chloro-2-(4-(1-methyl-2-(pyrrolidin-1-ylmethyl)-1H-imidazol-5-yl)phenoxy)benzyl)-13-(4-chlorobenzyl)-10-(hydroxymethyl)-7-methyl-3-(pyridin-2-ylmethyl)-1,6,9,12-tetraazabicyclo[11.3.1]heptadecane-2,5,8,11-tetraone (Compound 1)

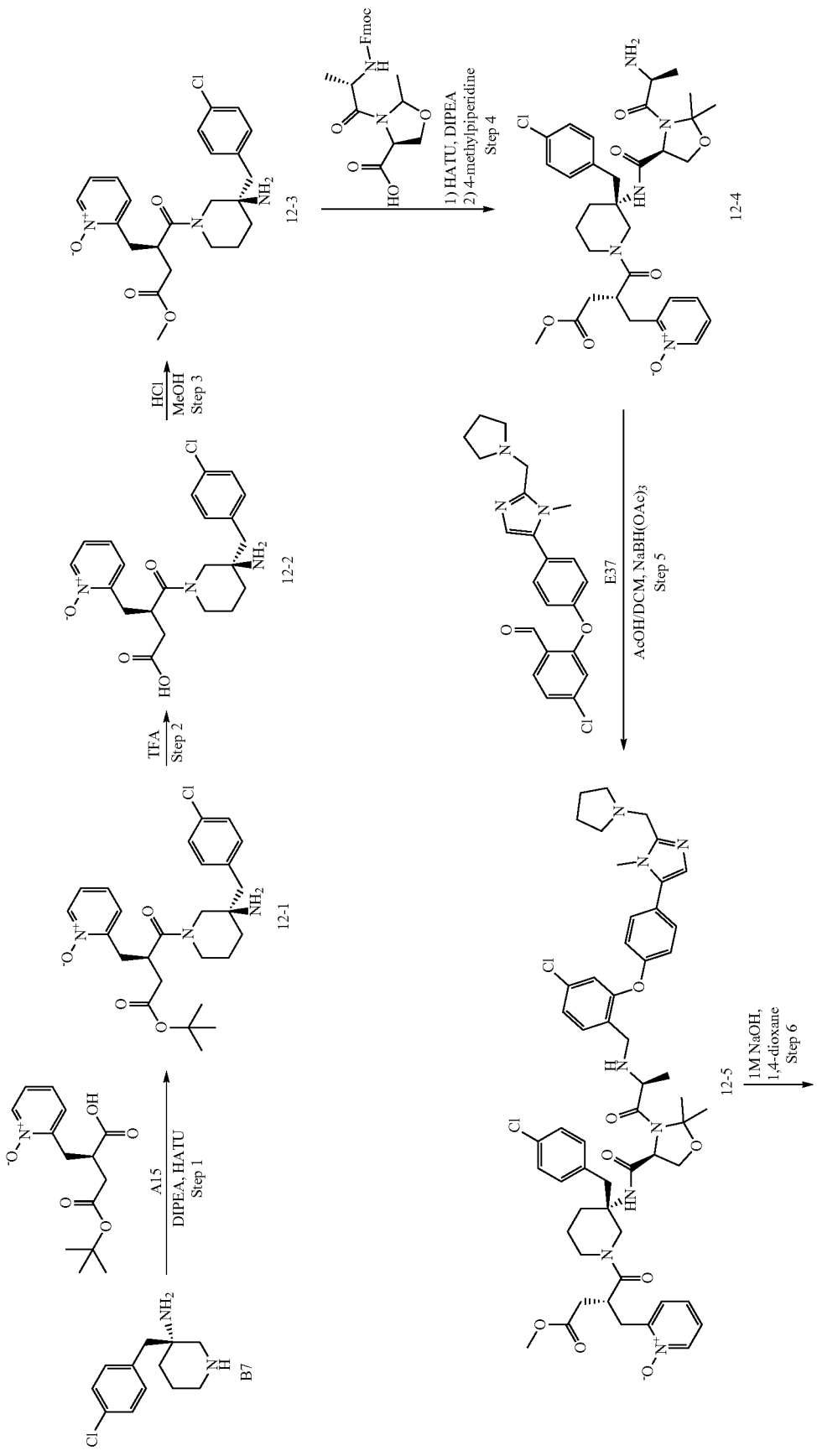

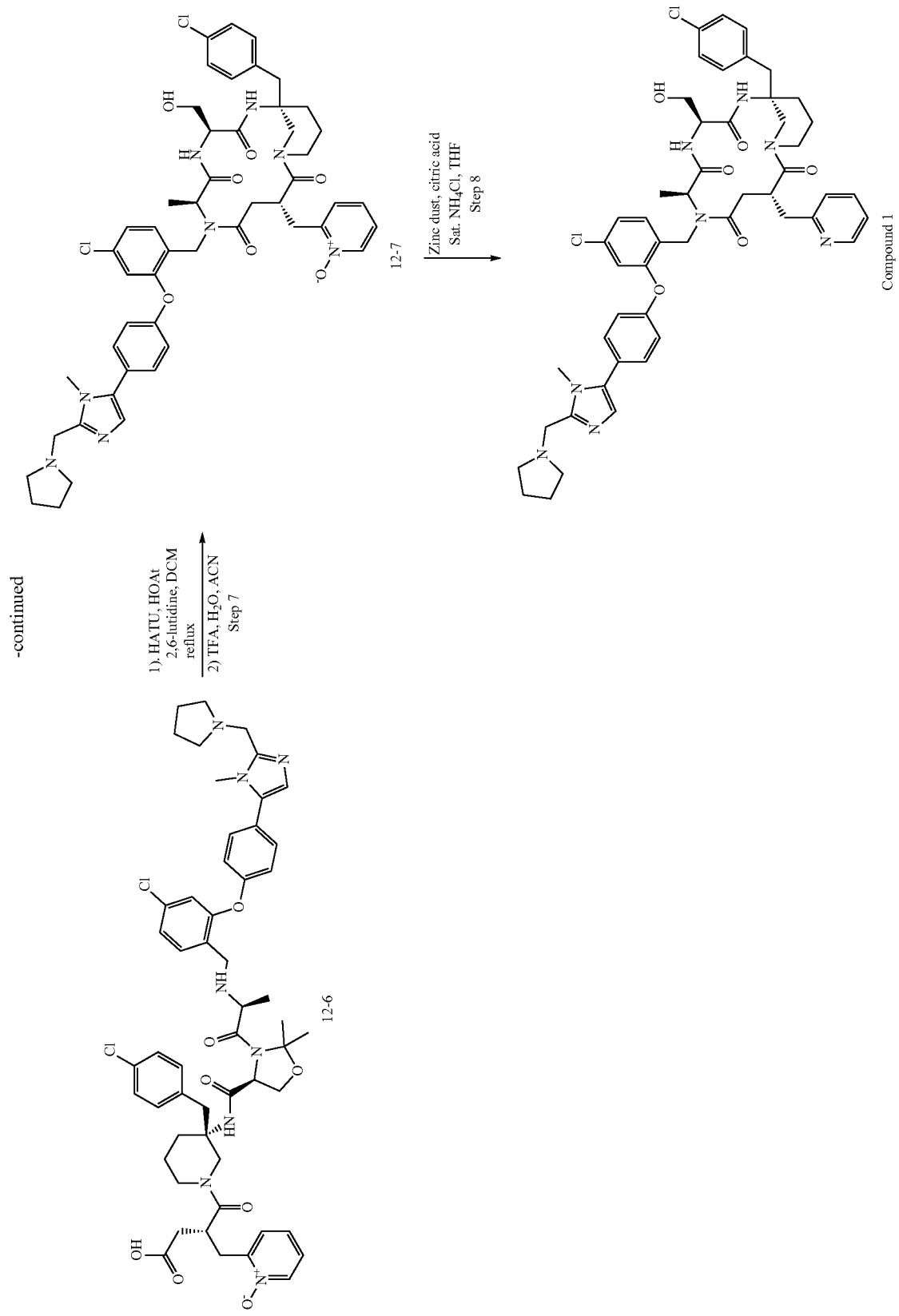

Step 1. 2-((R)-2-((R)-3-Amino-3-(4-chlorobenzyl) piperidine-1-carbonyl)-4-(tert-butoxy)-4-oxobutyl) pyridine 1-oxide (12-1)

To a solution of A15 (1.696 g, 6.03 mmol) in anhydrous ACN (40 mL) was added DIPEA (4.74 mL, 27.1 mmol), E37 (1.80 g, 6.03 mmol), and HATU (2.98 g, 7.84 mmol). The resulting mixture was stirred at RT overnight, and then partitioned between EtOAc (100 mL) and 5% aq. NaHCO$_3$ (100 mL). The organic phase was dried over Na$_2$SO$_4$, filtered, and concentrated. The crude material was purified by flash column chromatography on silica gel (eluting with 0-10% DCM/MeOH) to afford 12-1 as a yellow solid after concentrating the pure fractions (2.63 g, 5.39 mmol, 89% yield). Analytical Method 5, $t_R$=0.92 min., [M+H]$^+$=488.4.

Step 2. 2-((R)-3-((R)-3-amino-3-(4-chlorobenzyl) piperidin-1-yl)-2-(carboxymethyl)-3-oxopropyl)pyridine 1-oxide (12-2)

To 12-1 (2.63 g, 5.39 mmol) in anhydrous DCM (8 mL) was added TFA (8.30 mL, 108 mmol). The resulting mixture was stirred at RT for 6 h, then concentrated, and dried thoroughly to afford 12-2 (2.9 g, 5.39 mmol, ~ quantitative yield). The crude product was used in the next step without purification. Analytical Method 5, $t_R$=0.50 min., [M+H]$^+$=432.3.

Step 3. 2-((R)-2-((R)-3-Amino-3-(4-chlorobenzyl) piperidine-1-carbonyl)-4-methoxy-4-oxobutyl)pyridine 1-oxide (12-3)

To a solution of 12-2 (2.9 g, 5.39 mmol) in anhydrous MeOH (13 mL) was added 4M HCl in dioxane (13.5 mL, 53.9 mmol). The resulting mixture was stirred at RT for overnight and then concentrated under reduced pressure. The crude product was purified by reverse-phase column chromatography (eluting with 0-100% water/ACN with 0.1% NH$_4$OH) to afford 12-3 (766 mg, 1.72 mmol, 32% yield) after concentrating the pure fractions. Analytical Method 5, $t_R$=0.75 min., [M+H]$^+$=446.3.

Step 4. 2-((R)-2-((R)-3-((S)-3-((S)-2-aminopropanoyl)-2,2-dimethyloxazolidine-4-carboxamido)-3-(4-chlorobenzyl)piperidine-1-carbonyl)-4-methoxy-4-oxobutyl)pyridine 1-oxide (12-4)

To a solution of Fmoc-Ala-Ser[psi(Me,Me)pro]-OH (403 mg, 0.92 mmol) in DMA (5 mL) was added HATU (350 mg, 0.92 mmol) and DIPEA (0.21 mL, 1.20 mmol). The solution was stirred for 2 min at RT and then a solution of 12-3 (410 mg, 0.92 mmol) in DMA (3 mL) was added. The resulting mixture was stirred at RT for overnight 4-methylpiperidine (3 mL) was then added. The reaction mixture was stirred at RT for 30 min and then subsequently concentrated to dryness under reduced pressure. The crude material was purified by reverse-phase column chromatography (eluting with 0-60% water/ACN with 0.1% NH$_4$OH) to afford 12-4 (360 mg, 0.60 mmol, 61% yield) after free drying down the pure fractions. Analytical Method 5, $t_R$=0.84 min., [M+H]$^+$=644.5.

Step 5. 2-((R)-2-((R)-3-((S)-3-((S)-2-((4-Chloro-2-(4-(1-methyl-2-(pyrrolidin-1-ylmethyl)-1H-imidazol-5-yl)phenoxy)benzyl)amino)propanoyl)-2,2-dimethyloxazolidine-4-carboxamido)-3-(4-chlorobenzyl)piperidine-1-carbonyl)-4-methoxy-4-oxobutyl)pyridine 1-oxide (12-5)

To a mixture of 12-4 (360 mg, 0.60 mmol) and E37 (332 mg, 0.84 mmol) in DCM (15 mL) was added AcOH (0.13 mL, 2.24 mmol). The resulting mixture was stirred for at RT for 1 h and sodium triacetoxyborohydride (592 mg, 2.79 mmol) was then added. The reaction mixture was stirred for 2 h and then EtOAc (60 mL) was added. The organic phase was washed with 5% aq. Na$_2$CO$_3$ (50 mL×2), dried over Na$_2$SO$_4$, filtered, and concentrated to dryness to afford 12-5 (572 mg, 0.60 mmol, crude) as a brown oil. The product was used in the next step without purification. Analytical Method 5, $t_R$=1.18 min., [M+H]$^+$=1023.6.

Step 6. 2-((R)-2-(Carboxymethyl)-3-((R)-3-((S)-3-((S)-2-((4-chloro-2-(4-(1-methyl-2-(pyrrolidin-1-ylmethyl)-1H-imidazol-5-yl)phenoxy)benzyl)amino) propanoyl)-2,2-dimethyloxazolidine-4-carboxamido)-3-(4-chlorobenzyl)piperidin-1-yl)-3-oxopropyl)pyridine 1-oxide (12-6)

To a mixture of 12-5 (572 mg, 0.60 mmol) in dioxane (10 mL) and H$_2$O (2.5 mL) and cooled to 0° C. was added 1 M NaOH (2.23 mL, 2.23 mmol). The resulting mixture was stirred at RT for 2 h. Additional NaOH (1M, up to 3.3 mL) was added and stirring was continued at RT until starting material was consumed by LCMS. The reaction mixture was quenched with AcOH (0.96 mL, 16.8 mmol) and 50 mL of NaHCO$_3$, and extracted with EtOAc (×2). Brine was added to the aqueous phase and back extracted with EtOAc once more. The combined organic phases were dried over sodium sulfate, filtered, and concentrated. The crude material was purified by reverse-phase column chromatography (eluting with 0-100% water/ACN with 0.1% NH$_4$OH) to afford 12-6 (436 mg, 0.43 mmol, 77% yield) after freeze drying the pure fractions. Analytical Method 5, $t_R$=0.84 min., [M+H]$^+$=1009.4.

Step 7. 2-(((3R,7S,10S,13R)-6-(4-chloro-2-(4-(1-methyl-2-(pyrrolidin-1-ylmethyl)-1H-imidazol-5-yl)phenoxy)benzyl)-13-(4-chlorobenzyl)-10-(hydroxymethyl)-7-methyl-2,5,8,11-tetraoxo-1,6,9,12-tetraazabicyclo[11.3.1]heptadecan-3-yl)methyl) pyridine 1-oxide (12-7)

Step 7-1: To a solution of 12-6 (436 mg, 0.43 mmol) in DCM (250 mL) was added 2,6-lutidine (1.51 mL, 12.9 mmol), HOAt (58.8 mg, 0.43 mmol) and HATU (657 mg, 1.73 mmol). The resulting mixture was heated to reflux for 19 h in a 48° C. heating bath and then cooled to RT and concentrated to dryness. The obtained residue was partitioned between EtOAc (100 mL) and 5% aq. NaHCO$_3$ (50 mL). The organic phase was washed with 5% aq. NaHCO$_3$ (2×50 mL) and brine (50 mL), dried over Na$_2$SO$_4$, filtered, and concentrated to dryness under reduced pressure. Analytical Method 5: $t_R$=1.17 min; [M+H]$^+$=991.3.

Step 7-2: To the crude product from Step 7-1 in a mixture of ACN/H$_2$O (5:3) (16 mL) and cooled to 0° C. in an ice bath was added a pre-chilled solution of TFA (3.9 mL, 51.3 mmol) dropwise and the resulting mixture was stirred at RT for 75 min. A mixture of saturated NaHCO$_3$/1M Na$_2$CO$_3$ was added to basify the reaction and the resulting slurry was extracted with EtOAc (×2). The combined organic phases were washed with brine, dried over sodium sulfate, filtered, and concentrated to afford 12-7 (137 mg, 0.14 mmol, ~ quantitative yield). The product was used directly in the next step without further purification. Analytical Method 5, $t_R$=1.02 min., [M+H]$^+$=951.6.

Step 9. (3R,7S,10S,13R)-6-(4-chloro-2-(4-(1-methyl-2-(pyrrolidin-1-ylmethyl)-1H-imidazol-5-yl)phenoxy)benzyl)-13-(4-chlorobenzyl)-10-(hydroxymethyl)-7-methyl-3-(pyridin-2-ylmethyl)-1,6,9,12-tetraazabicyclo[11.3.1]heptadecane-2,5,8,11-tetraone (Compound 1)

To a solution of 12-7 (137 mg, 0.14 mmol) in THF (40 mL) was added saturated NH₄Cl (13.3 mL), zinc dust (1.8 g, 27.1 mmol) and citric acid (1464 mg, 7.62 mmol) and the resulting mixture was stirred at RT for 30 min to afford a biphasic mixture. The organic phase was collected and the remaining aqueous phase was washed with 50 mL of DCM. The combined organic phases were concentrated to dryness and the resulting residue was taken up in DCM and washed with a 5% NaHCO₃ solution. The organic phase was separated, dried over sodium sulfate, filtered, and concentrated to afford a crude product. The crude material was purified by reverse-phase column chromatography (eluting with 0-100% water/ACN with 0.1% NH₄OH) to afford Compound 1 (137 mg, 0.14 mmol, 34% yield) after freeze drying the pure fractions. Analytical Method 2, $t_R$=2.71 min., [M+H]⁺=935.7.

Example 8.33: Synthesis of (3R,7S,10S,13R)-6-(4-Chloro-2-(4-(2-((dimethylamino)methyl)-1-methyl-1H-imidazol-5-yl)phenoxy)benzyl)-13-(4-chlorobenzyl)-10-(hydroxymethyl)-7,12-dimethyl-3-(pyridin-2-ylmethyl)-1,6,9,12-tetraazabicyclo[11.3.1]heptadecane-2,5,8,11-tetraone (Compound 18)

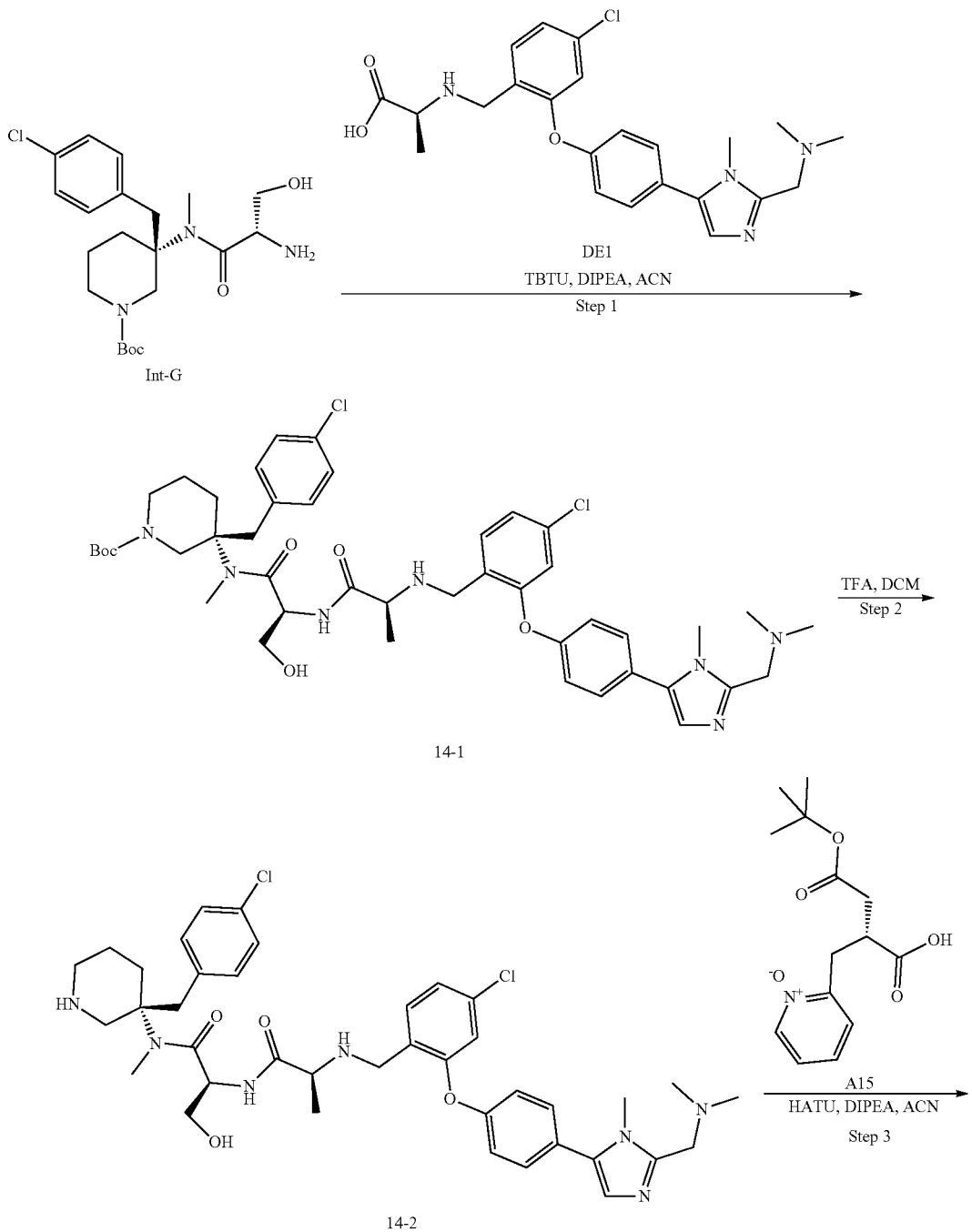

-continued
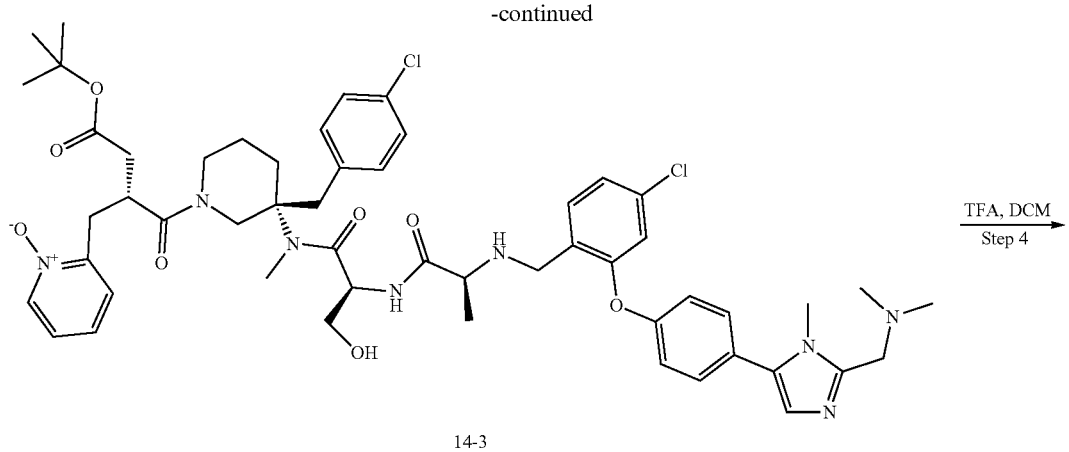
14-3
TFA, DCM
Step 4
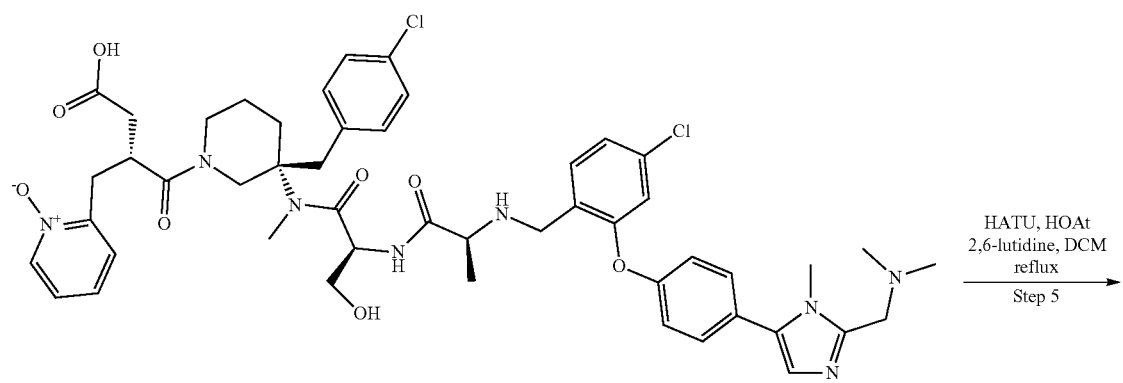
14-4
HATU, HOAt
2,6-lutidine, DCM
reflux
Step 5
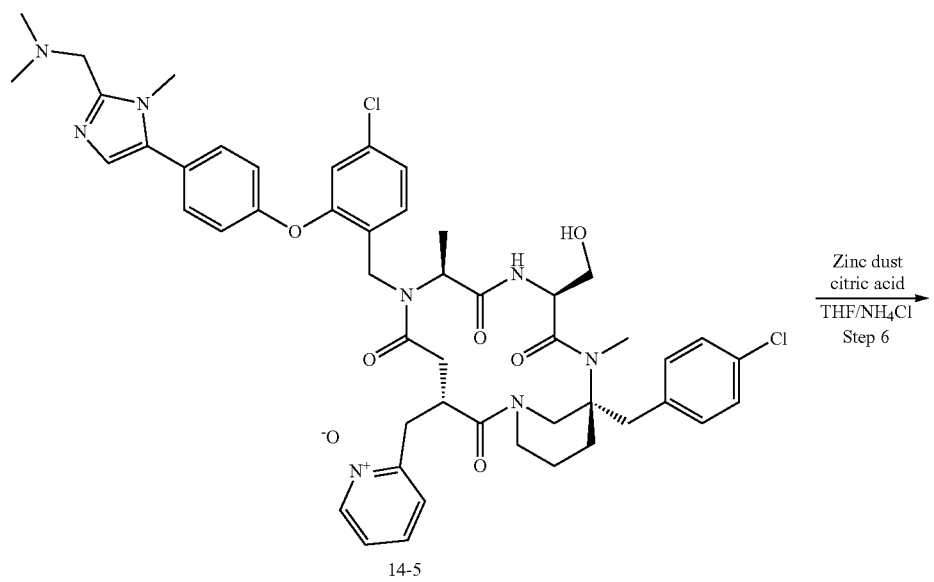
14-5
Zinc dust
citric acid
THF/NH₄Cl
Step 6

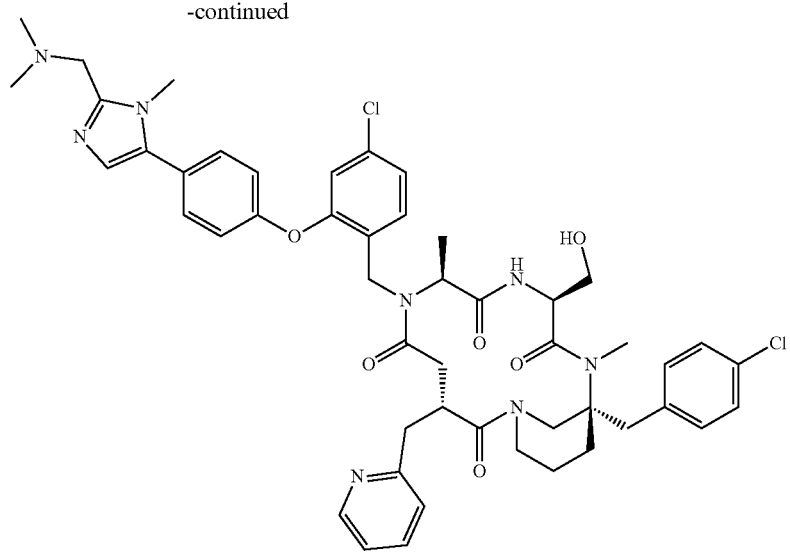

Compound 18

Step 1. (R)-tert-Butyl 3-((S)-2-((S)-2-((4-chloro-2-(4-(2-((dimethylamino)methyl)-1-methyl-1H-imidazol-5-yl)phenoxy)benzyl)amino)propanamido)-3-hydroxy-N-methylpropanamido)-3-(4-chlorobenzyl)piperidine-1-carboxylate (14-1)

To intermediate DE1 (59.3 mg, 0.134 mmol) in ACN (5 mL) was added DIPEA (0.070 mL, 0.401 mmol) and TBTU (43.0 mg, 0.134 mmol). The resulting mixture was stirred at rt for 5 min before Intermediate G (57 mg, 0.134 mmol) was added. The reaction mixture was stirred for 1.5 h and then was diluted with 10 mL of sat. NaHCO$_3$ and 10 mL of water and extracted with 2×15 mL of DCM. The combined organic phases were dried over sodium sulfate, and concentrated to afford 14-1 (114 mg, 0.134 mmol) as an oil. This oil was used directly in the next step without further purification. Analytical Method 5, $t_R$=1.03 min., [M+H]$^+$=850.4.

Step 2. (S)-2-((S)-2-((4-Chloro-2-(4-(2-((dimethylamino)methyl)-1-methyl-1H-imidazol-5-yl)phenoxy)benzyl)amino)propanamido)-N—((R)-3-(4-chlorobenzyl)piperidin-3-yl)-3-hydroxy-N-methylpropanamide (14-2)

To a solution of 14-1 (114 mg, 0.134 mmol) in DCM (3 mL) was added TFA (1.032 mL, 13.40 mmol). The resulting solution was stirred at RT for 1 h and then concentrated to dryness. The resulting oil (14-2, 101 mg, 0.135 mmol, ~ quantitative yield) was in the next step without further purification. Analytical Method 5, $t_R$=1.13 min., [M+H]$^+$=750.4.

Step 3. 2-((R)-4-(tert-Butoxy)-2-((R)-3-((S)-2-((S)-2-((4-chloro-2-(4-(2-((dimethylamino)methyl)-1-methyl-1H-imidazol-5-yl)phenoxy)benzyl)amino)propanamido)-3-hydroxy-N-methylpropanamido)-3-(4-chlorobenzyl)piperidine-1-carbonyl)-4-oxobutyl)pyridine 1-oxide (14-3)

To a solution of A15 in 3 mL of ACN was added DIPEA (0.09 mL, 0.54 mmol) and HATU (51.2 mg, 0.14 mmol). The resulting mixture was stirred at RT for 5 min before a solution of 14-2 (101 mg, 0.135 mmol) in 2 mL of ACN was added. The reaction mixture was stirred for 30 min before being quenched with a NaHCO$_3$ solution and extracted with 2×15 mL of EtOAc. The combined organic phases were dried over sodium sulfate, filtered, and concentrated to afford 14-3 as a yellow oil (136 mg, 0.135 mmol, and ~ quantitative yield). The product was used in the next step without further purification. Analytical Method 5, $t_R$=1.13 min., [M+H]$^+$=1013.7.

Step 4. 2-((R)-2-(Carboxymethyl)-3-((R)-3-((S)-2-((S)-2-((4-chloro-2-(4-(2-((dimethylamino)methyl)-1-methyl-1H-imidazol-5-yl)phenoxy)benzyl)amino)propanamido)-3-hydroxy-N-methylpropanamido)-3-(4-chlorobenzyl)piperidin-1-yl)-3-oxopropyl)pyridine 1-oxide (14-4)

To a solution of 14-3 (136 mg, 0.135 mmol) in DCM (2 mL) was added TFA (2.07 mL, 26.8 mmol) and the resulting mixture was stirred at RT for 2 h and then concentrated under reduced pressure to dryness. The crude material was taken up in DMSO and purified by reverse-phase column chromatography (eluting with 0-50% water/ACN with 0.1% NH$_4$OH) to afford 14-4 (47 mg, 0.05 mmol, 34% yield) after freeze drying the pure fractions. Analytical Method 5, $t_R$=0.78 min., [M+H]$^+$=957.4.

Step 5. 2-(((3R,7S,10S,13R)-6-(4-Chloro-2-(4-(2-((dimethylamino)methyl)-1-methyl-1H-imidazol-5-yl)phenoxy)benzyl)-13-(4-chlorobenzyl)-10-(hydroxymethyl)-7,12-dimethyl-2,5,8,11-tetraoxo-1,6,9,12-tetraazabicyclo[11.3.1]heptadecan-3-yl)methyl)pyridine 1-oxide (14-5)

To a solution of 14-4 (40 mg, 0.04 mmol) in DCM (50 mL) was added 2,6-lutidine (0.15 mL, 1.25 mmol), HOAt (5.7 mg, 0.04 mmol), and HATU (63.5 mg, 0.17 mmol). The resulting mixture was heated to reflux for 4 h in a 48° C., and then cooled to RT and concentrated. The obtained residue was partitioned between EtOAc (15 mL) and 5% NaHCO$_3$ (15 mL). The organic phase was washed with 5% NaHCO$_3$ (2×15 mL) and brine (15 mL), dried over Na$_2$SO$_4$, filtered, and concentrated to dryness under reduced pressure to afford 14-5 (43 mg, 0.04 mmol, ~quantitative yield). The product was used in the next step without further purification. Analytical Method 5, $t_R$=0.97 min., [M+H]$^+$=939.4.

Step 6. (3R,7S,10S,13R)-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-7,12-dimethyl-3-(pyridin-2-ylmethyl)-1,6,9,12-tetraazabicyclo[11.3.1]heptadecane-2,5,8,11-tetraone (Compound 18)

To a solution of 14-5 (43 mg, 0.04 mmol) in THF (5 mL) was added saturated NH$_4$Cl (1.7 mL) solution, zinc dust (194 mg, 2.97 mmol), and citric acid (160 mg, 0.84 mmol). The resulting mixture was stirred at RT for 30 min to afford a biphasic mixture. The organic phase was collected and the remaining aqueous mixture was washed with 5 mL of DCM. The combined organic phases were concentrated to dryness, and the resulting residue was taken up in DCM and washed with a 5% NaHCO$_3$ solution. The organic phase was separated, dried over sodium sulfate, filtered, and concentrated to afford a crude product. The crude material was purified by HPLC (eluting with 0-100% water/ACN with 0.1% NH$_4$OH as buffer) to afford Compound 18 (12 mg, 0.01 mmol, 27% yield) as a white powder after freeze drying the pure fractions. Analytical Method 2, t$_R$=2.60 min., [M+H]$^+$=923.6.

Example 8.34: Synthesis of (3R,7S,10S,13R)-6-(4-Chloro-2-(4-(1-methyl-2-(pyrrolidin-1-ylmethyl)-1H-imidazol-5-yl)phenoxy)benzyl)-13-(4-chlorobenzyl)-10-((difluoromethoxy)methyl)-7-methyl-3-(pyridin-2-ylmethyl)-1,6,9,12-tetraazabicyclo[11.3.1]heptadecane-2,5,8,11-tetraone (Compound 30)

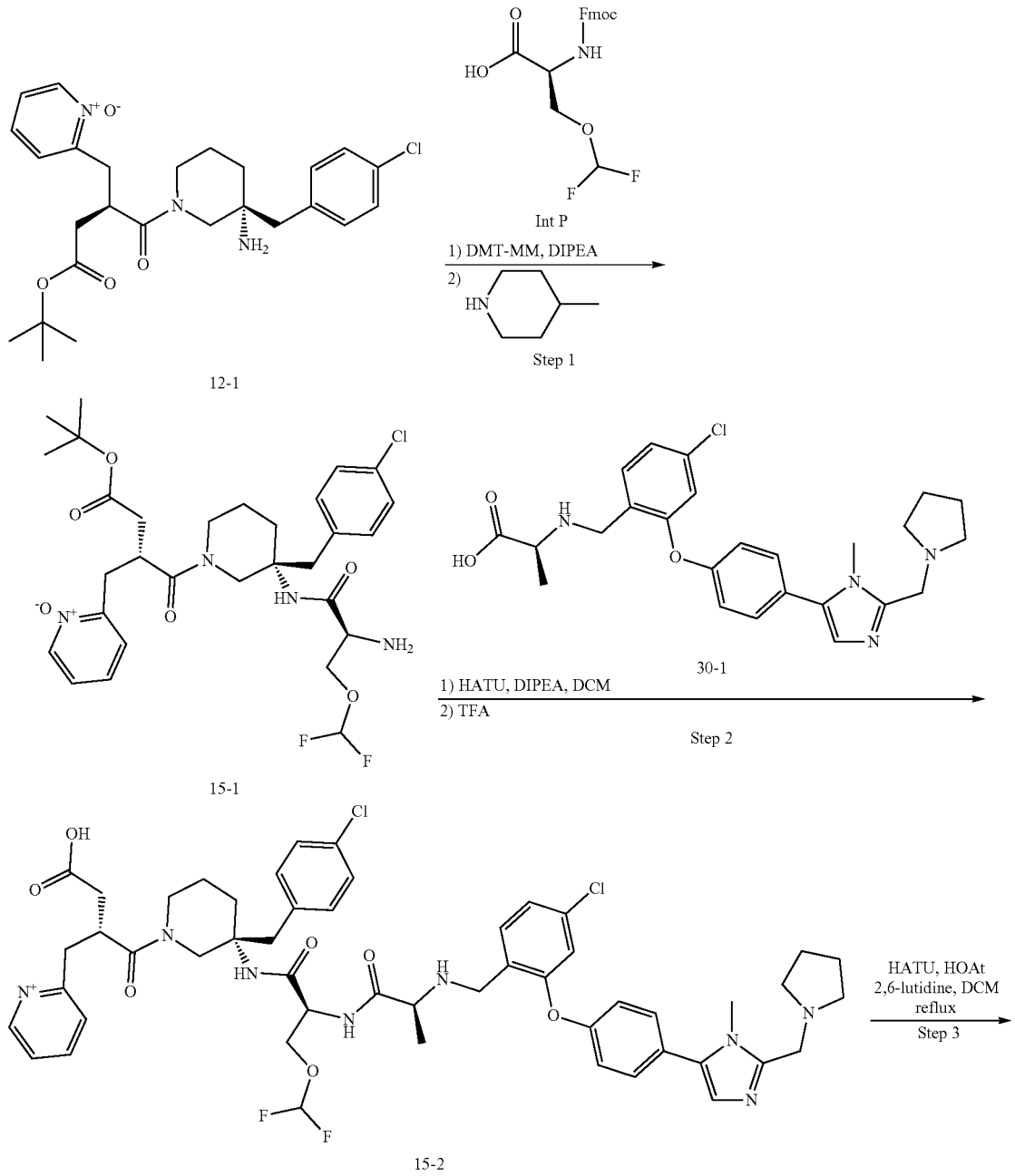

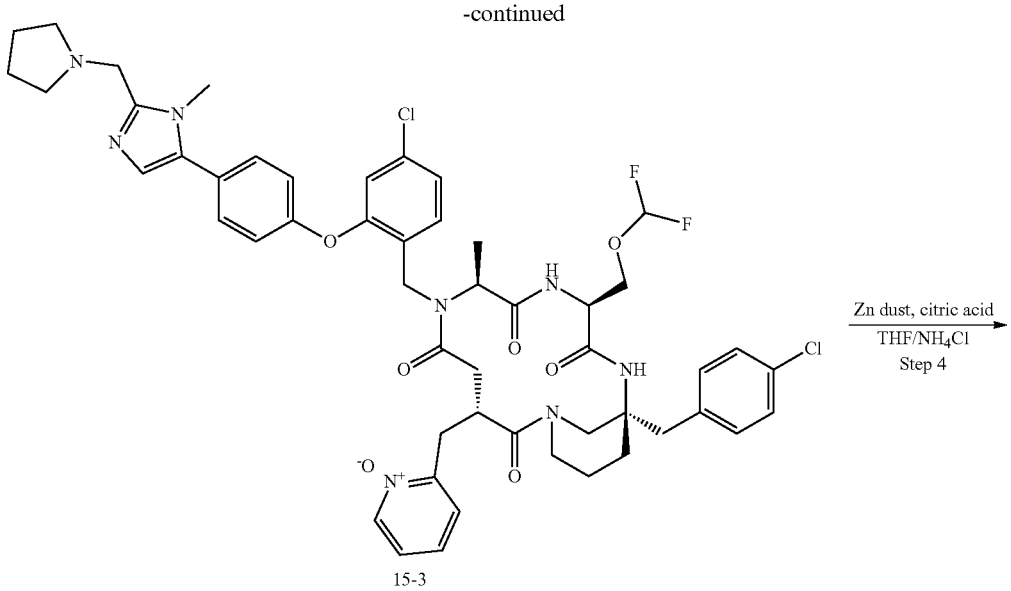

15-3

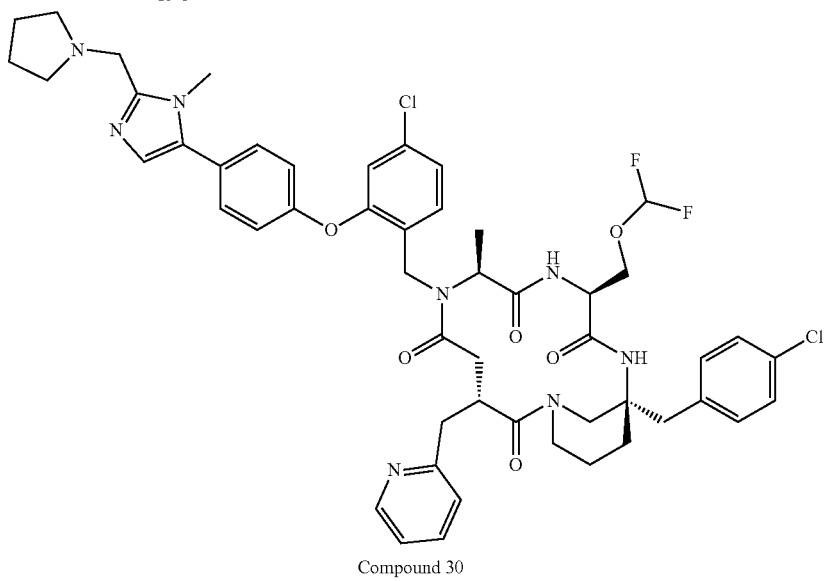

Compound 30

Step 1. 2-((R)-2-((R)-3-((S)-2-Amino-3-(difluoromethoxy)propanamido)-3-(4-chlorobenzyl)piperidine-1-carbonyl)-4-(tert-butoxy)-4-oxobutyl)pyridine 1-oxide (15-1)

To a solution of 12-1 (250 mg, 0.51 mmol) in THF (5 mL) was added Intermediate P (773 mg, 2.05 mmol) and DIPEA (0.54 mL, 3.07 mmol), followed by DMT-MM (354 mg, 1.28 mmol). The resulting mixture was stirred at RT for 1 h. before 4-methylpiperidine (0.61 mL, 5.12 mmol) was added. The reaction mixture was stirred at RT for 30 min and then concentrated to dryness under reduced pressure. The resulting crude material was purified by reverse-phase column chromatography (eluting with 0-100% water/ACN with 0.1% NH$_4$OH) to afford 15-1 (131 mg, 0.21 mmol, 41% yield) after freeze drying of the pure fractions. Analytical Method 5, t$_R$=1.27 min., [M+H]$^+$=625.3.

Step 2. 2-((R)-2-(Carboxymethyl)-3-((R)-3-((S)-2-((S)-2-((4-chloro-2-(4-(1-methyl-2-(pyrrolidin-1-ylmethyl)-1H-imidazol-5-yl)phenoxy)benzyl)amino)propanamido)-3-(difluoromethoxy)propanamido)-3-(4-chlorobenzyl)piperidin-1-yl)-3-oxopropyl)pyridine 1-oxide (15-2)

To a solution of 15-1 (187 mg, 0.30 mmol) in DCM (15 mL) was added DIPEA (0.16 mL, 0.90 mmol), 30-1 (140 mg, 0.30 mmol), and HATU (114 mg, 0.30 mmol) and the resulting mixture was stirred at RT for 3 h. TFA (4.60 mL, 59.7 mmol) was added and stirring was continued for 90 min. The reaction mixture was then concentrated under reduced pressure and the crude material was purified by reverse-phase column chromatography (eluting with 0-100% water/ACN with 0.1% NH$_4$OH) to afford 15-2 (183 mg, 0.18 mmol, 60% yield) after freeze drying the pure fractions. Analytical Method 5, t$_R$=0.82 min., [M+H]$^+$=1019.7.

Step 3. 2-(((3R,7S,10S,13R)-6-(4-Chloro-2-(4-(1-methyl-2-(pyrrolidin-1-ylmethyl)-1H-imidazol-5-yl)phenoxy)benzyl)-13-(4-chlorobenzyl)-10-((difluoromethoxy)methyl)-7-methyl-2,5,8,11-tetraoxo-1,6,9,12-tetraazabicyclo[11.3.1]heptadecan-3-yl)methyl)pyridine 1-oxide (15-3)

To a solution of 15-2 (167 mg, 0.16 mmol) in DCM (100 mL) was added 2,6-lutidine (0.57 mL, 4.91 mmol), HOAt (22.3 mg, 0.16 mmol) and HATU (249 mg, 0.66 mmol) and the resulting mixture was heated to reflux overnight in a 48° C. The reaction mixture was cooled to RT and concentrated. The resulting residue was partitioned between EtOAc (100 mL) and 5% NaHCO$_3$ (100 mL). The organic phase was washed with 5% NaHCO$_3$ (2×50 mL) and brine (50 mL), dried over Na$_2$SO$_4$, filtered, and concentrated to dryness under reduced pressure to afford 15-3 (164 mg, 0.16 mmol, ~quantitative yield). The product was used in the next step without further purification. Analytical Method 5, $t_R$=1.16 min., [M+H]$^+$=1001.6.

Step 4. (3R,7S,10S,13R)-6-(4-Chloro-2-(4-(1-methyl-2-(pyrrolidin-1-ylmethyl)-1H-imidazol-5-yl)phenoxy)benzyl)-13-(4-chlorobenzyl)-10-((difluoromethoxy)methyl)-7-methyl-3-(pyridin-2-ylmethyl)-1,6,9,12-tetraazabicyclo[11.3.1]heptadecane-2,5,8,11-tetraone (Compound 30)

To a solution of 15-3 (164 mg, 0.16 mmol) in THF (20 mL) was added saturated NH$_4$Cl (6.7 mL), zinc dust (685 mg, 10.5 mmol), and citric acid (566 mg, 2.95 mmol). The resulting mixture was stirred at RT for 30 min to afford a biphasic mixture. The organic phase was collected and the remaining aqueous phase was washed with 50 mL of DCM. The combined organic phases were concentrated to dryness, and the resulting residue was taken up in DCM and washed with a 5% NaHCO$_3$ solution. The organic phase was separated, dried over sodium sulfate, filtered, and concentrated. The crude material was purified by reverse-phase column chromatography (eluting with 0-100% water/ACN with 0.1% NH$_4$OH) to afford the desired product with minor impurities. The material was purified again by HPLC (eluting with 0-100% water/ACN with 0.1% NH$_4$OH as modifier) to afford Compound 30 (63 mg, 0.06 mmol, 37% yield) as a white powder after freeze drying the pure fractions. Analytical Method 2, $t_R$=3.04 min., [M+H]$^+$=985.4.

Example 8.35: Synthesis of 2-(((3R,7S,10S,13R)-6-(4-Chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-2,5,8,11-tetraoxo-1,6,9,12-tetraazabicyclo[11.3.1]heptadecan-3-yl)methyl)pyridine 1-oxide (Compound 66)

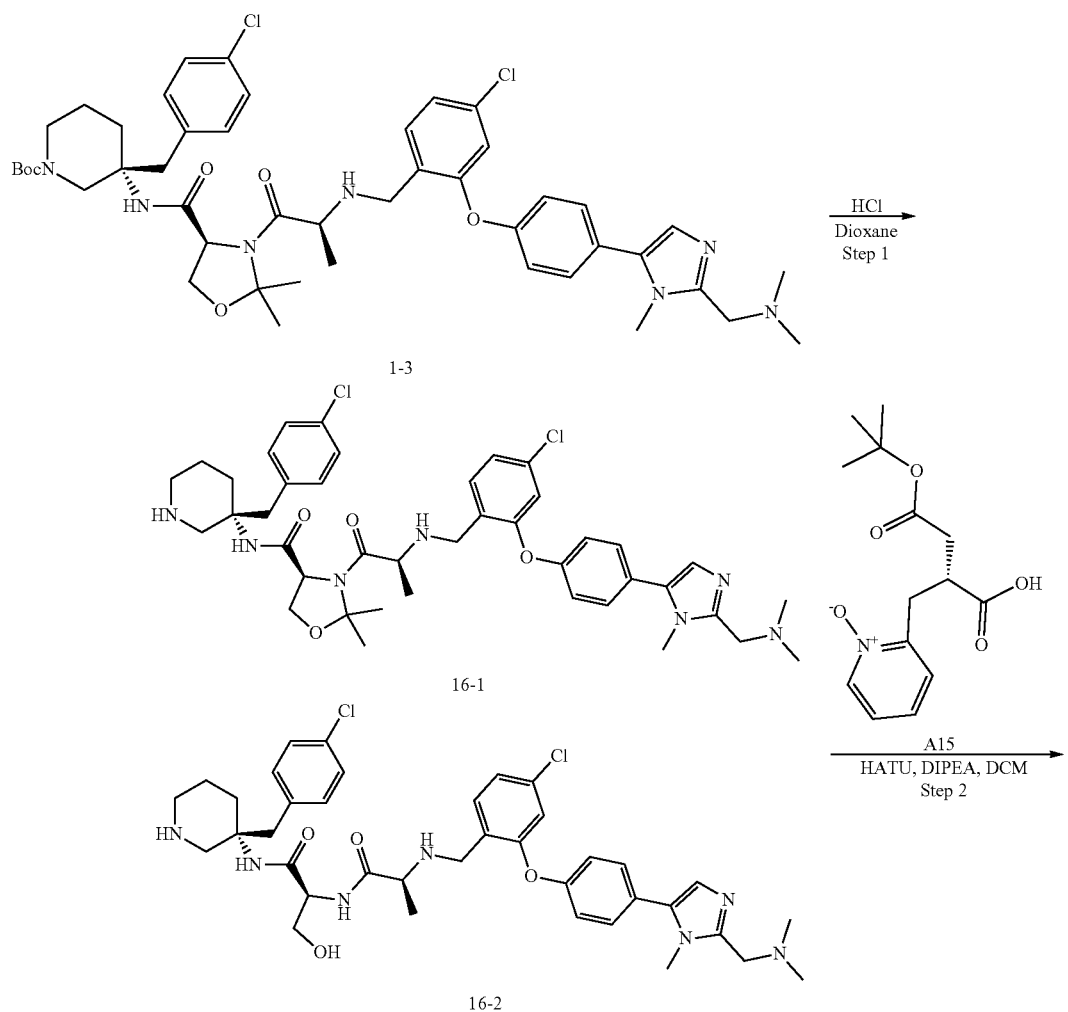

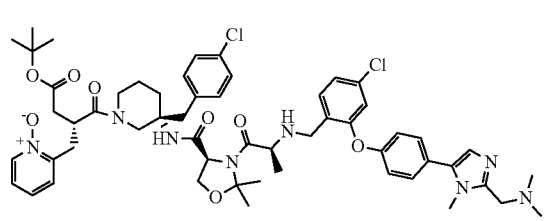

16-3

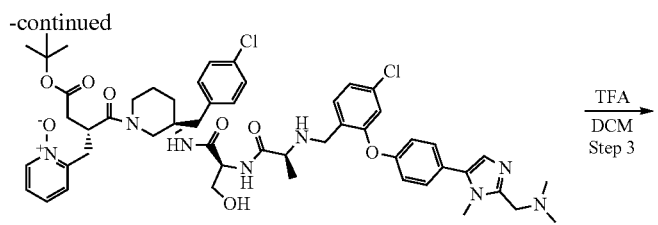

16-4

TFA
DCM
Step 3

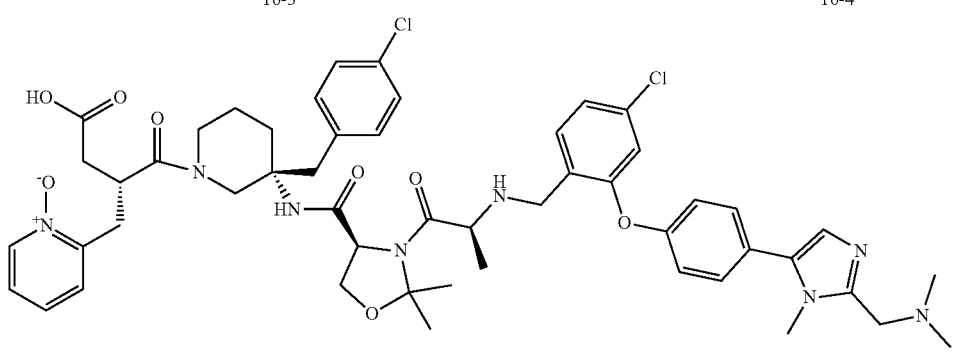

16-5 i. HATU, HOAt, 2,6-lutidine
DCM, 40° C.
ii. TFA, DCM/H₂O, rt

Step 4

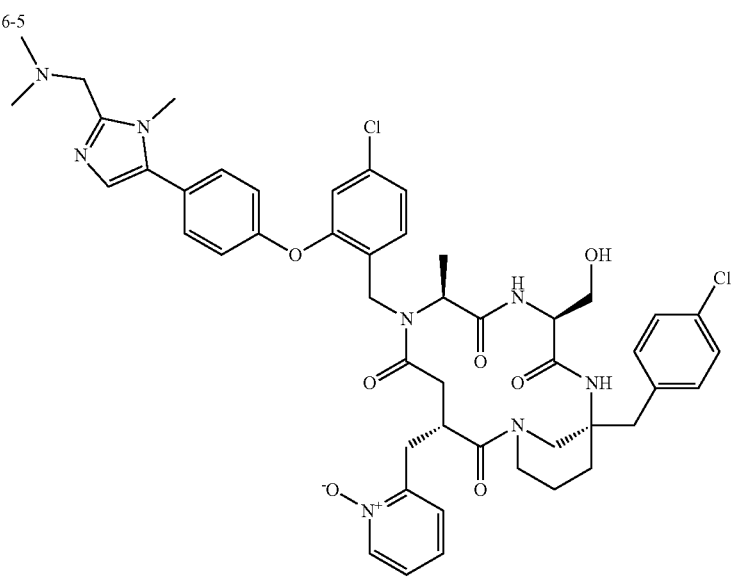

Compound 66

Step 1. (S)-3-((4-chloro-2-(4-(2-((dimethylamino) methyl)-1-methyl-1H-imidazol-5-yl)phenoxy)benzyl)-L-alanyl)-N—((R)-3-(4-chlorobenzyl)piperidin-3-yl)-2,2-dimethyloxazolidine-4-carboxamide (16-1) and (S)-2-((S)-2-((4-chloro-2-(4-(2-((dimethylamino)methyl)-1-methyl-1H-imidazol-5-yl)phenoxy)benzyl)amino)propanamido)-N—((R)-3-(4-chlorobenzyl)piperidin-3-yl)-3-hydroxypropanamido (16-2)

4 N HCl in dioxane (1.0 mL, 4.00 mmol) was added to 1-3 (105.2 mg, 0.12 mmol) in a round bottom flask charged with a magnetic stir bar. Additional dioxane (3 mL) was then added in one portion via syringe. The resulting mixture was allowed to stir at RT for 2.5 h and then concentrated in vacuo to provide 88 mg of a white solid containing a 60/40 mixture of 16-1 (Analytical Method 5, $t_R$=1.21 min., [M+H]⁺=776.4) and 16-2 (Analytical Method 5, $t_R$=1.09 min., [M+H]⁺=736.3) by LCMS. The product mixture was taken on to the next step without further purification.

Step 2. 2-((R)-4-(tert-Butoxy)-2-((R)-3-((S)-3-((4-chloro-2-(4-(2-((dimethylamino)methyl)-1-methyl-1H-imidazol-5-yl)phenoxy)benzyl)-L-alanyl)-2,2-dimethyloxazolidine-4-carboxamido)-3-(4-chlorobenzyl)piperidine-1-carbonyl)-4-oxobutyl) pyridine 1-oxide (16-3) and 2-((R)-4-(tert-Butoxy)-2-((R)-3-((S)-2-((S)-2-((4-chloro-2-(4-(2-((dimethylamino)methyl)-1-methyl-1H-imidazol-5-yl)phenoxy)benzyl)amino)propanamido)-3-hydroxypropanamido)-3-(4-chlorobenzyl) piperidine-1-carbonyl)-4-oxobutyl)pyridine 1-oxide (16-4)

A15 (34 mg, 0.12 mmol) was added in one portion via syringe as a solution in DCM (4 mL) to a 60/40 crude mixture of 16-1 and 16-2 (88 mg, 0.12 mmol) in a round bottom flask charged with a magnetic stir bar. DIPEA (0.126 mL, 0.12 mmol) was then added in one portion via syringe, followed by the addition of HATU (59 mg, 0.16 mmol). The resulting mixture was stirred at RT overnight, then diluted with DCM, and washed with saturated NH$_4$Cl (×2) and brine. The organic phase was dried over Na$_2$SO$_4$, filtered, and concentrated in vacuo to provide a pale yellow oil, which contained both 16-3 (Analytical Method 5, $t_R$=1.23 min., [M+H]$^+$=1039.7) and 16-4 (Analytical Method 5, $t_R$=1.12 min., [M+H]$^+$=999.6) by LCMS. The crude mixture was taken on to the next step without further purification (assumed quantitative yield for reagent calculations in the next step).

Step 3. 2-((R)-2-(Carboxymethyl)-3-((R)-3-((S)-3-((4-chloro-2-(4-(2-((dimethylamino)methyl)-1-methyl-1H-imidazol-5-yl)phenoxy)benzyl)-L-alanyl)-2,2-dimethyloxazolidine-4-carboxamido)-3-(4-chlorobenzyl)piperidin-1-yl)-3-oxopropyl)pyridine 1-oxide (16-5)

TFA (0.925 mL, 12.00 mmol) was added in one portion via syringe to the crude mixture containing 16-3 and 16-4 (0.12 mmol) in DCM (4 mL) in a round bottom flask charged with a magnetic stir bar. The resulting mixture was stirred at RT under a N$_2$ atmosphere for 2 h and then concentrated in vacuo. The obtained residue was taken up in DCM, and concentrated in vacuo again to provide a crude yellow residue. This process was repeated (×2) to remove the residual TFA. The crude product was taken up in DMSO (3 mL), filtered, and purified via reverse phase HPLC (30×100 mm 5 m column, eluting with 15-40% MeCN:H$_2$O with 5 mM NH$_4$OH, 2×1.5 mL injections, 75 mL/min) to provide 13.2 mg (11% yield) of 16-5 as a white powder after freeze drying the product containing fractions. Analytical Method 5, $t_R$=0.80 min., [M+H]+=983.6.

Step 4. 2-(((3R,7S,10S,13R)-6-(4-Chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-2,5,8,11-tetraoxo-1,6,9,12-tetraazabicyclo[11.3.1]heptadecan-3-yl)methyl) pyridine 1-oxide (Compound 66)

2,6-lutidine (0.016 mL, 0.13 mmol) was added in one portion via syringe to 16-5 (13.2 mg, 0.01 mmol) in DCM (13 mL) in a round bottom flask charged with a magnetic stir bar. HOAt (3.7 mg, 0.03 mmol) was then added, followed by the addition of HATU (10.2 mg, 0.03 mmol. The resulting mixture was heated to 40° C. overnight and then diluted with EtOAc. The organic phase was washed with saturated NaHCO$_3$ (×3) and brine, dried over Na$_2$SO$_4$, filtered, and concentrated in vacuo. The crude material was transferred to a glass vial and taken up in DCM (0.5 mL). H$_2$O (0.3 mL) was added, followed by TFA (0.2 mL, 2.60 mmol) at RT. The reaction mixture was allowed to stir for 45 min and then partially concentrated in vacuo. The resulting residue was taken up in DMSO, filtered, and purified by reverse phase HPLC (30×100 mm 5 m column, eluting with 35-60% MeCN:H$_2$O with 5 mM NH$_4$OH, 1×1.5 mL injection, 75 mL/min) to provide 0.6 mg (5%) of Compound 66 as a white solid after freeze drying the product containing fractions. Analytical Method 4, $t_R$=1.63 min., [M+H]$^+$=925.5.

Example 8.36: Synthesis of (3R,7S,10S,13R)-6-(4-Chloro-2-(4-(2-((dimethylamino)methyl)-1-methyl-1H-imidazol-5-yl)phenoxy)benzyl)-13-(4-chlorobenzyl)-10-(methoxymethyl)-7-methyl-3-((6-methylpyridin-2-yl)methyl)-1,6,9,12-tetraazabicyclo[11.3.1]heptadecane-2,5,8,11-tetraone (Compound 4)

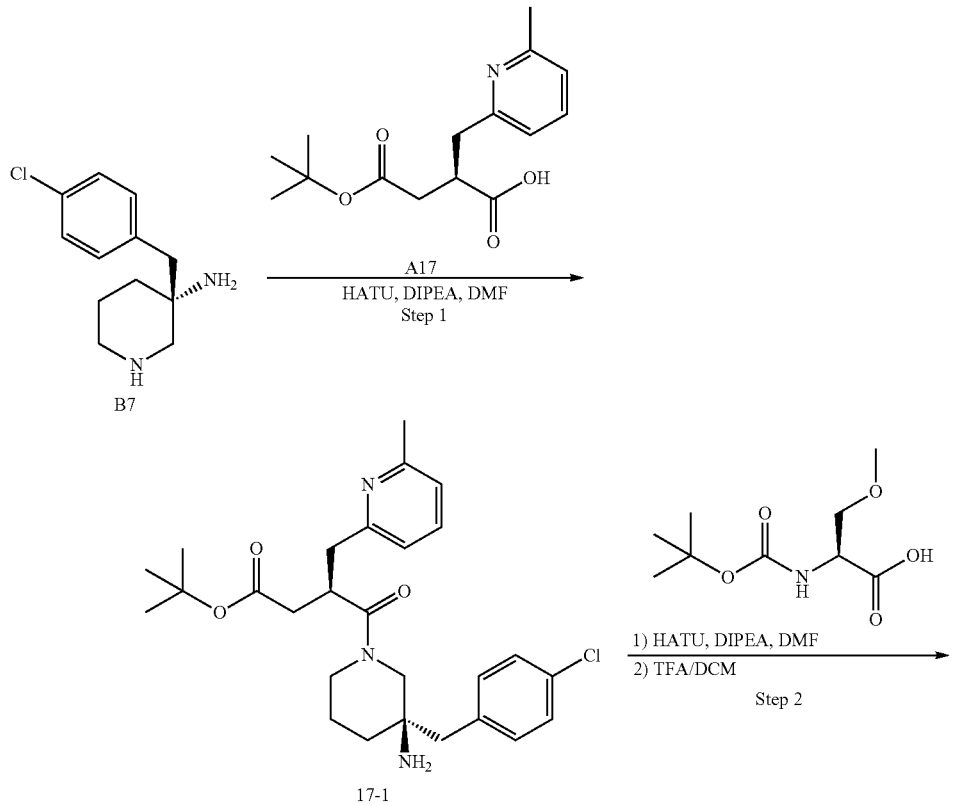

-continued
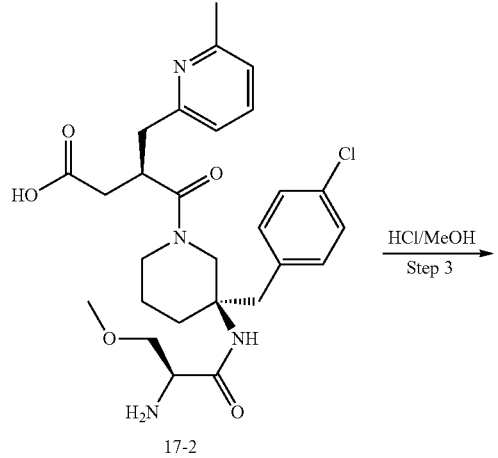
17-2
HCl/MeOH
Step 3
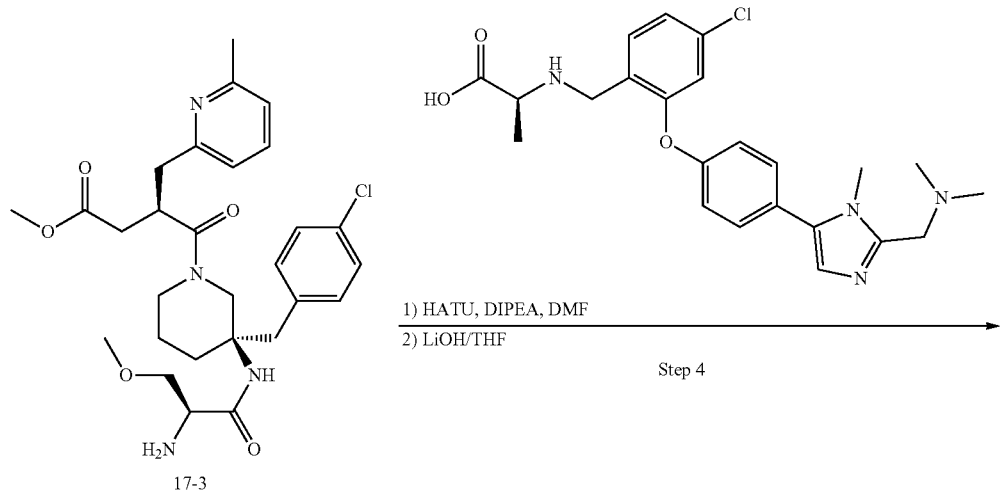
17-3
1) HATU, DIPEA, DMF
2) LiOH/THF
Step 4
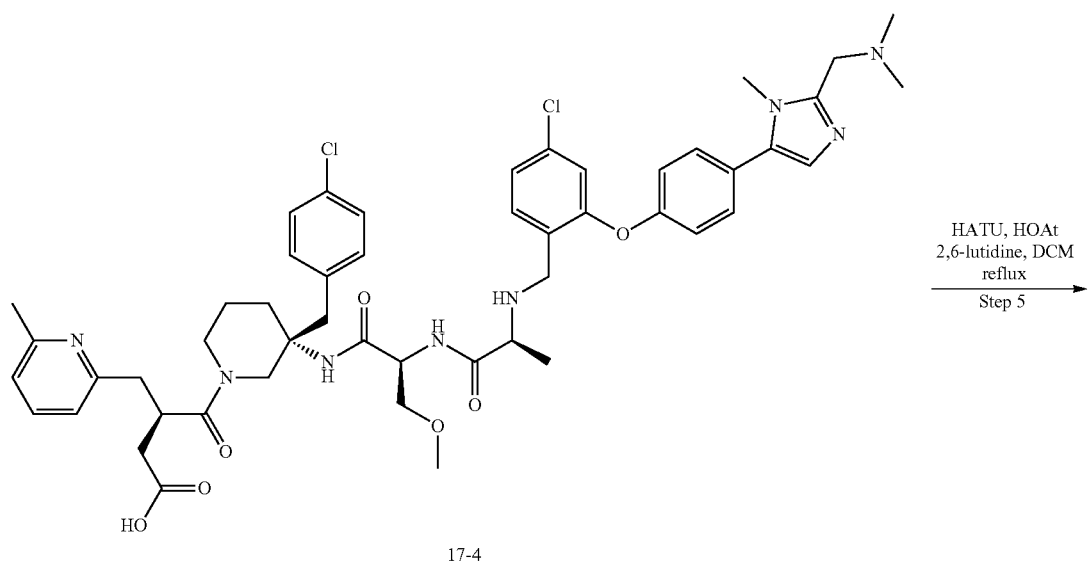
17-4
HATU, HOAt
2,6-lutidine, DCM
reflux
Step 5

-continued

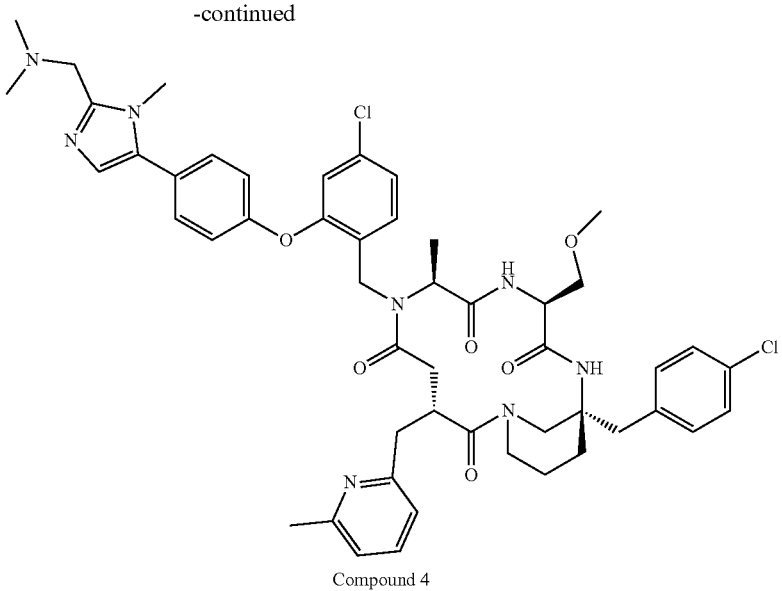

Compound 4

Step 1. tert-Butyl (R)-4-((R)-3-amino-3-(4-chlorobenzyl)piperidin-1-yl)-3-((6-methylpyridin-2-yl)methyl)-4-oxobutanoate (17-1)

To a solution of A17 (523 mg, 1.68 mmol) in anhydrous DMF (20 mL) was added DIPEA (1.47 mL, 8.40 mmol) and B7 (500 mg, 1.68 mmol) at 0° C. followed by HATU (703 mg, 1.85 mmol) and the resulting mixture was warmed to RT and stirred for 2 h. EtOAc was added and the reaction mixture was washed with a 5% aq. NaHCO$_3$ solution, saturated NaHCO$_3$ solution, and brine. The organic phase was dried over Na$_2$SO$_4$, filtered, and concentrated. The crude material was purified by reverse-phase column chromatography (eluting with 0-100% water/ACN with 0.1% NH$_4$OH, product elute ~80% ACN) to afford 17-1 as a dark material after freeze drying the pure fractions (637 mg, 78% yield). The material contained a major impurity and was carried to the next step without additional purification. Analytical Method 5, $t_R$=1.12 min., [M+H]$^+$=486.3.

Step 2. (R)-4-((R)-3-((S)-2-amino-3-methoxypropanamido)-3-(4-chlorobenzyl)piperidin-1-yl)-3-((6-methylpyridin-2-yl)methyl)-4-oxobutanoic acid (17-2)

To a mixture of 17-1 (315 mg, 0.65 mmol) in anhydrous DMF (5 mL) was added a solution of (S)-2-((tert-butoxycarbonyl)amino)-3-methoxypropanoic acid (170 mg, 0.78 mmol), DIPEA (0.34 mL, 1.94 mmol) and a solution of HATU (296 mg, 0.78 mmol in 4 mL) in DMF) and the resulting mixture was stirred at RT for 4 h. EtOAc was added and the reaction mixture was washed with a solution of NaHCO$_3$ and brine. The organic phase was dried over Na$_2$SO$_4$, filtered, and concentrated. The crude product was purified by flash column chromatography on silica gel (eluting with 20-100% EtOAc/heptane, product eluted out ~ 100% EtOAc) to afford 17-2 as a light brown oil after concentrating the pure fractions (445 mg, 85% yield). Analytical Method 5, $t_R$=0.60 min., [M+H]$^+$=531.4.

Step 3. methyl (R)-4-((R)-3-((S)-2-Amino-3-methoxypropanamido)-3-(4-chlorobenzyl)piperidin-1-yl)-3-((6-methylpyridin-2-yl)methyl)-4-oxobutanoate (17-3)

To a solution of 17-2 (378 mg, 0.55 mmol) in anhydrous DCM (1 mL) was added TFA (2.12 mL, 27.5 mmol). The resulting mixture was stirred at RT for 2-3 h and then concentrated to dryness under reduced pressure and dried under high vacuum to afford 17-3 (418 mg, quantitative yield). Analytical Method 5, $t_R$=0.96 min., [M+H]$^+$=545.3.

Step 4. (R)-4-((R)-3-((S)-2-((S)-2-((4-Chloro-2-(4-(2-((dimethylamino)methyl)-1-methyl-1H-imidazol-5-yl)phenoxy)benzyl)amino)propanamido)-3-methoxypropanamido)-3-(4-chlorobenzyl)piperidin-1-yl)-3-((6-methylpyridin-2-yl)methyl)-4-oxobutanoic acid (17-4)

Step 4-1: To a solution of 17-3 (248 mg, 0.45 mmol) in anhydrous DMF (8 mL) was added DE1 (222 mg, 0.50 mmol), DIPEA (0.25 mL, 1.43 mmol) and HATU (208 mg, 0.55 mmol) and the resulting mixture was stirred at RT for 2-3 h. EtOAc was added and the reaction mixture was washed with a solution of sodium carbonate and brine. The organic phase was dried over Na$_2$SO$_4$, filtered, and concentrated. The crude product was purified by reverse-phase column chromatography (eluting with 0-100% water/ACN, 0.1% NH$_4$OH, product eluted around 90% ACN) to afford the desired product. The pooled fractions was concentrated to remove excess ACN and extracted twice with EtOAc. The organic phase was dried over Na$_2$SO$_4$, filtered, and concentrated to afford the methyl ester as a white foam (441 mg, 37% yield).

Step 4-2: To the methyl ester from Step 4-1 (164 mg, 0.17 mmol) in THF (6 mL) and water (1.5 mL) and cooled in an ice bath was added LiOH (1 N, 0.25 mL, 0.51 mmol). The resulting mixture was stirred at RT for 2 h before being quenched by the addition of aq. HCl (0.51 mL, 0.507 mmol) and a solution of NaHCO$_3$ (to adjust pH to 7-8). The reaction mixture was extracted with EtOAc (×2) and the combined organic phases were dried over sodium sulfate, filtered, and concentrated to afford 17-4 as a white gummy solid after drying (162 mg, 87% yield). The product was carried to the next step without purification. Analytical Method 5, $t_R$=1.79 min., [M+H]⁺=955.7.

Step 5. (3R,7S,10S,13R)-6-(4-chloro-2-(4-(2-((dimethylamino)methyl)-1-methyl-1H-imidazol-5-yl)phenoxy)benzyl)-13-(4-chlorobenzyl)-10-(methoxymethyl)-7-methyl-3-((6-methylpyridin-2-yl)methyl)-1,6,9,12-tetraazabicyclo[11.3.1]heptadecane-2,5,8,11-tetraone (Compound 4)

To a solution of 17-4 (141 mg, 0.15 mmol) in DCM (150 mL) was added 2,6-lutidine (0.5 mL, 4.29 mmol), HOAt (20.1 mg, 0.15 mmol), and HATU (224 mg, 0.59 mmol). The resulting mixture was heated to reflux for overnight in a 48° C., cooled to RT and concentrated to dryness. The obtained residue was purified by reverse-phase column chromatography (eluting with 0-100% water/can with 0.1% NH₄OH, then 50-100% water/IPA with 0.1% NH₄OH, product eluted 60% IPA) to afford the desired product after concentrating the pure fractions. The product was purified again using basic HPLC to afford Compound 4 as a white solid after freeze drying the pure fractions (64 mg, 45% yield). Analytical Method 2, $t_R$=2.83 min., [M+H]⁺=937.3.

The compounds in Table 25 were synthesized according to the procedure described in Example 8.36 for Compound 4 from the respective intermediates shown in Tables 1-7 and described above in Example 8.

TABLE 25

| Cmd No. | Structure | LCMS |
|---|---|---|
| 17 | 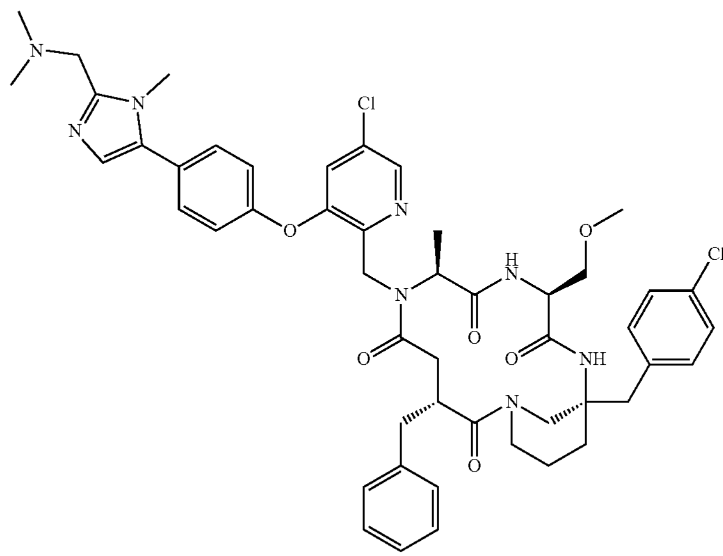 [SMILES: COC[C@@H]1NC(=O)[C@H](C)N(Cc2ncc(Cl)cc2Oc2ccc(-c3cnc(CN(C)C)n3C)cc2)C(=O)C[C@@H](Cc2ccccc2)C(=O)N2CCC[C@@](Cc3ccc(Cl)cc3)(C2)NC1=O] | Analytical Method 2<br>$t_R$ = 2.95 min.<br>[M + H]⁺ = 923.0 |
| 35 | 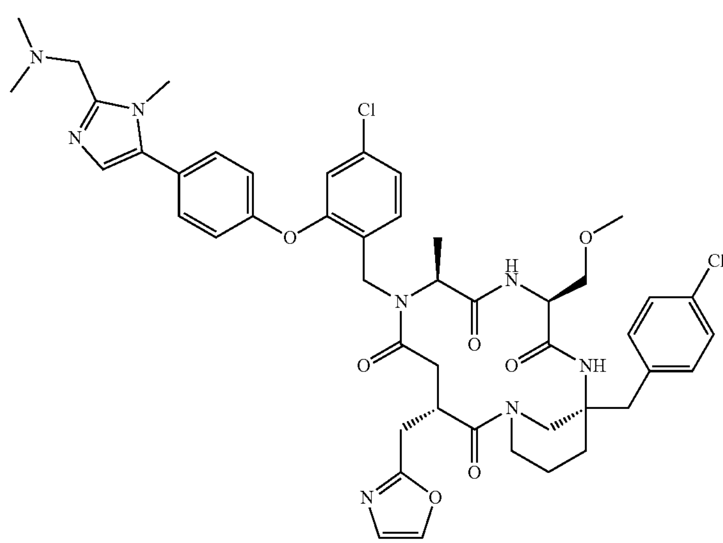 [SMILES: COC[C@@H]1NC(=O)[C@H](C)N(Cc2ccc(Cl)cc2Oc2ccc(-c3cnc(CN(C)C)n3C)cc2)C(=O)C[C@@H](Cc2ncco2)C(=O)N2CCC[C@@](Cc3ccc(Cl)cc3)(C2)NC1=O] | Analytical Method 2<br>$t_R$ = 2.66 min.<br>[M + H]⁺ = 913.4 |

TABLE 25-continued
| Cmd No. | Structure | LCMS |
|---|---|---|
| 44 | 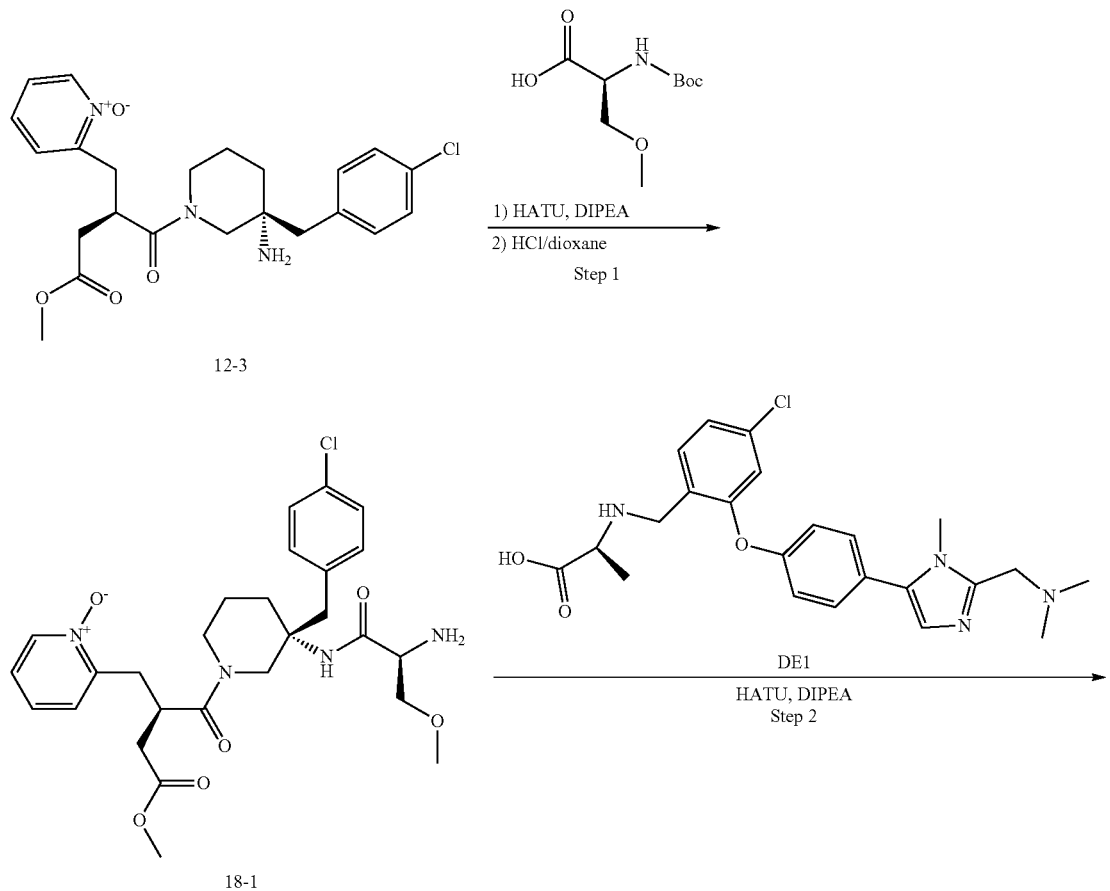 | Analytical Method 2<br>$t_R$ = 2.53 min.<br>$[M + H]^+$ = 953.5 |
Example 8.37: Synthesis of (3R,7S,10S,13R)-6-(4-Chloro-2-(4-(2-((dimethylamino)methyl)-1-methyl-1H-imidazol-5-yl)phenoxy)benzyl)-13-(4-chlorobenzyl)-10-(methoxymethyl)-7-methyl-3-(pyridin-2-ylmethyl)-1,6,9,12-tetraazabicyclo[11.3.1]heptadecane-2,5,8,11-tetraone (Compound 21)

-continued
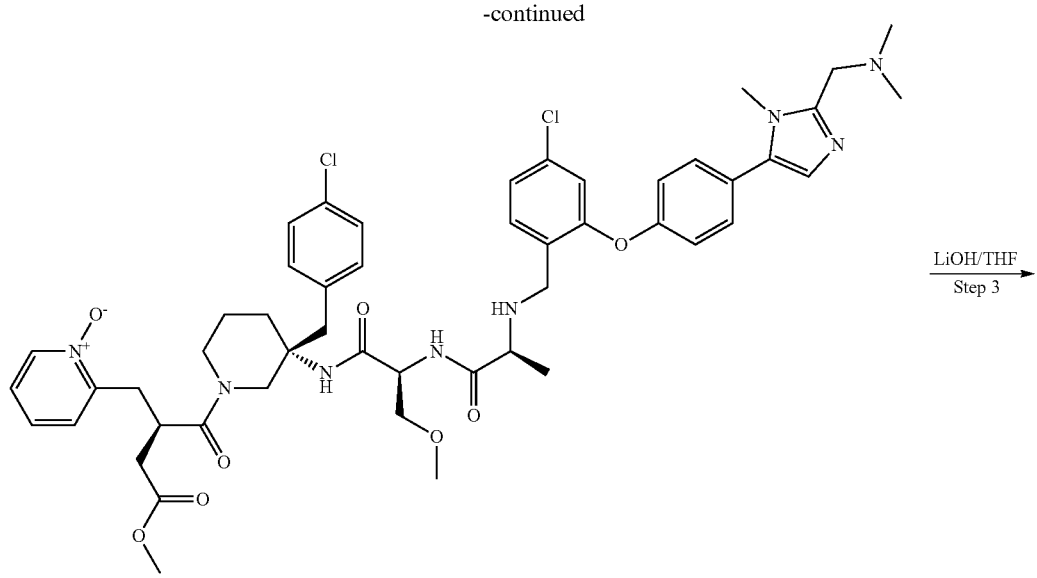
18-2
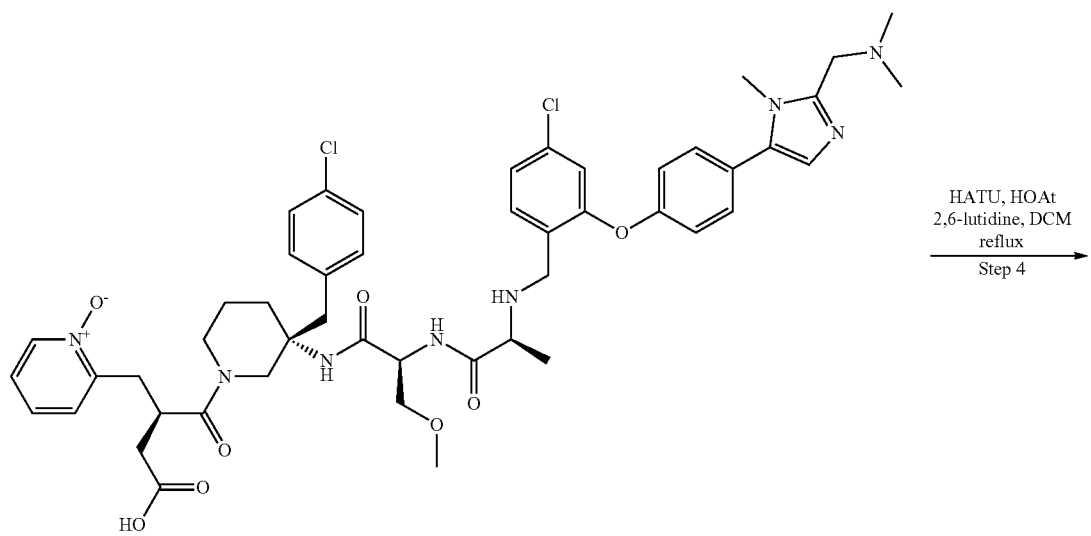
18-3

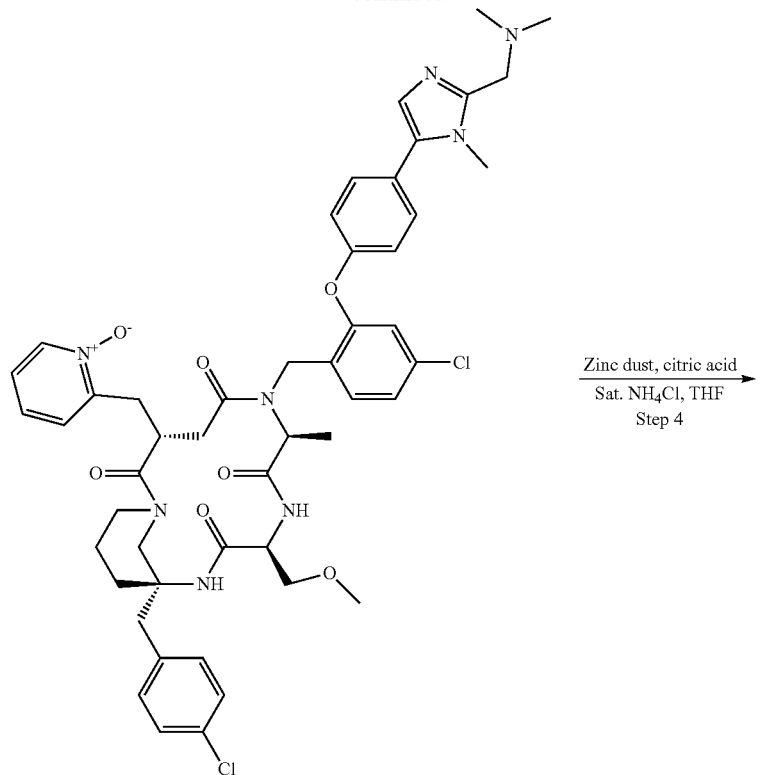
18-4
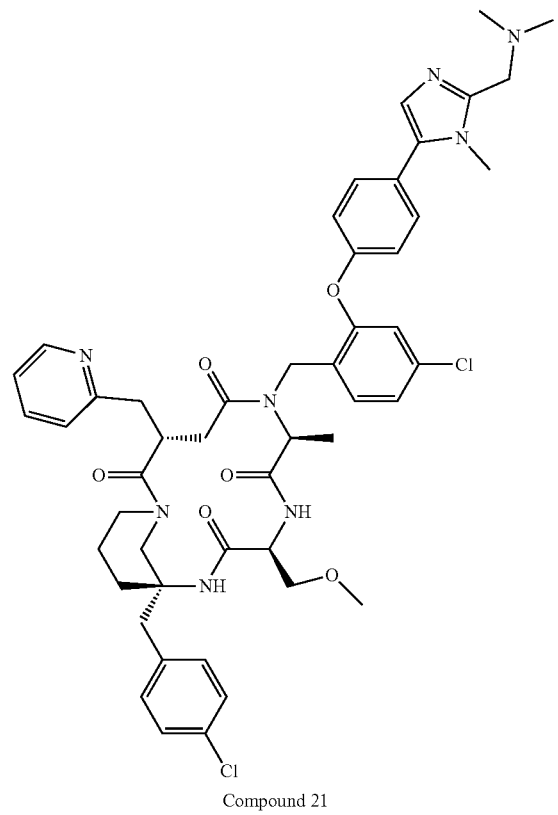
Compound 21

Step 1. 2-((R)-2-((R)-3-((S)-2-((tert-Butoxycarbonyl)amino)-3-methoxypropanamido)-3-(4-chlorobenzyl)piperidine-1-carbonyl)-4-methoxy-4-oxobutyl)pyridine 1-oxide (18-1)

Step 1-1: To a solution of 12-3 (168 mg, 0.38 mmol) in anhydrous DMF (3 mL) was added of (S)-2-((tert-butoxycarbonyl)amino)-3-methoxypropanoic acid (99 mg, 0.45 mmol) and DIPEA (0.2 mL, 1.14 mmol) and the resulting mixture was stirred at RT. A solution of HATU (172 mg, 0.45 mmol) in DMF (3 mL) was added and stirring was continued for overnight. EtOAc was added and the reaction mixture was washed with a solution of sodium carbonate and twice with brine. The organic phase was dried over $Na_2SO_4$, filtered, and concentrated. The crude product was purified by flash column chromatography on silica gel (eluting with 0-100% EtOAc/Heptane, product eluted as a broad peak ~100% EtOAc, the remaining product was eluted out by using 5% MeOH in EtOAc) to afford the interim product which was used directly in the following step without further purification (233 mg, 96%).

Step 1-2: To the product from Step 1-1 (233 mg, 0.36 mmol) in dioxane (1 mL) was added a solution of HCl in dioxane (5 mL, 20.0 mmol) and the resulting mixture was stirred at RT for 1 h. The reaction mixture was concentrated under reduced pressure, and dried under high vacuum to afford 18-1 as a crude product (238 mg, ~quantitative yield), which was used in the next step without purification. Analytical Method 7, $t_R$=0.68 min., $[M+H]^+$=547.4.

Step 2. 2-((R)-2-((R)-3-((S)-2-((S)-2-((4-Chloro-2-(4-(2-((dimethylamino)methyl)-1-methyl-1H-imidazol-5-yl)phenoxy)benzyl)amino)propanamido)-3-methoxypropanamido)-3-(4-chlorobenzyl)piperidine-1-carbonyl)-4-methoxy-4-oxobutyl)pyridine 1-oxide (18-2)

To a mixture of 18-1 (238 mg, 0.37 mmol) in anhydrous DMF (6 mL) was added DE1 (195 mg, 0.44 mmol), DIPEA (0.32 mL, 1.83 mmol) and HATU (167 mg, 0.44 mmol) and the resulting mixture was stirred at RT for 2 h. EtOAc was added and the reaction mixture was washed with a solution of sodium carbonate, brine. The organic phase was dried over $Na_2SO_4$, filtered, and concentrated. The crude product was purified by reverse-phase column chromatography (eluting with 10-100% $H_2O$/ACN with 0.1% $NH_4OH$, product eluted ~75% ACN) to afford the desired product. The pure fractions was concentrated down, extracted with EtOAc twice, dried over $Na_2SO_4$, filtered, and concentrated to afford 18-2 after drying under high vacuum (172 mg, 48%). Analytical Method 5, $t_R$=1.08 min., $[M+H]^+$=971.4.

Step 3. 2-((R)-2-(Carboxymethyl)-3-((R)-3-((S)-2-((S)-2-((4-chloro-2-(4-(2-((dimethylamino)methyl)-1-methyl-1H-imidazol-5-yl)phenoxy)benzyl)amino)propanamido)-3-methoxypropanamido)-3-(4-chlorobenzyl)piperidin-1-yl)-3-oxopropyl)pyridine 1-oxide (18-3)

To 18-2 (172 mg, 0.18 mmol) in anhydrous THF (4 mL) and water (1 mL) and cooled in an ice bath was added LiOH (0.25 mL, 0.50 mmol). The cooling bath was removed and the mixture was stirred at RT for 4 h. HCl (1N) was then added to adjust the pH to between 7-8. The resulting mixture was then extracted with EtOAc (×2) and DCM (×2). The combined organic phases were dried over sodium sulfate, filtered, and concentrated to afford 18-3 as a white foam after drying under high vacuum (162 mg, 96% yield). Analytical Method 5, $t_R$=0.77 min., $[M+H]^+$=957.4.

Step 4. 2-(((3R,7S,10S,13R)-6-(4-Chloro-2-(4-(2-((dimethylamino)methyl)-1-methyl-1H-imidazol-5-yl)phenoxy)benzyl)-13-(4-chlorobenzyl)-10-(methoxymethyl)-7-methyl-2,5,8,11-tetraoxo-1,6,9,12-tetraazabicyclo[11.3.1]heptadecan-3-yl)methyl)pyridine 1-oxide (18-4)

To a mixture of 18-3 (162 mg, 0.17 mmol) in DCM (100 mL) at RT was added HOAt (23 mg, 0.17 mmol), HATU (257 mg, 0.68 mmol) and 2,6-lutidine (0.59 mL, 5.07 mmol). The resulting mixture was heated to reflux for overnight (bath temp 50° C.) and then cooled to rt and concentrated to dryness under reduced pressure. The crude product was then taken up in EtOAc and washed with a 5% $NaHCO_3$ solution. Some product precipitated out of the organic phase and was dissolved with ACN after decanting away the aq. phase. The organic phase was concentrated to afford a crude material, which was purified by reverse phase column (eluting with 0-100% water/ACN with 0.1% $NH_4OH$, product eluted ~80% ACN). The pure fractions were concentrated down and extracted with EtOAc (×2). The organic phase was dried over sodium sulfate, filtered, and concentrated to afford 18-4 after high vacuum drying (88 mg, 55% yield). Analytical Method 5, $t_R$=1.03 min., $[M+H]^+$=939.6.

Step 5. (3R,7S,10S,13R)-6-(4-Chloro-2-(4-(2-((dimethylamino)methyl)-1-methyl-1H-imidazol-5-yl)phenoxy)benzyl)-13-(4-chlorobenzyl)-10-(methoxymethyl)-7-methyl-3-(pyridin-2-ylmethyl)-1,6,9,12-tetraazabicyclo[11.3.1]heptadecane-2,5,8,11-tetraone (Compound 21)

To a solution of 18-4 (88 mg, 0.09 mmol) in THF (9 mL) was added saturated $NH_4Cl$ (3.00 mL), zinc dust (392 mg, 5.99 mmol), and citric acid (324 mg, 1.68 mmol). The resulting mixture was stirred at RT for 1.5 h and then filtered through a pad of Celite®. EtOAc was added and the mixture was washed with a saturated solution of NaHCO₃. The phases were separated and the aqueous phase was back extracted twice with EtOAc. The combined organic phases were concentrated. The crude product was purified by basic HPLC to afford Compound 21 after freeze drying the pure fractions (30 mg, 34% yield). Analytical Method 2, $t_R$=2.76 min., [M+H]⁺=923.6.

Example 8.38: Synthesis of (3R,7S,10S,13R)-3-((E)-but-2-en-1-yl)-6-(4-Chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-1,6,9,12-tetraazabicyclo[11.3.1]heptadecane-2,5,8,11-tetraone (Compound 40)

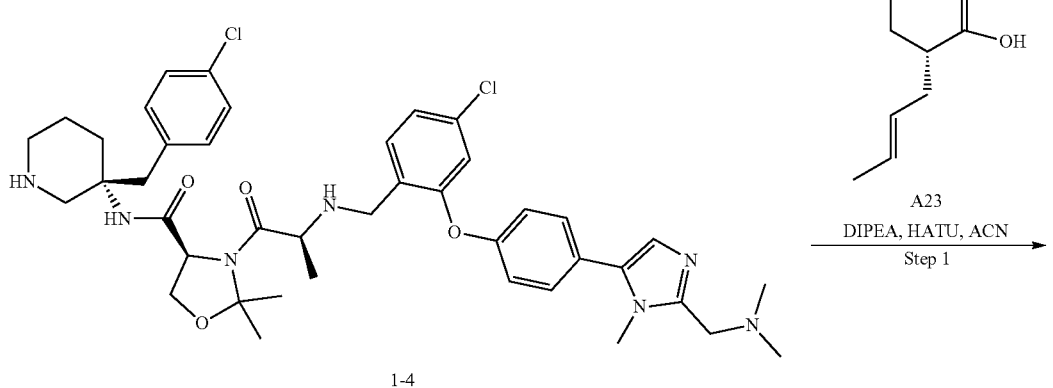

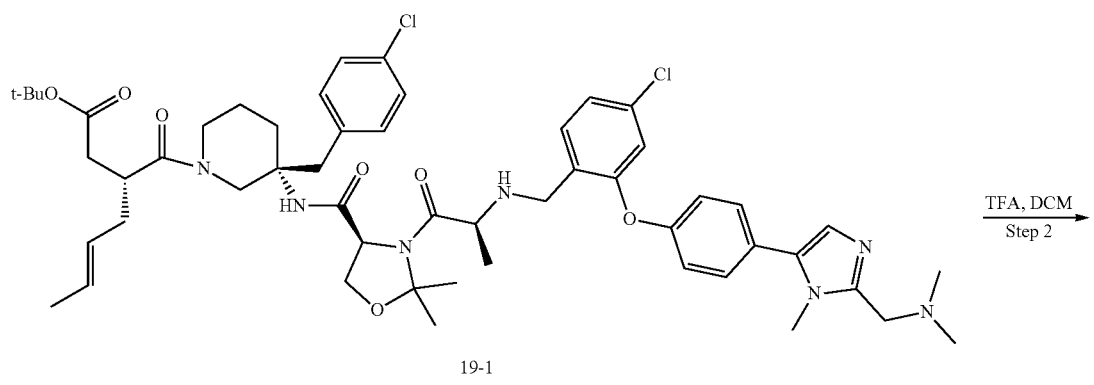

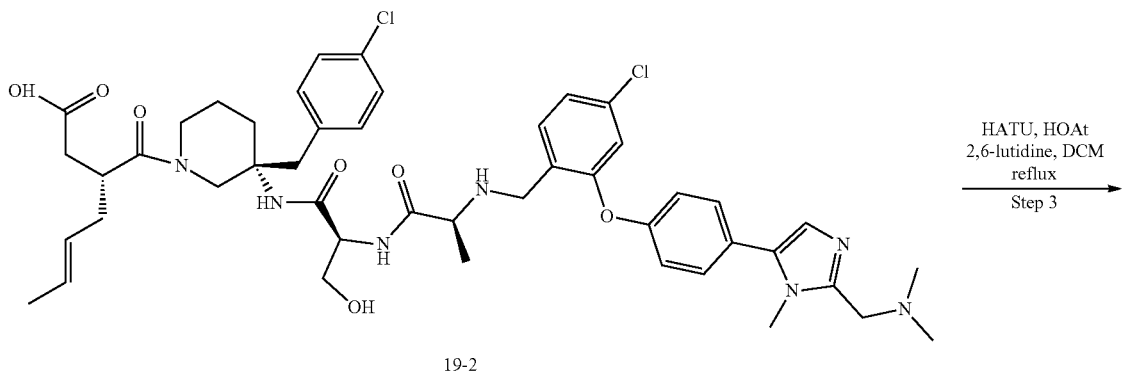

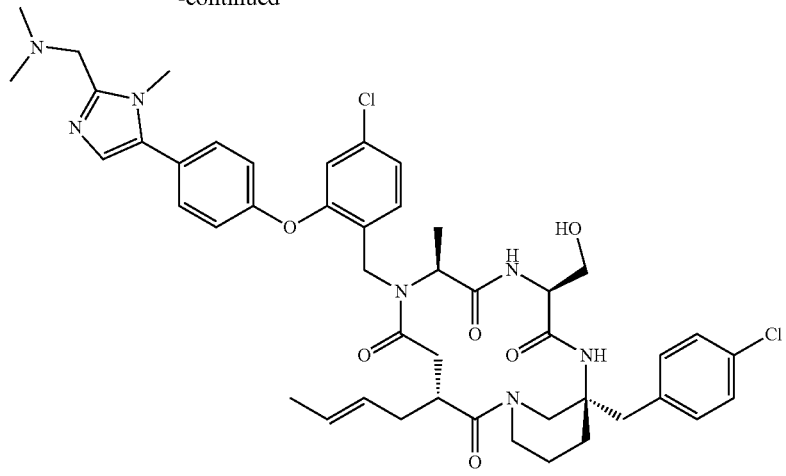

Compound 40

Step 1. (R,E)-tert-Butyl 3-((R)-3-((S)-3-((S)-2-((4-choro-2-(4-(2-((dimethylamino)methyl)-methyl-1H-imidazol-5-yl)phenoxy)benzyl)amino)propanoyl)-2,2-dimethyloxazolidine-4-carboxamido)-3-(4-chlorobenzyl)piperidine-1-carbonyl)hept-5-enoate (19-I)

To a solution of A23 (106 mg, 0.46 mmol) in DMF (1.5 mL) was added DIPEA (0.20 mL, 1.16 mmol) and HATU (184 mg, 0.48 mmol). The resulting mixture was stirred at RT for 5 min before being added to a solution of 1-4 (300 mg, 0.39 mmol) in DMF (2 m. The reaction mixture was stirred for 2 h and then quenched with a 5% sodium bicarbonate solution and extracted with EtOAc. The organic phase was washed with 5% sodium bicarbonate and brine respectively, dried over sodium sulfate, filtered and concentrated to afford 19-I as a foam after drying under high vacuum (390 mg, assume quantitative yield). The material was used in the next step without purification. Analytical Method 5, $t_R$=1.41 min. [M+H]$^+$=986.8.

Step 2. (R,E)-3-((R)-3-((S)-2-((S)-2-((4-Chloro-2-(4-(2-(dimethylamino)methyl)-1-methyl-1H-imidazol-5-yl)phenoxy)benzyl)amino)propanamido)-3-hydroxypropanamido)-3-(4-chlorobenzyl)piperidine-1-carbonyl)hept-5-enoic acid (19-2)

To a solution of 19-I (390 mg, 0.40 mmol) in DCM (3 mL) and cooled in an ice bath was added TFA (3 mL, 38.9 mmol) dropwise. The cooling bath was then removed and the resulting mixture was stirred at RT for 3 h. Water and ACN were added (1:1 ratio, 4 mL) and stirring was continued at RT for another 2 h. The reaction mixture was concentrated and the obtained residue was taken up in DCM with stirring Sodium carbonate was added to adjust the pH of the aq. phase to slightly basic. The organic phase was then collected and the aqueous phase was back extracted with DCM again. The combined organic phases were dried over sodium sulfate, filtered, and concentrated to afford 19-2 as a light yellow foam (333 mg, 95% yield). The product was carried to the next step without purification. Analytical Method 5, $t_R$=0.81 min., [M+H]+=890.3.

Step 3. (3R,7S,10S,13R)-3-((E)-but-2-en-1-yl)-6-(4-Chloro-2-(4-(2-((dimethylamino)methyl)-1-methyl-1H-imidazol-5-yl)phenoxy)benzyl)-13-(4-chlorobenzyl)-10-(hydroxymethyl)-7-methyl-1,6,9,12-tetraazabicyclo[11.3.1]heptadecane-2,5,8,11-tetraone (Compound 40)

To a solution of 19-2 (278 mg, 0.31 mmol) in DCM (140 mL) was added HOAt (42.5 mg, 0.31 mmol), HATU (475 mg, 1.25 mmol) and 2,6-lutidine (0.8 mL, 6.87 mmol). The resulting mixture was heated to reflux for (bath temp 50° C.) overnight, then cooled to RT, and washed with a 5% aq. sodium bicarbonate solution. The organic phase was separated and concentrated to dryness to afford a crude product, which was purified by basic HPLC (water/ACN, w/ammonium hydroxide modifier) to afford Compound 40 as a white powder after freeze drying the pure fractions (18 mg, 6.4% yield). Analytical Method 2, $t_R$=2.92 min., [M+H]$^+$=872.2.

The compound in Table 26 was synthesized according to the procedure described in Example 8.38 for Compound 40 from the respective intermediates shown in Table 1-7 and described above in Example 8.

TABLE 26
| Cmd No. | Structure | LCMS |
|---|---|---|
| 66 | 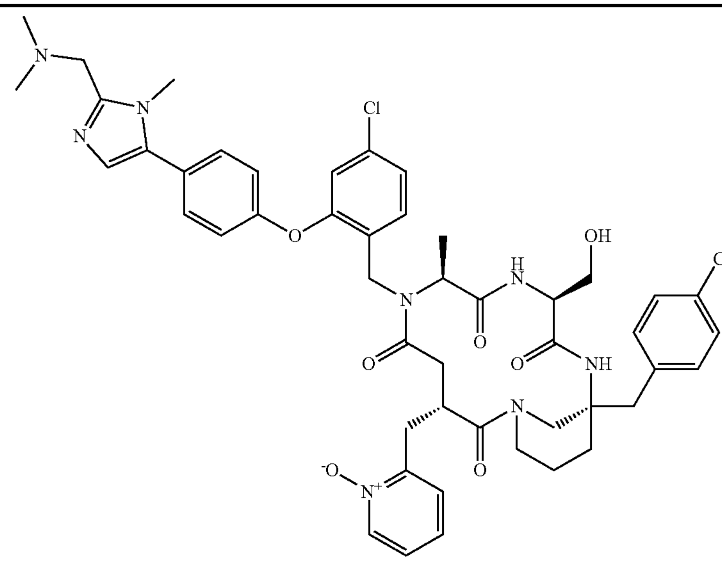 | Analytical Method 4<br>$t_R$ = 1.63 min.<br>$[M + H]^+$ = 925.5 |
Example 8.38: Synthesis of (3S,7S,10S,13R)-6-(4-Chloro-2-(4-(2-((cyclobutylamino)methyl)-1-methyl-1H-imidazol-5-yl)phenoxy)-6-fluorobenzyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone (Compound 45)
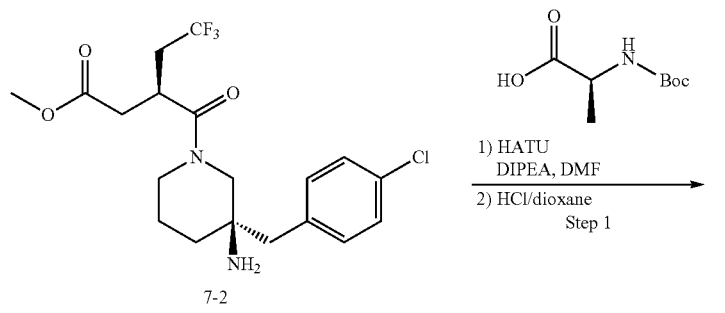
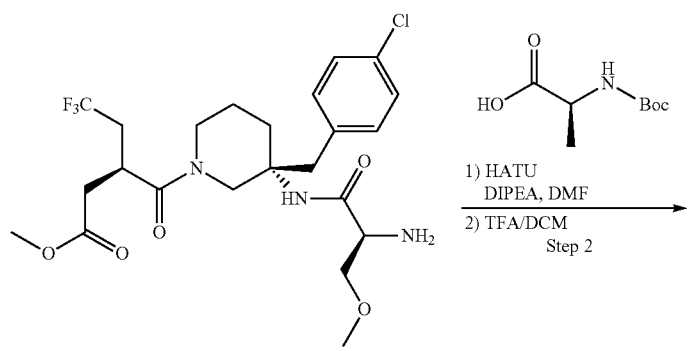

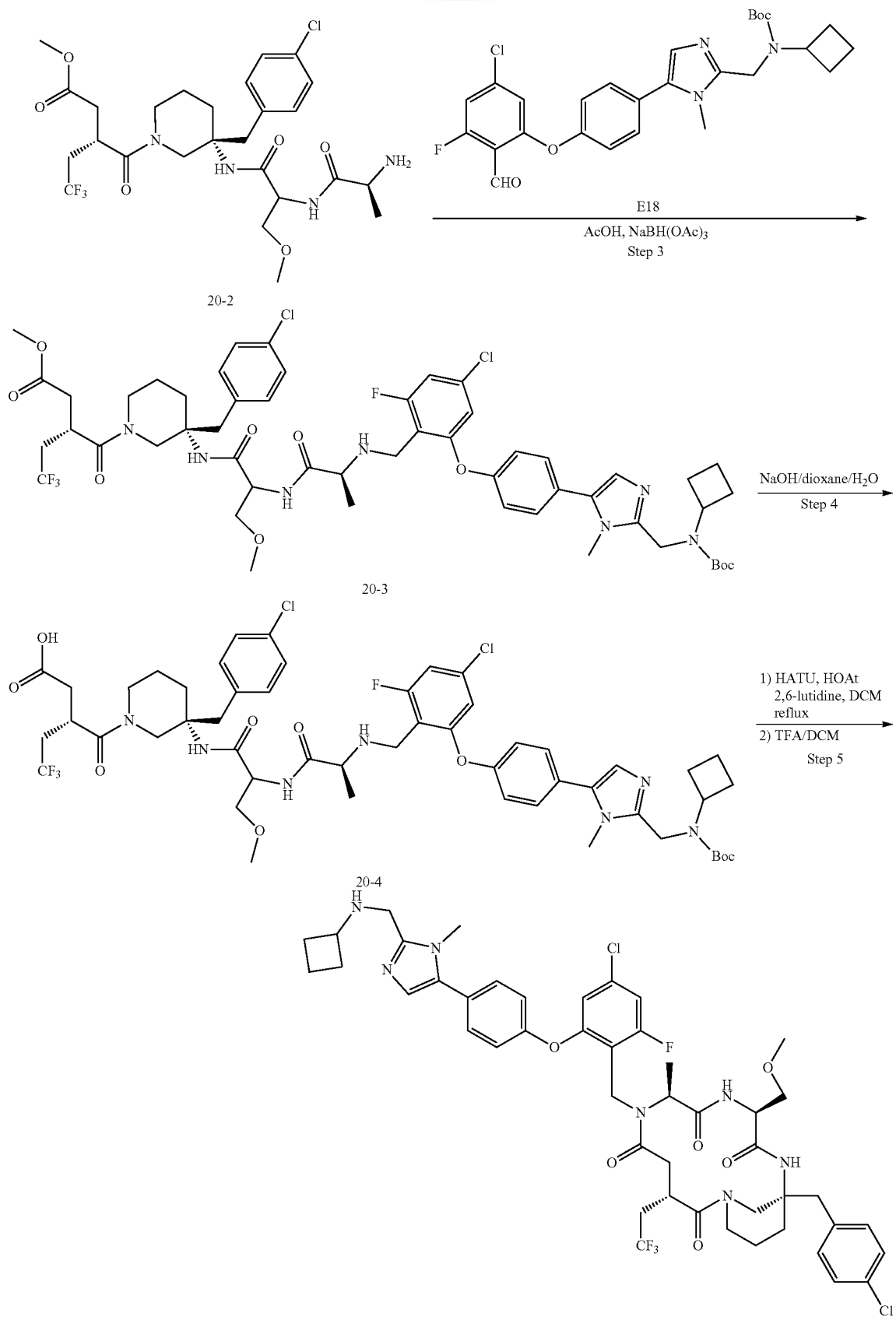

Step 1. (S)-Methyl 3-((R)-3-((S)-2-Amino-3-methoxypropanamido)-3-(4-chlorobenzyl)piperidine-1-carbonyl)-5,5,5-trifluoropentanoate (20-1)

Step 1-1: To a solution of (S)-2-((tert-butoxycarbonyl)amino)-3-methoxypropanoic acid (1.30 g, 5.92 mmol) in DMF (25 mL) was added HATU (2.47 g, 6.51 mmol) and DIPEA (3.10 mL, 17.7 mmol). The resulting mixture was stirred for 2 min before a solution of 7-2 (2.49 g, 5.92 mmol) in DMF (5 mL) was added. The reaction mixture was stirred at RT for overnight to complete the reaction. EtOAc was added and the mixture was washed with a 5% aq. sodium bicarbonate solution (×2) and then brine. The organic phase was dried over sodium sulfate, filtered, and concentrated to afford the interim product as a dark brown oil after drying (3.9 g, ~quantitative. yield). The material was used in the next step without further purification.

Step 1-2: To a solution of the product from Step 1-1 (1.7 g, 2.73 mmol) in DCM (5 mL) was added TFA (4.21 mL, 54.7 mmol) dropwise at RT. The resulting mixture was stirred for 2 h and subsequently concentrated. The obtained residue was taken up in DCM and washed with a saturated solution of sodium bicarbonate. The organic phase was collected, dried over sodium sulfate, filtered, and concentrated to afford 20-1 as a crude red foam after drying (1 g, 70% yield). The material was carried to the next step without purification. Analytical Method 2, $t_R$=2.16 min., [M+H]$^+$=522.3

Step 2. (S)-Methyl 3-((R)-3-((S)-2-((S)-2-aminopropanamido)-3-methoxypropanamido)-3-(4-chlorobenzyl)piperidine-1-carbonyl)-5,5,5-trifluoropentanoate (20-2)

Step 2-1: To a solution of Boc-Ala-OH (0.36 g, 1.92 mmol) in DMF (10 mL) was added HATU (0.80 g, 2.11 mmol) and DIPEA (1.0 mL, 5.75 mmol). The resulting mixture was stirred for 2 min before a solution of 20-1 (1 g, 1.92 mmol) in DMF (5 mL) was added. The reaction mixture was stirred at RT for 1 h. EtOAc was added and the mixture was washed with a 5% sodium bicarbonate solution twice and then brine. The organic phase was dried over sodium sulfate, filtered, and concentrated to afford a dark brown oil. The crude material was purified by reverse-phase column chromatography (eluting with 0-100% water/ACN with 0.1% NH$_4$OH modifier, product eluted ~80% ACN). The reaction was repeated with the same scale, combined to afford the interim product after concentrating all the pure fractions (1.3 g, 99% yield).

Step 2-2: To a solution of the product from Step 2-1 (1.3 g, 3.03 mmol) in DCM (3 mL) was added TFA (3 mL, 40.2 mmol) dropwise. The resulting mixture was then stirred at RT for overnight. MeOH was then added, and the mixture was stirred for 1 h before being concentrated. The resulting residue was taken up in EtOAc and washed with 5% sodium bicarbonate. The aqueous phase was back extracted with EtOAc again and the combined organic phases were dried over sodium sulfate, filtered, and concentrated to afford example 20-2 as a light yellow foam (1.09 g, 98% yield). The product was used in the next step without purification. Analytical Method 5, $t_R$=0.97 min., [M+H]$^+$=593.3

Step 3. (S)-Methyl 3-((R)-3-((S)-2-((S)-2-((2-(4-(2-(((tert-butoxycarbonyl)(cyclobutyl)amino)methyl)-1-methyl-1H-imidazol-5-yl)phenoxy)-4-chloro-6-fluorobenzyl)amino)propanamido)-3-methoxypropanamido)-3-(4-chlorobenzyl)piperidine-1-carbonyl)-5,5,5-trifluoropentanoate (20-3)

To a round bottom flask containing 20-2 (265 mg, 0.45 mmol) and E18 (230 mg, 0.45 mmol) was added DCM (10 ml) and acetic acid (0.10 ml, 1.79 mmol) and the resulting mixture was stirred at RT for 1 h. Sodium triacetoxyborohydride (474 mg, 2.24 mmol) was added and stirring was continued at RT for overnight. The reaction mixture was then concentrated and the obtained residue was taken up in EtOAc and washed with a half saturated solution of sodium carbonate twice and brine. The organic phase was dried over Na$_2$SO$_4$, filtered, and concentrated to dryness to provide 20-3 as an oil (488 mg, assume quantitative yield). The material was carried to the next step without purification. Analytical Method 5, $t_R$=1.46 min., [M+H]$^+$=1090.4.

Step 4. (S)-3-((R)-3-((S)-2-((S)-2-((2-(4-(2-(((tert-Butoxycarbonyl)(cyclobutyl)amino)methyl)-1-methyl-1H-imidazol-5-yl)phenoxy)-4-chloro-6-fluorobenzyl)amino)propanamido)-3-methoxypropanamido)-3-(4-chlorobenzyl)piperidine-1-carbonyl)-5,5,5-trifluoropentanoic acid (20-4)

To a round bottom flask containing 20-3 (488 mg, 0.45 mmol) in dioxane (8 mL) and water (2 mL) and cooled in an ice bath was added sodium hydroxide (1M, 1.79 ml, 1.79 mmol) dropwise. The cooling bath was removed and the resulting mixture was stirred at RT for 3 h. The reaction mixture was then cooled using an ice bath and quenched with a solution of HCl (1M, 1.34 ml, 1.34 mmol) in water (2 ml). The mixture was stirred at RT for 15 min, and subsequently freeze dried to afford a crude solid. The solid was taken up in ACN and purified by reverse-phase column chromatography (eluting with 0-100% water/ACN, with 0.1% NH$_4$OH as modifier, product eluted ~50% ACN). The pure fractions were concentrated down to afford a white slurry and extracted (×3) with a solution of 10% MeOH in EtOAc. The organic phases were combined, dried over sodium sulfate, filtered, and concentrated to afford 20-4 as a white solid (200 mg, 42% yield). Analytical Method 5, $t_R$=1.01 min., [M+H]$^+$=1076.0.

Step 5. (3S,7S,10S,13R)-6-(4-Chloro-2-(4-(2-((cyclobutylamino)methyl)-1-methyl-1H-imidazol-5-yl)phenoxy)-6-fluorobenzyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone (Compound 45)

Step 5-1: To a solution of 20-4 (200 mg, 0.19 mmol) in DCM (250 mL) was added 2,6-lutidine (0.5 mL, 4.29 mmol), HOAt (25.3 mg, 0.19 mmol) and HATU (282 mg, 0.74 mmol). The resulting mixture was heated in a 45° C. heating bath overnight, then cooled to RT, filtered, and concentrated. The obtained residue was taken up in EtOAc, washed with saturated NaHCO₃ and brine. The organic phase was dried over Na₂SO₄, filtered, and concentrated to afford the product as an oil (197 mg, ~quantitative yield). The material was taken to the next step directly without purification.

Step 5-2: To a solution of the product from Step 5-1 (197 mg, 0.19 mmol) in DCM (2 mL) and cooled to 0° C. in an ice bath was added TFA (2 mL, 26.0 mmol) dropwise and the resulting mixture was stirred at RT for 1 h. The reaction mixture was then concentrated and the obtained residue was taken up in EtOAc. The organic phase was washed with a saturated solution of sodium bicarbonate, dried over sodium sulfate, filtered, and concentrated. The crude product was purified by basic HPLC (water/ACN, ammonium hydroxide as modifier) to afford Compound 45 as a white solid after freeze drying the clean fractions (42.6 mg, 23% yield). Analytical Method 2, $t_R$=3.08 min., [M+H]⁺=958.3.

Example 8.39: Synthesis of (3R,7S,10S,13R)-3-Benzyl-6-(4-chloro-2-((6-(2-((dimethylamino)methyl)-1-methyl-1H-imidazol-5-yl)pyridin-3-yl)oxy)benzyl)-13-(4-chlorobenzyl)-10-(methoxymethyl)-7,12-dimethyl-1,6,9,12-tetraazabicyclo[11.3.1]heptadecane-2,5,8,11-tetraone (Compound 27)

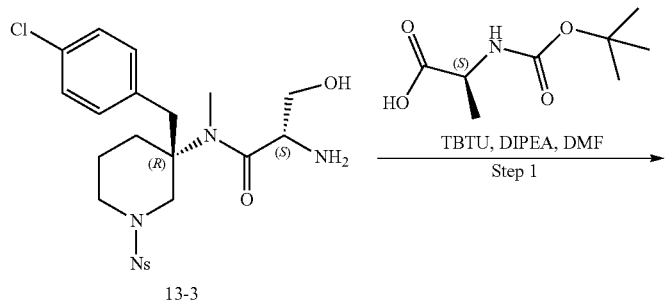

13-3

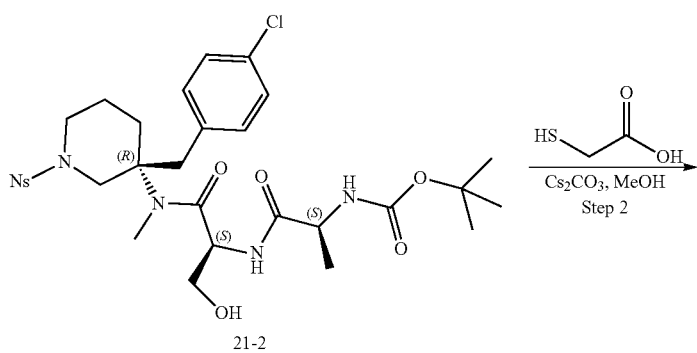

21-2

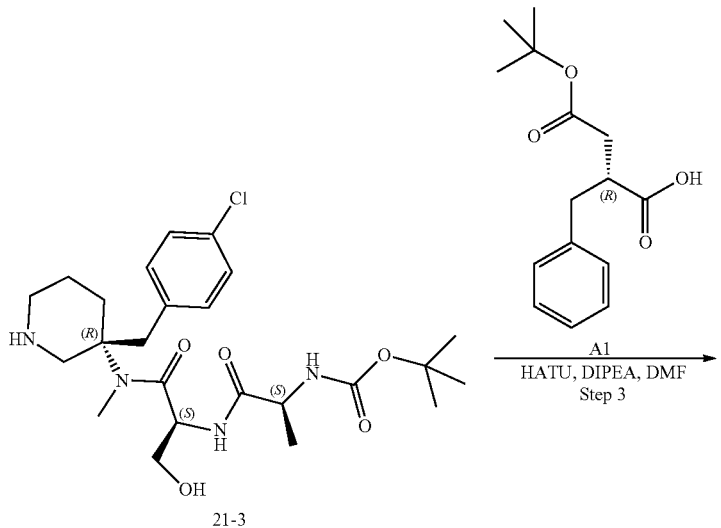

21-3

-continued
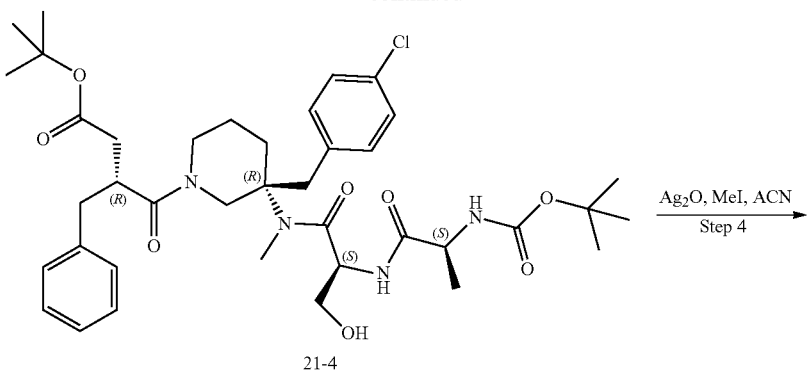
21-4
Ag₂O, MeI, ACN
Step 4 →
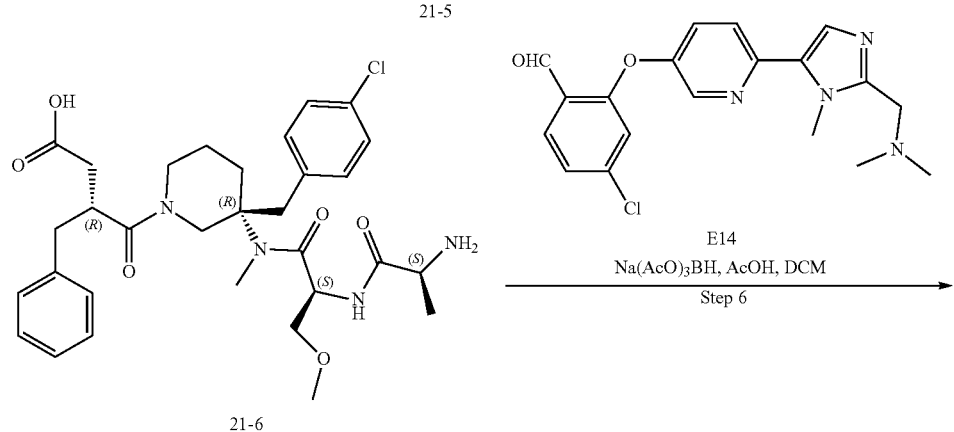
21-5
TFA
Step 5 →
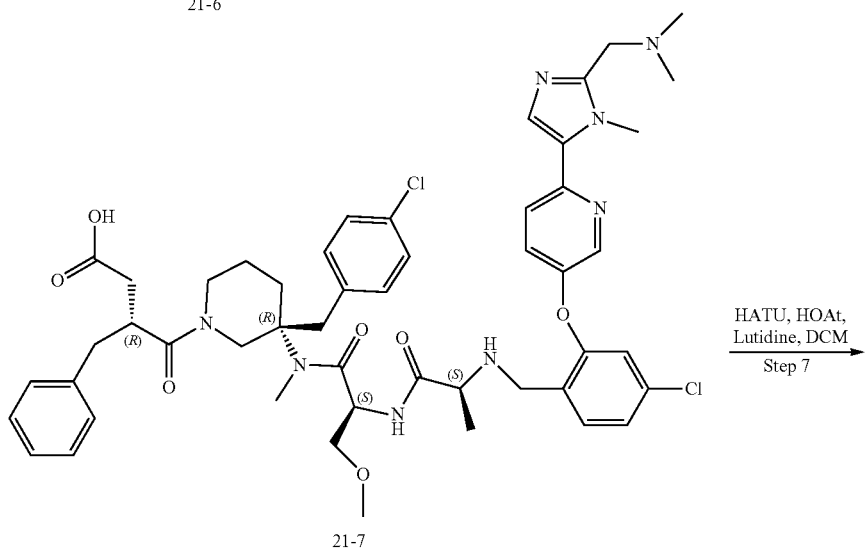
21-6
E14
Na(AcO)₃BH, AcOH, DCM
Step 6 →
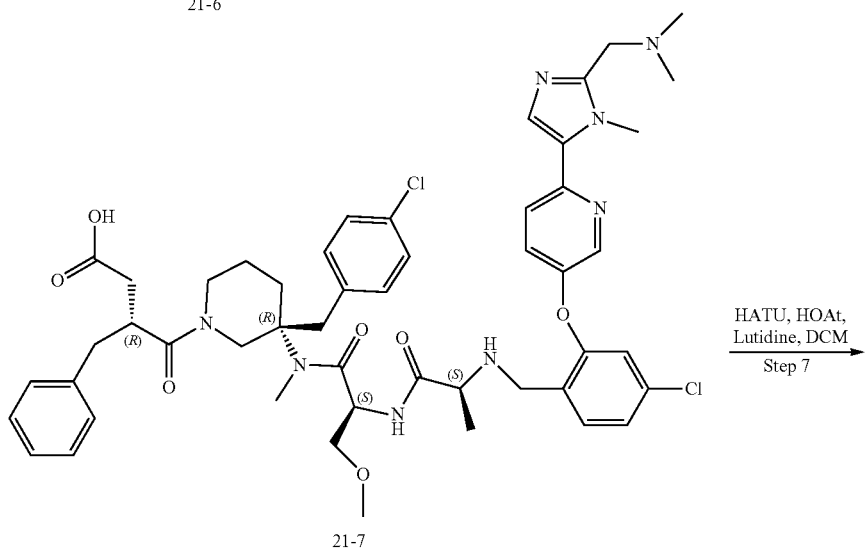
21-7
HATU, HOAt,
Lutidine, DCM
Step 7 →

-continued

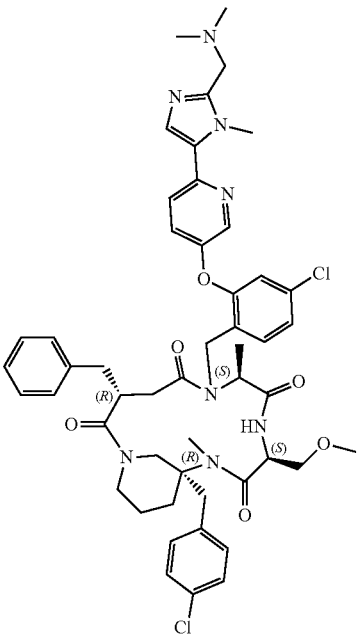

Compound 27

Step 1. tert-Butyl ((S)-1-(((S)-1-(((R)-3-(4-Chlorobenzyl)-1-((4-nitrophenyl)sulfonyl)piperidin-3-yl)(methyl)amino)-3-hydroxy-1-oxopropan-2-yl)amino)-1-oxopropan-2-yl)carbamate (21-2)

To a solution of (S)-2-((tert-butoxycarbonyl)amino)propanoic acid (0.31 g, 1.61 mmol) in DMF (6 mL) was added DIPEA (0.85 mL, 4.84 mmol) and TBTU (0.52 g, 1.61 mmol). The resulting mixture was stirred at room temperature for 2 min. before being added to a solution of 13-3 (0.82 g, 1.61 mmol) containing DIPEA (0.84 mL, 4.84 mmol) in DCM (6 mL) and cooled in a dry-ice bath. The reaction mixture was warmed to RT gradually, stirred for 30 min, and then added to a mixture of saturated NaHCO$_3$ and water to form a biphasic mixture. The organic phase was separated, and the aqueous portion was back-extracted twice with DCM. The combined organic phases were washed with brine, dried over sodium sulfate, filtered, and concentrated to afford 21-2 as a crude product (1.1 g, assumed quantitative yield). The crude product was used directly without further purification. Analytical Method 5, $t_R$=1.10 min., [M+H]$^+$=682.2

Step 2. tert-Butyl ((S)-1-(((S)-1-(((R)-3-(4-chlorobenzyl)piperidin-3-yl)(methyl)amino)-3-hydroxy-1-oxopropan-2-yl)amino)-1-oxopropan-2-yl)carbamate (21-3)

To a solution of 21-2 (1.09 g, 1.6 mmol) in MeOH (75 mL) at RT was added mercaptoacetic acid (0.45 mL, 6.40 mmol) and Cs$_2$CO$_3$ (3.65 g, 11.2 mmol). The resulting mixture was stirred at room temperature for 40 min (LCMS observed the formation of an isomeric product), then poured into 200 mL of cold water and extracted with 2×80 mL of EtOAc (brine was added to assist the partition). The combined organic phases were washed with 5% NaHCO$_3$ solution twice, dried over sodium sulfate, filtered, and concentrated to afford 21-2 as a crude yellow foam after drying under high vacuum (594 mg, 75% yield). The product was used in the next step without purification. Analytical Method 5, $t_R$=0.98 min., [M+H]$^+$=497.4.

Step 3. tert-Butyl (R)-3-benzyl-4-((R)-3-((S)-2-((S)-2-((tert-butoxycarbonyl)amino)propanamido)-3-hydroxy-N-methylpropanamido)-3-(4-chlorobenzyl)piperidin-1-yl)-4-oxobutanoate (21-4)

To a solution of A1 (190 mg, 0.72 mmol) in ACN (8 mL) was added DIPEA (0.63 mL, 3.59 mmol) and HATU (273 mg, 0.72 mmol). The resulting mixture was stirred at room temperature for 5 min. before being added to a solution of 21-3 (594 mg, 1.19 mmol) in ACN (8.00 mL) at 0° C. The reaction mixture was stirred at room temperature for 30 min and subsequently concentrated. The residue was purified by flash column chromatography on silica gel (eluting with 0-100% EtOAc/Heptane, product eluted ~ 80% EtOAc) to afford 21-4 after concentrating the clean fractions (430 mg, 80% yield). Analytical Method 5, $t_R$=1.28 min., [M+H]$^+$=743.6.

Step 4. tert-Butyl (R)-3-benzyl-4-((R)-3-((S)-2-((S)-2-((tert-butoxycarbonyl)amino)propanamido)-3-methoxy-N-methylpropanamido)-3-(4-chlorobenzyl)piperidin-1-yl)-4-oxobutanoate (21-5)

To a solution of 21-4 (200 mg, 0.270 mmol) in ACN (4 mL) was added Ag$_2$O (312 mg, 1.34 mmol) and MeI (0.168 mL, 2.69 mmol). The resulting mixture was stirred at room temperature under an atmosphere of nitrogen in the dark overnight to complete the reaction. The reaction mixture was then filtered through a pad of Celite® and concentrated to afford 21-5 (~quantitative yield). The product was carried to the next step without purification. Analytical Method 5, $t_R$=1.34 min., [M+H]$^+$=757.6.

Step 5. (R)-4-((R)-3-((S)-2-((S)-2-Aminopropanamido)-3-methoxy-N-methylpropanamido)-3-(4-chlorobenzyl)piperidin-1-yl)-3-benzyl-4-oxobutanoic acid (21-6)

To a solution of 21-5 (0.401 g, 0.53 mmol) in DCM (2 mL) was added TFA (4.08 ml, 53.0 mmol) dropwise. The resulting mixture was stirred at room temperature for 2 hour and subsequently concentrated. The obtained residue was taken up in toluene and concentrated again (this was repeated for a total of 3 times to ensure TFA removal) to afford 21-6 after drying under high vacuum (156 mg, assumed quantitative yield). The solid was carried to the next step without purification. Analytical Method 5, $t_R$=0.64 min., [M+H]$^+$=601.5.

Step 6. (R)-3-Benzyl-4-((R)-3-((S)-2-((S)-2-((4-chloro-2-((6-(2-((dimethylamino)methyl)-1-methyl-1H-imidazol-5-yl)pyridin-3-yl)oxy)benzyl)amino)propanamido)-3-methoxy-N-methylpropanamido)-3-(4-chlorobenzyl)piperidin-1-yl)-4-oxobutanoic acid (21-7)

To a solution of 21-6 (156 mg, 0.26 mmol) in anhydrous DCM (5 mL) was added E14 (96 mg, 0.26 mmol) and acetic acid (0.02 ml, 0.39 mmol). The resulting mixture was stirred at room temperature overnight and then sodium triacetoxyborohydride (220 mg, 1.04 mmol) was added. The reaction mixture was stirred at RT for 1.5 h and subsequently quenched with water and MeOH and concentrated. The crude residue was purified by reverse-phase column chromatography (eluting with 20-50% ACN/water with 0.1% TFA) to afford example 21-7 as a white solid after freeze drying the pure fractions (130 mg, 52% yield). Analytical Method 5, $t_R$=0.80 min., [M+H]$^+$=955.6.

Step 7. (3R,7S,10S,13R)-3-Benzyl-6-(4-chloro-2-((6-(2-((dimethylamino)methyl)-1-methyl-1H-imidazol-5-yl)pyridin-3-yl)oxy)benzyl)-13-(4-chlorobenzyl)-10-(methoxymethyl)-7,12-dimethyl-1,6,9,12-tetraazabicyclo[11.3.1]heptadecane-2,5,8,11-tetraone (Compound 27)

To a stirred mixture of 21-7 (130 mg, 0.14 mmol), HATU (207 mg, 0.54 mmol) and HOAt (27.8 mg, 0.20 mmol) in DCM (130 mL) at RT was added 2,6-lutidine (0.32 mL, 2.72 mmol). The resulting mixture was heated to 40° C. for 4 h, then cooled to RT, and washed twice with water. The organic phase was concentrated to afford a crude product which was purified by basic HPLC (eluting with water/ACN with 0.1% NH$_4$OH, product eluted ~75% ACN) to afford Compound 27 as a white solid after freeze drying the pure fractions (25 mg, 19% yield). Analytical Method 2, $t_R$=3.12 min., [M+H]$^+$=937.6.

The compounds in Table 27 were synthesized according to the procedure described in Example 8.39 for Compound 27 from the respective intermediates shown in Tables 1-7 and described above in Example 8.

TABLE 27

| Cmd No. | Structure | LCMS |
|---------|-----------|------|
| 85 | 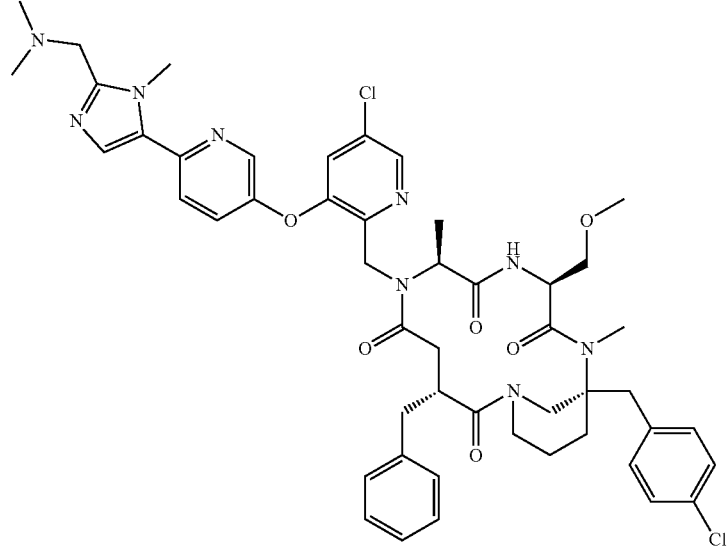 [SMILES: COC[C@@H]1NC(=O)[C@H](C)N(Cc2ncc(Cl)cc2Oc2ccc(-c3cnc(CN(C)C)n3C)nc2)C(=O)C[C@@H](Cc2ccccc2)C(=O)N2CCC[C@@](Cc3ccc(Cl)cc3)(C2)N(C)C1=O] | Analytical Method 2<br>$t_R$ = 2.91 min.<br>[M + H]$^+$ = 938.3 |

TABLE 27-continued
| Cmd No. | Structure | LCMS |
|---|---|---|
| 157 | 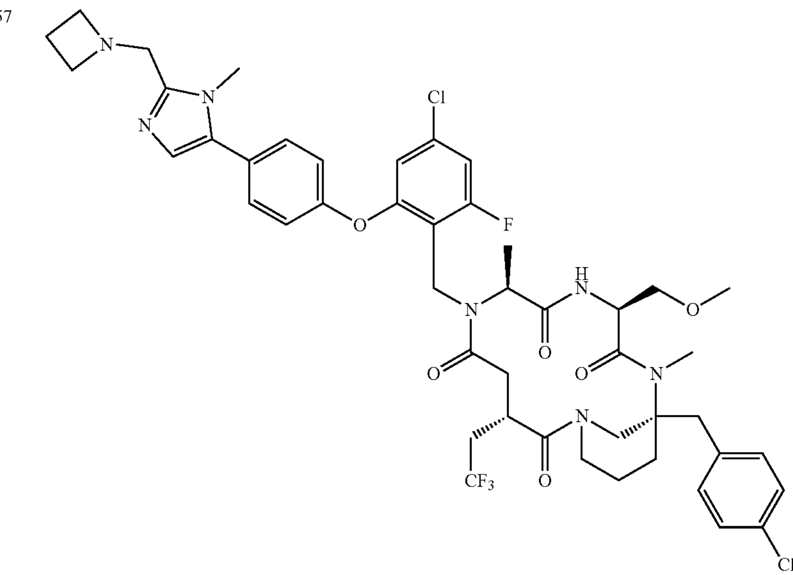 | Analytical Method 2<br>$t_R$ = 3.07 min.<br>[M + H]$^+$ = 958.1 |
Example 8.40: Synthesis of (3R,7S,10S,13R)-3-Benzyl-10-(((tert-Butyldimethylsilyl)oxy)methyl)-6-(4-chloro-2-((6-(2-((dimethylamino)methyl)-1-methyl-1H-imidazol-5-yl)pyridin-3-yl)oxy)benzyl)-13-(4-chlorobenzyl)-7,12-dimethyl-1,6,9,12-tetraazabicyclo[11.3.1]heptadecane-2,5,8,11-tetraone (Compound 71)
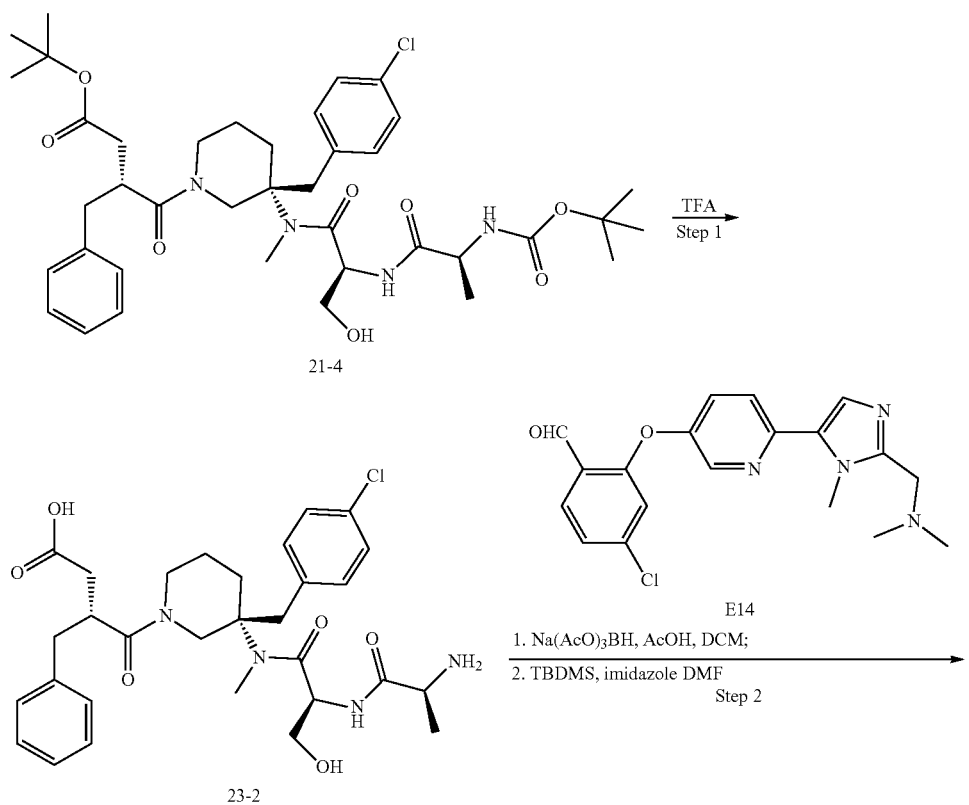

-continued

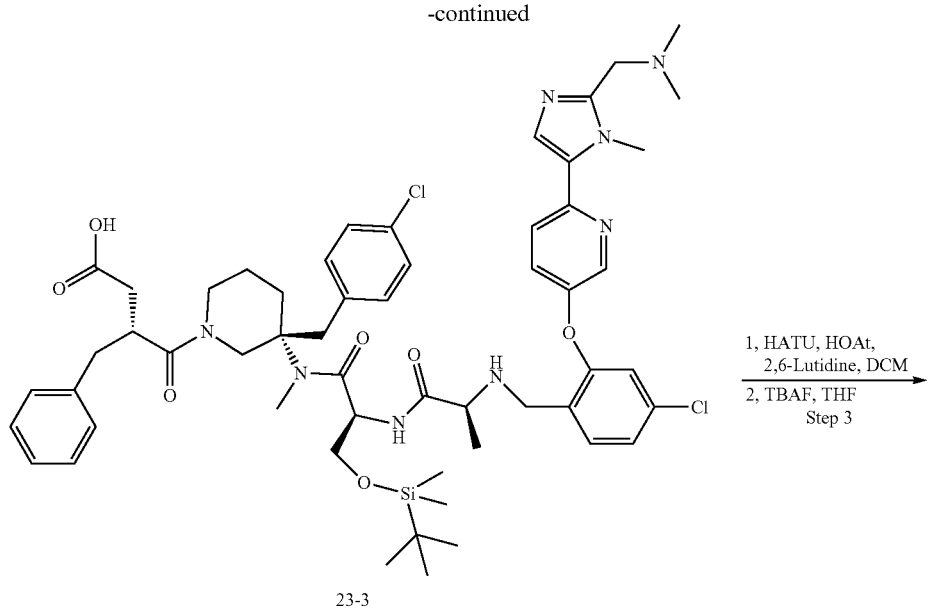

23-3

1, HATU, HOAt,
2,6-Lutidine, DCM
2, TBAF, THF
Step 3

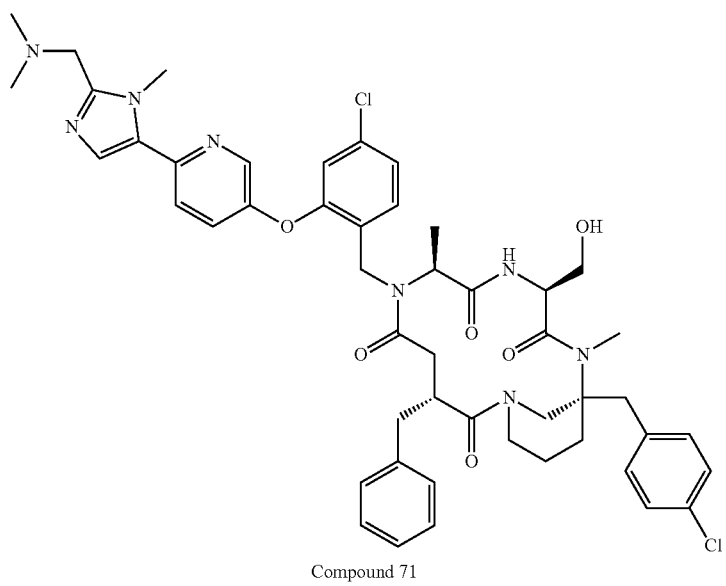 [SMILES: C[C@H]1C(=O)N[C@@H](CO)C(=O)N(C)[C@@]2(Cc3ccc(Cl)cc3)CCCN(C2)C(=O)[C@H](Cc2ccccc2)CC(=O)N1Cc1ccc(Cl)cc1Oc1ccc(-c2cnc(CN(C)C)n2C)nc1]

Compound 71

Step 1. (R)-4-((R)-3-((S)-2-((S)-2-Aminopropanamido)-3-hydroxy-N-methylpropanamido)-3-(4-chlorobenzyl)piperidin-1-yl)-3-benzyl-4-oxobutanoic acid (23-2)

To a solution of 21-4 (2.45 g, 3.30 mmol) in anhydrous EtOAc (30 ml) was added TFA (229 ml, 296 mmol) dropwise. The resulting mixture was stirred at room temperature for 1 h and subsequently concentrated. The obtained residue was dried thoroughly under high vacuum to provide 23-2 (1.9 g, ~quantitative yield). The product was used in the next step without purification. Analytical Method 5, $t_R$=0.62 min., $[M+H]^+$=587.3.

Step 2. (R)-3-Benzyl-4-((R)-3-((S)-3-((tert-butyldimethylsilyl)oxy)-2-((S)-2-((4-chloro-2-((6-(2-((dimethylamino)methyl)-1-methyl-1H-imidazol-5-yl)pyridin-3-yl)oxy)benzyl)amino)propanamido)-N-methylpropanamido)-3-(4-chlorobenzyl)piperidin-1-yl)-4-oxobutanoic acid (23-3)

Step 2-1: To a solution of 23-2 (82 mg, 0.14 mmol) in anhydrous DCM (6 ml), was added E14 (40 mg, 0.11 mmol) and acetic acid (0.025 ml, 0.43 mmol). DIPEA (0.1 mL) was then added to make the mixture homogenous and the resulting solution was stirred at RT for 2 h. Na(AcO)$_3$BH (114 mg, 0.54 mmol) was added in one portion and stirring was continued for 1.5 h. The reaction mixture was quenched by the addition of water and then concentrated. The crude product was purified by reverse-phase column chromatography (eluting with 30-50% ACN/water with 0.1% NH$_4$OH) to afford the interim product after concentrating the clean fractions (50 mg, 48% yield).

Step 2-2: To a solution of the intermediate from Step 2-1 (50 mg, 0.05 mmol) and imidazole (72.3 mg, 1.06 mmol) in DMF (2 mL) was added TBDMS (60 mg, 0.40 mmol). The resulting mixture was stirred at room temperature for 16 h. A half saturated NaHCO$_3$ solution (10 mL) was added, followed by solid K$_2$CO$_3$ (50 mg) and stirring was continued at RT for 1 h. The reaction mixture was then extracted with EtOAc and the organic phase was dried over sodium sulfate, filtered, and concentrated. The crude product was purified by reverse-phase column chromatography (eluting with 0-100% ACN/water with 0.1% NH$_4$OH) to afford 23-2 as a white solid after freeze drying the clean fractions (35 mg, 24% yield). Analytical Method 5, $t_R$=1.03 min., [[M+H]$^+$/2]$^+$=433.5.

Step 3. (3R,7S,10S,13R)-3-Benzyl-10-(((tert-butyldimethylsilyl)oxy)methyl)-6-(4-chloro-2-((6-(2-((dimethylamino)methyl)-1-methyl-1H-imidazol-5-yl)pyridin-3-yl)oxy)benzyl)-13-(4-chlorobenzyl)-7,12-dimethyl-1,6,9,12-tetraazabicyclo[11.3.1]heptadecane-2,5,8,11-tetraone (Compound 71)

Step 3-1: To a round bottom flask containing 23-3 (35 mg, 0.03 mmol), HATU (50.4 mg, 0.13 mmol) and HOAt (6.8 mg, 0.05 mmol) was added DCM (35 mL) and the resulting mixture was stirred at RT for a few minutes. 2,6-lutidine (0.08 mL, 0.66 mmol) was added and stirring was continued at 40° C. for 16 h. The reaction mixture was cooled to RT and water (30 ml) was added. The organic phase was drained off and concentrated. The obtained residue was taken up in 100 mL of EtOAc and the organic phase was washed with water (50 mL) and brine (50 ml), dried over Na$_2$SO$_4$, filtered, concentrated. The crude residue was dried under high vacuum to afford the crude cyclized product.

Step 3-1: The product from Step 3-1 was directly taken up in THF (3 mL) was added TBAF (1 N in THF, 0.28 mL, 0.28 mmol). The resulting mixture was stirred at room temperature for 4 h and then concentrated. The crude residue was purified by reverse-phase column chromatography (eluting 50-90% ACN/water with 0.1% TFA) to afford the desired product after freeze drying the pure fractions. The product was purified again by basic HPLC (eluting with ACN/water with 0.1% NH$_4$OH) to afford Compound 71 as a white powder after freeze drying the pure fractions (9 mg, 29% yield). Analytical Method 2, $t_R$=2.89 min., [M+H]$^+$=923.5.

The compounds in Table 28 were synthesized according to the procedure described in Example 8.40 for Compound 71 from the respective intermediates shown in Tables 1-7 and described above in Example 8.

TABLE 28

| Cmd No. | Structure | LCMS |
|---|---|---|
| 79 | 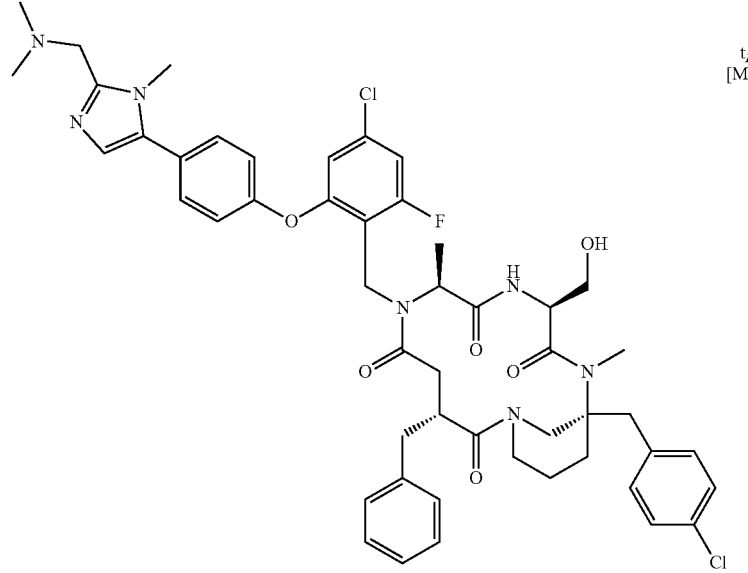 | Analytical Method 2 $t_R$ = 3.02 min. [M + H]$^+$ = 940.7 |

TABLE 28-continued
| Cmd No. | Structure | LCMS |
|---|---|---|
| 99 | 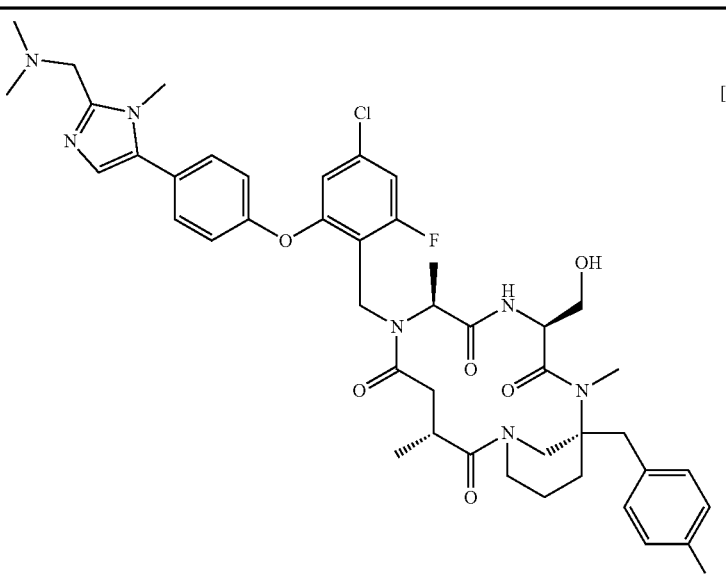 | Analytical Method 2<br>$t_R = 0.90$<br>$[M + H]^+ = 864.5$ |
Example 8.41: Synthesis of (2S,5S,8R,12S)-8-(4-Chlorobenzyl)-12-((S)-2,3-dihydro-1H-inden-1-yl)-1-(2-(4-(2-((dimethylamino)methyl)-1-methyl-1H-imidazol-5-yl)phenoxy)-4-ethylbenzyl)-5-(hydroxymethyl)-2,7,10-trimethyl-1,4,7,10-tetraazacyclotetradecane-3,6,11,14-tetraone (Compound 119)
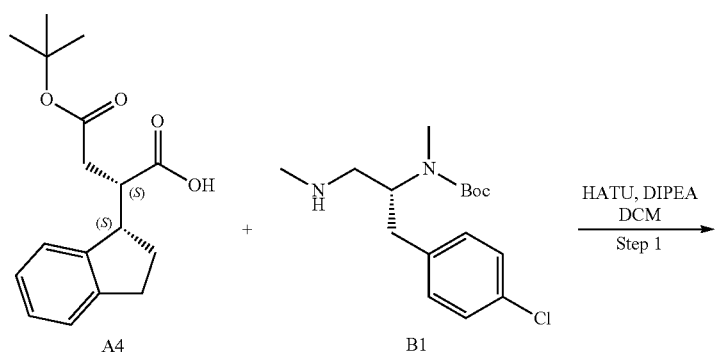
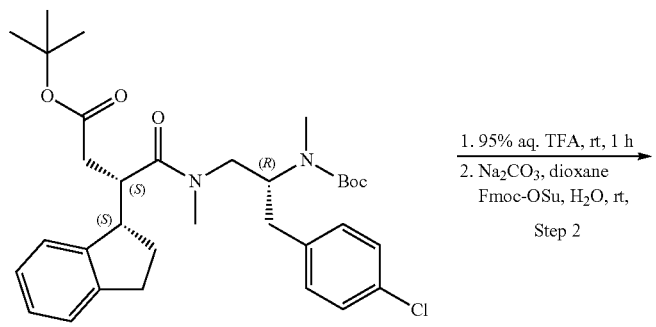
24-2

-continued
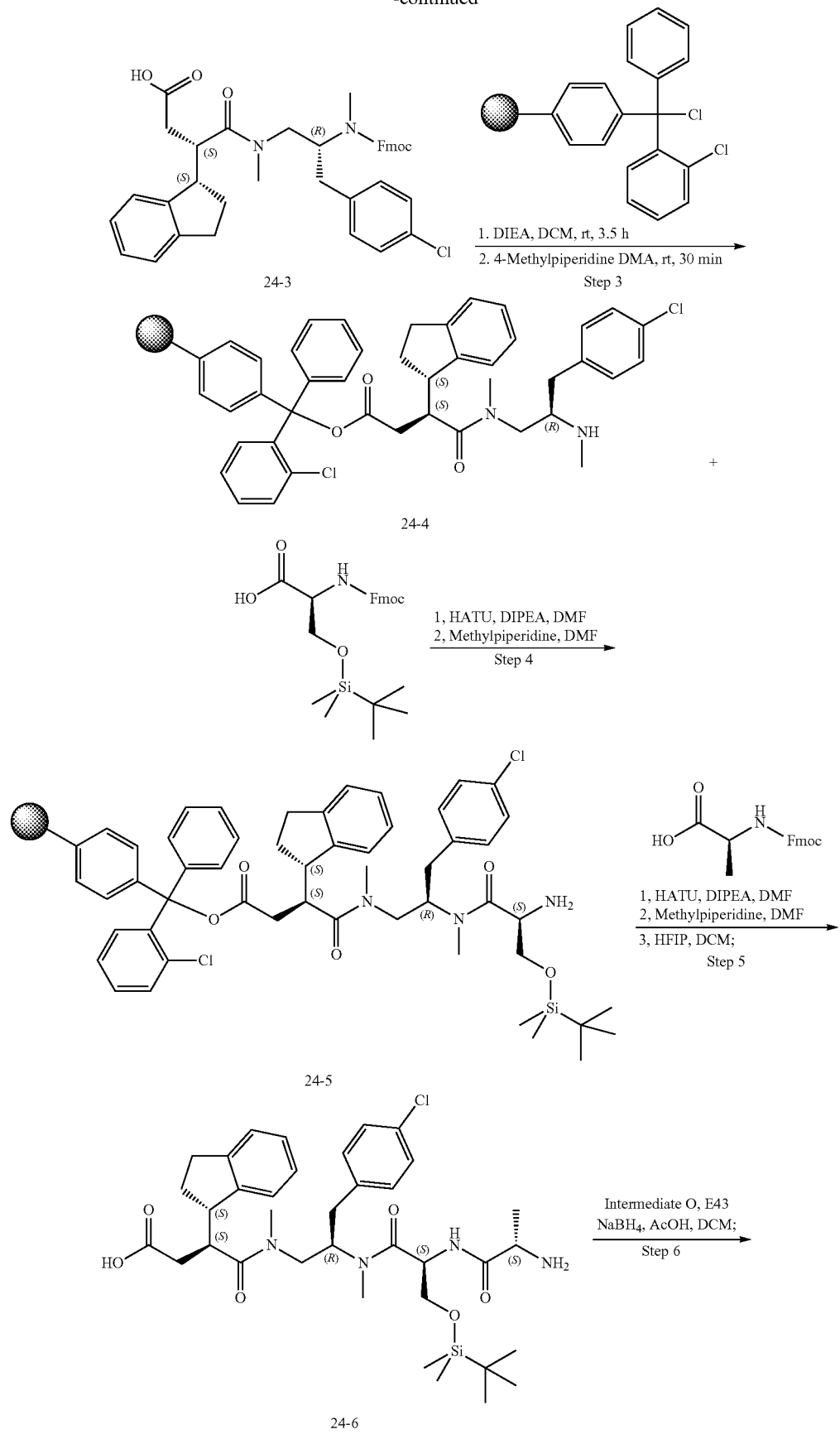

-continued

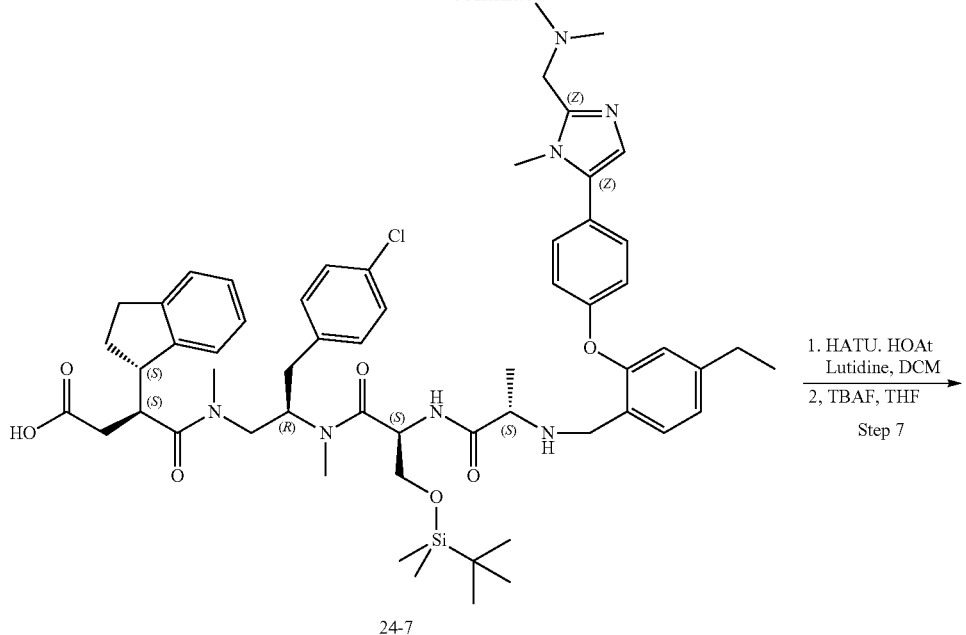

24-7

1. HATU, HOAt
   Lutidine, DCM
2. TBAF, THF

Step 7

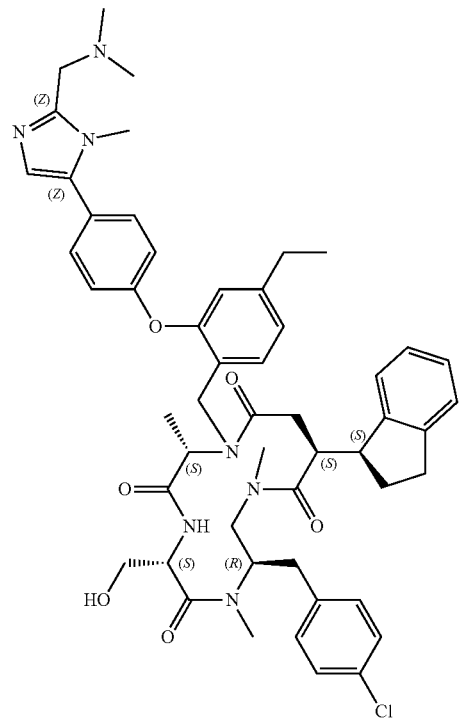

Compound 119

Step 1. (S)-4-(((R)-2-((tert-Butoxycarbonyl)(methyl) amino)-3-(4-chlorophenyl)propyl)(methyl)amino)-3-((S)-2,3-dihydro-1H-inden-1-yl)-4-oxobutanoic acid (24-2)

To a mixture of A4 (2.05 g, 5.37 mmol) and HATU (2.24 g, 5.90 mmol) suspended in DCM (30 mL) was added DIPEA (3.75 mL, 21.5 mmol) and the resulting mixture was stirred at RT for 30 min. A solution of B1 (2.8 g, 8.85 mmol) in DCM (30 mL) was added and stirring was continued at RT for 16 h. The reaction mixture was then concentrated and the residue was partitioned between EtOAc (50 mL) and 5% aq. NaHCO$_3$ (10 mL). The organic phase was washed with 5% aq. NaHCO$_3$ (3×10 mL) and brine (10 mL), dried over Na$_2$SO$_4$, filtered, and concentrated to afford 24-2 as a beige oil (3.1 g, assume quantitative yield). The crude product was used in the next step without purification. Analytical Method 5, $t_R$=1.48 min., MS [M+H]$^+$=585.5.

Step 2. (S)-4-(((R)-2-((((9H-Fluoren-9-yl)methoxy) carbonyl)(methyl)amino)-3-(4-chlorophenyl)propyl) (methyl)amino)-3-((S)-2,3-dihydro-1H-inden-1-yl)- 4-oxobutanoic acid (24-3)

To a round bottom flask containing 24-2 (3.10 g, 5.30 mmol) was added TFA (20.4 mL, 265 mmol). The resulting solution was stirred for 1 h at room temperature, and then concentrated to dryness in vacuo. The obtained residue was dissolved in dioxane (50 mL) and a solution of 0.5 M aq. $Na_2CO_3$ (74.2 mL, 37.1 mmol) and Fmoc-OSu (4.82 g, 14.3 mmol, in 5 mL dioxane) was added. The resulting mixture was stirred at RT for 16 h before being quenched with a 1 M aqueous HCl solution (40 mL). The reaction mixture was then concentrated and the residue was taken up in EtOAc (200 mL). The phases were separated. The organic phase was washed with brine (50 mL), dried over $Na_2SO_4$, filtered, and concentrated to dryness in vacuo. The crude product was purified by flash column chromatography on silica gel (eluting 30-90% Heptane/EtOAc with 1% acetic acid) to afford the desired product as an oily residue after concentrating the pure fractions. The product was then taken up in a mixture of ACN (10 mL) and water (3 ml) and freeze dried to afford 24-3 as a white solid (3.23 g, 66% yield). Analytical Method 5, $t_R$=0.86 min., $[M+H]^+$=650.7.

Step 3. Resin loaded (3S)-(2-chlorophenyl)(phenyl) (p-tolyl)methyl-4-(((R)-3-(4-chlorophenyl)-2-(methylamino)propyl)(methyl)amino)-3-((S)-2,3-dihydro- 1H-inden-1-yl)-4-oxobutanoate (24-4)

Step 3.1: 2-Chlorotrityl chloride resin (7.75 g, 12.4 mmol) was first washed thoroughly with DCM. To the resin was then added a solution of 24-3 (3.2 g, 4.96 mmol) in DCM (30 mL) containing DIEA (4.33 mL, 24.8 mmol). The resulting slurry was shaken at room temperature for 3.5 h and then the solution was drained off. The resulting resin was washed sequentially with a solution of DCM/MeOH/DIPEA (17:2:1, 30 mL), 30 mL of DCM, and finally 30 mL of DMA.

Step 3.2: Fmoc-removal—To the resin from Step 3.1 was added a solution of 4-methylpiperidine in DMF (25%, 40 mL) and the resulting suspension was shaken at room temperature for 90 min. The slurry was then drained and the process was repeated twice, washing the resin with more 4-methylpiperidine/DMF solution. The resin was then washed DMF (3×50 mL), followed by DCM (3×50 mL) and was dried in vacuo to afford the corresponding resin-loaded product 24-4, which was used in the next step without further purification.

Step 4. Resin loaded (6S,9R,13S)-(2-chlorophenyl) (phenyl)(p-tolyl)methyl 6-amino-9-(4-chlorobenzyl)-13-((S)-2,3-dihydro-1H-inden-1-yl)-2,2,3,3,8, 11-hexamethyl-7,12-dioxo-4-oxa-8,11-diaza-3- silapentadecan-15-oate (24-5)

Step 4-1: To resin 24-4 (4.96 mmol) was added a solution of Fmoc-Ser(BSI)-OH (3.29 g, 7.44 mmol), HATU (2.83 g, 7.44 mmol), DIPEA (2.60 mL, 14.88 mmol) in DMF (60 mL). The resulting slurry was then shaken at room temperature overnight and then drained. The resin was washed sequentially with DMF (6×50 mL) and DCM (6×50 mL). The washing process was repeated once more to afford the resin intermediate which was used directly in the next step.

Step 4-2: Fmoc-removal—To the resin from Step 4-1 was added a solution of 4-methylpiperidine in DMF (25%, 50 mL) and the resulting suspension was shaken at room temperature for 1.5 h. The slurry was then drained and the process was repeated once more with another solution of 4-methylpiperidine/DMF for 1 h. The resin was then washed with DMF (3×50 mL), DCM (4×50 mL) and dried in vacuo to afford 24-5. The resin was used in the next step without further purification. MS $[M+H]^+$=630.2 (A small amount of resin was cleaved for analysis purpose).

Step 5. (6S,9R,13S)-6-((S)-2-Aminopropanamido)- 9-(4-chlorobenzyl)-13-((S)-2,3-dihydro-1H-inden-1- yl)-2,2,3,3,8,11-hexamethyl-7,12-dioxo-4-oxa-8,11- diaza-3-silapentadecan-15-oic acid (24-6)

Step 5-1: Coupling of Fmoc-Ala-OH— To a mixture of Fmoc-L-Ala-OH (2.32 g, 7.44 mmol), HATU (2.83 g, 7.44 mmol) in DMF (70 mL) was added DIPEA (2.6 mL, 14.9 mmol). The resulting solution was stirred for a few minutes and then added to a shaking funnel containing resin 24-5 (4.57 g, 4.96 mmol). The suspension was shaken at RT for 17 h before being drained and washed with DMF (3×50 mL). The resulting resin was directly used in the next step.

Step 5-2: Fmoc-removal—To the resin from Step 5-1 was added a solution of 4-methylpiperidine in DMF (25%, 40 mL) and the suspension was shaken at RT for 10 min. The slurry was then drained and the process was repeated twice with more 4-methylpiperidine solution. The remaining resin was then washed with DMF (3×50 mL) and DCM (3×50 mL) to afford the corresponding resin-loaded product, which was used in the next step without further purification.

Step 5-3: Cleavage from resin—To the resin from Step 5-2 was added a solution of hexafluoro-2-propanol in DCM (25%, 40 mL). The resulting suspension was shaken at RT for 15 min and then the solution was drained off and the filtrate collected. This procedure was repeated two additional times with hexafluoro-2-propanol solution. The remaining resin was washed with DCM (2×40 mL). All of the organic phases were combined and concentrated to dryness. The crude material was purified by reverse-phase column chromatography (eluting with 30-50% ACN/water with 0.1% $NH_4OH$) to afford 24-6 as an orange oil after concentrating the clean fractions (1.75 g, 2.49 mmol, 50.3% yield). Analytical Method 2, $t_R$=2.11 min., $[M+H]^+$=701.3.

Step 6. (3S,6S,9R,13S)-6-(((tert-Butyldimethylsilyl) oxy)methyl)-9-(4-chlorobenzyl)-13-((S)-2,3-di- hydro-1H-inden-1-yl)-1-(2-(4-(2-((dimethylamino) methyl)-1-methyl-1H-imidazol-5-yl)phenoxy)-4- ethylphenyl)-3,8,11-trimethyl-4,7,12-trioxo-2,5,8,11- tetraazapentadecan-15-oic acid (24-7)

To a round bottom flask containing 24-6 (578 mg, 0.82 mmol) was added a solution of E43 (300 mg, 0.82 mmol) in 60 mL of anhydrous DCM. The resulting mixture was stirred at room temperature overnight and then concentrated. The obtained residue was subsequently taken up in MeOH (60 mL) and the cloudy mixture was stirred while cooled in an ice bath. Sodium borohydride (94 mg, 2.47 mmol) was then slowly added in portions and stirring was continued while cooled in ice bath for 30 min. The reaction mixture was quenched with water (1 mL), treated with acetic acid (0.07 mL, 1.24 mmol) at RT for 30 min and then concentrated. The crude product was purified by reverse-phase column chromatography (eluting with 0-100% ACN/water with 0.1% NH$_4$OH) to afford the desired product after freeze drying the pure fractions. The product was then taken up in EtOAc (500 mL) and the organic phase was washed with water (150 ml). The organic phase was separated and the aqueous phase was back-extracted with more EtOAc (200 ml). The combined organic phases were dried with sodium sulfate, filtered, concentrated, dried under high vacuum to afford 24-7 (0.70 g, 81% yield). Analytical Method 5, $t_R$=1.08 min., [M+H]$^+$=1049.8

Step 7. (2S,5S,8R,12S)-8-(4-Chlorobenzyl)-12-((S)-2,3-dihydro-1H-inden-1-yl)-1-(2-(4-(2-((dimethylamino)methyl)-1-methyl-1H-imidazol-5-yl)phenoxy)-4-ethylbenzyl)-5-(hydroxymethyl)-2,7,10-trimethyl-1,4,7,10-tetraazacyclotetradecane-3,6,11,14-tetraone (Compound 119)

Step 7.1: To a round bottom flask containing 24-7 (0.75 g, 0.72 mmol), HATU (1.09 g, 2.86 mmol) and HOAt (0.15 g, 1.07 mmol) was added anhydrous DCM (715 mL) and the resulting mixture was stirred at RT for a few minutes and 2,6-lutidine (1.67 mL, 14.3 mmol) was added. The reaction was heated to 39° C. for 5 h and then cooled to RT. Water (50 mL) was added to afford a biphasic mixture. The organic phase was separated, washed with water, and concentrated. The residue was dried under high vacuum to afford the interim cyclized intermediate, which was used directly in the next step without purification.

Step 7.2: To a round bottom flask containing the intermediate from Step 7.1 in THF (20 mL) was added TBAF (1 N in THF, 3.0 mL, 3.0 mmol) and the resulting mixture was stirred at RT for 16 h. Water (20 mL) was added, followed by EtOAc (100 mL). The organic phase was separated and concentrated to dryness. The obtained residue was purified by reverse-phase column chromatography (eluting with 50-80% isopropanol/water with 0.1% NH$_4$OH) to afford Compound 119 as a white powder after freeze drying the pure fractions (373 mg, 55% yield). Analytical Method 2, $t_R$=3.01 min., [M+H]$^+$=916.8. During the purification process, isomeric Compounds 121 (15 mg) and 118 (28 mg) were also obtained.

The compounds in Table 29 were synthesized according to the procedure described in Example 8.41 for Compound 119 starting from starting from A4 and Intermediate N.

TABLE 29

| Cmd No. | Structure | LCMS |
|---|---|---|
| 118 | 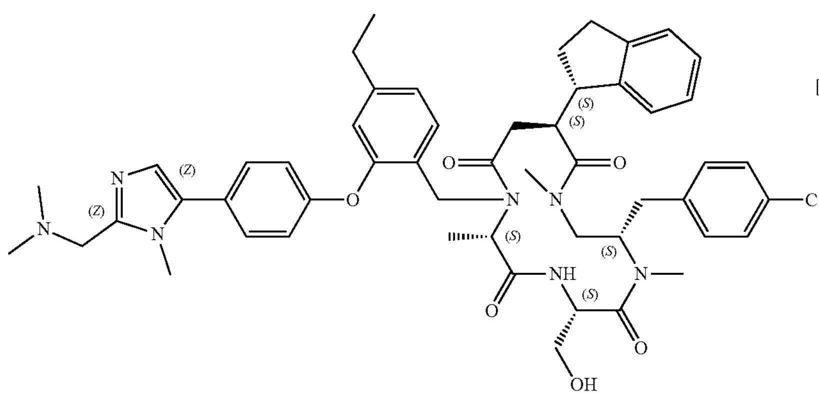 | Analytical Method 2 $t_R$ = 3.00 min. [M + H]$^+$ = 916.9 |
| 121 | 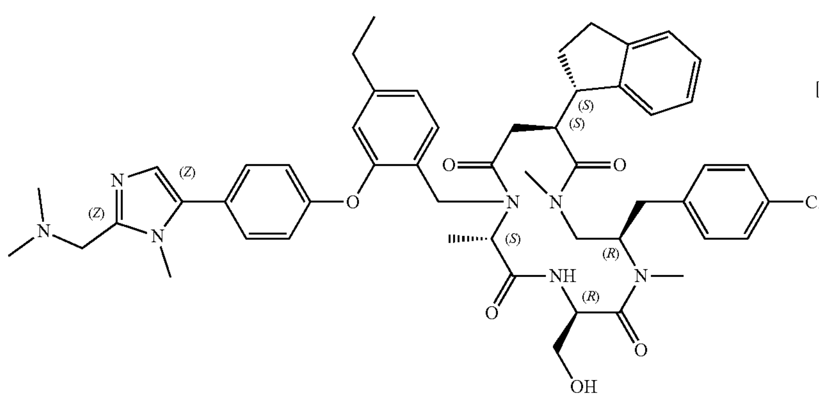 | Analytical Method 2 $t_R$ = 3.01 min. [M + H]$^+$ = 916.8 |

Example 8.42: Synthesis of (3S,7S,10S,13R)-6-(2-(4-(2-(((tert-Butyl(methyl)amino)methyl)-1-methyl-1H-imidazol-5-yl)phenoxy)-4-chloro-6-fluorobenzyl)-13-(4-chlorobenzyl)-10-(methoxymethyl)-7-methyl-3-(2,2,2-trifluoroethyl)-1,6,9,12-tetraazabicyclo[11.3.1]heptadecane-2,5,8,11-tetraone (Compound 137)

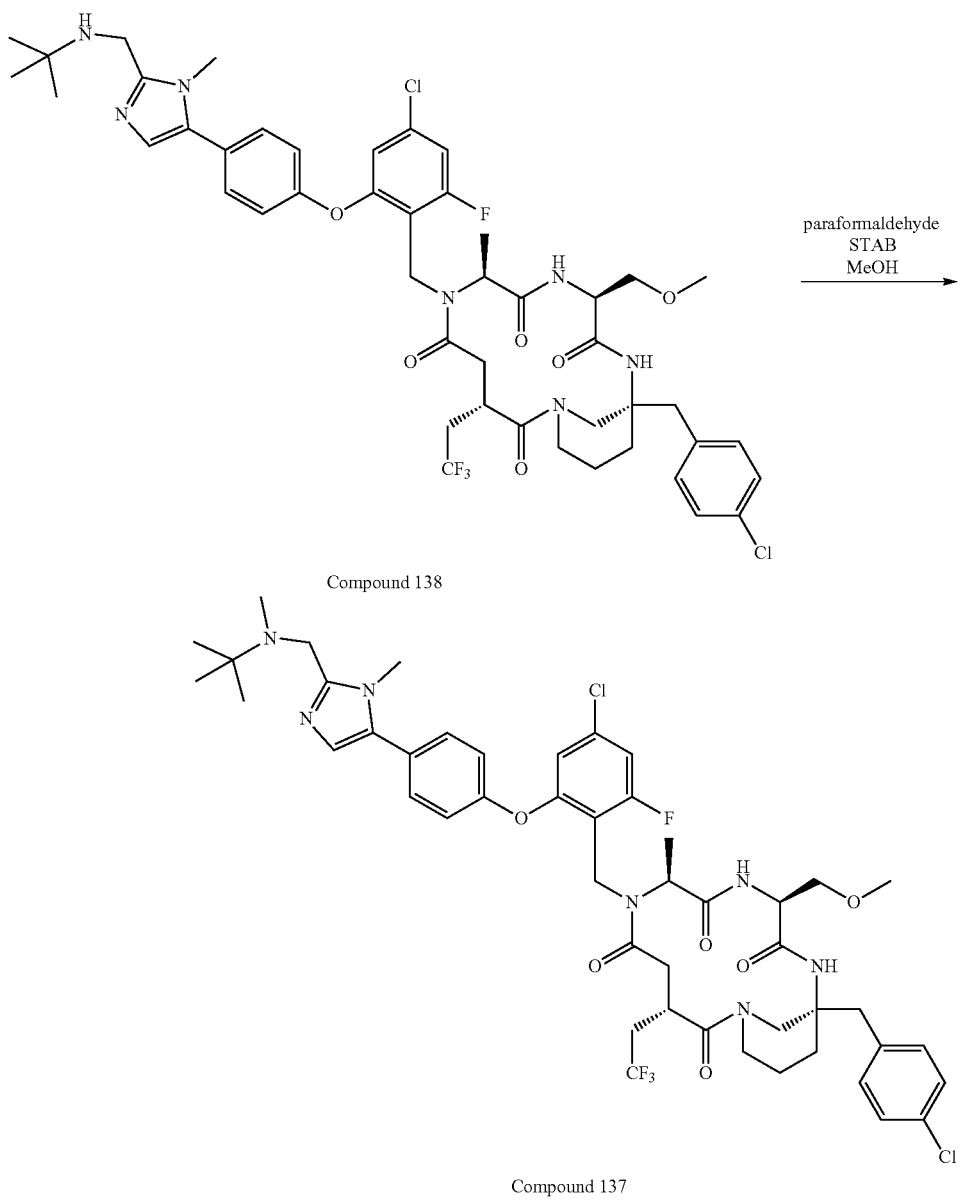

To a reaction vial containing paraformaldehyde (566 mg, 18.8 mmol) was added anhydrous MeOH (22 mL). The resulting slurry was sonicated under ultrasound for a few minutes and then stirred vigorously at RT for 1 hr. Compound 138 (181 mg, 0.19 mmol) was then added and stirring was continued at RT for 1 h. Sodium triacetoxyborohydride (798 mg, 3.77 mmol) was added and the reaction mixture stirred at RT for 30 min. Additional sodium triacetoxyborohydride was added (up to a total of 40 eq.) until complete consumption of starting material was observed. The reaction mixture was then filtered and the filtrate was concentrated under reduced pressure (bath 30° C.) to afford a clear oil. The material was taken up in DCM and washed with a saturated solution of sodium bicarbonate. The slightly basic aqueous portion (pH~8) was washed with DCM (×2) and the combined organic phases were dried over sodium sulfate, filtered, and concentrated. The crude material was purified by flash column chromatography on silica gel (eluting with DCM/MeOH, product elute ~10%) to afford a white film after concentrating the pure fractions. The resulting material was taken up in a 1:1 mixture of ACN and water, freeze dried to afford Compound 137 as a white powder (173 mg, 89% yield). Analytical Method 3, $t_R$=1.17 min., [M+H]$^+$=974.4.

The compounds in Table 30 were synthesized according to the procedure described in Example 8.42 for Compound 137 from the respective intermediates shown in Tables 1-7 and described above in Example 8.

TABLE 30
| Cmd No. | Structure | LCMS |
|---|---|---|
| 139 | 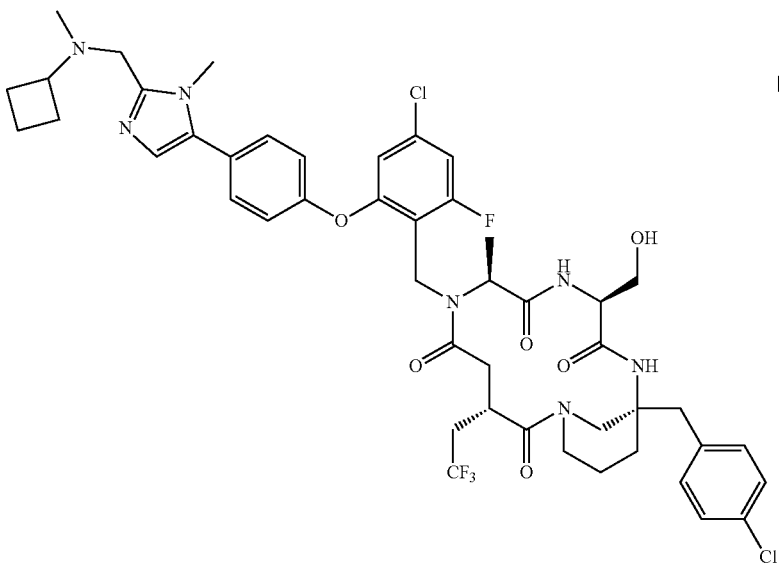 [SMILES: C[C@H]1C(=O)N[C@@H](CO)C(=O)N[C@@]2(Cc3ccc(Cl)cc3)CCCN(C2)C(=O)[C@H](CC(F)(F)F)CC(=O)N1Cc1c(F)cc(Cl)cc1Oc1ccc(-c2cnc(CN(C)C3CCC3)n2C)cc1] | Analytical Method 3<br>$t_R$ = 1.12 min.<br>$[M + H]^+$ = 958.4 |
| 141 | 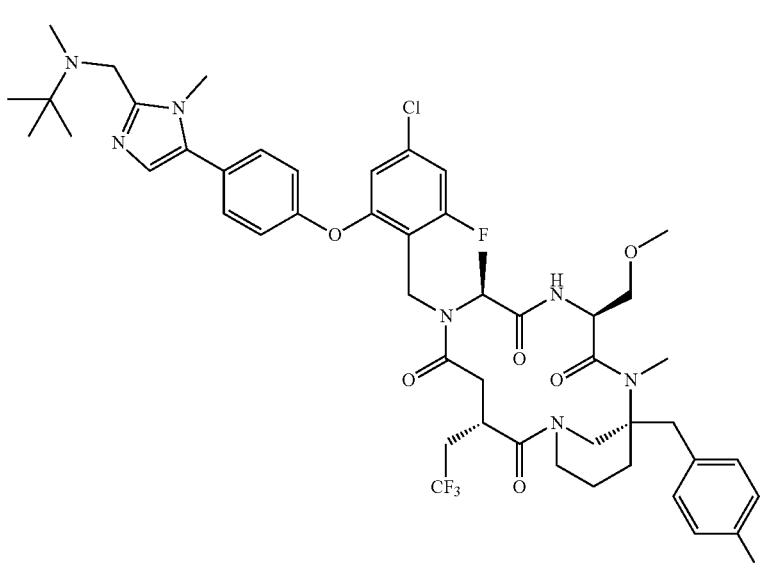 | Analytical Method 2<br>$t_R$ = 3.45 min.<br>$[M + H]^+$ = 988.7 |

TABLE 30-continued
| Cmd No. | Structure | LCMS |
|---|---|---|
| 143 | 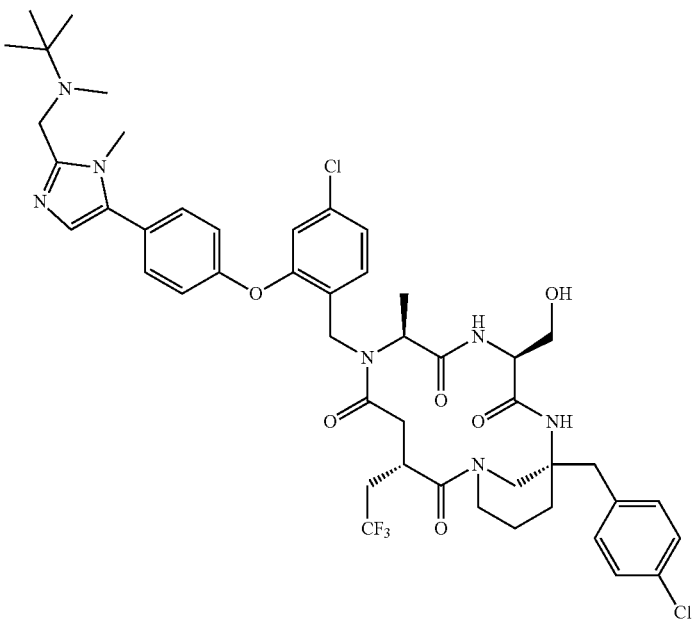 [SMILES: C[C@H]1C(=O)N[C@@H](CO)C(=O)N[C@@]2(Cc3ccc(Cl)cc3)CCCN(C2)C(=O)[C@H](CC(F)(F)F)CC(=O)N1Cc1ccc(Cl)cc1Oc1ccc(-c2cnc(CN(C)C(C)(C)C)n2C)cc1] | Analytical Method 4<br>$t_R$ = 2.08 min.<br>$[M + H]^+$ = 942.4 |
| 160 | 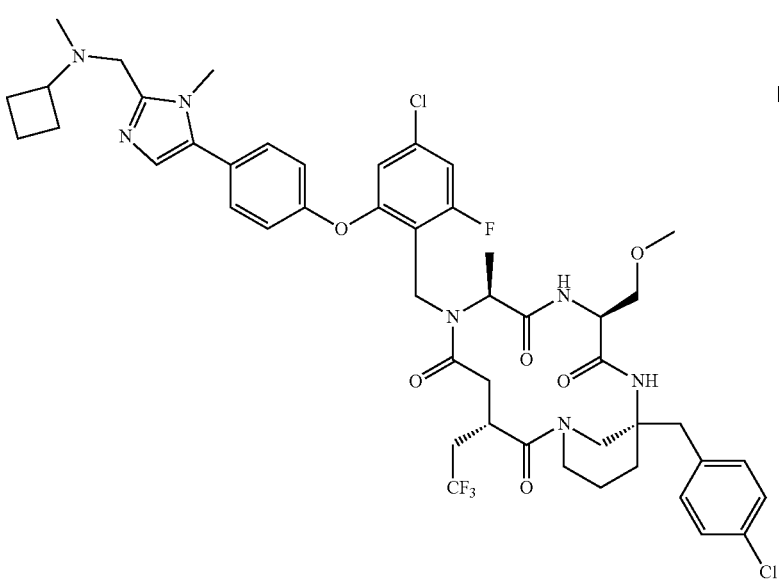 [SMILES: COC[C@@H]1NC(=O)[C@H](C)N(Cc2c(F)cc(Cl)cc2Oc2ccc(-c3cnc(CN(C)C4CCC4)n3C)cc2)C(=O)C[C@@H](CC(F)(F)F)C(=O)N2CCC[C@@](Cc3ccc(Cl)cc3)(C2)NC1=O] | Analytical Method 3<br>$t_R$ = 1.17 min.<br>$[M + H]^+$ = 972.4 |

TABLE 30-continued
| Cmd No. | Structure | LCMS |
|---|---|---|
| 162 | 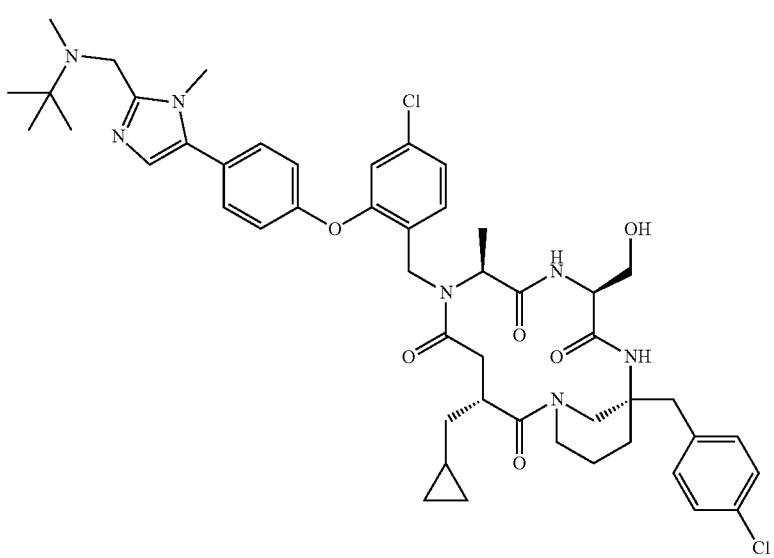 [SMILES: C[C@H]1C(=O)N[C@@H](CO)C(=O)N[C@@]2(Cc3ccc(Cl)cc3)CCCN(C2)C(=O)[C@H](CC2CC2)CC(=O)N1Cc1ccc(Cl)cc1Oc1ccc(-c2cnc(CN(C)C(C)(C)C)n2C)cc1] | Analytical Method 2<br>$t_R$ = 2.16 min.<br>$[M + H]^+$ = 914.4 |
| 163 | 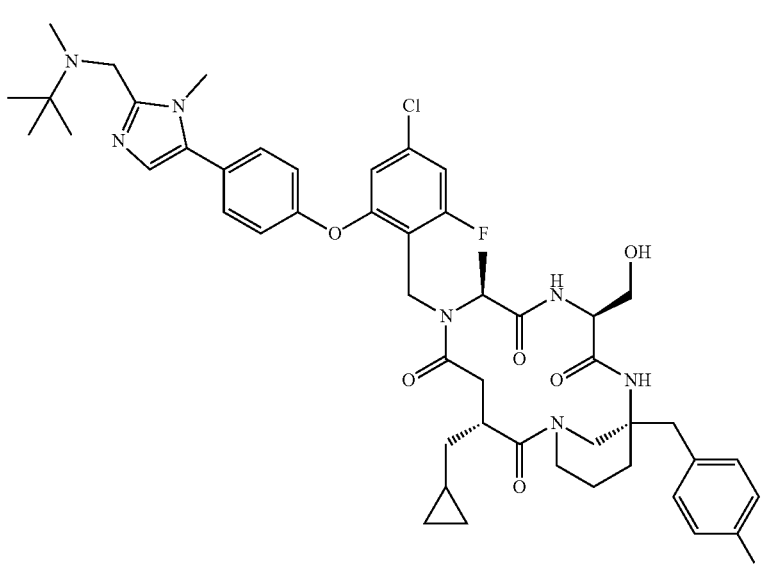 | Analytical Method 3<br>$t_R$ = 1.14 min.<br>$[M + H]^+$ = 932.4 |

| Cmd No. | Structure | LCMS |
|---|---|---|
| 169 | 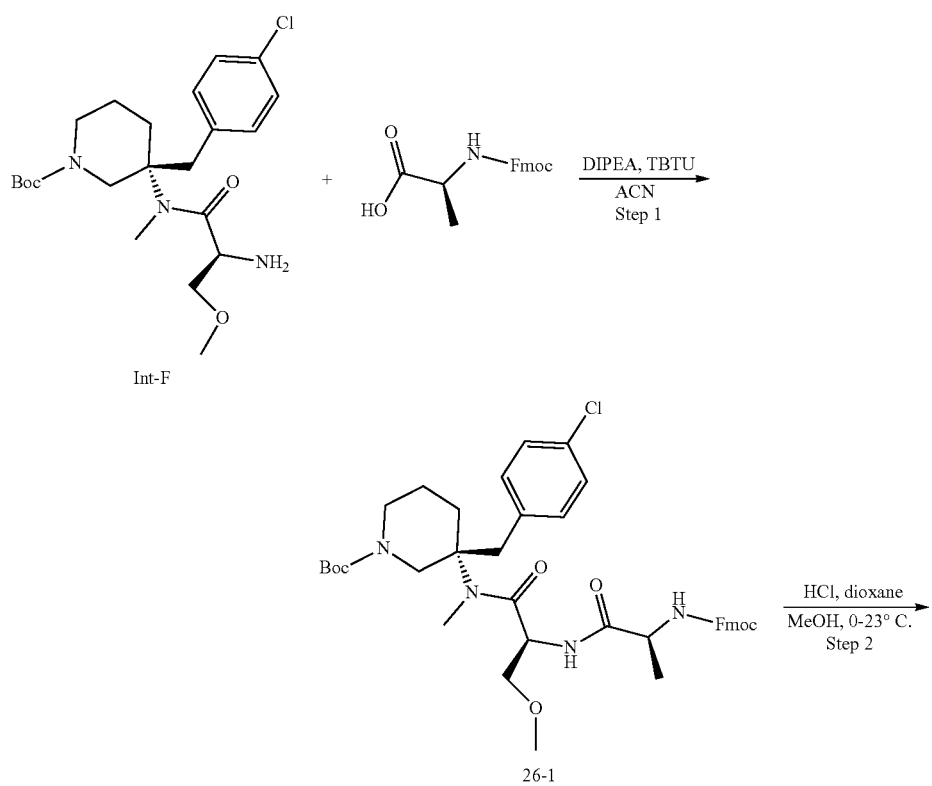 | Analytical Method 3<br>$t_R$ = 1.2 min.<br>$[M + H]^+$ = 996.4 |
Example 8.43: Synthesis of (3S,7S,10S,13R)-6-(2-(4-(2-((tert-Butylamino)methyl)-1-methyl-1H-imidazol-5-yl)phenoxy)-4-chloro-6-fluorobenzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone (Compound 136)

-continued
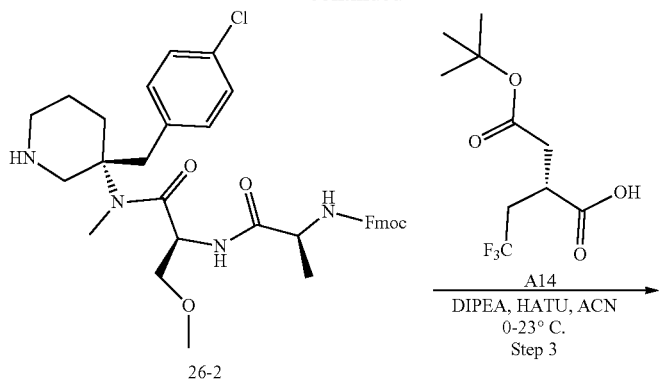
26-2
A14
DIPEA, HATU, ACN
0-23° C.
Step 3
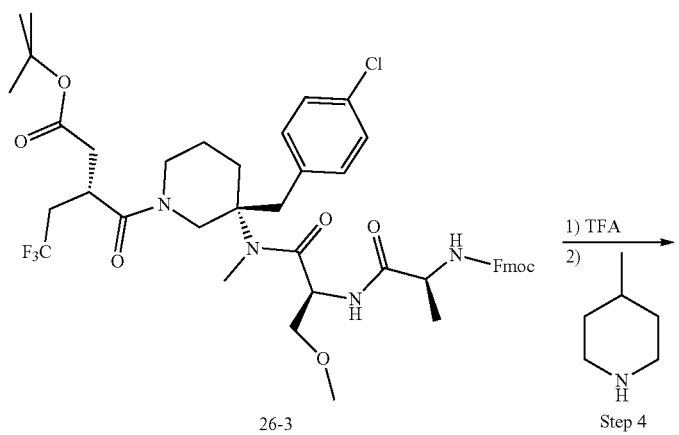
26-3
1) TFA
2) 4-methylpiperidine
Step 4
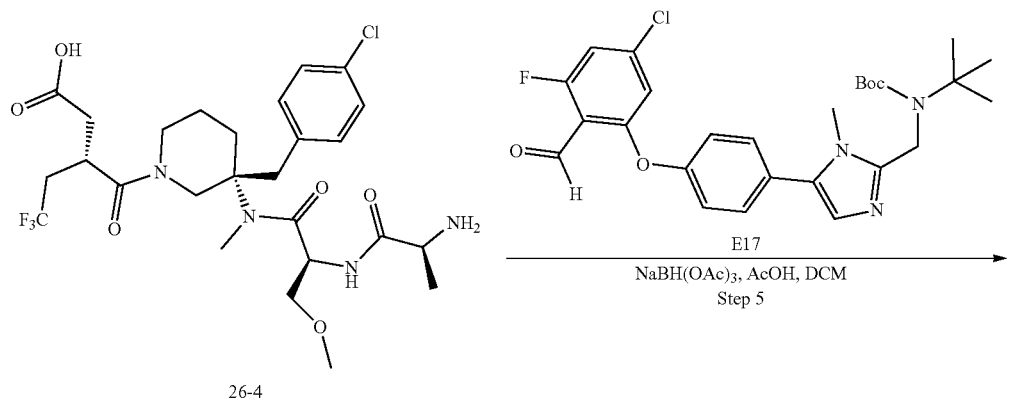
26-4
E17
NaBH(OAc)₃, AcOH, DCM
Step 5
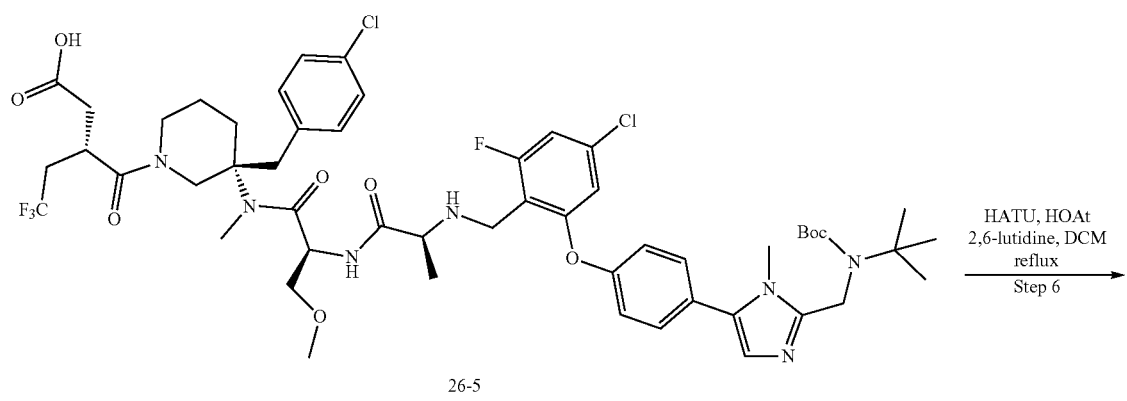
26-5
HATU, HOAt
2,6-lutidine, DCM
reflux
Step 6

-continued

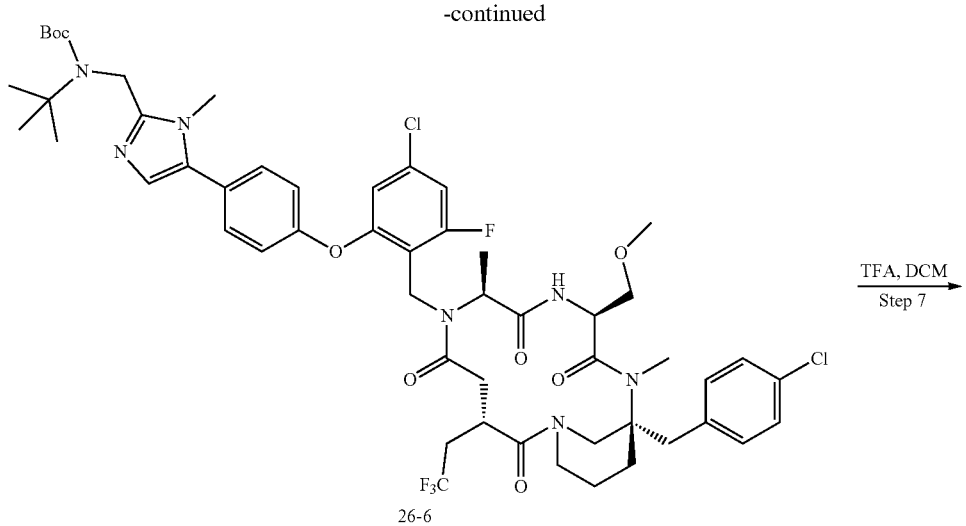

26-6

TFA, DCM
Step 7 →

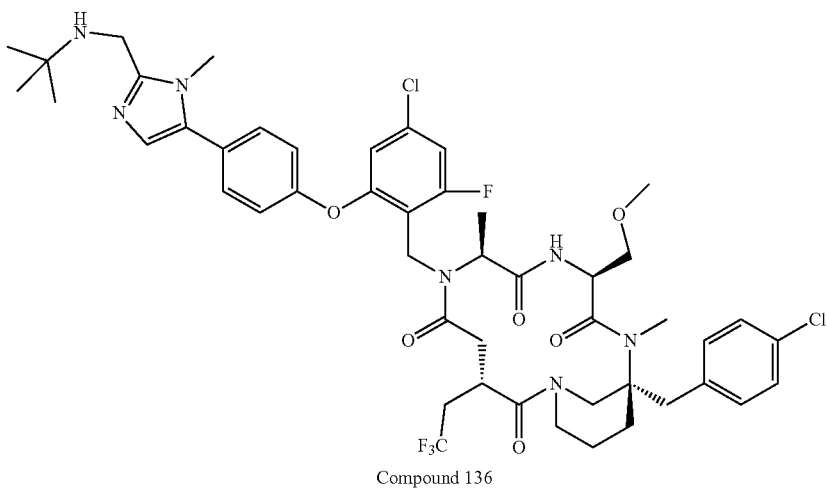 [SMILES: COC[C@@H]1NC(=O)[C@H](C)N(Cc2c(F)cc(Cl)cc2Oc2ccc(-c3cnc(CNC(C)(C)C)n3C)cc2)C(=O)C[C@@H](CC(F)(F)F)C(=O)N2CCC[C@@](Cc3ccc(Cl)cc3)(C2)N(C)C1=O]

Compound 136

Step 1. tert-Butyl (R)-3-((S)-2-((S)-2-((((9H-fluoren-9-yl)methoxy)carbonyl)amino)propanamido)-3-methoxy-N-methylpropanamido)-3-(4-chlorobenzyl)piperidine-1-carboxylate (26-1)

To a mixture of Fmoc-L-alanine (3.03 g, 9.74 mmol) and TBTU (3.13 g, 9.74 mmol) in ACN (100 mL) was added DIPEA (4.86 mL, 27.8 mmol). The resulting mixture was stirred at RT for 5 min. to afford a clear solution. Intermediate F (5.1 g, 9.27 mmol) was then added and stirring was continued at RT for 1 h. The reaction mixture was treated with water (30 mL) and then concentrated to remove excess organic solvent. The obtained residue was extracted with DCM (2×100 mL) and the organic phase was washed sequentially with saturated NaHCO$_3$, water and brine, dried over sodium sulfate, filtered, and concentrated to afford 26-1 as a crude product (6.95 g, assumed quantitative yield), which was used directly in the next step without purification. Analytical Method 3, $t_R$=1.34 min., [M+H]$^+$−100=633.4.

Step 2. (9H-fluoren-9-yl)methyl ((S)-1-(((S)-1-(((R)-3-(4-chlorobenzyl)piperidin-3-yl)(methyl)amino)-3-methoxy-1-oxopropan-2-yl)amino)-1-oxopropan-2-yl)carbamate (26-2)

To a solution of 26-1 (6.95 g, 9.48 mmol) in anhydrous MeOH (100 mL) at 0° C. was added a cold solution of HCl (4N in dioxane (71.1 mL, 284 mmol) dropwise. The cooling bath was then removed and the resulting mixture was stirred at RT for 1 h and concentrated in vacuo. The obtained residue was dried under high vacuum to afford 26-2 (6.35 g, ~ quantitative yield), which was be used in the next step without purification. Analytical Method 3, $t_R$=1.22 min., [M+H]$^+$=633.8.

Step 3. (S)-tert-Butyl 3-((R)-3-((S)-2-((S)-2-((((9H-fluoren-9-yl)methoxy)carbonyl)amino)propanamido)-3-methoxy-N-methylpropanamido)-3-(4-chlorobenzyl)piperidine-1-carbonyl)-5,5,5-trifluoropentanoate (26-3)

To a mixture of A14 (2.55 g, 9.95 mmol), HATU (3.78 g, 9.95 mmol) in ACN (100 mL) was added DIPEA (8.28 mL, 47.4 mmol). The resulting mixture was stirred at RT for a few minutes before being added to a chilled solution of 26-2 (6.35 g, 9.48 mmol) in ACN (100 mL) cooled in an ice bath. The cooling bath was removed and stirring was continued at RT for 60 min. The reaction mixture was then treated with 15 mL of water and concentrated. The residue was extracted twice with EtOAc (2×100 mL). The organic phase was washed sequentially with saturated $NaHCO_3$, water, and brine, dried over $Na_2SO_4$, filtered, and concentrated to afford 26-3 (8.26 g, ~quantitative yield). The material was carried to the next step without purification. Analytical Method 3, $t_R$=1.40 min., $[M+H]^+$=871.3.

Step 4. (S)-3-((R)-3-((S)-2-((S)-2-Aminopropanamido)-3-methoxy-N-methylpropanamido)-3-(4-chlorobenzyl)piperidine-1-carbonyl)-5,5,5-trifluoropentanoic acid (26-4)

Step 4.1: To a solution of 26-3 (8.26 g, 9.48 mmol) in DCM (100 mL) at 0° C. was slowly added TFA (21.91 mL, 284 mmol). The resulting mixture was stirred at RT for 2 h and a saturated $NaHCO_3$ solution was then added with stirring to afford a biphasic mixture. The organic phase was separated and the aqueous phase back extracted with more DCM. The combined organic phases were dried over $Na_2SO_4$, filtered, and concentrated to afford the interim product. The material was used in the next step without further purification without purification. MS $[M+H]^+$=815.4

Step 4.2: To the product from Step 4.1 in DCM (100 mL) was treated with 4-methylpiperidine (4.49 mL, 37.9 mmol) at 0° C. The cooling bath was removed and the resulting mixture was stirred at RT for 30 min. Another portion of 4-methylpiperidine (4.49 mL, 37.9 mmol) was then added and stirring was continued at RT for 60 min. The reaction mixture was then concentrated and the residue was purified by reverse-phase column chromatography (eluting with 0-100% ACN/water with 0.1% $NH_4OH$) to afford 26-4 after freeze drying the pure fractions (2.37 g, 40.9% yield). Analytical Method 2, $t_R$=1.19 min., $[M+H]^+$=593.5.

Step 5. (S)-3-((R)-3-((S)-2-((S)-2-((2-(4-(2-(((tert-Butoxycarbonyl)(tert-butyl)amino)methyl)-1-methyl-1H-imidazol-5-yl)phenoxy)-4-chloro-6-fluorobenzyl)amino)propanamido)-3-methoxy-N-methylpropanamido)-3-(4-chlorobenzyl)piperidine-1-carbonyl)-5,5,5-trifluoropentanoic acid (26-5)

To a mixture of 26-4 (304 mg, 0.51 mmol) and E17 (270 mg, 0.52 mmol) in DCM (8 mL) was treated with AcOH (0.09 mL, 1.57 mmol) and the resulting solution was stirred at RT for 1 h. Sodium $NaBH(OAc)_3$ (444 mg, 2.09 mmol) was added in one portion stirring was continued for 1.5 h. EtOAc (100 mL) was added and the organic phase was washed with a 5% $NaHCO_3$ solution (50 mL), dried over $Na_2SO_4$, filtered, and concentrated. The crude oily product was purified by reverse-phase column chromatography (eluting with 0-100% ACN/water with 0.1% $NH_4OH$) to afford 26-5 (373 mg, 0.321 mmol, 61% yield) as a white powder after freeze drying the pure fractions. Analytical Method 5, $t_R$=1.02 min., $[M+H]^+$=1092.1.

Step 6. tert-Butyl tert-butyl((5-(4-(5-chloro-2-(((3S,7S,10S,13R)-13-(4-chlorobenzyl)-10-(methoxymethyl)-7,12-dimethyl-2,5,8,11-tetraoxo-3-(2,2,2-trifluoroethyl)-1,6,9,12-tetraazabicyclo[11.3.1]heptadecan-6-yl)methyl)-3-fluorophenoxy)phenyl)-1-methyl-1H-imidazol-2-yl)methyl)carbamate (26-6)

To a solution of 26-5 (373 mg, 0.34 mmol) in anhydrous DCM (150 mL) was added 2,6-lutidine (1.19 mL, 10.2 mmol), HOAt (46.4 mg, 0.34 mmol), and HATU (519 mg, 1.36 mmol). The resulting mixture was heated to reflux overnight in a 45° C. heating bath. The reaction mixture was cooled to RT and subsequently concentrated. The obtained residue was partitioned between EtOAc (100 mL) and 5% aq. $NaHCO_3$ (50 mL). The separated organic phase was washed with 5% aq. $NaHCO_3$ (3×50 mL) and brine (50 mL), dried over $Na_2SO_4$, filtered, and concentrated to afford 26-6 as a crude oil (368 mg, assume quantitative yield). The product was used in the next step without further purification. Analytical Method 5, $t_R$=1.45 min., $[M+H]^+$=1074.7.

Step 7. (3S,7S,10S,13R)-6-(2-(4-(2-((tert-Butylamino)methyl)-1-methyl-1H-imidazol-5-yl)phenoxy)-4-chloro-6-fluorobenzyl)-13-(4-chlorobenzyl)-10-(methoxymethyl)-7,12-dimethyl-3-(2,2,2-trifluoroethyl)-1,6,9,12-tetraazabicyclo[11.3.1]heptadecane-2,5,8,11-tetraone (Compound 136)

To a pre-chilled solution of 26-6 (368 mg, 0.34 mmol) in anhydrous DCM (20 mL) was added TFA (3.95 mL, 51.3 mmol) dropwise and slowly. The cooling bath was removed and the resulting mixture was stirred at RT for 1 h. Additional TFA was added and stirring was continued for 1.5 h. The reaction mixture was added carefully to a saturated $NaHCO_3$ solution (100 mL) with stirring at RT and then extracted twice with EtOAc (2×100 mL). The organic phase was dried over sodium sulfate, filtered, and concentrated. The resulting oil was purified by reverse-phase column chromatography (eluting with 0-100% ACN/water with 0.1% TFA) to afford the desired product as a TFA salt. The product was then taken up in a mixture of EtOAc and $NaHCO_3$ and stirred at RT to for a few minutes. The organic phase was separated and concentrated to afford the desired product as a free base. The material was purified by basic HPLC (eluting with 0-100% ACN/water with 0.1% $NH_4OH$) and then by flash column chromatography on silica gel (eluting with 0-10% DCM/MeOH) to afford Compound 136 after concentrating the pure fractions (50 mg, 0.05 mmol, 14% yield). Analytical Method 3, $t_R$=1.14 min. $[M+H]^+$=974.4.

The compounds in Table 31 were synthesized according to the procedure described in Example 8.43 for Compound 136 from the respective intermediates shown in Tables 1-7 and described above in Example 8.

TABLE 31

| Cmd No. | Structure | LCMS |
|---|---|---|
| 173 | 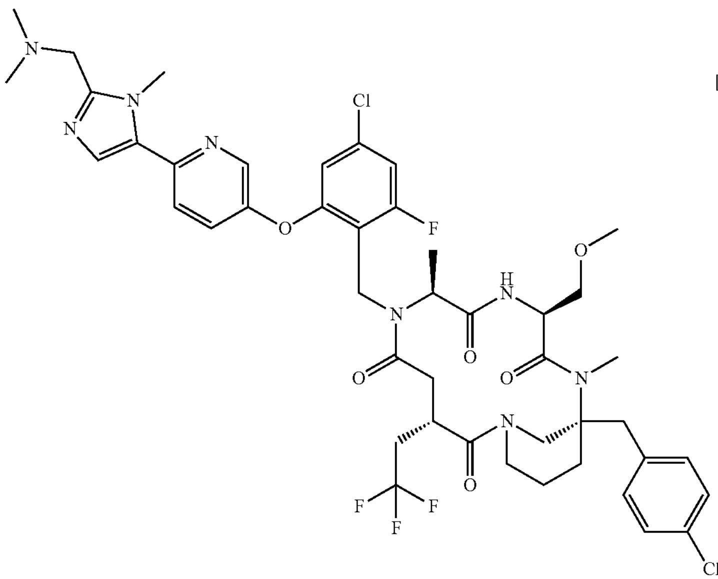 [SMILES: COC[C@@H]1NC(=O)[C@H](C)N(Cc2c(F)cc(Cl)cc2Oc2ccc(-c3cnc(CN(C)C)n3C)nc2)C(=O)C[C@@H](CC(F)(F)F)C(=O)N2CCC[C@@](Cc3ccc(Cl)cc3)(C2)N(C)C1=O] | Analytical Method 2<br>$t_R$ = 2.96 min.<br>$[M + H]^+$ = 947.34 |
| 176 | 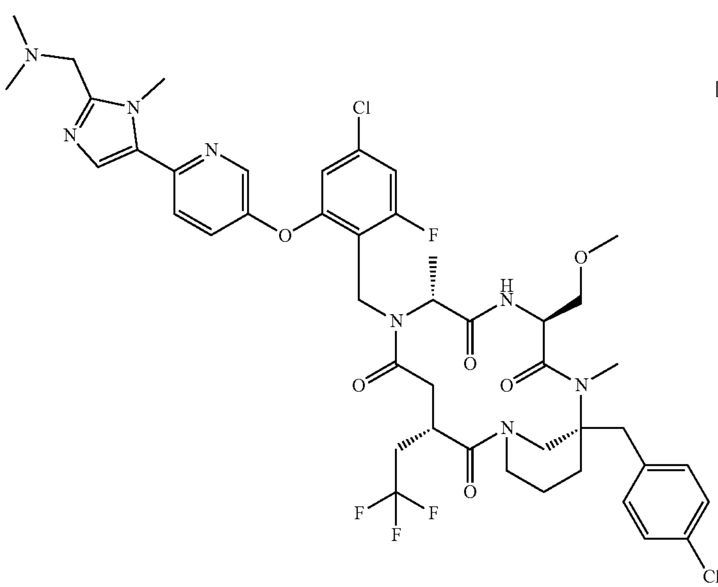 [SMILES: COC[C@@H]1NC(=O)[C@@H](C)N(Cc2c(F)cc(Cl)cc2Oc2ccc(-c3cnc(CN(C)C)n3C)nc2)C(=O)C[C@@H](CC(F)(F)F)C(=O)N2CCC[C@@](Cc3ccc(Cl)cc3)(C2)N(C)C1=O] | Analytical Method 2<br>$t_R$ = 2.9 min.<br>$[M + H]^+$ = 947.34 |

Example 8.44: (3R,7S,10S,13R)-6-(4-chloro-2-fluoro-6-(4-(1-methyl-2-((methylamino)methyl)-1H-imidazol-5-yl)phenoxy)benzyl)-13-(4-chlorobenzyl)-10-(methoxymethyl)-7,12-dimethyl-3-((6-methylpyridin-2-yl)methyl)-1,6,9,12-tetraazabicyclo[11.3.1]heptadecane-2,5,8,11-tetraone (Compound 167)
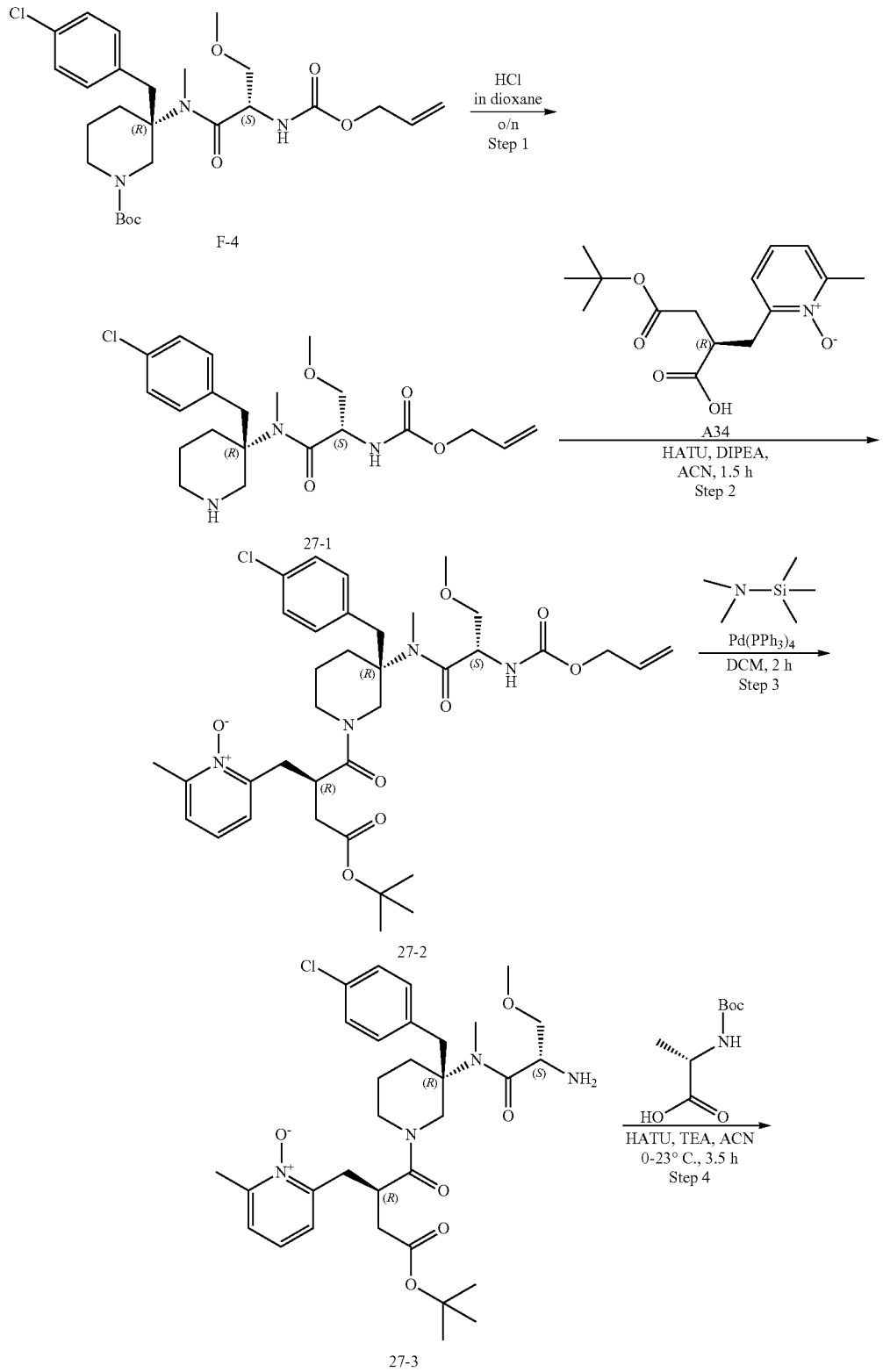

-continued
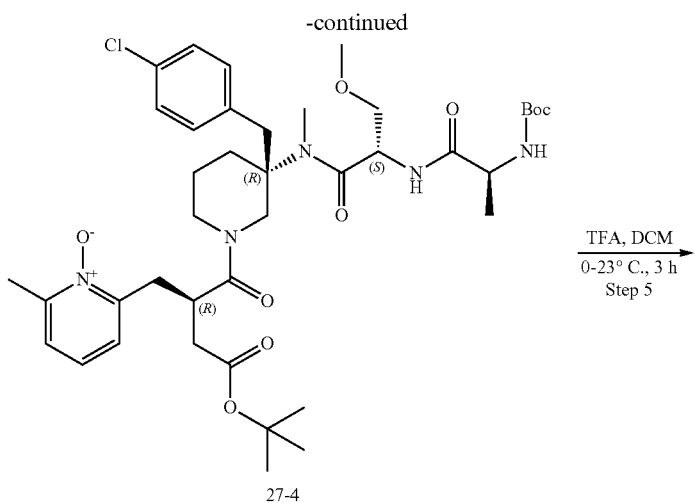
27-4
TFA, DCM
0-23° C., 3 h
Step 5
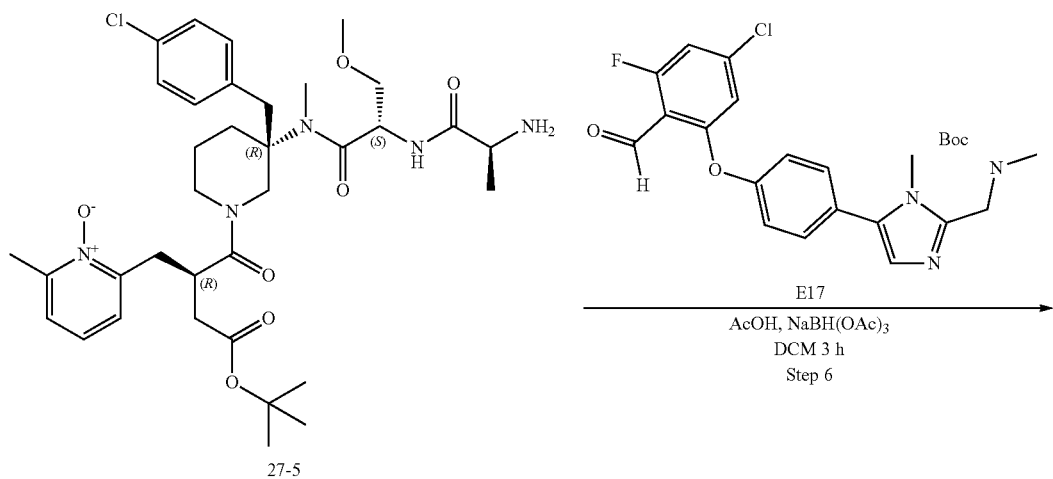
27-5
E17
AcOH, NaBH(OAc)$_3$
DCM 3 h
Step 6
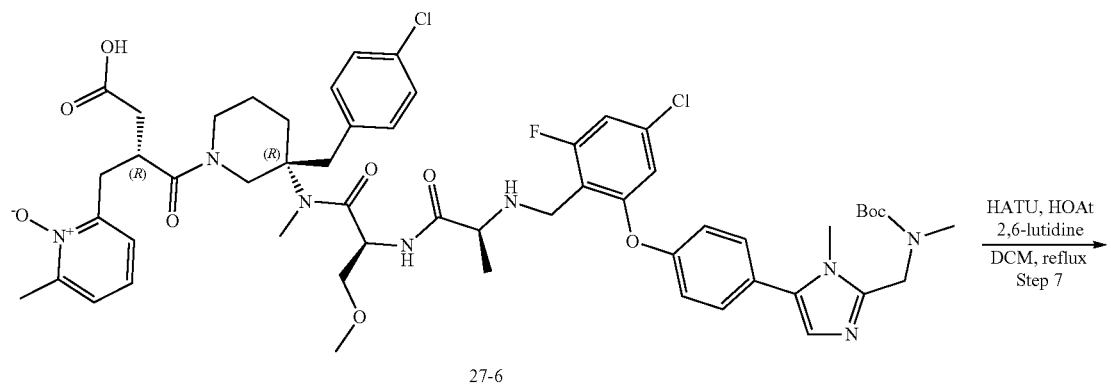
27-6
HATU, HOAt
2,6-lutidine
DCM, reflux
Step 7

-continued
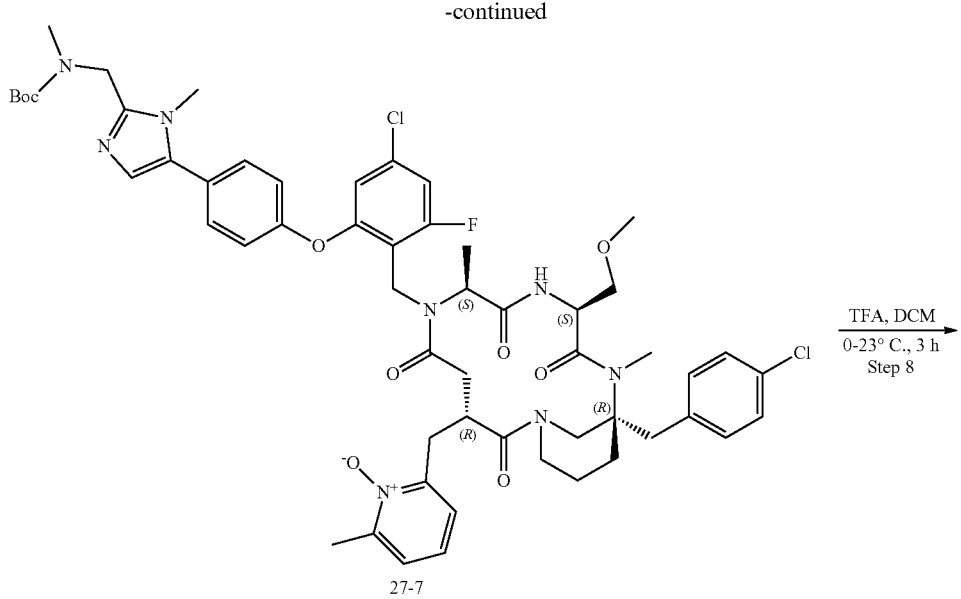
27-7
TFA, DCM
0-23° C., 3 h
Step 8
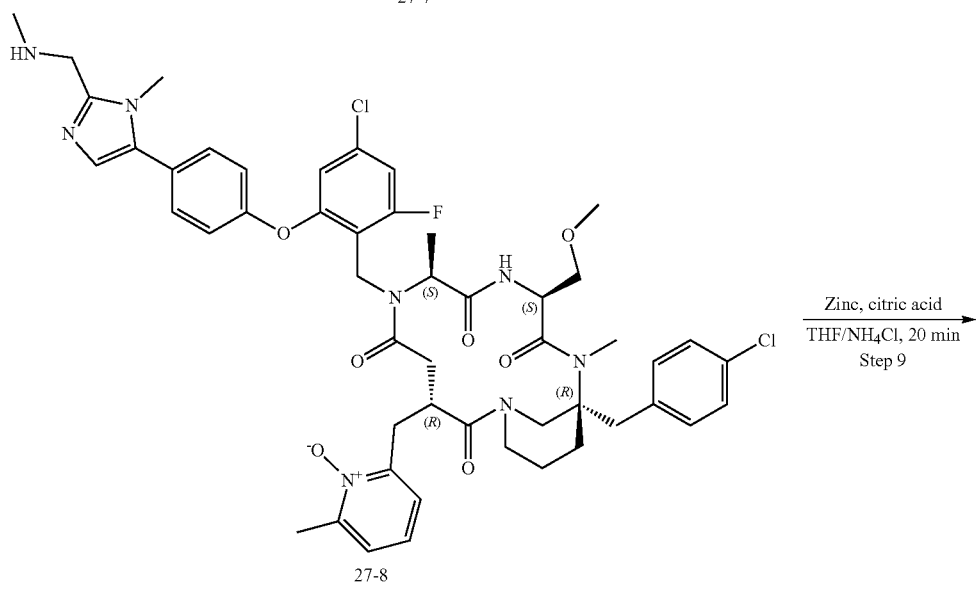
27-8
Zinc, citric acid
THF/NH4Cl, 20 min
Step 9
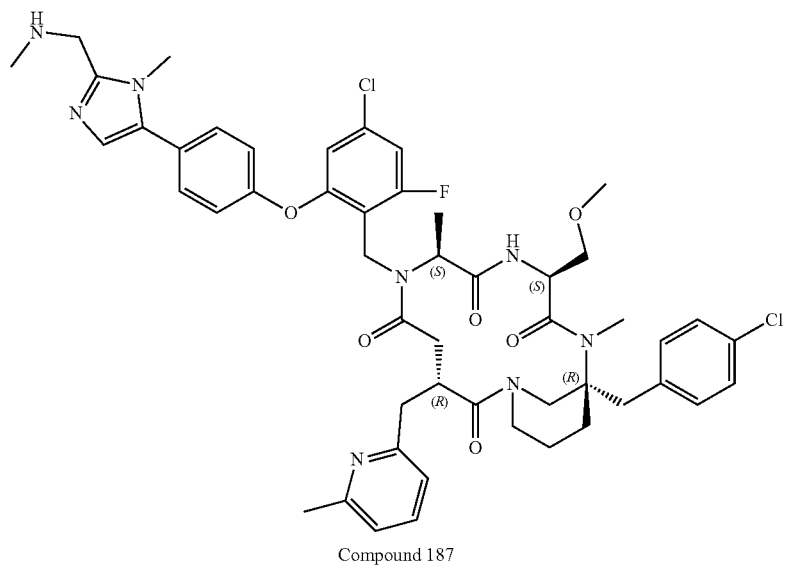
Compound 187

Step 1: Allyl ((S)-1-(((R)-3-(4-chlorobenzyl)piperidin-3-yl)(methyl)amino)-3-methoxy-1-oxopropan-2-yl)carbamate (27-1)

To a solution of F-4 (2.049 g, 3.91 mmol) in anhydrous 1,4-dioxane (7 mL) at 0° C. was added HCl in 1,4-dioxane (5.87 mL, 23.46 mmol). The cooling bath was removed and the resulting mixture was stirred at rt for overnight. Once LCMS showed complete consumption of starting materials, the reaction mixture was concentrated to afford 27-1 as a white solid which was used in next step without purification. Analytical method 5, $t_R$=1.02 min, [M+H]$^+$=424.3.

Step 2: 2-((R)-2-((R)-3-((S)-2-(((allyloxy)carbonyl)amino)-3-methoxy-N-methylpropanamido)-3-(4-chlorobenzyl)piperidine-1-carbonyl)-4-(tert-butoxy)-4-oxobutyl)-6-methylpyridine 1-oxide (27-2)

To a mixture of 27-1 (1.8 g, 3.91 mmol) and A34 (1.212 g, 4.11 mmol) in ACN (10 mL) at 0° C. was added DIPEA (2.049 mL, 11.73 mmol) and HATU (1.561 g, 4.11 mmol). The cooling bath was removed and the reaction was stirred at rt for 1.5 h. Once LCMS showed complete consumption of starting materials, the reaction mixture was diluted with 100 mL of EtOAc and washed with 3×100 mL of 5% NaHCO$_3$ and brine, dried over sodium sulfate, filtered, and concentrated to afford 27-2 as a brown foam-like solid which was used in next step without purification. Analytical method 5, $t_R$=1.10 min, [M+H]$^+$=701.6.

Step 3: 2-((R)-2-((R)-3-((S)-2-amino-3-methoxy-N-methylpropanamido)-3-(4-chlorobenzyl)piperidine-1-carbonyl)-4-(tert-butoxy)-4-oxobutyl)-6-methylpyridine 1-oxide (27-3)

To a solution of 27-2 (2.74 g, 3.91 mmol) in DCM (30 mL) was added N,N,1,1,1-pentamethylsilanamine (3.13 mL, 19.55 mmol) and Pd(PPh$_3$)$_4$ (0.339 g, 0.293 mmol) and the resulting mixture was stirred at rt for 2 h. Once LCMS showed complete consumption of starting materials, the reaction mixture was then concentrated. The resulting brown oil was diluted with 100 mL of EtOAc and washed with 3×100 mL of 5% NaHCO$_3$, and brine, dried over sodium sulfate, filtered and concentrated under reduced pressure overnight to afford 27-3 as a yellow foaming solid (~100% yield) which was used in next step without purification. Analytical method 5, $t_R$=0.97 min, [M+H]$^+$=617.3.

Step 4: 2-((R)-4-(tert-butoxy)-2-((R)-3-((S)-2-((S)-2-((tert-butoxycarbonyl)amino)propanamido)-3-methoxy-N-methylpropanamido)-3-(4-chlorobenzyl)piperidine-1-carbonyl)-4-oxobutyl)-6-methylpyridine 1-oxide (27-4)

To a solution of 27-3 (2.413 g, 3.91 mmol) in anhydrous ACN (20 mL) at 0° C. was added Boc-L-alanine (0.777 g, 4.11 mmol), TEA (1.090 mL, 7.82 mmol) and HATU (1.561 g, 4.11 mmol). The cooling bath was removed and the resulting mixture was stirred at rt for 3.5 h. Once LCMS showed complete consumption of starting materials, the reaction mixture was diluted with 100 mL of EtOAc and washed with 3×100 mL of 5% NaHCO$_3$ and brine, dried over sodium sulfate, filtered and concentrated under reduced pressure overnight to afford 27-4 as a yellow foam-like solid as the desired product which was used in next step without purification. Analytical method 5, $t_R$=1.11 min, [M+H]$^+$=788.3.

Step 5: 2-((R)-3-((R)-3-((S)-2-((S)-2-aminopropanamido)-3-methoxy-N-methylpropanamido)-3-(4-chlorobenzyl)piperidin-1-yl)-2-(carboxymethyl)-3-oxopropyl)-6-methylpyridine 1-oxide (27-5)

To a solution of 27-4 (3.08 g, 3.91 mmol) in anhydrous DCM (12 mL) at 0° C. was added TFA (12.05 mL, 156 mmol)). The resulting mixture was stirred at 0° C. for 1 h and then warming to rt and stirred for 3 h. Once LCMS showed complete consumption of starting materials, the reaction mixture was concentrated under reduced pressure and purified by ISCO column chromatography on a 415 g C18 column (eluting with 0-50% ACN in water buffered with 0.1% NH$_4$OH; product came out at 40% ACN,) to afford 27-5 (1.01 g, 1.598 mmol, 40.9% yield) after lyophilization. Analytical method 5, $t_R$=0.51 min, [M+H]$^+$=632.3.

Step 6: 2-((R)-3-((R)-3-((S)-2-((S)-2-((2-(4-(2-((((tert-butoxycarbonyl)(methyl)amino)methyl)-1-methyl-1H-imidazol-5-yl)phenoxy)-4-chloro-6-fluorobenzyl)amino)propanamido)-3-methoxy-N-methylpropanamido)-3-(4-chlorobenzyl)piperidin-1-yl)-2-(carboxymethyl)-3-oxopropyl)-6-methylpyridine 1-oxide (27-6)

To a solution of 27-5 (267 mg, 0.422 mmol) in DCM (10 mL) was added E17 (200 mg, 0.422 mmol) and acetic acid (0.072 mL, 1.266 mmol). The resulting mixture was stirred for 1 h at rt, and NaBH(OAc)$_3$ (358 mg, 1.688 mmol) was then added. The reaction mixture was stirred for additional 2 h at rt. Once LCMS showed complete consumption of starting materials, the reaction mixture was diluted with 100 mL of EtOAc, washed with 50 mL of 5% NaHCO$_3$, dried over Na$_2$SO$_4$, filtered, and concentrated. The crude oily product was purified by ISCO column chromatography on a C18 column (eluting with 0-100% ACN in water with 0.1% NH$_4$OH as buffer) to afford 27-6 (224 mg, 0.205 mmol, 48.7% yield) after lyophilization. Analytical method 2, $t_R$=1.97 min, [M+H]$^+$=1089.1.

Step 7: 2-(((3R,7S,10S,13R)-6-(2-(4-(2-(((tert-butoxycarbonyl)(methyl)amino)methyl)-1-methyl-1H-imidazol-5-yl)phenoxy)-4-chloro-6-fluorobenzyl)-13-(4-chlorobenzyl)-10-(methoxymethyl)-7,12-dimethyl-2,5,8,11-tetraoxo-1,6,9,12-tetraazabicyclo[11.3.1]heptadecan-3-yl)methyl)-6-methylpyridine 1-oxide (27-7)

To a solution of 27-6 (224 mg, 0.205 mmol) in anhydrous DCM (100 mL) were added 2,6-lutidine (0.718 mL, 6.16 mmol), HOAt (28.0 mg, 0.205 mmol), and HATU (313 mg, 0.822 mmol) and the resulting mixture was refluxed overnight in a 45° C. heating bath. Once LCMS showed complete consumption of starting materials, the reaction mixture was concentrated and the resulting residue was partitioned between EtOAc (100 mL) and 5% aq. NaHCO$_3$ (100 mL). The separated organic phase was washed with 5% aq. NaHCO$_3$ (2×50 mL) and brine (50 mL), dried over Na$_2$SO$_4$, filtered and concentrated. The crude oil (27-7) was carried on to the next step without purification. Analytical method 5, $t_R$=1.19 min, [M+H]$^+$=1071.1.

Step 8: 2-(((3R,7S,10S,13R)-6-(4-chloro-2-fluoro-6-(4-(1-methyl-2-((methylamino)methyl)-1H-imidazol-5-yl)phenoxy)benzyl)-13-(4-chlorobenzyl)-10-(methoxymethyl)-7,12-dimethyl-2,5,8,11-tetraoxo-1,6,9,12-tetraazabicyclo[11.3.1]heptadecan-3-yl)methyl)-6-methylpyridine 1-oxide (27-8)

To a solution of 27-7 (220 mg, 0.205 mmol) in anhydrous DCM (10 mL) at 0° C. was added TFA (2.371 mL, 30.8 mmol) and the cooling bath was then removed. The resulting mixture was stirred at rt for 3 h. Once LCMS showed complete consumption of starting materials, the reaction mixture was poured into 100 mL of sat. NaHCO$_3$ and extracted with 100 mL of DCM. The separated organic phase was dried with sodium sulfate, filtered, and concentrated under reduced pressure to afford 27-8 as oil, which was used in next step without purification. Analytical method 5, $t_R$=1.06 min, [M+H]$^+$=971.2.

Step 9: (3R,7S,10S,13R)-6-(4-chloro-2-fluoro-6-(4-(1-methyl-2-((methylamino)methyl)-1H-imidazol-5-yl)phenoxy)benzyl)-13-(4-chlorobenzyl)-10-(methoxymethyl)-7,12-dimethyl-3-((6-methylpyridin-2-yl)methyl)-1,6,9,12-tetraazabicyclo[11.3.1]heptadecane-2,5,8,11-tetraone (Compound 167)

To a solution of 27-8 (199 mg, 0.205 mmol) in THF (20 mL) was added sat. NH$_4$Cl (6.7 mL), Zinc dust (803 mg, 12.28 mmol) and citric acid (708 mg, 3.69 mmol) and the resulting mixture was stirred at rt for 20 min. Once LCMS showed complete consumption of starting materials, the clear biphasic reaction solution was poured out and the top organic phase was separated (added 2×20 mL of THF to extract any remaining product). The combined organics were concentrated and the residue was diluted in 100 mL of DCM/100 mL of 5% NaHCO$_3$ and partitioned in a separatory funnel overnight. The separated aqueous phase was extracted with 50 mL of DCM. The combined organic phases were dried over sodium sulfate, filtered, and concentrated. The resulting oil was purified by ISCO column chromatography on a 150 g C18 column (eluting with 0-50% ACN in water with 0.1% TFA) to the TFA salt of desired product as a white power after lyophilization. The product was repurified by prep HPLC to afford Compound 167 (21 mg, 0.021 mmol, 10.19% yield) after lyophilization. Analytical method 2, $t_R$=2.76 min, [M+H]$^+$=955.0.

The compounds in Table 32 were synthesized according to the procedure described in Example 8.44 for Compound 167 from the respective intermediates shown in Tables 1-7 and described above in Example 8.

TABLE 32

| Cmd No. | Structure | LCMS |
|---|---|---|
| 172 | 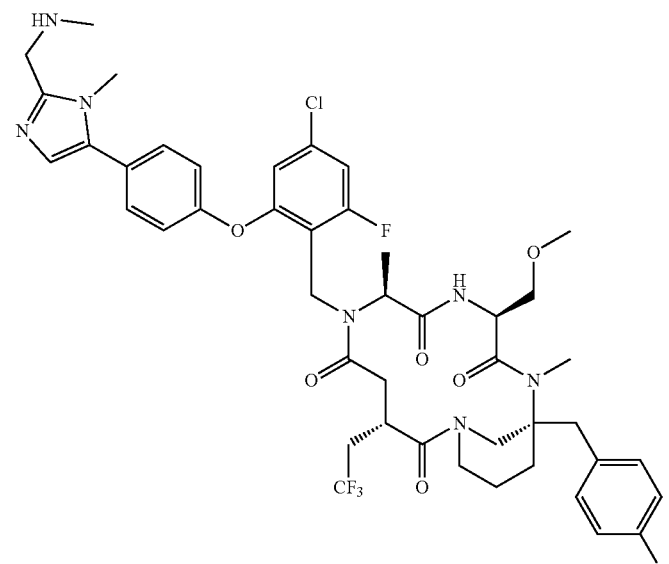 | Analytical Method 2<br>$t_R$ = 2.89 min.<br>[M + H]$^+$ = 932.5 |

Example 8.45: (3R,7S,10S,13R)-6-(4-chloro-2-(4-(2-((dimethylamino)methyl)-1-methyl-1H-imidazol-5-yl)phenoxy)-6-fluorobenzyl)-13-(4-chlorobenzyl)-10-(hydroxymethyl)-7,12-dimethyl-3-((6-methylpyridin-2-yl)methyl)-1,6,9,12-tetraazabicyclo[11.3.1]heptadecane-2,5,8,11-tetraone (Compound 170)

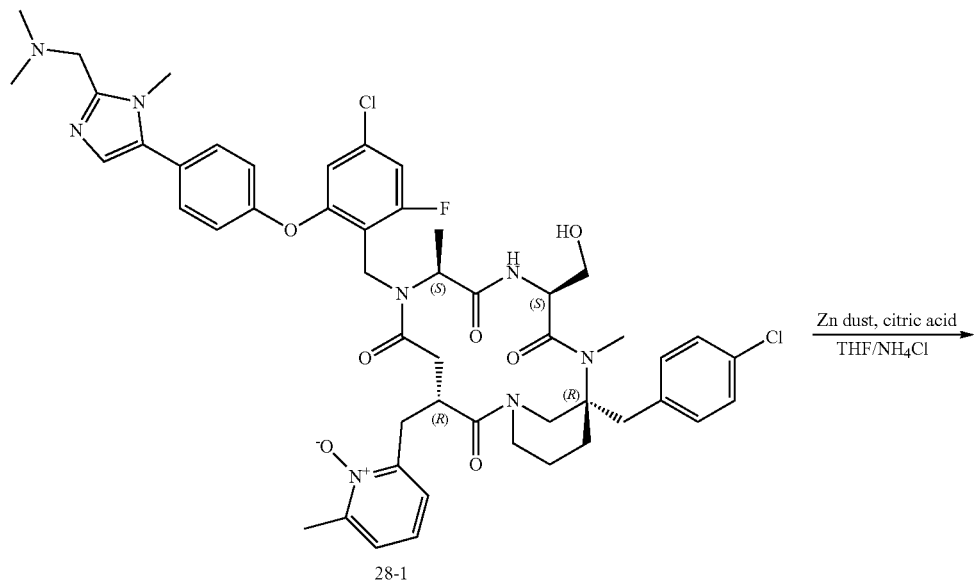

28-1

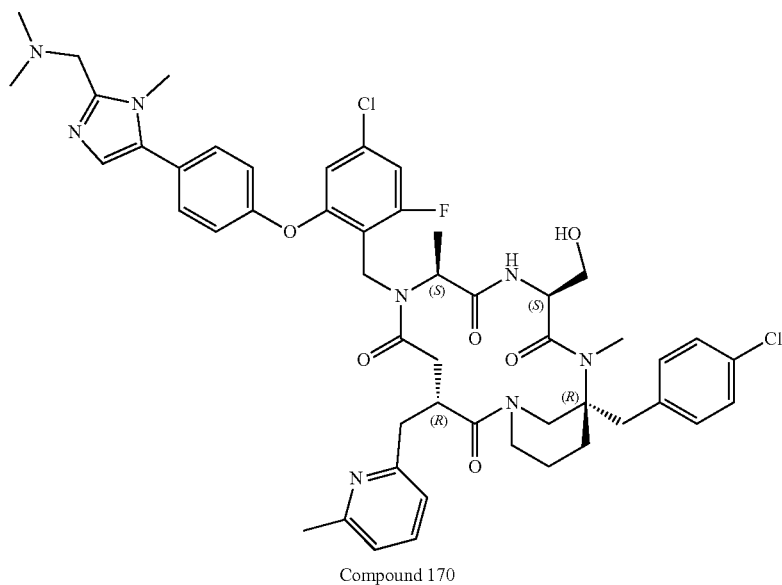

Compound 170

The title Compound 170 was prepared according to the procedure described in Example 8.28, Step 9 for Compound 32 starting from 28-1. Intermediate 28-1 was prepared according to the procedure described in Example 8.22 for Compound 82.

(3S,7S,10S,13R)-6-(2-(4-(2-((tert-butylamino)methyl)-1-methyl-1H-imidazol-5-yl)phenoxy)-4-chloro-6-fluorobenzyl)-13-(4-chlorobenzyl)-3-(3,3-difluorocyclobutyl)-10-(methoxymethyl)-7,12-dimethyl-1,6,9,12-tetraazabicyclo[11.3.1]heptadecane-2,5,8,11-tetraone (Compound 165)
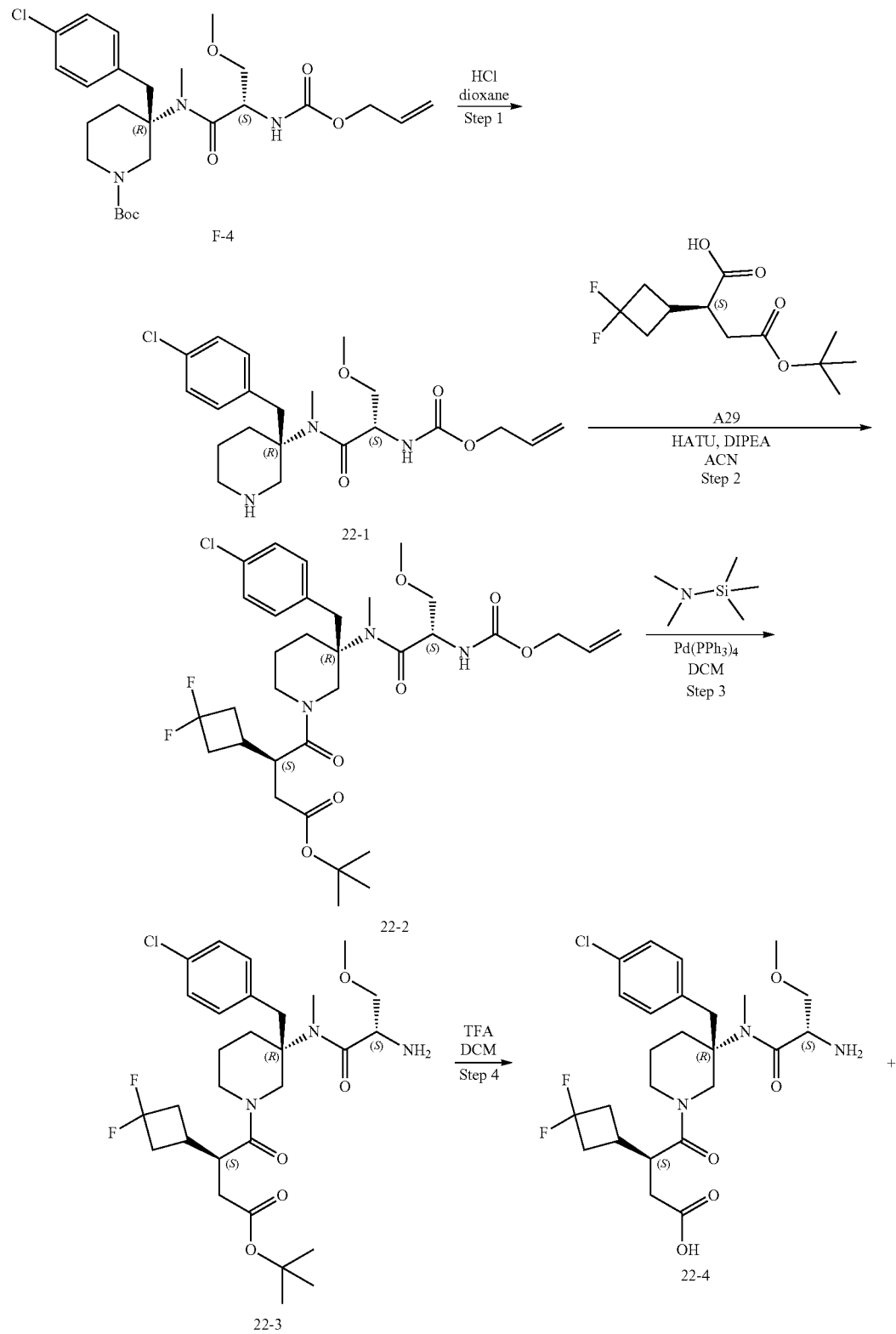

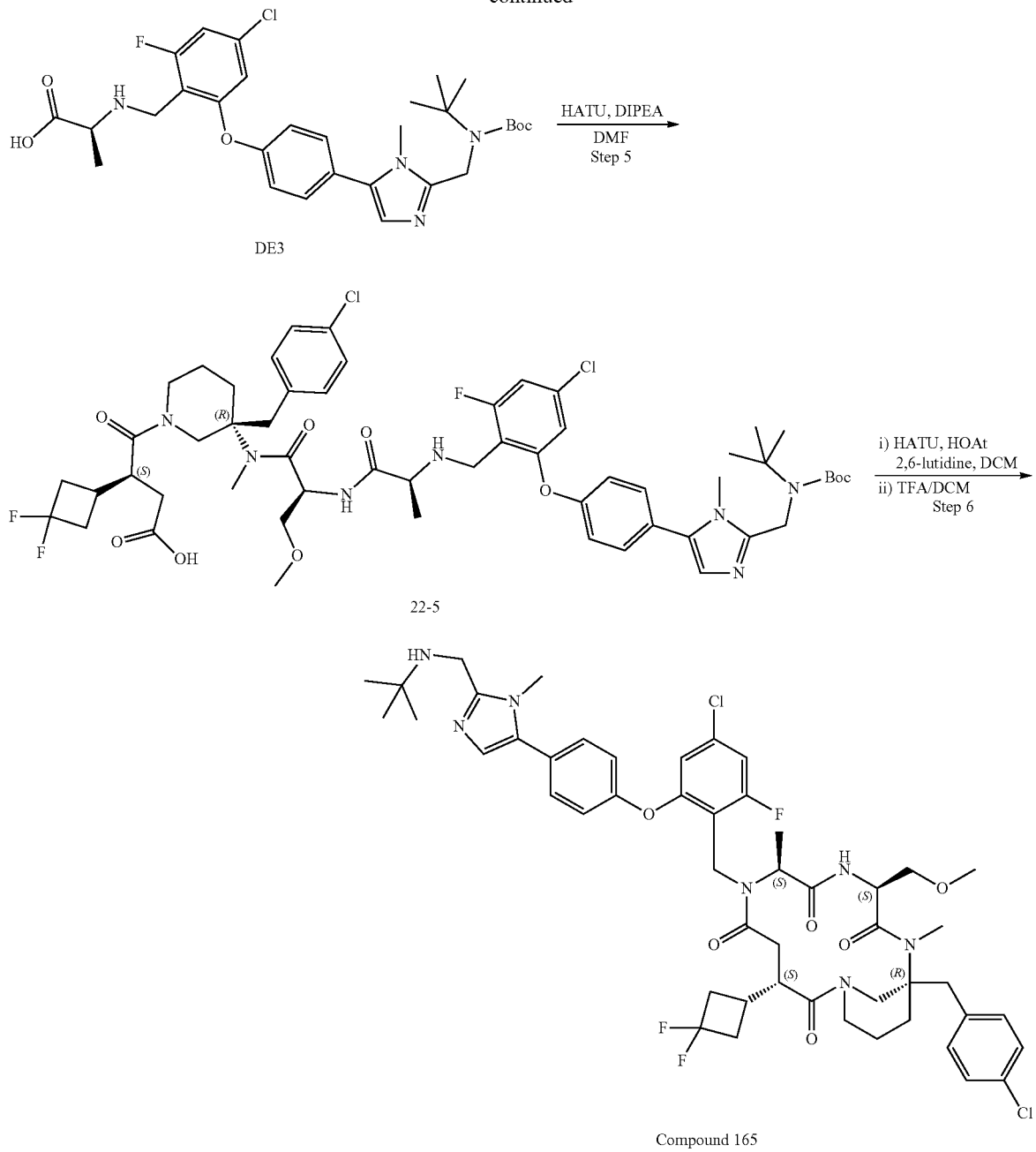

Compound 165

Step 1: Allyl ((S)-1-(((R)-3-(4-chlorobenzyl)piperidin-3-yl)(methyl)amino)-3-methoxy-1-oxopropan-2-yl)carbamate (22-1)

To a solution of intermediate F-4 (6.92 g, 13.21 mmol) in anhydrous 1,4-Dioxane (Volume: 40 mL) at 0° C. was added 4M HCl in 1,4-dioxane (19.82 mL, 79 mmol). The cooling bath was removed and the resulting mixture was stirred at room temperature overnight. The resulting mixture was concentrated under reduced pressure overnight to afford provide 22-1 (5.84 g, 12.68 mmol, 96% yield) as a white solid which was used in the next step without purification. Analytical method 5, $t_R$=0.99 min, [M+H]$^+$=424.1.

Step 2: Tert-butyl (S)-4-((R)-3-((S)-2-(((allyloxy)carbonyl)amino)-3-methoxy-N-methylpropanamido)-3-(4-chlorobenzyl)piperidin-1-yl)-3-(3,3-difluorocyclobutyl)-4-oxobutanoate (22-2)

To a solution of A29 (3.64 g, 13.79 mmol) in ACN (Volume: 50 mL) at 0° C. was added DIPEA (8.76 mL, 50.1 mmol) and HATU (5.24 g, 13.79 mmol). The cooling bath was removed and the resulting mixture was stirred at room temperature for 10 min. The reaction mixture was cooled to 0° C. again before 22-1 (5.77 g, 12.53 mmol) was added. The resulting was stirred at room temperature for 3 h and additional A29 (320 mg, 0.1 eq) and HATU (470 mg, 0.1 eq)

were added and stirring was continued for an additional 2 h. The resulting mixture was concentrated and the obtained residue was taken up in 200 mL of EtOAc. The organic phase was washed with 3×150 mL of 5% NaHCO$_3$ solution and 150 mL of brine, dried over sodium sulfate, and filtered, and concentrated. The crude product was purified by flash column chromatography on silica gel (eluted with 0-100% EtOAc in heptane) to afford 22-2 (5.2 g, 7.76 mmol, 61.9% yield) as a white foam-like solid after concentrating the pure fractions under reduced pressure. Analytical method 5, $t_R$=1.29 min, [M+H]$^+$=614.2 (as carboxylic acid).

Step 3: Tert-butyl (S)-4-((R)-3-((S)-2-amino-3-methoxy-N-methylpropanamido)-3-(4-chlorobenzyl)piperidin-1-yl)-3-(3,3-difluorocyclobutyl)-4-oxobutanoate (22-3)

To a solution of 22-2 (1.7 g, 2.54 mmol) in anhydrous DCM (Volume: 20 mL) was added N,N,1,1,1-pentamethylsilanamine (2.032 mL, 12.68 mmol) and Pd(PPh$_3$)$_4$ (0.220 g, 0.190 mmol) and the resulting mixture was stirred at room temperature for 3 h. The reaction mixture was then concentrated and the residue was taken up in 100 mL of EtOAc. The organic phase was washed with 3×100 mL of 5% NaHCO$_3$ and brine, dried over sodium sulfate, filtered, and concentrated under reduced pressure to afford 22-3 (1.487 g, 2.54 mmol, ~100% yield) as a yellow foam. The product was used directly in the next step without further purification. Analytical method 5, $t_R$=1.15 min, [M+H]$^+$=586.2.

Step 4: (S)-4-((R)-3-((S)-2-amino-3-methoxy-N-methylpropanamido)-3-(4-chlorobenzyl)piperidin-1-yl)-3-(3,3-difluorocyclobutyl)-4-oxobutanoic acid (22-4)

To a solution of 22-3 (2.087 g, 3.56 mmol) in anhydrous DCM (14 mL) at 0° C. was added TFA (13.72 mL, 178 mmol). The cooling bath was removed and the resulting solution was stirred at room temperature for 30 min. Toluene (50 mL) was then added and the reaction mixture was concentrated. The resulting brown residue was purified by reverse phase flash column chromatography (eluting with 0-50% ACN in water with 0.1% NH$_4$OH) to afford 22-4 (1.543 g, 2.88 mmol, 81% yield) after freeze drying the pure fractions. Analytical method 2, $t_R$=1.21 min, [M+H]$^+$=530.0.

Step 5: (S)-4-((R)-3-((S)-2-((S)-2-((2-(4-(2-(((tert-butoxycarbonyl)(tert-butyl)amino)methyl)-1-methyl-1H-imidazol-5-yl)phenoxy)-4-chloro-6-fluorobenzyl)amino)propanamido)-3-methoxy-N-methylpropanamido)-3-(4-chlorobenzyl)piperidin-1-yl)-3-(3,3-difluorocyclobutyl)-4-oxobutanoic acid (22-5)

To a solution of DE3 (881 mg, 1.496 mmol) in DMF (30 mL) was added DIPEA (0.442 ml, 2.53 mmol) and HATU (569 mg, 1.496 mmol) and the resulting yellow solution was stirred at RT for 15 min. 22-4 (610 mg, 1.151 mmol) then was added as a solid stirring was continued at RT for 15 min. The reaction mixture was then taken up in EtOAc and washed with brine (×2). The organic phase was dried over sodium sulfate, filtered, and concentrated. The crude material was purified by reverse flash column chromatography (eluting with 0-80% water/ACN with 0.1% NH$_4$OH) to afford 22-5 (2.5 g, 2.27 mmol, 95%) as an off white powder after freeze drying down the pure fractions. Analytical method 5, $t_R$=0.93 min, [M+H]$^+$=1100.8.

Step 6: (3S,7S,10S,13R)-6-(2-(4-(2-((tert-butylamino)methyl)-1-methyl-1H-imidazol-5-yl)phenoxy)-4-chloro-6-fluorobenzyl)-13-(4-chlorobenzyl)-3-(3,3-difluorocyclobutyl)-10-(methoxymethyl)-7,12-dimethyl-1,6,9,12-tetraazabicyclo[11.3.1]heptadecane-2,5,8,11-tetraone (Compound 165)

Step 6-1: To a 1 L round bottom flask containing 22-5 (1.3 g, 1.181 mmol) in DCM (650 mL) at room temperature and with stirring was added HATU (1.796 g, 4.72 mmol), HOAt (0.161 g, 1.181 mmol) and 2,6-lutidine (4.13 ml, 35.4 mmol). The resulting mixture was stirred at room temperature for 15 min and then heated to 42° C. The reaction mixture was then cooled to room temperature and filtered. The filtrate was concentrated down to about ⅓ of the volume and washed with a half-saturated NaHCO$_3$ solution. The organic phase was then dried over sodium sulfate, filtered, and concentrated. The crude material was purified by flash column chromatography (eluting with 0-10% DCM/MeOH) to afford the cyclized product (2.16 g, 1.99 mmol, 86%) after drying down the pure fractions. Analytical method 5, $t_R$=1.43 min, [M+H]$^+$=1084.8.

Step 6-2: Deprotection step—To a round bottom flask containing the cyclized product from Step 6-1 (2.16 g, 1.994 mmol) was added DCM (40 mL). The resulting clear solution was cooled in an ice bath and TFA (7.68 ml, 100 mmol) was added dropwise slowly. Once complete consumption of the starting materials was observed, the ice bath was removed and the reaction mixture was stirred at room temperature for 1 h and then added dropwise to a pre-cooled solution of saturated NaHCO$_3$ (105 ml, 120 mmol) in an ice bath. The reaction mixture was stirred at room temperature for 1 h or until gas evolution ceased and then poured into a separatory funnel and was shaken until no sound of gas evolution. The organic phase was separated and the aqueous portion was back extracted with DCM (×1). The combined organic phases were dried over sodium sulfate, filtered, and concentrated to afford a viscous oil. The crude product was purified by flash column chromatography (eluting with 0-20% DCM/MeOH) to afford Compound 165 as a white solid (1.55 g, 1.56 mmol, 78%, major product; Analytical Method 3, $t_R$=1.13 min., [M+H]$^+$=982.4) and Compound 166 (127 mg, 0.14 mmol, 6.8%, minor product, see Table 33) as a white solid after concentration and freeze drying.

TABLE 33
| Cmd No. | Structure | LCMS |
|---|---|---|
| 166 | 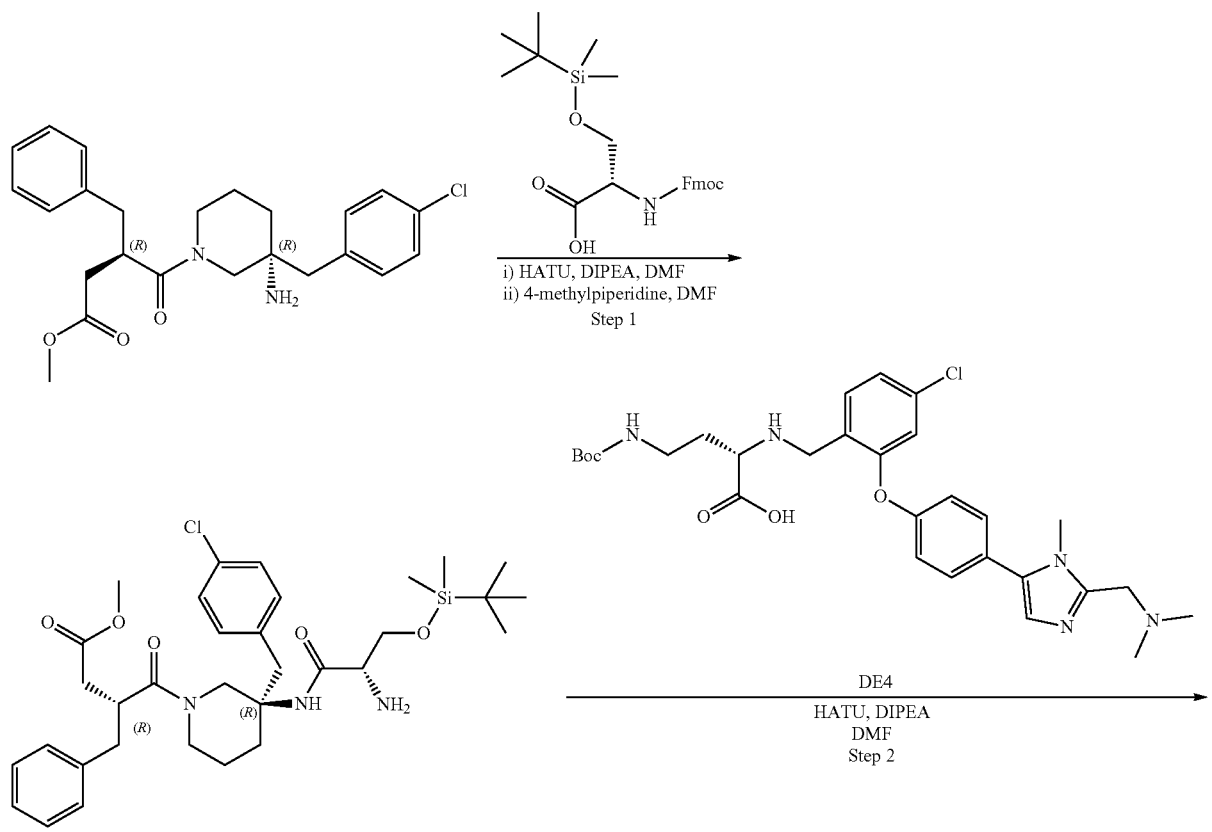 | Analytical Method 3<br>$t_R = 1.08$ min.<br>$[M + H]^+ = 926.3$ |
Example 8.46: (3R,7S,10S,13R)-7-(2-aminoethyl)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-1,6,9,12-tetraazabicyclo[11.3.1]heptadecane-2,5,8,11-tetraone (Compound 178)

-continued
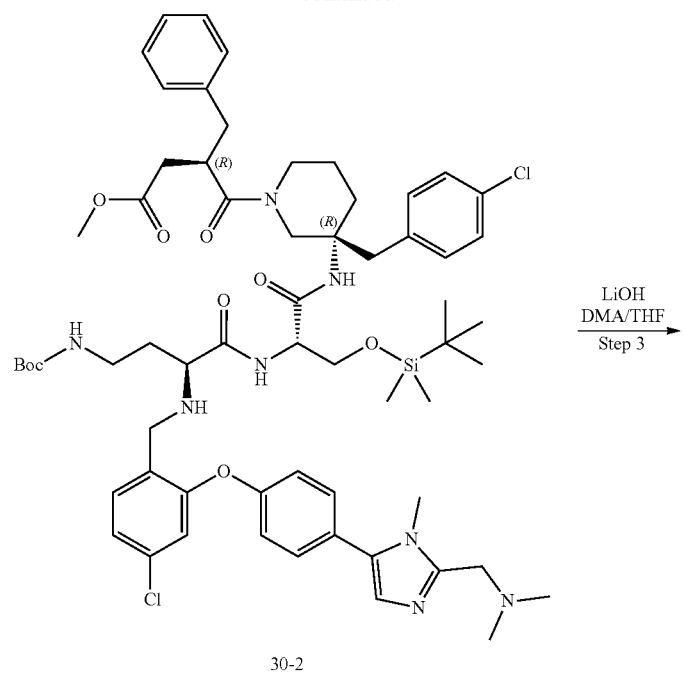
30-2
LiOH
DMA/THF
Step 3
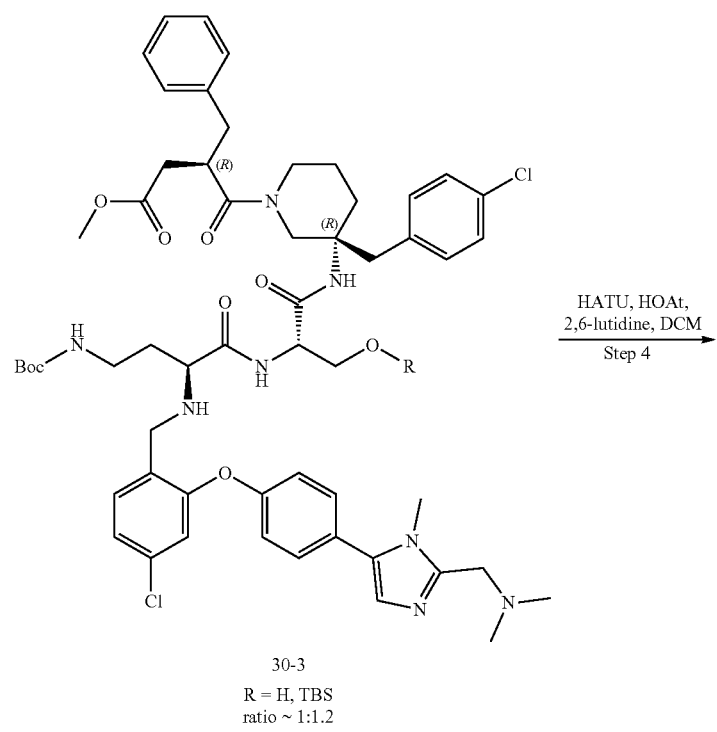
30-3
R = H, TBS
ratio ~ 1:1.2
HATU, HOAt,
2,6-lutidine, DCM
Step 4

-continued
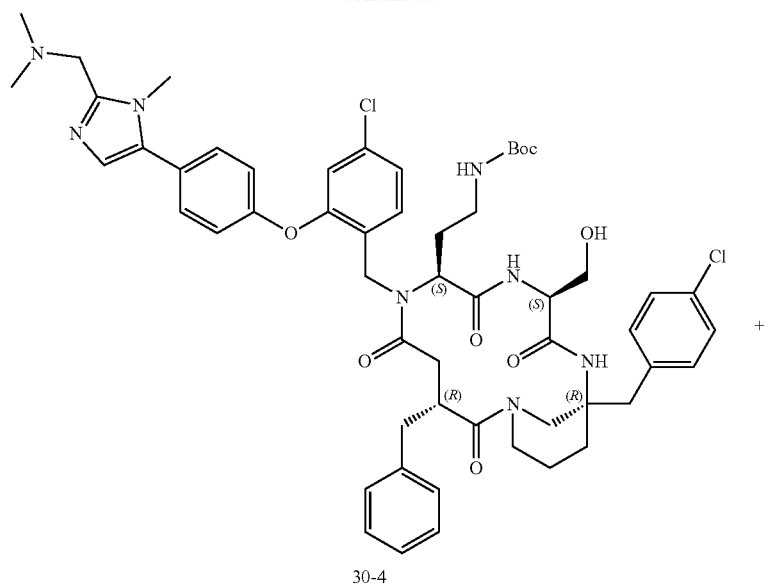
30-4
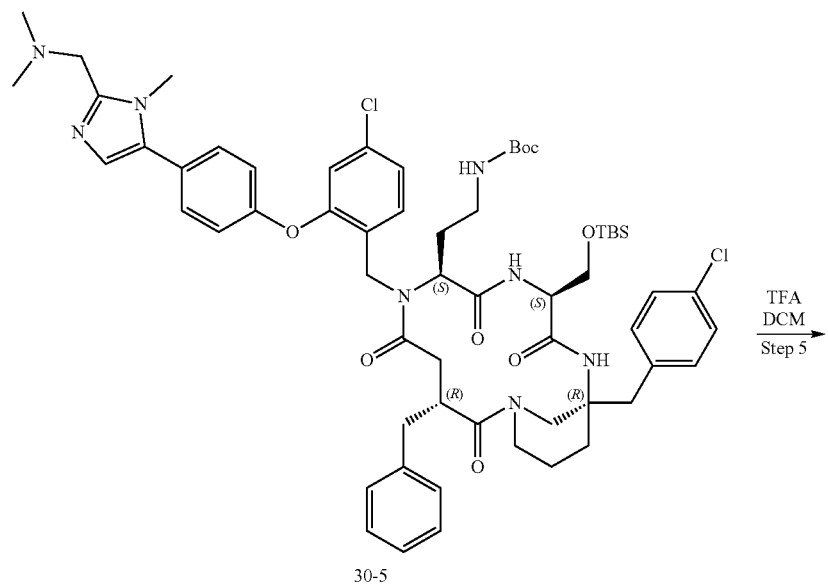
30-5

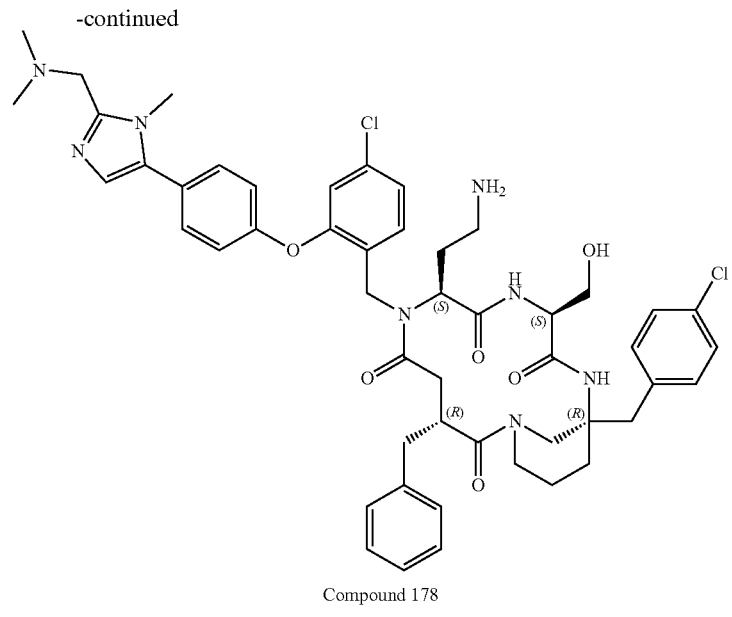

Compound 178

Step 1: (R)-methyl 4-((R)-3-((S)-2-amino-3-((tert-butyldimethylsilyl)oxy)propanamido)-3-(4-chlorobenzyl)piperidin-1-yl)-3-benzyl-4-oxobutanoate (30-1)

To a solution of Fmoc-Ser(OtBMe₂Si)OH (548 mg, 1.242 mmol) in DMA (5 mL) was added HATU (455 mg, 1.197 mmol) and DIPEA (0.789 mL, 4.52 mmol). The resulting mixture was stirred for 2 min at room temperature and then added to a solution of intermediate M-2 (484 mg, 1.129 mmol, in 3 mL of DMA). The reaction mixture was stirred at room temperature for 3 h. Additional Fmoc-Ser(OtBMe₂Si)OH (88 mg, 0.200 mmol) and HATU (76 mg, 0.20 mmol) were added and stirring was continued overnight at room temperature. 4-methylpiperidine (0.8 mL, 6.77 mmol) was added and stirring was continued for 30 min. at room temperature. The reaction mixture was concentrated under reduced pressure (bath temperature 50° C.) and the residue was purified by reverse flash column chromatography (eluting with 5-90% water/ACN with 0.1% NH₄OH) to afford 30-1 (450 mg, 0.664 mmol, 59%) after freeze drying down the pure fractions. Analytical method 5, $t_R$=1.41 min, [M+H]⁺=630.5.

Step 2: (R)-methyl 3-benzyl-4-((R)-3-((S)-2-((S)-4-((tert-butoxycarbonyl)amino)-2-((4-chloro-2-(4-(2-((dimethylamino)methyl)-1-methyl-1H-imidazol-5-yl)phenoxy)benzyl)amino)butanamido)-3-((tert-butyldimethylsilyl)oxy)propanamido)-3-(4-chlorobenzyl)piperidin-1-yl)-4-oxobutanoate (30-2)

To a solution of DE4 (449 mg, 0.785 mmol) and 30-1 (450 mg, 0.714 mmol) in DMA (5 mL) was added DIPEA (0.374 mL, 2.142 mmol). The resulting solution was stirred for 2 min at room temperature and then a solution of HATU (299 mg, 0.785 mmol) in DMA (3 mL) was added. The reaction mixture was stirred at room temperature for 3 h. Additional DE4 (88 mg, 0.14 mmol) and HATU (76 mg, 0.20 mmol) were added and stirring was continued at room temperature overnight. The resulting mixture was concentrated under reduced pressure and the residue was purified by flash column chromatography (eluting with 98/2 to 85/15 DCM/MeOH with 0.3% triethylamine) to afford 30-2 (760 mg, 0.642 mmol, 90% yield) as the major product after concentrating the pure fractions. Analytical method 5, $t_R$=1.55 min, [M+H]⁺=1184.1.

Step 3: Mixture of (R)-3-benzyl-4-((R)-3-((S)-2-((S)-4-((tert-butoxycarbonyl)amino)-2-((4-chloro-2-(4-(2-((dimethylamino)methyl)-1-methyl-1H-imidazol-5-yl)phenoxy)benzyl)amino)butanamido)-3-((tert-butyldimethylsilyl)oxy)propanamido)-3-(4-chlorobenzyl)piperidin-1-yl)-4-oxobutanoic acid and (R)-3-benzyl-4-((R)-3-((S)-2-((S)-4-((tert-butoxycarbonyl)amino)-2-((4-chloro-2-(4-(2-((dimethylamino)methyl)-1-methyl-1H-imidazol-5-yl)phenoxy)benzyl)amino)butanamido)-3-hydroxypropanamido)-3-(4-chlorobenzyl)piperidin-1-yl)-4-oxobutanoic acid (30-3)

To a solution of 30-2 (770 mg, 0.65 mmol) in DMA (5 mL) was added water (1 mL) and THF (4 mL). The resulting mixture was stirred at room temperature and then a solution of LiOH (1.300 mL, 1.300 mmol) was added. The reaction mixture was stirred at room temperature for 3 h. Additional LiOH (1.300 mL, 1.300 mmol) was added and stirring was continued at room temperature overnight (LCMS indicated a mixture of desire product as well as the de-silyl alcohol R=H). The reaction mixture was cooled in an ice bath, the pH was neutralized (pH=7) by the addition of 1N HCl, and then concentrated under reduced pressure (bath maintained at 30° C.). The residue was taken up in 250 mL of EtOAc. The organic phase was washed with water and brine, dried over Na₂SO₄, filtered, and concentrated to afford 30-3 (770 mg, white solid) as a mixture of two products (R=H and TBS, ratio 1:1.2). The mixture was used in the next step without additional purification. R=TBS, Analytical method 2, $t_R$=2.41 min, [M+H]⁺=1171.7. R=H, Analytical method 2, $t_R$=1.98 min, [M+H]⁺=1055.1.

Step 4:Tert-butyl (2-((3R,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-2,5,8,11-tetraoxo-1,6,9,12-tetraazabicyclo[11.3.1]heptadecan-7-yl)ethyl)carbamate (30-4) and Tert-butyl (2-((3R,7S,10S,13R)-3-benzyl-10-(((tert-butyldimethylsilyl)oxy)methyl)-6-(4-chloro-2-(4-(2-((dimethylamino)methyl)-1-methyl-1H-imidazol-5-yl)phenoxy)benzyl)-13-(4-chlorobenzyl)-2,5,8,11-tetraoxo-1,6,9,12-tetraazabicyclo[11.3.1]heptadecan-7-yl)ethyl)carbamate (30-5)

To a 1 L round bottom flask containing a solution of the mixture 30-3 (770 mg, 0.658 mmol) in DCM (700 mL) was added 2,6-lutidine (2.3 mL, 19.74 mmol), HOAt (107 mg, 0.790 mmol) and HATU (1001 mg, 2.63 mmol). The resulting mixture was heated to 50° C. in a heating bath for 4 h and then at 38° C. with stirring overnight. The reaction mixture was then concentrated to dryness under reduced pressure and the residue was partitioned between EtOAc (400 mL) and 5% aq. NaHCO$_3$ (30 mL). The organic phase was washed with 5% aq. NaHCO$_3$ (2×25 mL) and brine (30 mL), dried over Na$_2$SO$_4$, filtered, and concentrated. The crude material was purified by reverse flash column chromatography (eluting with 5-60% water/ACN with 0.1% trifluoroacetic acid) to afford 30-4 as a white solid (300 mg, 0.21 mmol, 32% yield, Analytical method 2, $t_R$=3.22 min, [M+H]$^+$=1039.4) and 30-5 (360 mg, 0.30 mmol, 45% yield, Analytical method 5, $t_R$=1.55 min, [M+H]$^+$=1153.7) as a white solid after freeze drying down the respective pure fractions.

Step 5:(1S,3R,7S,10S,13R)-7-(2-aminoethyl)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-1,6,9,12-tetraazabicyclo[11.3.1]heptadecane-2,5,8,11-tetraone (Compound 178)

To a round bottom flask containing 30-5 (350 mg, 0.304 mmol) in anhydrous dioxane (6 mL) and cooled in an ice bath was added 4.0 N hydrogen chloride in dioxane (2 mL, 8.00 mmol). The ice bath was then removed and the resulting mixture was stirred at room temperature for 16 h. The reaction mixture was concentrated under reduced pressure to afford an off-white solid which was purified by reverse flash column chromatography (eluting with 5-50% water/ACN with 0.1% trifluoroacetic acid) to afford Compound 178 (200 mg, 0.181 mmol, 59.5%), Analytical method 3, $t_R$=0.94 min., [M+H]$^+$=937.39.

Example 8.47: (3S,7S,10S,13R)-6-(4-chloro-2-fluoro-6-(4-(1-methyl-2-((methylamino)methyl)-1H-imidazol-5-yl)phenoxy)benzyl)-13-(4-chlorobenzyl)-10-(hydroxymethyl)-7,12-dimethyl-3-(2,2,2-trifluoroethyl)-1,6,9,12-tetraazabicyclo[11.3.1]heptadecane-2,5,8,11-tetraone trifluoroacetate (Compound 177)

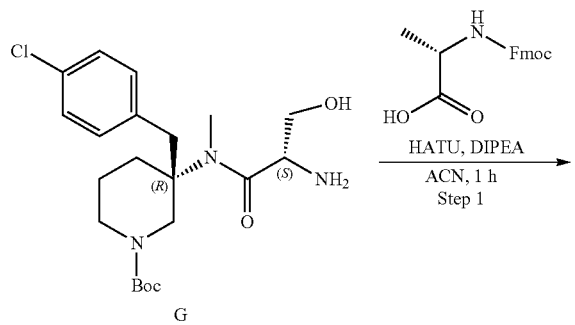

G

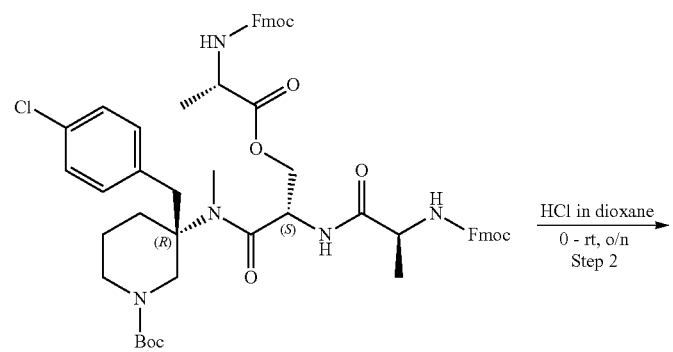

31-1

-continued
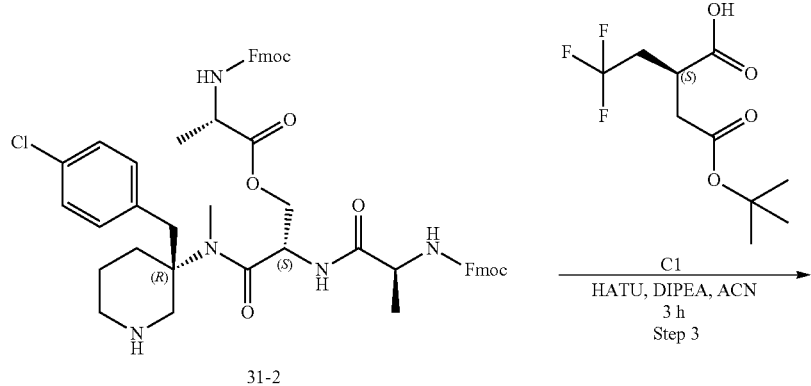
31-2
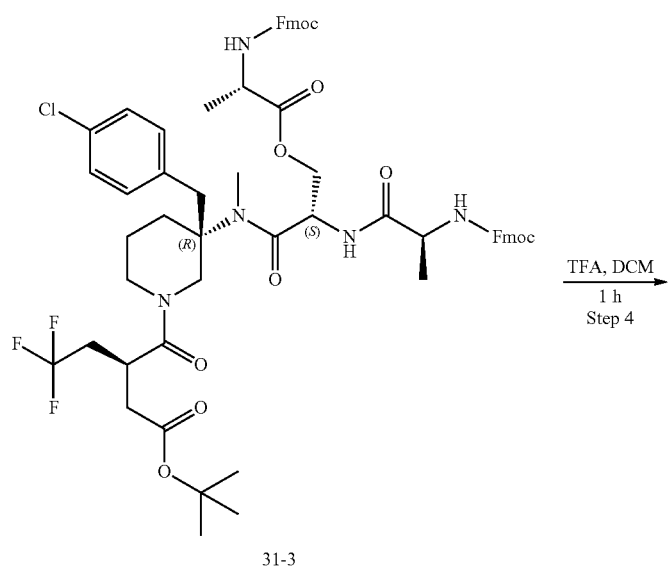
31-3
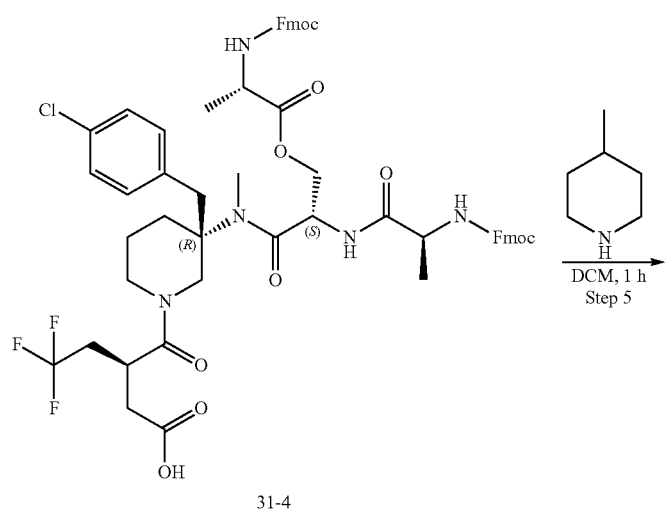
31-4

-continued
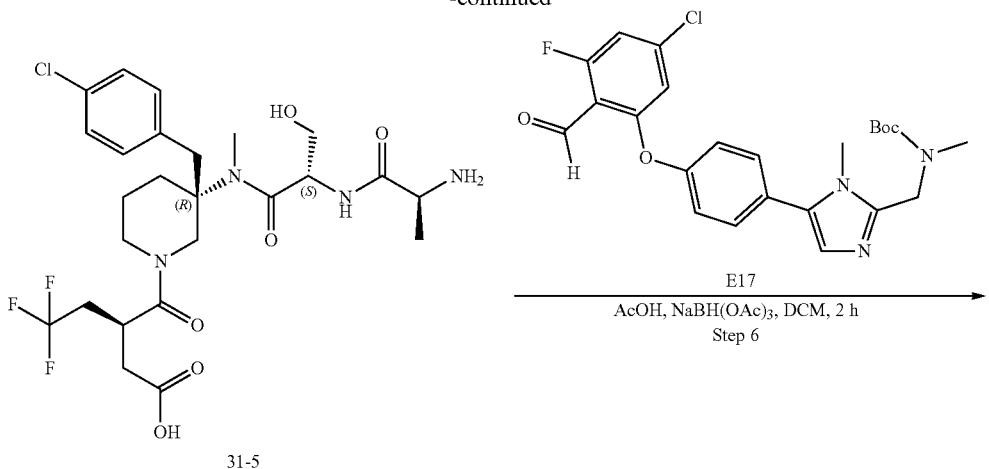
31-5
E17
AcOH, NaBH(OAc)₃, DCM, 2 h
Step 6
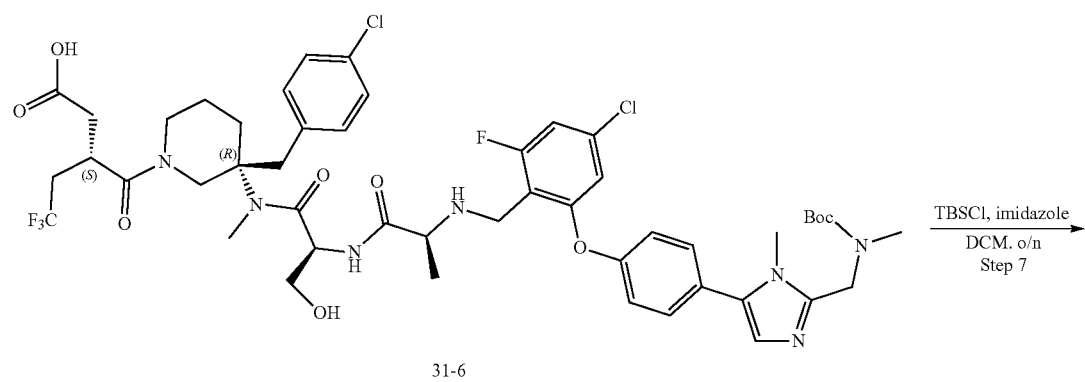
31-6
TBSCl, imidazole
DCM. o/n
Step 7
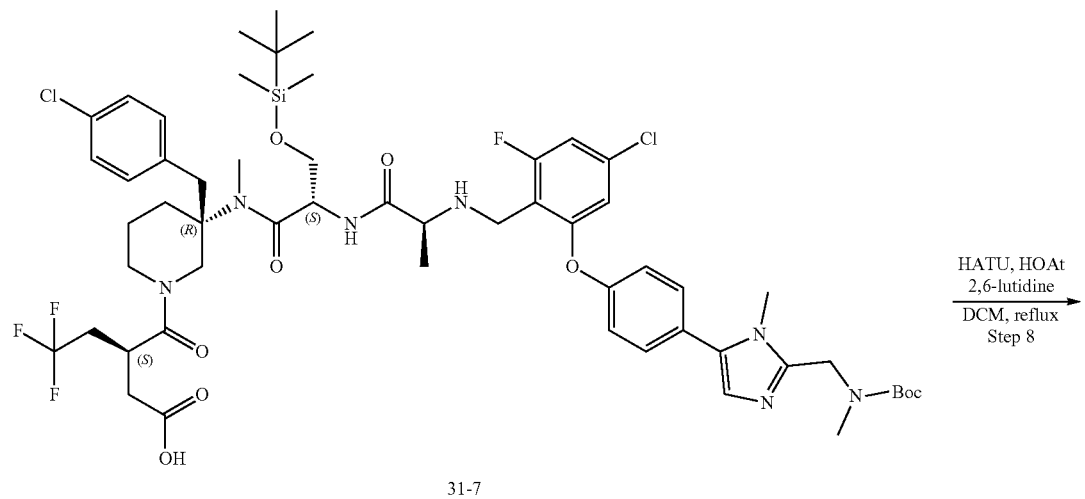
31-7
HATU, HOAt
2,6-lutidine
DCM, reflux
Step 8

-continued

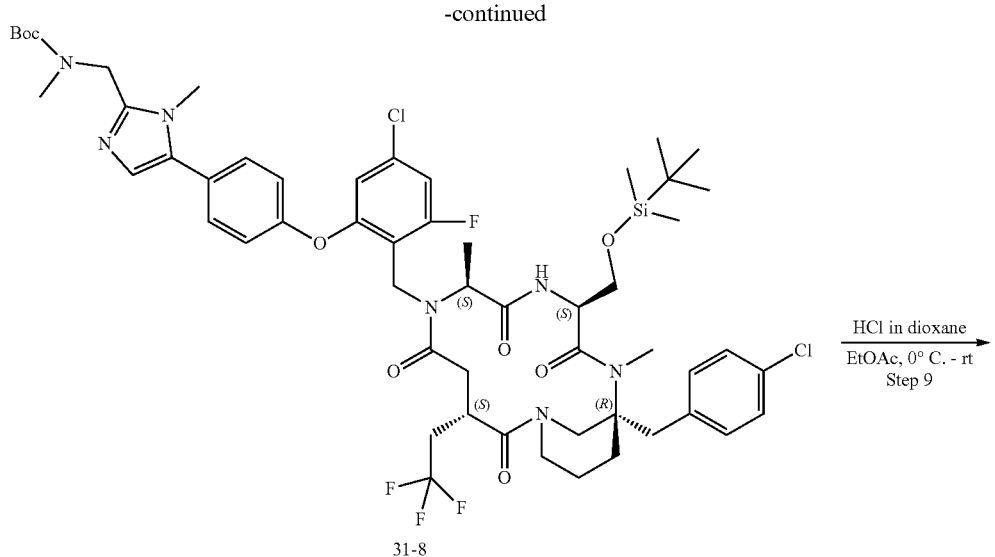

31-8

HCl in dioxane
EtOAc, 0° C. - rt
Step 9

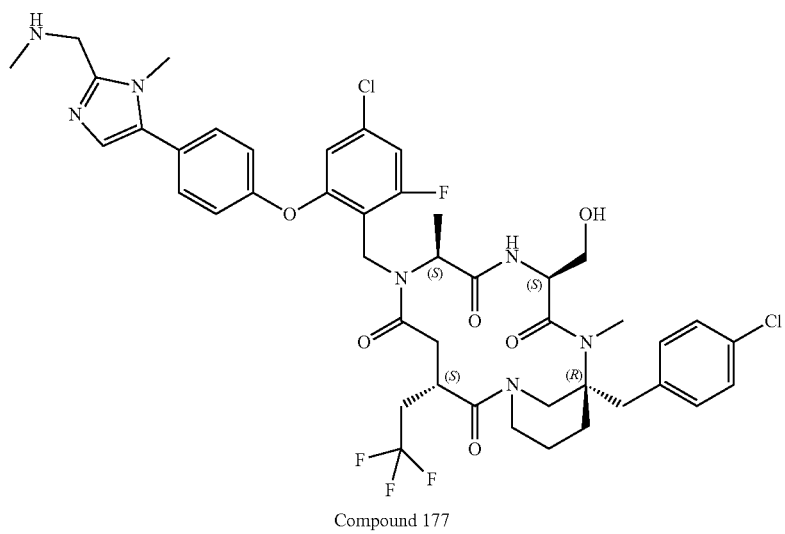

Compound 177

Step 1: Tert-butyl (R)-3-((S) 3 (((((9H-fluoren-9-yl)
methoxy)carbonyl)-L-alanyl)oxy)-2-((S)-2-((((9H-
fluoren-9-yl)methoxy)carbonyl)amino)propana-
mido)-N-methylpropanamido)-3-(4-chlorobenzyl)
piperidine-1-carboxylate (31-1)

To a solution of Intermediate G (291 mg, 0.588 mmol) and Fmoc-Ala-OH (187 mg, 0.600 mmol) in acetonitrile (30 mL) was added DIPEA (0.205 mL, 1.176 mmol) at rt, followed by HATU (228 mg, 0.600 mmol). The resulting mixture was stirred at rt for 1 h. Once the desired product was observed as a major product, the acetonitrile was removed under reduced pressure. The crude residue was dissolved in 300 mL of EtOAc and washed with 40 mL of saturated NaHCO₃ aq. solution. The separated organic phase was washed with brine, dried with sodium sulfate, filtered, and concentrated. The obtained residue was dissolved in DCM and purified by ISCO column chromatography on a 40 g silica gel column (eluting with 10-100% EtOAc in Heptane) to afford 31-1 (210 mg, 0.207 mmol) as a foaming solid. Analytical method 5, $t_R$=1.51 min, [M+H(−Boc)]⁺=971.2.

Step 2: (S)-2-((S)-2-((((9H-fluoren-9-yl)methoxy)
carbonyl)amino)propanamido)-3-(((R)-3-(4-chlo-
robenzyl)piperidin-3-yl)(methyl)amino)-3-oxopropyl
(((9H-fluoren-9-yl)methoxy)carbonyl)-L-alaninate
(31-2)

To a solution of 31-1 (210 mg, 0.207 mmol) in anhydrous ethyl acetate (7 mL) under atmosphere of nitrogen was added 4M hydrogen chloride in dioxane (1 ml, 4.00 mmol) in portions at 0° C. The resulting mixture was stirred at 0° C. for 1 h and then at rt for overnight. Once the desired product was observed by LCMS, the reaction mixture was concentrated and the resulting solid was dried under reduced pressure and then freeze dried to afford 31-2 (192.5 mg, 0.172 mmol, 83% yield). Analytical method 5, $t_R$=1.45 min, [M+H]⁺=912.6.

Step 3: Tert-butyl (S)-3-((R)-3-((S)-3-(((((9H-fluoren-9-yl)methoxy)carbonyl)-L-alanyl)oxy)-2-((S)-2-(((((9H-fluoren-9-yl)methoxy)carbonyl)amino)propanamido)-N-methylpropanamido)-3-(4-chlorobenzyl)piperidine-1-carbonyl)-5,5,5-trifluoropentanoate (31-3)

To a solution of 31-2 (192.5 mg, 0.179 mmol) and C1 (45.9 mg, 0.179 mmol) in acetonitrile (20 mL) was added DIPEA (0.094 mL, 0.538 mmol), followed HATU (68.2 mg, 0.179 mmol) and the resulting mixture was stirred at rt for 3 h. Once the desired product was observed by LCMS, the acetonitrile was removed under reduced pressure and the crude residue was dissolved in 200 mL of EtOAc. The organic phase was washed with 30 mL of 5% NaHCO$_3$, 30 mL of saturated NH$_4$OH solution. The separated organic phase was washed with brine (2×30 mL), dried with sodium sulfate, filtered, and concentrated under reduced pressure to afford 31-3 (220 mg, 0.172 mmol, 96% yield) which was used in the next step without purification. Analytical method 5, t$_R$=1.54 min, [M+H]$^+$=971.2. Analytical method 5, t$_R$=1.54 min, [M+H]$^+$=not observed due to lack of ionization.

Step 4: (S)-3-((R)-3-((S)-3-(((((9H-fluoren-9-yl)methoxy)carbonyl)-L-alanyl)oxy)-2-((S)-2-((((9H-fluoren-9-yl)methoxy)carbonyl)amino)propanamido)-N-methylpropanamido)-3-(4-chlorobenzyl)piperidine-1-carbonyl)-5,5,5-trifluoropentanoic acid (31-4)

To a solution of 31-3 (220 mg, 0.172 mmol) in anhydrous DCM (4 ml) under atmosphere of nitrogen was added TFA (1.06 ml, 13.76 mmol) in portions at rt. The reaction mixture was stirred at rt for 1 h and 30 min and then cooled to 0° C. and diluted with 20 mL of DCM and 5 mL of water. Na$_2$CO$_3$ (1.893 ml, 3.79 mmol) solution was added slowly to adjust the pH to 6.5-7. The resulting mixture was extracted with 15/85 isopropanol/DCM (120 mL). The organics were dried with Na$_2$SO$_4$ and concentrated to dryness to afford 31-4 (220 mg, 86% pure) which as used in next step without purification. Analytical method 5, t$_R$=1.00 min, [M+H]$^+$=1094.8.

Step 5: (S)-3-((R)-3-((S)-2-((S)-2-aminopropanamido)-3-hydroxy-N-methylpropanamido)-3-(4-chlorobenzyl)piperidine-1-carbonyl)-5,5,5-trifluoropentanoic acid (31-5)

To a solution of 31-4 (220 mg, 86% pure) in DCM (9 mL) at rt, was added 4-methylpiperidine (1 mL, 7.86 mmol) dropwise. The reaction mixture was stirred at rt for 1 h, and then concentrated and diluted with 50/50 acetonitrile/water (10 mL). The resulting mixture was filtered through a pad of Celite® which was washed with acetonitrile/water. The filtrates was concentrated and the obtained residue was mixed with 2 mL of ACN and 1M NaHCO$_3$ (1.0 mL, 1.000 mmol). The crude product was purified by ISCO column chromatography using a C18 column (100 g) (eluting with ACN/water with 0.1% NH$_4$OH) to afford 31-5 (77 mg, 0.133 mmol, 73% yield) as a white solid after freeze drying. Analytical method 7, t$_R$=0.73 min, [M+H]$^+$=579.2.

Step 6: (S)-3-((R)-3-((S)-2-((S)-2-((2-(4-(2-(((tert-butoxycarbonyl)(methyl)amino)methyl)-1-methyl-1H-imidazol-5-yl)phenoxy)-4-chloro-6-fluorobenzyl)amino)propanamido)-3-hydroxy-N-methylpropanamido)-3-(4-chlorobenzyl)piperidine-1-carbonyl)-5,5,5-trifluoropentanoic acid (31-6)

To a solution of 31-5 (77 mg, 0.133 mmol) in DCM (12 mL) was added E17 (66.2 mg, 0.140 mmol) and the resulting solution was stirred for 1 h at rt. NaBH(OAc)$_3$ (85 mg, 0.399 mmol) was added, followed by acetic acid (0.023 mL, 0.399 mmol) and stirring was continued for an additional 1 h at rt. Once LCMS showed complete consumption of starting material, acetic acid (0.023 mL, 0.399 mmol) and 0.1 mL water were added to quench the reaction. The mixture was diluted with 100 mL of a mixture DCM/IPA (80/20), washed with 20 mL of 5% NaHCO$_3$ and 20 mL of brine, dried over Na$_2$SO$_4$, filtered, and concentrated. The crude product was purified by ISCO column chromatography using a 100 g C18 column (eluting with 5-70% ACN in water, 0.1% NH$_4$OH) to afford 31-6 (86 mg, 0.079 mmol, 59.2% yield) after lyophilization. Analytical method 5, t$_R$=0.88 min, [M+H]$^+$=1036.7.

Step 7: (S)-3-((R)-3-((S)-2-((S)-2-((2-(4-(2-(((tert-butoxycarbonyl)(methyl)amino)methyl)-1-methyl-1H-imidazol-5-yl)phenoxy)-4-chloro-6-fluorobenzyl)amino)propanamido)-3-((tert-butyldimethylsilyl)oxy)-N-methylpropanamido)-3-(4-chlorobenzyl)piperidine-1-carbonyl)-5,5,5-trifluoropentanoic acid (31-7)

t-Butyldimethylsilylchloride (50.0 mg, 0.332 mmol) was added dropwise at 0° C. to a solution of 31-6 (86 mg, 0.083 mmol) and imidazole (16.94 mg, 0.249 mmol) in DCM (20 mL). The resulting mixture was stirred at rt for 16 h. Additional imidazole (200 mg, 2.93 mmol) and t-butyldimethylsilylchloride (440 mg, 2.90 mmol) was added and stirring was continued at rt for 5 h. Imidazole (100 mg, 1.46 mmol) and t-butyldimethylsilylchloride (220 mg, 1.46 mmol) was again added, and stirring was continued at rt for another 18 h. Once LCMS showed complete consumption of starting material, the reaction mixture was transferred to a 500 mL separatory funnel and 200 mL of DCM was added. The organic phase was washed with water (40 mL) and brine (40 mL), dried over Na$_2$SO$_4$, filtered, and concentrated. The crude residue was loaded on a C18 column (eluting with 5-70% ACN/water (5-70%) with NH$_4$OH). The product containing fractions were freeze dried to afford 31-7 (50 mg, 0.040 mmol, 48.2% yield). Analytical method 2, t$_R$=2.53 min, [M+H]$^+$=1051.2.

Step 8. Tert-butyl ((5-(4-(2-(((3S,7S,10S,13R)-10-(((tert-butyldimethylsilyl)oxy)methyl)-13-(4-chlorobenzyl)-7,12-dimethyl-2,5,8,11-tetraoxo-3-(2,2,2-trifluoroethyl)-1,6,9,12-tetraazabicyclo[11.3.1]heptadecan-6-yl)methyl)-5-chloro-3-fluorophenoxy)phenyl)-1-methyl-1H-imidazol-2-yl)methyl)(methyl)carbamate (31-8)

To a solution of 31-7 (62 mg, 0.054 mmol) in anhydrous DCM (40 mL) was added 2,6-lutidine (0.094 mL, 0.808 mmol) and HOAt (7.33 mg, 0.054 mmol). The resulting mixture was stirred at rt for 2 min and then HATU (106 mg, 0.215 mmol) was added. The reaction mixture was then heated in a 46° C. heating bath for 7 h. The crude mixture was filtered and the filtrate was concentrated. The obtained residue was dissolved in 60 mL of EtOAc. The organic phase was washed with 10 mL of 5% NaHCO$_3$ solution and 10 mL of brine, dried over Na$_2$SO$_4$, filtered, and concentrated. The crude product was purified by ISCO column chromatography on a silica gel column (eluting with DCM: 15% MeOH/DCM 0.3% TEA) to afford 31-8 (56 mg, 0.045 mmol, 84% yield). Analytical method 5, t$_R$=1.60 min, [M+H]$^+$=1143.7.

Step 9. (3S,7S,10S,13R)-6-(4-chloro-2-fluoro-6-(4-(1-methyl-2-((methylamino)methyl)-1H-imidazol-5-yl)phenoxy)benzyl)-13-(4-chlorobenzyl)-10-(hydroxymethyl)-7,12-dimethyl-3-(2,2,2-trifluoroethyl)-1,6,9,12-tetraazabicyclo[11.3.1]heptadecane-2,5,8,11-tetraone (Compound 177)

To a solution of 31-8 (56 mg, 0.045 mmol) in EtOAc (3.5 mL) was added 4M hydrogen chloride in dioxane (0.5 mL, 2.000 mmol) at 0° C. The cooling bath was removed and the resulting mixture was stirred at rt for 2 h. The reaction mixture was stored at 4° C. and then concentrated at rt. The residue was dissolved in ACN/water (60/40) and purified by reverse phase column chromatography on a C18 column (eluting with ACN/Water with 0.1% TFA). The product fractions were freeze dried to afford Compound 177 (8.2 mg, 7.15 μmol, 15.72% yield). Analytical method 2, $t_R$=2.68 min, $[M+H]^+$=919.2.

Example 8.47: Synthesis of Tert-butyl (R)-3-((S)-2-((S)-2-aminopropanamido)-3-(difluoromethoxy)-N-methylpropanamido)-3-(4-chlorobenzyl)piperidine-1-carboxylate (Intermediate L)

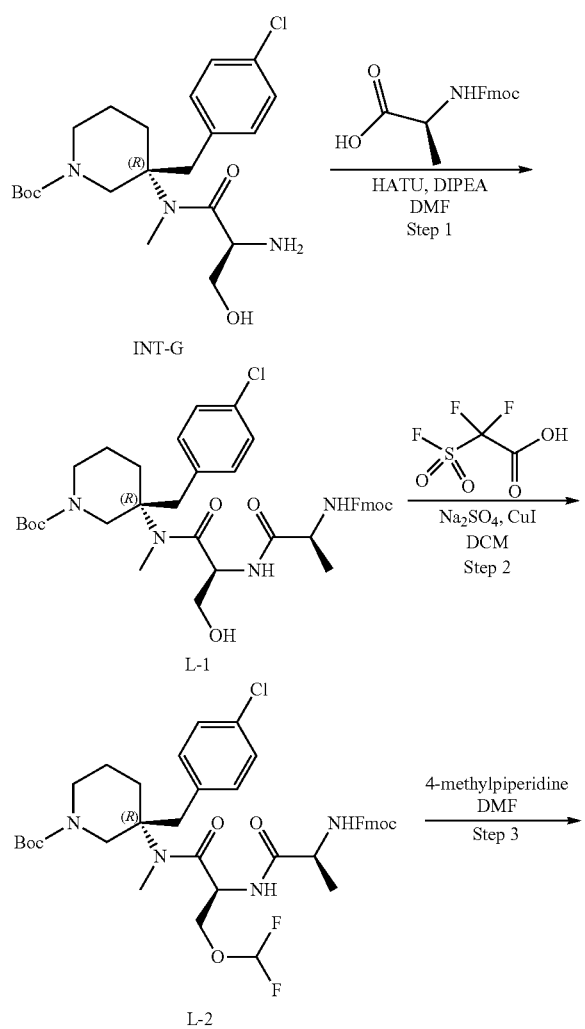

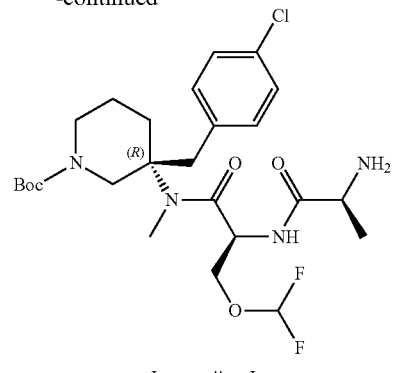

Intermediate L

Step 1. Tert-butyl (R)-3-((S)-2-((S)-2-((((9H-fluoren-9-yl)methoxy)carbonyl)amino)propanamido)-3-hydroxy-N-methylpropanamido)-3-(4-chlorobenzyl)piperidine-1-carboxylate (L-1)

To a vial containing Intermediate G (250 mg, 0.59 mmol) and Fmoc-Ala-OH (183 mg, 0.59 mmol) was added DMF (4 mL). DIPEA (0.154 mL, 0.880 mmol), followed by HATU (223 mg, 0.59 mmol). The resulting mixture was stirred at room temperature overnight. The reaction mixture was taken up in EtOAc and washed with a half-saturated solution of sodium bicarbonate and brine. The organic phase was dried over sodium sulfate, filtered, and concentrated. The crude material was purified by flash column (eluting 0-100% EtOAc/Heptane) to afford L-1 (364 mg, 0.51 mmol, 86%) as a foam after drying down the pure fractions.

Step 2. Tert-butyl (R)-3-((S)-2-((S)-2-((((9H-fluoren-9-yl)methoxy)carbonyl)amino)propanamido)-3-(difluoromethoxy)-N-methylpropanamido)-3-(4-chlorobenzyl)piperidine-1-carboxylate (L-2)

To a 20 mL vial containing a mixture of L-1 (364 mg, 0.506 mmol), sodium sulfate (71.9 mg, 0.506 mmol) and copper(I) iodide (96 mg, 0.506 mmol) was added ACN (2 mL). The resulting mixture was stirred at 60° C. and then treated with a solution of 2,2-difluoro-2-(fluorosulfonyl)acetic acid (0.078 mL, 0.759 mmol) in anhydrous acetonitrile (ACN, 2 mL) slowly over 45 min (using a syringe pump). The reaction mixture was then stirred for 30 min, filtered, and washed with DCM. The filtrate was then washed water (×1), dried over sodium sulfate, filtered, and concentrated. The crude material was purified by silica gel flash column chromatography (eluting with 0-30% DCM/EtOAc) to afford L-2 (169 mg, 0.220 mmol, 43.4% yield) as a white foam after drying down the pure fractions.

Step 3. Tert-butyl (R)-3-((S)-2-((S)-2-aminopropanamido)-3-(difluoromethoxy)-N-methylpropanamido)-3-(4-chlorobenzyl)piperidine-1-carboxylate (Intermediate L)

To a vial containing L-2 (169 mg, 0.220 mmol) in ACN (2 mL) was added 4-methylpiperidine (0.778 ml, 6.59 mmol) cooled in an ice bath. After the addition, the ice bath was removed and the resulting mixture was stirred at room temperature for 2 h and then concentrated. The resulting crude product was purified by silica gel flash column chromatography (eluting with 0-20% DCM/MeOH) to afford INT L (99 mg, 0.18 mmol, 82%) as a foam after drying down the pure fractions.

Example 9: Postmodification

In this section, modifications done after cyclization of the linear peptides are described.

Example 9.1: Synthesis of (2S,5S,8R,12R)-12-benzyl-1-(4-chloro-2-(4-(1-methyl-2-(pyrrolidin-1-ylmethyl)-1H-imidazol-5-yl)phenoxy)benzyl)-8-(4-chlorobenzyl)-2,7,10-trimethyl-5-(2-oxopropyl)-1,4,7,10-tetraaza-cyclotetradecane-3,6,11,14-tetraone hydrochloride (Compound 129)

and DIC (5.5 µL, 0.035 mmol) and the resulting mixture was stirred at rt for 45 h. Additional DMAP (0.7 mg, 5.4 µmol), 2,2-dimethyl-1,3-dioxane-4,6-dione (0.8 mg, 5.4 µmol) and DIC (0.9 µL, 5.4 µmol) were added and stirring at rt was continued for 20 h.

Step 2: 80% aq. TFA (2 mL) was added to the mixture from Step 1. The reaction mixture was stirred for 5 h at rt and then concentrated to dryness in vacuo. The residue was dissolved in DCM (2 mL) and 80% aq. TFA (2 mL), and the resulting mixture was stirred for 16 h at rt and 2 h at 50° C., then concentrated to dryness in vacuo.

Step 3. The residue from Step 2 was dissolved in ACN/H$_2$O (1:1) (4 mL). The resulting solution was stirred at rt for 16 and at 50° C. for 2 h and then concentrated to dryness in vacuo. The crude product was purified by preparative reverse-phase HPLC (eluent A: 0.1% TFA in H$_2$O; eluent B:

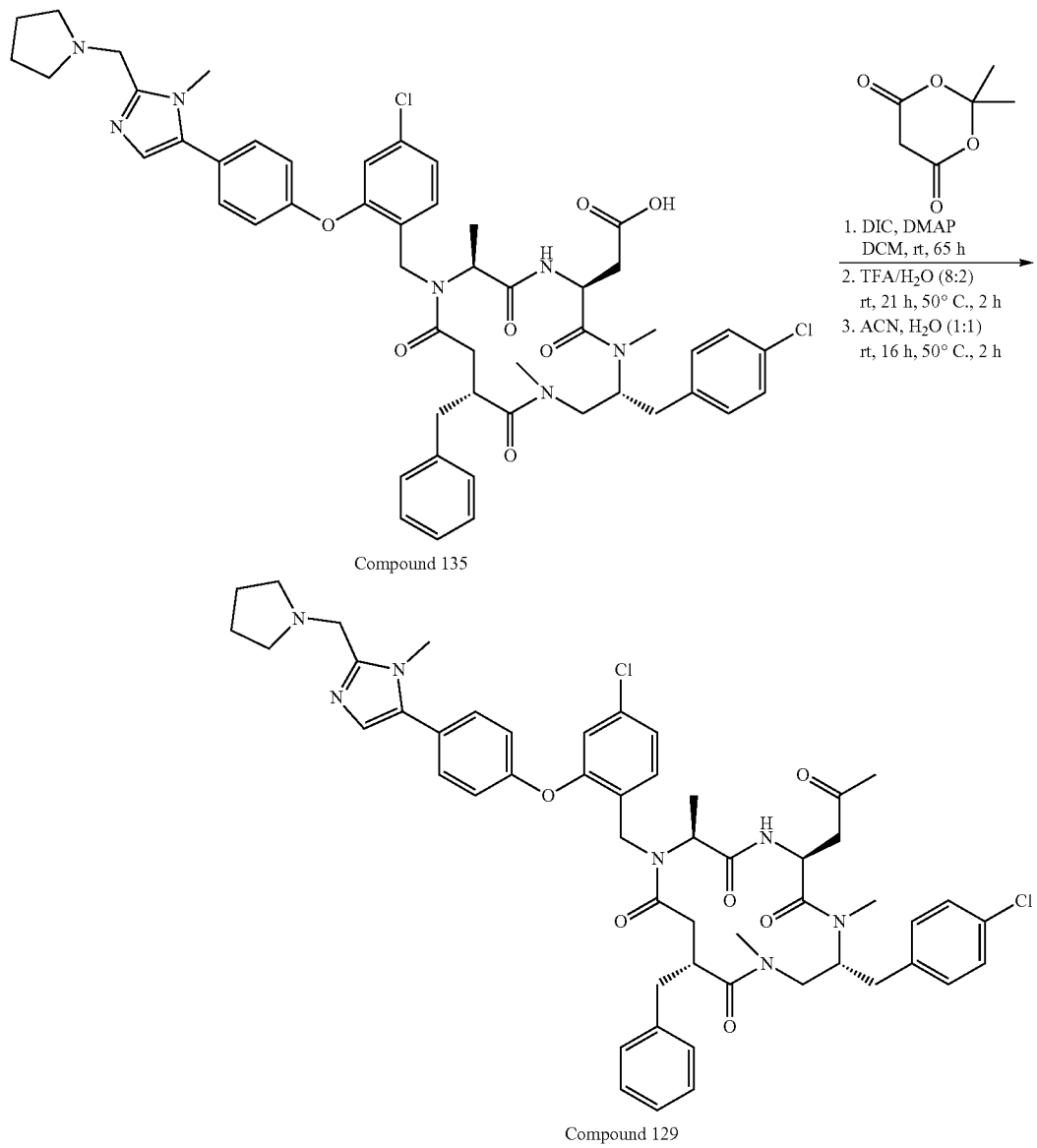

Compound 135

Compound 129

Step 1: To Compound 135 (32 mg, 0.027 mmol) dissolved in DCM (2 mL) was added DMAP (5.0 mg, 0.041 mmol), 2,2-dimethyl-1,3-dioxane-4,6-dione (5.1 mg, 0.035 mmol)

ACN). Pure fractions were combined and lyophilized. The product was dissolved in EtOAc (40 mL) and the organic phase was washed with 5% aq. NaHCO$_3$ (2×5 mL) and brine (5 mL), dried over Na₂SO₄, filtered, and concentrated to dryness in vacuo. The residue was dissolved in ACN/H₂O (1:1) (20 mL) and 0.023 M aq. HCl (5.1 mL) was added. After lyophilization, the hydrochloride salt of Compound 129 (18.4 mg, 0.017 mmol, 64% yield) was obtained as a white solid. Analytical method 9; $t_R$=5.15 min; [M+H]⁺=948.4.

Example 9.2: Synthesis of (2S,5S,8R,12S)-2-(3-(azetidin-1-yl)-3-oxopropyl)-1-(4-chloro-2-(4-(1-methyl-2-(pyrrolidin-1-ylmethyl)-1H-imidazol-5-yl)phenoxy)benzyl)-8-(4-chlorobenzyl)-12-((R)-3,3-dimethyl-2,3-dihydro-1H-inden-1-yl)-5-(methoxymethyl)-7,10-dimethyl-1,4,7,10-tetraazacyclotetradecane-3,6,11,14-tetraone hydrochloride (Compound 132)

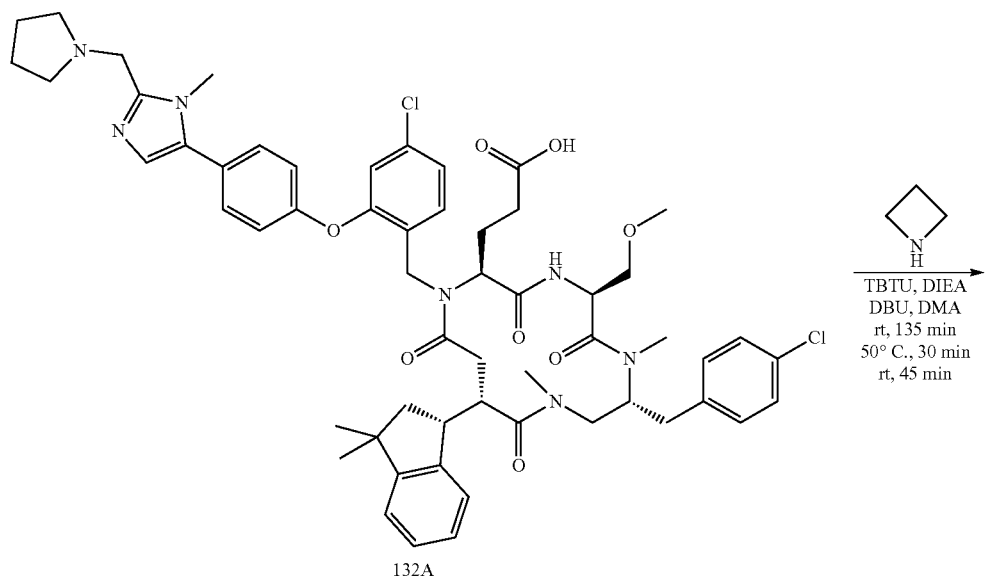

132A

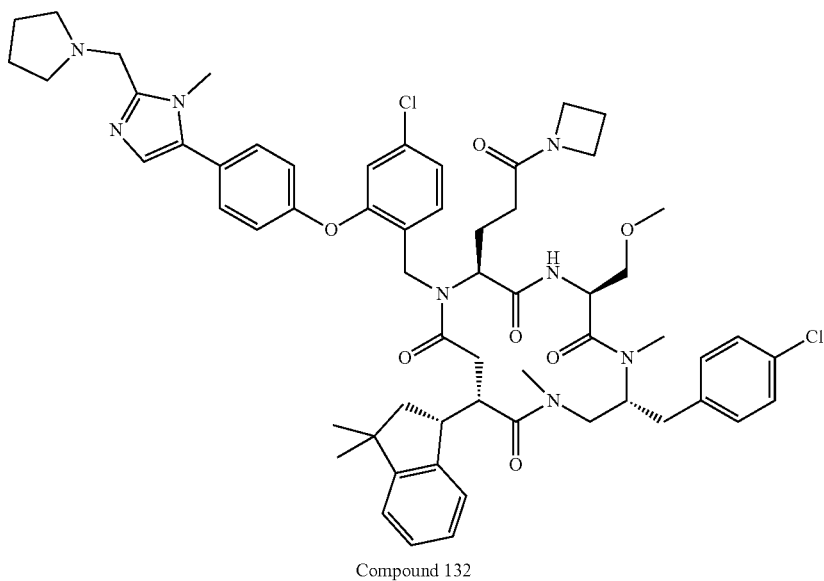

Compound 132

132A (40.6 mg, 0.032 mmol) and TBTU (15.3 mg, 0.048 mmol) were dissolved in DMA (1.5 mL) and DIEA (0.011 mL, 0.064 mmol) and the resulting mixture was stirred at rt for 2 min. A suspension of azetidine HCl (4.5 mg, 0.048 mmol) in DMA (0.5 mL) and DIEA (8.3 µl, 0.048 mmol) was added and stirring was continued for 30 min at rt. Additional TBTU (5.03 mg, 0.016 mmol) and DIEA (2.7 µl, 0.016 mmol) were added, followed by addition of a suspension of azetidine HCl (1.5 mg, 0.016 mmol) in DMA (0.1 mL) and DIEA (2.7 µl, 0.016 mmol). The reaction mixture was stirred for 105 min at rt and 30 min at 50° C. Azetidine HCl (4.4 mg, 0.047 mmol) in DMA (0.5 mL) and DBU (7.1 µl, 0.047 mmol) were again added at rt and stirring was continued for 45 min at rt. The reaction mixture was quenched by addition of MeOH (1 mL) and H₂O and the product was isolated by preparative reverse-phase HPLC (eluent A: 0.1% TFA in H₂O; eluent B: ACN). Pure fractions were combined and lyophilized. The product was dissolved in EtOAc (50 mL) and the organic phase was washed with 5% aq. NaHCO₃ (2×5 mL) and brine, dried over Na₂SO₄, filtered, and concentrated to dryness in vacuo. The residue was dissolved in ACN/H₂O (1:1) (20 mL) and 0.016 M aq. HCl (5.1 mL) was added. After lyophilization, the hydrochloride salt of Compound 132 (14 mg, 0.011 mmol, 34% yield) was obtained as a white solid. Analytical method 9; $t_R$=5.29 min; [M+H]⁺=1087.5.

Example 9.2: Synthesis of (3S,7S,10S,13R)-6-(4-chloro-2-(4-(1-methyl-2-(1-methyl-2,5-dihydro-1H-pyrrol-3-yl)-1H-imidazol-5-yl)phenoxy)benzyl)-13-(4-chlorobenzyl)-3-((S)-2,3-dihydro-1H-inden-1-yl)-10-(hydroxymethyl)-7-methyl-1,6,9,12-tetraazabicyclo[11.3.1]heptadecane-2,5,8,11-tetraone hydrochloride (Compound 77)

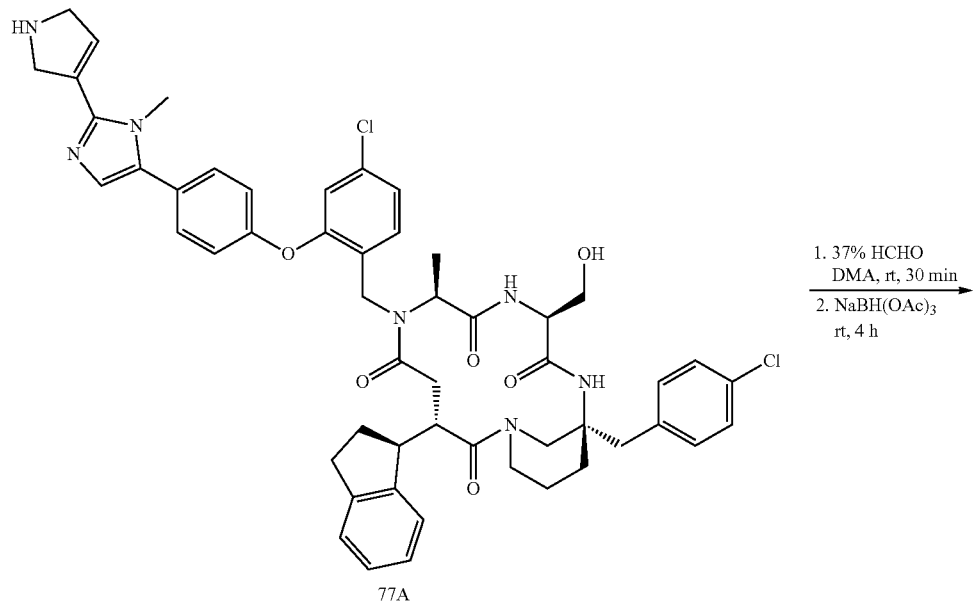

77A

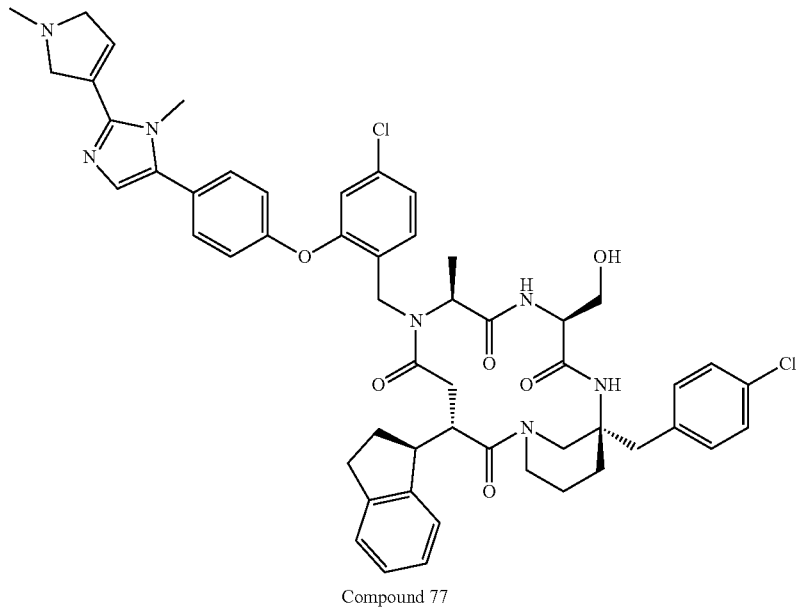

Compound 77

To 77A dissolved in DMA (2 mL) was added 37% formaldehyde solution (0.019 ml, 0.261 mmol) and the resulting solution was stirred for 30 min at rt. NaBH(OAc)$_3$ was then added and stirring was continued at rt for 2 h 30 min Additional 37% formaldehyde solution (6.5 µl, 0.087 mmol) was added and the resulting mixture was stirred for 10 min at rt. NaBH(OAc)$_3$ was again added and stirring at rt was continued for 80 min. The reaction mixture was quenched with H$_2$O (2 mL) and the product was isolated by preparative reverse-phase HPLC (eluent A: 0.01 M HCl in H$_2$O; eluent B: ACN). Pure fractions were combined and lyophilized to afford Compound 77 (30 mg, 0.030 mmol, 34% yield) as a white solid. Analytical method 14; $t_R$=4.48 min; [M+H]$^+$=958.4.

Example 10: PCSK9 Ligand Binding Assay

The PCSK9 binding of the compounds of the disclosure were measured using a time resolved fluorescence resonance energy transfer (TR-FRET) assay. This time resolved fluorescence resonance energy transfer (TR-FRET) assay measures the ability of a compound of the present disclosure to interfere with the binding of human PCSK9 to human LDLR, providing measures of both potency (IC$_{50}$) and efficacy (A$_{max}$).

Materials
 Human PCSK9
 Human PCSK9 Alexa Fluor 647
 Human LDLR extracellular domain-Europium Kryptate
 Proxi plate-low volume assay plate (PerkinElmer #6008280)
 Greiner V-bottom (Greiner BioOne #781280)
 Assay Buffer
 20 mM HEPES, pH 7.5
 150 mM NaCl
 1 mM CaCl$_2$
 0.01% v/v Tween20
 0.01% w/v BSA A master compound plate was prepared in a Greiner V bottom plate by diluting compounds of the disclosure in dimethylsulfoxide to the correct concentration for the desired top concentration based on the desired final concentration: for a 30 uM final concentration the master plate concentration is 1.5 mM (68 uL DMSO+12 uL 10 mM of a compound of the disclosure), for a 10 uM final concentration the master plate concentration is 0.5 mM (76 uL DMSO+4 uL 10 mM of a compound of the disclosure), for a 3 uM final concentration the master plate concentration is 150 uM (69 uL DMSO+1 uL 10 mM of a compound of the disclosure). These solutions were pipetted into columns 1 and 11 of the compound plate. Threefold serial dilutions were generated in columns 2-10 and 12-20 of the compound plate by transferring 10 uL into 20 uL of DMSO. Columns 21 and 22 of the compound plate were negative controls containing DMSO alone.

An intermediate plate was generated in a Greiner V bottom plate by transferring 8 uL from each well of the master plate into a corresponding well containing 92 uL of assay buffer and mixing thoroughly.

A Proxi plate-low volume assay plate was used for the assay. To all wells of the plate was added 10 uL of 16 nM Human PCSK9 Alexa Fluor 647, followed by 5 uL from the intermediate plate. For the positive control wells in columns 23 and 24 of the plate, 5 uL of unlabeled human PCSK9 was added at 4 uM in assay buffer containing 8% DMSO. Following a 30 minute incubation, 5 uL of 4 nM Human LDLR extracellular domain-Europium Kryptate was added and the mixture was incubated for an additional 2 hours.

The TR-FRET signal was measured on an EnVision or PheraStar instrument with a 60 ms delay, 330 nm excitation and 665 nm emission (FRET), and 330 nM excitation and 615 nm (Europium). The FRET ratio (FRET/Europium) was used for calculations.

Data Analysis

No inhibition (0%) was observed from the wells containing DMSO (Control) in columns 21 and 22 of the compound plate. Full inhibition (100%) was observed from the wells containing 1 uM human PCSK9 (Control) in columns 23 and 24 of the plate. Data is expressed as percent inhibition: (value—0%)/(100%-0%).

TABLE 34

PCSK9 activity of cyclic polypeptides of the present disclosure in the PCSK9 Fret assay.

| Cmd No. | PCSK9 FRET Assay IC$_{50}$ (uM) | Max % inhibition |
| --- | --- | --- |
| 1 | 0.000562 | 103.2 |
| 2 | 0.000847 | 112.5 |
| 3 | 0.000452 | 113.9 |
| 4 | 0.000558 | 106.4 |
| 5 | 0.000400 | 101.9 |
| 6 | 0.000956 | 119.9 |
| 7 | 0.000401 | 107.3 |
| 8 | 0.000465 | 104.7 |
| 9 | 0.000220 | 111.3 |
| 10 | 0.000152 | 115.5 |
| 11 | 0.000351 | 110.0 |
| 12 | 0.000152 | 112.8 |
| 13 | 0.000549 | 112.1 |
| 14 | 0.000632 | 102.7 |
| 15 | 0.000342 | 119.0 |
| 16 | 0.000529 | 97.5 |
| 17 | 0.000327 | 102.6 |
| 18 | 0.000549 | 104.5 |
| 19 | 0.000450 | 105.3 |
| 20 | 0.000187 | 117.5 |
| 21 | 0.000470 | 107.0 |
| 22 | 0.000159 | 101.9 |
| 23 | 0.000463 | 109.3 |
| 24 | 0.000277 | 115.7 |
| 25 | 0.000438 | 100.8 |
| 26 | 0.000480 | 98.3 |
| 27 | 0.000627 | 111.0 |
| 28 | 0.000612 | 114.2 |
| 29 | 0.000970 | 119.8 |
| 30 | 0.000819 | 106.2 |
| 31 | 0.001104 | 98.3 |
| 32 | 0.000447 | 105.8 |
| 33 | 0.001054 | 113.0 |
| 34 | 0.000509 | 101.6 |
| 35 | 0.000914 | 105.0 |
| 36 | 0.000584 | 104.5 |
| 37 | 0.000445 | 112.0 |
| 38 | 0.000715 | 106.4 |
| 39 | 0.000383 | 113.2 |
| 40 | 0.000600 | 107.8 |
| 41 | 0.000556 | 105.9 |
| 42 | 0.000596 | 108.3 |
| 43 | 0.000405 | 110.0 |
| 44 | 0.001184 | 105.2 |
| 45 | 0.000816 | 103.7 |
| 46 | 0.000568 | 112.3 |
| 47 | 0.000820 | 97.0 |
| 48 | 0.000596 | 102.8 |
| 49 | 0.000631 | 102.2 |
| 50 | 0.000510 | 108.7 |
| 51 | 0.001115 | 101.3 |
| 52 | 0.000610 | 112.5 |
| 53 | 0.000700 | 107.4 |
| 54 | 0.000624 | 109.4 |
| 55 | 0.000742 | 96.0 |
| 56 | 0.000425 | 101.7 |
| 57 | 0.000763 | 115.6 |
| 58 | 0.000367 | 106.6 |
| 59 | 0.000572 | 103.6 |
| 60 | 0.000476 | 106.6 |
| 61 | 0.000623 | 109.3 |

TABLE 34-continued

PCSK9 activity of cyclic polypeptides of the present disclosure in the PCSK9 Fret assay.

| Cmd No. | PCSK9 FRET Assay IC$_{50}$ (uM) | Max % inhibition |
|---|---|---|
| 62 | 0.000963 | 110.7 |
| 63 | 0.000851 | 117.9 |
| 64 | 0.001161 | 99.7 |
| 65 | 0.000621 | 109.2 |
| 66 | 0.000673 | 104.2 |
| 67 | 0.000334 | 104.2 |
| 68 | 0.001618 | 95.0 |
| 69 | 0.000781 | 70.1 |
| 70 | 0.001478 | 110.7 |
| 71 | 0.000754 | 102.6 |
| 72 | 0.000837 | 100.1 |
| 73 | 0.001362 | 95.0 |
| 74 | 0.001733 | 99.1 |
| 75 | 0.000758 | 113.3 |
| 76 | 0.000810 | 101.7 |
| 77 | 0.000979 | 71.9 |
| 78 | 0.000859 | 99.2 |
| 79 | 0.000819 | 108.3 |
| 80 | 0.000624 | 106.6 |
| 81 | 0.000950 | 105.6 |
| 82 | 0.000370 | 108.5 |
| 83 | 0.000347 | 112.4 |
| 84 | 0.001679 | 101.9 |
| 85 | 0.001408 | 101.7 |
| 86 | 0.000941 | 99.4 |
| 87 | 0.000580 | 111.7 |
| 88 | 0.003163 | 99.0 |
| 89 | 0.001508 | 104.5 |
| 90 | 0.001711 | 99.2 |
| 91 | 0.001834 | 104.8 |
| 92 | 0.002372 | 104.1 |
| 93 | 0.001395 | 103.0 |
| 94 | 0.000978 | 107.7 |
| 95 | 0.001880 | 102.5 |
| 96 | 0.002215 | 96.3 |
| 97 | 0.002083 | 91.2 |
| 98 | 0.002406 | 108.6 |
| 99 | 0.002861 | 116.6 |
| 100 | 0.002359 | 95.5 |
| 101 | 0.001943 | 98.3 |
| 102 | 0.001380 | 100.8 |
| 103 | 0.002075 | 98.4 |
| 104 | 0.001837 | 69.1 |
| 105 | 0.006122 | 97.0 |
| 106 | 0.008521 | 105.1 |
| 107 | 0.007834 | 105.6 |
| 108 | 0.009323 | 104.6 |
| 109 | 0.011150 | 82.0 |
| 110 | 0.010157 | 102.2 |
| 111 | 0.011402 | 102.4 |
| 112 | 0.013515 | 98.8 |
| 113 | 0.021584 | 102.5 |
| 114 | 0.021412 | 95.9 |
| 115 | 0.024971 | 99.0 |
| 116 | 0.019724 | 104.9 |
| 117 | 0.035134 | 98.9 |
| 118 | 0.059598 | 95.2 |
| 119 | 0.031317 | 94.0 |
| 120 | 0.061156 | 102.4 |
| 121 | 0.091485 | 92.9 |
| 122 | 0.094331 | 96.9 |
| 123 | 0.346011 | 84.4 |
| 124 | 0.102446 | 96.8 |
| 125 | 0.102587 | 92.2 |
| 126 | 0.612336 | 100.1 |
| 127 | 0.138173 | 94.3 |
| 128 | 0.250492 | 89.8 |
| 129 | 0.204711 | 87.3 |
| 130 | 0.878852 | 99.3 |
| 131 | 0.281120 | 91.9 |
| 132 | 0.231350 | 100.3 |
| 133 | 1.492230 | 76.9 |
| 134 | 0.490074 | 93.6 |
| 135 | 0.630564 | 91.3 |
| 136 | 0.00026 | 113.0 |
| 137 | 0.00030 | 113.0 |
| 138 | 0.00018 | 114.0 |
| 139 | 0.00015 | 113.0 |
| 140 | 0.00145 | 109.6 |
| 141 | 0.00178 | 112.3 |
| 142 | 0.00091 | 111.1 |
| 143 | 0.00128 | 113.6 |
| 144 | 0.00396 | 113.1 |
| 145 | 0.00095 | 112.3 |
| 146 | 0.00057 | 111.4 |
| 147 | 0.00072 | 110.6 |
| 148 | 0.00109 | 111.9 |
| 149 | 0.00075 | 111.4 |
| 150 | 0.00085 | 105.4 |
| 151 | 0.00569 | 107.5 |
| 152 | 0.00329 | 103.4 |
| 153 | 0.00093 | 100.4 |
| 154 | 0.00071 | 104.6 |
| 155 | 0.00095 | 101.4 |
| 156 | 0.00921 | 100.8 |
| 157 | 0.00118 | 104.7 |
| 158 | 0.00096 | 110.3 |
| 159 | 0.00125 | 114.0 |
| 160 | 0.00163 | 113.8 |
| 161 | 0.00033 | 115.5 |
| 162 | 0.00130 | 114.4 |
| 163 | 0.00121 | 111.6 |
| 164 | 0.00090 | 109.6 |
| 165 | 0.00093 | 113.3 |
| 166 | 0.00074 | 98.1 |
| 167 | 0.00090 | 108.6 |
| 168 | 0.00081 | 114.9 |
| 169 | 0.00085 | 113.1 |
| 170 | 0.00073 | 115.0 |
| 171 | 0.00103 | 107.8 |
| 172 | 0.00057 | 104.8 |
| 173 | 0.00137 | 107.7 |
| 174 | 0.00220 | 110.7 |
| 175 | 0.00256 | 114.7 |
| 176 | 0.07631 | 86.3 |
| 177 | 0.05268 | 108.8 |
| 178 | 0.00266 | 104.3 |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:
1. A compound of Formula (Ig):

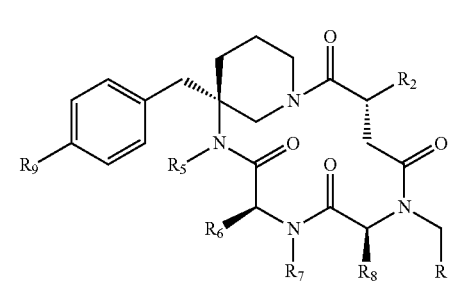

wherein:
$R_1$ is $(C_6-C_{10})$aryl substituted with —$OR_{10}$ and substituted with one to three $R_{11}$;
$R_2$ is H, $(C_1-C_6)$alkyl, $(C_2-C_6)$alkenyl, $(C_1-C_6)$haloalkyl, —$NR_{12}R_{13}$, $(C_3-C_7)$carbocyclyl, $(C_3-C_7)$cycloalkenyl, 5- to 7-membered heterocyclyl comprising 1-3 heteroatoms selected from N, O, and S, $(C_6-C_{10})$aryl, or 5- or 6-membered heteroaryl comprising 1-3 heteroatoms selected from N, O, and S, wherein the alkyl is optionally substituted with one or more $R_{18}$, and the carbocyclyl, $(C_3-C_7)$cycloalkenyl, heterocyclyl, aryl and heteroaryl are optionally substituted with one or more $R_{19}$;
$R_5$ and $R_7$ are each independently H, D, $(C_1-C_6)$alkyl, $(C_1-C_6)$alkoxy, $(C_1-C_6)$haloalkyl, $(C_1-C_6)$haloalkoxy, or $(C_1-C_6)$hydroxyalkyl, wherein the $(C_1-C_6)$alkyl is optionally substituted with one or more D;
$R_6$ is $(C_1-C_6)$alkyl, $(C_1-C_6)$alkoxy, $(C_1-C_6)$haloalkyl, $(C_1-C_6)$haloalkoxy, or $(C_1-C_6)$hydroxyalkyl, wherein the alkyl is optionally substituted with one or more substituents each independently selected from $(C_1-C_6)$alkoxy, $(C_1-C_6)$haloalkoxy, —$C(O)(C_1-C_6)$alkyl, —$C(O)OH$, and —$C(O)O(C_1-C_6)$alkyl;
$R_8$ is H, $(C_1-C_6)$alkyl, or $(C_1-C_6)$haloalkyl, wherein the alkyl is optionally substituted with one or more substituents each independently selected from $(C_3-C_7)$carbocyclyl, 4- to 7-membered heterocyclyl comprising 1-3 heteroatoms selected from N, O, and S, —$NR_{16}R_{17}$, and —$C(O)NR_{16}R_{17}$;
$R_9$ is halogen, $(C_1-C_6)$alkyl, $(C_1-C_6)$alkoxy, $(C_1-C_6)$haloalkyl, $(C_1-C_6)$haloalkoxy, —OH, or CN;
$R_{10}$ is $(C_6-C_{10})$aryl or 5- or 6-membered heteroaryl comprising 1-3 heteroatoms selected from N, O, and S, wherein the aryl and heteroaryl are optionally substituted with one or more $R_{22}$;
each $R_{11}$ is independently at each occurrence halogen, $(C_1-C_6)$alkyl, $(C_1-C_6)$alkoxy, $(C_1-C_6)$haloalkyl, $(C_1-C_6)$haloalkoxy, —OH, or CN;
$R_{12}$ and $R_{13}$ are each independently H or $(C_1-C_6)$alkyl;
$R_{16}$ and $R_{17}$ are each independently H or $(C_1-C_6)$alkyl, or $R_{16}$ and $R_{17}$ together with the nitrogen atom to which they are attached form a 4- to 7-membered heterocyclyl ring optionally comprising 1-2 additional heteroatoms selected from N, O, and S;
each $R_{18}$ is independently at each occurrence $(C_3-C_7)$carbocyclyl, 5- to 7-membered heterocyclyl comprising 1-3 heteroatoms selected from N, O, and S, $(C_6-C_{10})$aryl, or 5- or 6-membered heteroaryl comprising 1-3 heteroatoms selected from N, O, and S, wherein the carbocyclyl, heterocyclyl, aryl and heteroaryl are optionally substituted with one or more $R_{20}$;
each $R_{19}$ is independently at each occurrence halogen, $(C_1-C_6)$alkyl, $(C_1-C_6)$alkoxy, $(C_1-C_6)$haloalkyl, $(C_1-C_6)$haloalkoxy, —OH, or CN; or
two $R_{19}$ together, when on adjacent atoms, form a $(C_6-C_{10})$aryl or 5- or 6-membered heteroaryl ring comprising 1-3 heteroatoms selected from N, O, and S, wherein the aryl and heteroaryl are optionally substituted with one or more substituents each independently selected from halogen, $(C_1-C_6)$alkyl, $(C_1-C_6)$alkoxy, $(C_1-C_6)$haloalkyl, $(C_1-C_6)$haloalkoxy, —OH, and CN;
each $R_{20}$ is independently at each occurrence halogen, $(C_1-C_6)$alkyl, $(C_1-C_6)$alkoxy, $(C_1-C_6)$haloalkyl, $(C_1-C_6)$haloalkoxy, oxo, —OH, or CN; or
when $R_{18}$ is a carbocyclyl or a heterocyclyl, two $R_{20}$, when attached to the same carbon atom, together form =(O);
$R_{21}$ is H or $(C_1-C_6)$alkyl;
each $R_{22}$ is independently at each occurrence halogen, $(C_1-C_6)$alkyl, $(C_1-C_6)$alkoxy, $(C_1-C_6)$haloalkyl, $(C_1-C_6)$haloalkoxy, —OH, CN, $(C_6-C_{10})$aryl, or 5- or 6-membered heteroaryl comprising 1-3 heteroatoms selected from N, O, and S, wherein the aryl and heteroaryl are optionally substituted with one or more $R_{23}$;
each $R_{23}$ is independently at each occurrence halogen, $(C_1-C_6)$alkyl, $(C_1-C_6)$alkoxy, $(C_1-C_6)$haloalkyl, $(C_1-C_6)$haloalkoxy, —$CH_2(OCH_2CH_2)_{1-3}OCH_2CH_3$, —OH, CN, or 4- to 7-membered heterocyclyl comprising 1-3 heteroatoms selected from N, O, and S, wherein the heterocyclyl is optionally substituted with one or more substituents each independently selected from halogen, $(C_1-C_6)$alkyl, $(C_1-C_6)$alkoxy, $(C_1-C_6)$haloalkyl, $(C_1-C_6)$haloalkoxy, —OH, —$C(O)R_{24}R_{25}$, —$NR_{24}C(O)R_{25}$, —$NH_2$, —$NH(C1-C_6)$alkyl, and —$N((C_1-C_6)$alkyl$)_2$, and the alkyl is optionally substituted with —$NR_{24}R_{25}$ or a 4- to 7-membered heterocyclyl comprising 1-3 heteroatoms selected from N, O, and S optionally substituted with one or more substituents each independently selected from halogen, $(C_1-C_6)$alkyl, $(C_1-C_6)$alkoxy, $(C_1-C_6)$haloalkyl, $(C_1-C_6)$haloalkoxy, —OH, —$NH_2$, —$NH(C_1-C_6)$alkyl, and —$N((C_1-C_6)$alkyl$)_2$; and
$R_{24}$ and $R_{25}$ are each independently H, $(C_1-C_6)$alkyl, or $(C_3-C_7)$carbocyclyl optionally substituted with one to two $(C_1-C_6)$alkyl;
or a pharmaceutically acceptable salt, hydrate, solvate, prodrug, stereoisomer, N-oxide, or tautomer thereof.

2. The compound according to claim 1, wherein $R_5$ is H or $(C_1-C_6)$alkyl.

3. The compound according to claim 1 or 2, wherein $R_5$ is $(C_1-C_6)$alkyl.

4. The compound according to any one of claims 1-3, wherein $R_7$ is H or $(C_1-C_6)$alkyl.

5. The compound according to any one of claims 1-4, wherein $R_7$ is H.

6. The compound according to any one of claims 1-5, wherein $R_9$ is halogen.

7. The compound according to any one of claims 1-6, wherein $R_9$ is chloro.

8. The compound according to any one of claims 1-7, wherein $R_a$ is $(C_1-C_6)$alkyl optionally substituted with one to three substituents each independently selected from $(C_3-C_7)$carbocyclyl, 4- to 7-membered heterocyclyl comprising 1-3 heteroatoms selected from N, O, and S, —$NR_{16}R_{17}$, and —$C(O)NR_{16}R_{17}$.

9. The compound according to any one of claims 1-8, wherein $R_8$ is $(C_1-C_6)$alkyl.

10. The compound according to any one of claims 1-9, wherein $R_1$ is phenyl substituted with —$OR_{10}$ and optionally substituted with one to three $R_{11}$.

11. The compound according to any one of claims 1-10, wherein $R_{10}$ is phenyl substituted with one to three $R_{22}$.

12. The compound according to claim 1 selected from:
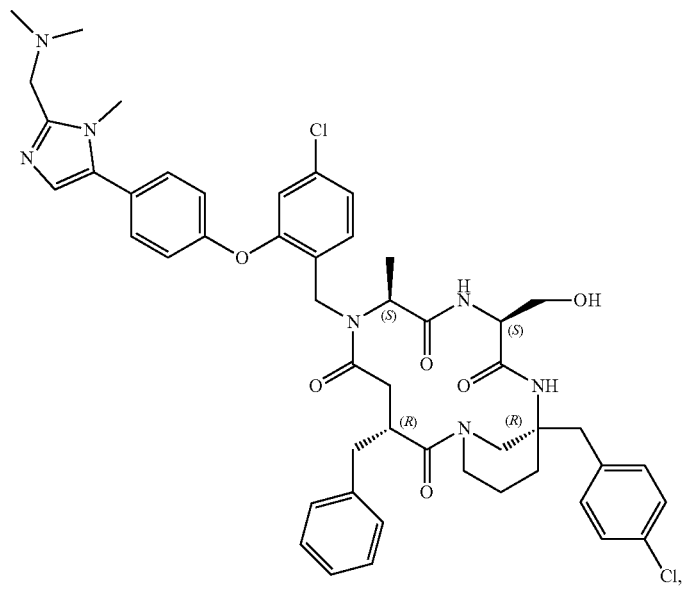
(Cmd No. 50)
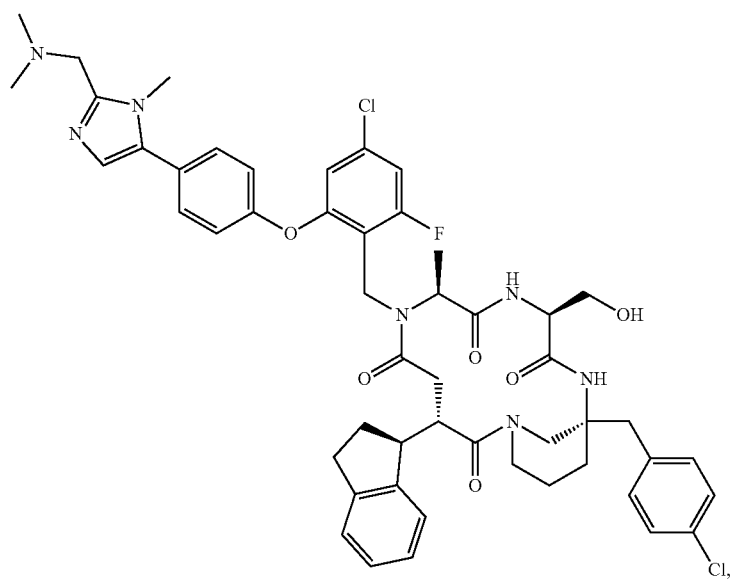
(Cmd No. 49)

-continued
(Cmd No. 53)
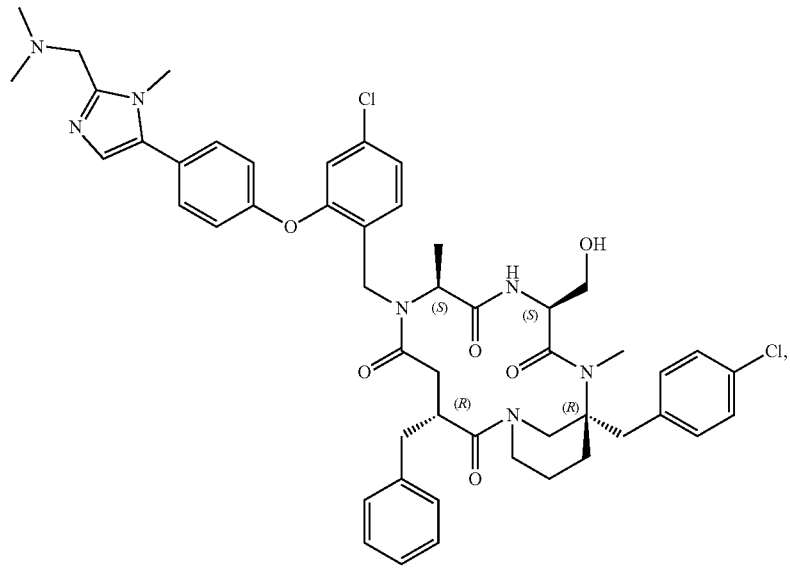
(Cmd No. 11)
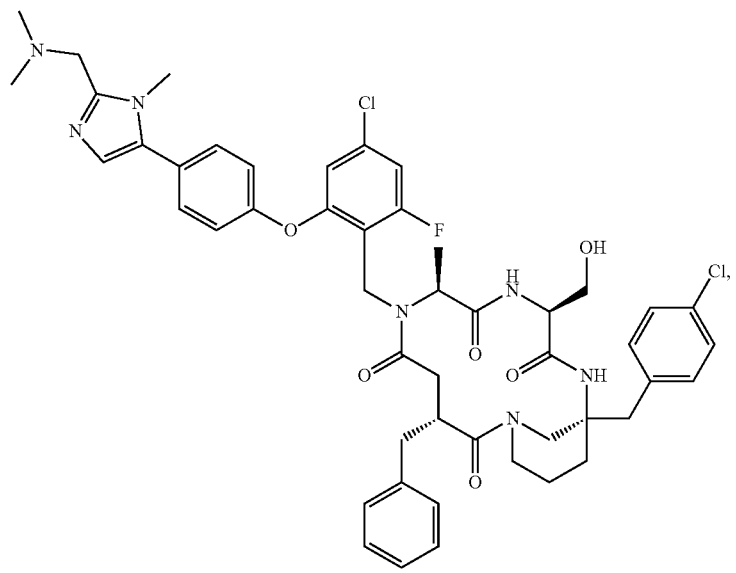

(Cmd No. 79)
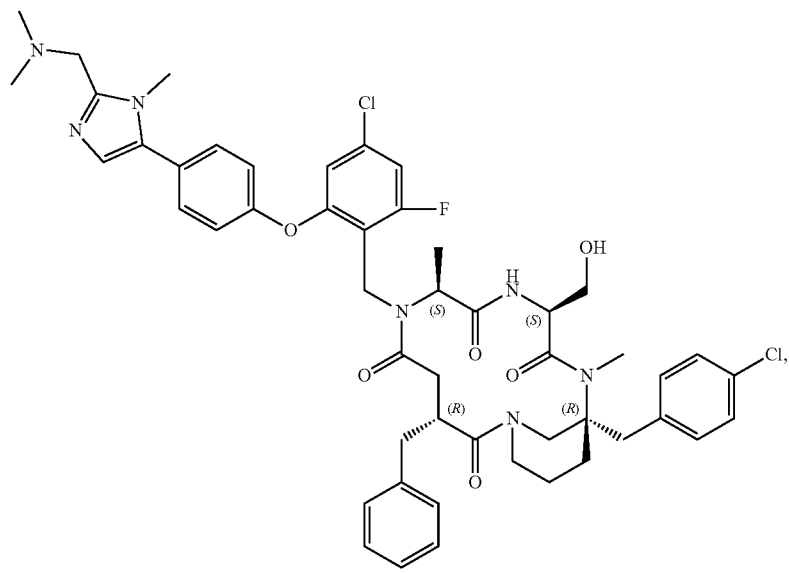
(Cmd No. 22)
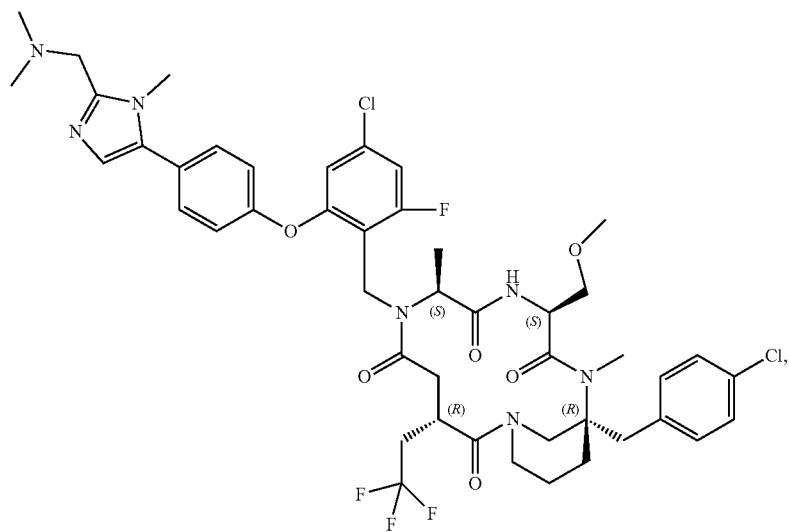
(Cmd No. 82)
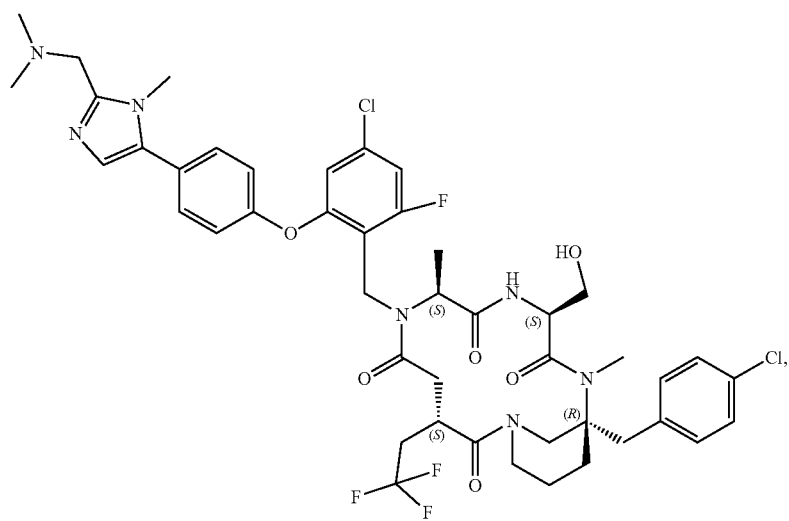

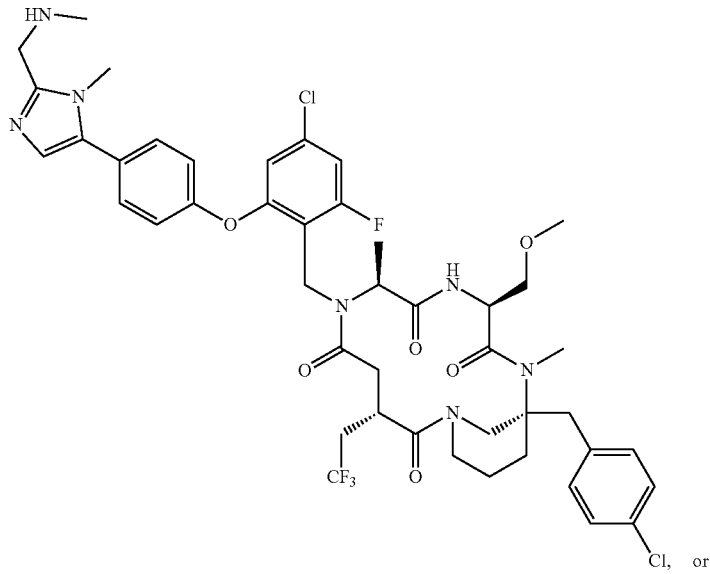

(Cmd No. 172)

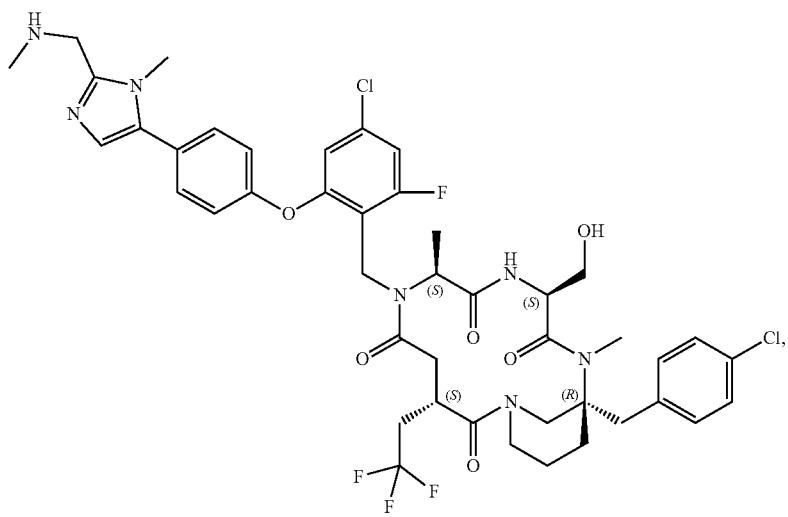

(Cmd No. 177)

or a pharmaceutically acceptable salt, hydrate, solvate, prodrug, stereoisomer, N-oxide, or tautomer thereof.

13. A pharmaceutical composition comprising a therapeutically effective amount of a compound according to any one of the claims 1-12, or a pharmaceutically acceptable salt thereof, and a pharmaceutically acceptable carrier or excipient.

14. The pharmaceutical composition according to claim 13 further comprising at least one additional pharmaceutical agent.

15. A method of modulating PCSK9 comprising administering to a patient in need thereof a compound according to any one of claims 1-12, or a pharmaceutically acceptable salt thereof.

16. A method of inhibiting PCSK9 comprising administering to a patient in need thereof a compound according to any one of claims 1-12, or a pharmaceutically acceptable salt thereof.

17. A method of inhibiting PCSK9 activity comprising administering to a patient in need thereof a compound according to any one of claims 1-12, or a pharmaceutically acceptable salt thereof.

18. A method for treating a PCSK9-mediated disease or disorder comprising the step of administering to a patient in need thereof a therapeutically effective amount of a compound according to any one of the claims 1-12, or a pharmaceutically acceptable salt thereof.

19. The method according to claim 18, wherein said PCSK9-mediated disease or disorder is selected from hypercholesterolemia, hyperlipidemia, hypertriglyceridemia, sitosterolemia, atherosclerosis, arteriosclerosis, coronary heart disease, peripheral vascular disease, vascular inflammation, and xanthoma.

20. A method of reducing LDL-C in a patient in need thereof, the method comprising administering a therapeutically effective amount of a compound of any one of claims 1-12, or a pharmaceutically acceptable salt thereof to the patient, thereby reducing LDL-C in the patient.

* * * * *